US011510886B2

(12) United States Patent
González-Canudas

(10) Patent No.: US 11,510,886 B2
(45) Date of Patent: Nov. 29, 2022

(54) METFORMIN AMINO ACID COMPOUNDS AND METHODS OF USING THE SAME

(71) Applicant: Laboratorios Silanes S.A. DE C.V., Mexico City (MX)

(72) Inventor: Jorge González-Canudas, Mexico City (MX)

(73) Assignee: LABORATORIOS SILANES, S.A. DE C.V., Mexico City (MX)

( * ) Notice: Subject to any disclaimer, the term of this patent is extended or adjusted under 35 U.S.C. 154(b) by 0 days.

(21) Appl. No.: 16/337,994

(22) PCT Filed: Sep. 29, 2017

(86) PCT No.: PCT/IB2017/056034
§ 371 (c)(1),
(2) Date: Mar. 29, 2019

(87) PCT Pub. No.: WO2018/060962
PCT Pub. Date: Apr. 5, 2018

(65) Prior Publication Data
US 2020/0222343 A1    Jul. 16, 2020

Related U.S. Application Data

(60) Provisional application No. 62/402,921, filed on Sep. 30, 2016.

(51) Int. Cl.
| | | |
|---|---|---|
| *A61K 31/155* | (2006.01) | |
| *C07C 279/26* | (2006.01) | |
| *A61K 9/14* | (2006.01) | |
| *A61K 45/06* | (2006.01) | |
| *A61P 3/10* | (2006.01) | |
| *A61K 31/198* | (2006.01) | |
| *A61K 47/18* | (2017.01) | |

(52) U.S. Cl.
CPC ............ *A61K 31/155* (2013.01); *A61K 9/145* (2013.01); *A61K 31/198* (2013.01); *A61K 47/183* (2013.01); *A61P 3/10* (2018.01); *C07C 279/26* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,903,141 A | 9/1975 | Just et al. | |
| 3,957,853 A | 5/1976 | Bohuon | |
| 4,028,402 A | 6/1977 | Fischer et al. | |
| 4,835,184 A | 5/1989 | Hugelin et al. | |
| 8,703,183 B2 | 4/2014 | Lara | |
| 8,853,259 B2* | 10/2014 | Mylari ................. | C07D 339/04 514/440 |
| 2005/0158374 A1 | 7/2005 | Wong et al. | |
| 2008/0031964 A1 | 2/2008 | Messadek | |
| 2012/0219623 A1* | 8/2012 | Meinicke ................ | A61P 25/00 424/465 |
| 2014/0018419 A1 | 1/2014 | Mylari et al. | |
| 2017/0119841 A1* | 5/2017 | Mathias ............. | C07K 5/06069 |

FOREIGN PATENT DOCUMENTS

| | | |
|---|---|---|
| WO | WO 2005/065675 | 7/2005 |
| WO | WO 2006/086856 | 8/2006 |
| WO | WO 2008/061456 | 5/2008 |
| WO | WO 2008/093984 | 8/2008 |
| WO | WO 2009/038396 | 3/2009 |
| WO | WO 2009/144527 | 12/2009 |
| WO | WO 2011/051974 | 5/2011 |
| WO | WO 2018/060959 | 4/2018 |

OTHER PUBLICATIONS

Mencarelli et al., "Goodpasture Antigen-binding Protein/Ceramide Transporter Binds to Human Serum Amyloid P-Component and Is Present in Brain Amyloid Plaques" The Journal of Biological Chemistry vol. 287 No. 18 pp. 14897-14911 (Year: 2012).*

Scotland et al., "Mitochondrial energetic and AKT status mediate metabolic effects and apoptosis of metformin in human leukemic cells" Leukemia vol. 27 pp. 2129-2138 (Year: 2013).*

Rena et al., "Molecular mechanism of action of metformin: old or new insights?" Diabetologia vol. 56 pp. 1898-1906 (Year: 2013).*

Definition of "Complex" from https://www.brittanica.com/science/complex-in-chemistry (Year: 2011).*

Yadav et al., "Co-Crystals: A Novel Approach to Modify Physicochemical Properties of Active Pharmaceutical Ingredients" Indian Journal of Pharmaceutical Sciences, vol. 71 No. 4 pp. 359-370 (Year: 2009).*

Brunmair, B., et al., "Thiazolidinediones, Like Metformin, Inhibit Respiratory Complex I: A Common Mechanism Contributing to Their Antidiabetic Actions?" *Diabetes* 53:1052-1059, 2004, American Diabetes Association, United States.

Buzzai, M., et al., "Systemic Treatment with the Antidiabetic Drug Metformin Selectively Impairs p53-Deficient Tumor Cell Growth," *Cancer Res.* 67(14):6745-6752, 2007, Science Publishing Group, United States.

Hardie, D.G., "Neither LKB1 Nor AMPK Are the Direct Targets of Metformin," *Gastroenterology* 131:973, 2006, Elsevier, Netherlands.

Kim, Y.D., et al., "Metformin Inhibits Hepatic Gluconeogenesis Through AMP-Activated Protein Kinase-Dependent Regulation of the Orphan Nuclear Receptor SHP," *Diabetes* 57:307-314, 2008, American Diabetes Association, United States.

Natali, A., et al., "Effects of metformin and thiazolidinediones on suppression of hepatic glucose production and stimulation of glucose update in type 2 diabetes: a systematic review," *Diabetologia* 49:434-441, 2006, Springer-Verlag, Germany.

(Continued)

*Primary Examiner* — Eric Olson
(74) *Attorney, Agent, or Firm* — Sterne, Kessler, Goldstein & Fox

(57) ABSTRACT

The present invention relates to metformin amino acid compounds (SLNs), pharmaceutical compositions thereof, and methods of using them for the treatment of hyperglycemia, diabetes, and Type 2 diabetes. The compounds can be synthesized using the processes disclosed herein.

4 Claims, 144 Drawing Sheets

(56) References Cited

OTHER PUBLICATIONS

Figure 1:
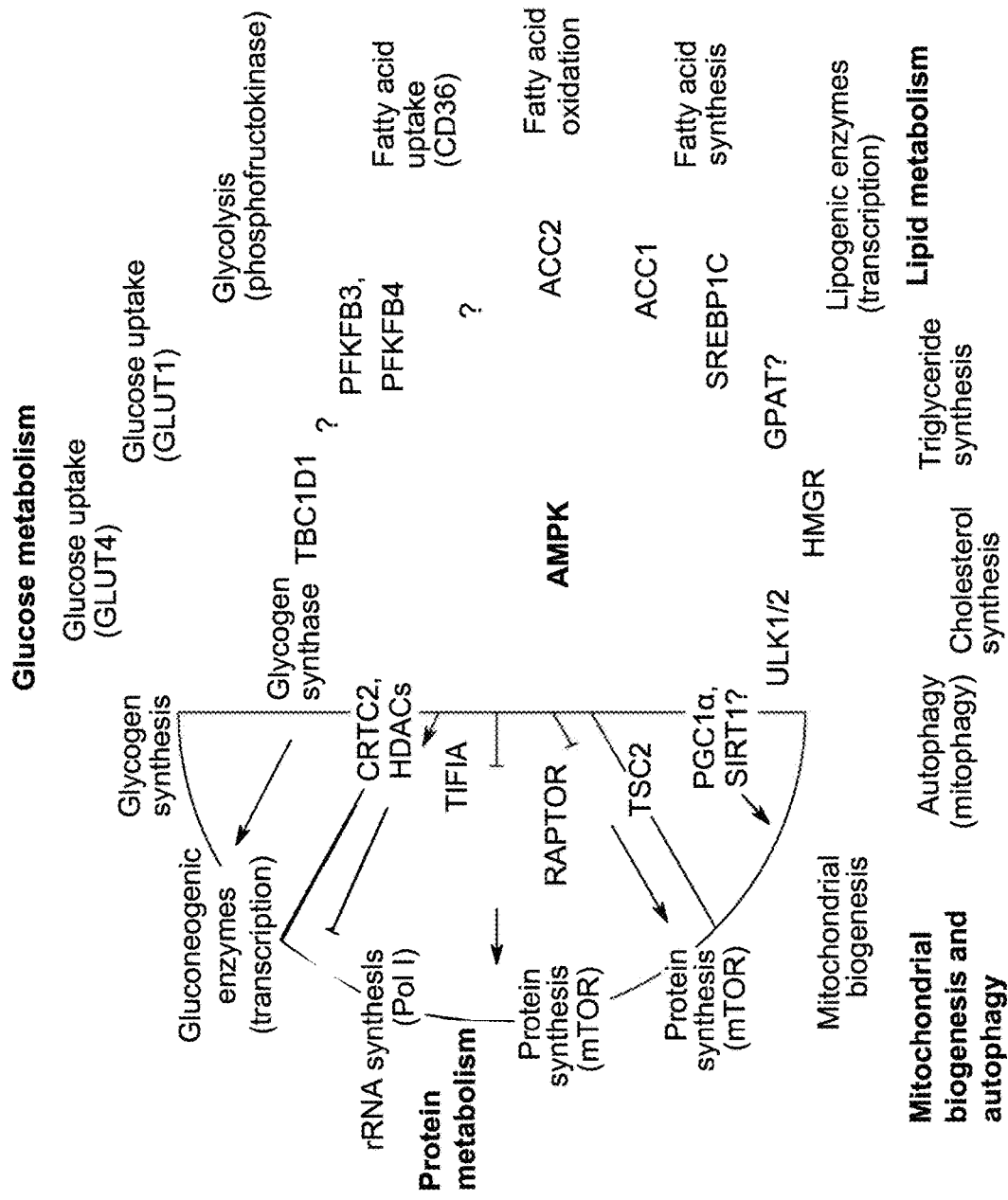

Ouyang, J., et al., "Metformin Activates AMP Kinase through Inhibition of AMP Deaminase," *J. Biol. Chem.* 286(1):1-11, 2011, American Society for Biochemistry and Molecular Biology, Inc., United States.

Zhang, Y., et al., "Metfoiinin interacts with AMPK through binding to γ subunit," *Mol. Cell Biochem.* 368:69-76, 2012, Springer Science+Business Media, LLC, United States.

Bogan, J. S., et al., "Functional cloning of TUG as a regulator of GLUT4 glucose transporter trafficking," *Nature* 425:727-733, Nature Publishing Group, United Kingdom (Oct. 2003).

Fioranelli, M., et al., "Twenty-five years of studies and trials for the therapeutic application of IL-10 imunomodulating properties. From high doses administration to low dose medicine new paradigm," *Journal of Integrative Cardiology* 1(1):2-6, Open Access Text, United Kingdom (Dec. 2014).

Galadari, S., et al., "Role of ceramide in diabetes mellitus: evidence and mechanisms," *Lipids Health Disease* 12:98-114, Springer Nature, United States (Jul. 2013).

Granero, F., et al., "A human-specific TNF-responsive promoter for Goodpasture antigen-binding protein," *FEBS Journal* 272(20):5291-5305, John Wiley & Sons, United States (Oct. 2005).

Granero-Moltó, F., et al., "Goodpasture Antigen-binding Protein and Its Spliced Variant, Ceramide Transfer Protein, Have Different Functions in the Modulation of Apoptosis during Zebrafish Development," *Journal of Biological Chemistry* 283(29):20495-20504, American Society for Biochemistiy and Molecular Biology, Inc., United States (Jul. 2008).

Hla, T., et al., "C16:0-Ceramide Signals Insulin Resistance," *Cell Metabolism* 20(5):703-705, Elsevier Inc., United States (Nov. 2014).

Jembrek, M. J., et al., "Ceramides in Alzheimer's Disease: Key Mediators of Neuronal Apoptosis Induced by Oxidative Stress and Aβ Accumulation," *Oxidative Medicine and Cellular Longevity* 2015:1-17, Hindawi Publishing Corporation, Egypt (May 2015).

Kramer, H. F., et al., "AS160 Regulates Insulin-and Contraction-stimulated Glucose Uptake in Mouse Skeletal Muscle," *Journal of Biological Chemistry* 281(42):31478-31485, American Society for Biochemistry and Molecular Biology, Inc., United States (published online Aug. 2006, published in print Oct. 2006).

Lee, J. O., et al., "Metformin Regulates Glucose Transporter 4 (GLUT4) Translocation through AMP-activated Protein Kinase (AMPK)-mediated Cb1/CAP Signaling in 3T3-L1 Preadipocyte Cells," *Journal of Biological Chemistry* 287(53):44121-44129, American Society for Biochemistry and Molecular Biology, Inc., United States (published online Nov. 2012, published in print Dec. 2012).

Miralem, T., et al., "Human Biliverdin Reductase Suppresses Goodpasture Antigen-binding Protein (GPBP) Kinase Activity," *Journal of Biological Chemistry* 285(17):12551-12558, American Society for Biochemistiy and Molecular Biology, Inc., United States (published online Feb. 2010, published in print Apr. 2010).

Mosser, D. M., et al., "Interleukin-10: new perspectives on an old cytokine," *Immunological Reviews* 226:205-218, Blackwell Munksgaard, United Kingdom (Dec. 2008).

Raya, A., et al., "Characterization of a Novel Type of Serine/Threonine Kinase That Specifically Phosphorylates the Human Goodpasture Antigen," *Journal of Biological Chemistry* 274(18):12642-12649, American Society for Biochemistry and Molecular Biology, Inc., United States (Apr. 1999).

Raya, A., et al., "Goodpasture Antigen-binding Protein, the Kinase That Phosphorylates the Goodpasture Antigen, Is an Alternatively Spliced Variant Implicated in Autoimmune Pathogenesis," *Journal of Biological Chemistry* 275(51):40392-40399, American Society for Biochemistry and Molecular Biology, Inc., United States (Dec. 2000).

Revert, F., et al., "Goodpasture Antigen-binding Protein Is a Soluble Exportable Protein that Interacts with Type IV Collagen," *Journal of Biological Chemistry* 283(44):30246-30255, American Society for Biochemistry and Molecular Biology, Inc., United States (published online Sep. 2008, published in print Oct. 2008).

Sawada, M., et al., "Molecular mechanisms of TNF-α-induced ceramide formation in human glioma cells: P53-mediated oxidant stress-dependent and -independent pathways," *Cell Death Differentiation* 11(9):997-1008, Nature Publishing Group, United Kingdom (Sep. 2004).

Sharma, K., et al., "The yins and yangs of ceramide," *Cell Res.* 9:1-10, Nature Publishing Group, United Kingdom (Mar. 1999).

Turpin, S.M., et al., "Obesity-Induced CerS6-Dependent C16:0 Ceiamide Production Promotes Weight Gain and Glucose Intolerance," *Cell Metab.* 20(4):678-686, Elsevier, Inc., United States (Oct. 2014).

Xia, J. Y., et al., "The adipokine/ceramide axis: Key aspects of insulin sensitization," *Biochimie* 96:130-139, Elsevier, Inc., United States (published online Aug. 2013, published in print Jan. 2014).

International Search Report and Written Opinion for International Application No. PCT/IB2017/056031, ISA/US, Commissioner for Patents, Alexandria, Virginia, dated Jan. 17, 2018, 12 pages.

International Search Report and Written Opinion for International Application No. PCT/IB2017/056034, ISA/US, Commissioner for Patents, Alexandria, Virginia, dated Apr. 12, 2018, 8 pages.

\* cited by examiner

Figuer 5 anti-GPBP mAb-N27

| Grade | Description | Morphology |
|---|---|---|
| 0 | • Unchanged | Not shown |
| 1 | • Minimal changes<br>• Slight mesangial and/or glomerular basement membrane expansion rate. | Not shown |
| 2 | • Glomerular cell proliferation<br>• Slight mesangial matrix and/or glomerular basement membrane expansion rate | 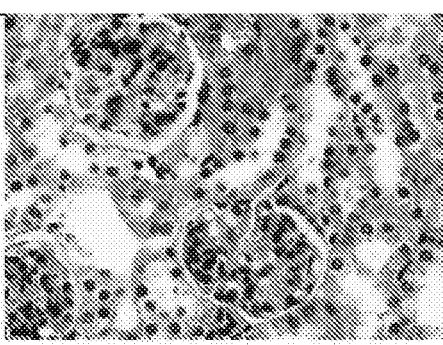 |
| 3 | • Pronounced glomerular cell proliferation<br>• Moderate mesangial expansion and/or basement membrane enlargement that occludes capillaries<br>• Lobulated glomeruli<br>• Small tubular atrophy | 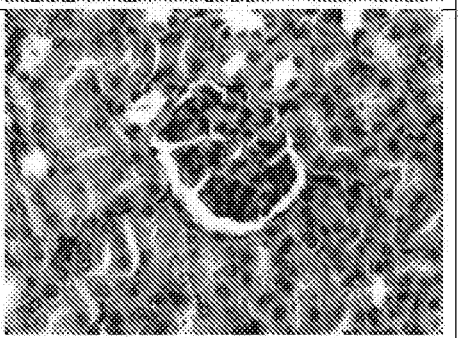 |
| 4 | • Total or partial glomerular sclerosis<br>• Pronounced tubular atrophy<br>• Interstitial inflammatory infiltrates | 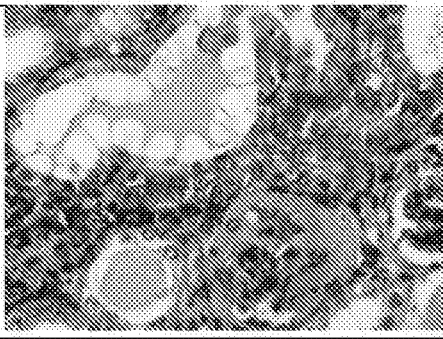 |

Figure 82

Figure 94B:
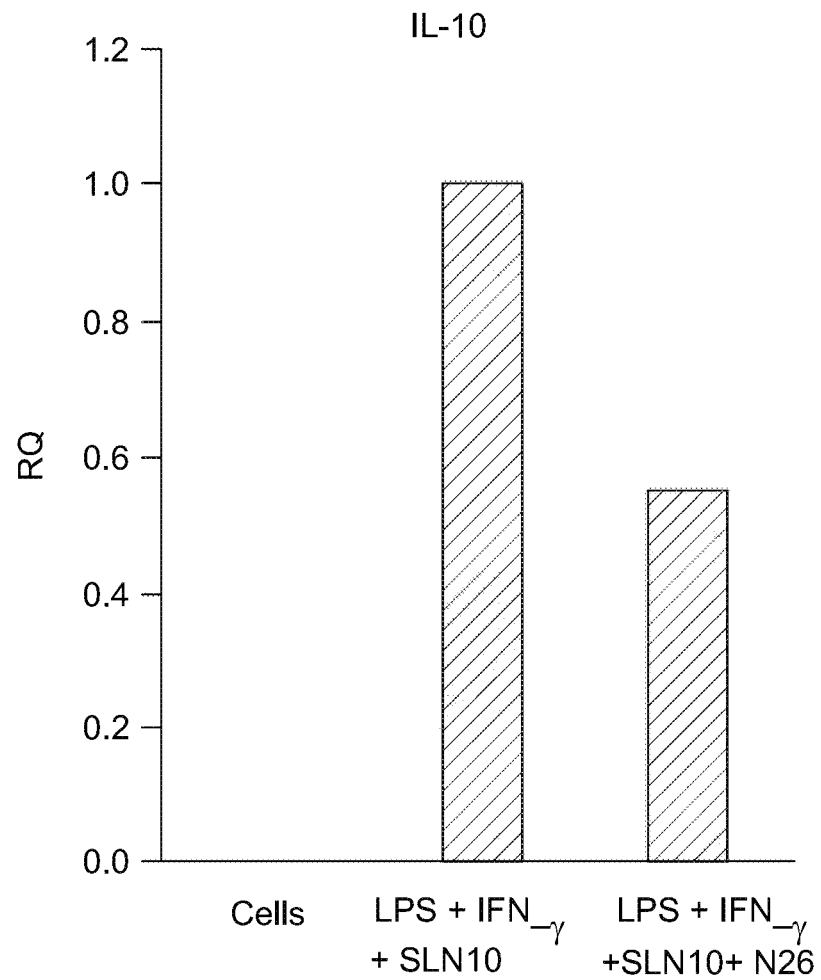

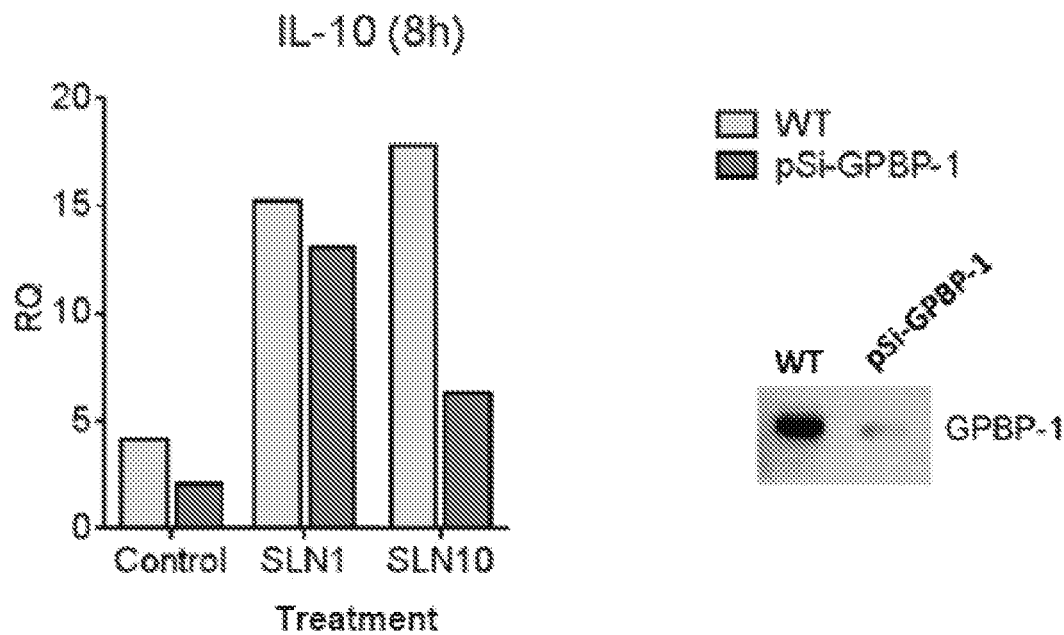
Figure 93
Figure 94A
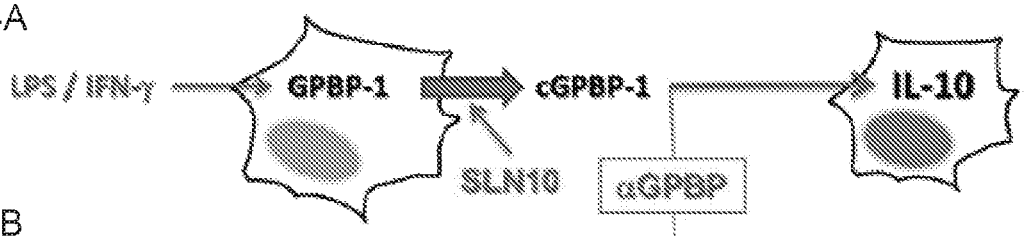
Figure 94B
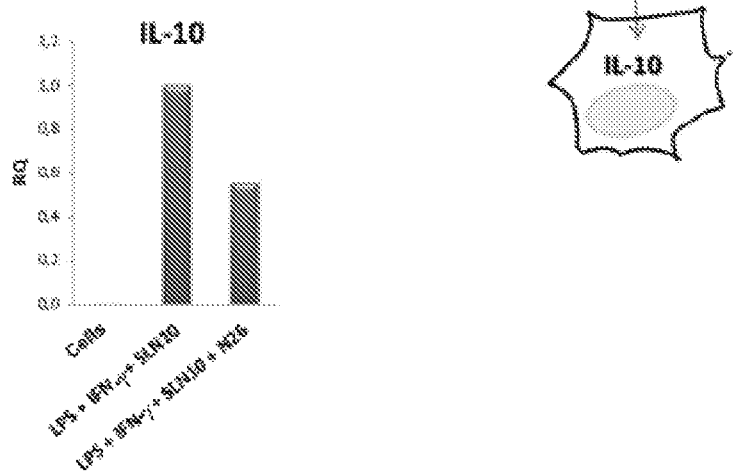

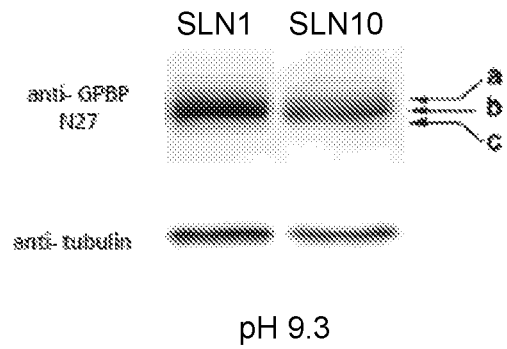
Figure 111
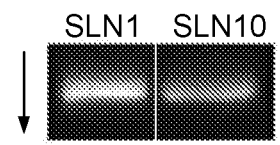
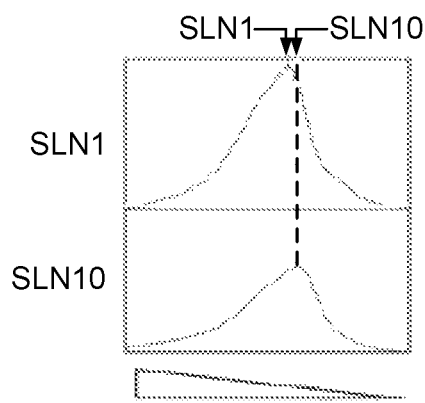
Figure 112

DIPHENFORMIN ASPARTATE
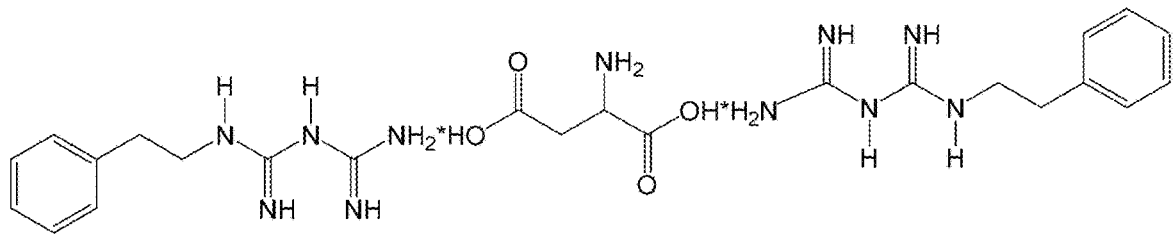
METFORMIN VALINATE
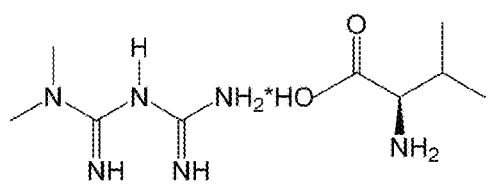
METFORMIN ISOLEUCINATE
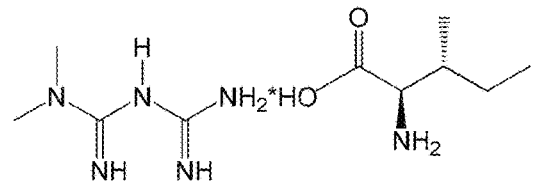
METFORMIN LYSINATE
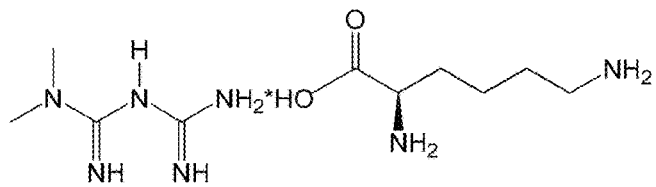
METFORMIN ALANINATE
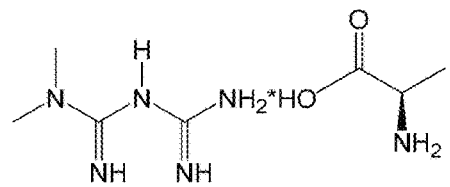
METFORMIN ASPARAGINATE
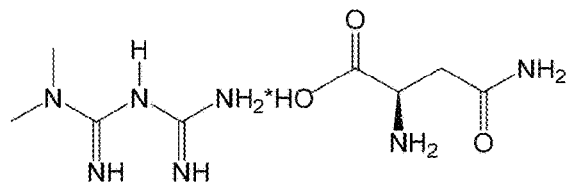
METFORMIN LEUCINATE
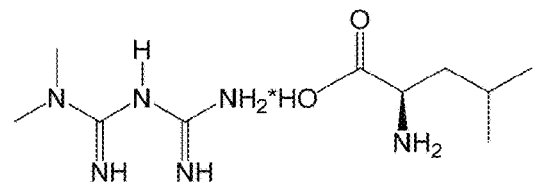
METFORMIN THREONINATE
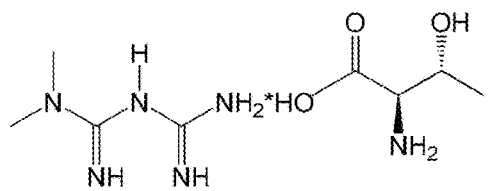
Figure 138

METFORMIN AMINO ACID COMPOUNDS AND METHODS OF USING THE SAME

FIELD OF INVENTION

This invention relates to metformin amino acid compounds, which are useful for the treatment and control of hyperglycemia, diabetes, and diabetes mellitus. Additionally, it relates to pharmaceutical compositions comprising the compounds.

BACKGROUND OF THE INVENTION

Diabetes is currently one of the most expensive chronic diseases, and it is a condition that has reached epidemic proportions worldwide. The International Diabetes Federation (IDF) estimates that more than 190 million people in the world have diabetes, and it has predicted that by 2025 this figure will rise to 330 million, mainly because of population growth, aging, urbanization, and sedentary lifestyle. Diabetes complications are a cause of mortality and are associated with multiple organ damage or failure. Additionally, Type 2 diabetes mellitus patients also have a significantly higher risk of coronary disease, peripheral vascular disease, cerebrovascular disease, as well as arterial hypertension, dyslipidemia, and obesity. Diabetes mellitus is a syndrome characterized by an alteration in glucose metabolism identified by hyperglycemia that occurs because of an impaired insulin secretion or the combination of peripheral resistance to insulin and a reduced compensatory secretion. Type 2 diabetes mellitus (T2DM) is the most common type, and it results from an insulin resistance (mainly the one produced by visceral obesity) with a defective insulin secretion.

According to the last consensus by the American Diabetes Association (ADA) and the European Association for the Study of Diabetes (EASD), achieving specific goals in glycemia control may reduce morbidity considerably. Thus, effective hyperglycemia treatment has become a main priority. Before, treatment of diabetes was centered on hyperglycemia control, but new therapies are focusing as well on controlling dyslipidemia, hypertension, hypercoagulability, obesity, and insulin resistance.

Biguanides are the first choice among drug products for T2DM treatment, since they reduce not only glucose, but also cholesterol levels and patients' weight, lowering the risks of micro and macroangiopathic and cardiovascular complications. Today, the biguanide component most commonly used is metformin hydrochloride (hereon in the text and figures it will be also referred to herein as SLN1), which is converted into hydrochloric acid when ingested, due to the anion release in the solution; this contributes to the typical gastrointestinal symptomatology observed in this drug: diarrhea, flatulence, abdominal malaise, and dyspepsia. Due to its relatively short half-life, it should be administered every 12 hours, which may often reduce treatment adherence and stimulate disease progression.

Biguanides are a group of drugs that reduce glucose levels in blood serum, eliminating hepatic glucose production and promoting glucose absorption by the skeletal muscle. metformin ((Glucophage®), 3-(diaminomethylidene)-1,1-Dimethylguanidine), belongs to the drug class of biguanides and increases insulin sensitivity, which is why it is currently the most prescribed drug and the most used clinically. Metformin does not increase insulin secretion by the pancreas; thus, there is minimum risk of developing hypoglycemia.

Metformin does not trigger insulin release, increases glucose metabolism in tissue (anaerobic glycolysis), reduces hepatic gluconeogenesis, and inhibits the absorption of glucose, amino acids, and other intestinal components. It depends on the AMP-activated protein kinase, which controls energy metabolism.

Metformin activity has been reported to inhibit hepatic gluconeogenesis and glycogenolysis, and increase insulin sensitivity to $IP_3$ kinase receptors. Metformin activates the AMP-dependent protein kinase, a hepatic enzyme that plays a key role in the insulin signaling pathway, energy regulation throughout the body, and the metabolism of glucose and fats. A recent study (Y. D. Kim, K. G. Park, Y. S. Lee, Metformin inhibits hepatic gluconeogenesis through AMP-activated protein kinase-dependent regulation of theorphan nuclear receptor SHP, *Diabetes* 57, 306-14 [2008]) suggests that metformin activity occurs through AMP activation, necessary for increasing the SHP transcription factor, which inhibits the expression of the hepatic gluconeogenesis genes PEPCK and 25 GLC-6-Pase. Studies suggest that metformin increases cytosolic adenosine monophosphate (AMP), in contrast to variations in total AMP or the relationship of total AMP/ATP. Further activity by metformin has also been reported, as well as its use for preventing and treating cancer caused by p53 gene impairment (M. Buzzai, et al., Systemic treatment with the antidiabetic drug metformin selectively impairs p53 gene-deficient tumor cell growth, *Cancer Res.*, 67, 30 [2007]).

There is also evidence that metformin improves sensitivity to insulin by increasing insulin receptor tyrosine kinase activity, promoting glycogen synthesis, and increasing the number and transport capacity of GLUT4 transporters in the plasma membrane. Additionally, it has been demonstrated that in certain organisms, metformin has an effect on mitochondrial activity. Metformin has a minimal inhibitory effect on complex I of the oxidative phosphorylation; it has antioxidative properties and activates glucose-6-phosphate dehydrogenase (G6PDH) and the AMP- or AMPK-activated protein kinase. The importance of AMPK as a mechanism in metformin activity is related to its role in regulating lipid and carbohydrate metabolism. In adipose tissue, metformin inhibits lipolysis, while promoting fatty acid re-esterification.

AMPK: Master Metabolic Regulator

AMP(AMPK)-stimulated protein kinase was discovered as an enzyme that inhibited acetyl-CoA carboxylase (ACC) and 3-hydroxy-3-methyl-glutaryl-CoA reductase (HMG-CoA reductase) preparations, induced by AMP. AMPK induces a cascade of events in cells in response to their constant energy changes. The role of AMPK in cell energy charge regulation makes this enzyme important in keeping energy homeostasis. Recent evidence shows that AMPK activity may be also regulated by physiological stimuli, regardless of the cell energy charge, including nutrients and hormones (FIG. 1).

Once activated, AMPK-mediated phosphorylation changes cells from a state in which they actively consume ATP (fatty acid and cholesterol biosynthesis) to a state in which they actively produce ATP (fatty acid and glucose oxidation). These events occur quickly, and are referred to as short-term regulation processes. AMPK activation has also long-term effects on the expression of genes and protein synthesis. Other relevant activities attributed to AMPK are: insulin synthesis and secretion regulation in pancreatic β cells and the modulation of hypothalamic functions involved in satiety regulation.

AMPK Structure

AMPK is a trimeric enzyme formed by a catalytic subunit-α and non-catalytic subunits β and γ. There are two genes that code for isoforms of subunits α and β (α1, α2, β1, and β2), and three genes that code for subunits γ (γ1-γ3). Isoform α2 is the AMPK subunit that is predominantly found in skeletal and cardiac muscles, whereas isoforms α1 and α2 are distributed in a balanced way. Isoform α1 is predominant in pancreatic β cells.

Half of the N-terminal in α subunits has a catalytic domain typical in serine/threonine kinase. Interaction with subunits α and γ is carried out with half of the C-terminal in α subunits. The central part of subunits γ has a binding domain for glycogen. This domain is closely related to the N-terminal in iso-amylases and is distantly related to domains of phosphatase subunits directed to glycogen and different proteins that bind to starch. AMPK proximity to glycogen supply enables it to make rapid changes in glycogen metabolism in response to changes in metabolic demands.

AMPK Regulation

AMPK gets activated by phosphorylation from one or more AMPK kinases (AMPKKs). When no phosphorylation occurs, no AMPK activity for its substrates is detected. AMPK phosphorylation occurs in threonine 172 (Thr 172) of the α subunit, which is located in the activation loop. The $Ca^{2+}$/calmodulin(CaMKKb)-dependent kinase kinase-β is a kinase that activates and phosphorylates AMPK in response to high calcium concentrations. Recent data have shown that threonine kinase, LBK1, is necessary for AMPK activation in response to stress. Activity loss of LBK1 in the liver of adult mice leads to complete activity impairment of AMPK, and it is associated with hyperglycemia.

Figure 2:
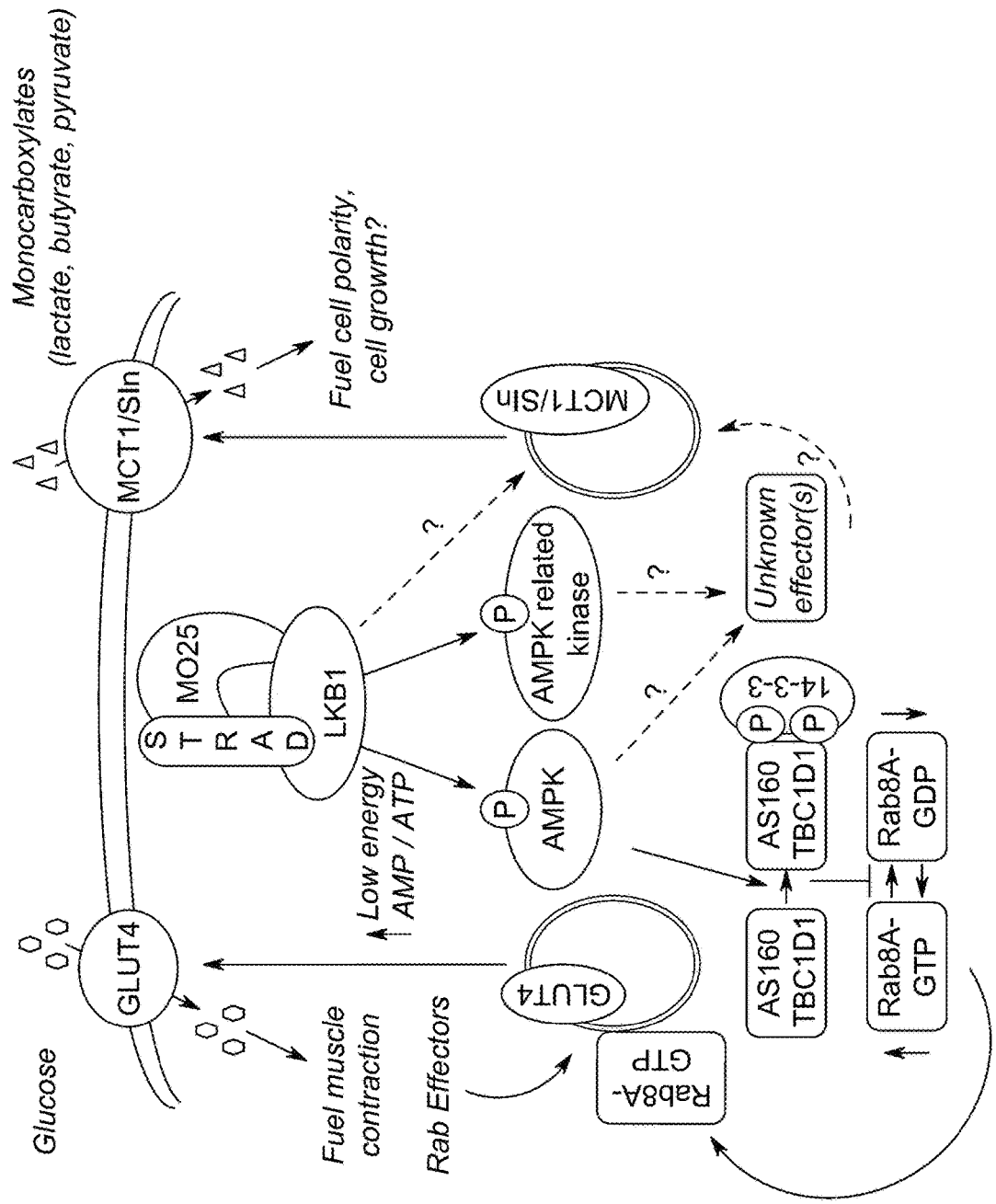

Hyperglycemia occurs partially as an increase in gluconeogenic gene transcription. Especially important is the increase in the peroxisome proliferator-activated receptor-γ (PPAR-γ) co-activator 1α (PGC-1α) expression involved in gluconeogenesis. Reduction in PGC-1α activity makes glucose blood levels return to normal in mice with low LBK1. It has been also demonstrated that AMPK is activated by receptors that are coupled to phospholipase C-β (PLC-β) and by cytokines secreted by adipose tissue (adipokines), such as leptin and adiponectin (FIG. 2).

AMPK Targets

Signaling cascades initiated by AMPK activation have an impact on glucose and lipid metabolism, gene expression, and protein synthesis. These effects are more important for the metabolic event regulation in the liver, skeletal muscle, adipose tissue, and pancreas.

Most of AMPK's known targets have been included, as well as several metabolic pathways whose flow is affected by AMPK activation. Arrows indicate positive effects of AMPK, and T lines indicate inhibiting effects.

Glucose uptake by muscles represents >70% of the glucose taken from blood in humans. Therefore, it should be evident that this event is extremely important for general glucose homeostasis, as, indeed, glucose uptake by both heart and adipocytes may not be excluded from the equation. An important fact related to muscles glucose uptake is that this process is notably impaired in subjects with Type 2 Diabetes. Glucose uptake increases dramatically in response to stress (e.g. ischemia) and exercise, and it is stimulated via transporter recruitment in the cell membrane, primarily GLUT4, which is induced by insulin. The recruitment of insulin-independent receptors also occurs in the skeletal muscle in response to contraction (exercise). AMPK activation plays an important role in initiating GLUT4 recruitment in the cell membrane, although this is not exclusive of AMPK activation. Furthermore, it has been demonstrated that AMPK regulates glucose transportation via GLUT1 transporter. An increase in glucose uptake results in increased glycolysis and ATP production.

Considering that stress and exercise are powerful inducers of AMPK activity in skeletal muscle—additional regulators of its activity—drugs such as thiazolidinediones (PPAR-γ activators) and metformin, which exert part of their effects through AMPK activity regulation, were identified. As it was previously indicated, AMPK activity by phosphorylation via LKB1 is essential in glucose flux and homeostasis regulation. Metformin action in reducing glucose levels requires AMPK activity in the liver for this function. This is true for several adipokines either for stimulation or inhibition of AMPK: leptin and adiponectin have demonstrated to stimulate AMPK activation, whereas resistin inhibits AMPK activation.

Inside the skeletal muscle and heart, AMPK activation leads to phosphorylation and inhibition of acetyl-CoA carboxylase (ACC). This inhibition results in a drop in malonyl-CoA levels, which is an inhibitor of carnitine palmitoyltransferase I (CPT I). A concomitant increase in β-oxidation of fatty acids in the mitochondria will occur due to the drop in CPT I levels. An increase in fatty acids oxidation, e.g., a glycolysis increase, and in ATP production, will lead to increase ATP production. Apart from ACC, it has been demonstrated that AMPK phosphorylates and, thus, regulates the activities of HMG-CoA reductase (HMGR); lipase sensitive to hormones (HSL); glycerophosphate acyltransferase (GPAT); malonyl-CoA decarboxylase (MCD); glycogen synthase (GS); and creatine kinase (CK). Therefore, the effects of AMPK activation affect not only glucose homeostasis and fatty acids metabolism, but also all energy homeostasis, including glycogen metabolism, as well as cholesterol and creatine phosphate metabolism.

AMPK activation effects in the heart also include endothelial nitric oxide synthase phosphorylation (eNOs) in cardiac endothelium. AMPK-mediated eNOs phosphorylation leads to an increase of its activity and, consequently, to nitric oxide production (NO), which provides an association between metabolic stress and cardiac function. In platelets, insulin action leads to an increase in eNOs activity, due to its phosphorylation by AMPK. Activation in NO production in platelets leads to a reduction in platelet aggregation induced by thrombin, thus limiting pro-coagulating effects in platelet activation. Platelet response to insulin activity clearly indicates why insulin activity alteration is an important factor contributing to metabolic syndrome development.

AMPK activation not only produces its effects on enzymatic activity via phosphorylation, but also generates other notable effects on several glycolytic and lipogenic enzymes in the liver and adipose tissue. PPARγ (peroxisome proliferator-activated receptor γ) is a target of pharmaceutical drugs, such as the thiazolidinedione class type, used in Type 2 diabetes treatment, which may be itself an AMPK target. The transcription co-activator, p300, is phosphorylated by AMPK, which inhibits the p300 interaction not only with PPARγ, but also with the retinoic acid receptor, retinoic X receptor, and thyroid receptor. Another AMPK transcription target is the FKHR protein, (known as Fox01). Fox01 is involved in the activation of glucose-6-phosphatase expression, and therefore, Fox01 activity impairment in response to AMPK activation will lead to a reduction in glucose secretion by the liver.

AMPK Relevance in Type 2 Diabetes

A fuel loss is produced in obesity metabolism and this alteration is one of the main pathogenic factors of Type 2 Diabetes. Insulin resistance associated with Type 2 diabetes is more severe at the level of skeletal muscle, since this is where glucose and fatty acids are used. Thus, AMPK activation in skeletal muscle could offer important benefits in the Type 2 diabetes pharmacologic treatment. As previously indicated, Metformin exerts some of its effects through AMPK activation.

In the skeletal muscle, AMPK phosphorylates PGC1α, generating a greater mitochondrial biogenesis and fatty acid oxidation. Both effects of PGC1α require SIRT1. Additionally, AMPK-activated PGC1α results in an increase in GLUT4, present in cell membranes of skeletal muscles that are responsible for increasing glucose capture; AMPK activates fatty acid oxidation in the liver, through PGC1α activation as well as its effects on other lipogenesis enzymes, as it has been previously described (e.g. SREBP and FAS).

GPBP/CERT in Diabetes

GPBP/CERT (Goodpasture antigen-binding Protein) is also known as CERT (ceramide transfer protein); CERTL (ceramide transfer protein); STARD11 is a kinase serine/threonine that phosphorylates the non-collagenous domain (NCI) of the α3 chain of Type IV collagen in basal membranes. This domain is also known as Goodpasture's autoantigen, since it is the specific target of auto-antibodies that cause glomerulonephritis and pulmonary hemorrhage in Goodpasture Syndrome.

The coding gene for GPBP/CERT, COL4A3BP, expresses three polypeptides: GPBP/CERT1 (CERT1), GPBP/CERT2 (STARD11), and GPBP/CERT3.

GPBP/CERT1 is a protein that is secreted into the extracellular media and that regulates the organization of Type IV collagen net; GPBP/CERT2 is located in the cytosol and its main function involves transferring ceramide between the endoplasmic reticulum and the Golgi apparatus; it participates in the phosphorylated and dephosphorylated forms in intracellular signaling mechanisms, and regulates protein secretion as Type IV collagen; and GPBP/CERT3 is an isoform bound to the external wall of the plasma membrane, that regulates GPBP/CERT1 exportation. In the striated muscle, where alternative isoforms are not expressed, GPBP/CERT1 remains in the cytoplasm and regulates myofibrillar organization through its interaction with a new protein family denominated GIP proteins (GPBP/CERT interacting proteins). In summary, GPBP/CERT1 regulates protein assembly in both intracellular and extracellular behavior.

Ceramides and Insulin Resistance

The evidence of several studies shows that ceramides play an important role in diabetes by means of at least three different mechanisms: inducing apoptosis in pancreatic β cells, increasing insulin resistance, and reducing insulin genetic expression. Recent studies have linked high intracellular ceramide levels as key mediators in insulin resistance. This type of lipids are composed by a sphingosine column conjugated with a fatty acid derivate, and they are found in all cell types. On the other hand, it should be noted that lipids' role in insulin resistance has been widely observed, and it is an accepted mechanism. It is still under research if plasma circulating lipids or lipid accumulation in insulin-dependent cell types should be considered as a triggering mechanism in the insulin resistance phenomenon.

Consumption of food rich in saturated fatty acids, such as butter, cream, and red meat, has become common in Western diet. Therefore, ceramides play a more important and clinically relevant role in individuals with diet-induced obesity, observed in developed nations, than previously assumed.

Ceramides are generated by 3 different pathways (FIG. 4): 1) De novo; 2) by direct generation via sphingomyelin division by sphingomyelinase; or, 3) by "salvage pathway" through direct decomposition of sphingolipids in sphingosine, which can be converted in ceramides by the ceramide synthase. Alterations in enzymatic activity in any of these steps can dramatically alter intracellular levels of these lipid fractions, a process that may be beneficial or fatal for the cell, depending on the physiological conditions. Since these three pathways may be active in a parallel manner, their inhibition may have either deep consequences or a marginal effect in cellular physiology, depending on cell type, development state or nutritional state.

Ceramides are essential for the phospholipid bilayer development in the cell membrane. Besides this structural role, ceramides also play an important role in cell signaling, inflammation, and apoptosis. Once generated, ceramides are common precursors of a series of complex sphingolipids, and they may also be glycosylated, deacetylated, and phosphorylated to produce a variety of metabolites and signaling molecules. The de novo ceramide generation pathway can be induced by a diet rich in saturated fat, an increase in diet serins, oxidative stress and oxidized LDL. Additionally, it has been demonstrated that inflammatory cytokines, such as TNFα and IL-1, may increase serine palmitoyltransferase (SPT) enzyme expression and activity, leading to an increase in de novo ceramide synthesis.

Human plasma and murine are a rich source of ceramides, which circulate in the 0.5-10 μM micromolar range. Around 75% of these ceramides are contained in VLDL and LDL particles, and the rest in HDL. Due to its stable association with these lipoproteins, scientists may hypothesize that the primary source of circulating ceramides is the liver. This hypothesis has already been proven. However, the matter regarding the information that plasma ceramide levels reveal is far from being solved. So far, plasma ceramides are used as useful biomarkers for metabolic dysfunction.

Several clinical studies have reported high levels of circulating ceramides in Type 2 Diabetes patients, and these levels were correlated with the severity of insulin resistance. These studies are supported by in vivo evidence that reveals that LDL particles containing ceramides are able to induce insulin resistance when administered to non-obese mice. Other studies have shown that total levels of ceramides are correlated with several parameters related to insulin resistance, as high circulating levels of TNFα and IL-6. It has been also observed that plasma ceramide levels subsequent to gastric bypass were lower, as well as TNFα plasma levels. These reductions were correlated with a dramatic improvement in sensitivity to insulin in these patients. Together, these studies help to establish a relationship among circulating ceramides, inflammation, and subsequent insulin resistance in different obesity and Type 2 Diabetes stages.

Insulin activity is mediated through the insulin receptor (IR), which propagates its activity via three pathways: 1) the phosphatidylinositol 3-kinase (PI3k), 2) the mitogen-activated protein kinase (MAPK), and 3) Cb1 (CAP) associated protein. The first pathway (PI3k) is in charge primarily of glucose transportation, and it is significantly distorted by ceramides. Insulin receptor is a tyrosine-kinase receptor that has two extracellular α subunits and two β transmembrane subunits. After insulin binding to the α subunit of the receptor, the insulin receptor is subject to an autophosphorylation of tyrosine residues in the intracellular β domain The insulin receptor substrate (IRS) has a binding domain to phosphotyrosine that recognizes activated IR and leads to the phosphorylation of tyrosine and IRS activation. (FIG. 5) After several reactions, protein kinase B (PKB, also called AKT) is activated, and this promotes its relocation in the cytosol, causing the translocation of the glucose transporter GLUT4 in the plasma membrane. This stimulates glucose uptake. AKT also phosphorylates and inactivates glycogen synthase-kinase-3 (GSK3), an enzyme involved in glycogen synthase inactivation. This results in an increase of glycogen storage. To summarize, insulin receptor activation (IR) leads to AKT activation, which, once activated, reduces plasma glucose by inducing cell glucose uptake, glycogen synthesis, and protein and fatty acid synthesis. AKT acts also by inhibiting gluconeogenesis. Ceramides cause insulin resistance by inhibiting AKT; similarly, they reduce GLUT4.

Macrophages are primarily known for their role in the immune system. Macrophage infiltration in adipose tissue in obesity plays a fundamental role in insulin resistance. As obesity progresses, macrophages change from an alternative activated anti-inflammatory phenotype (M2) to a more classically activated anti-inflammatory phenotype (M1). M1 macrophages produce a large number of pro-inflammatory cytokines, including TNFα, which may increase ceramides levels in several tissues. Ceramide function and role in macrophages has been subject of investigation with a great amount of literature addressing ceramides as mediators in several key physiological processes in macrophages.

Adipose tissue was once considered a simple triglyceride reservoir, but it is now recognized as an active endocrine organ that plays an important role in insulin resistance pathogenesis associated with obesity. Adipose tissue also expresses insulin receptors and is responsible for taking a portion of plasma glucose. TNFα, which is up-regulated in adipose tissue during obesity, may induce resistance to insulin by mitigating its signaling at the insulin receptor level and suppressing the expression of the glucose transporter that responds to insulin, GLUT4. It is believed that TNFα induces these effects by mediating ceramide synthesis. The resulting increase in intracellular ceramide levels correlates with a 60% decrease of GLUT4. Furthermore, it has been observed that 3T3-L1 adipocytes treatment with C8-ceramide (a ceramide analog) also reduces GLUT4, which suggests that there is a signaling pathway, initiated by ceramides in adipocytes, that plays a role in facilitating TNFα control in GLUT4 expression.

Several clinical studies have reported that there are high ceramide serum levels in Type 2 diabetes patients that correlate with the severity of insulin resistance. These correlated studies are supported by in vivo evidence that shows that LDL particles containing ceramides were capable of inducing insulin resistance when injected in slim mice. Insulin stimulus increased glucose uptake and reduced CERT-mediated ceramide transportation in L6 myotubes exposed to these ceramides. Other studies have demonstrated that total high ceramide levels correlate with several parameters involved in insulin resistance and an increase in pro-inflammatory cytokines, such as TNFα and interleukin-6. Additionally, a reduction in plasma ceramide levels and TNFα levels following a gastric bypass has been observed. This reduction correlated with a dramatic improvement in sensitivity to insulin in these patients. Together, these studies help to establish ceramides as central mediators in inflammation and insulin resistance in different obesity and Type 2 diabetes stages.

Type 2 Diabetes

Type 2 diabetes is a chronic and inflammatory disease that affects mainly obese individuals; it is preceded by peripheral insulin resistance as a result of low insulin production by pancreatic β cells. One of the main causes of peripheral insulin resistance is an existing low-intensity chronic inflammatory tissue state. In obese individuals, macrophages are drawn by adipocytes, and could represent up to 40% of tissue cells. These macrophages are activated and secrete pro-inflammatory cytokines, such as tumor necrosis factor alpha (TNFα) and interleukins. The pro-inflammatory phenotype of the activated macrophages is known as M1; it is mainly characterized by the secretion and synthesis of IL-1β and other pro-inflammatory mediators, such as iNOs and TNFα; it is also known that the M1 macrophage synthetizes and secretes GPBP. Activated macrophages tend to self-limit in time, and they differentiate into an M2 anti-inflammatory phenotype, which secretes other cytokines, including IL-10 and arginase.

Within the extensive therapeutic repertoire of diabetes treatment, the biguanides family is characterized by the prevention of insulin release, increase of glucose metabolism in tissue (anaerobic glycolysis), and reduction of hepatic gluconeogenesis. Additionally, metformin improves sensitivity to insulin by increasing insulin receptor tyrosine kinase activity, promoting glycogen synthesis, and increasing GLUT4 transporter capacity and quantity in the plasma membrane. Metformin hydrochloride (SLN1) is a well known biguanide with anti-inflammatory, antidiabetic and anti-tumoral activity; however, its mode of action has not been properly used or completely characterized; this opens a new scenario in treatment forms for diabetes, as physiological processes involved in this type of metabolic disorders are understood.

Also, metformin is highly unstable, and thus, it is marketed mainly as hydrochloride; it is formed in the reaction site, from released hydrochloride by dimethylamine hydrochloride—one of the reagents in the synthesis process. Nevertheless, literature has presented many other compounds, such as Belgian Patent No. BE 568513, which describes compounds formed by adding several acids, including metformin hydrochloride. U.S. Pat. No. 4,028,402, addresses metformin dichloroacetate and other biguanides; U.S. Pat. No. 4,835,184, addresses para-chloro-phenoxyacetic acid; U.S. Pat. No. 3,957,853, addresses acetylsalicylic acid salt. application U.S. Pub. No. 2005/0158374, describes metformin associated with fatty acids, which contribute to enhanced absorption in the intestinal tract. This metformin associated with fatty acid derivatives, such as laureate, succinate, capric acid, palmitate, etc., increases absorption in the lower intestinal tract Plasma concentrations of these compounds measured in rats in g/mL, with respect to time in hours, show greater bioavailability of metformin compounds not bound to fatty acids.

Other documents include European Patent No. 1039890 which describes several dicarboxylic acid salts, in combination with another antidiabetic agent; this patent describes metformin fumarate, metformin succinate and metformin malate. Korean patent WO 2008/093984 addresses acetate compounds; International Publication No. WO2008/061456 addresses metformin folate. U.S. Pat. No. 4,835,184, describes metformin p-chlorophenol oxyacetate. French Patent Nos. 2320735 and 2037002 describe metformin pamoate. U.S. Pat. No. 3,957,853 describes metformin p-chlorophenol oxyacetate. German Patent Nos. 2357864 and 1967138 describe metformin derived from nicotinic acid. Japanese Patent No. 64008237 addresses metformin hydroxy acid, including aliphatic dicarboxylic hydroxy acids, such as meso-tartaric acid, tartaric acid, mesoxalic acids, and oxidized maleate. International Pub. No. WO 2009/038396 addresses dicarboxylic acids, such as malonate, glutarate, adipate, and malate. U.S. Pat. No. 3,903,141 and International Pub. No. WO2009/144527, among others, address adamantane acid, these may be located in the cited patents referred to in this document or in their corresponding databases.

Betaines are compounds whose molecular formula $(CH_3)_3N^+(CH_2)_nCOO^-$, has an amino group trisubstituted by three methyls, or a "quaternary amine", and n may be equal to a number from 1 to 5. U.S. 2008/0031964, WO 2006/086856, and WO 2005/065675 relate to betaines compounds such as lipidic betaines, and betaine lipids, as well as pharmaceutically acceptable salts from these betaines, compositions thereof and methods of using the compounds for treating disorders such as diabetes. Betaines are different compounds from the compounds disclosed herein.

Proposed Solution to the Literature in the Present Invention

There are well documented experiences about the regulation of glucose uptake in cells for energy, growth, and proliferation. In this sense, scientists have observed that insulin is not the only one having these properties; other molecules have glucose uptake properties or even the molecular signaling that stimulates glucose uptake. These mechanisms are still under research; however, it is known that a variety of agents may activate glucose transportation into cells, even translocation of transporters at the cell membrane level, such as hormones and bioactive molecules, regardless of insulin levels. Therefore, glucose level control is not a simple event that could be attributed to insulin alone; it is a complex process that involves a variety of physiological regulators.

The compounds disclosed herein are formed by metformin and an amino acid, also known as SLNs. Exemplary SLNs include metformin lysinate, metformin aspartate, metformin isoleucinate, metformin alaninate, metformin valinate, metformin asparaginate, metformin threoninate, and metformin leucinate. Metformin glycinate, an SLN also known as SLN2, is disclosed in U.S. Pat. No. 8,703,138.

The use of the SLNs (e.g., metformin lysinate, also known as SLN10) as a new molecule, or other amino acids, instead of the widely known metformin hydrochloride, is extremely important to define its assimilation pathway. New compounds in this invention take into account the presence of an amino acid to open a new assimilation pathway or route. There are experimental results showing that the assimilation pathway is different between the typical hydrochloride and compounds such as metformin lysinate. This reflects the unexpected major importance of these components and the therapeutic advantage that this represents, an advantage achieved by more than just enhanced solubility. Compounds in this invention (referred to as SLNs) have a molecular target in the glucose regulation mechanism that is identified and used to present compounds and drugs that contain them for the treatment of diabetes mellitus, for example, beyond the already known metformin pharmacology. Thus, this invention has an activity that exceeds, with several benefits, known pharmacological virtues offered by metformin hydrochloride.

Particularly, for compounds in this invention, known also as SLNs, the ionized component is not the one acting differently; instead, when a new assimilation form comes into play, a new chemical entity appears that is internalized through a different mechanism. By taking advantage of SLNs' properties, these new compounds may be assimilated through a pathway that is different from the known metformin pathway, or may act through a receptor that is different from the one corresponding to separated compounds (ionized); this results in a different mode of action that has not been reported nor suggested in the literature about metformin pharmacology.

The present invention shows that metformin amino acid compounds (biguanides), such as metformin lysinate (SLN10), are compounds that are different from metformin hydrochloride for Type 2 Diabetes, operating by inhibiting GPBP kinase activity. In this invention, it is disclosed that:
1. SLN10 has a different electronic structure from metformin SLN1 that confronts GPBP and inhibits its kinase activity; and 2. SLN10 promotes glucose transporter translocation to membranes and glucose uptake (anti-hyperglycemic and anti-hypoglycemic activities), and limit the inflammatory response (anti-inflammatory activity) by inhibiting GPBP kinase activity.

There are four protein complexes involved: AMPK, GPBP, LKB1, and AS160, characterized by the mode of action of compounds of this invention, such as metformin aspartate, metformin isoleucinate, metformin alaninate, metformin valinate, metformin asparaginate, metformin threoninate, metformin leucinate, or metformin lysinate, which are essential in the regulation of GLUT4 expression as well as energy and glucose metabolism.

The development of new medications that contribute to glucose control, together with existing therapies, as well as changes in lifestyle, have broadened treatment options for Type II Diabetes. However, the main problems are the need for an adequate indication for each patient and the lack of treatment adherence; thus, the disease's progression ends up causing complications, specific to this condition, and finally death, with high social and economic costs.

In the present invention, drugs comprising selected compounds from the group consisting of metformin aspartate, metformin isoleucinate, metformin alaninate, metformin valinate, metformin asparaginate, metformin threoninate, metformin leucinate, and metformin lysinate, more particularly metformin lysinate, these participate and intervene in AMPK, GPBP/CERT and LKB1 activity in the following manner:

They inhibit GPBP/CERT activity
They increase LKB1 activity
They inhibit GPBP/CERT and LKB1 cross-activation
Increases IL10 synthesis
They translocate glucose transporter GLUT4 more efficiently
They act via VAPA-VAMP2 interaction; and/or
They participate in AS160 regulation where AMPK increases GPBP/CERT activity; and GPBP/CERT and LKB1 power, in a synergic way, its kinase activity (reducing insulin and leptin levels, and improving lipid profile).

Therefore, pharmaceutical drugs of the present invention contain new compounds (SLNs), which are biguanides, selected from the group consisting of metformin aspartate, metformin isoleucinate, metformin alaninate, metformin valinate, metformin asparaginate, metformin threoninate, metformin leucinate, and metformin lysinate, more particularly metformin lysinate; they have unique physicochemical characteristics, a distinct mode of action different from metformin hydrochloride's, translocating GLUT4 more efficiently, with a better anti-inflammatory profile; also, they reduce insulin and leptin levels in Type 2 diabetes models.

Drugs of the present invention containing metformin amino acid compounds (SLNs), which are biguanides, selected from the group consisting of metformin aspartate, metformin isoleucinate, metformin alaninate, metformin valinate, metformin asparaginate, metformin threoninate, metformin leucinate, and metformin lysinate, more particularly metformin lysinate, have an anti-hyperglycemic effect as coadjuvant on prevention, treatment and control of Type 2 diabetes in adults, as well as children and adolescents, always associated with diet and exercise.

Likewise, these drugs contain metformin amino acid compounds (SLNs), which are biguanides, selected from the group consisting of mMetformin aspartate, metformin isoleucinate, metformin alaninate, metformin valinate, metformin asparaginate, metformin threoninate, metformin leucinate and metformin lysinate, more particularly the group comprising metformin lysinate, for Type II diabetes mellitus control, with an immediate release mechanism for a more effective treatment and less adverse effects.

The present application discloses also pharmaceutical compositions comprising a compound of the present invention, or a pharmaceutically acceptable salt, solvate, and/or ester thereof, in combination with at least one additional therapeutic agent, and a pharmaceutically acceptable carrier or excipient.

In a modality, the present invention also describes drugs containing metformin amino acid compounds (SLNs), which are biguanides, selected from the group consisting of metformin aspartate, metformin isoleucinate, metformin alaninate, metformin valinate, metformin asparaginate, metformin threoninate, metformin leucinate, and metformin lysinate, more particularly metformin lysinate, solvates, hydrates, and/or polymorphs thereof.

The present invention is also directed to an optimized, robust, and useful formulation in preventing, treating and controlling Type 2 Diabetes. The formulation is replicable and has the required quality, stability and effectiveness for its purpose.

SUMMARY OF THE INVENTION

The present invention provides a compound which comprises metformin and an amino acid, forming a metformin amino acid compound, wherein the amino acid is selected from the group consisting of aspartate, isoleucinate, alaninate, valinate, asparaginate, threoninate, leucinate, and lysinate.

In some embodiments, the metformin amino acid compound is metformin asparatate. In some embodiments, the metformin amino acid compound is metformin isoleucinate. In some embodiments, the metformin amino acid compound is metformin alaninate. In some embodiments, the metformin amino acid compound is metformin valinate. In some embodiments, the metformin amino acid compound is metformin asparaginate. In some embodiments, the metformin amino acid compound is metformin threoninate. In some embodiments, the metformin amino acid compound is metformin leucinate. In some embodiments, the metformin amino acid compound is metformin lysinate.

The present invention also provides a pharmaceutical composition comprising a therapeutically effective amount of a metformin amino acid compound.

In some embodiments, the metformin amino acid compound in the pharmaceutical composition is metformin asparatate. In some embodiments, the metformin amino acid compound in the pharmaceutical composition is metformin isoleucinate. In some embodiments, the metformin amino acid compound in the pharmaceutical composition is metformin alaninate. In some embodiments, the metformin amino acid compound in the pharmaceutical composition is metformin valinate. In some embodiments, the metformin amino acid compound in the pharmaceutical composition is metformin asparaginate. In some embodiments, the metformin amino acid compound in the pharmaceutical composition is metformin threoninate. In some embodiments, the metformin amino acid compound in the pharmaceutical composition is metformin leucinate. In some embodiments, the metformin amino acid compound in the pharmaceutical composition is metformin lysinate.

In some embodiments, the pharmaceutical composition further comprises a pharmaceutically acceptable carrier, vehicle, diluent, or combination thereof.

In some embodiments, the pharmaceutical composition is in the form of a tablet, a caplet, a gel, a paste, a powder, an extended-release granule, a capsule, an extended-release tablet, a liquid, an effervescent tablet, a suspension, a syrup, an aerosol, or a spray.

In some embodiments, the therapeutically effective amount in the pharmaceutical composition is from about 100 mg to about 2.4 g. In some embodiments, the therapeutically effective amount in the pharmaceutical composition is from about 100 mg to about 1100 mg. In some embodiments, the therapeutically effective amount in the pharmaceutical composition is from about 400 mg to about 700 mg.

In some embodiments, the pharmaceutical composition further comprises an excipient.

In some embodiments, the excipient in the pharmaceutical composition is microcrystalline cellulose, anhydrous dibasic calcium phosphate, sodium starch glycolate, magnesium stearate, or combination thereof.

In some embodiments, the pharmaceutical composition further comprises another anti-hyperglycemic agent. In some embodiments, the pharmaceutical composition further comprises another anti-hyperglycemic agent selected from the group consisting of glyburide, glipizide, glimepiride, acarbose, miglitol, troglitazone, and insulin.

The present invention also provides a method of producing a metformin amino acid compound, wherein the metformin amino acid compound is metformin asparatate, metformin isoleucinate, metformin alaninate, metformin valinate, metformin asparaginate, metformin threoninate, metformin leucinate, or metformin lysinate, comprising:

(a) preparing the free base of metformin from a metformin compound;

(b) admixing the metformin free base of (a) with an amino acid at a temperature from about 0° C. to about 60° C.

In some embodiments, in the method of producing a metformin amino acid compound, about one equivalent of the metformin free base is reacted with about one equivalent of the amino acid, wherein the amino acid is selected from the group consisting of isoleucinate, alaninate, valinate, asparaginate, threoninate, leucinate, and lysinate.

In some embodiments, in the method of producing a metformin amino acid compound, about one equivalent of the metformin free base is reacted with about two equivalents of the amino acid, wherein the amino acid is aspartate.

In some embodiments, the method of producing a metformin amino acid compound further comprises:

(c) stirring the metformin free base and the amino acid for from about 30 minutes to about 30 hours.

In some embodiments, the method of producing a metformin amino acid compound further comprises:

(d) filtering the admixture of metformin base and amino acid; and (e) concentrating the filtrate of (d).

In some embodiments, in the method of producing a metformin amino acid compound, the metformin compound is metformin hydrochloride.

The present invention provides a method for treating hyperglycemia in a subject in need thereof, comprising administering to the subject a therapeutically effective amount of a metformin amino acid compound, wherein the metformin amino acid compound is metformin aspartate, metformin isoleucinate, metformin alaninate, metformin valinate, metformin asparaginate, metformin threoninate, metformin leucinate, or metformin lysinate. In some embodiments, the metformin amino acid compound is metformin lysinate.

In some embodiments, the therapeutically effective amount is from about 100 mg to about 2.4 mg. In some embodiments, the therapeutically effective amount is from about 100 mg to about 1100 mg. In some embodiments, the therapeutically effective amount is from about 500 mg to about 700 mg.

The present invention provides a method for treating diabetes in a subject in need thereof, comprising administering to the subject a therapeutically effective amount of a metformin amino acid compound, wherein the metformin amino acid compound is metformin aspartate, metformin isoleucinate, metformin alaninate, metformin valinate, metformin asparaginate, metformin threoninate, metformin leucinate, or metformin lysinate. In some embodiments, the metformin amino acid compound is metformin lysinate.

In some embodiments, the therapeutically effective amount is from about 100 mg to about 2.4 mg. In some embodiments, the therapeutically effective amount is from about 100 mg to about 1100 mg. In some embodiments, the therapeutically effective amount is from about 500 mg to about 700 mg.

In some embodiments, the diabetes treated by the method is diabetes mellitus. In some embodiments, the diabetes treated by the method is Type 2 diabetes.

The present invention also provides a method for treating symptoms, complications, and disorders associated with diabetes in a subject in need thereof, comprising administering to the subject a therapeutically effective amount of the metformin amino acid compound, wherein the metformin amino acid compound is metformin aspartate, metformin isoleucinate, metformin alaninate, metformin valinate, metformin asparaginate, metformin threoninate, metformin leucinate, or metformin lysinate. In some embodiments, the metformin amino acid compound is metformin lysinate.

In some embodiments, the therapeutically effective amount is from about 100 mg to about 2.4 mg. In some embodiments, the therapeutically effective amount is from about 100 mg to about 1100 mg. In some embodiments, the therapeutically effective amount is from about 500 mg to about 700 mg.

In some embodiments, the disorder associated with diabetes is dyslipidemia, hypertension, hypercoagulability, obesity, or insulin resistance.

The present invention also provides a method for treating proteinuria in a subject in need thereof, comprising administering to the subject a therapeutically effective amount of a metformin amino acid compound, wherein the metformin amino acid compound is metformin aspartate, metformin isoleucinate, metformin alaninate, metformin valinate, metformin asparaginate, metformin threoninate, metformin leucinate, or metformin lysinate. In some embodiments, the metformin amino acid compound is metformin lysinate.

In some embodiments, the subject of methods described herein is a mammal. In other embodiments, the subject is a human.

In some embodiments, the therapeutically effective amount is from about 100 mg to about 2.4 mg. In some embodiments, the therapeutically effective amount is from about 100 mg to about 1100 mg. In some embodiments, the therapeutically effective amount is from about 500 mg to about 700 mg.

Type 2 diabetes affects mainly obese people, and it develops after the appearance of peripheral insulin resistance derived from a deficient insulin production by pancreatic β cells. One of the main causes of peripheral insulin resistance is an existing low-intensity chronic inflammatory tissue state (Lumeng C N, Saltiel A R. *J Clin Invest.* 2011; 121:2111-7). In overfed obese individuals, macrophages are drawn by adipocytes and may represent up to 40% of tissue cells (Weisberg S P, McCann D, Desai M, Rosenbaum M, Leibel R L, Ferrante A W Jr. *J Clin Invest.* 2003; 112:1796-808). These macrophages are activated and secrete pro-inflammatory cytokines, such as TNF-α, which act as a paracrine in surrounding tissue and provokes insulin resistance by inhibitory phosphorylation of IRS-1 by c-Jun N terminal kinase (JNK) and IB kinase (IKK). When cytokine secretion is too high, their plasma levels may increase and have an endocrine effect, causing insulin resistance in distant tissues, e.g. muscle and liver (Osborn O, Olefsky J M. *Nat Med* 2012; 18:363-74).

In general, macrophage activation occurs in two steps (Rock K L, Latz E, Ontiveros F, Kono H. *Annu Rev Immunol.* 2010; 28:321-42; Strowig T, Henao-Mejia J, Elinav E, Flavell R. *Nature.* 2012; 481:278-86). In the first step, LPS or TNFα initiate a signaling cascade through their corresponding membrane receptors, activating TNFα, a class of transcription factors, which promote not only pro-IL-1β synthesis, but also GPBP activation and synthesis (Granero F, Revert F, Revert-Ros F, Lainez S, Martinez-Martinez P, Saus J. *FEBS J.* 2005; 272:5291-305; Miralem T, Gibbs P E, Revert F, Saus J, Maines M D. *J Biol Chem.* 2010; 285:12551-8). In the second step, an additional signal, such as ATP, doxorubicin, IC, glucose, cholesterol crystals, or uric acid, among others, activates the inflammasome (caspase-1) and the processing and secretion of IL-1β is initiated. Interestingly, our studies have demonstrated that doxorubicin, a known inflammasome activator (Sauter K A, Wood L J, Wong J, Iordanov M, Magun B E. *Cancer Biol Ther.* 2011; 11:1008-16), induces GPBP secretion (Saus J, Revert F, Merino R, Merino J, Revert-Ros F. (2012). Appl. No. PCT/EP2012/052923. Publication No. WO2012/113785). The activated macrophage pro-inflammatory phenotype is known as M1, and it is characterized by the synthesis and secretion of IL-1β and other pro-inflammatory mediators, such as iNOs and TNF-α (Edin S, Wikberg M L, Dahlin A M, Rutegård J, Öberg Å, Oldenborg P A, Palmqvist R. *PLoS One.* 2012; 7:e47045); morcover, it is also known that macrophage M1 synthetizes and secretes GPBP (Saus J, Revert F, Merino R, Merino J, Revert-Ros F. (2012). Appl. No. PCT/EP2012/052923. Publication No. WO2012/113785). Activated macrophages tend to self-limit in time, and they differentiate into an M2 anti-inflammatory phenotype, which secretes other cytokines, among which IL-10 and arginase are the most important (for further review, see Biswas & Mantovani *Nat Immunol.* 2010; 11:889-96). Transition from M1 to M2 is mediated by receptor TLR4 internalization in LPS-stimulated cells and activation of the promoter of cytokines, such as IL-10 (Iyer S S, Ghaffari A A, Cheng G. *J Immunol.* 2010; 185:6599-607). Studies have demonstrated that extracellular GPBP behaves as a pro-inflammatory cytokine, typical in M1 state, and promotes M1-M2 transition. In this respect, progressive accumulation of GPBP regulates macrophage activation to M1 (pro-inflammatory) (Saus J, Revert F, Merino R, Merino J, Revert-Ros F. (2012). Appl. No. PCT/EP2012/052923. Publication No. WO2012/113785) and its subsequent transformation to M2 (anti-inflammatory).

Metformin is a biguanide that not only promotes glucose uptake, but also inhibits hepatic gluconeogenesis (Natali A, Ferrannini E. *Diabetologia.* 2006; 49:434-41), as do compounds of the present invention, e.g. metformin lysinate. Inhibition of hepatic gluconeogenesis has been used Type 2 diabetes, but the mode of action of metformin has not been completely defined. Although it activates AMPK through a rise in intracellular concentration of 5'-AMP, the identity of its pharmacologic target is still a matter of debate. Complex T in the mitochondrial electronic transportation chain (Brunmair B, Staniek K, Gras F, Scharf N, Althaym A, Clara R, Roden M, Gnaiger E, Nohl H, Waldhäusl W, Fürnsinn C. *Diabetes.* 2004; 53:1052-9) and AMP deaminase (Ouyang J, Parakhia R A, Ochs R S. *J Biol Chem.* 2011; 286:1-11) have been described as metformin effectors. Although scientists have discarded AMPK as a direct target (Hardie D G. *Gastroenterology.* 2006; 131:973), Metformin interacts with its subunit (Zhang Y, Wang Y, Bao C, Xu Y, Shen H, Chen J, Yan J, Chen Y. *Mol Cell Biochem.* 2012; 368:69-76). More recent evidence has demonstrated that the pharmacokinetics and pharmacodynamics for metformin biguanide compounds (e.g. metformin glycinate) are different from those of metformin hydrochloride (Lara Ochoa, J M F. (2008). Appl. No. PCT/IB2008/002665. Publication No. WO/2009/144527); however, so far the mode of action and pharmacologic targets of metformin biguanide compounds have not been characterized or exploited.

Insulin resistance is a common feature in three pathologically related metabolic disorders, which have reached epidemic levels: Type 2 diabetes, obesity, and metabolic syndrome; thus, promoting Insulin sensitivity is an important goal within the therapeutic frame. Insulin receptor substrates (IRS) regulate insulin physiological activity (Tamemoto H, Kadowaki T, Tobe K, Yagi T, Sakura H, Hayakawa T, Terauchi Y, Ueki K, Kaburagi Y, Satoh S, et al. *Nature.* 1994; 372:182-6). According to this proposal, deletion of IRS2 in mice causes diabetes due to a reduced development in the pancreatic cell mass and to absence of proliferation from developed cells in response to peripheral insulin resistance (Withers D J, Gutierrez J S, Towery H, Burks D J, Ren J M, Previs S, Zhang Y, Bernal D, Pons S, Shulman G I, Bonner-Weir S, White M F. *Nature.* 1998; 391:900-4). Moreover, IRS2 deficiency causes hepatic resistance to insulin and a defective suppression of hepatic production of glucose (Withers D J, Gutierrez J S, Towery H, Burks D J, Ren J M, Previs S, Zhang Y, Bernal D, Pons S, Shulman G I, Bonner-Weir S, White M F. *Nature.* 1998; 391:900-4; Kubota N, Tobe K, Terauchi Y, Eto K, Yamauchi T, Suzuki R, Tsubamoto Y, Komeda K, Nakano R, Miki H, Satoh S, Sekihara H, Sciacchitano S, Lesniak M, Aizawa S, Nagai R, Kimura S, Akanuma Y, Taylor S I, Kadowaki T. *Diabetes.* 2000; 49:1880-9; Previs S F, Withers D J, Ren J M, White M F, Shulman G I. *J Biol Chem.* 2000; 275:38990-4). β cell islets coming from Type 2 diabetes patients express a lower quantity of IRS2 than control islets; this indicates that the molecule also plays an essential role in the development of diabetes in humans (Gunton J E, Kulkarni R N, Yim S, Okada T, Hawthorne W J, Tseng 25 Y H, Roberson R S, Ricordi C, O'Connell P J, Gonzalez F J, Kahn C R. *Cell.* 2005; 122:337-49). IRS2$^{-/-}$ male mice often die before 12 weeks due to diabetes complications, whereas IRS2$^{-/-}$ females develop a more benign diabetes form, and many survive up to 6 months. It is important to highlight that IRS2$^{-/-}$ females develop moderate obesity, partly because they eat more than control females; this suggests that IRS2$^{-/-}$ regulates the hypothalamic control of intake. According to this hypothesis, these females showed higher levels of leptin and leptin resistance (Burks D J, Font de Mora J, Schubert M, Withers D J, Myers M G, Towery H H, Altamuro S L, Flint C L, White M F. *Nature.* 2000; 407: 377-82), suggesting that IRS2 could be a convergence point in leptin and insulin signaling pathways. Finally, recent studies have demonstrated a reduction of basal lipolysis in IRS2$^{-/-}$ females, which is consistent with the moderate obesity they develop (Garcia-Barrado M J, Iglesias-Osma M C, Moreno-Viedma V, Pastor Mansilla M F, Gonzalez S S, Carretero J, Moratinos J, Burks D J. *Biochem Pharmacol.* 2011; 81:279-88).

The present invention addresses and describes how metformin amino acid compounds, e.g. metformin lysinate, pharmacologically operate through GPBP. The present invention discloses and explains that the different electronic structure of these metformin molecules (SLNs) confront cytosolic GPBP and inhibit its kinase activity differently. This inhibiting characteristic is somewhat responsible for the pharmacological (anti-hyperglycemic and anti-inflammatory) differential activity that SLNs deploy in the IRS2$^{-/-}$ model of Type 2 diabetes.

Hence, the present invention describes and protects new active principles, and their synthesis; they are new-generation biguanides, which exhibit advantages over the commercial compound, metformin hydrochloride. Conceptual pharmacologic studies are described, and their results are compared to those obtained with commercial metformin hydrochloride; favorable results have been obtained, showing that new active principles can be widely used for treating diabetes mellitus.

The assimilation pathway of the metformin amino acid compounds (SLNs) of the present invention is different from that of metformin hydrochloride. This indicates that the ionized compound is not the one acting differently, but rather that the existence of a new assimilation pathway shows a new chemical entity that is subsequently internalized by a different and differentiated mechanism. The compounds disclosed herein also act through pathways and/or through different receptors in addition to the pathways of metformin hydrochloride, and thus have modes of action that are different from the modes of action of Metformin hydrochloride.

metformin amino acid compounds may be selected among metformin aspartate, metformin isoleucinate, metformin alaninate, metformin valinate, metformin asparaginate, metformin threoninate, metformin leucinate, and metformin lysinate. In some embodiments, the metformin amino acid compound is metformin lysinate.

Several mechanism studies were conducted in order to demonstrate that the metformin amino acid compounds of the present invention, e.g. metformin lysinate:

are molecules that differ from metformin hydrochloride and that operate by inhibiting GPBP kinase activity;
  have an electronic structure that differs from metformin hydrochloride's electronic structure;
  confront GPBP and inhibit its kinase activity;
  promote glucose transporter translocation to membranes and glucose uptake (anti-hyperglycemic and anti-hypoglycemic activities);
  limit the inflammatory response (anti-inflammatory activity) by inhibiting GPBP kinase activity; and
  reduce peripheral insulin resistance in animal models of Type 2 diabetes due to their inhibiting action on GPBP kinase activity.

There are four protein complexes involved: AMPK, GPBP, LKB1, and AS160, characterized by the mode of action of compounds of this invention, such as metformin glycinate, aspartate, isoleucinate, alaninate, valinate, asparaginate, threoninate, leucinate, or lysinate, which are essential in the regulation of GLUT4 expression as well as energy and glucose metabolism.

Some embodiments of the present invention are directed to SLN compounds and compositions and/or formulations containing SLN compounds, wherein the SLN compound is selected from the group consisting of metformin aspartate, metformin isoleucinate, metformin alaninate, metformin valinate, metformin asparaginate, metformin threoninate, metformin leucinate, or metformin lysinate, more particularly metformin lysinate. Their solvates, hydrochlorides and/or polymorphs are included. Compounds in the invention are involved and intervene in AMPK, GPBP/CERT, and LKB1 activity in the following way:

They inhibit GPBP/CERT activity;
They increase LKB1 activity;
They inhibit GPBP/CERT and LKB1 cross-activation;
They have a different immune response modulation profile, increases IL10 synthesis;
They translocate glucose transporter GLUT4 more efficiently;
They act via VAPA-VAMP2 interaction; and/or
They participate in AS160 regulation.

where AMPK increases GPBP/CERT activity; and GPBP/CERT and LKB1 power, in a synergic way, its kinase activity (reducing insulin and leptin levels, and improving lipids profile).

The present invention is also directed to optimized, robust, and useful drugs, compositions and/or formulations in preventing, treating and controlling Type 2 diabetes, for example. These are replicable and have the required quality, stability and effectiveness for their purpose.

The present invention is also directed to drugs that contain compounds selected from the group consisting of metformin aspartate, metformin isoleucinate, metformin alaninate, metformin valinate, metformin asparaginate, metformin threoninate, metformin leucinate, or metformin lysinate, more particularly metformin lysinate: these have unique physicochemical characteristics and a distinct mode of action different from metformin hydrochloride's, translocating GLUT4 more efficiently, with a better anti-inflammatory profile; also, they reduce insulin and leptin levels in Type 2 diabetes models.

Drugs in the present invention containing new compounds (SLNs), which are new-generation biguanides, selected from the group comprising metformin aspartate, metformin isoleucinate, metformin alaninate, metformin valinate, metformin asparaginate, metformin threoninate, metformin leucinate, or metformin lysinate, more particularly the group comprising metformin lysinate, have an anti-hyperglycemic effect as coadjuvant on prevention, treatment and control of Type 2 diabetes in adults, as well as children and adolescents, always associated with diet and exercise.

Likewise, these drugs containing new compounds (SLNs), which are new-generation biguanides, selected from the group comprising metformin aspartate, metformin isoleucinate, metformin alaninate, metformin valinate, metformin asparaginate, metformin threoninate, metformin leucinate, or metformin lysinate, more particularly metformin lysinate, are used for controlling Type 2 diabetes, with an immediate release mechanism, resulting in a more effective treatment, with less adverse effects.

In one embodiment, the present application discloses pharmaceutical compositions comprising a compound of the present invention, or a pharmaceutically acceptable salt, solvate, and/or ester thereof, in combination with at least one additional therapeutic agent, and a pharmaceutically acceptable carrier or excipient. The additional therapeutic agent is selected among other antidiabetic drugs, such as sulfonylureas, iDPP4, SGL2, thiazolidinediones (TZD), insulin, glinides, etc.

Another objective in the present invention is to use compositions, formulations and/or drugs containing compounds, such as metformin aspartate, metformin isoleucinate, metformin alaninate, metformin valinate, metformin asparaginate, metformin threoninate, leucinate, metformin lysinate (new-generation biguanides) for Type 2 diabetes control, with an immediate release mechanism for a more effective treatment and fewer adverse effects. Besides, such compositions, formulations and/or drugs have unique physicochemical characteristics, a distinct mode of action different from metformin hydrochloride's, translocating GLUT4 more efficiently, with a better anti-inflammatory profile; also, they reduce insulin and leptin levels in Type 2 diabetes models.

Another objective in the present invention is to use compositions, formulations and/or drugs containing new compounds (new-generation biguanides, SLNs), such as metformin aspartate, metformin isoleucinate, metformin alaninate, metformin valinate, metformin asparaginate, metformin threoninate, metformin leucinate, or metformin lysinate.

In the present invention, such compounds, as well as compositions, formulations and/or drugs containing them, have an anti-hyperglycemic effect as coadjuvant on prevention, treatment and control of Type 2 diabetes in adults, as well as children and adolescents, always associated with diet and exercise.

In the present invention, such compounds, as well as compositions, formulations and/or drugs containing them, are also useful for preventing, treating, and controlling Type 2 diabetes in obese or overweight patients, including patients that have failed to follow a diet or exercise regimen, with sulfonylureas failure; and for preventing, treating and controlling Type 2 diabetes in patients on sulfonylureas therapy with a weight gain tendency; likewise, they are useful for preventing, treating, and controlling Type 2 diabetes in patients with lipid metabolism disorders secondary to diabetes.

In one embodiment, the compound is metformin lysinate, which is useful as an anti-hyperglycemic agent and as a coadjuvant compound in preventing, treating and controlling Type 2 diabetes in adults, as well as children and adolescents.

In some embodiments, the dosage form to administer the compounds and pharmaceutical compositions is a tablet, caplet, gel, paste, powder, extended-release granule, capsule, extended-release tablet, liquid with buffering agents, effervescent tablet, suspension, syrup, spray, or others. In some embodiments, the dosage form of the compounds and pharmaceutical compositions is as a tablet.

In some embodiments, the compounds and pharmaceutical compositions are administered orally, by intravenous injection, by intramuscular injection, nasally, by intraperitoneal injection, or sublingually. In some embodiments, the compounds and pharmaceutical compositions are administered orally.

In the present invention, one modality of drugs, formulations and dosage forms may contain from about 100 mg to about 2.4 g of at least one metformin amino acid compound, which are biguanides, selected from the group consisting of metformin aspartate, metformin isoleucinate, metformin alaninate, metformin valinate, metformin asparaginate, metformin threoninate, metformin leucinate, or metformin lysinate, solvates, hydrates, and/or polymorphs thereof. In some embodiments, the dosage form and optionally comprises an excipient, a carrier, or a pharmaceutically acceptable vehicle. In some embodiments, the metformin amino acid compound is metformin lysinate.

In some embodiments, the pharmaceutical composition comprises a therapeutically effective amount of a metformin amino acid compound, wherein the amino acid is selected from the group consisting of aspartate, isoleucinate, alaninate, valinate, asparaginate, threoninate, leucinate, and lysinate, wherein the therapeutically effective amount is from about 100 mg to about 2.4 mg. In some embodiments, the therapeutically effective amount is from about 100 mg to about 1100 mg, about 100 mg and about 1000 mg, about 100 mg and about 800 mg, about 200 mg to about 700 mg, about 400 mg and about 700 mg, about S00 mg and about 700 mg, or from about 600 mg to about 700 mg. In some embodiments, the pharmaceutical composition comprises a therapeutically effective amount of a metformin amino acid compound, wherein the therapeutically effective amount is from about 500 mg to about 700 mg.

In some embodiments, the dosage form is a tablet. In some embodiments, the selected formulation for administering the metformin amino acid compound is an aqueous coated tablet prepared via wet granulation, containing from about 100 mg to about 2.4 g of at least one metformin amino acid compound. In some embodiments, the dosage form comprises from about 589-651 mg, from about 615-625 mg, or about 620 mg of at least one metformin amino acid compound. In some embodiments, the metformin amino acid compound is metformin lysinate.

In some embodiments, the selected dosage form for administering metformin amino acid compounds is an aqueous coated tablet prepared via wet granulation, containing from about 100 mg to about 2.4 g of at least one metformin amino acid compound. In some embodiments, the dosage form comprises from about 997.5-1102.5 mg, from about 1035-1075 mg, or about 1050 mg of at least one metformin amino acid compound. In some embodiments, the metformin amino acid compound is metformin lysinate.

In one additional embodiment, the present invention discloses the pharmacokinetic profiles of different metformin compounds after oral administration to female Sprague Dawley rats and evaluates the effect of said compounds on the glucokinetic profile after an oral glucose overload. In the present invention, the pharmacokinetic profile of different metformin compounds after a single oral administration as well as their effect on the glucokinetic profile after repeated oral administrations and an oral glucose overload in female Sprague Dawley rats were determined. Furthermore, possible differences in toxicity profile of said metformin compounds given orally to the animals for 5 days were also evaluated.

In order to achieve these aims, twenty one groups were established and named A-U. Groups B-K consisted of six animals which were single administered by oral gavage with the reference item metformin hydrochloride and with different SLNs at a dose of 250 mg/kg (referred to the metformin base), respectively. Thereafter, blood samples were collected at 0.5, 1, 2, 4, 8, and 24 hours post-test item administration. Plasma was extracted and stored at ca.−80° C. until the delivery to the bioanalytical test site, Pharmanalyt, for the bioanalysis. Each animal was bled three times and three animals per time point were used. Body weight was recorded before administration and clinical signs thereafter. The following pharmacokinetic parameters were calculated from the metformin base concentration quantified in plasma: maximum concentration ($C_{max}$), time of maximum concentration ($T_{max}$), and area under the time-concentration curve until the last sampling point $AUC_{(0-24)}$.

Groups L-U with four animals each were orally administered five times (once a day for five consecutive days) with the reference item and with the SLNs at a dose of 750 mg/kg (referred to metformin base), respectively. Two hours after the fifth administration, the animals received an oral glucose overload (3 g/kg) and the blood glucose level was measured at 0.25, 0.5, 1, 2, 3, 4 and 6 hours post-glucose overload. Additionally, daily clinical signs, the body weights on the first and the last administration days, and macroscopic observations at the necropsy of the animals were evaluated as toxicity parameters. An eleventh group of six animals was administered in the same manner with the vehicle (ultrapure water) and it served as control (group A).

Regarding the pharmacokinetics, the reference item metformin hydrochloride showed to be absorbed faster as its $C_{max}$ was achieved at 0.5 hour post-test item administration ($T_{max}$). Dimetformin aspartate, metformin leucinate and threoninate presented the $T_{max}$ at 1 h. The remaining metformin compounds had its $T_{max}$ at 4 hours.

Considering the bioavailability, two tendencies of the administered metformin compounds could be distinguished: one group with a lower $AUC_{(0.5-24)}$ including dimetformin aspartate, metformin hydrochloride, metformin alaninate, metformin leucinate, metformin valinate and threoninate, and a second group showing a higher bioavailability and encompassing metformin isoleucinate, metformin lysinate, and metformin asparaginate.

In the study part for determining the effect of metformin compounds on the glucokinetic, the blood glucose level tended to be lower in animals treated with SLNs before and after the glucose overload compared to the administered with ultrapure water. Only a statistically significant decrease of the blood glucose level was observed with metformin isoleucinate previous the glucose overload and at 0.25, 0.5 and 3 hours thereafter, and with metformin alaninate at 1, 3, and 4 hours post-glucose overload. The glucokinetic profiles of all the tested compounds (including the reference item, metformin hydrochloride) were similar, and no significant differences were observed.

In addition, no adverse effect was observed in the animals from groups treated for five days with the different compounds at a metformin base dose of 750 mg/kg. Only the animal ID93 from the group administered with metformin lysinate had to be sacrificed for humane reasons, as it presented severe hypoglycemia throughout the fifth administration day.

Taking together the data obtained in the current study, it can be concluded that under the assay experimental conditions:

Concerning the maximum concentration of metformin base measured in plasma ($C_{max}$), no relevant differences were observed among the metformin compounds (e.g., SLNs) after a single dose of 250 mg/kg (referred to as metformin base). However, according to the time when $C_{max}$ occurs ($T_{max}$), two groups of metformin compounds could be distinguished: those where metformin was absorbed faster and included the reference item, metformin hydrochloride ($T_{max}$=0.5 hour), dimetformin aspartate, metformin leucinate, and threoninate ($T_{max}$=1 h), and those where metformin was absorbed more slowly comprising metformin isoleucinate, valinate, alaninate, lysinate, and asparaginate ($T_{max}$=4 hours). However, and regardless the groups distinguished above, the reference item, the Metformin hydrochloride, exhibited the lowest ($AUC_{(0-24)}$ 82.03 µg*h)/mL), when compared to rest of metformin compounds tested in the current study.

Two groups could be also established according to the bioavailability: a first one encompassing the metformin compounds of metformin isoleucinate, metformin lysinate, and metformin asparaginate with a higher bioavailability and a second one with lower availability including dimetformin aspartate together with metformin hydrochloride (reference item), metformin alaninate, metformin leucinate, metformin valinate, and metformin threoninate.

In general, metformin amino acidcompounds (SLNs) at a dose of 750 mg/kg (referred to metformin base) and administered for five days decreased in a non-statistically significant way the blood glucose level when compared to the vehicle, ultrapure water.

In general, metformin amino acid compounds (SLNs) at a dose of 750 mg/kg (referred to metformin base) and administered for five days prevented the blood glucose level increase induced by the oral glucose overload in a non-statistically significant way.

Regarding the effect of the metformin amino acid compounds on the glucokinetic profile, metformin isoleucinate and metformin alaninate showed a statistically significant decrease of the blood glucose levels at different times after the five test item administrations (750 mg/kg referred to metformin base) and oral glucose overload on the fifth day of treatment when compared to the vehicle (ultrapure water).

Similar effect on the glucokinetic profiles was shown by the reference item, metformin hydrochloride, and the rest of compounds as non-significant differences were observed after the five test item administrations (750 mg/kg referred to as metformin base) and oral glucose overload on the fifth day of treatment.

The metformin amino acid compounds (SLNs) at a dose of 750 mg/kg (referred to as metformin base) and administered for five days did not produce any adverse effects during the study period.

In another embodiment, the evaluation of the efficacy of different compounds of metformin (SLNs) to modulate glycemia in a rat model of streptozotocin-induced diabetes after daily oral administration for 14 consecutive days was also established in the present invention. The objective was to determine the efficacy of different compounds of metformin administered at the same dose calculated as base and to modulate glycemia in a rat model of streptozotocin-induced diabetes, when administered daily by oral route over a period of 14 consecutive days. The efficacy of a compound of diphenformin to modulate glycemia was also determined when administered with the same dosing regimen.

For this purpose, animals were treated with streptozotocin to induce diabetes prior to group distribution. Control animals were treated with vehicle. Blood glucose levels were measured before group distribution to confirm diabetic status and a total of 39 male rats were distributed in 13 groups as follows: normoglycemic animals treated with vehicle (group A), diabetic animals treated with vehicle (group B), diabetic animals treated with the reference item metformin hydrochloride (group C), diabetic animals treated with one of SLNs (groups C to K and M), and diabetic animals treated with a compound of diphenformin (group M).

Each experimental group contained a total number of 3 animals at the initiation of the study. Body weight was recorded at the time of diabetes induction, at the time of group distribution, the first day of Test item (TI)/Reference item (RI) administration and twice weekly thereafter until the end of the study. Clinical signs were recorded daily. Blood glucose levels were measured twice daily, one hour before TI/RI administration and again two hours after TI/RI administration. At the end of the study period, animals were bled before sacrifice and plasma glucose, triglycerides and total cholesterol levels were quantified. A body weight reduction was observed in all diabetic animals compared to normoglycemic animals. No effect on body weight of any of the metformin compounds, the reference item or the diphenformin compound was observed. Blood glucose levels before administration were similar among the experimental groups of diabetic animals and notably higher than blood glucose levels in normoglycemic rats. Treatment with reference item, compounds of metformin or the compound of diphenformin produced a transient reduction in blood glucose levels in diabetic rats.

Analysis of biochemical parameters showed statistically lower cholesterol levels in diabetic animals treated with vehicle compared to normoglycemic animals treated with vehicle. No statistically significant differences were observed on plasma glucose or triglycerides levels among experimental groups. Only 3 deaths were recorded throughout the study (one animal was found dead and two other animals were humanely sacrificed) and none of them were attributed to the TI/RI but rather to the diabetic condition of 30 of the animals.

Overall, treatment with compounds of metformin or diphenformin aspartate produced a transient reduction on blood glucose levels. No clear difference was observed in diabetic rats between treatment with the different compounds of metformin or the compound of diphenformin and treatment with the reference item metformin hydrochloride in all the parameters evaluated.

BRIEF FIGURES DESCRIPTION

The accompanying drawings, which are incorporated herein and form a part of the specification, illustrate the present invention and, together with the description, further serve to explain the principles of the invention and to enable a person skilled in the pertinent art to make and use the invention.

FIG. 1. Roles played by AMPK in several glucose, lipid and protein metabolism signaling pathways.

FIG. 2. Comparison of potential modes of action by which LKB1 controls the monocarboxylate transporters expression (lactate and pyruvate), and GLUT4.

Figure 3:
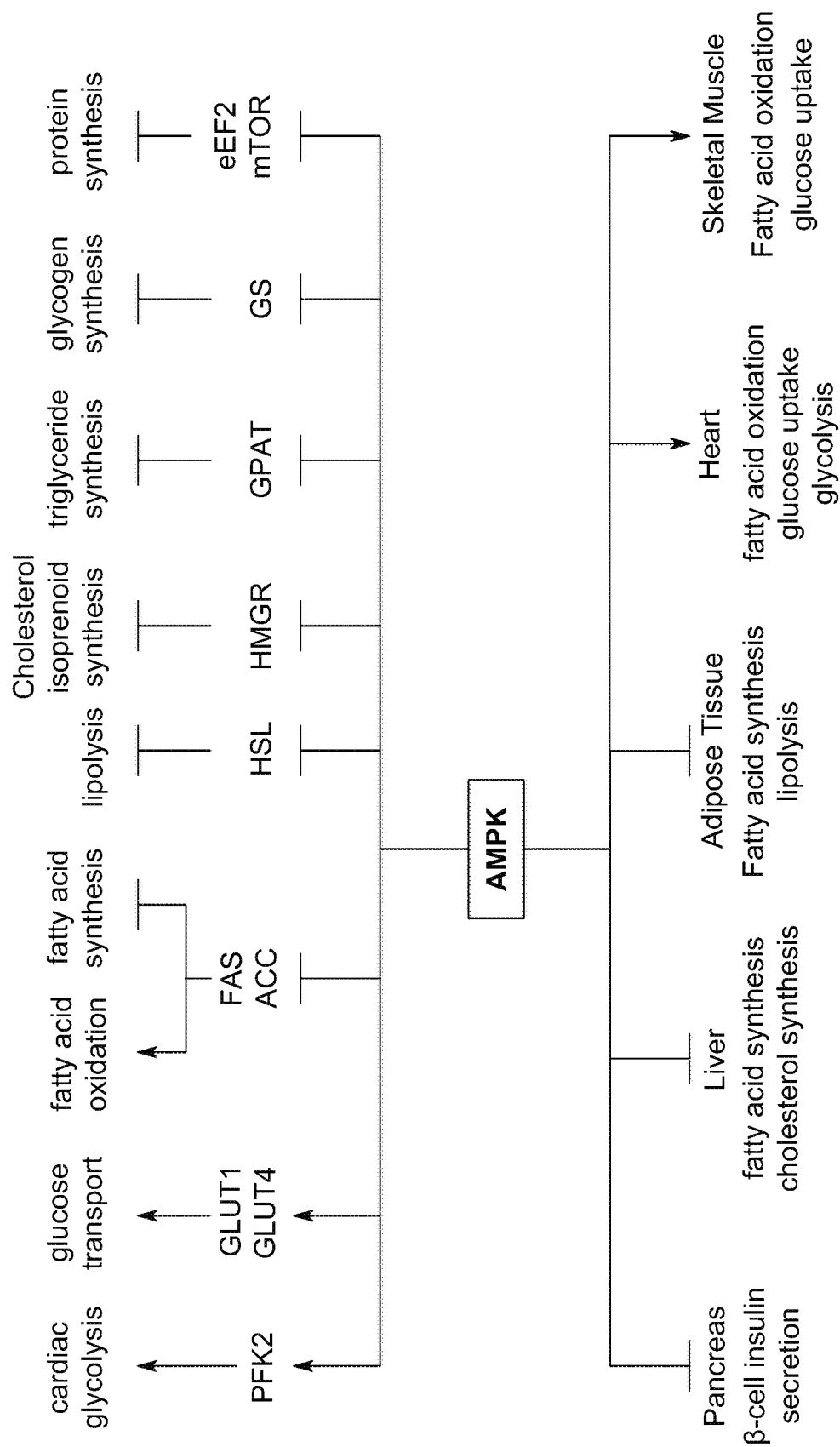

FIG. 3. Metabolic pathways involving AMPK.

Figure 4:
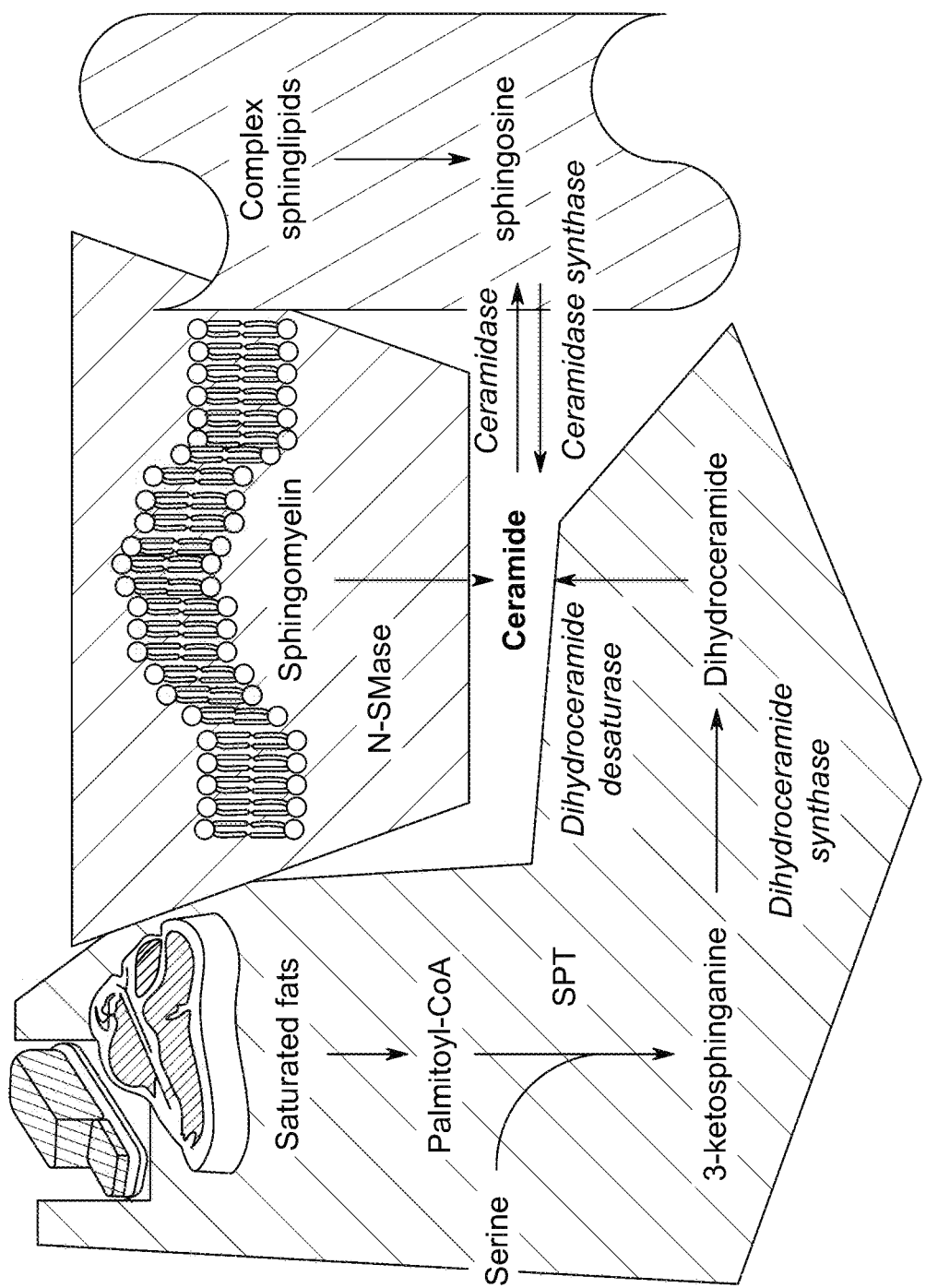

FIG. 4. Ceramides synthesis (J. Y. Xia et al. *Biochimie* 2014; 96:130-139).

Figure 5:
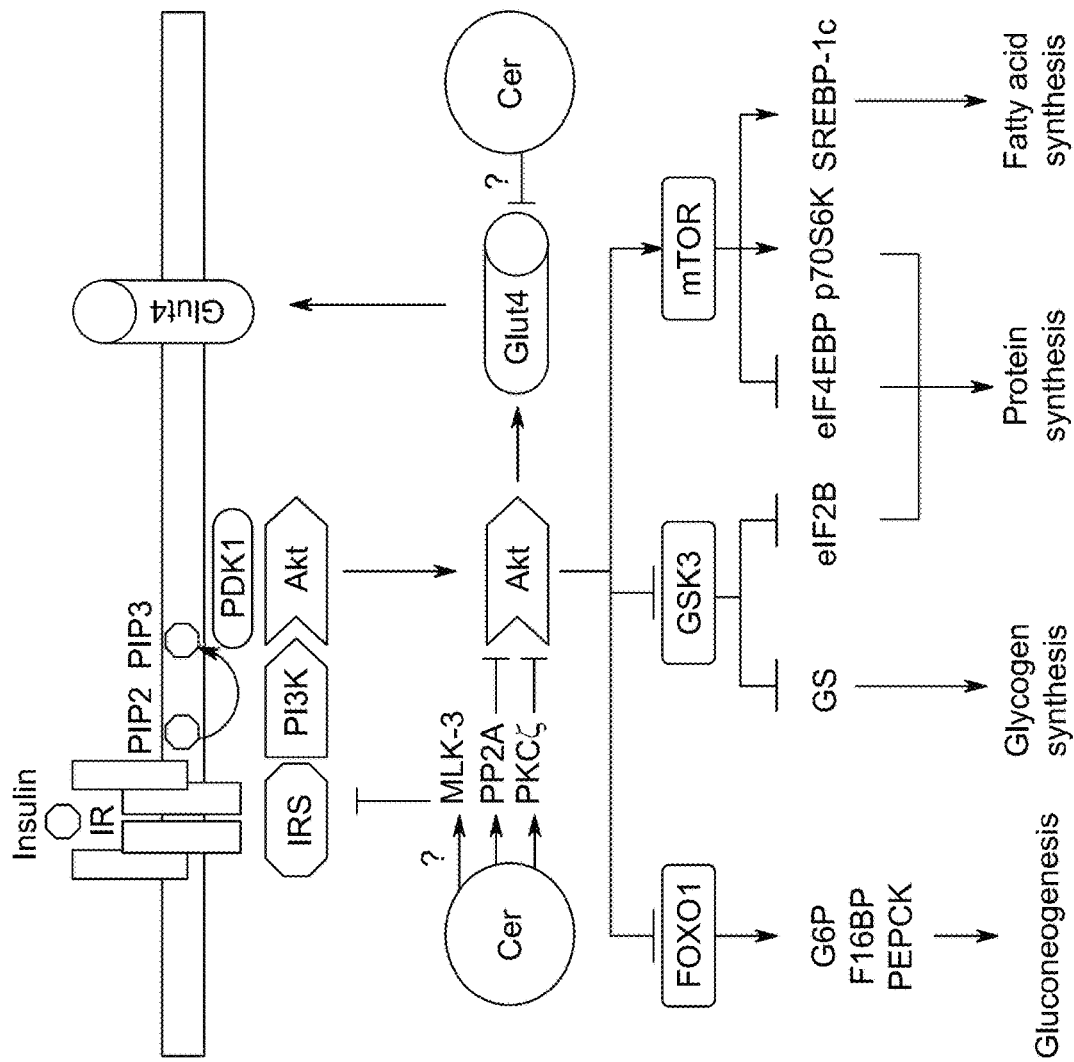

FIG. 5. Signaling pathways for insulin receptor.

Figure 6:
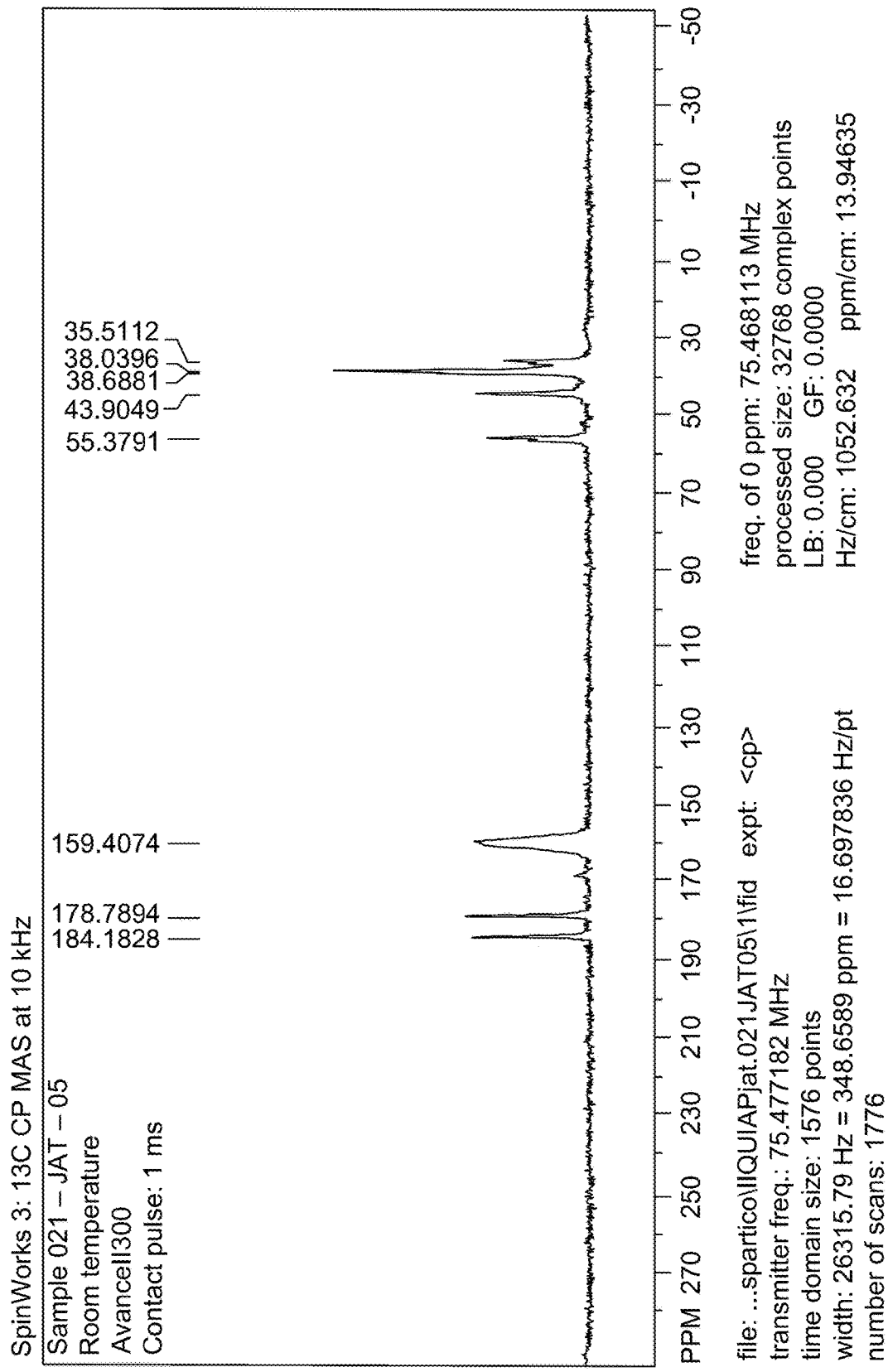

FIG. 6. Metformin aspartate. Solid-state $^{13}C$ nuclear magnetic resonance spectrum.

Figure 7:
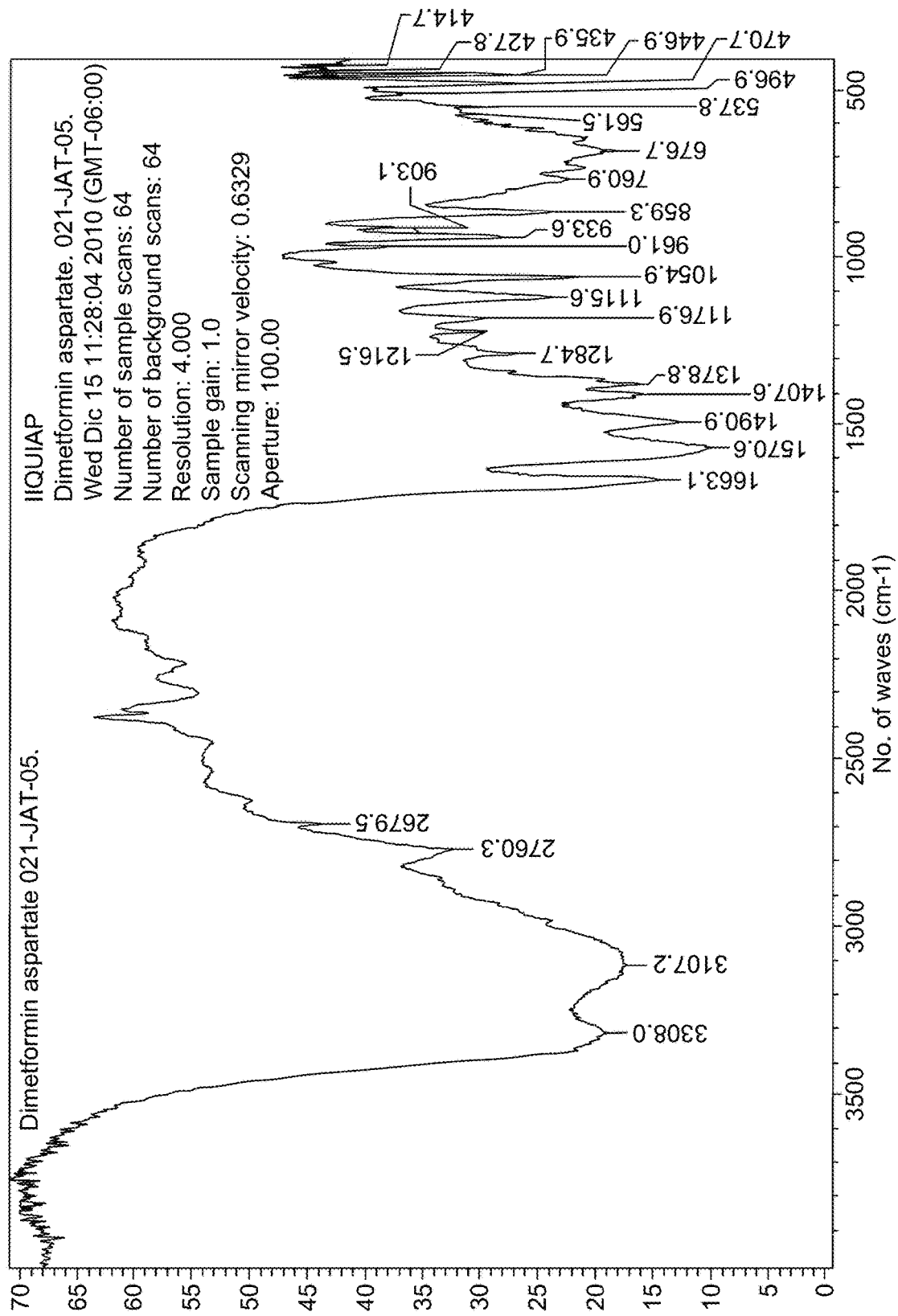

FIG. 7. Metformin aspartate. FT infrared spectrum

Figure 8:
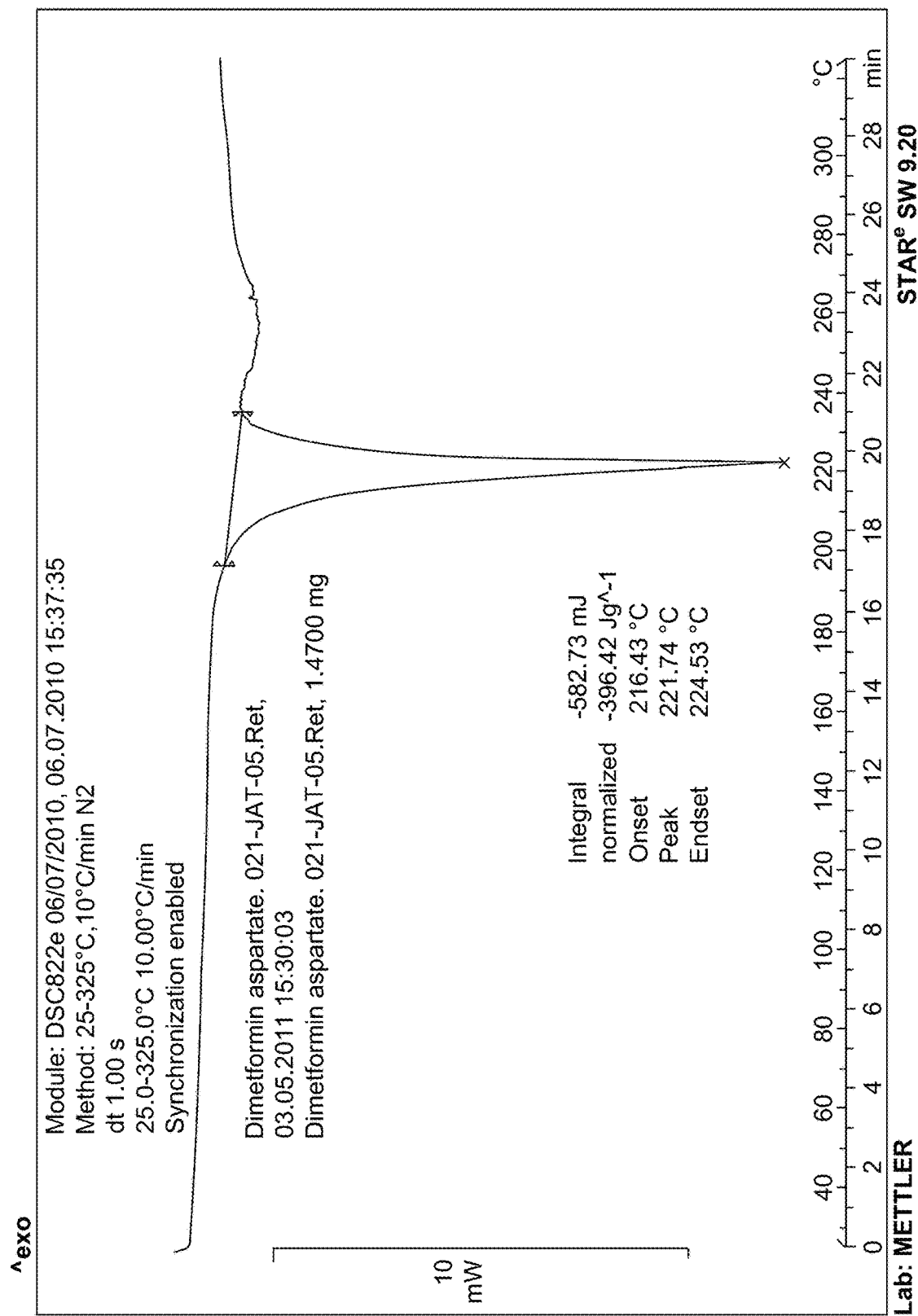

FIG. 8. Metformin aspartate. Differential scanning calorimetry (DSC).

Figure 9A:
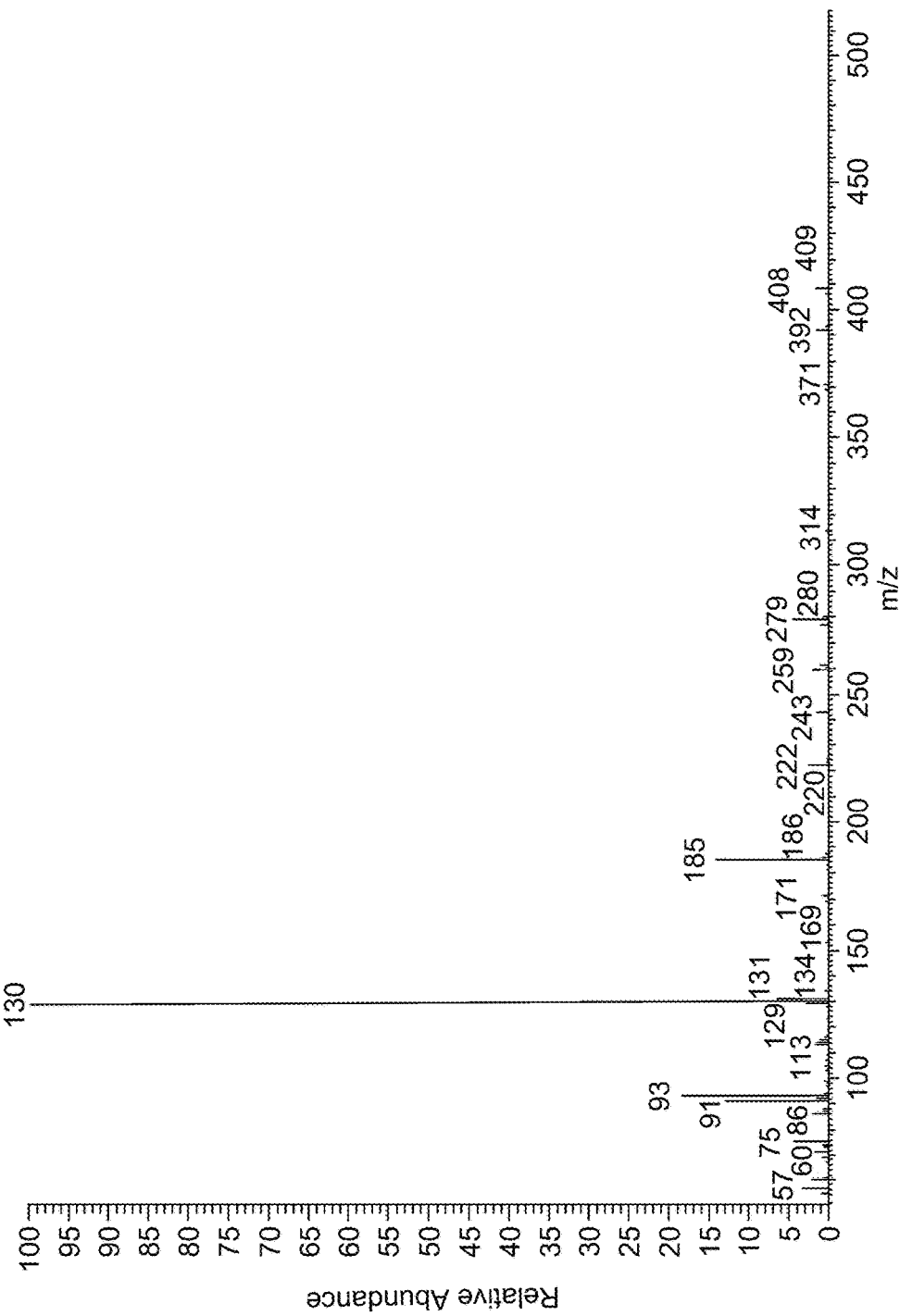
Figure 9B:
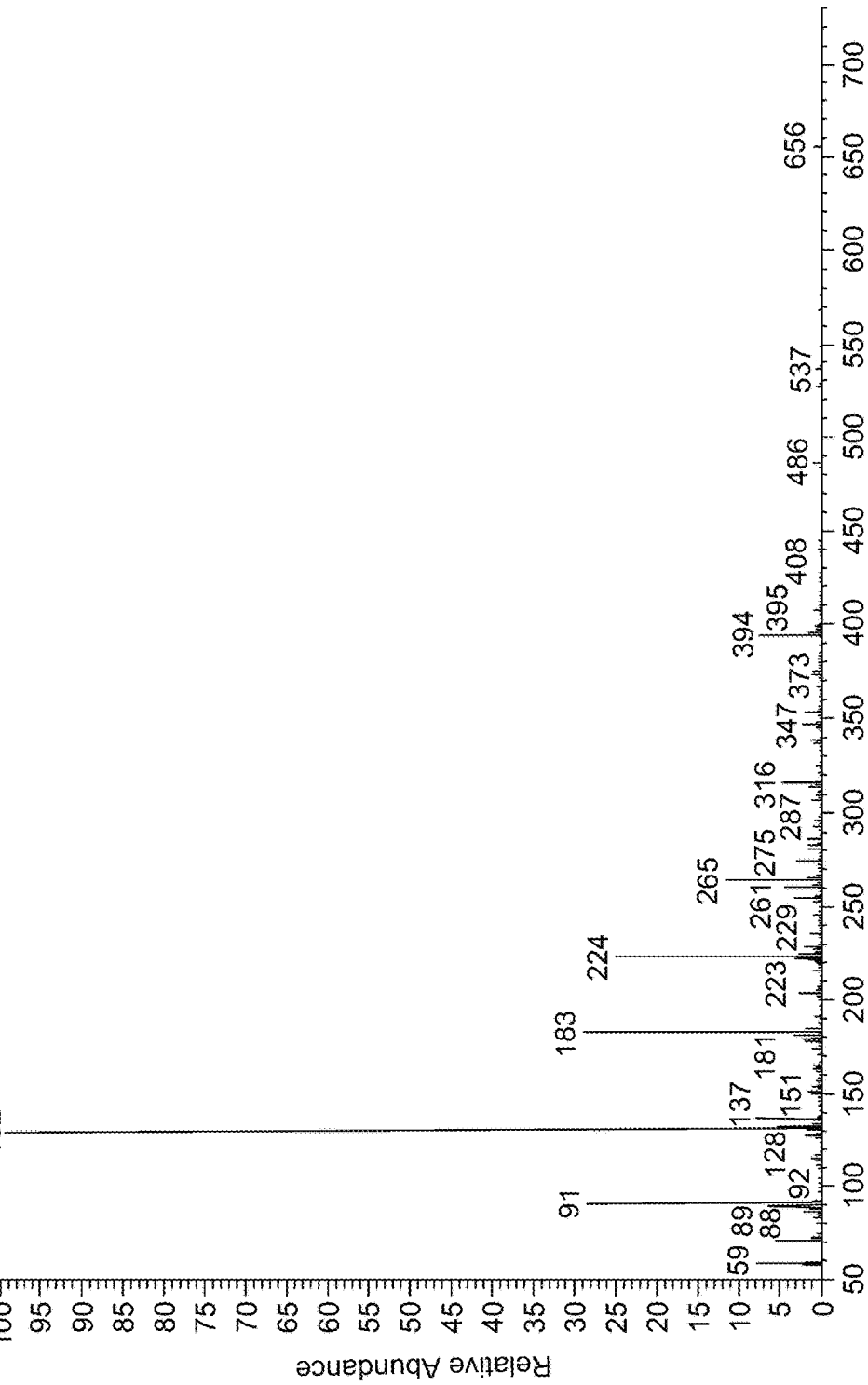

FIG. 9A-B. Metformin aspartate. $FAB^+$ (FIG. 9A) and FAB− (FIG. 9B) mass spectra.

Figure 10:
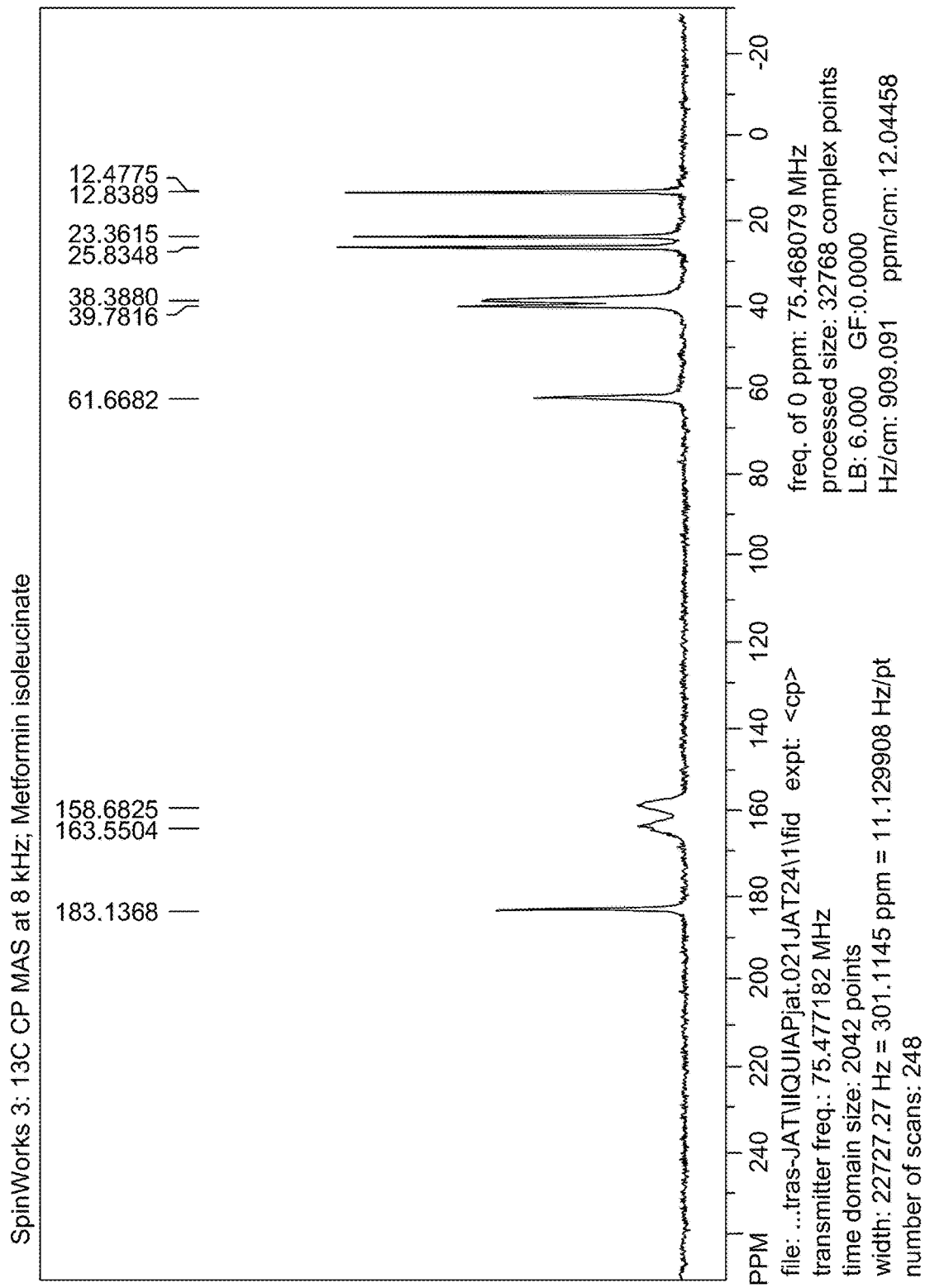

FIG. 10. Metformin isoleucinate. Solid-state $^{13}C$ nuclear magnetic resonance spectrum.

Figure 11:
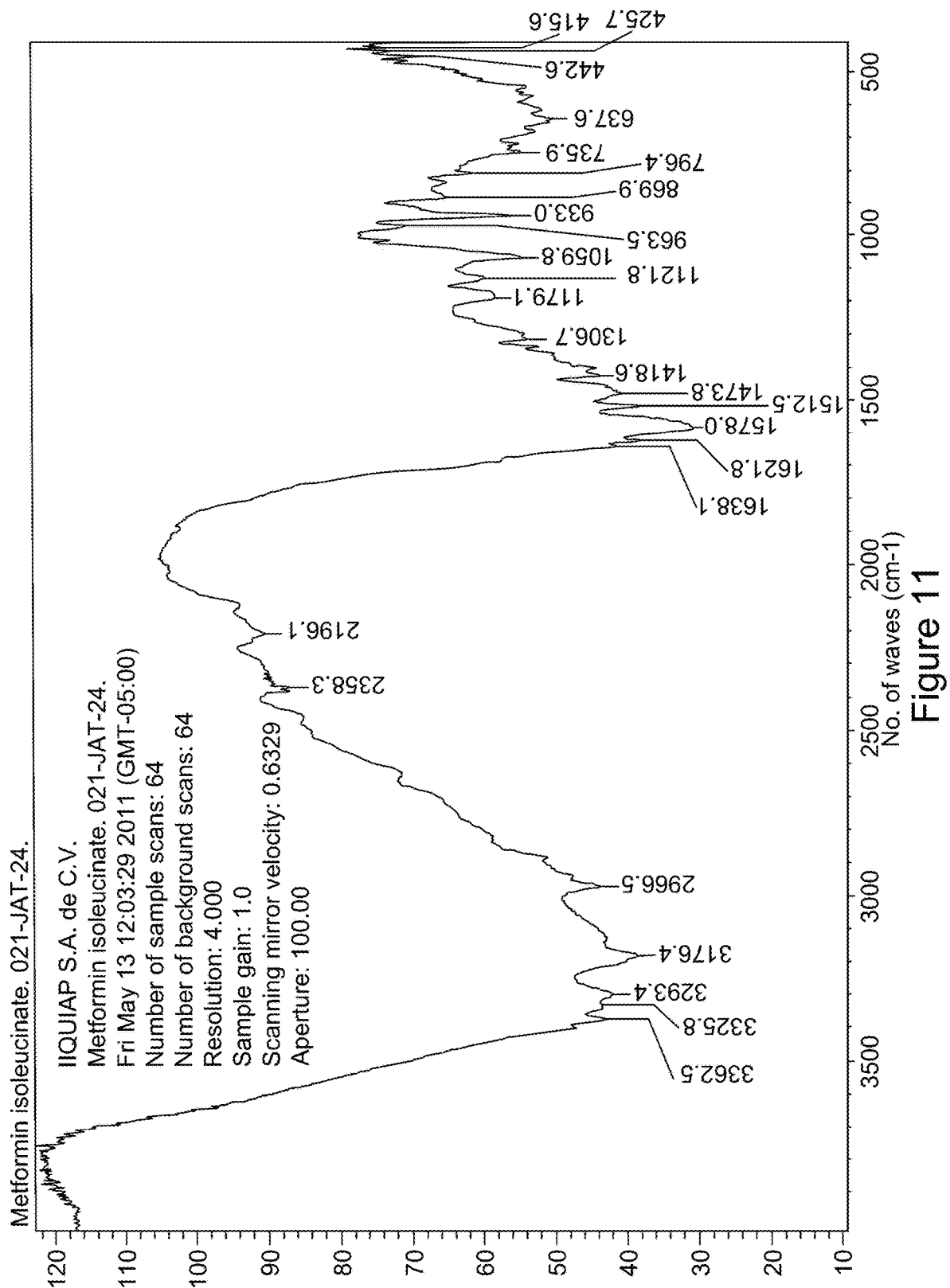

FIG. 11. Metformin isoleucinate. FT infrared spectrum

Figure 12:
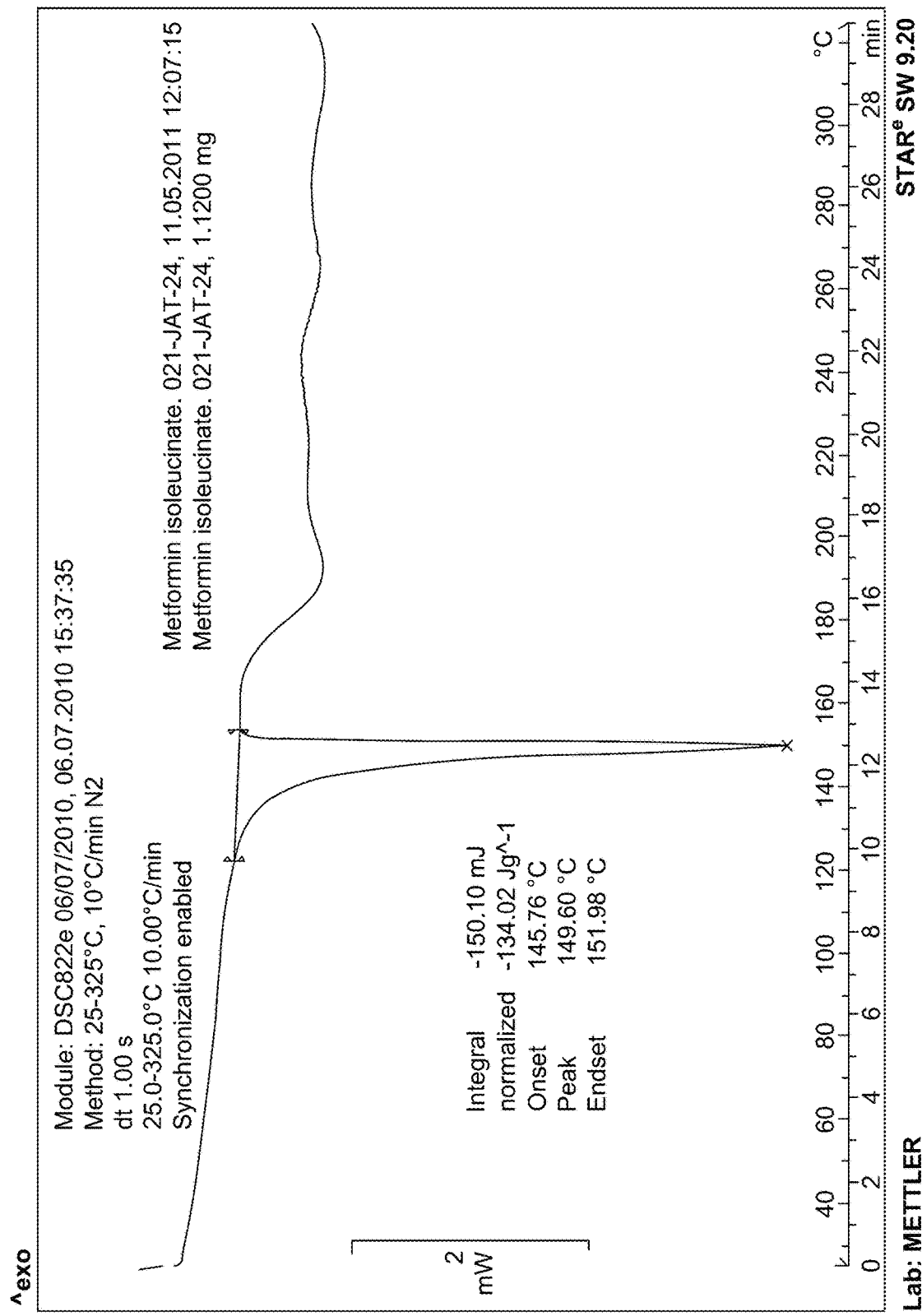

FIG. 12. Metformin isoleucinate. Differential scanning calorimetry (DSC).

Figure 13A:
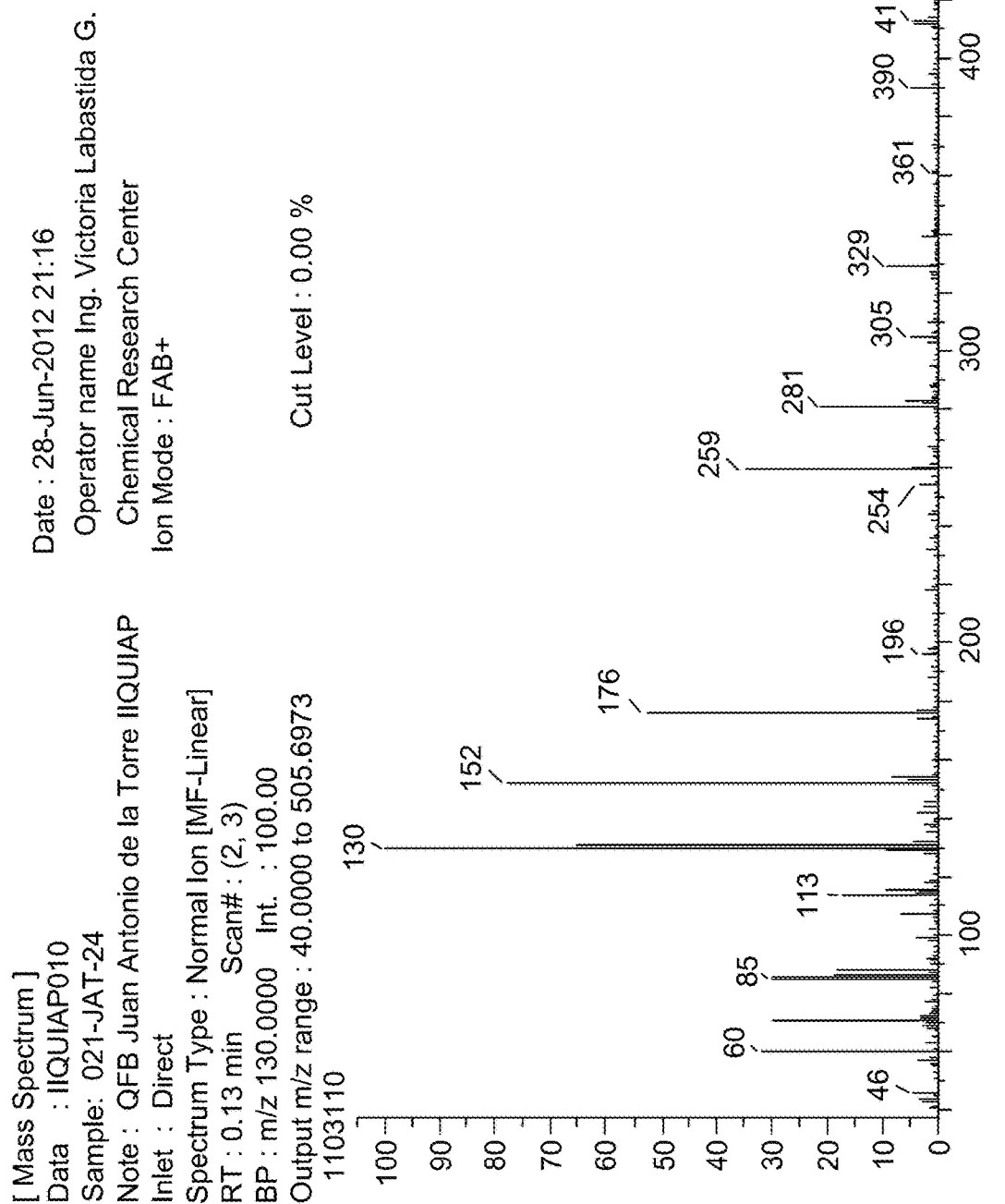
Figure 13B:
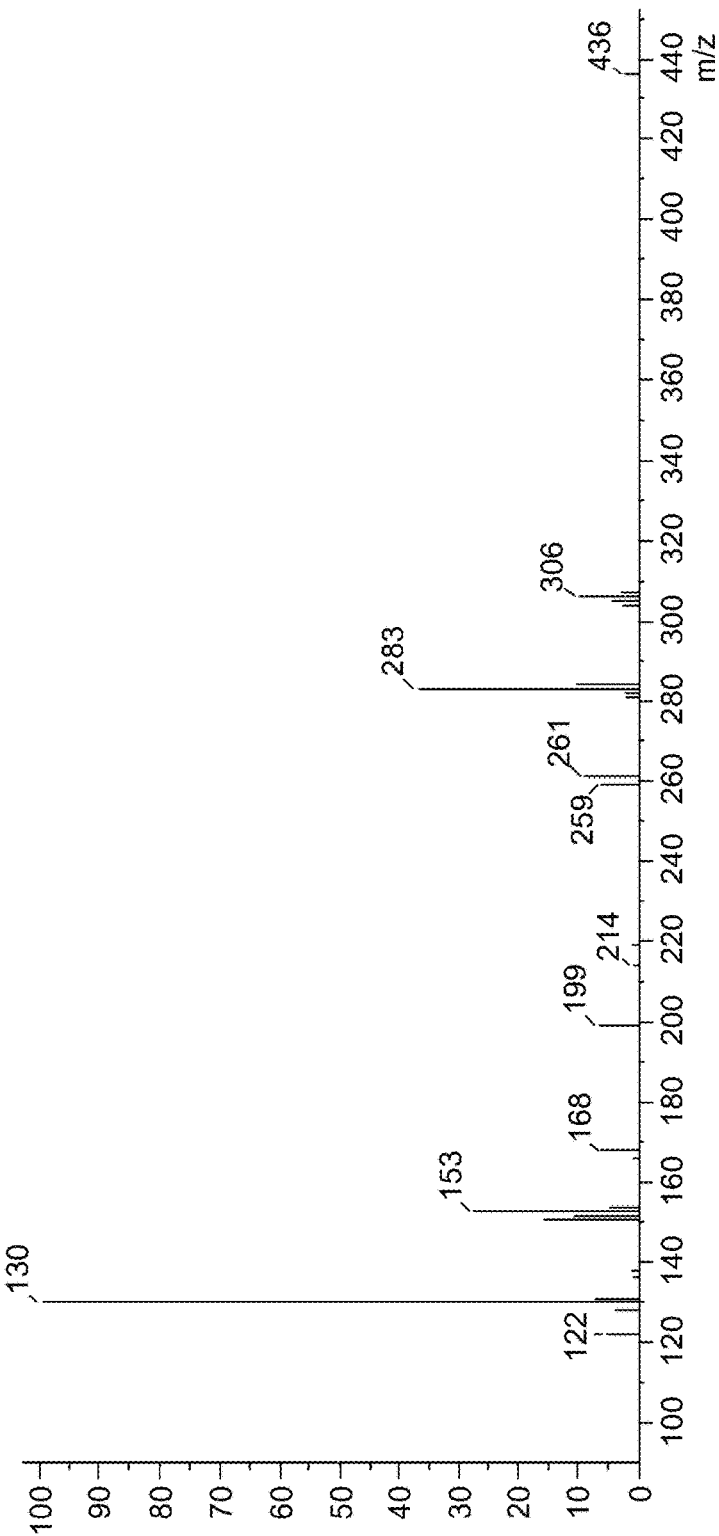

FIG. 13A-B. Metformin isoleucinate. $FAB^-$ (FIG. 13A) and $FAB^-$ (FIG. 13B) mass spectra.

Figure 14:
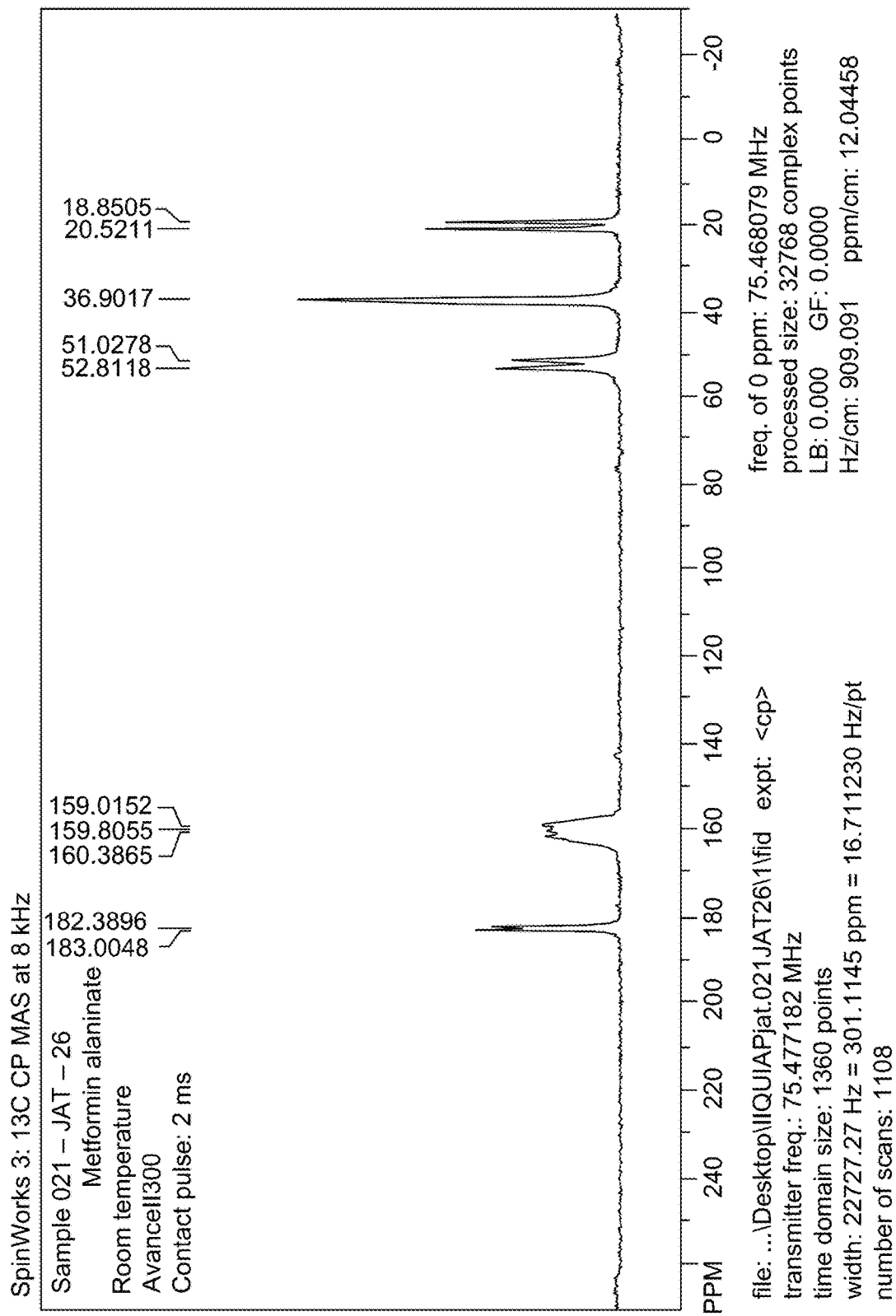

FIG. 14. Metformin alaninate Solid-state $^{13}$C nuclear magnetic resonance spectrum.

Figure 15:
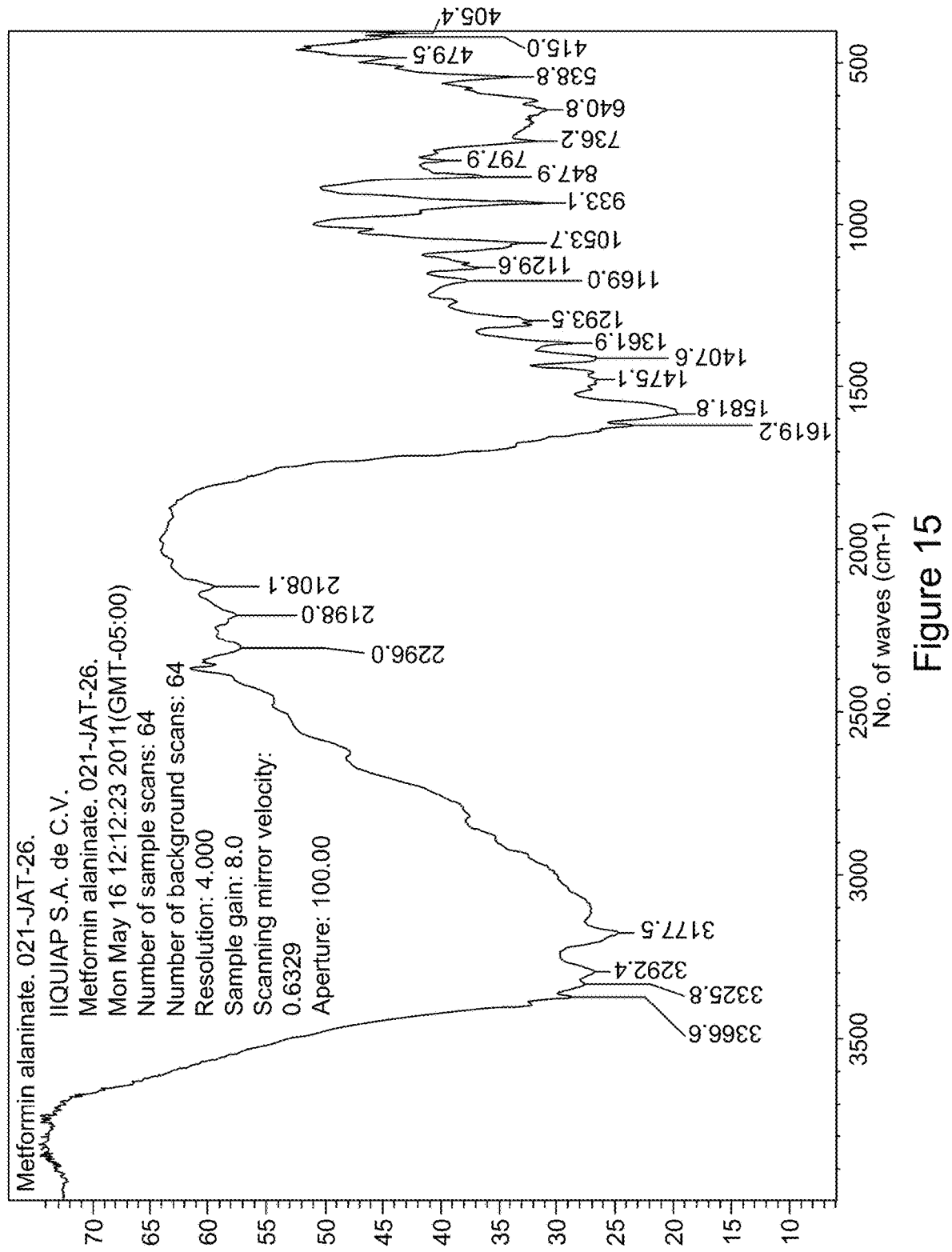

FIG. 15. Metformin alaninate. FT infrared spectrum.

Figure 16:
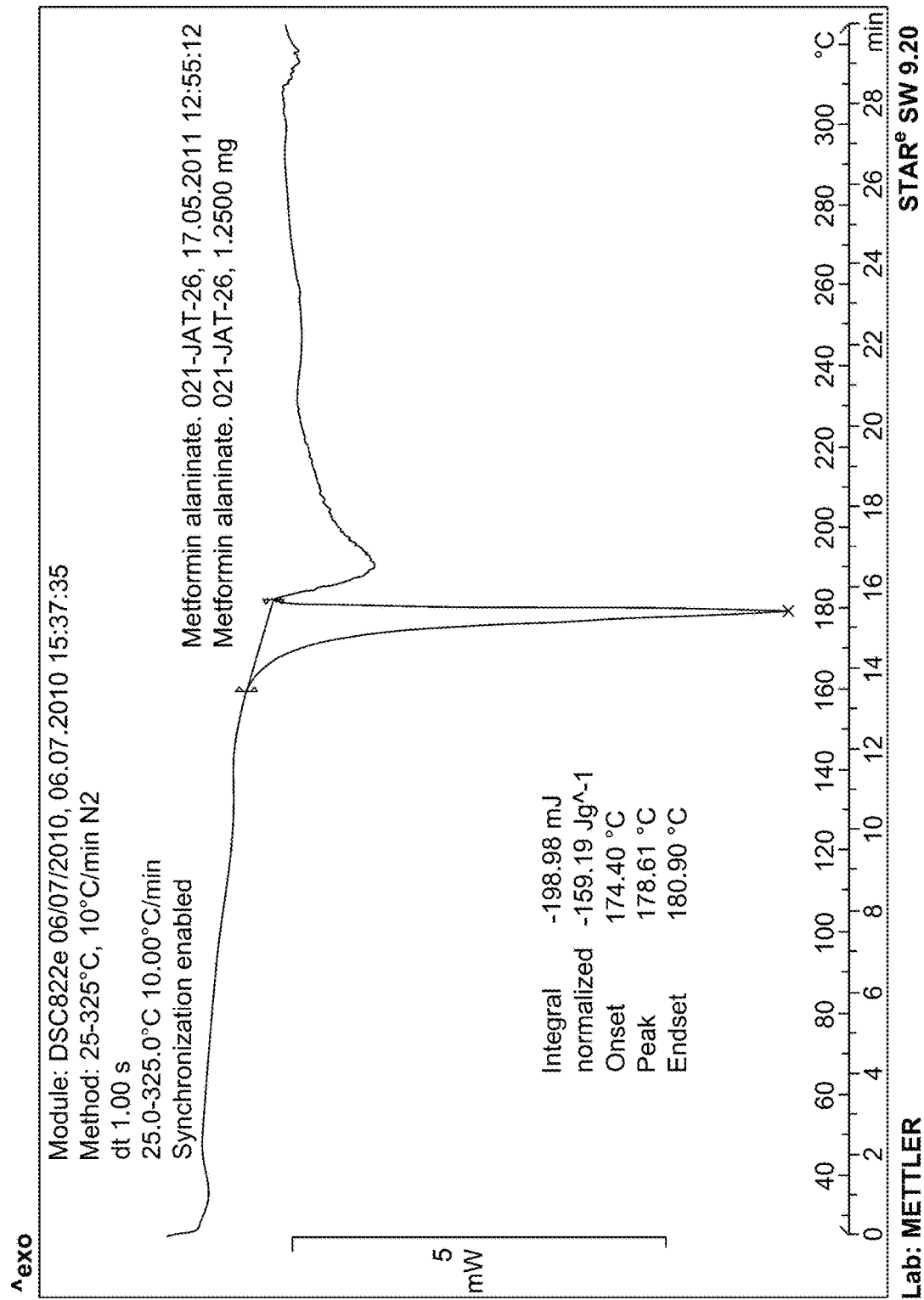

FIG. 16. Metformin alaninate. Differential scanning calorimetry (DSC).

Figure 17A:
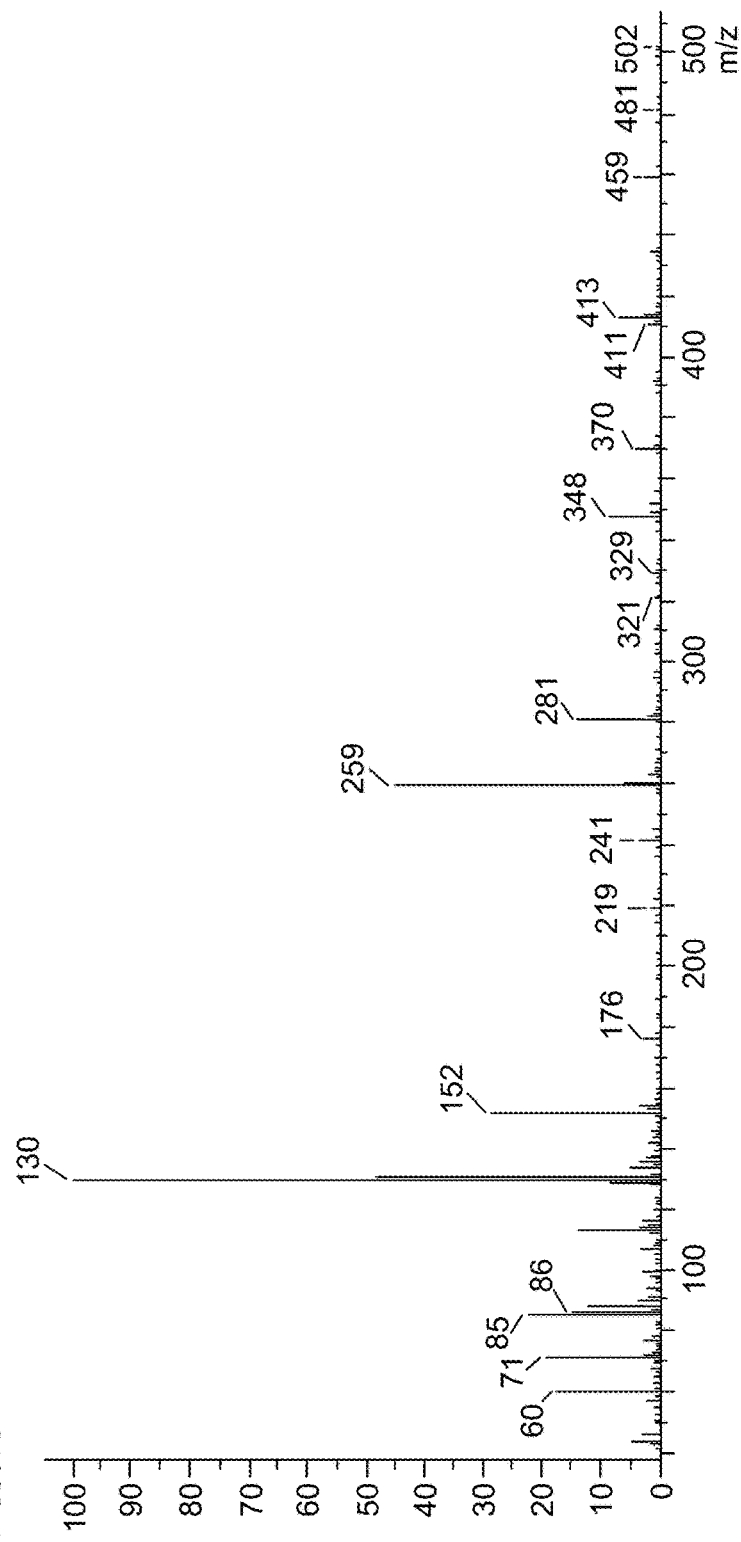
Figure 17B:
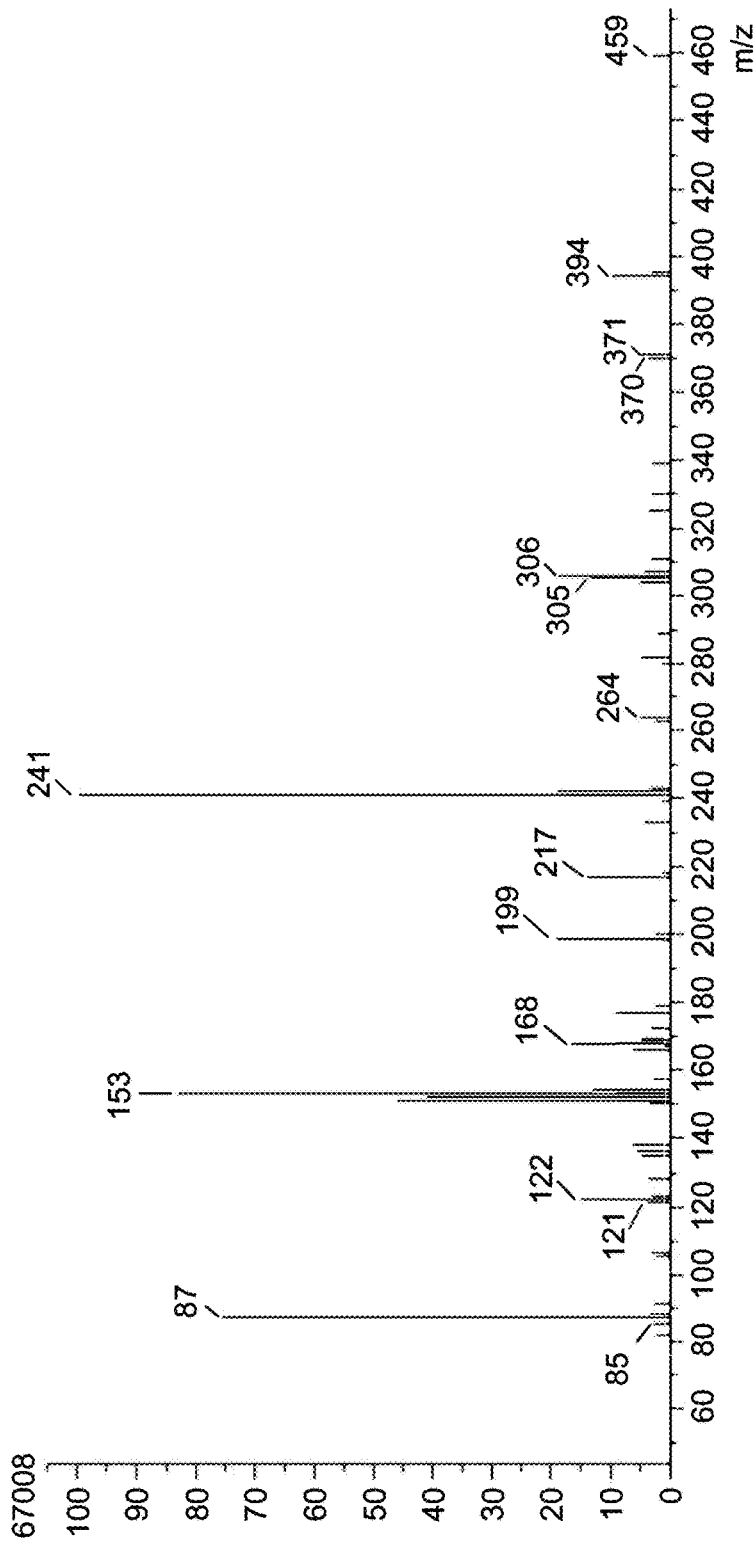

FIG. 17A-B. Metformin alaninate. FAB$^+$ (FIG. 17A) and FAB− (FIG. 17B) mass spectra.

Figure 18:
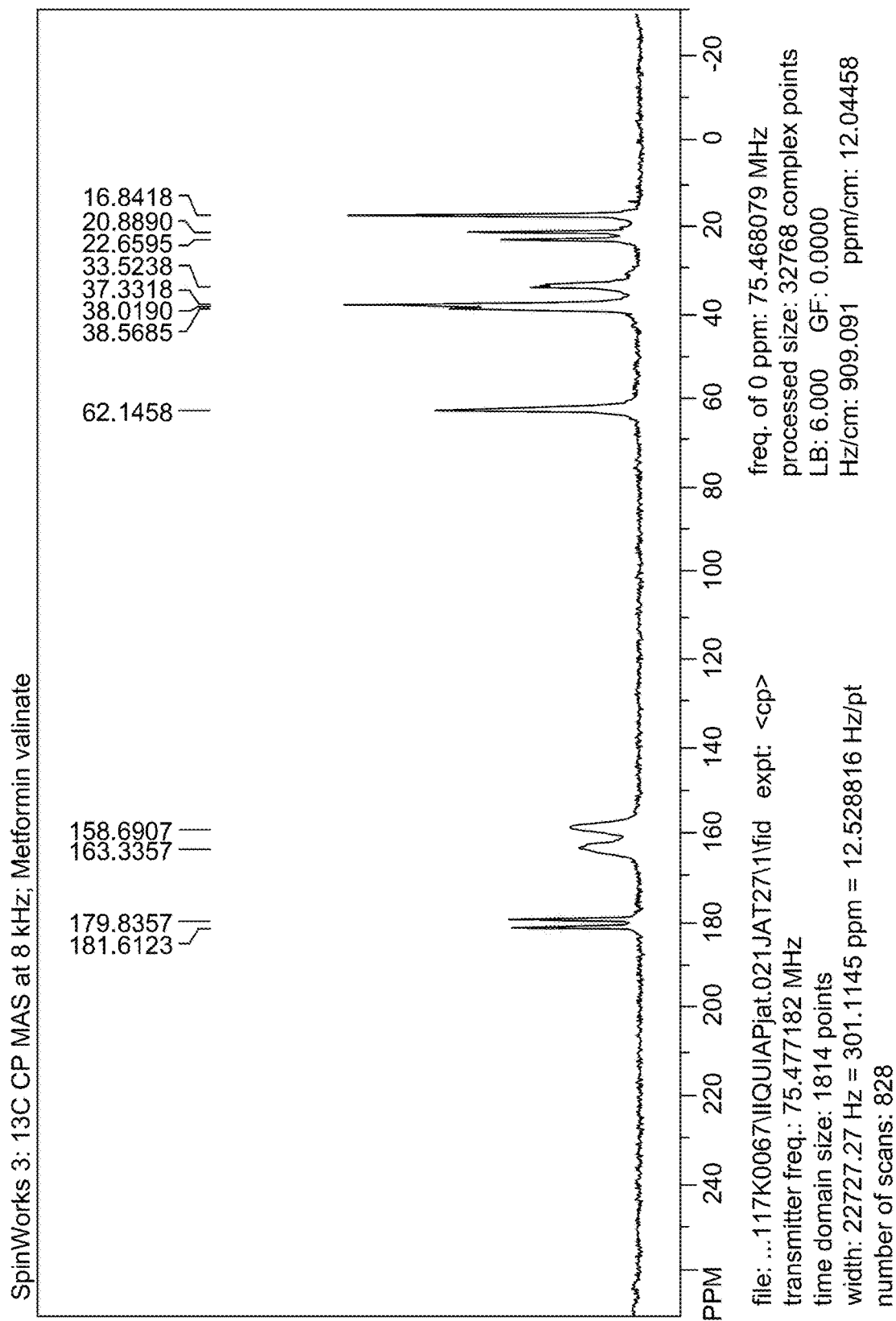

FIG. 18. Metformin valinate. Solid-state $^{13}$C nuclear magnetic resonance spectrum.

Figure 19:
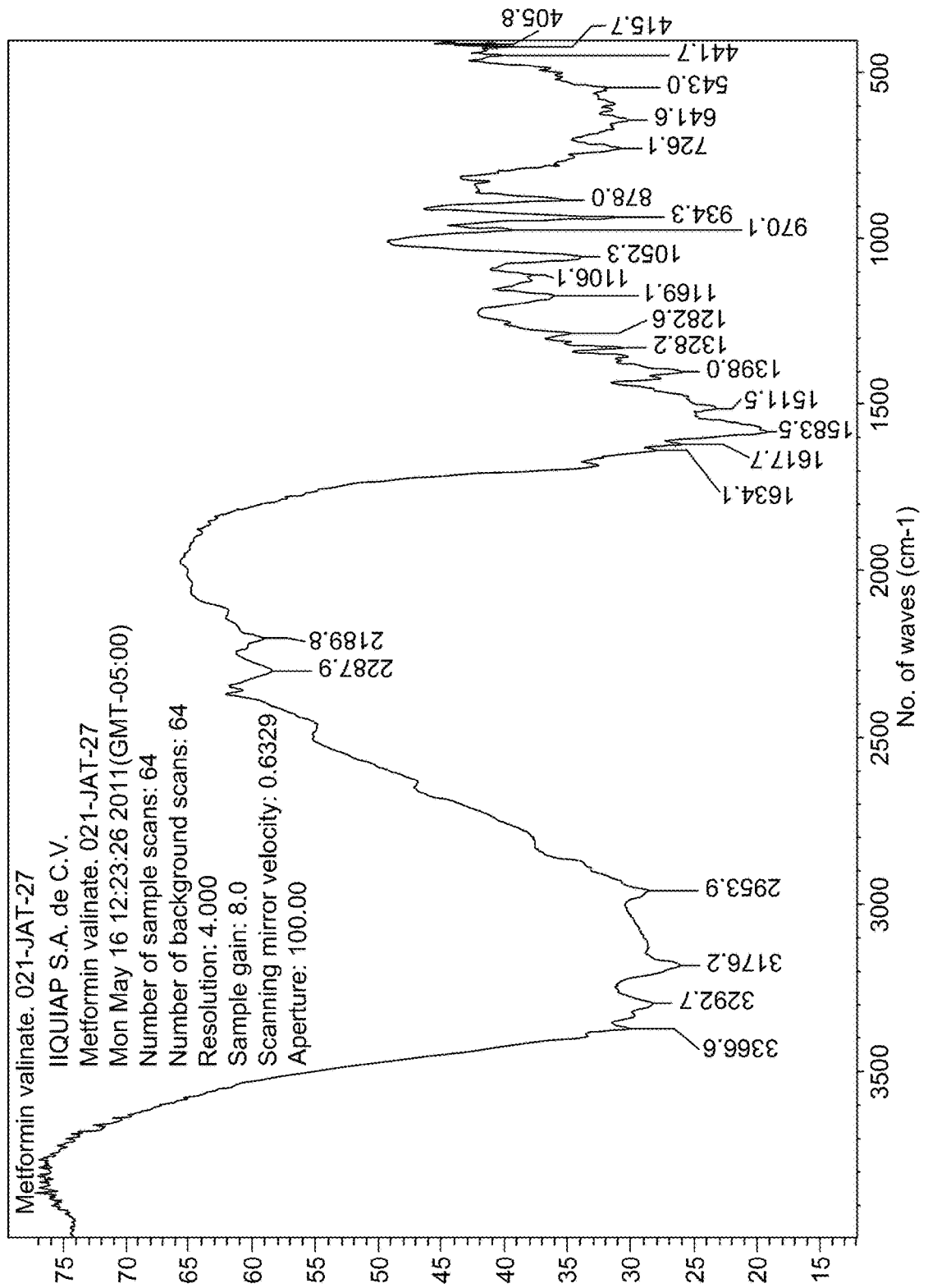

FIG. 19. Metformin valinate. FT infrared spectrum.

Figure 20:
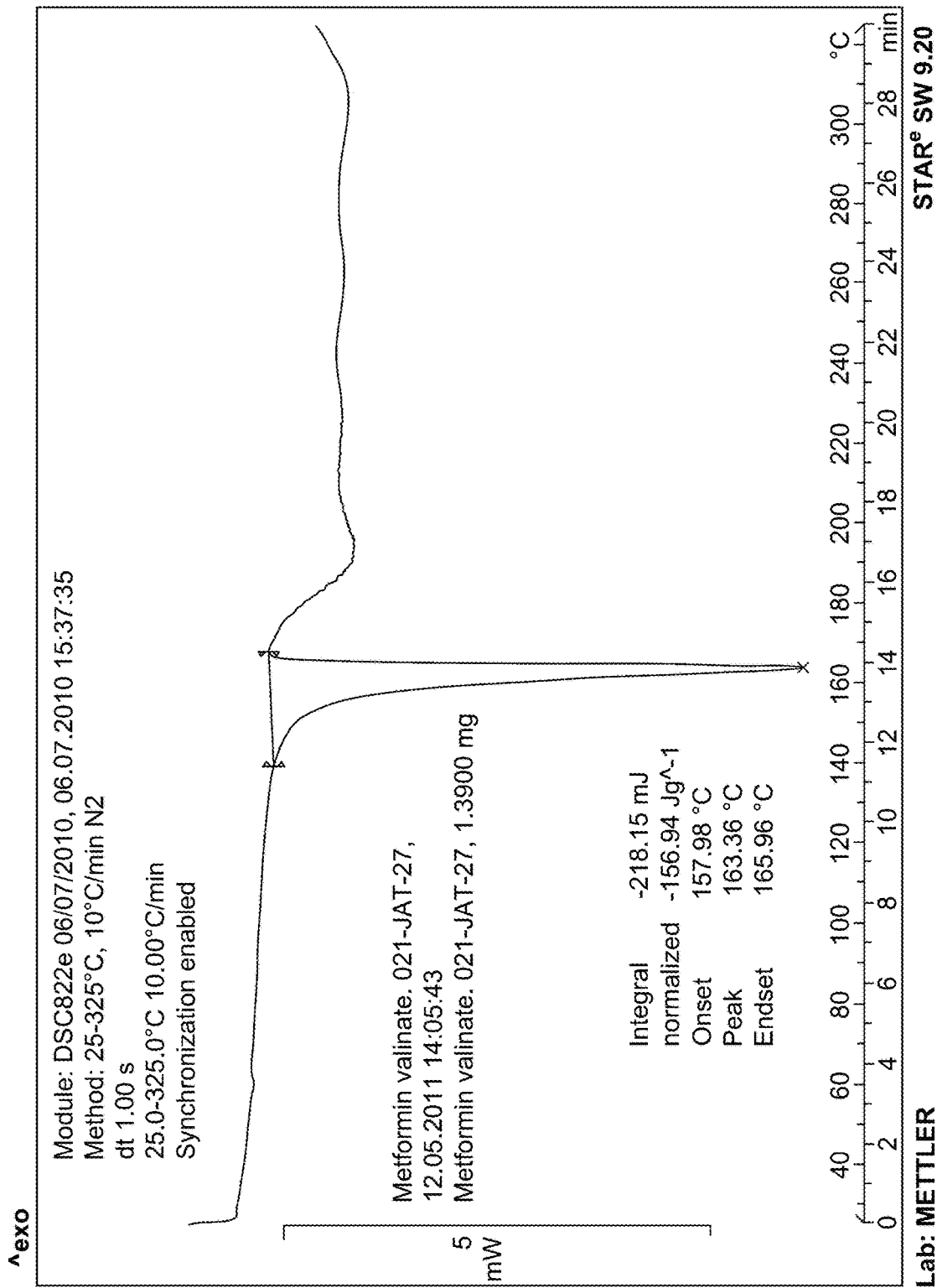

FIG. 20. Metformin valinate. Differential scanning calorimetry (DSC).

Figure 21A:
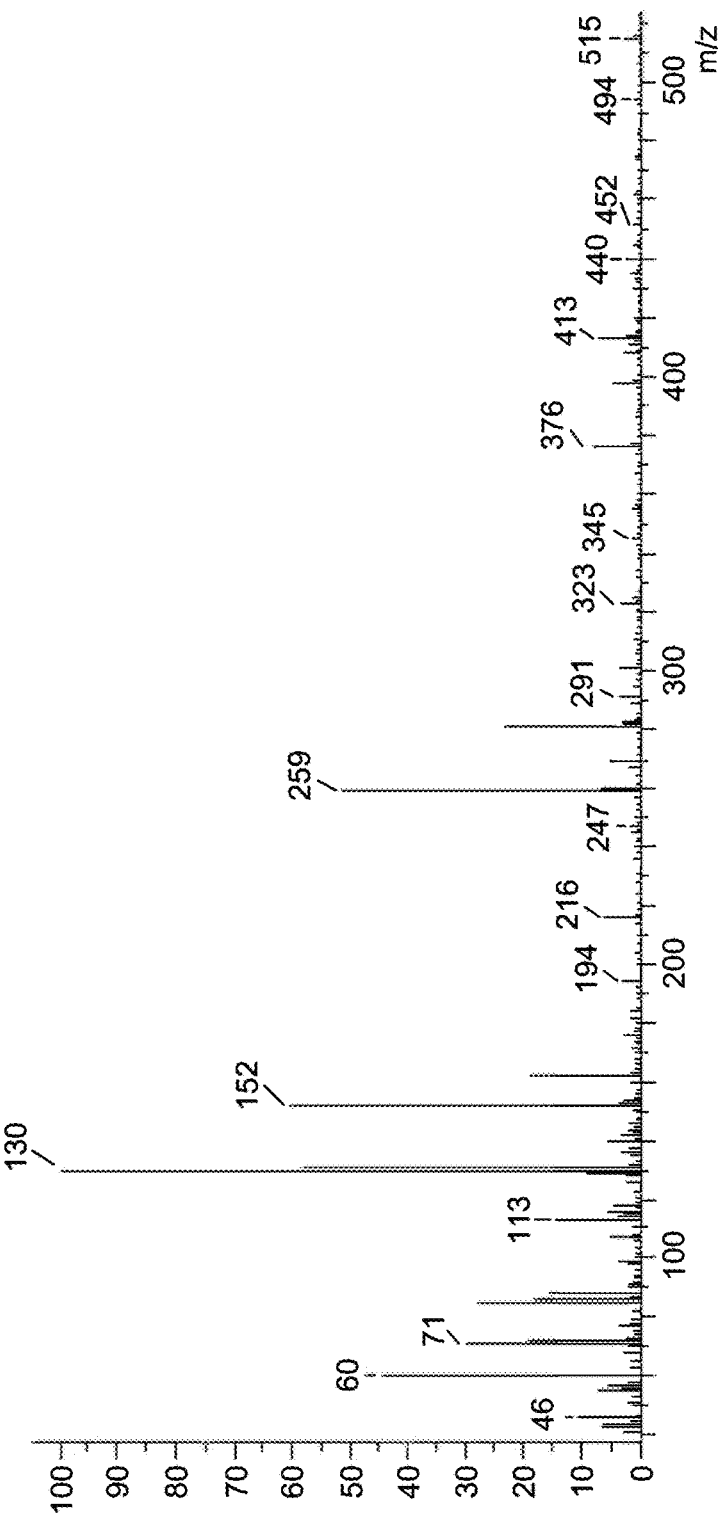
Figure 21B:
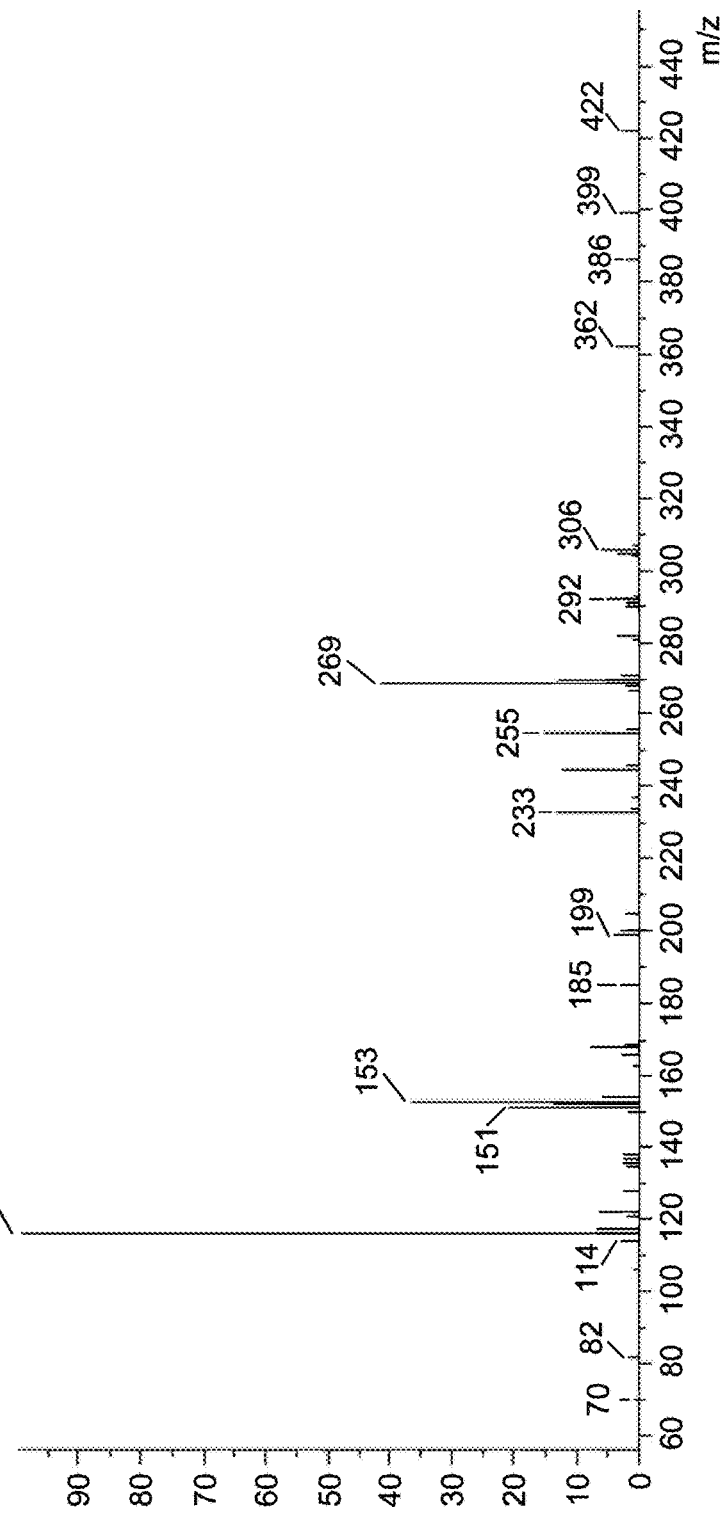

FIG. 21A-B. Metformin valinate. FAB$^+$ (FIG. 21A) and FAB− (FIG. 21B) mass spectra.

Figure 22:
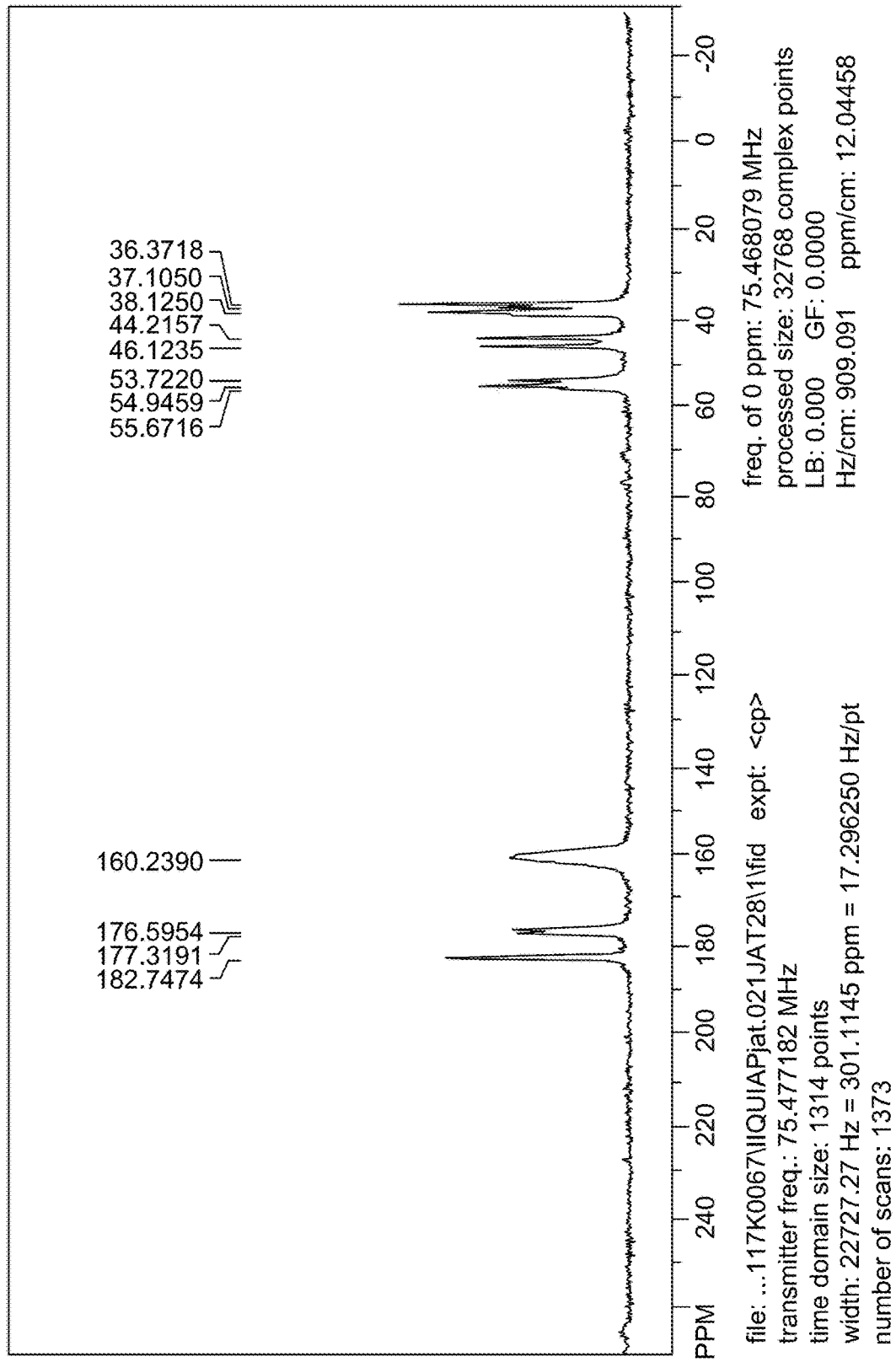

FIG. 22. Metformin asparaginate. Solid-state $^{13}$C nuclear magnetic resonance spectrum.

Figure 23:
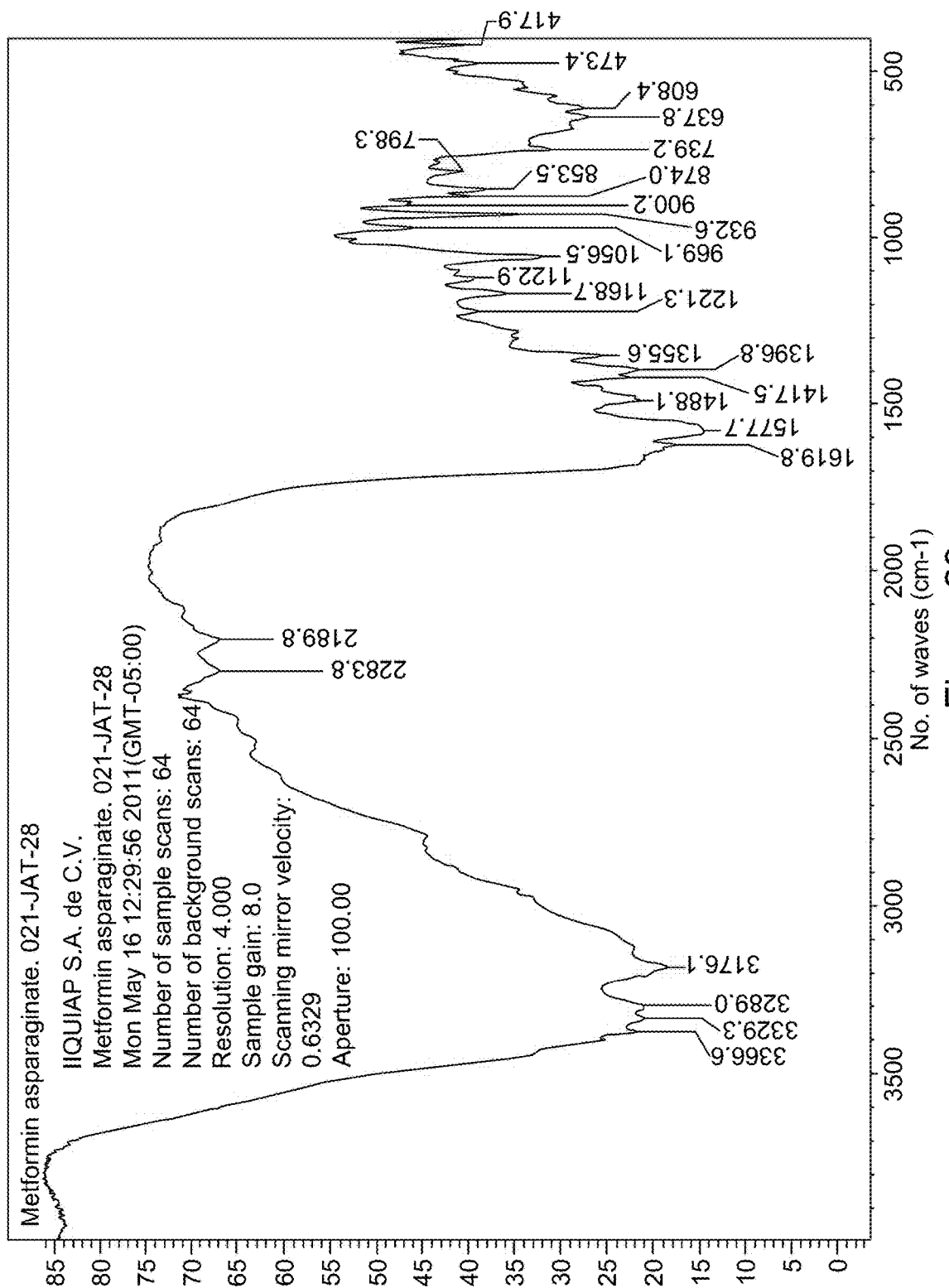

FIG. 23. Metformin asparaginate. FT infrared spectrum.

Figure 24:
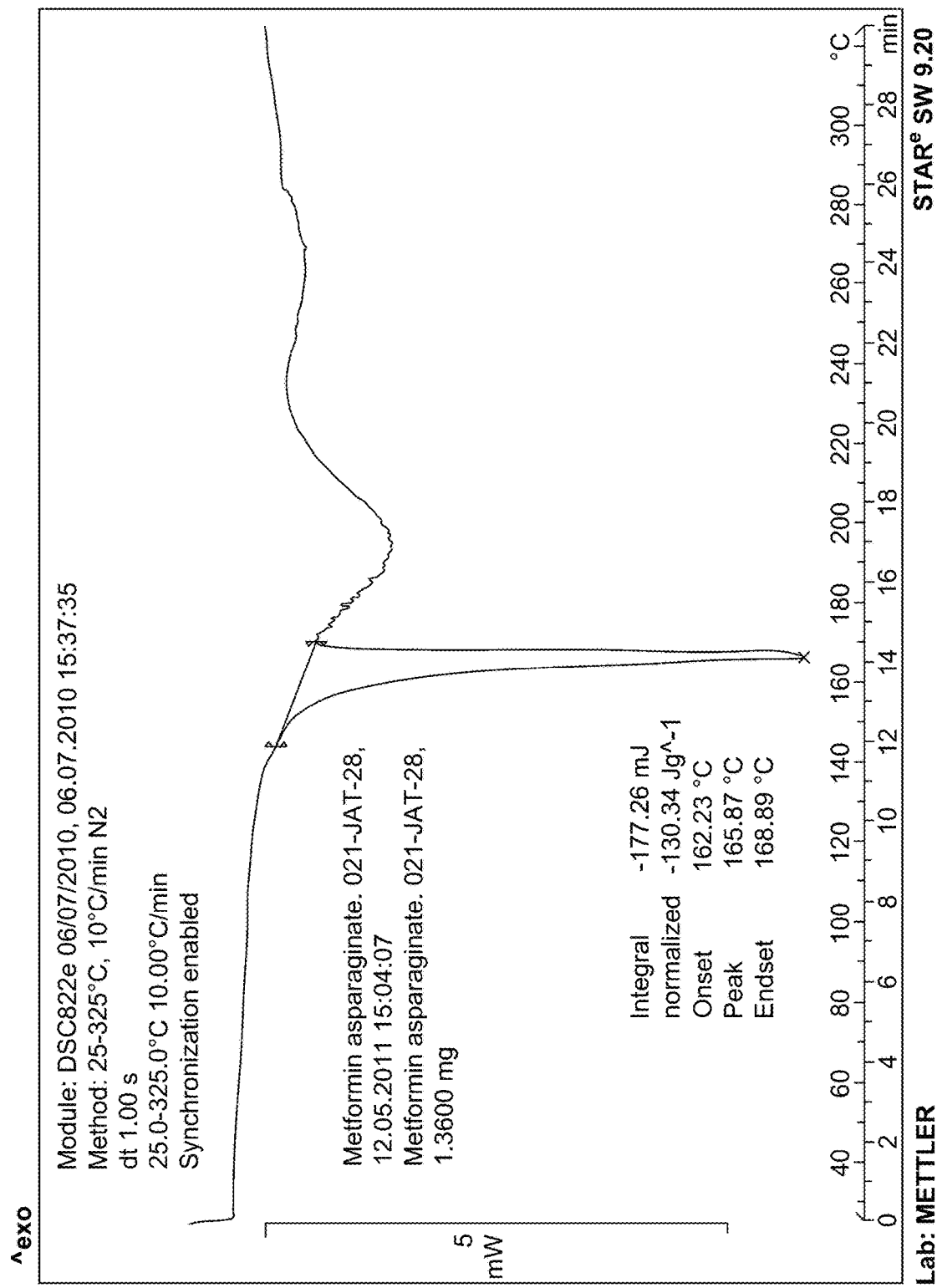

FIG. 24. Metformin asparaginate. Differential scanning calorimetry (DSC).

Figure 25A:
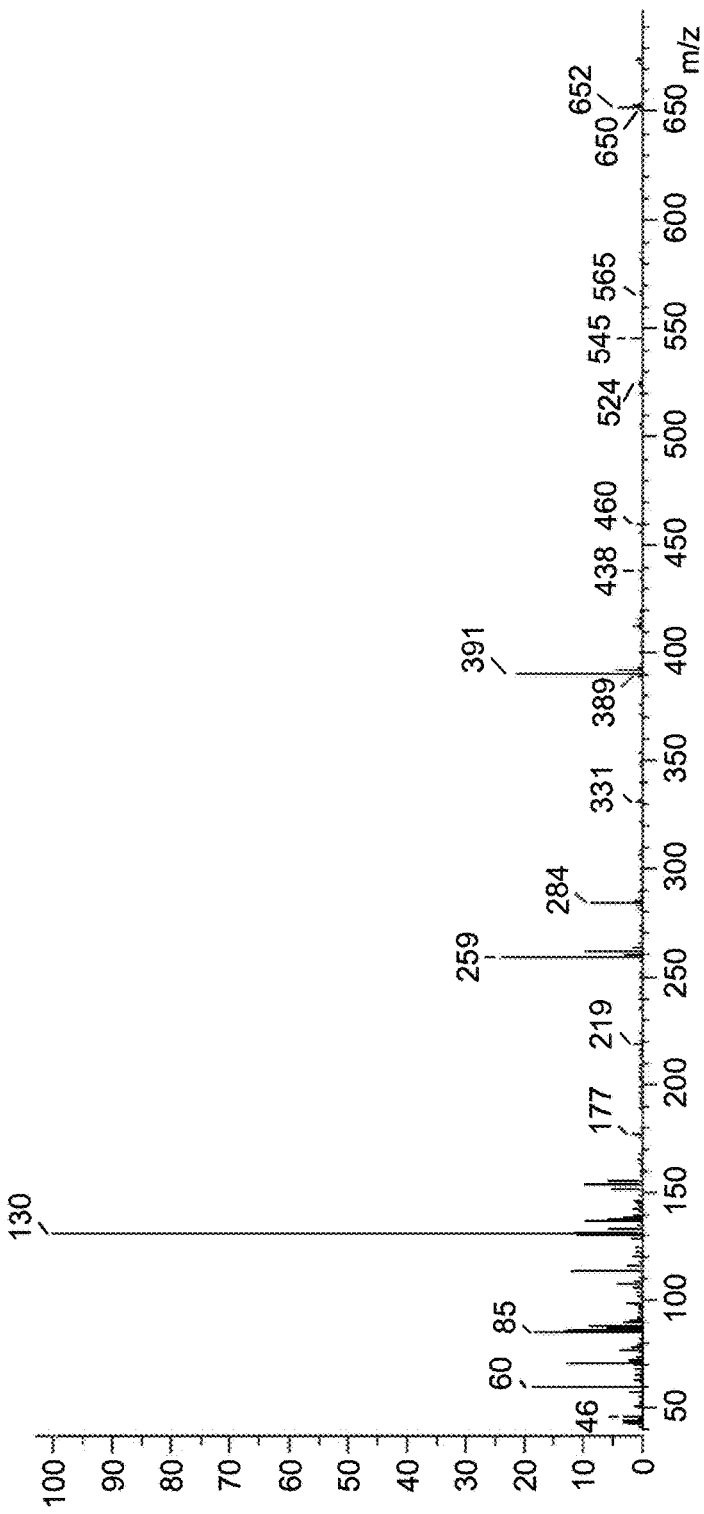
Figure 25B:
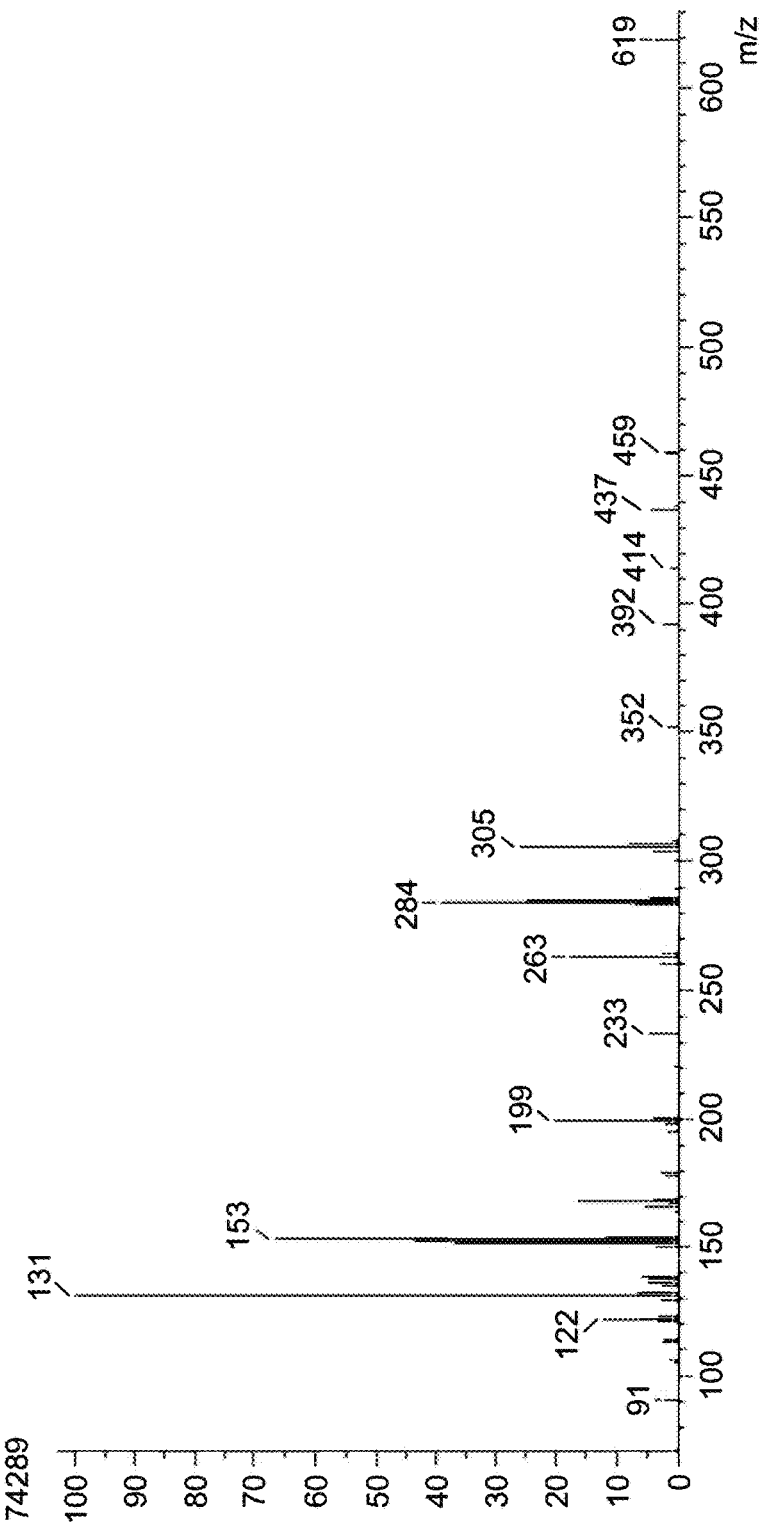

FIG. 25A-B. Metformin asparaginate. FAB$^+$ (FIG. 25A) and FAB− (FIG. 25B) mass spectra.

Figure 26:
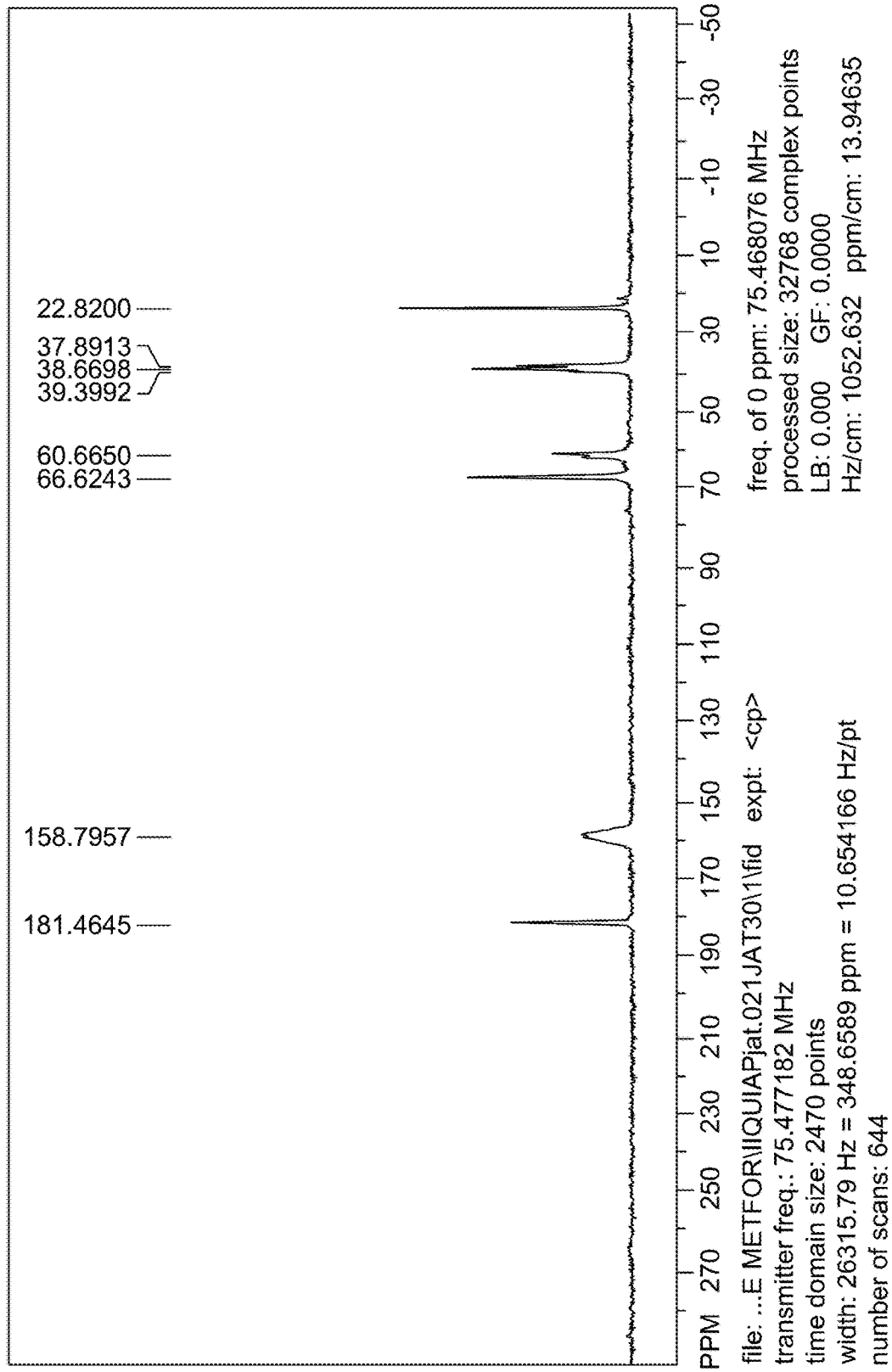

FIG. 26. Metformin threoninate. Solid-state $^{13}$C nuclear magnetic resonance spectrum.

Figure 27:
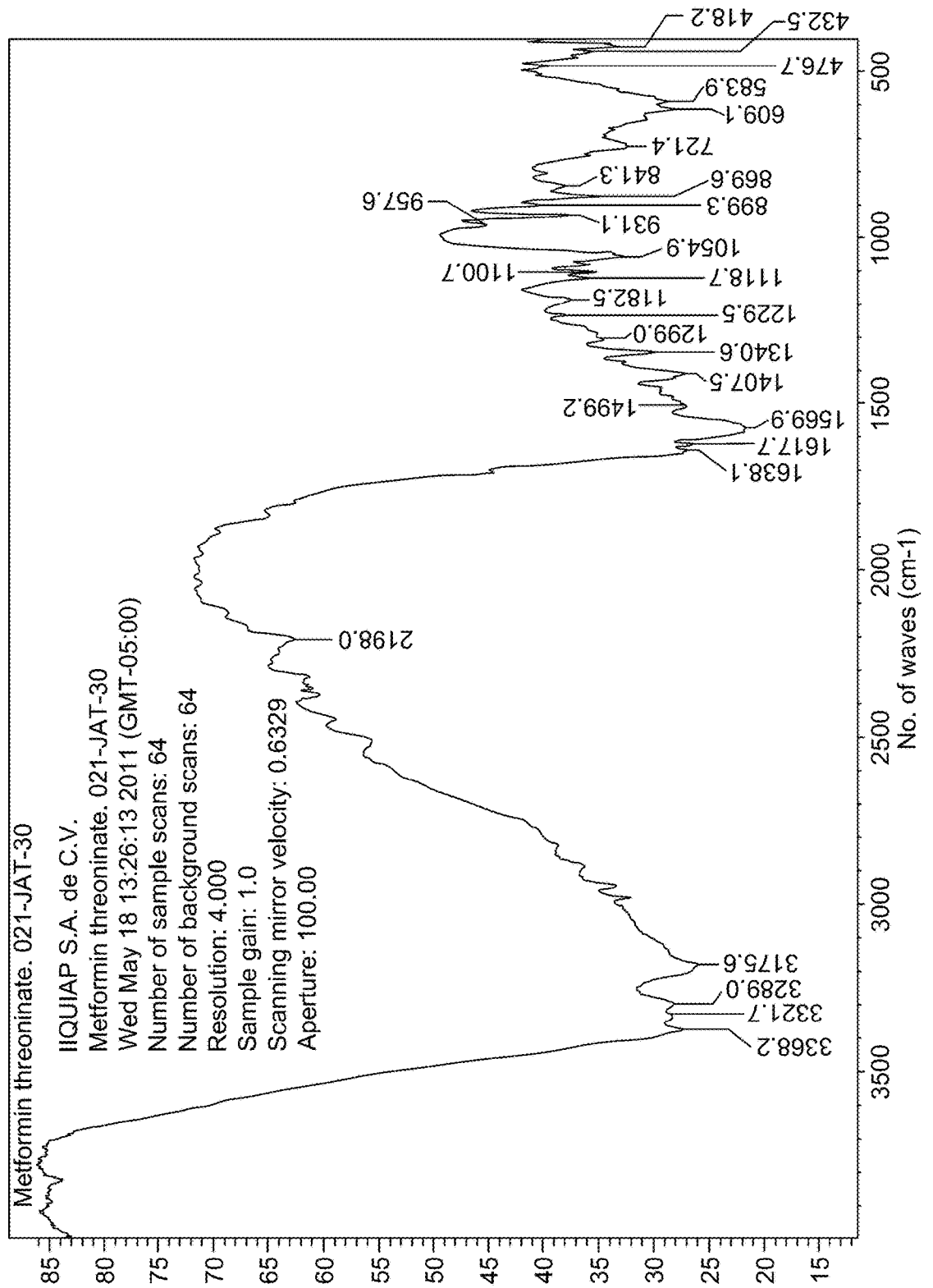

FIG. 27. Metformin threoninate. FT infrared spectrum.

Figure 28:
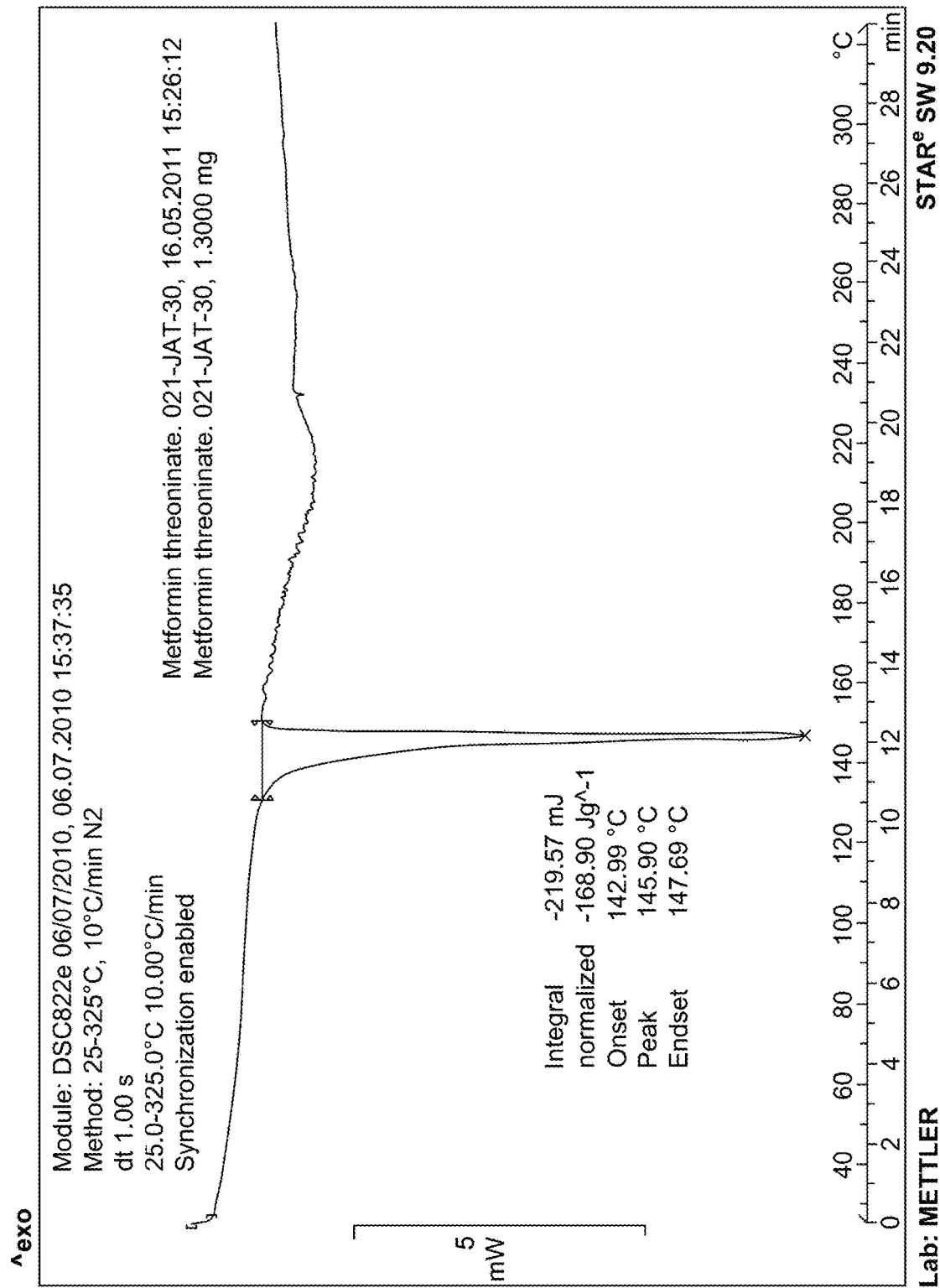

FIG. 28. Metformin threoninate. Differential scanning calorimetry (DSC).

Figure 29A:
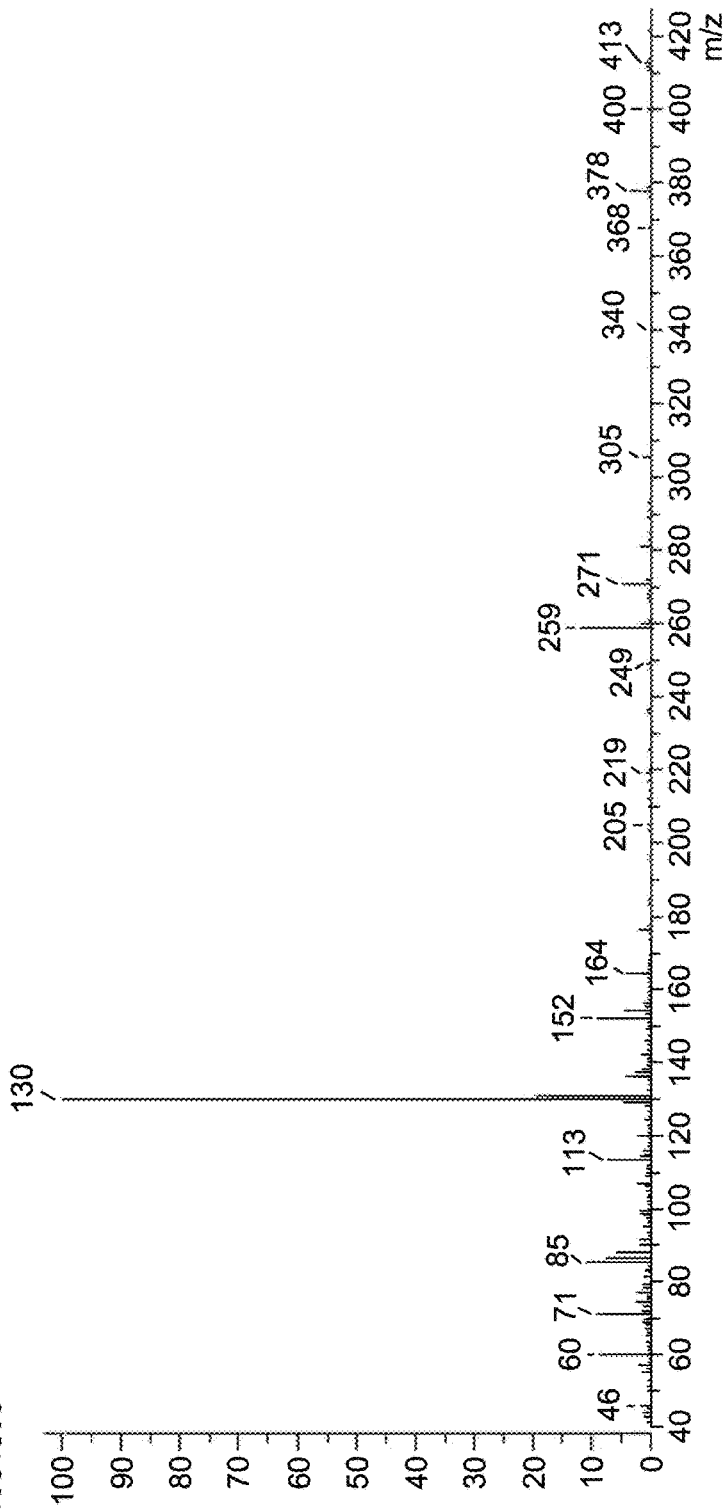
Figure 29B:
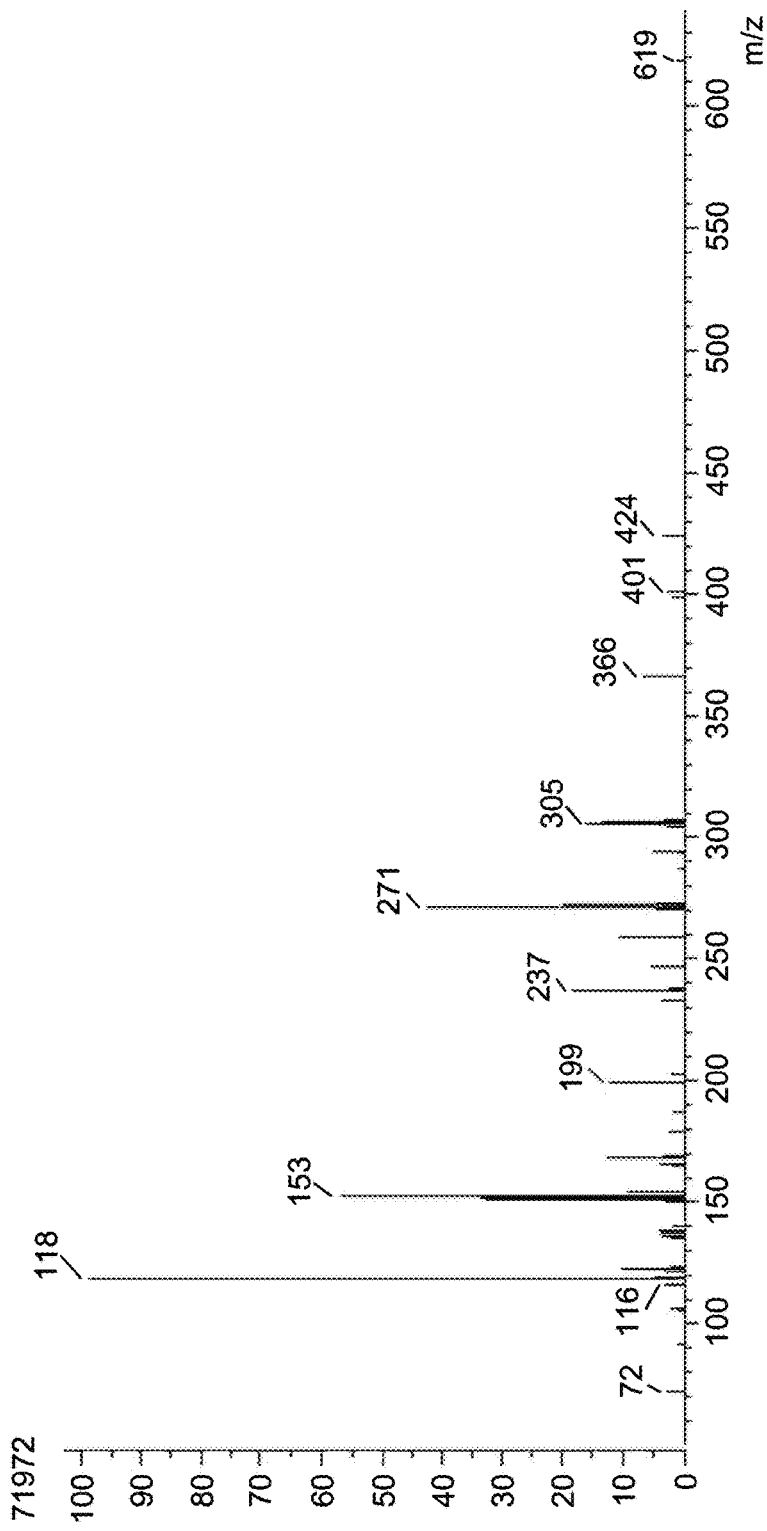

FIG. 29A-B. Metformin threoninate. FAB$^+$ (FIG. 29A) and FAB− (FIG. 29B) mass spectra.

Figure 30:
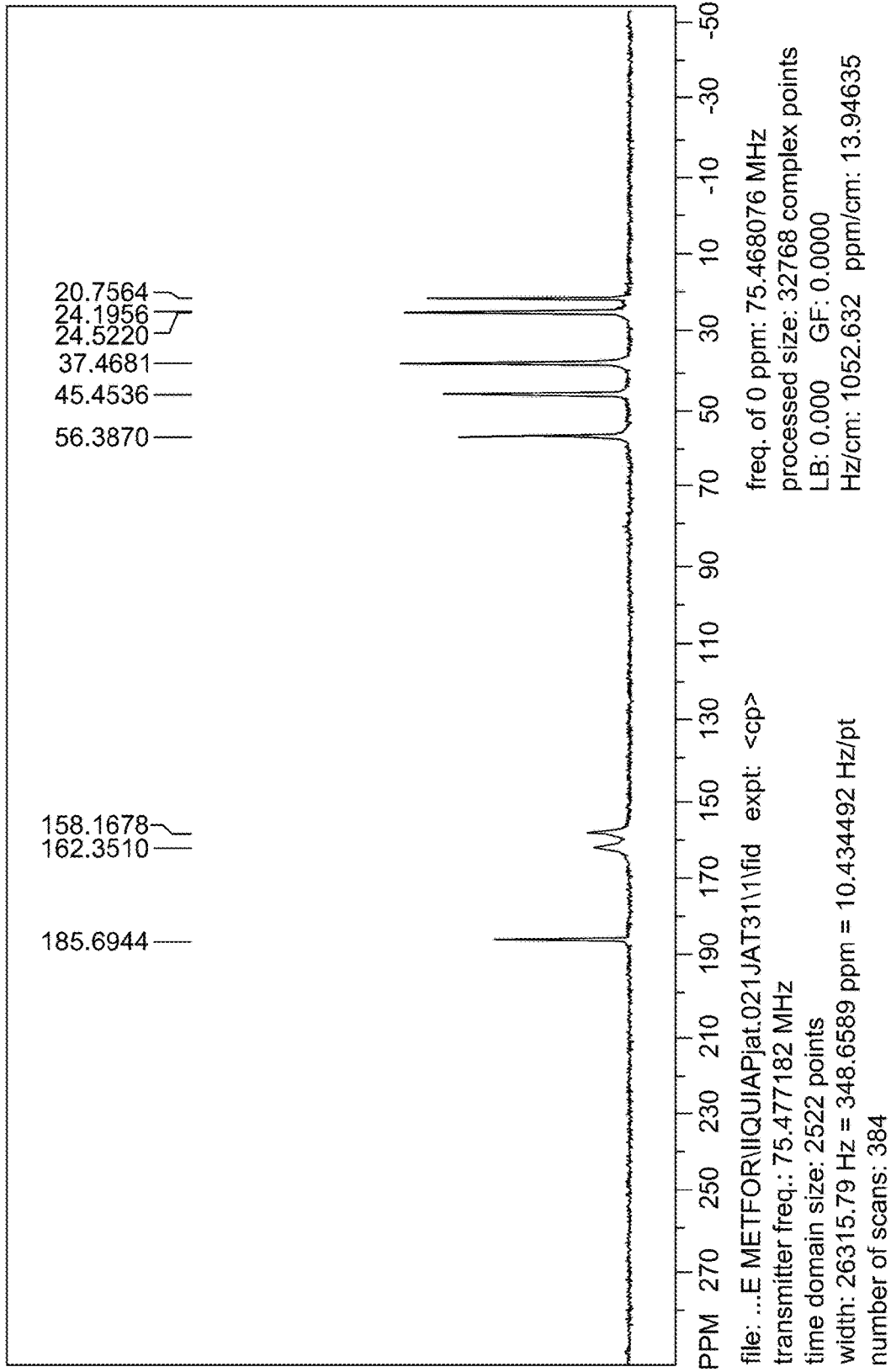

FIG. 30. Metformin leucinate. Solid-state $^{13}$C nuclear magnetic resonance spectrum.

Figure 31:
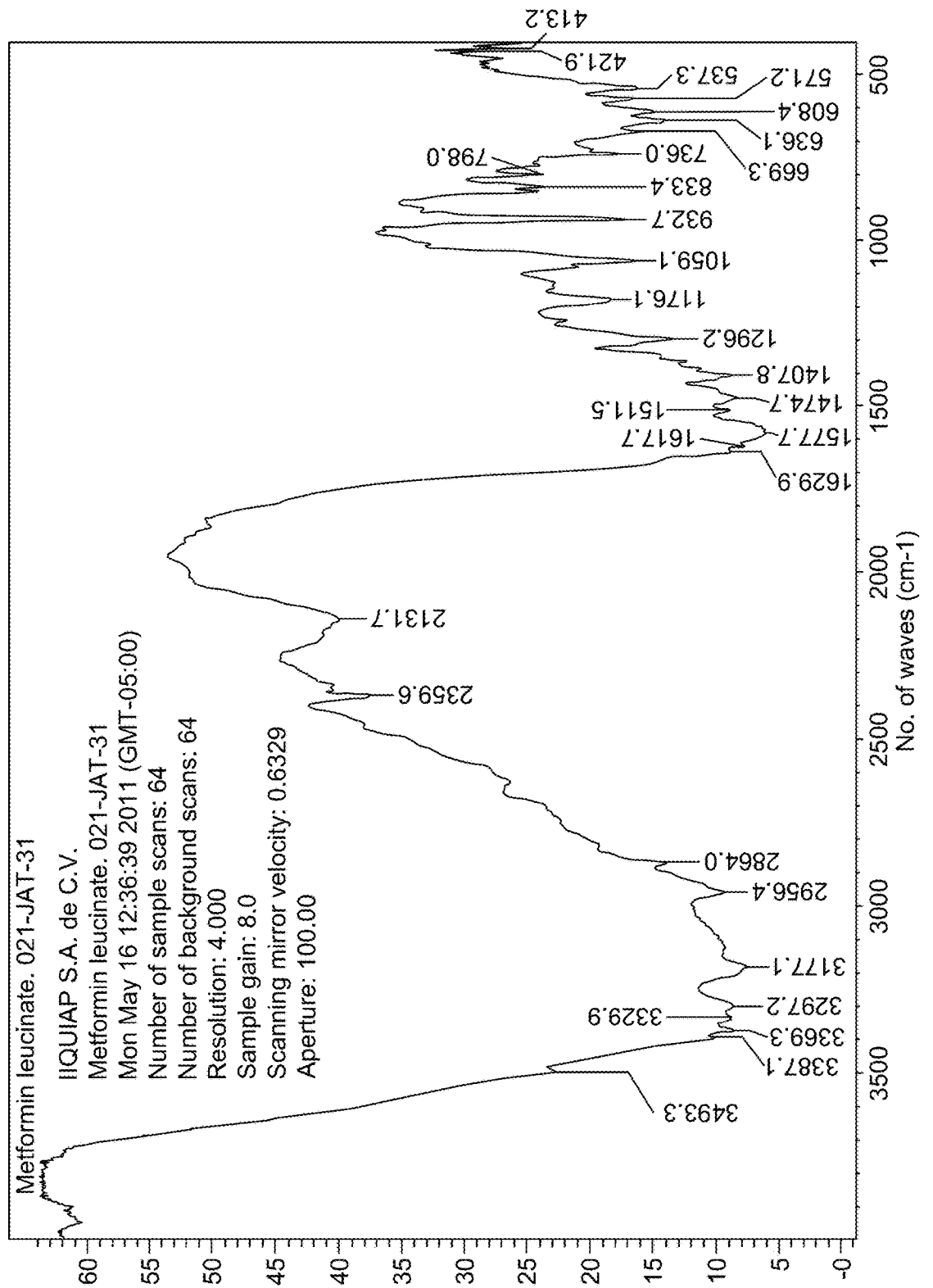

FIG. 31. Metformin leucinate. FT infrared spectrum.

Figure 32:
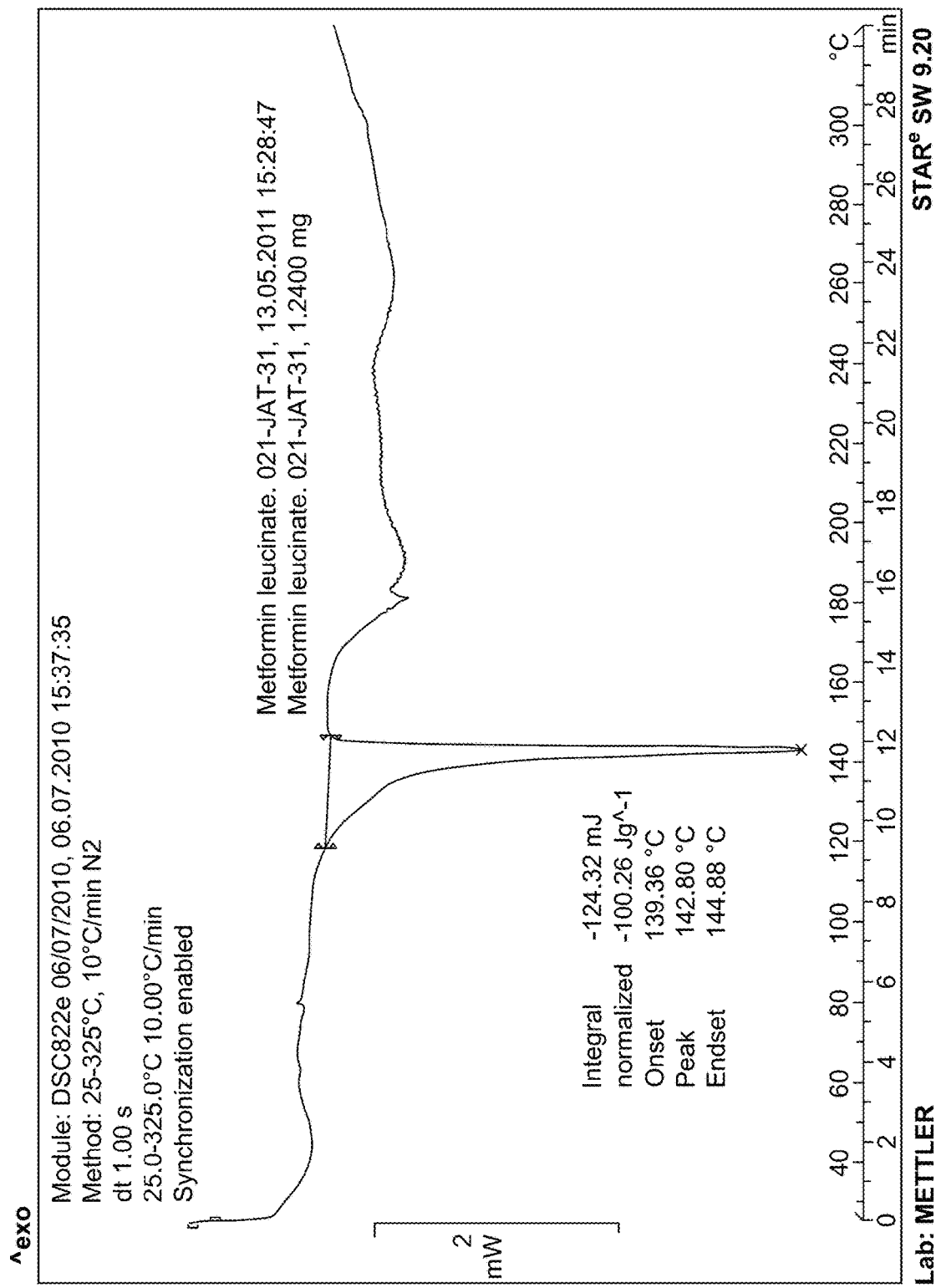

FIG. 32. Metformin leucinate. Differential scanning calorimetry (DSC).

Figure 33A:
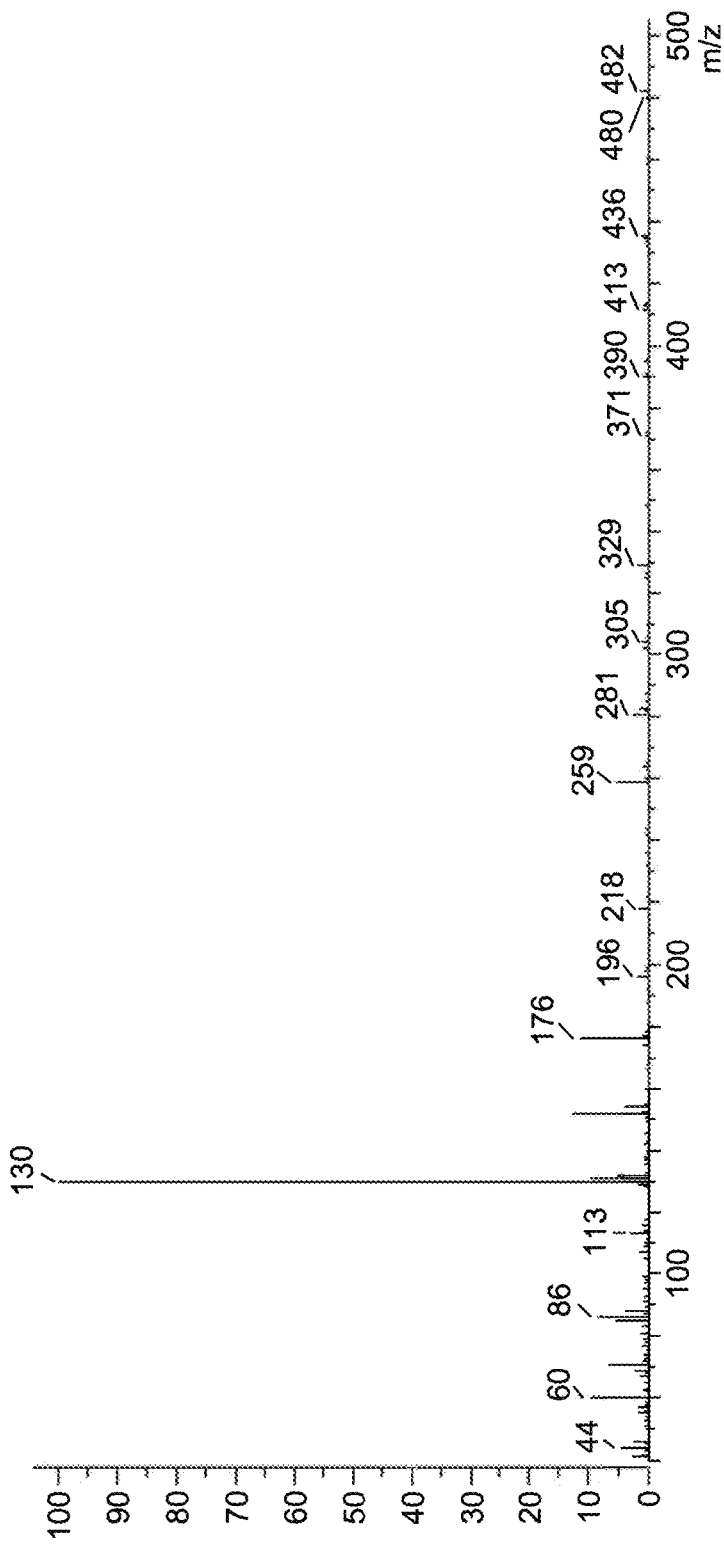
Figure 33B:
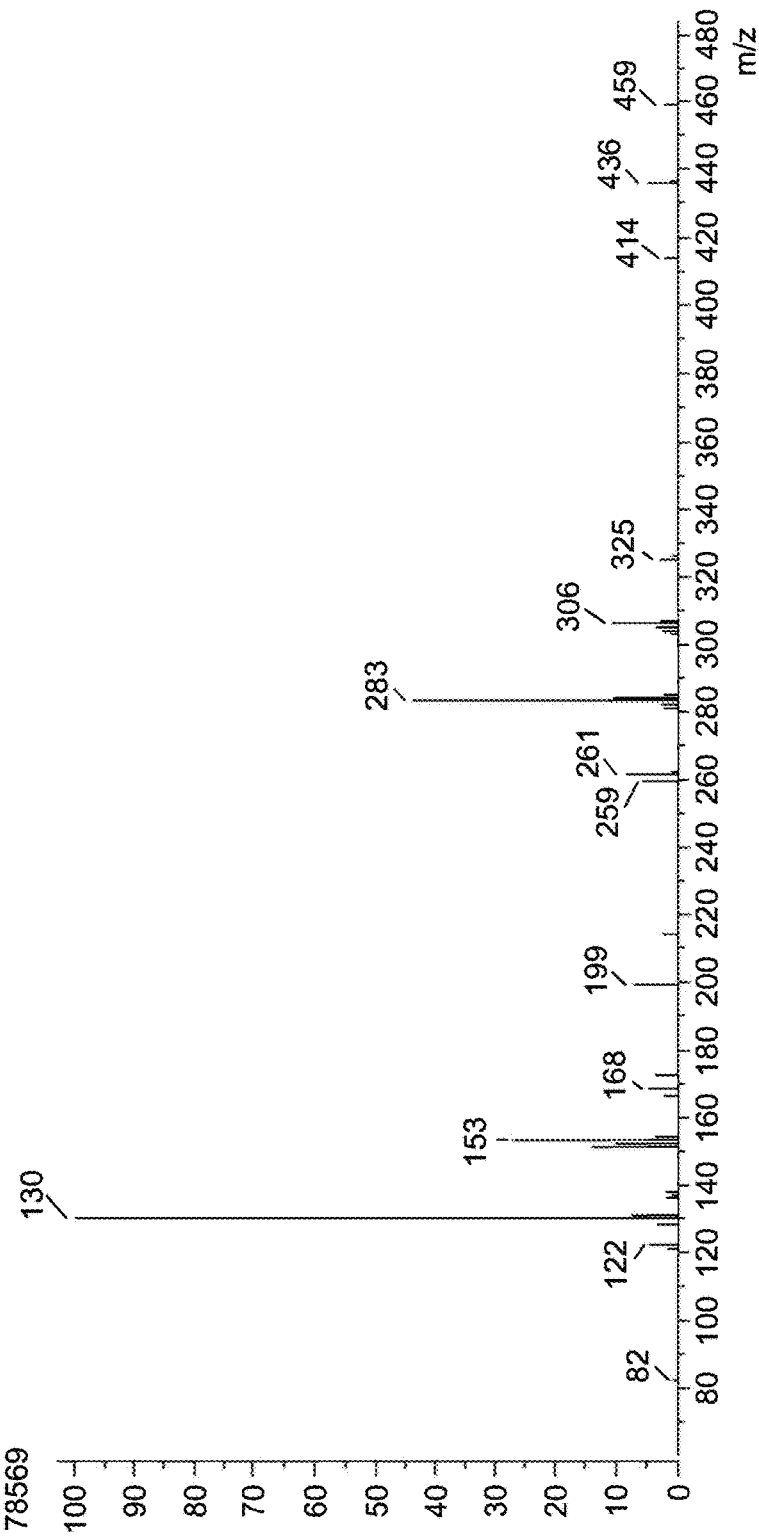

FIG. 33A-B. Metformin leucinate. FAB$^+$ (FIG. 33A) and FAB− (FIG. 33B) mass spectra.

Figure 34:
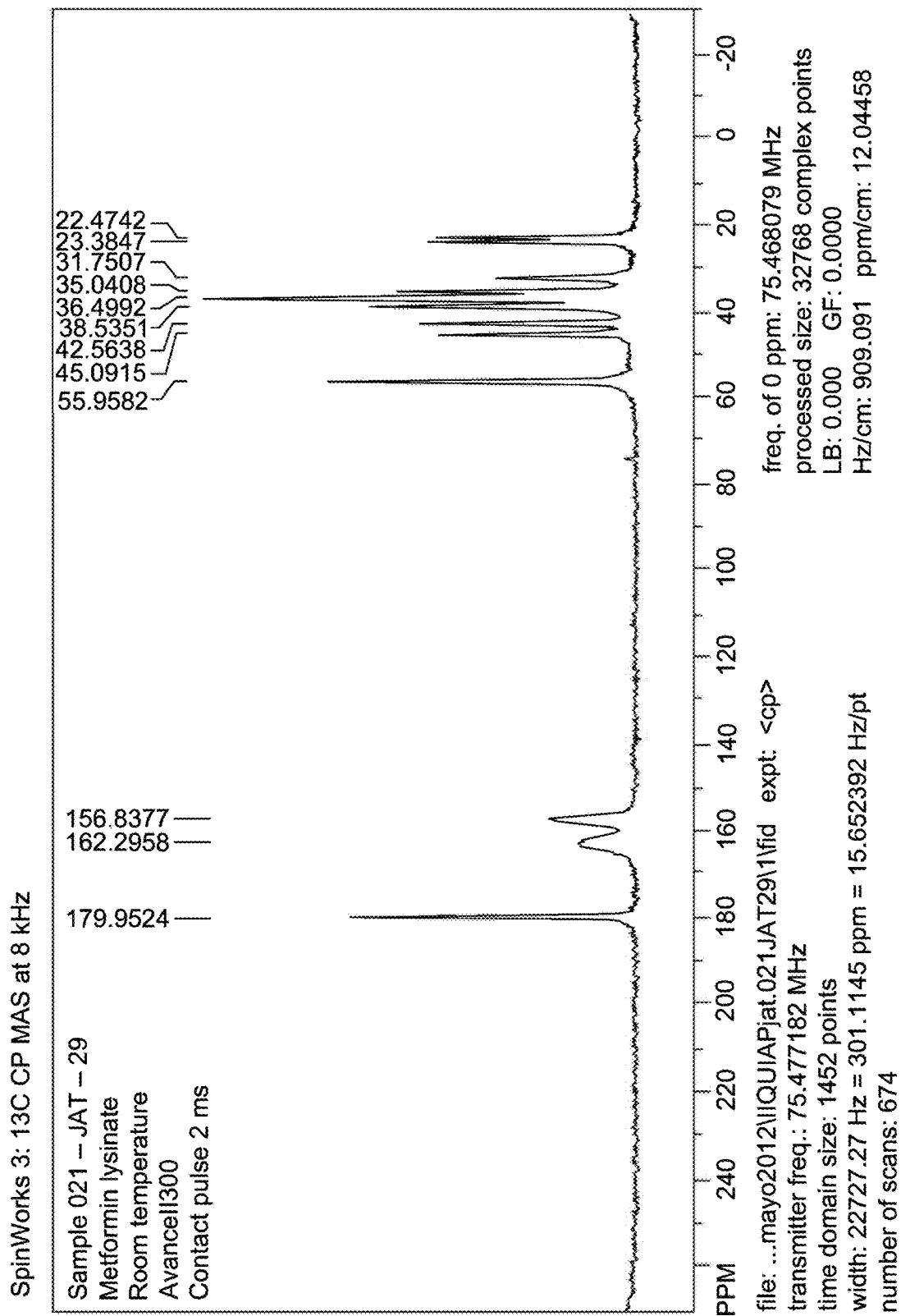

FIG. 34. Metformin lysinate. Solid-state $^{13}$C nuclear magnetic resonance spectrum.

Figure 35:
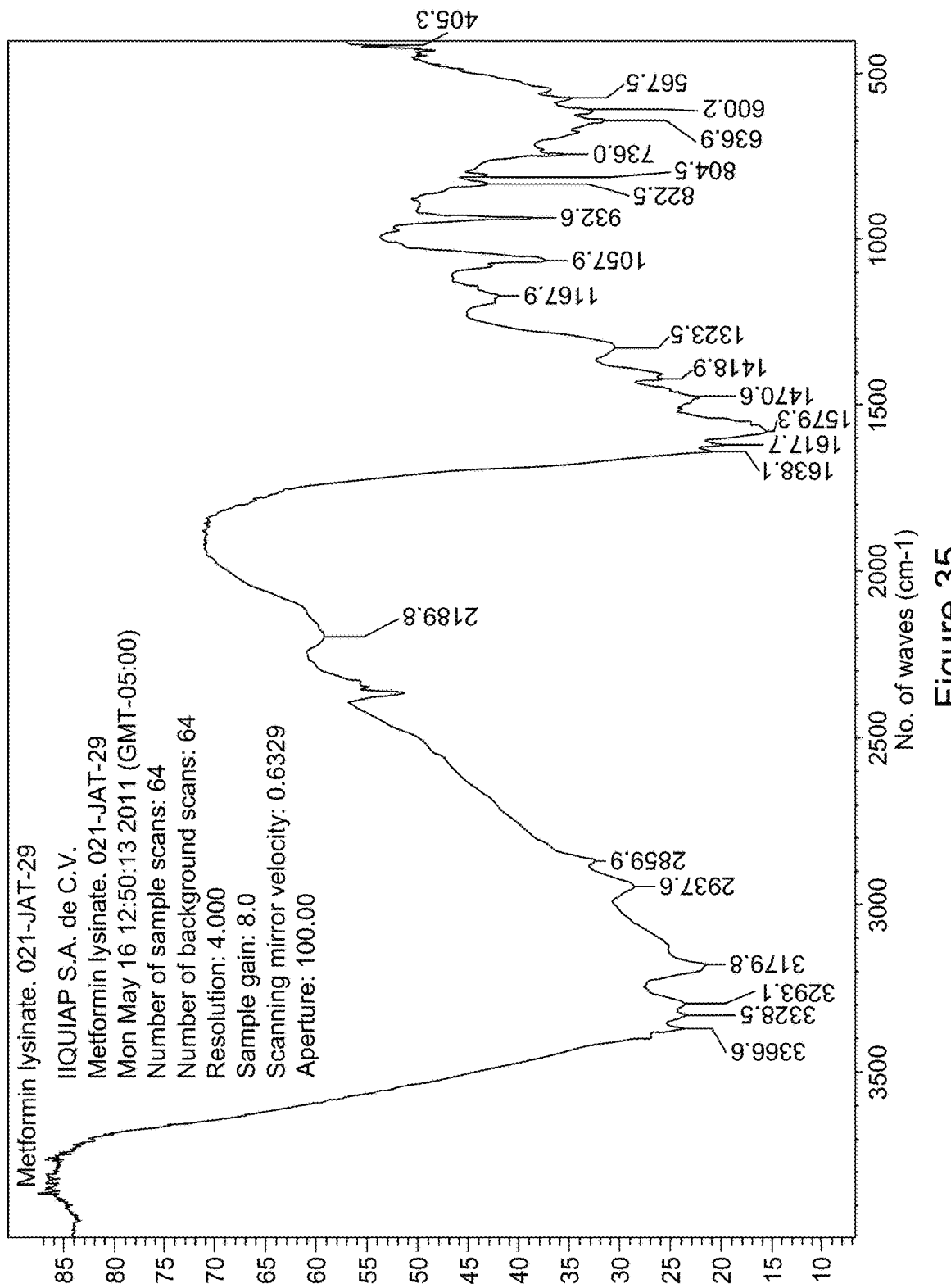

FIG. 35. Metformin lysinate. FT infrared spectrum.

Figure 36:
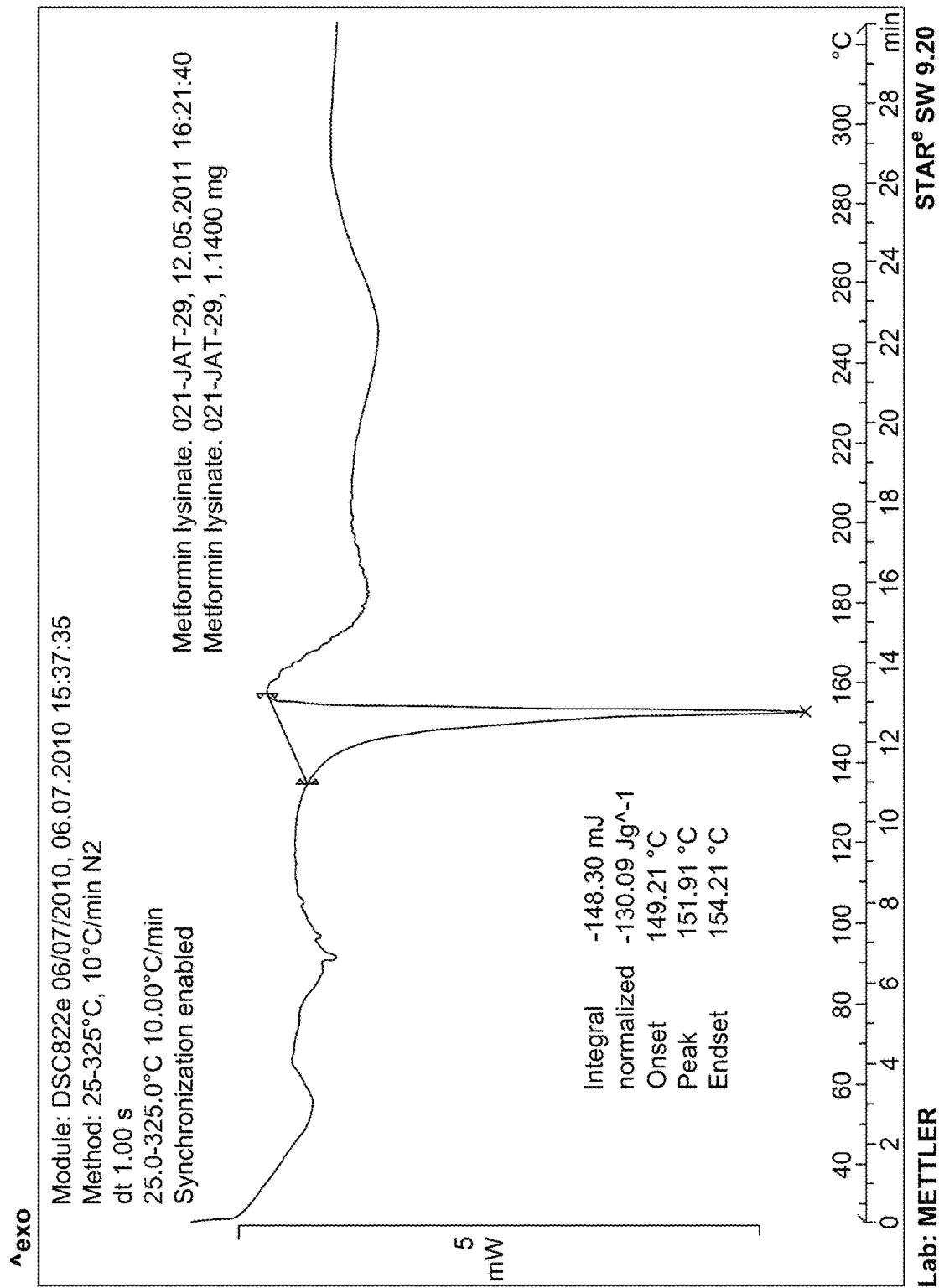

FIG. 36. Metformin lysinate. Differential scanning calorimetry (DSC).

Figure 37A:
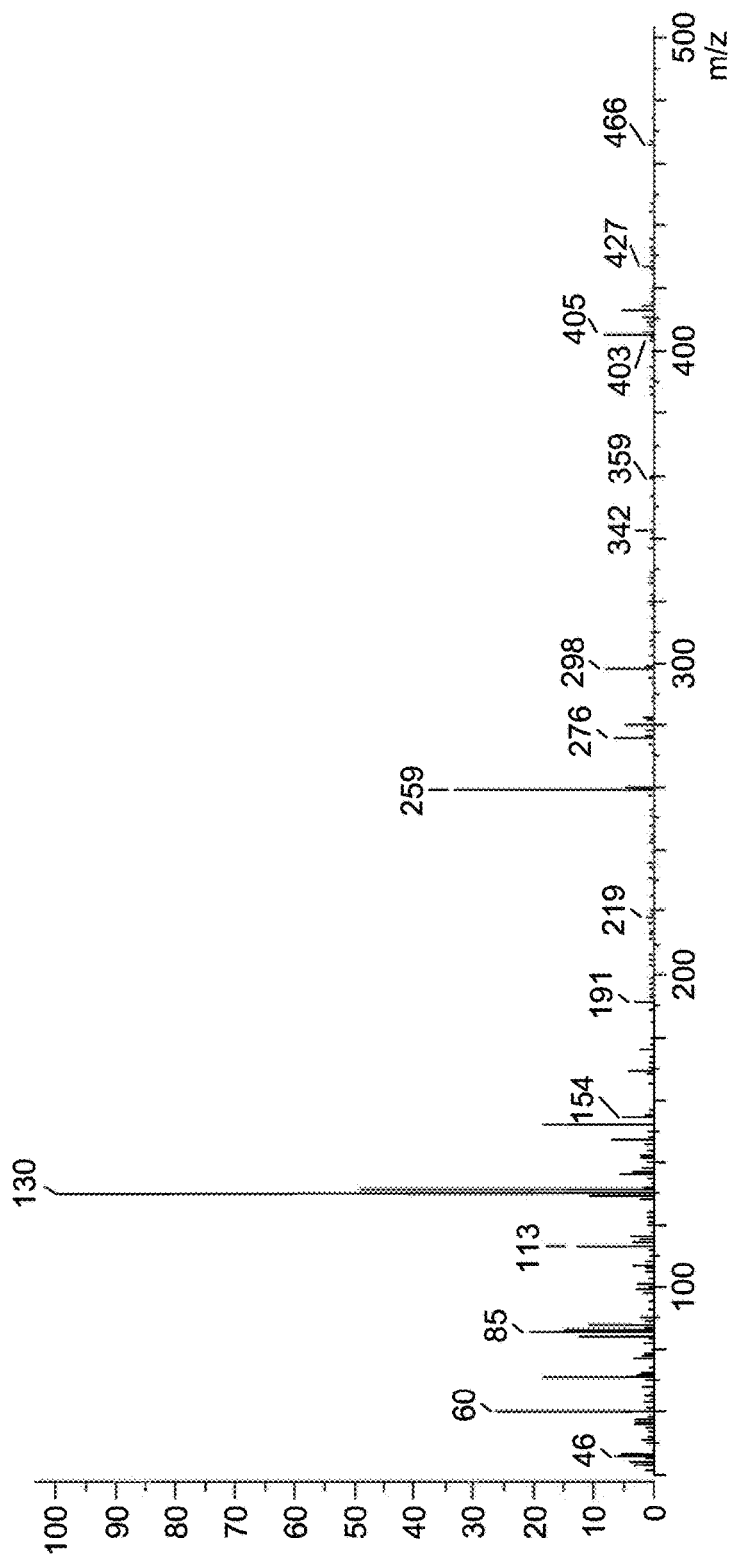
Figure 37B:
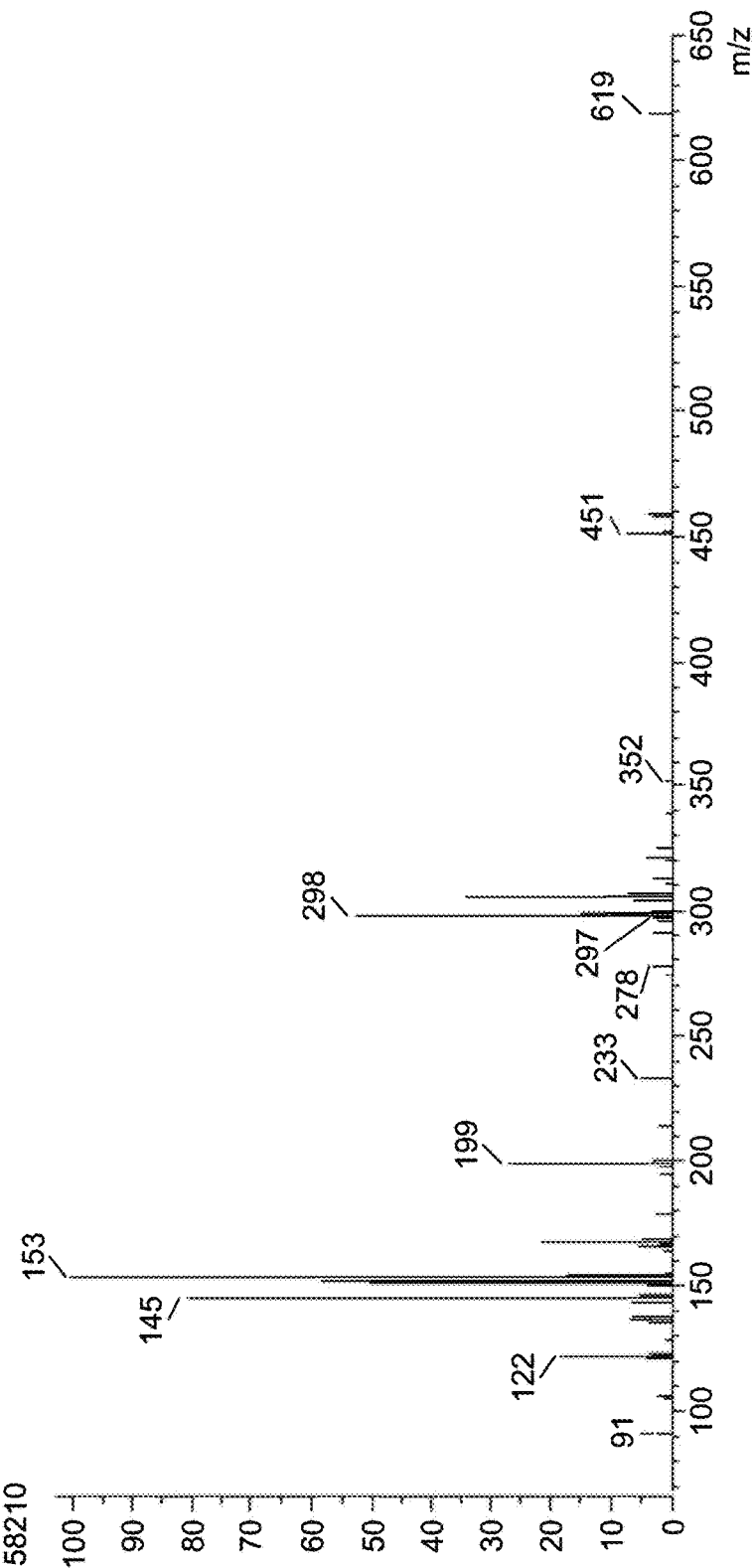

FIG. 37A-B. Metformin lysinate. FAB$^+$ (FIG. 37A) and FAB− (FIG. 37B) mass spectra.

Figure 38:
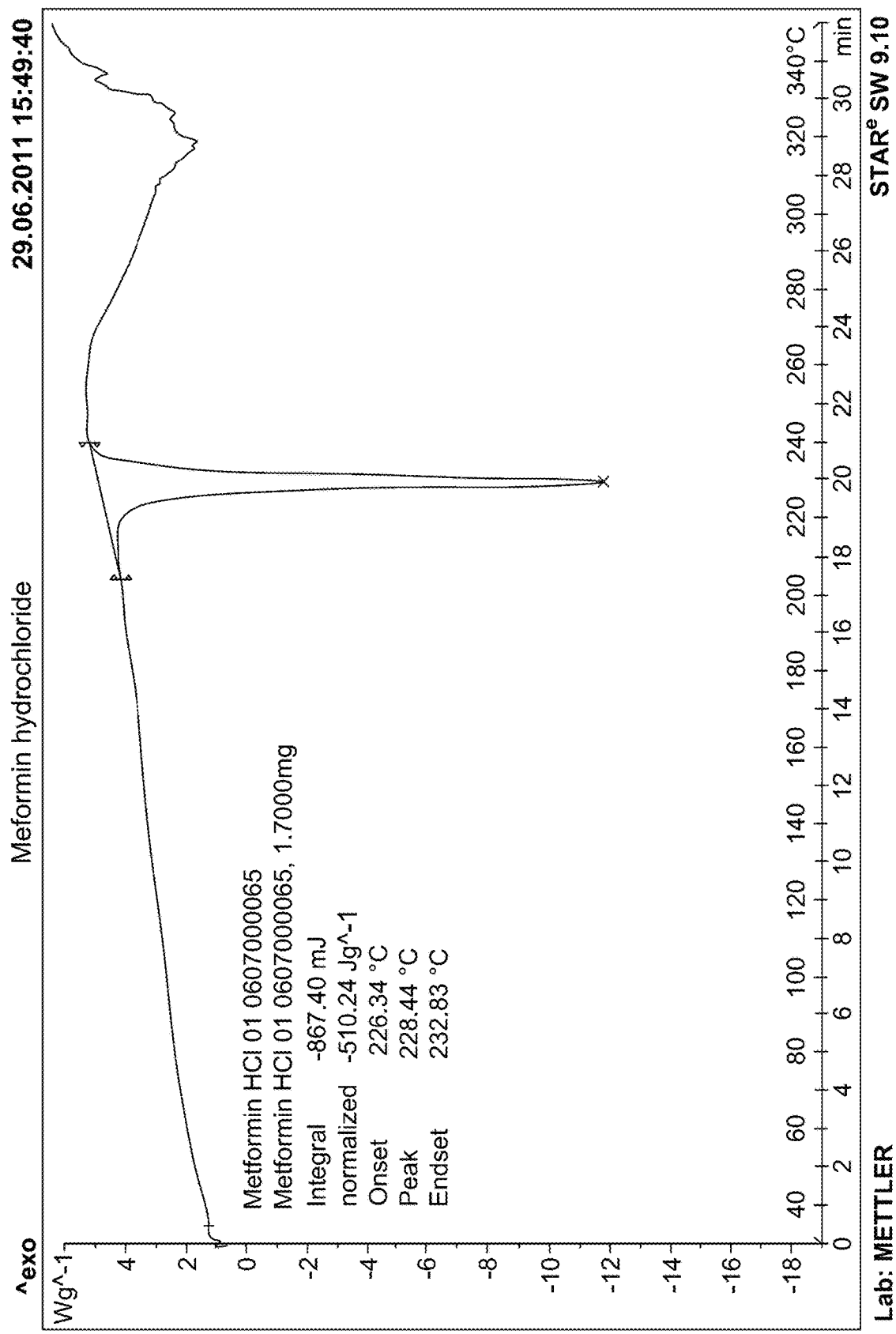

FIG. 38. Metformin hydrochloride. Differential scanning calorimetry (DSC).

Figure 39:
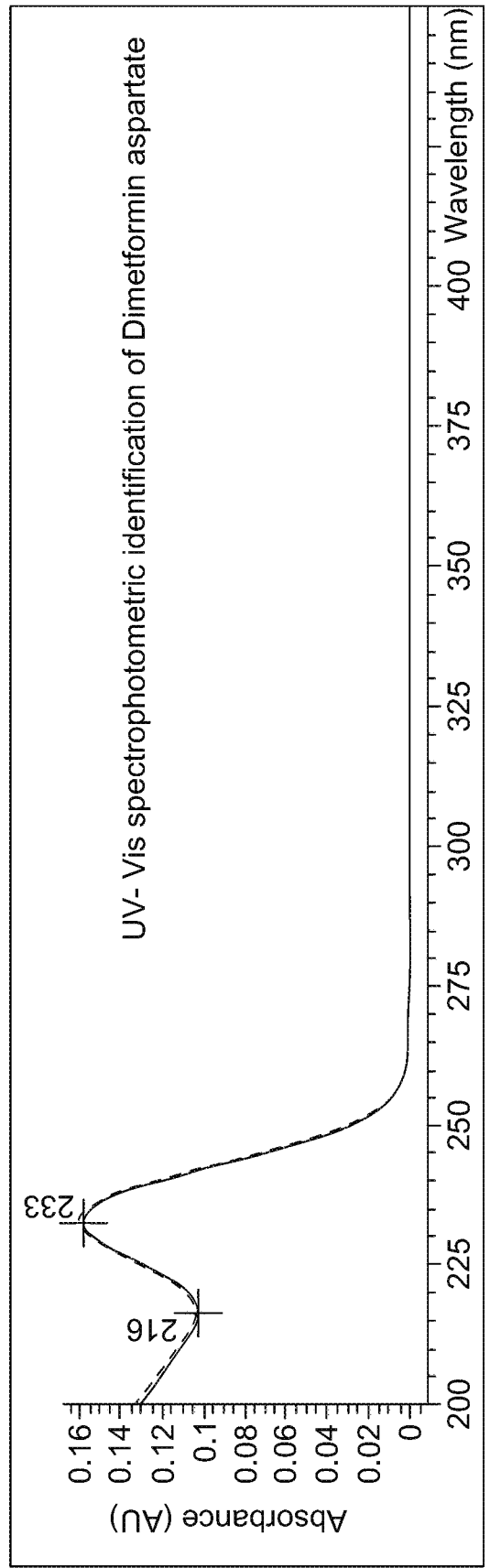

FIG. 39. Dimetformin aspartate identity through UV-Vis.

Figure 40:
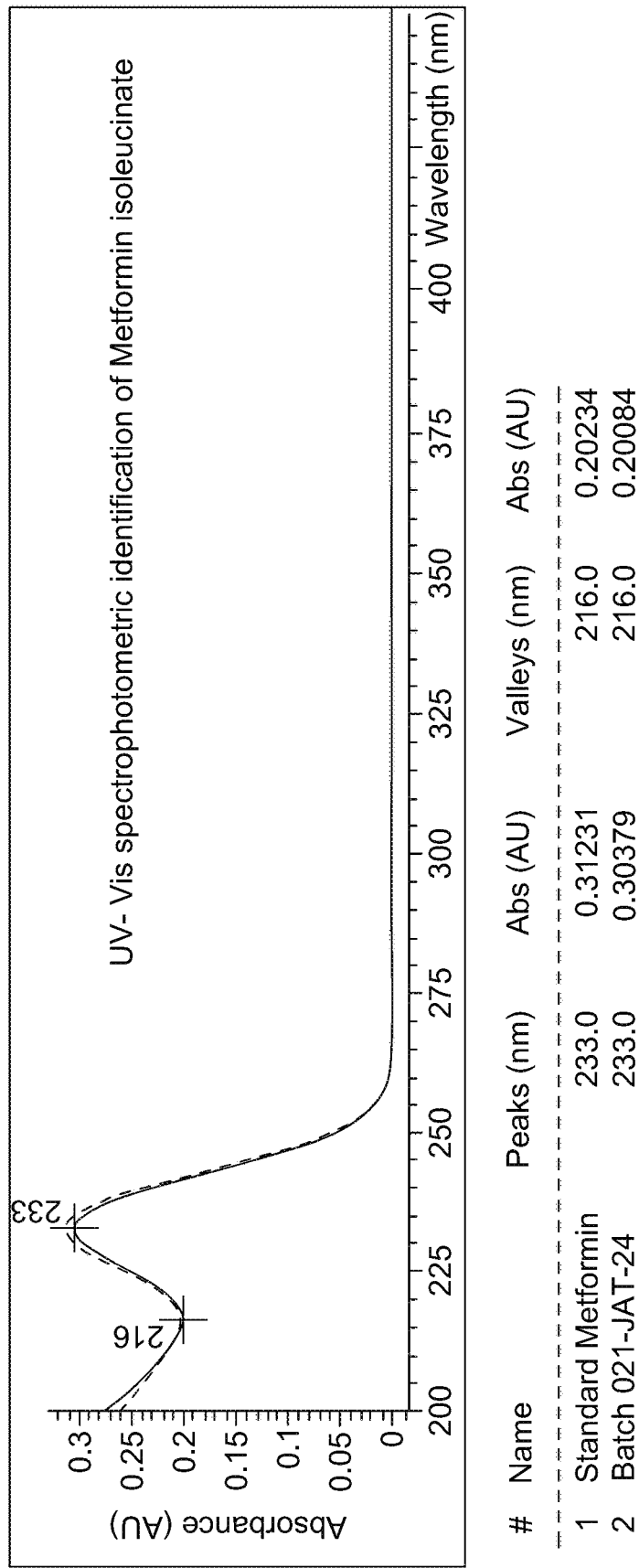

FIG. 40. Metformin isoleucinate identity through UV-Vis.

Figure 41:
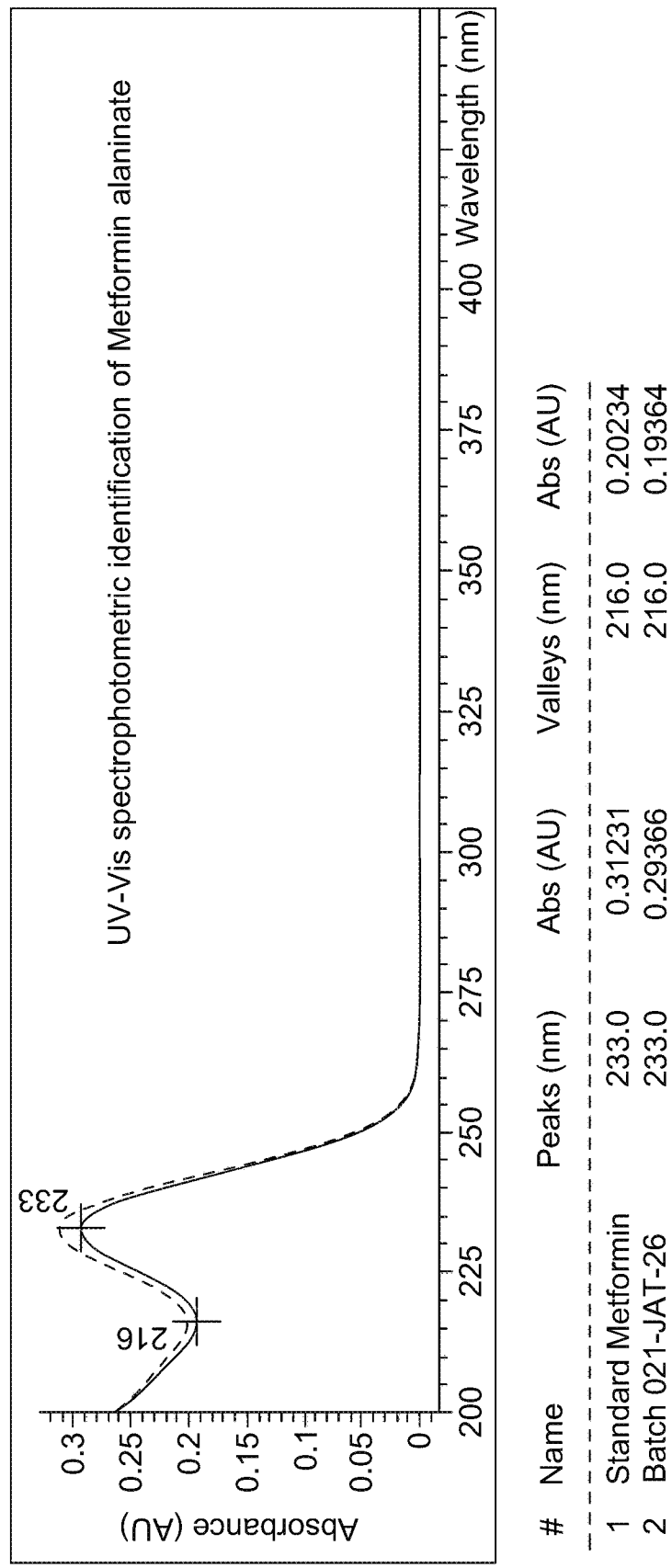

FIG. 41. Metformin alaninate identity through UV-Vis.

Figure 42:
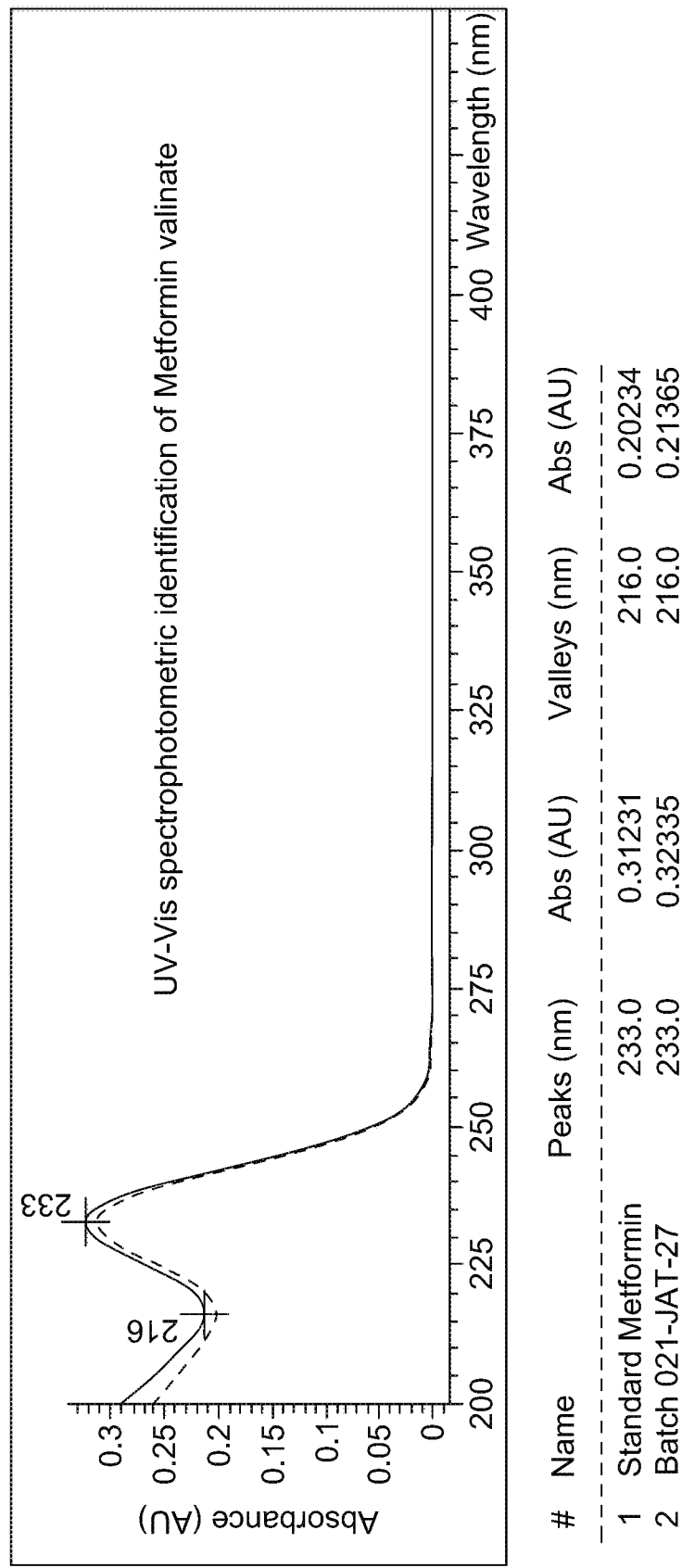

FIG. 42. Metformin valinate identity through UV-Vis.

Figure 43:
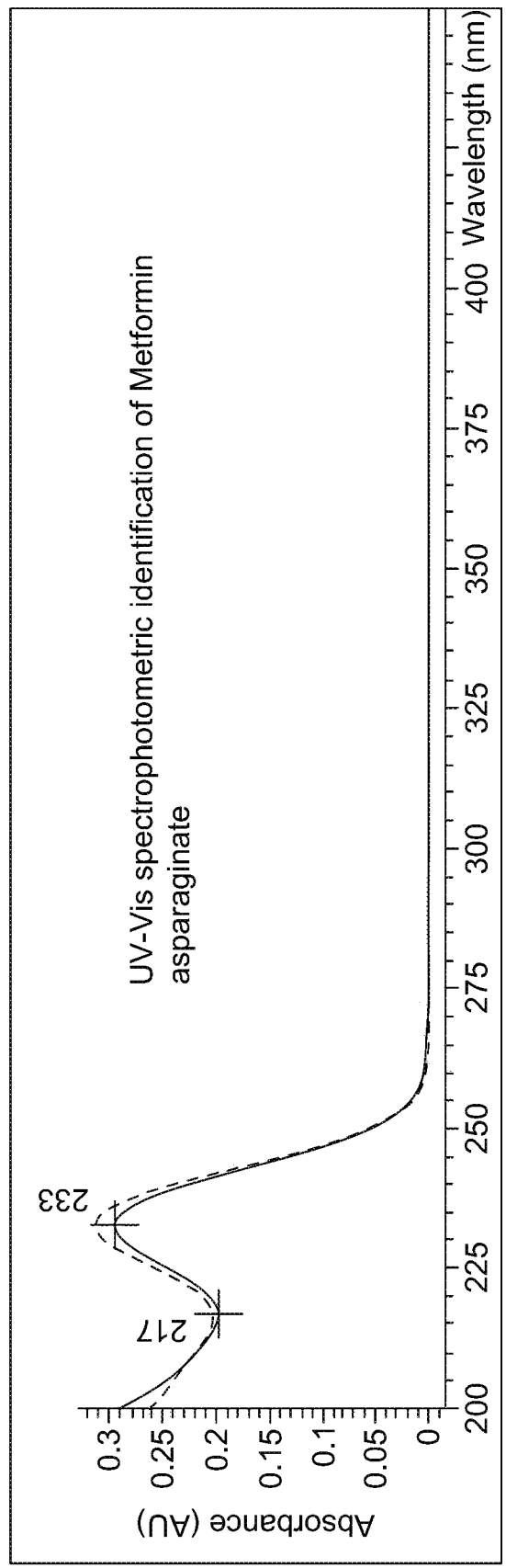

FIG. 43. Metformin asparaginate identity through UV-Vis.

Figure 44:
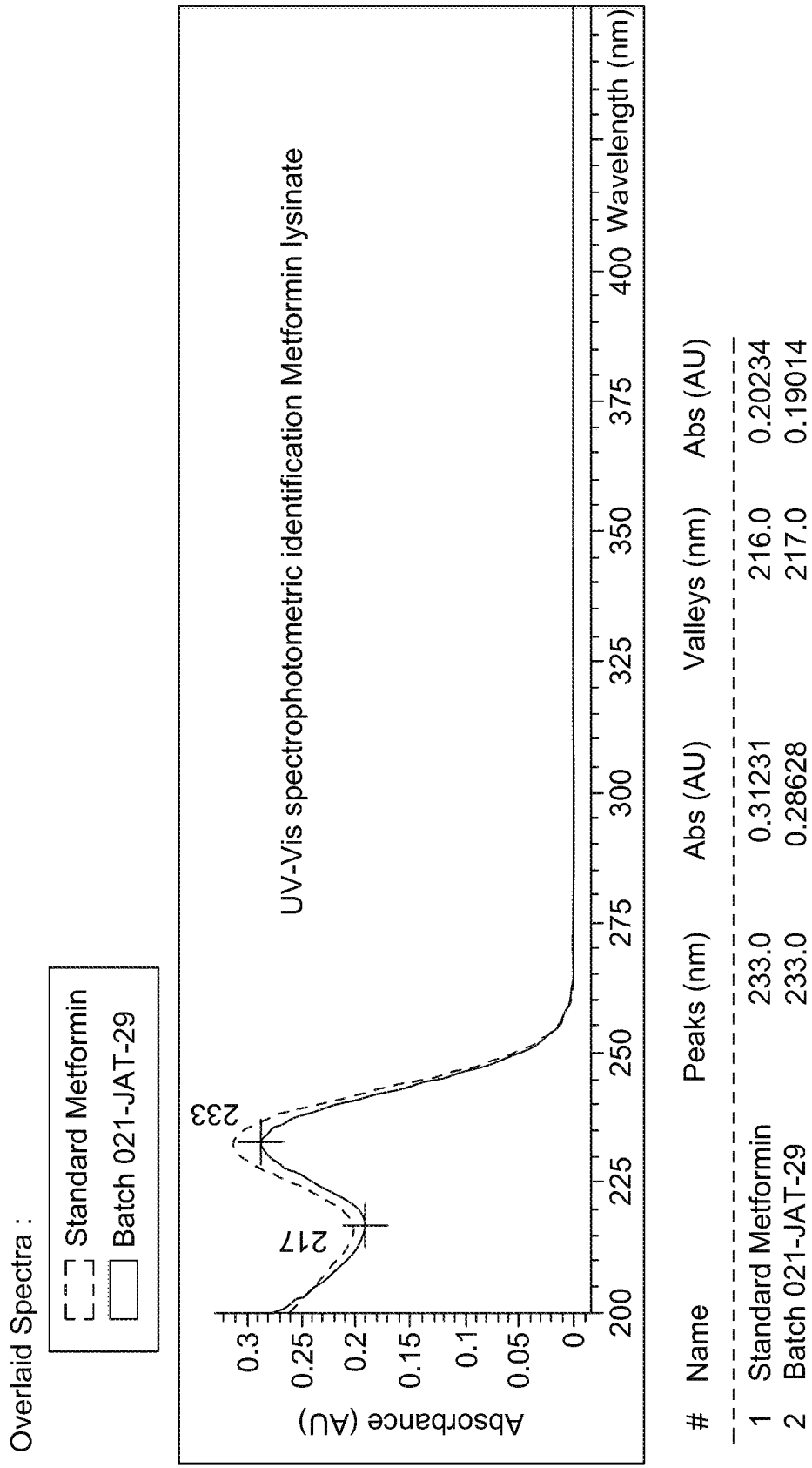

FIG. 44. Metformin lysinate identity through UV-Vis.

Figure 45:
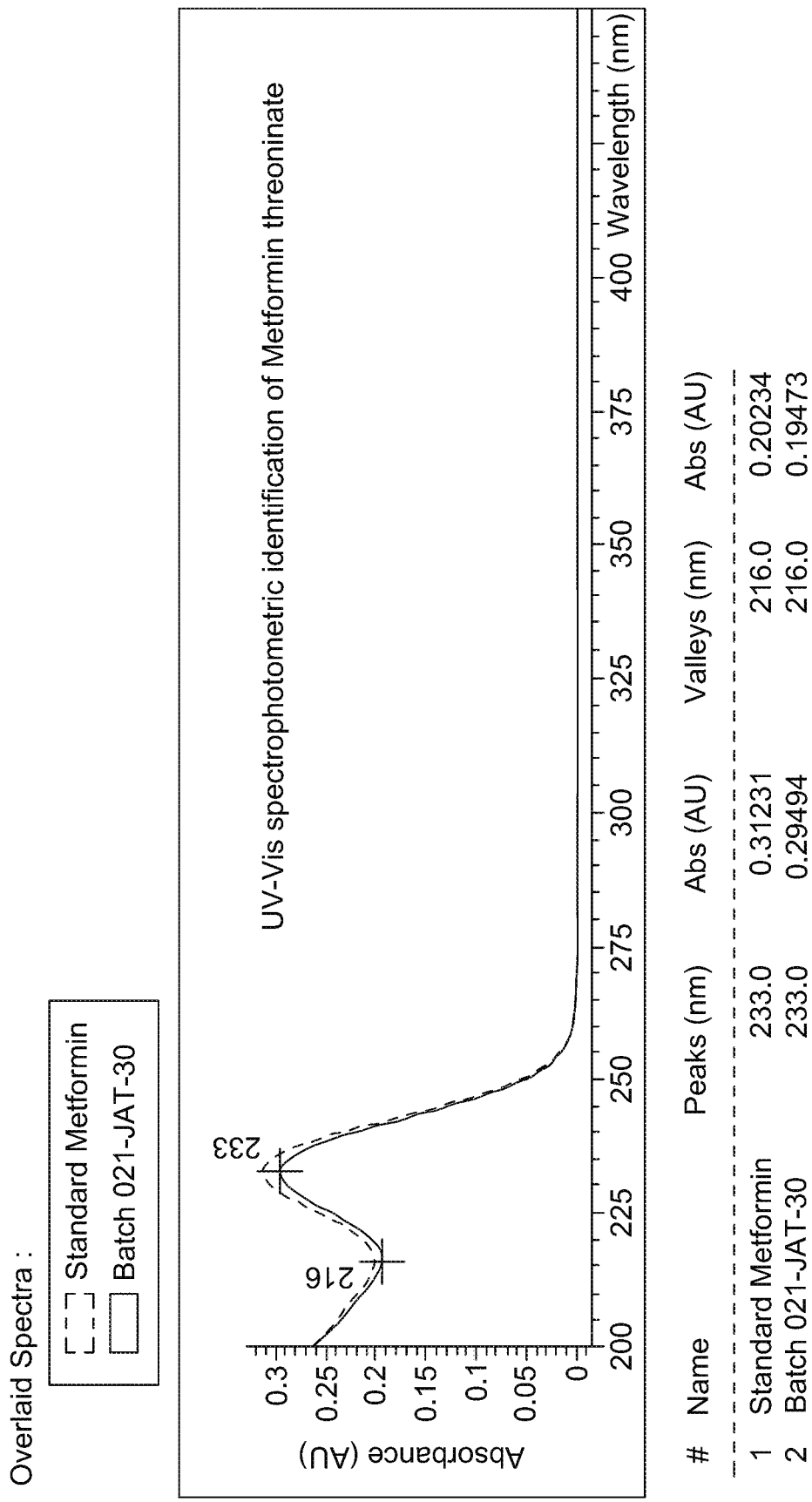

FIG. 45. Metformin threoninate identity through UV-Vis.

Figure 46:
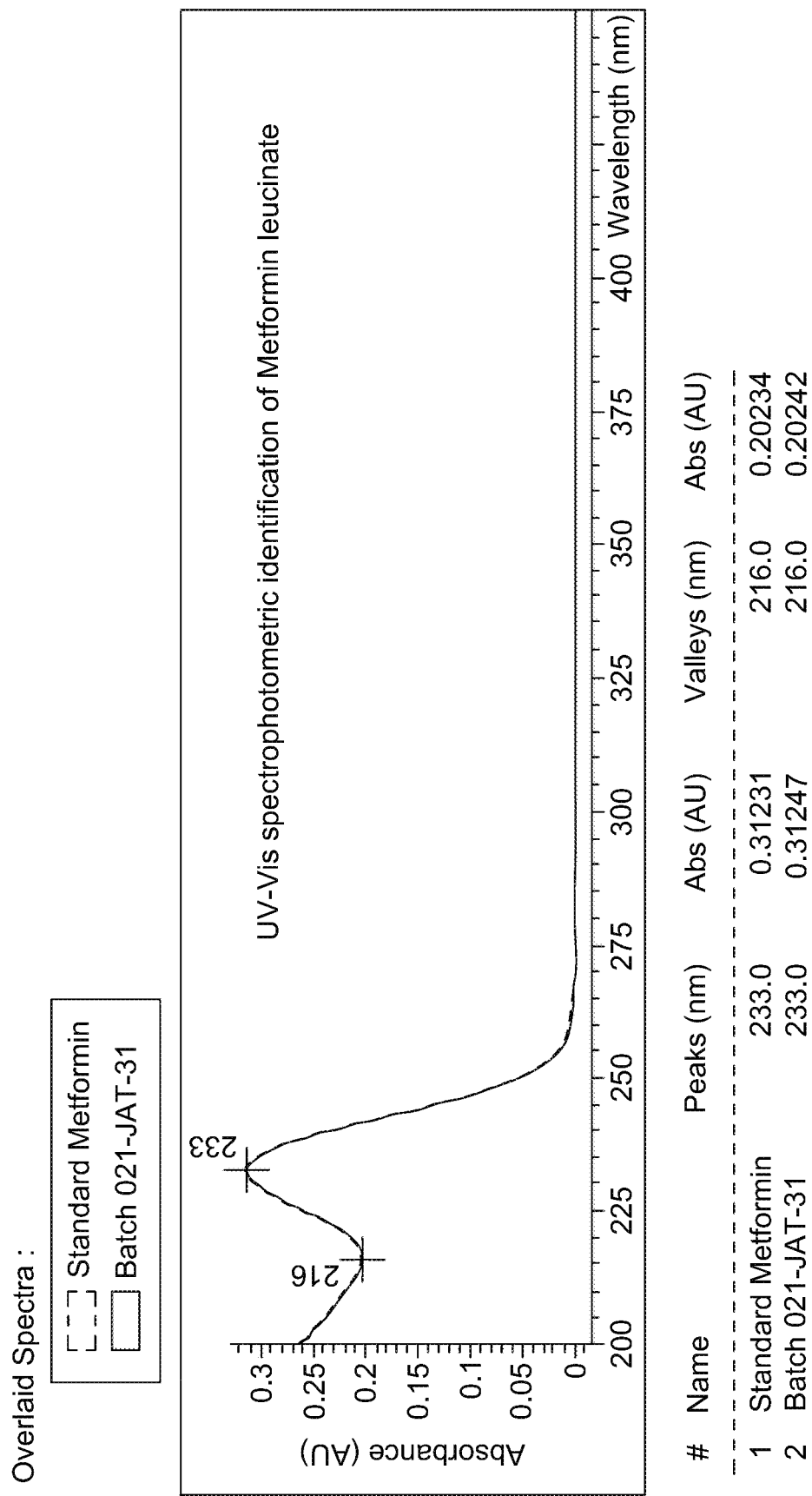

FIG. 46. Metformin leucinate identity through UV-Vis.

Figure 47:
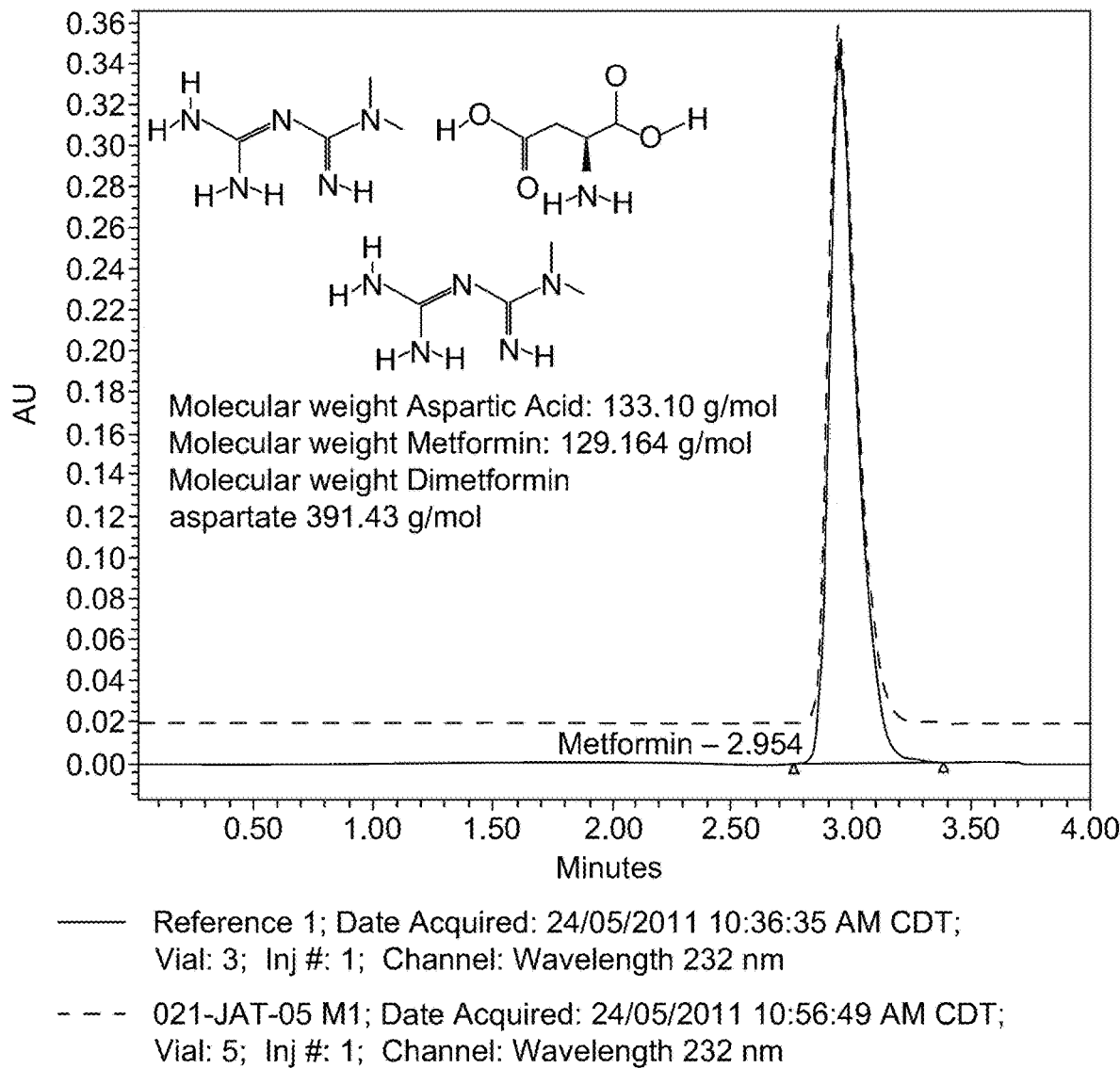

FIG. 47. Dimetformin aspartate identity through high-performance liquid chromatography.

Figure 48:
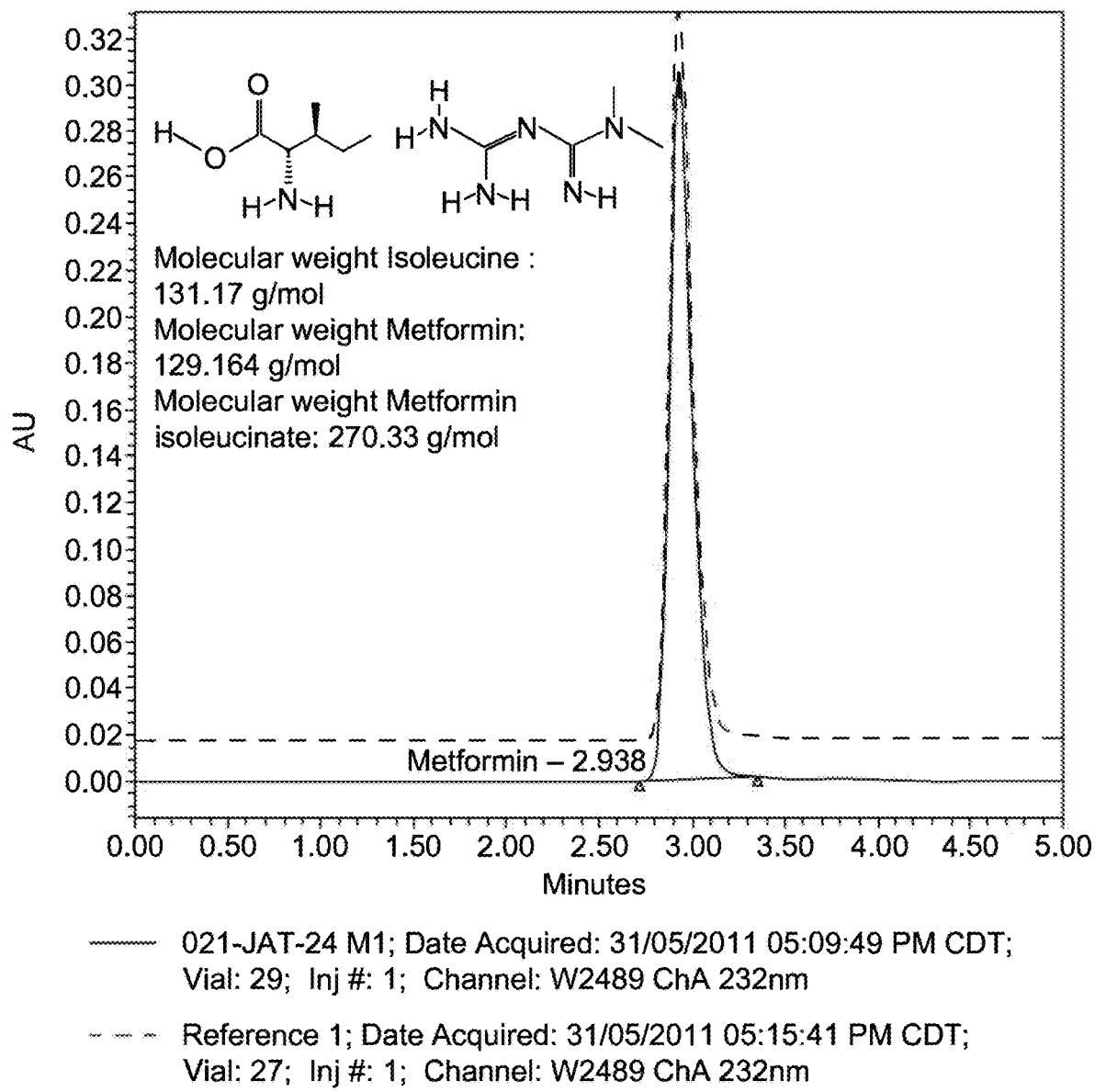

FIG. 48. Metformin isoleucinate identity through high-performance liquid chromatography.

Figure 49:
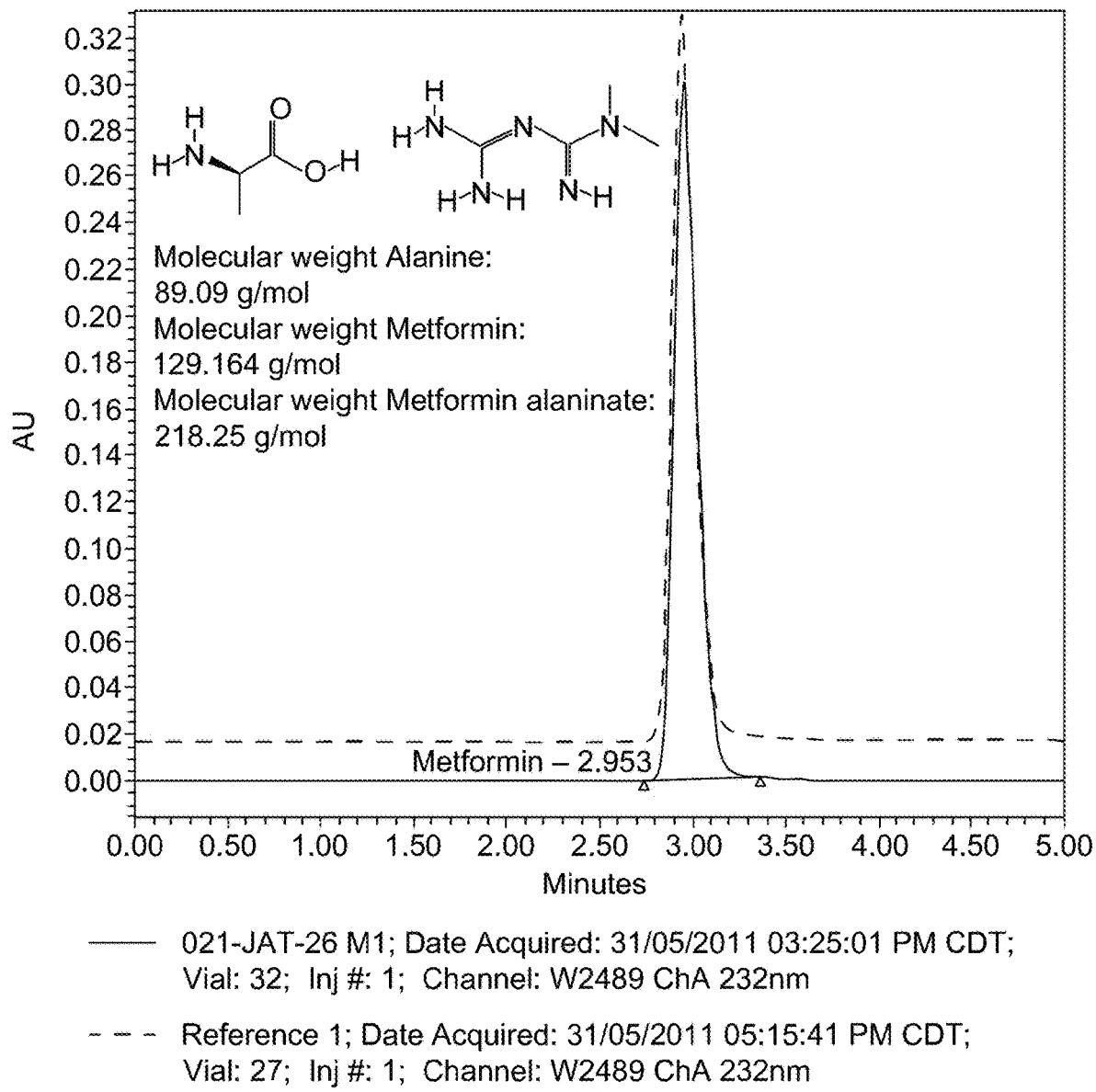

FIG. 49. Metformin alaninate identity through high-performance liquid chromatography.

Figure 50:
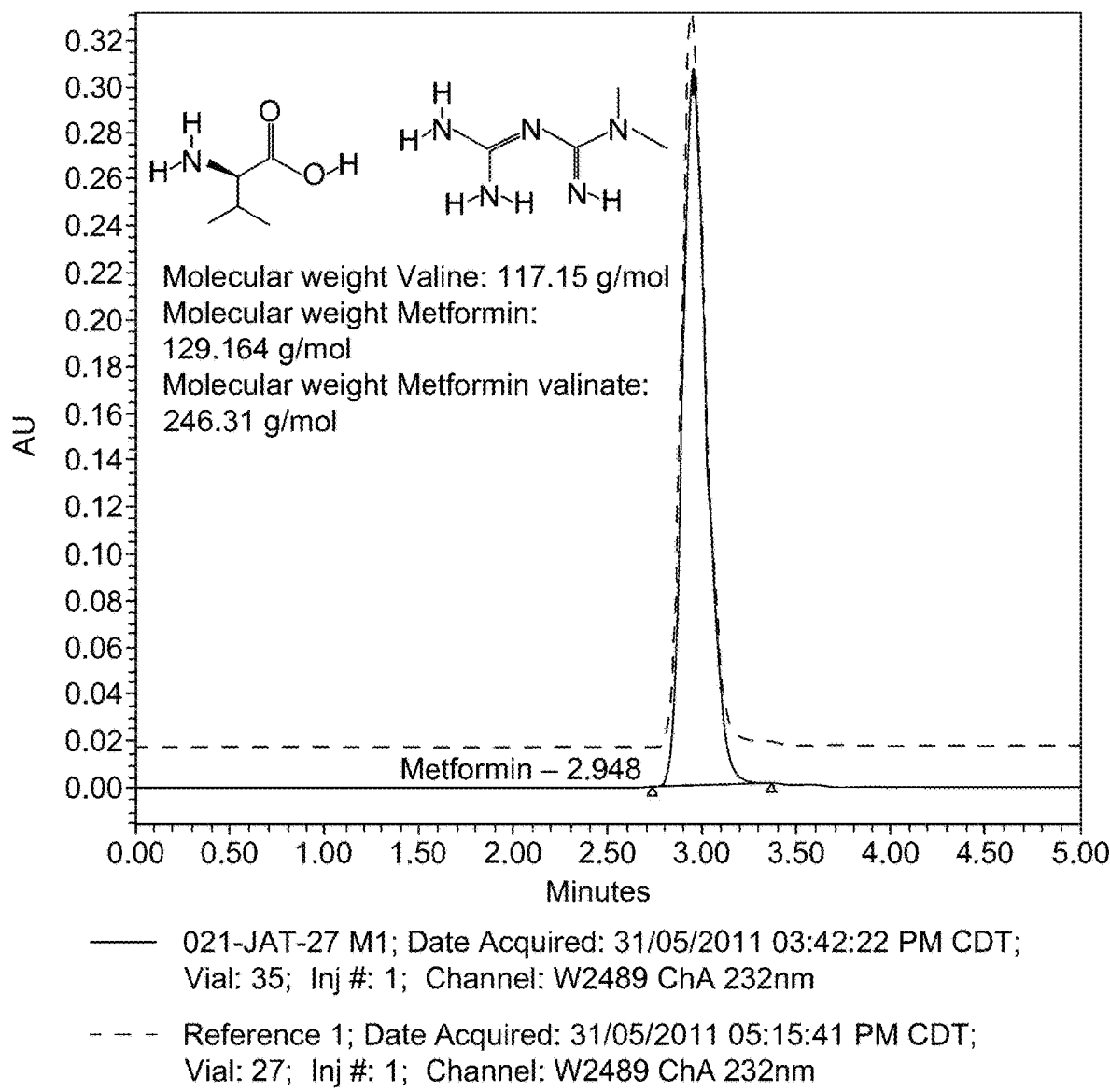

FIG. 50. Metformin valinate identity through high-performance liquid chromatography.

Figure 51:
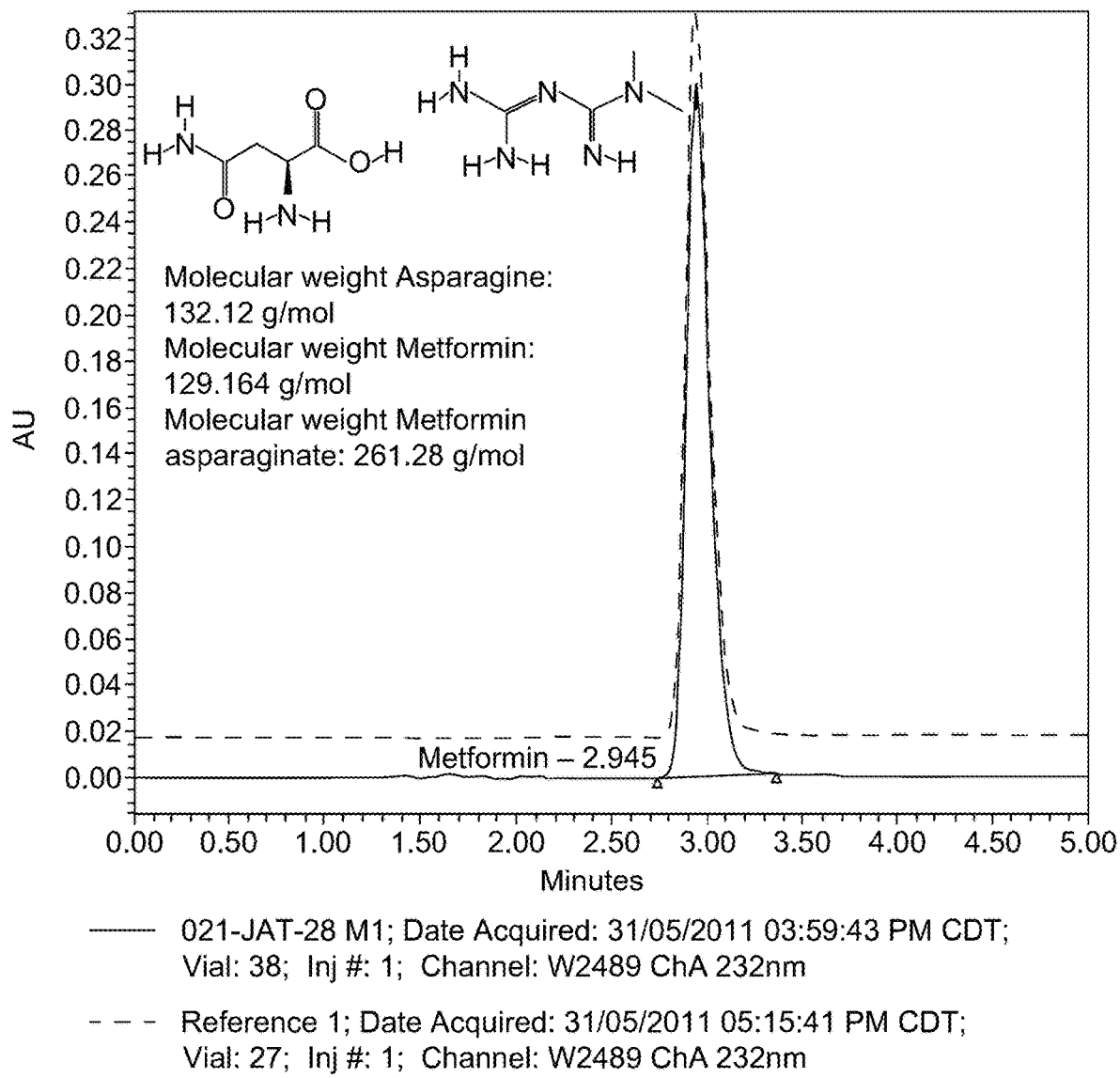

FIG. 51. Metformin asparaginate identity through high-performance liquid chromatography.

Figure 52:
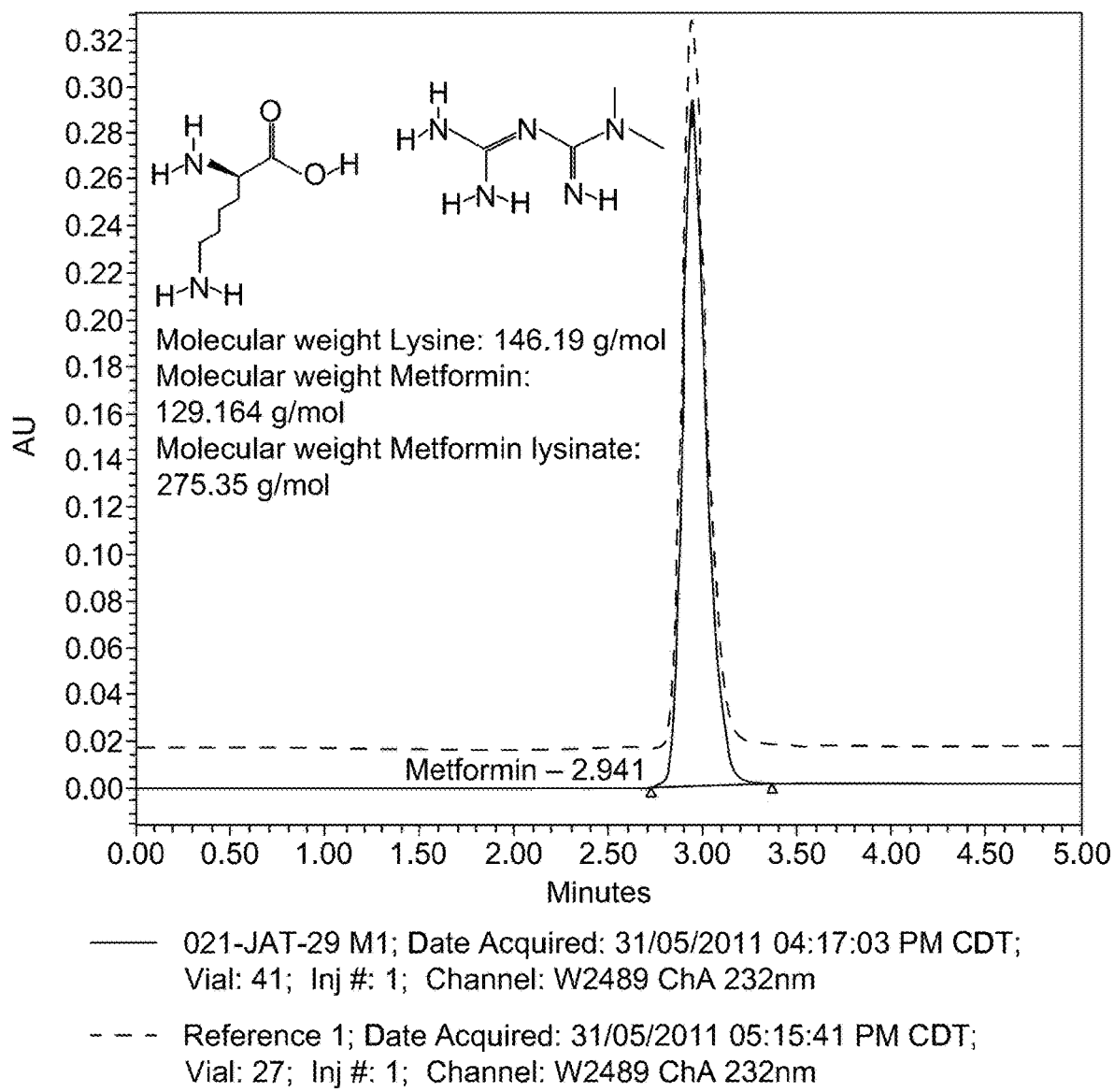

FIG. 52. Metformin lysinate identity.

Figure 53:
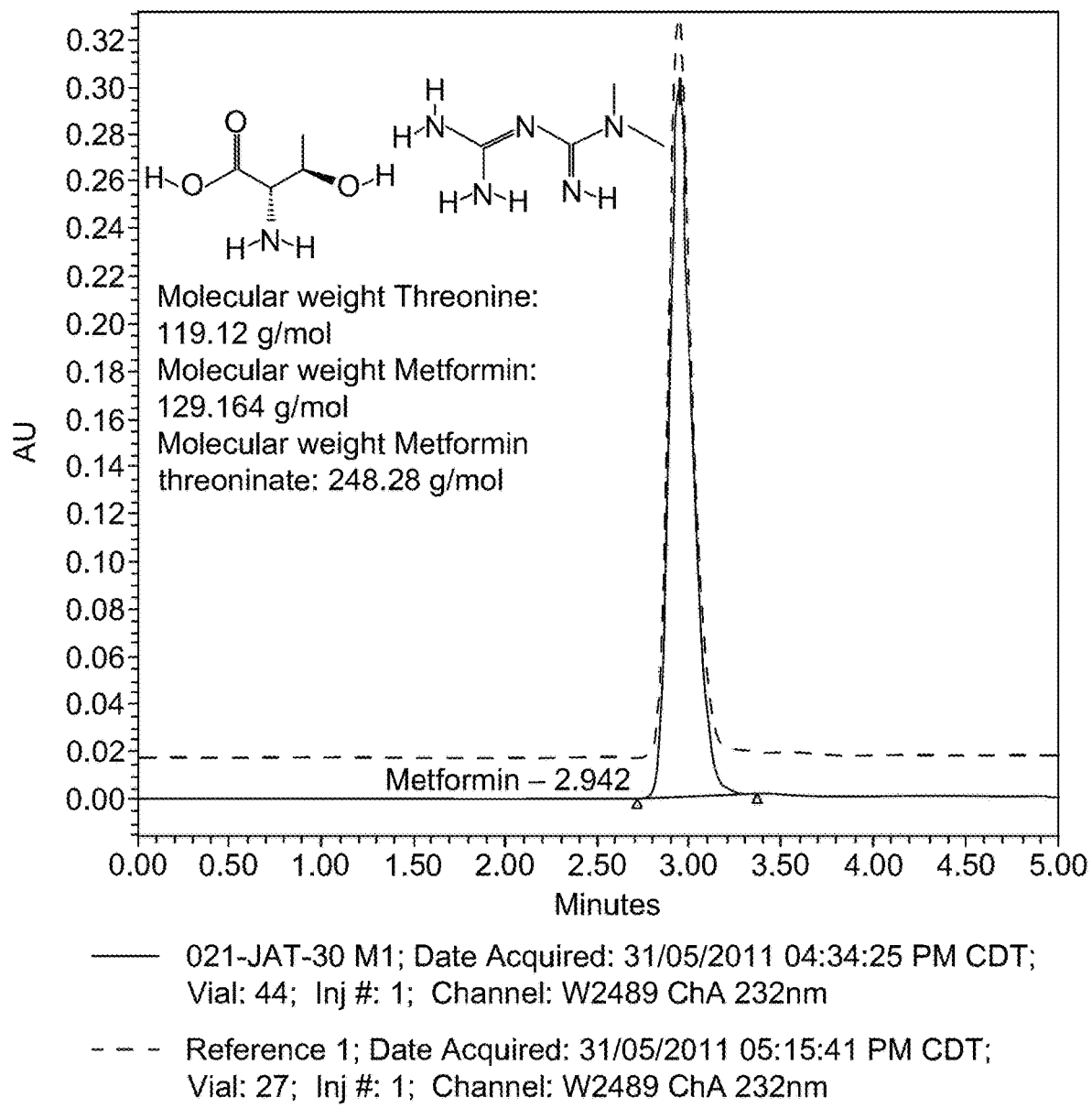

FIG. 53. Metformin threoninate identity through high-performance liquid chromatography.

Figure 54:
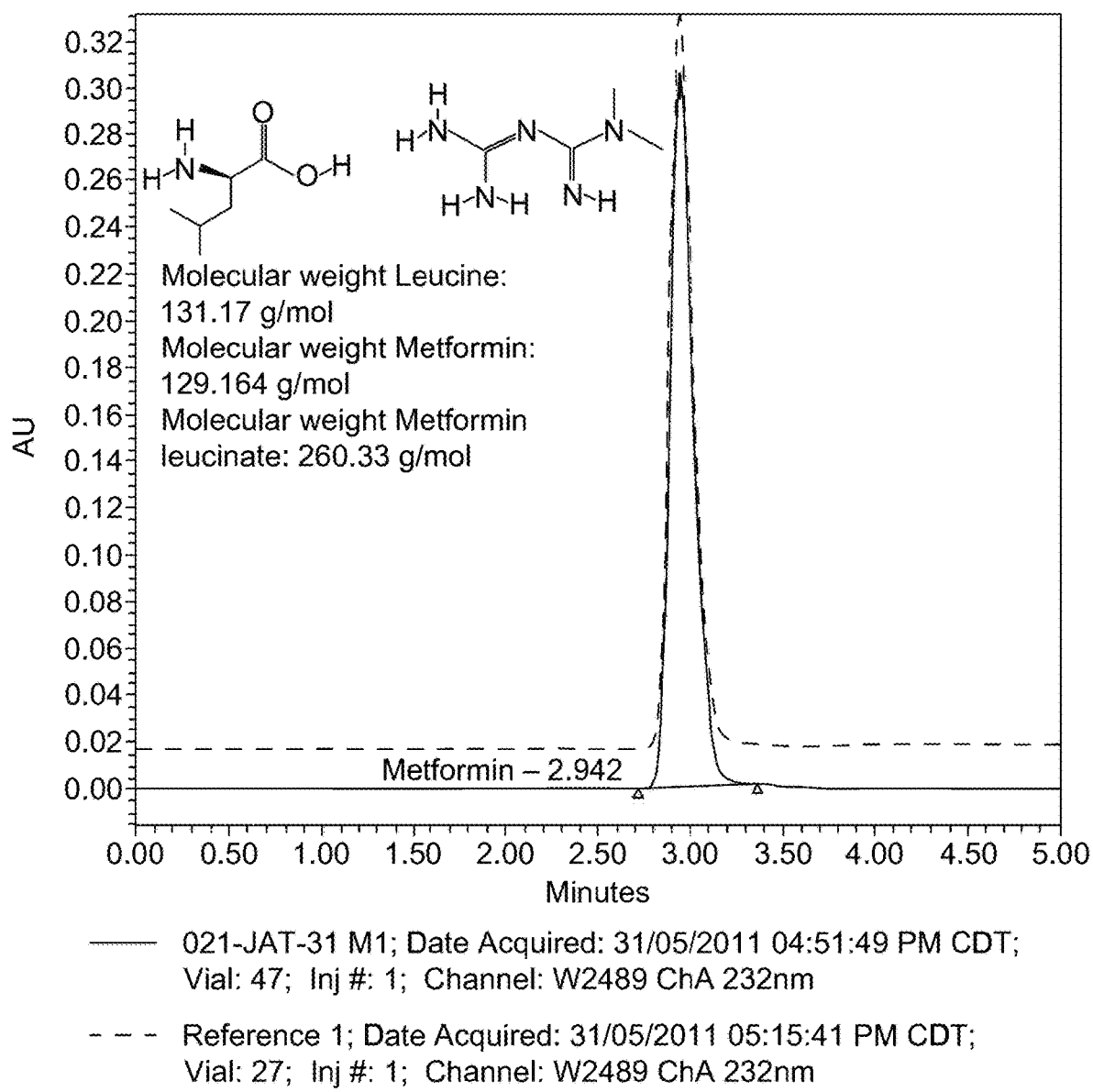

FIG. 54. Metformin leucinate identity through high-performance liquid chromatography.

Figure 55:
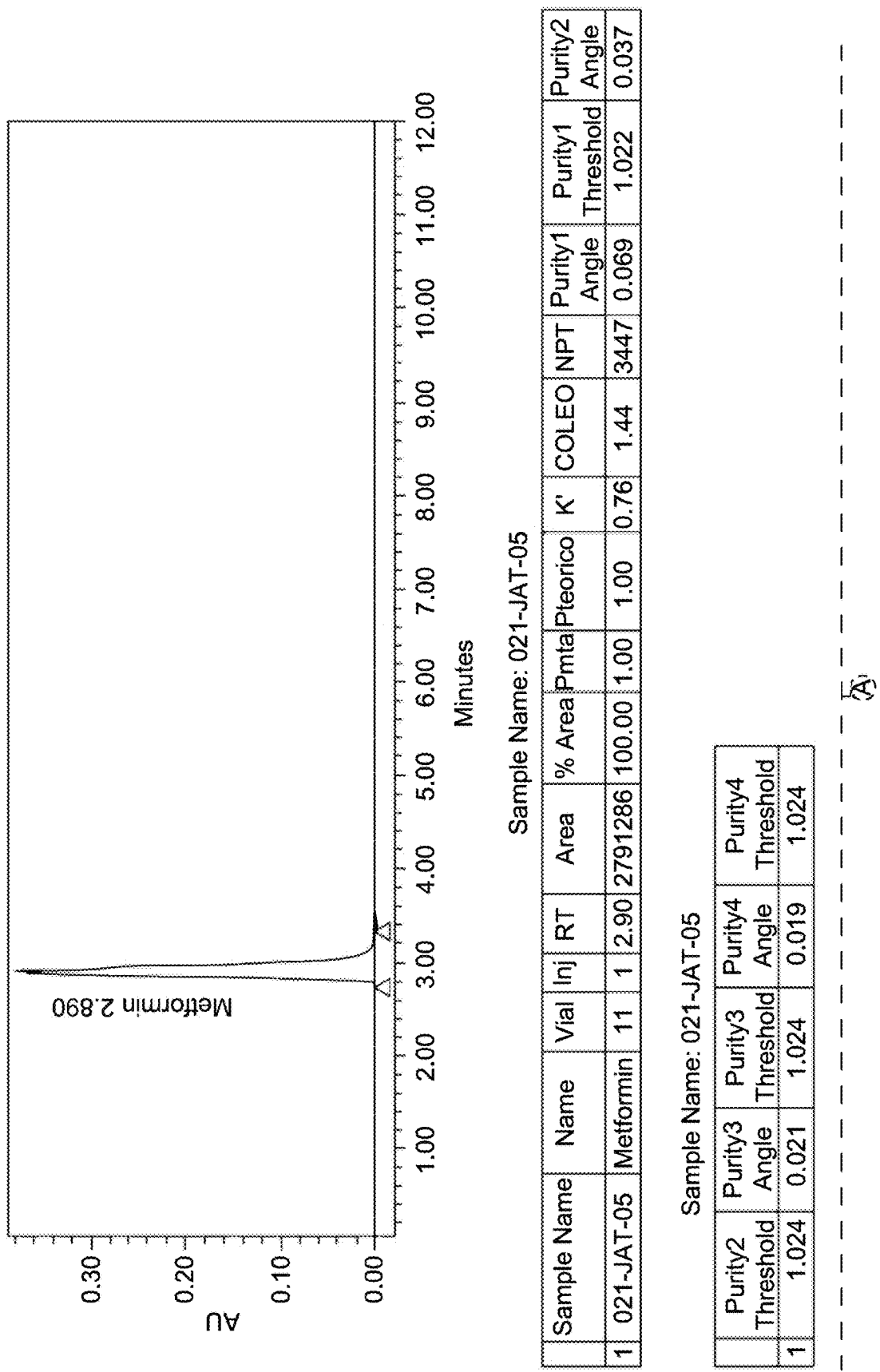
Figure 55:
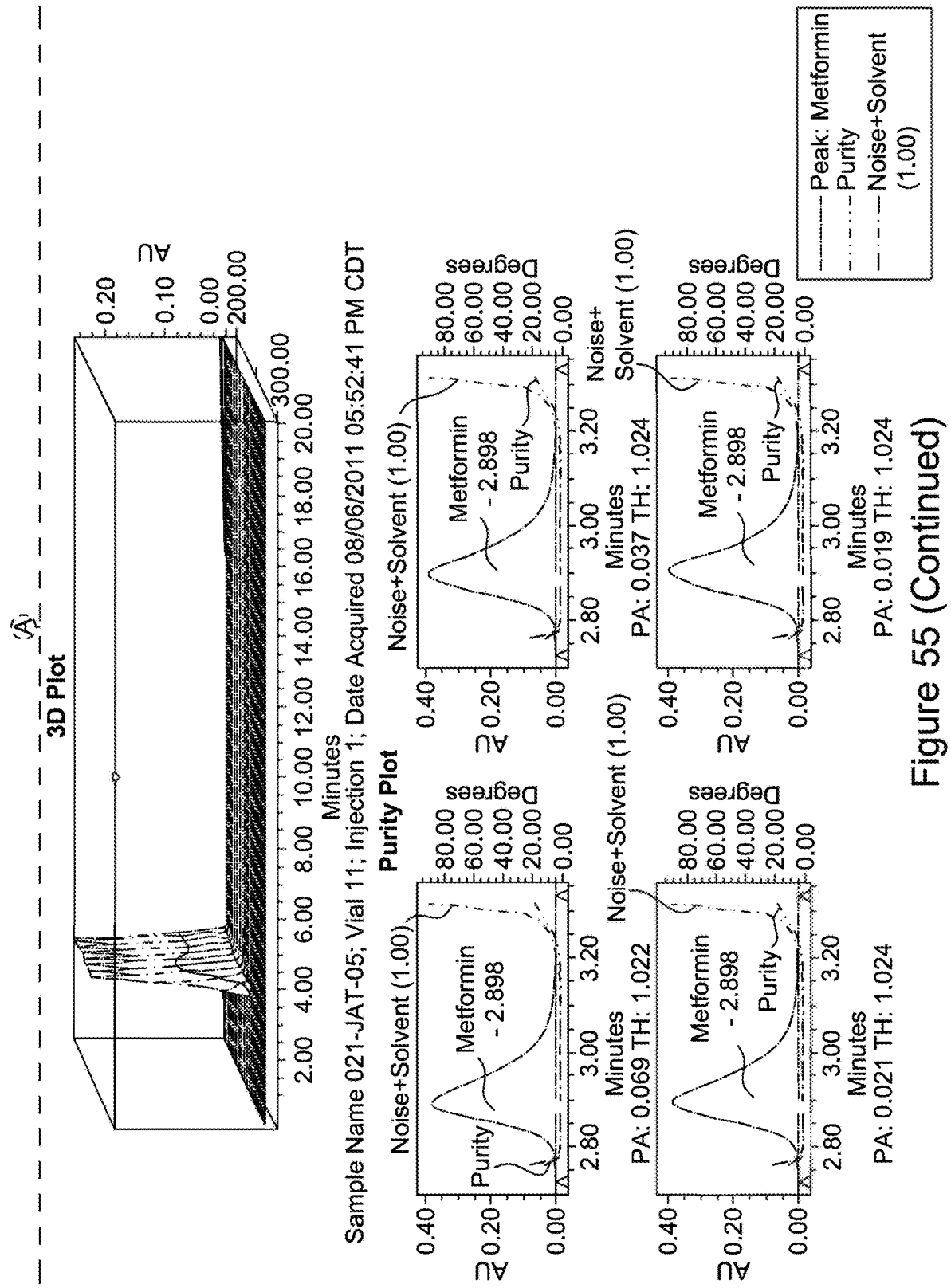

FIG. 55. Dimetformin aspartate peak purity and identity through high-performance liquid chromatography.

Figure 56:
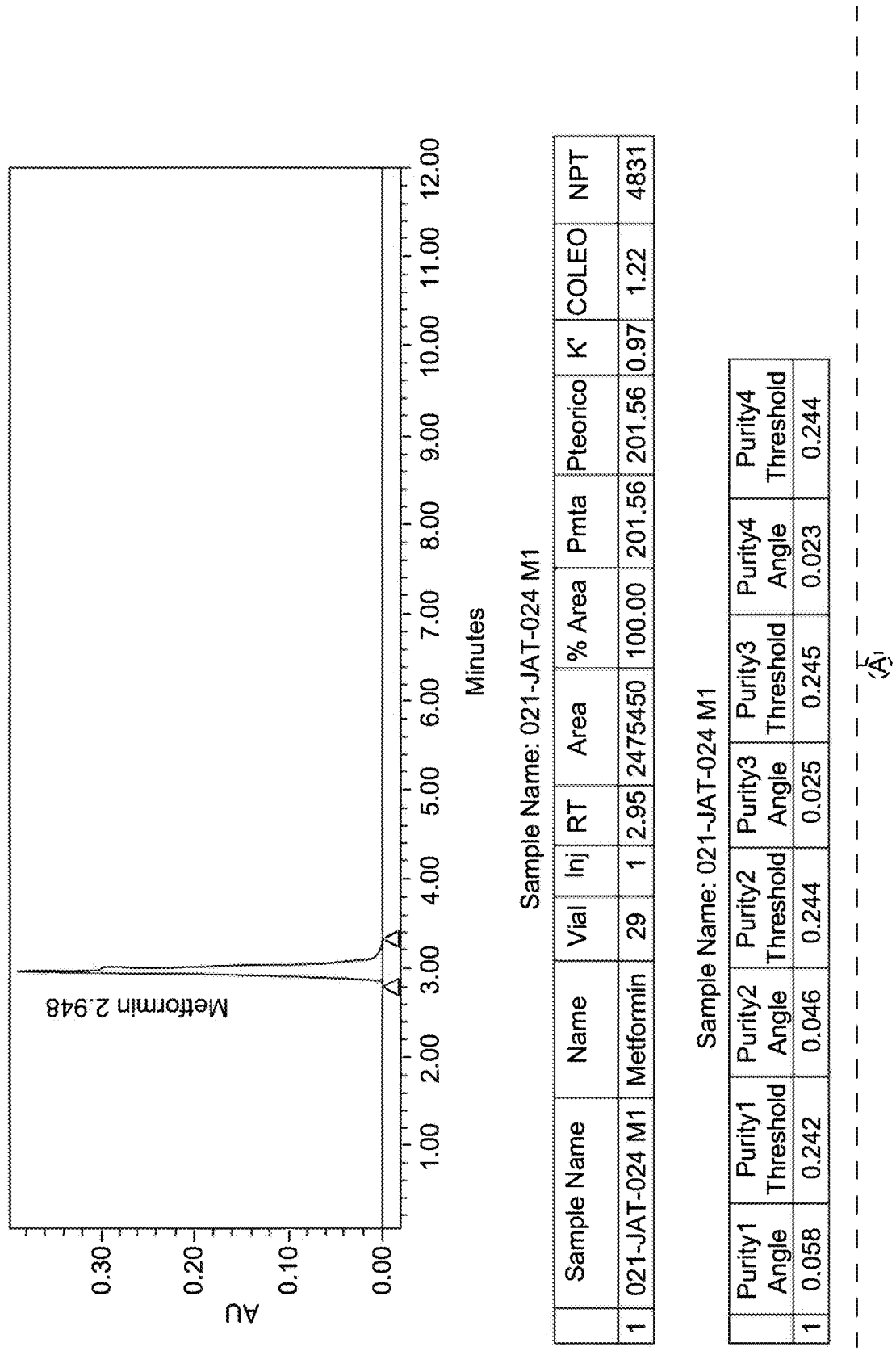
Figure 56:
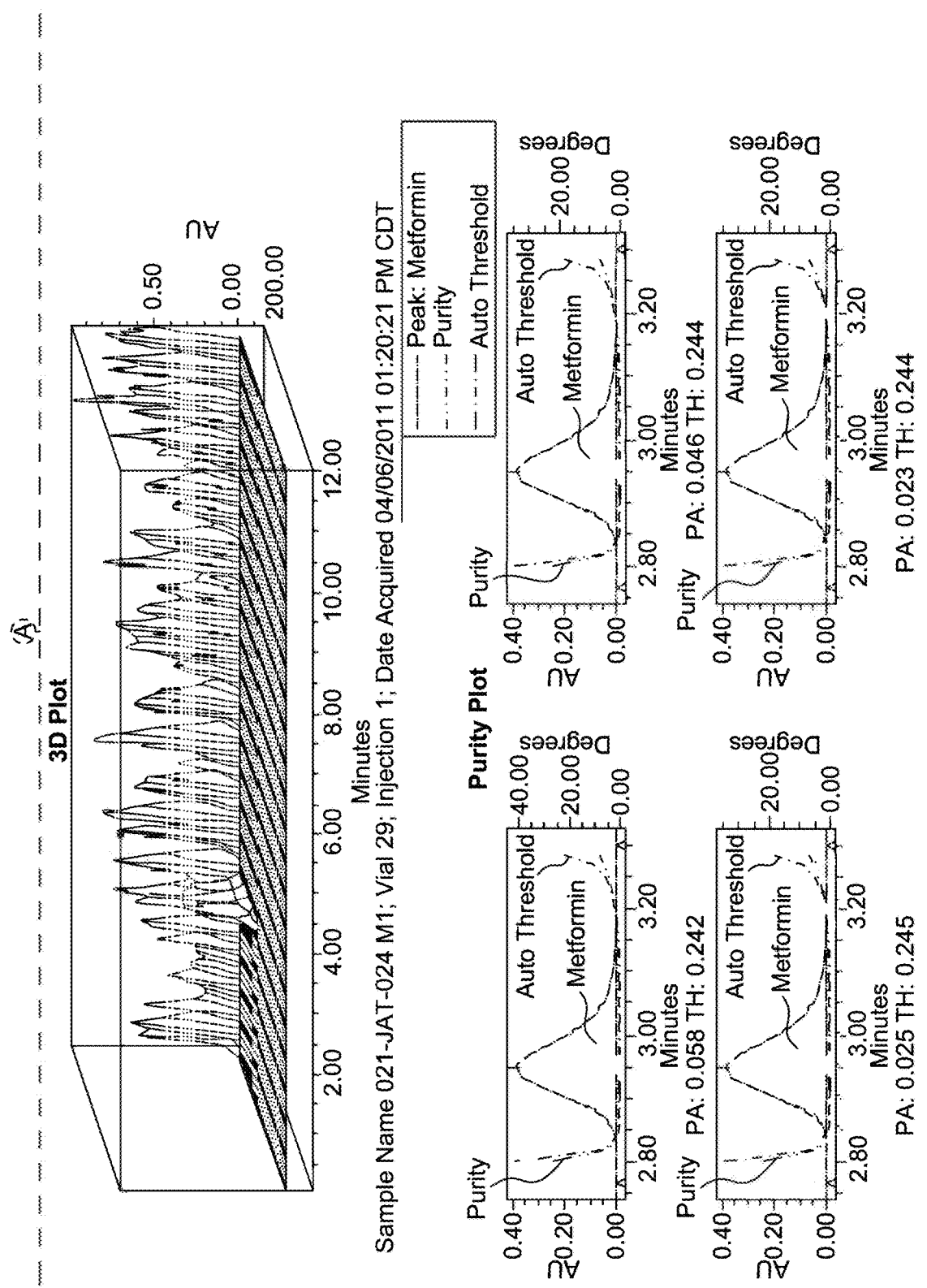

FIG. 56. Metformin isoleucinate peak purity and identity through high-performance liquid chromatography.

Figure 57:
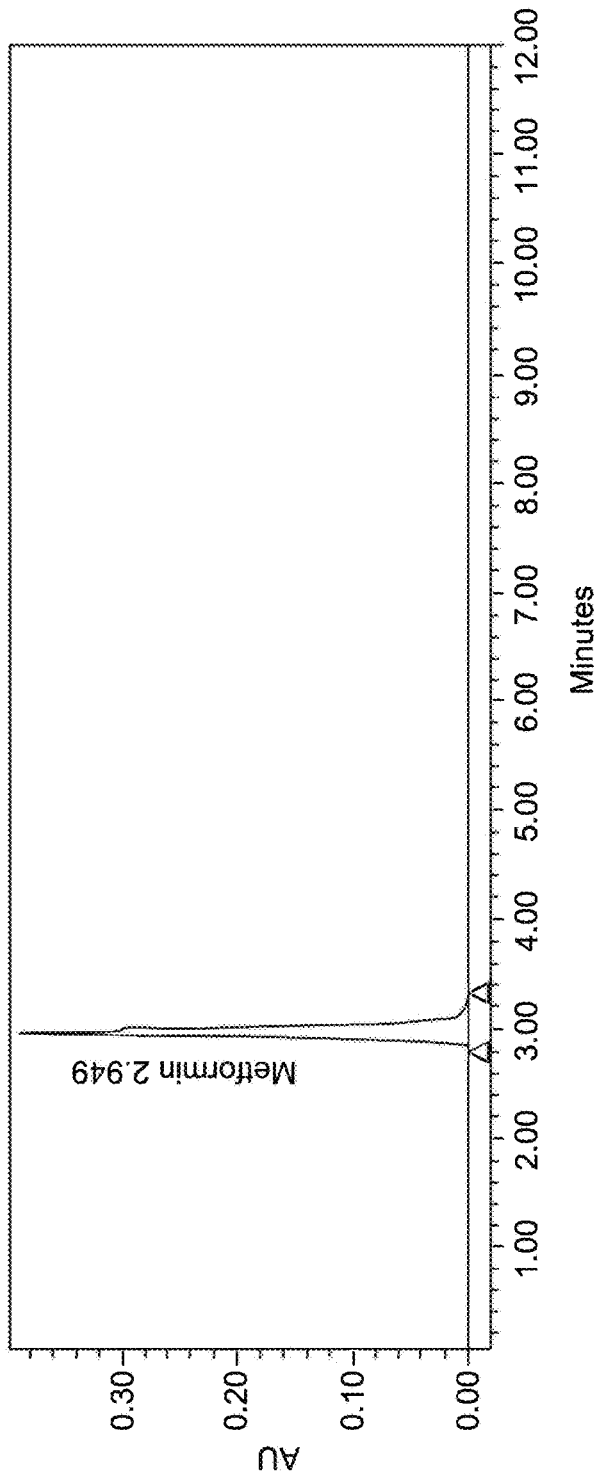
Figure 57:
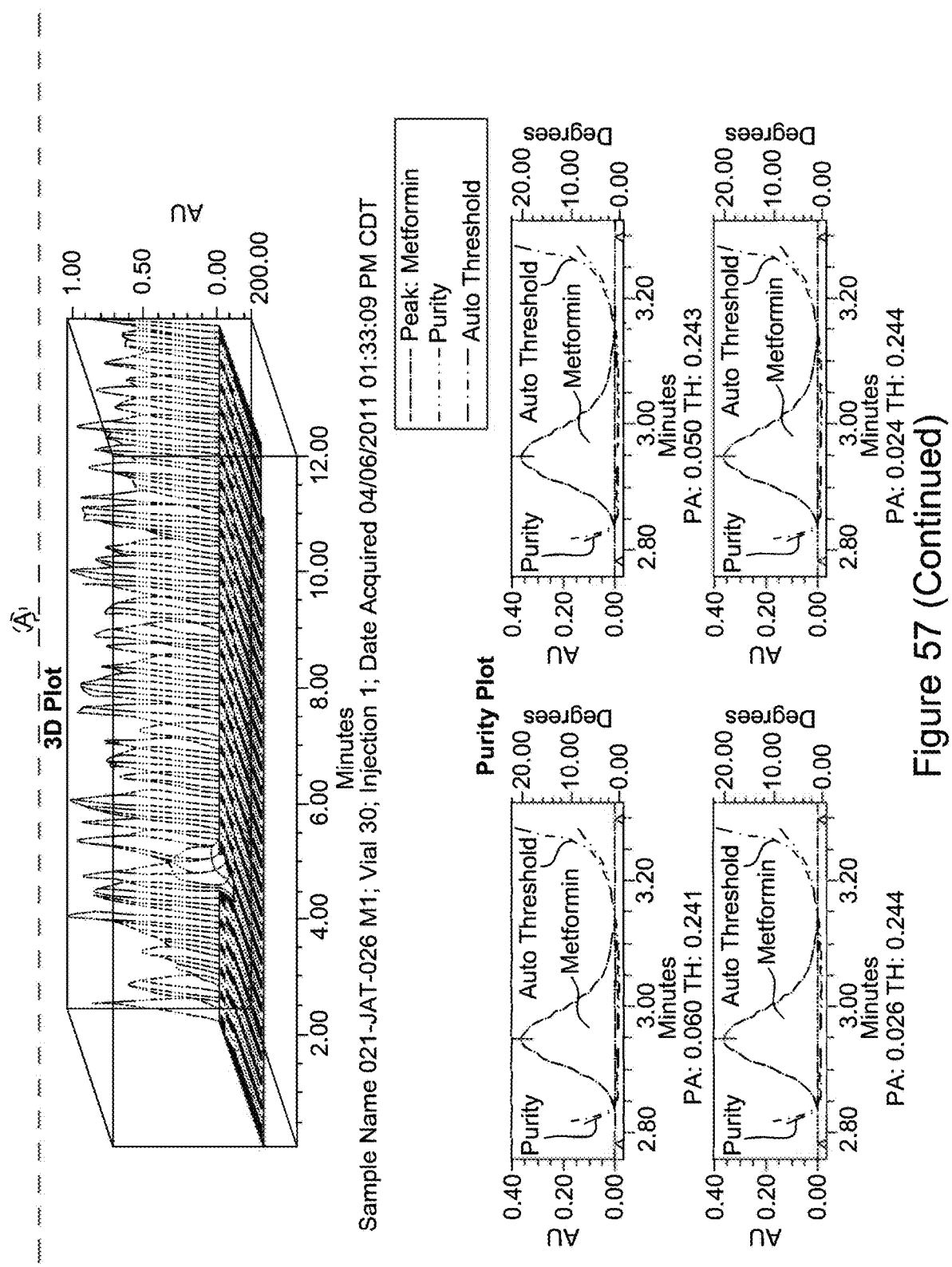

FIG. 57. Metformin alaninate peak purity and identity through high-performance liquid chromatography.

Figure 58:
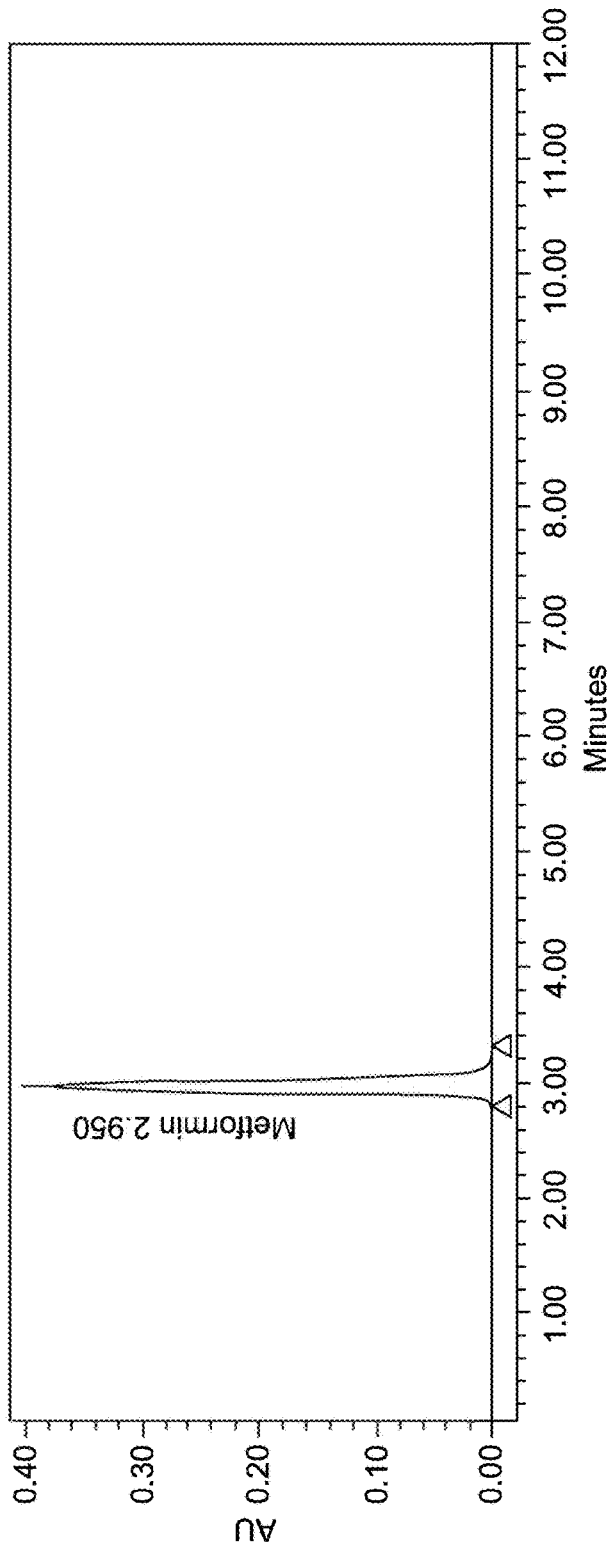
Figure 58:
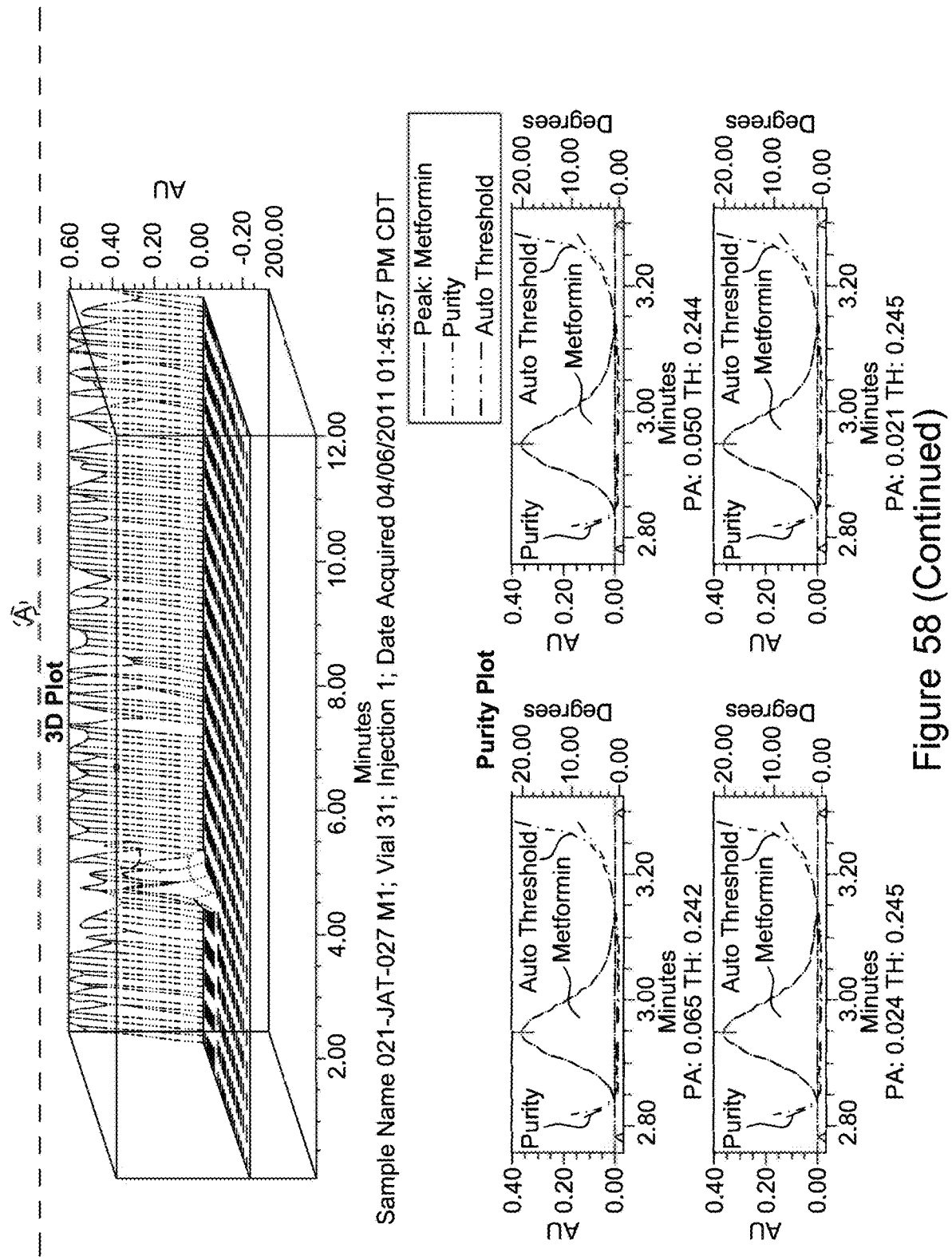

FIG. 58. Metformin valinate peak purity and identity through high-performance liquid chromatography.

Figure 59:
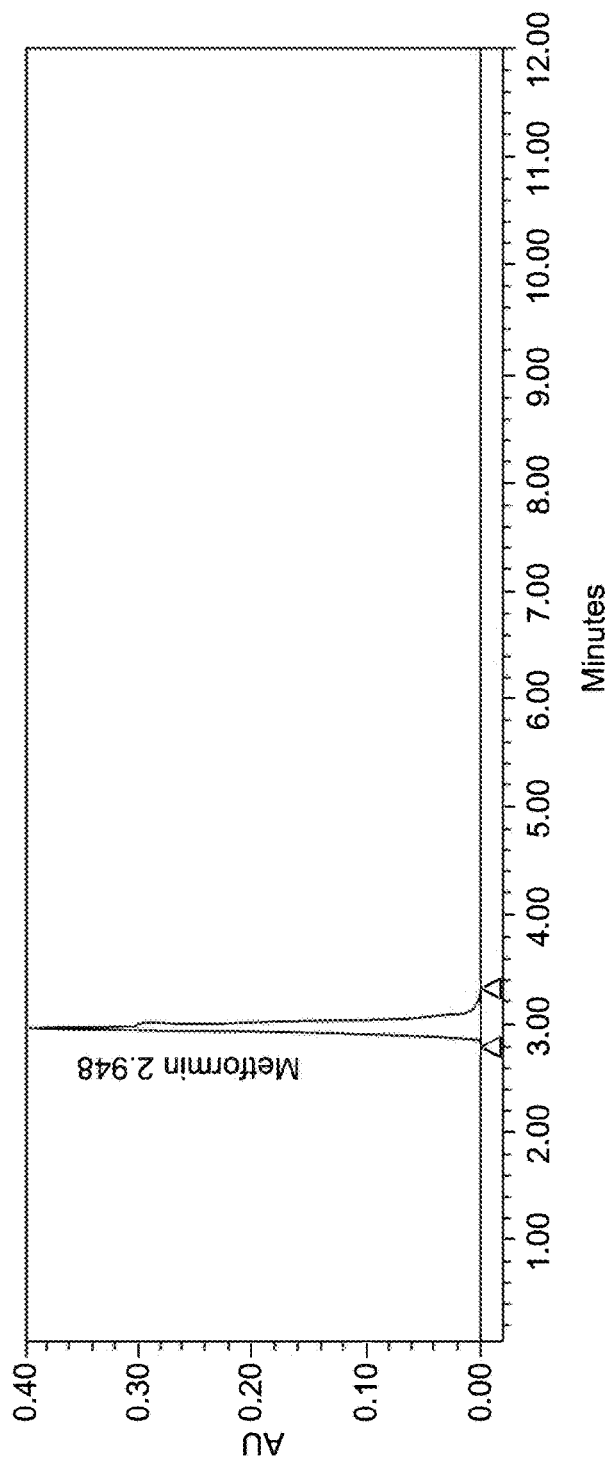
Figure 59:
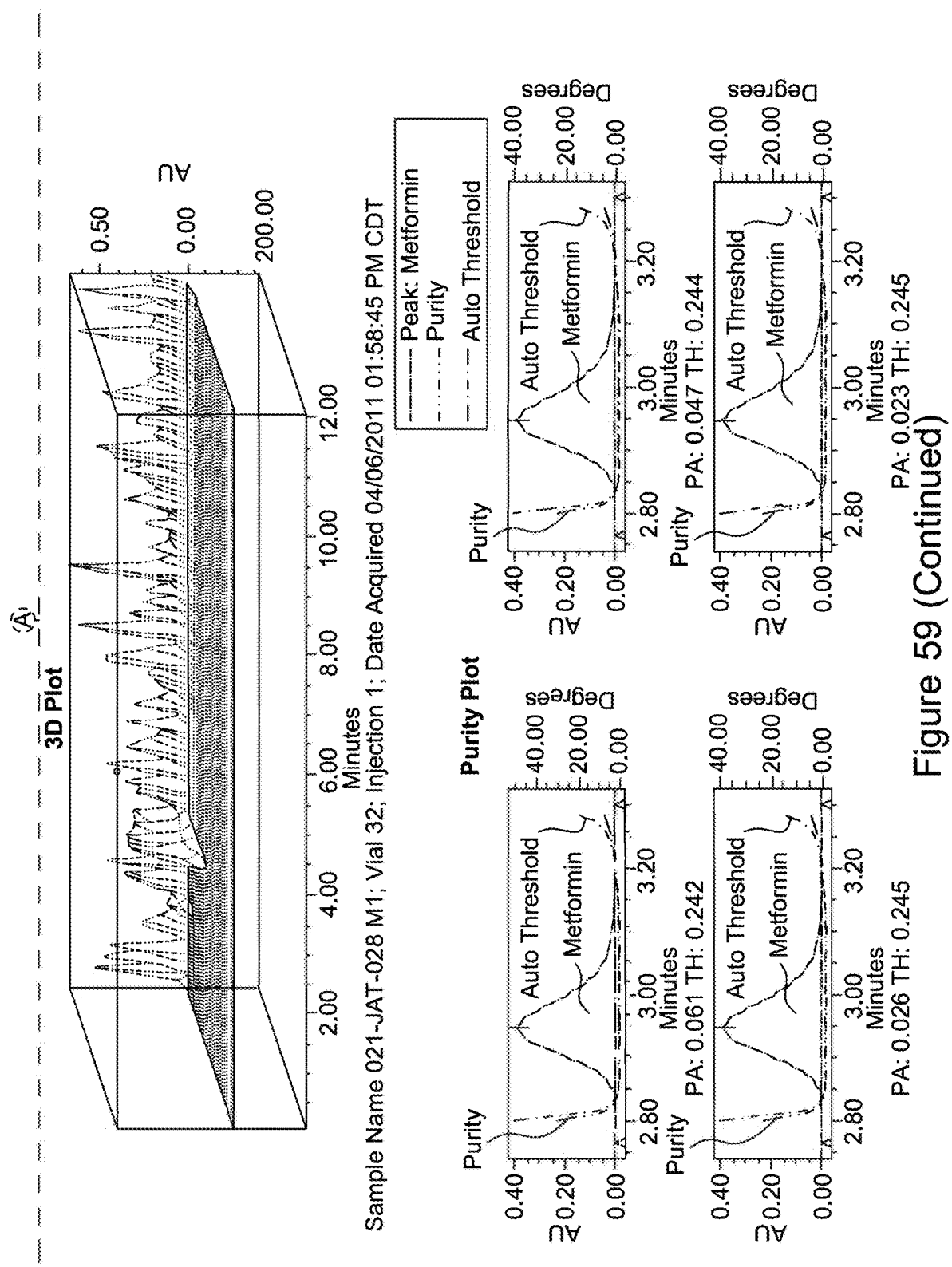

FIG. 59. Metformin asparaginate peak purity and identity through high-performance liquid chromatography.

Figure 60:
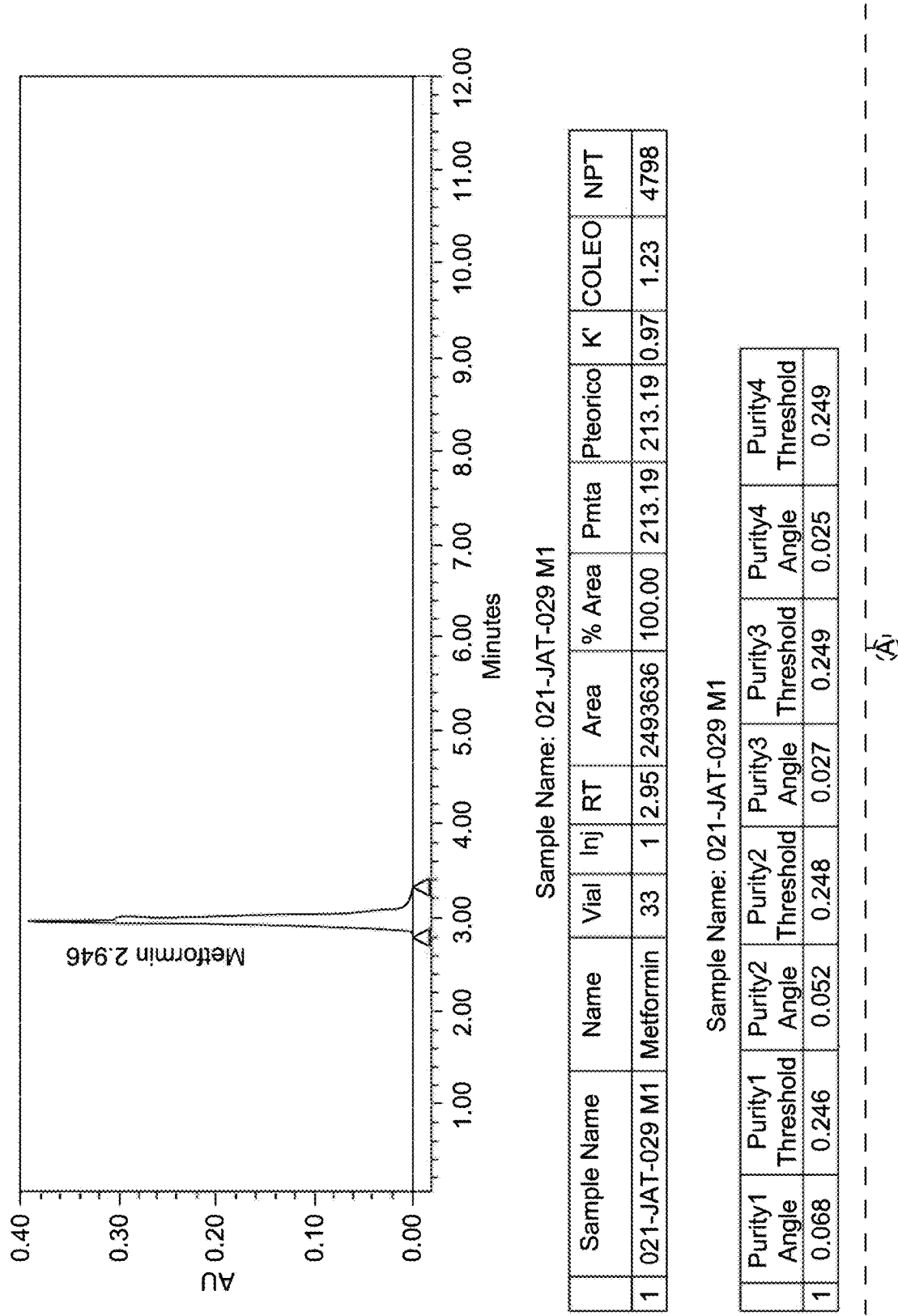
Figure 60:
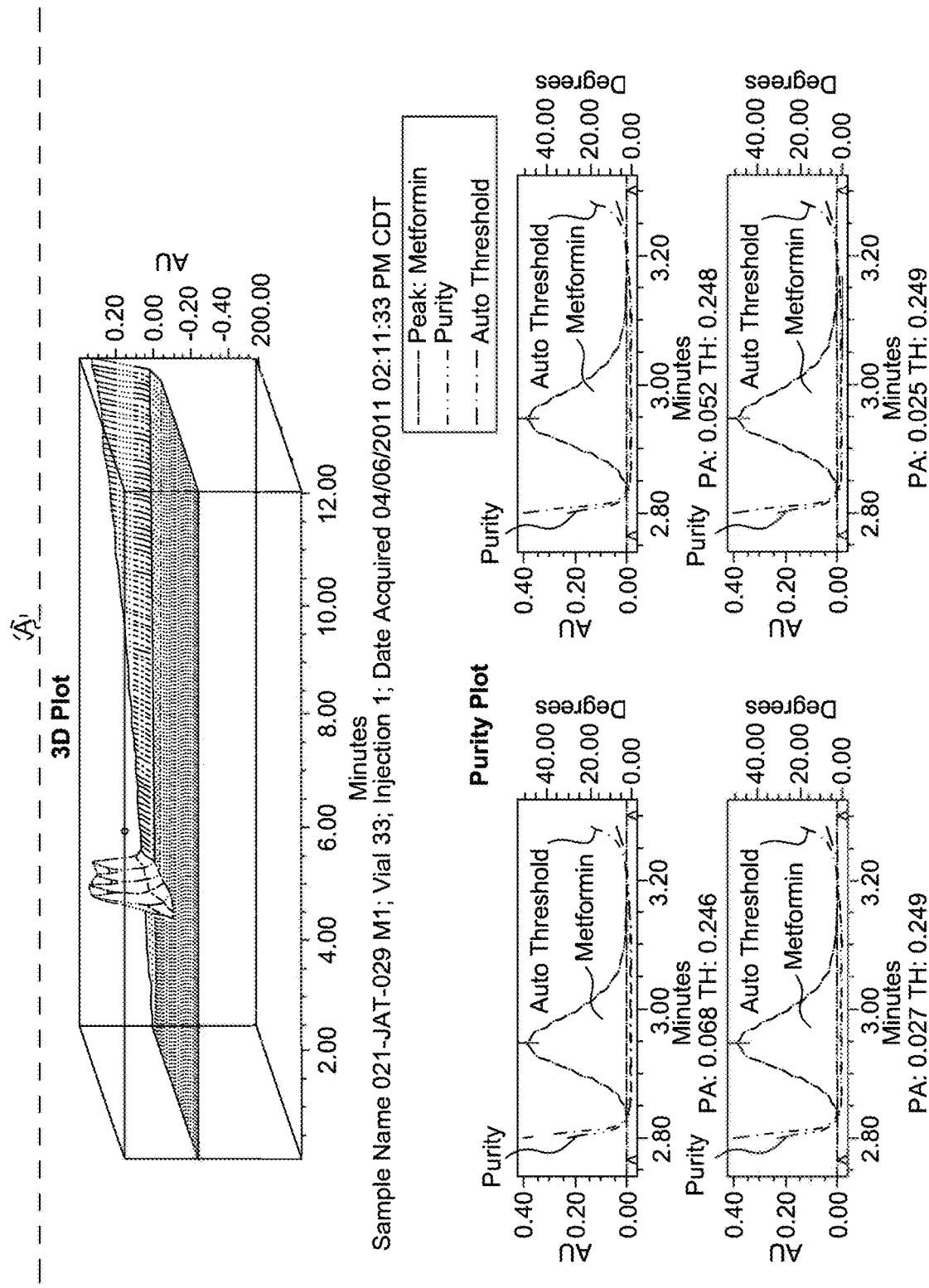

FIG. 60. Metformin lysinate peak purity and identity through high-performance liquid chromatography.

Figure 61:
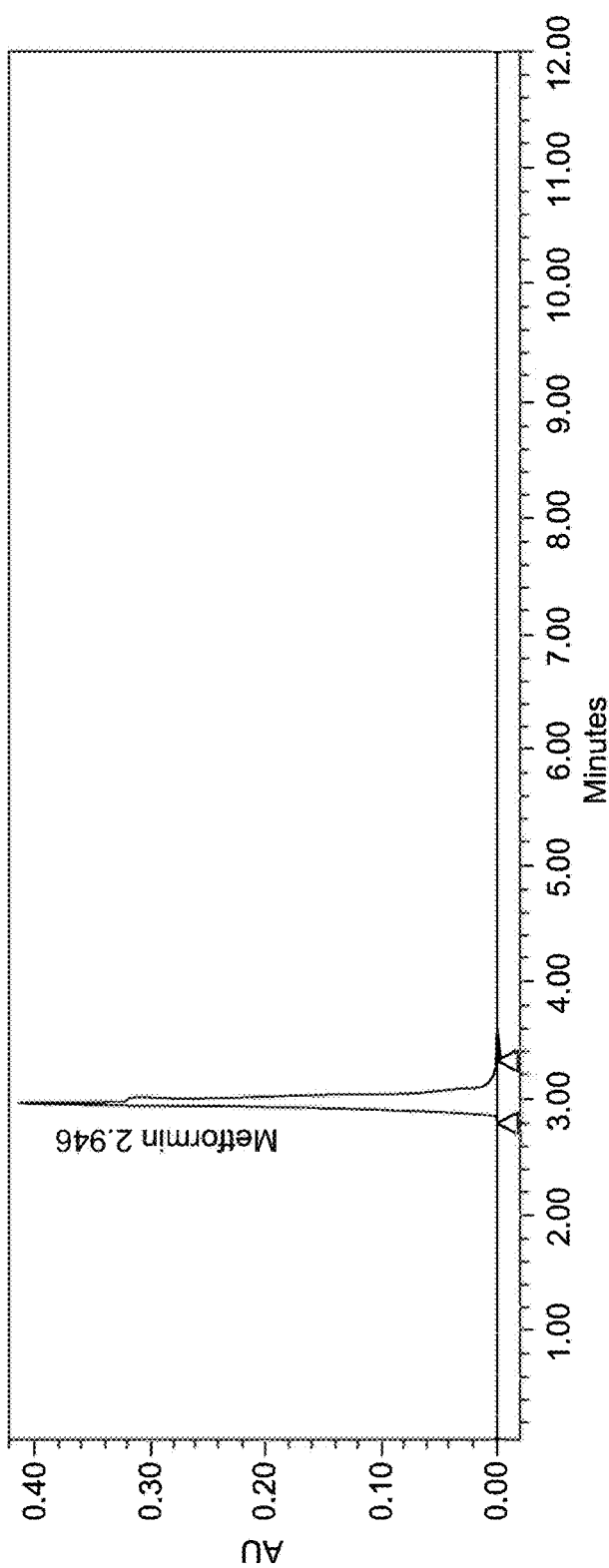
Figure 61:
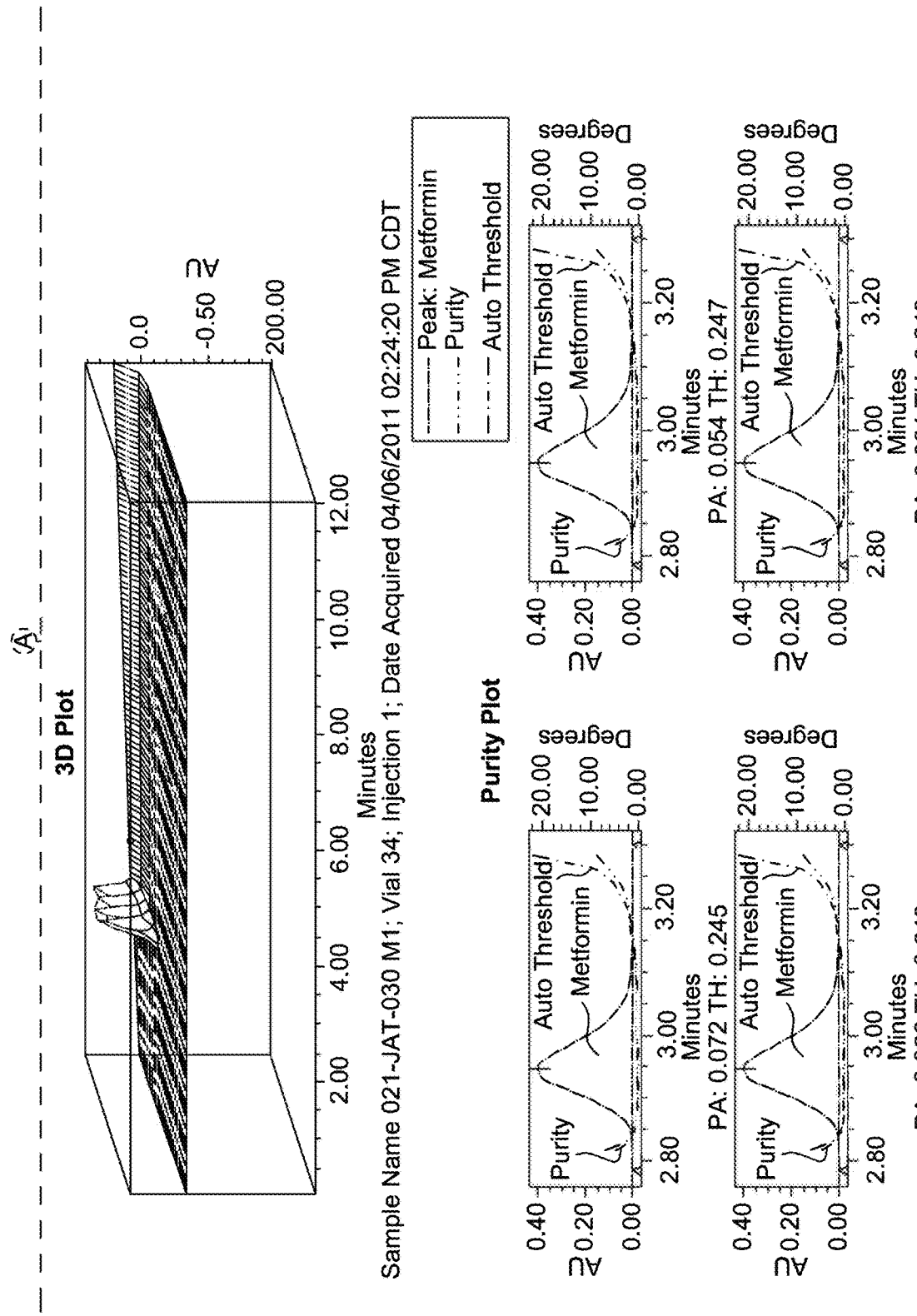

FIG. 61. Metformin threoninate peak purity and identity through high-performance liquid chromatography.

Figure 62:
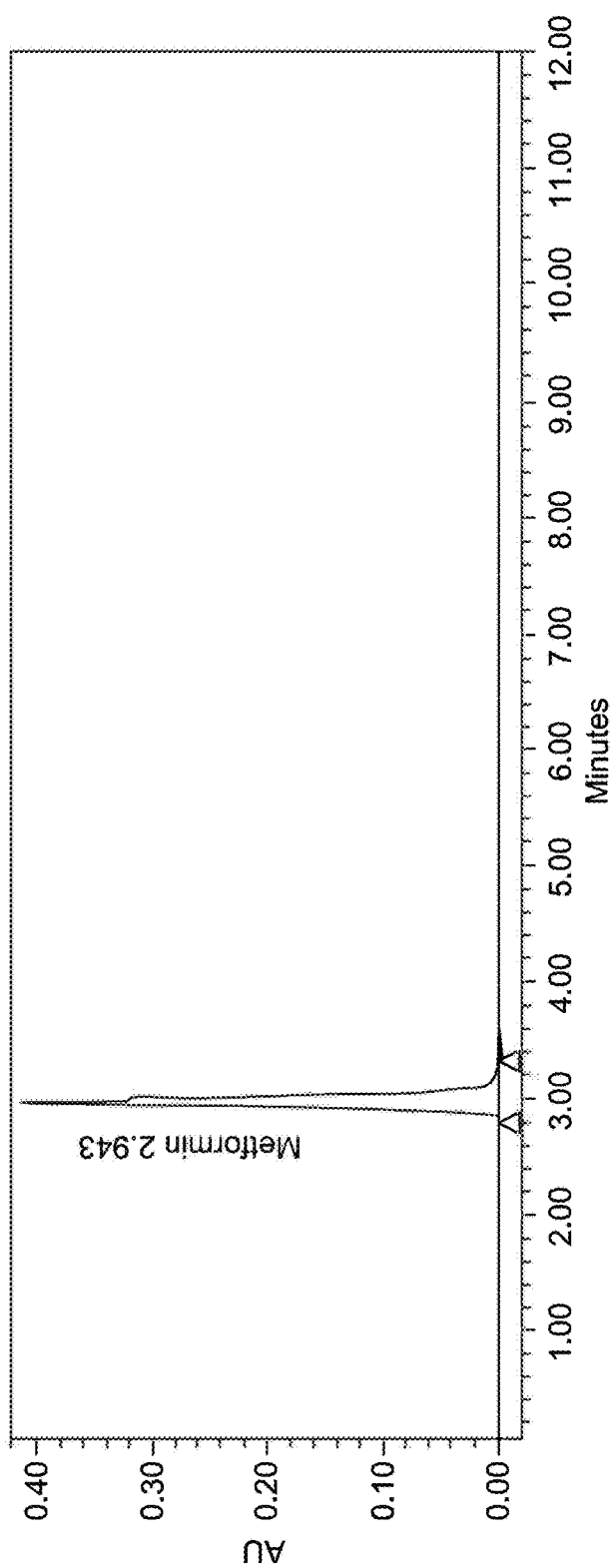
Figure 62:
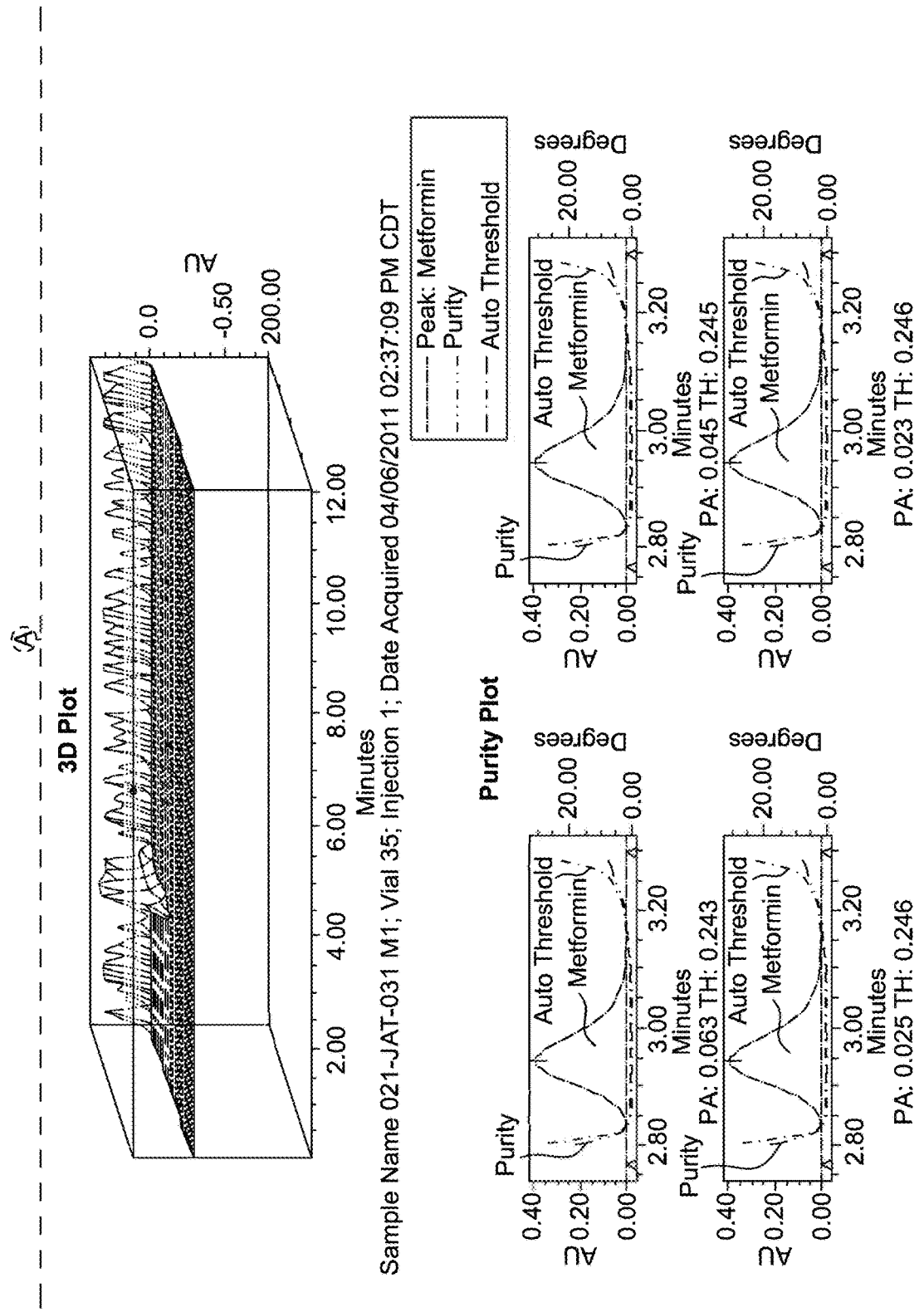

FIG. 62. Metformin leucinate peak purity and identity through high-performance liquid chromatography.

Figure 63:
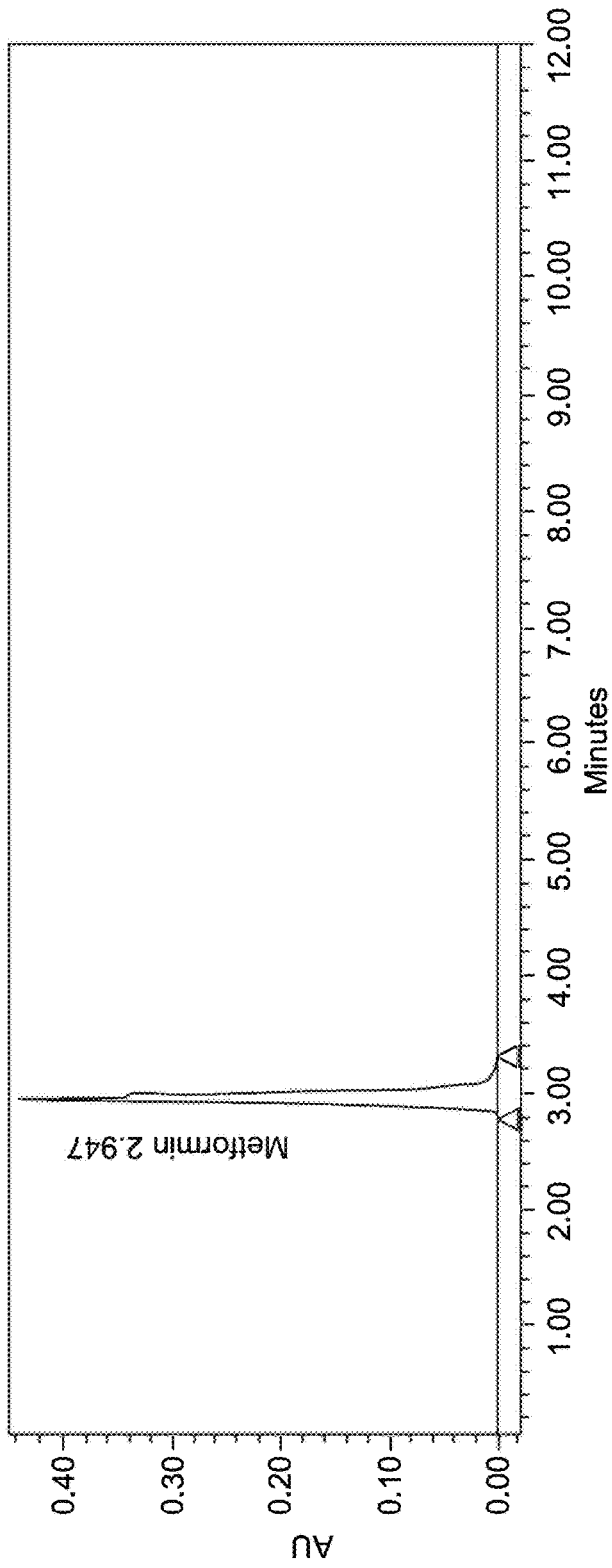
Figure 63:
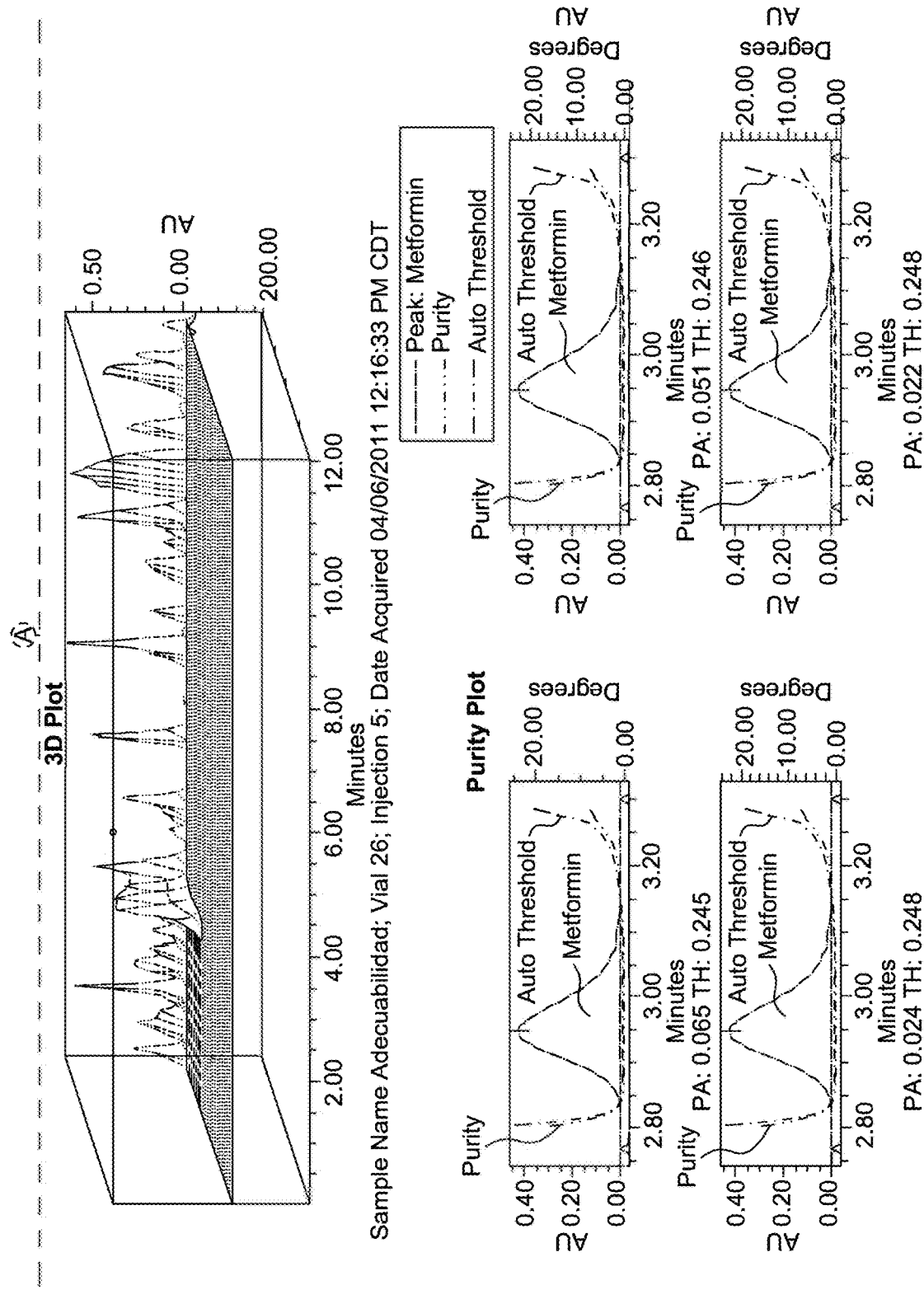

FIG. 63. Metformin hydrochloride peak purity and identity through high-performance liquid chromatography.

Figure 64:
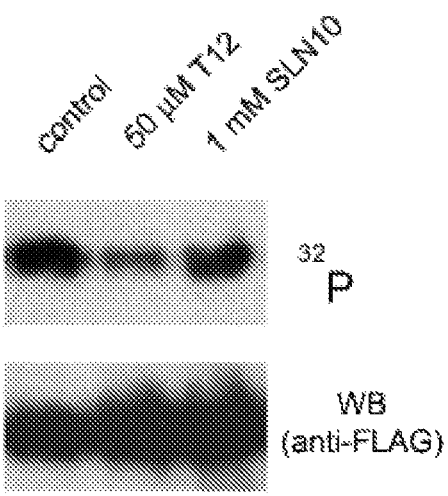

FIG. 64. Metformin lysinate (SLN10) inhibits GPBP in vitro kinase activity. Recombinant FLAG-GPBP, in similar quantities, expressed in yeast *Pichia pastoris* (Invitrogen) and purified with anti-FLAG resin (Sigma), as described above (Raya et al. *J Biol Chem.* 1999; 274:12642-9), were incubated in the absence (control) or presence of indicated concentrations of T12 or SLN10 (right) in the phosphorylation solution (final concentrations 25 mM β-glycerophosphate (pH 7.0), 0.5 mM EDTA, 0.5 mM EGTA, 8 mM MgCl$_2$, 5 mM MnCl$_2$, 1 mM DTT) without ATP for 10 minutes at room temperature (RT), after which [γ-32P]ATP was added (Perkin Elmer) (final concentration 0.132 μM). The reaction cocktails (25 μl) were incubated at 30° C. and stirred (350 rpm) for 15 minutes, then analyzed using PAGE standard procedures in the presence of SDS and β-mercaptoethanol, and electrotransferred to PVDF membrane (Immobilon P, Millipore). Membranes were then exposed to autoradiography (32P) and subsequently sent for incubation with anti-FLAG antibodies, peroxidase-labelled; ECL Prime (GE Healthcare) (WB anti-FLAG) was used for developing.

Figure 65:
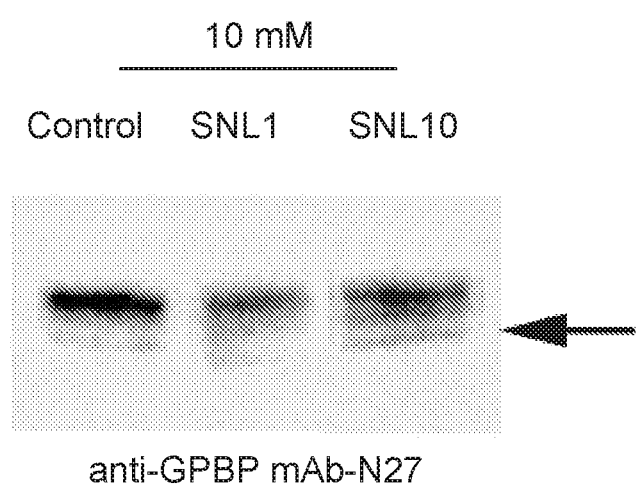

FIG. 65. SLN10 induce GPBP dephosphorylation ex vivo. Mice C2C12 myoblasts were differentiated in low serum concentration conditions (DMEM supplemented with 2% horse serum and penicillin/streptomycin) for 3 days at 37° C., and treated for 3 hours at the same temperature with compounds SLN1 (metformin hydrochloride) or SLN10, at the indicated concentrations, or with vehicle (control), with a subsequent lysis in Tris-HCl 50 mM, NaCl 150 mM, 1% Triton X-100, phenylmethylsulfonyl fluoride (PMSF) 1 mM, leupeptin 10 μg/mL for 30 minutes at 4° C. Cell lysates were centrifuged at 16000×g for 5 minutes at 4° C. and total protein concentration of supernatants was determined with Bradford Reagent (Bio-Rad). Similar quantities of each extract were analyzed using Western blot (SDS-PAGE and electrotransfer), with the indicated antibodies and chemiluminescence (ECL Prime, GE Healthcare). The arrow marks a dephosphorylated band, with higher abundance in SLN10-treated cells than in non-treated or SLN1-treated cells.

Figure 66:
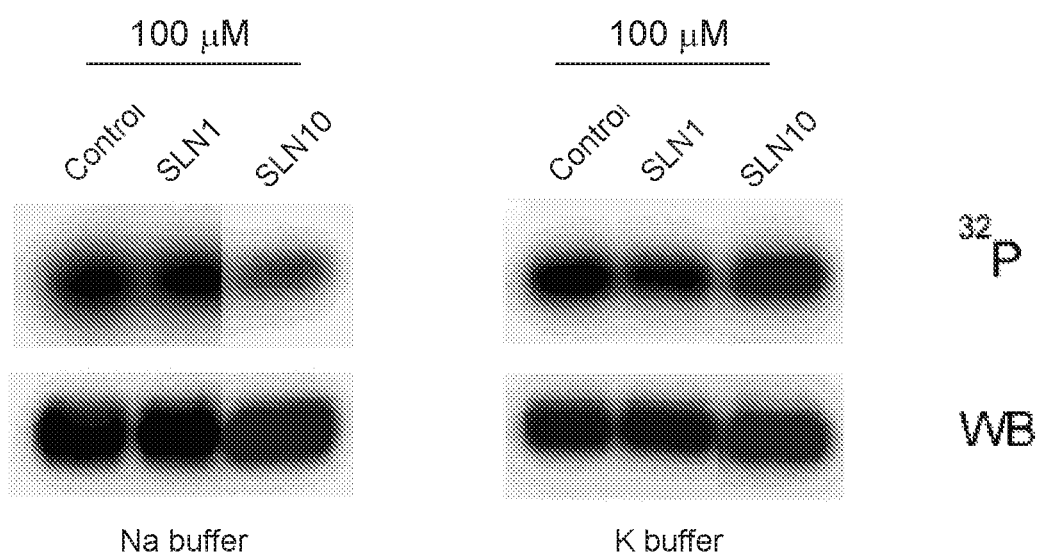

FIG. 66. The reaction medium composition determines the inhibiting activity of metformin amino acid compounds on GPBPs. SLN10 inhibits GPBP in Na buffer. This suggests that SLN10 inhibits GPBP in extracellular media, where Na ions are predominant. These results might reflect SLN10 capacity to induce GPBP secretion by macrophages.

Figure 67:
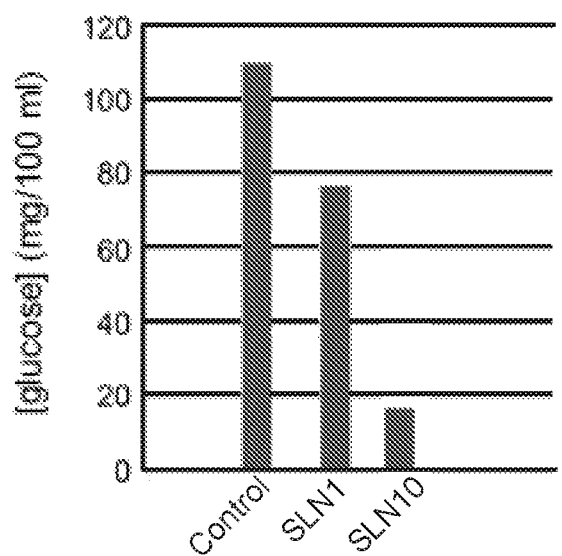

FIG. 67. Hypoglycemic activity ex vivo. Glucose concentration in myocyte culture medium, treated with the control, SLN1, or SLN10. C2C12 myoblast cultures were differentiated for 72 hours in DMEM supplemented with 2% horse serum and penicillin/streptomycin, with an initial glucose concentration of 450 mg/100 mL. In the last 18 hours of the differentiation process, cultures were incubated with SLN1 or SLN10 10 mM, or with the vehicle (control). The final glucose concentration in the culture medium was determined with a Glucocard (Arkray). Results show that SLN10 has a greater effect than SLN1, and that there is direct correspondence in the anti-hyperglycemic capacity of metformin amino acid compounds, e.g. Metformin lysinate (SLN10), and their activity as GPBP phosphorylation inhibitors (vide infra FIG. 73).

Figure 68A:
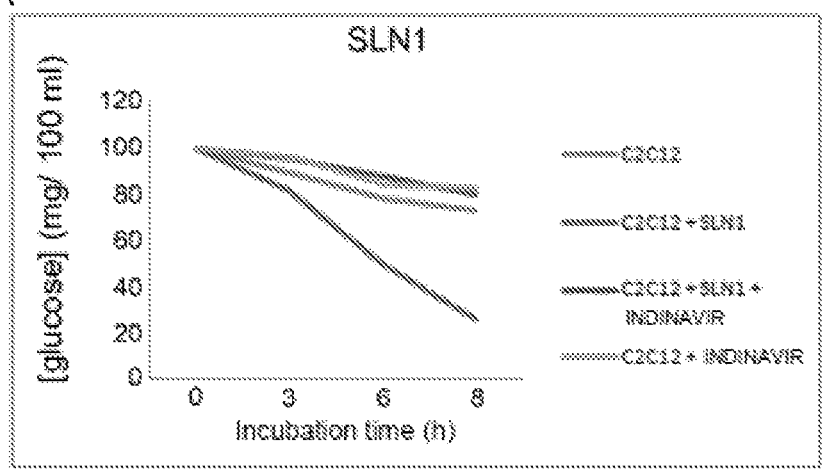
Figure 68B:
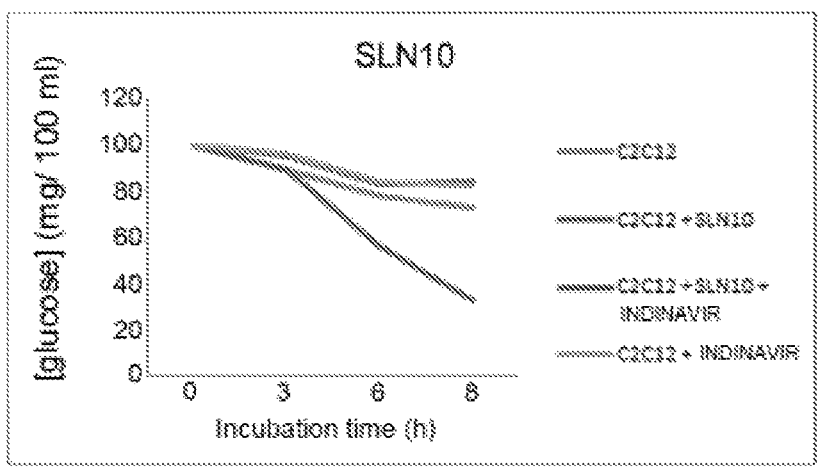

FIGS. 68A-B. Metformin amino acid compounds, such as metformin lysinate (SLN10), have an ex vivo hypoglycemic activity. C2C12 cells were differentiated in myotubes in DMEM supplemented with 2% horse serum and penicillin/streptomycin for 72 hours at 37° C. Glucose concentration in culture media was then adjusted to 100 mg/100 mL, and cultures were treated with SLN1 (FIG. 68A) or SLN10 (FIG. 68B) 10 mM, either in the presence or not of Indinavir (Sigma) 200 µM, a GLUT4 inhibitor. Glucose concentration in culture media was determined with a Glucocard (Arkray). Based on the results, scientists may deduce that in normoglycemia, SLN1 and SLN10 equally induce glucose consumption in myotubes, and that the effect is mediated by the GLUT4 transporter.

Figure 69:
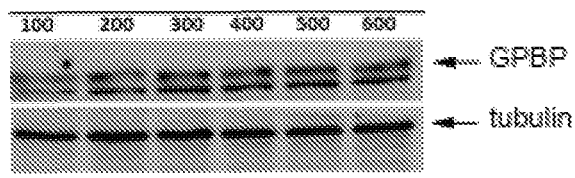

FIG. 69. Hyperglycemia induces GPBP expression in culture myotubes. C2C12 cells were differentiated for 5 days in DMEM supplemented with 2% horse serum and antibiotics. Cultures were washed with PBS and incubated for additional 24 hours with DMEM supplemented with 2% horse serum containing the indicated glucose concentrations. Cells were washed with PBS and lysed in Tris-HCl 50 mM, pH 7.0, NaCl 150 mM, 1% Triton X-100, PMSF 1 mM, and leupeptin 10 mg/mL for 30 minutes at 4° C. Cell lysates were cleared by centrifugation (16000×g, 5 minutes, 4° C.); the total protein concentration of supernatants was determined (Bio-Rad), and similar quantities of each extract (50 µg) were analyzed by Western blot with monoclonal anti-GPBP N27 antibodies and anti-tubulin antibodies (Sigma), as shown in the Figures above. The results show that hyperglycemia induces GPBP protein expression in myotubes.

Figure 70A:
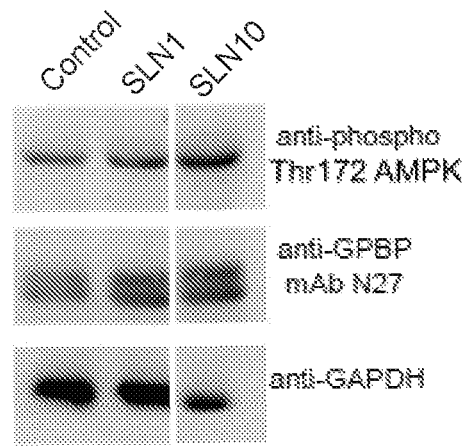
Figure 70B:
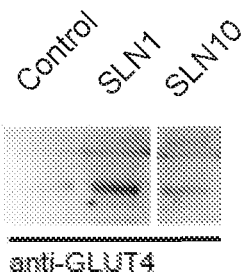
Figure 70C:
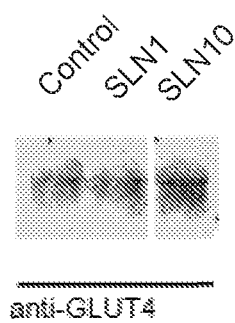

FIGS. 70A-C. Metformin amino acid compounds, like metformin lysinate (SLN10), induce AMPK activation and the accumulation of GLUT4 in the plasma membrane. Mice NIH-3T3-L1 pre-adipocytes, cultured in DMEM supplemented with 10% FBS and penicillin/streptomycin, were differentiated into adipocytes for 10 days according to the following protocol: 2 days in culture media supplemented with insulin 1 µg/mL, rosiglitazone 2 µM, dexamethasone 10 µM, 3-isobutyl-1-methylxanthine (IBMX) 100 µg/mL; 2 days in culture media supplemented with insulin 1 µg/mL; and 6 days in culture media. FIG. 70A shows a pictures of L1 adipocyte cultures were treated for 3 hours with SLN1 or SLN10 10 mM, or with vehicle (control), and then lysed with Tris-HCl 50 mM, NaCl 150 mM, 1% Triton X-100, PMSF 1 mM, leupeptin 10 µg/mL for 30 minutes at 4° C. Cell lysates were centrifuged at 16000×g for 5 minutes at 4° C. and total protein concentration of supernatants was determined with Bradford Reagent (Bio-Rad). Similar quantities of each extract were analyzed using Western blot (SDS-PAGE and electrotransfer), with the indicated antibodies and chemiluminescence (ECL Prime, GE Healthcare). FIGS. 70B-C show pictures of L1 adipocyte cultures treated as in FIG. 70A and exposed to fractioning for protein extraction from plasma membrane by a procedure described above (Nishiumi & Ashida. *Biosci Biotechnol Biochem.* 2007; 71:2343-6). Briefly, cells were washed with PBS and collected in solution A (Tris 50 mM, pH 8.0, DTT 0.5 mM, 0.1% Nonidet P-40, PMSF 1 mM, leupeptin 5 µg/mL, aprotinin 5 µg/mL, NaF 10 mM, $Na_3VO_4$ 1 mM) and lysed manually with a Dounce homogenizer (20 pestle movements). Homogenized solutions were centrifuged (1000×g, 10 minutes, 4° C.), cell precipitates were dispersed in solution A, without Nonidet P-40, stored in ice for 10 minutes, occasionally stirred, and centrifuged again (1000× g, 10 minutes, 4° C.). Resulting cell precipitates were then put into solution A, which contained 1% Nonidet P-40, stored in ice for 1 hour, with eventual stirring, and cleared (16000×g for 20 minutes at 4° C.). Supernatants were stored at −80° C. until analysis. Equivalent quantities of demembrane extracts were analyzed by Western blot with anti-GLUT4 (Abcam) antibodies. SLN10 activates AMPK and induces a GLUT4 accumulation in the plasma membrane.

Figure 71:
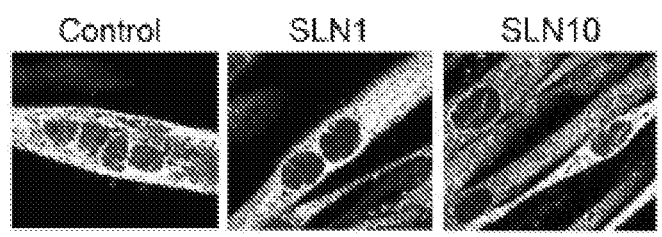

FIG. 71. Metformin amino acid compounds, such as metformin lysinate (SLN10), regulate LKB1 and GPBP distribution in myotubes. C2C12 cells were differentiated to myotubes for 5 days by incubation in DMEM medium, supplemented with 2% horse serum; then, cultures were treated for 3 hours with SLN1 or SLN10 10 mM, or with vehicle (control) at 37° C. Subsequently, cells were washed with PBS, and fixed with paraformaldehyde (4% in PBS) for 30 minutes at RM, permeabilized with Triton X-100 (0.2% in PBS) for 5 min at RM and then blocked with bovine serum albumin (BSA) (3% in PBS) for 30 min at RM. Afterwards, cells were incubated with monoclonal anti-GPBP N27 antibodies and with goat polyclonal anti-LKB1 antibodies (Santa Cruz Biotechnology) for 16 hours at 4° C. in a humidity chamber. Cells were washed with PBS (3×5 minutes) and incubated with antibodies against mouse IgG, conjugated with Alexa Fluor 488, and against goat IgG, conjugated with Alexa Fluor 546 (Molecular Probes) for 1 hour at RM in the dark. In this and in the following Figures showing confocal microscopy of cell cultures, all antibodies used were diluted in blocking solution. After incubation with antibodies, cells were washed with PBS (3×5 minutes) and mounting medium (Dako) in glass slides. Preparations were visualized with confocal microscopy and obtained images were analyzed with the WCIF ImageJ software as to detect colocalization points between GPBP and LKB1. GPBP appears in green, LKB1 in red, and colocalization points indicating similar and corresponding expression levels in both proteins appear in white. SLN10 seems to induce decolocalization in GPBP and LKB1.

Figure 72:
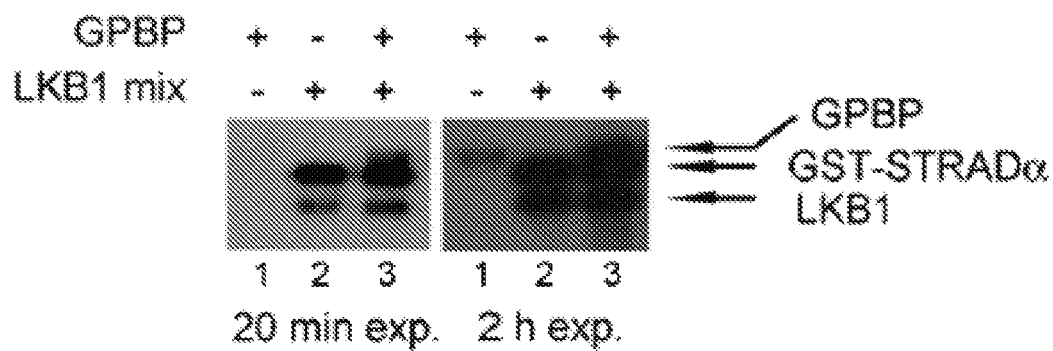

FIG. 72. GPBP and LKB1 are induced mutually. LAG-GPBP (270 ng), purified from yeast *Pichia pastoris*, and the activated LKB1 complex (LKB1 mix) (Millipore) (200 ng) containing LKB1, GST-STRADα, and GST-MO25, were incubated, either separately or in conjunction, in phosphorylation solution (β-glycerophosphate 25 mM (pH 7.0), EDTA 0.5 mM, EGTA 0.5 mM, $MgCl_2$ 8 mM, $MnCl_2$ 5 mM, DTT 1 mM, ATP[γ-32P] 0.132 µM), for 15 minutes at 30° C. with stirring (350 rpm) in a total volume of 25 µL. Reactions were stopped with a reducing loading buffer, analyzed by SDS-PAGE, and electrotransferred to PVDF membrane. Membranes were exposed to autoradiography during the indicated exposition times (exp.). Arrows show the identity of the bands observed in autoradiographs. Images show that GPBP and LKB1 mutually induce their phosphorylation.

Figure 73:
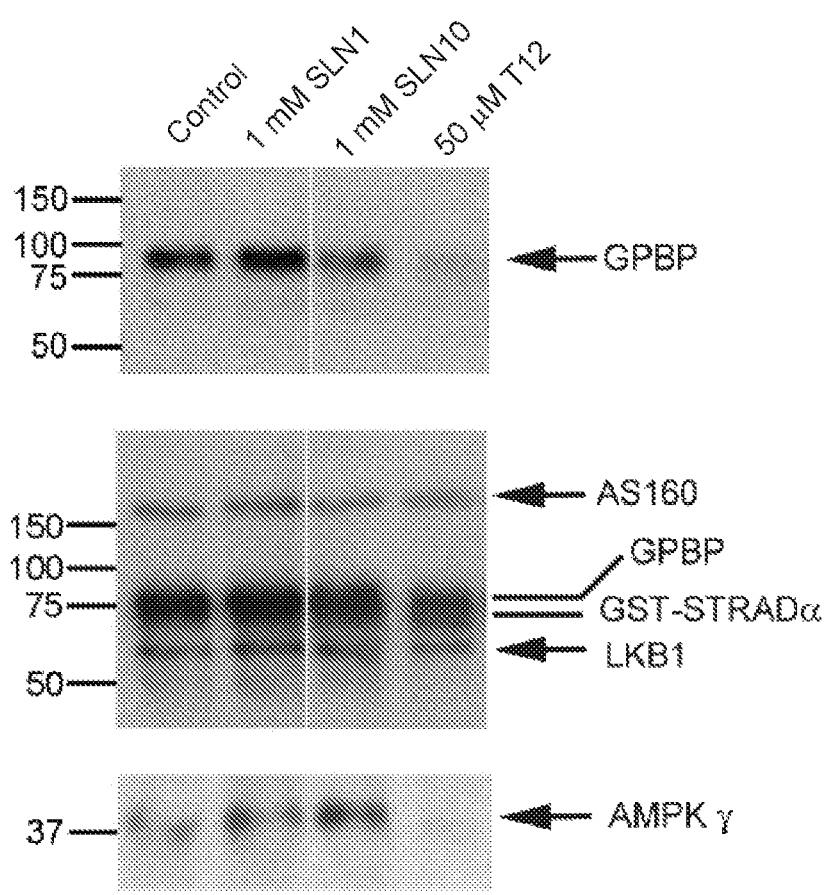

FIG. 73. In the presence of AMPK, GPBP inhibition activates LKB1. FLAG-GPBP (270 ng), activated LKB1 complex (LKB1 mix, 200 ng) (Millipore), activated AMPK (AMPKα, AMPKβ, AMPKλ, 200 ng) (Millipore) and AS160/TBC1D4 (Origene Technologies, 200 ng) were incubated in phosphorylation solution (β-glycerophosphate 25 mM, pH 7.0, EDTA 0.5 mM, EGTA 0.5 mM, MgCl$_2$ 8 mM, MnCl$_2$ 5 mM, DTT 1 mM) without ATP, either in the absence (Control) or in the presence of SLN1, SLN10, or T12 at indicated concentrations for 10 minutes at RM, after which [γ-32P] ATP (Perkin Elmer) (0.132 μM) was added. Reaction cocktails (25 μL) were incubated at 30° C. for 15 minutes, and stirred (350 rpm); then, they were analyzed by Western blot and autoradiography (shown), and revealed using antibodies (not shown) to identify phosphorylated polypeptides. Arrows and lines to the right of the image show the identity of phosphorylated polypeptides. Upper images and those in the middle come from autoradiographs taken at several exposure times. It can be observed that while SLN1 activates GPBP phosphorylation, SLN10 and T12 inhibit it increasingly. GPBP inhibition rises in coordination with STRADα phosphorylation and LKB1 substrate. No marking is observed with 32P in the AMPKα subunit, a LKB1 substrate, because the AMPK used (Millipore) is already activated.

Figure 74A:
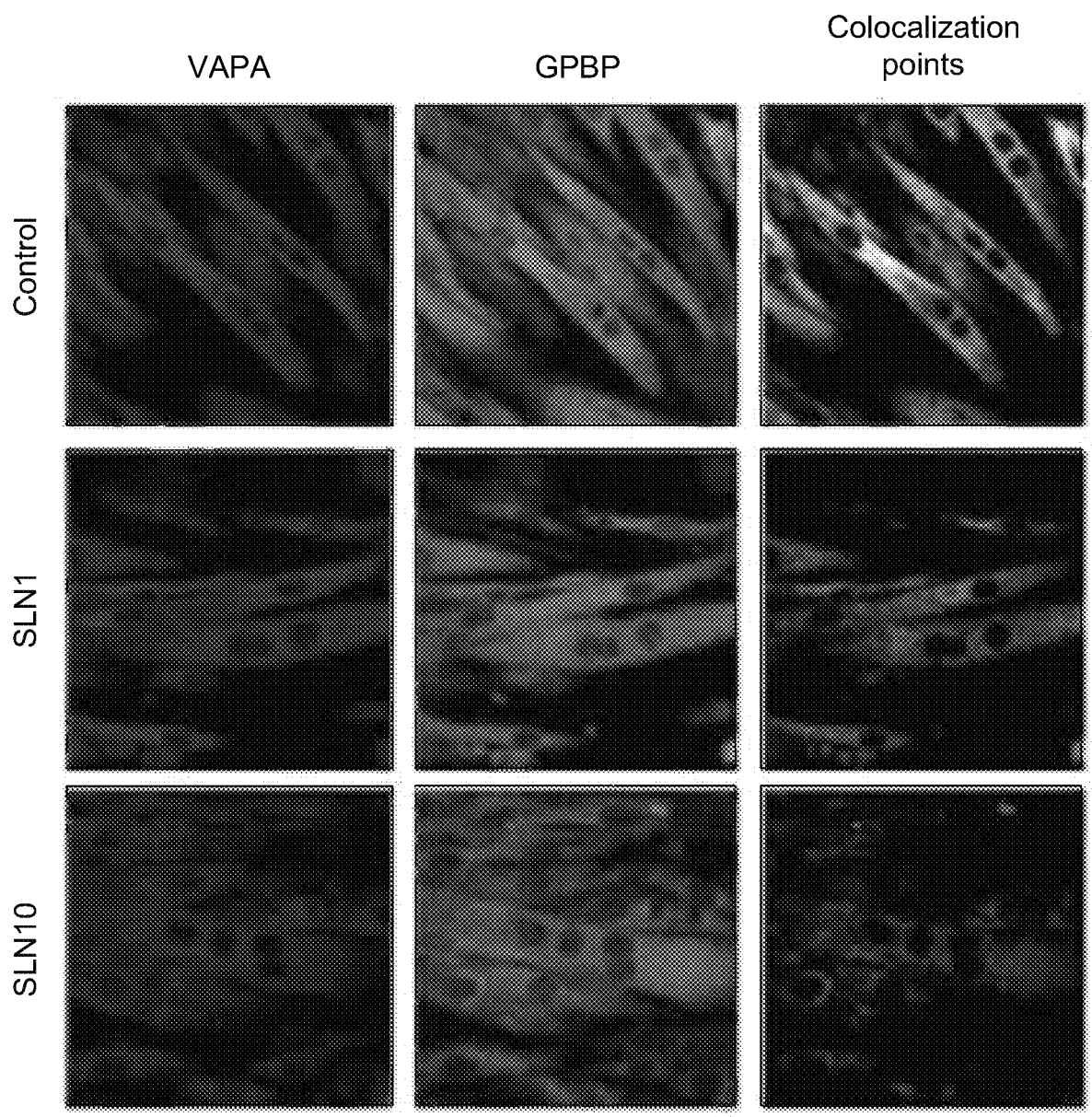

FIG. 74A. Metformin amino acid compounds, such as metformin lysinate (SLN10), reduce colocalization of GPBP with VAPA. In FIG. 74A, C2C12 cells were differentiated for 3 days in DMEM supplemented with 2% horse serum. For the last 16 hours of differentiation, cultures were treated with SLN1 or SLN10 10 mM, or with the corresponding vehicle; then, cells were washed, fixed, permeabilized, and blocked, as shown in FIG. 71, and incubated with mouse monoclonal anti-GPBP N27 antibodies and goat polyclonal anti-VAPA antibodies (Santa Cruz Biotechnology) for 2 hours at 37° C. in humidity chamber. Subsequently, cells were washed with PBS (3×5 minutes) and incubated with mouse secondary anti-IgG antibodies, conjugated with Alexa Fluor 488, and goat anti-IgG antibodies, conjugated with TRITC (Molecular Probes) for 1 hour at RM in the dark; then, cells were washed again with PBS (3×5 minutes) and mounted for confocal microscopy observation. Afterwards, the images obtained were analyzed with the WCIF ImageJ software to quantify colocalization quotient between GPBP and VAPA. In the third column, the points at which there are similar expression levels of both GPBP and VAPA appear in white.

Figure 74B:
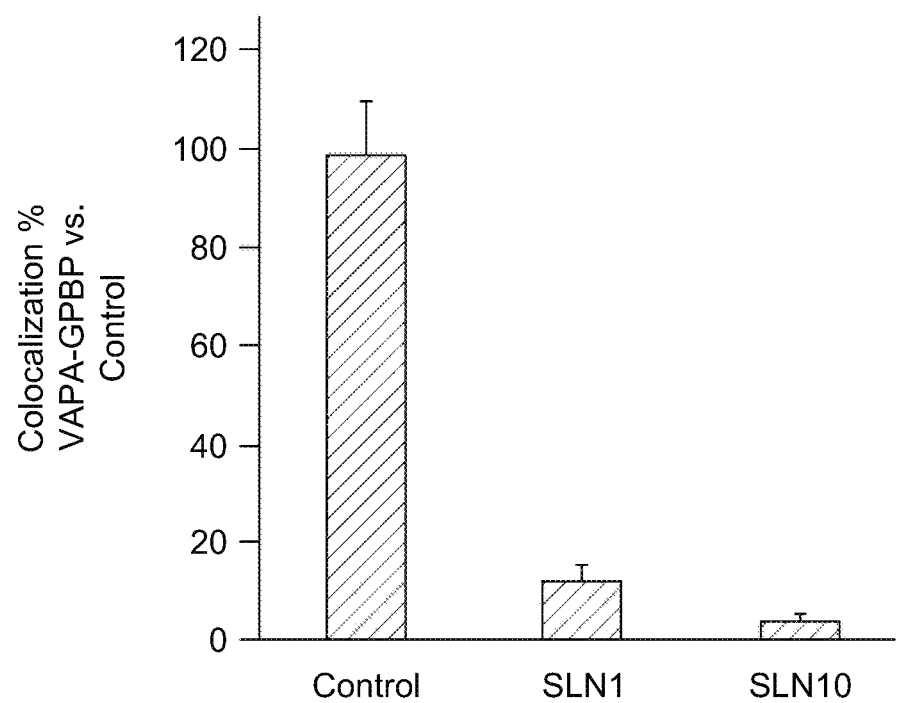

FIG. 74B. Shows a graph of the result of the quantitative analysis carried out with images obtained in FIG. 74A. The mean and standard deviations of the colocalization quotient, estimated with the WCIF ImageJ software for images of several non-treated cells (Control, n=2) and cells treated with SLN1 (n=2) or SLN10 (n=2), are shown. In cells treated with SLN1 or SLN10, colocalization of GPBP with VAPA was reduced significantly, compared with the one observed in control cells (p=0.0093 for Control vs. SLN1, p=0.0001 for Control vs. SLN10). SLN10 reduced colocalization between GPBP and VAPA more intensely than SLN1 (p=0.0283).

Figure 75:
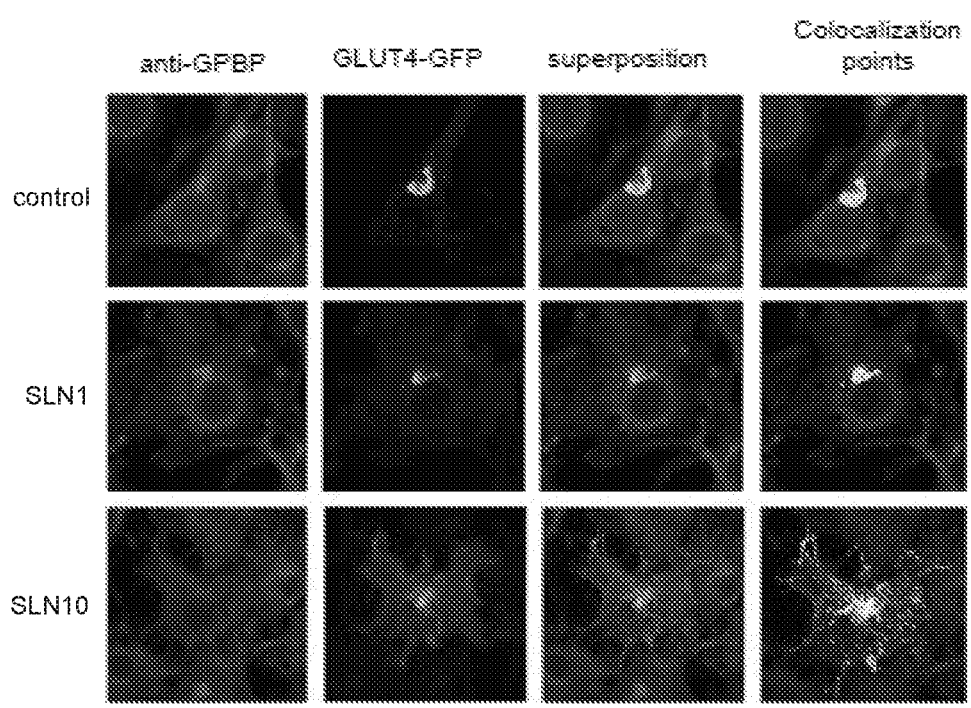

FIG. 75. Metformin amino acid compounds, such as metformin lysinate, induce GLUT4 transportation to plasma membrane. NIH-3T3-L1 cells were transfected with a construction expressing GLUT4 fused with Green Fluorescent Protein-GFP (Addgene). Transfected cells were selected by flow cytometry, taking advantage of GFP fluorescence, and cultured in DMEM supplemented with 10% FBS. Cultures were differentiated and treated as shown in FIGS. 70A-C, and prepared for confocal microscopy observation as shown in FIG. 71, using rabbit polyclonal anti-GPBP antibodies for 2 hours at 37° C. in humidity chamber, and rabbit secondary anti-IgG antibodies, conjugated with Alexa Fluor 647 (Molecular Probes) for 1 hour at RM in the dark. Images were analyzed with the WCIF ImageJ software to detect colocalization of GPBP (red) with GLUT4 (green). GLUT4-regulated transport stimulation to plasma membrane moved in decreasing order, SLN10 and SLN1, according to their capacity to inhibit GPBP kinase activity (vide supra FIGS. 74A-B).

Figure 76:
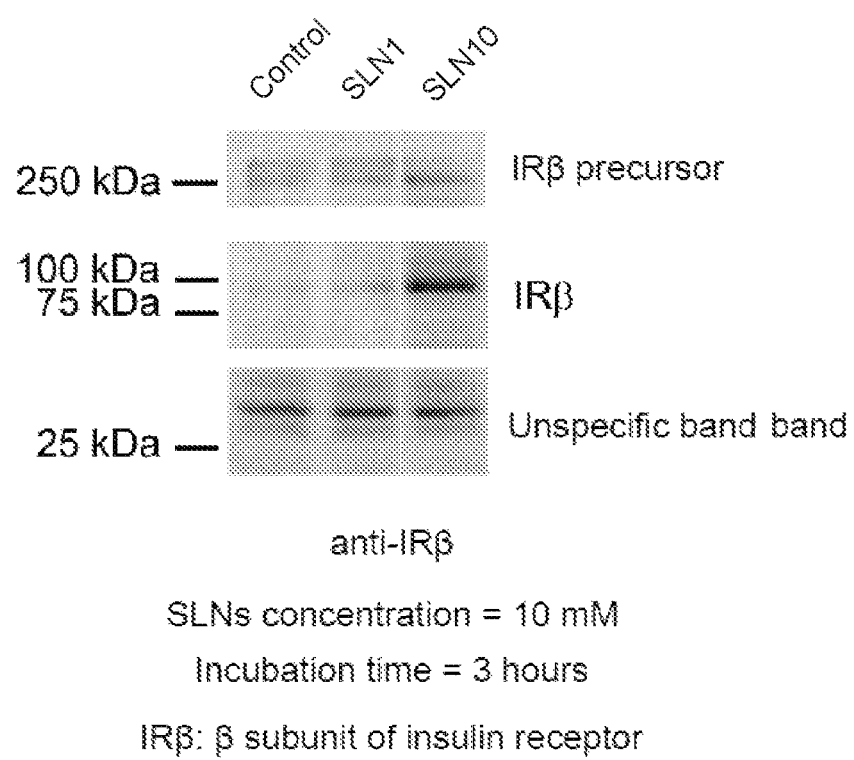

FIG. 76. Metformin lysinate promotes the accumulation of insulin receptor β subunit in plasma membrane. C2C12 cells were differentiated for 5 days in DMEM supplemented with 2% horse serum; then, cultures were treated for 3 hours with SLN1 or SLN10 10 mM, or with vehicle (control) at 37° C. Afterwards, cells were washed with PBS and their membrane proteins were extracted, as shown in FIG. 70B. Similar quantities of each extract were analyzed by Western blot with insulin receptor subunit (IRP) specific antibodies. SLN10 promotes the accumulation of insulin receptor in the plasma membrane, and it is expected that, consequently, they activate insulin pathways.

Figure 77:
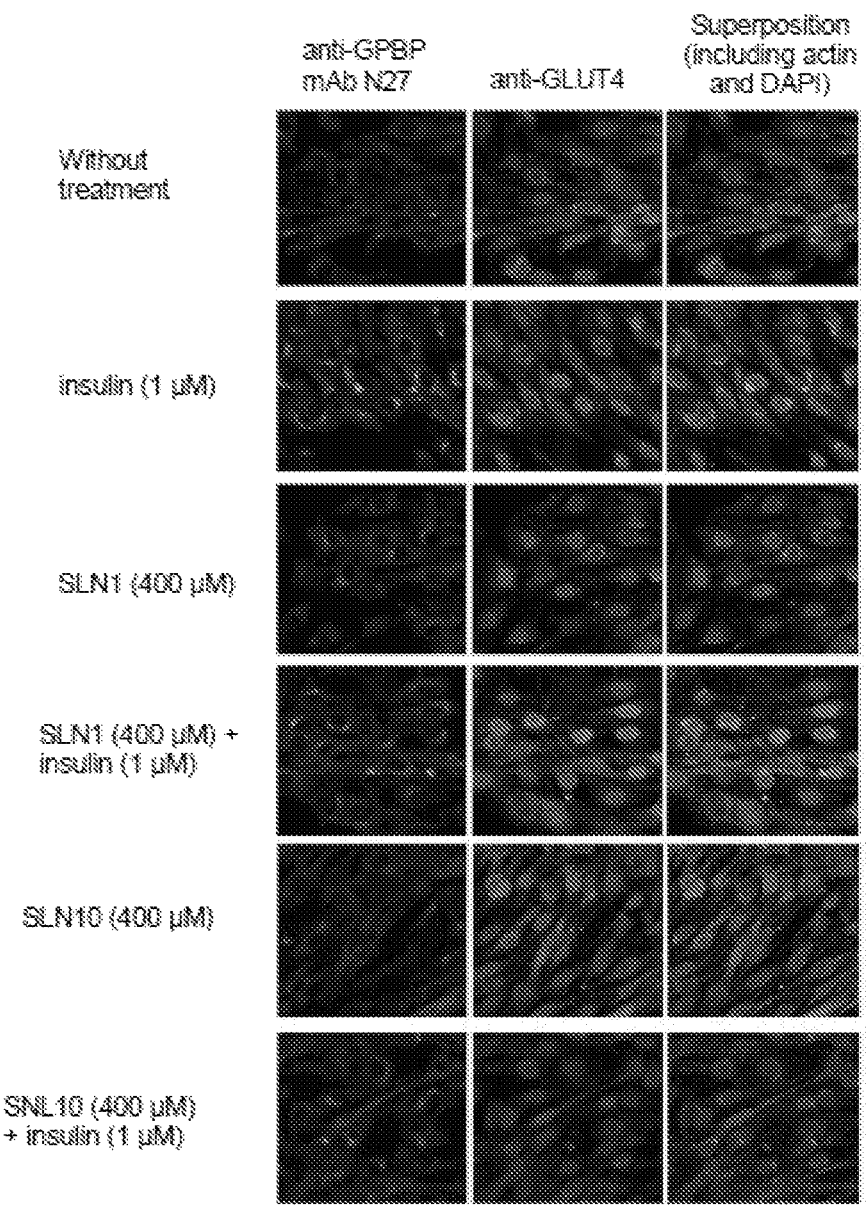

FIG. 77. Effects of no treatment, insulin, SLN1, SLN1 and insulin, SLN10, and SLN10 and insulin on GPBP-1 and GLUT-4 distribution in non-fused C2C12 cells after a 30 minute treatment.

Figure 78:
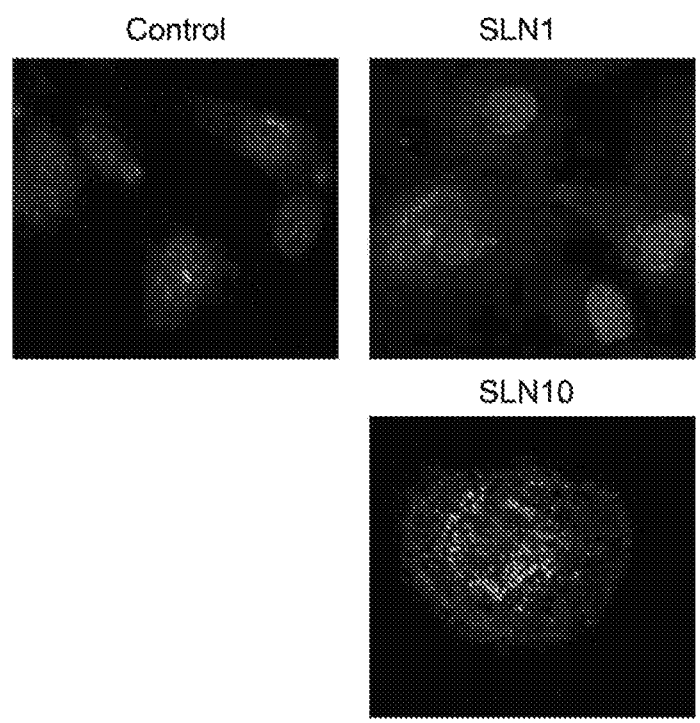

FIG. 78. C2C12 cells that expressed GLUT4-GFP constitutively were incubated with SLN1 or SLN10 10 mM, or with the corresponding vehicle (control), and GLUT4 distribution was analyzed by using immunofluorescence and confocal microscopy.

Figure 79:
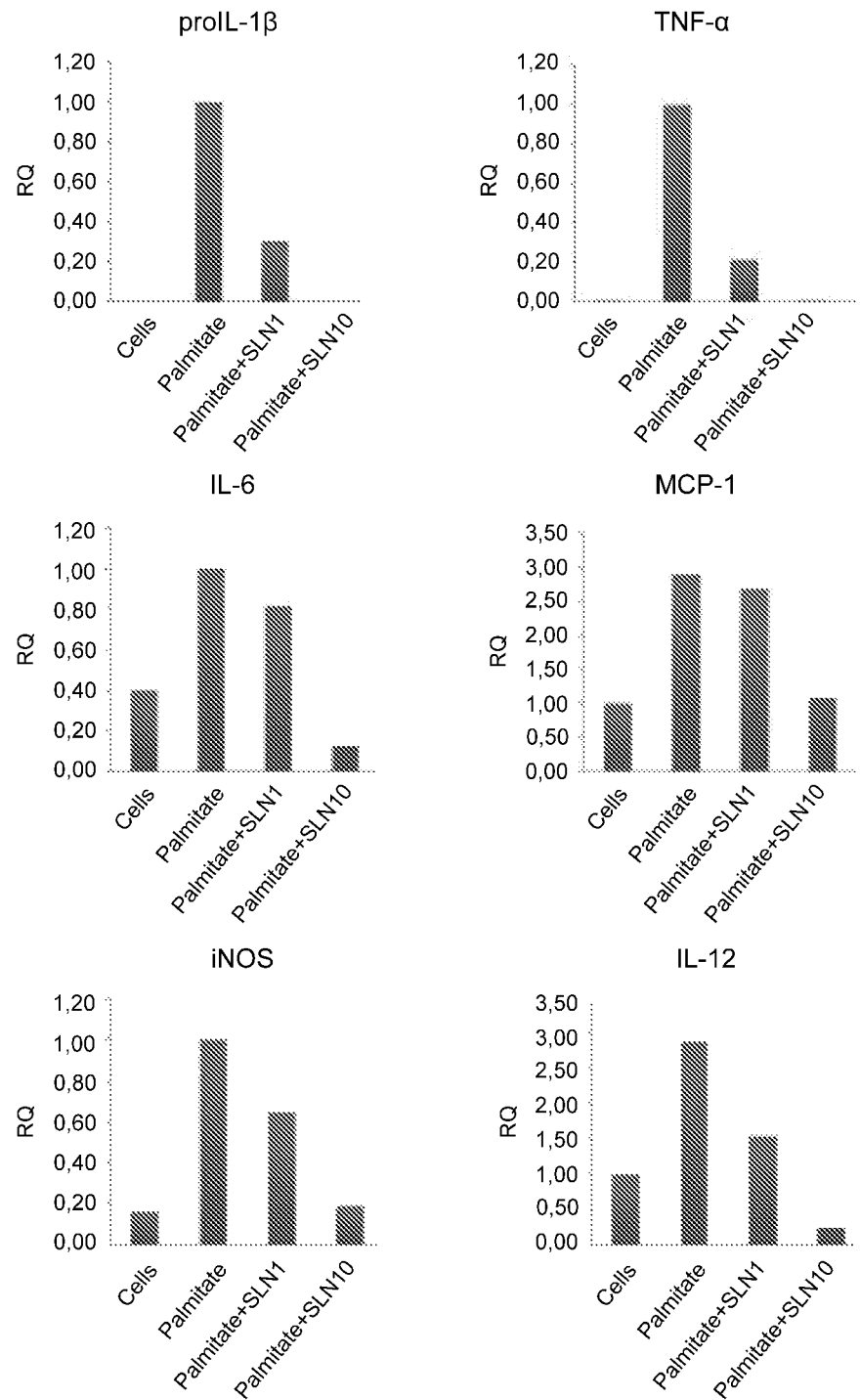

FIG. 79. Treatment with metformin amino acid compounds, such as metformin lysinate, reduce pro-inflammatory cytokines, with an efficacy that is consistent with their capacity to inhibit GPBP in vitro kinase activity. Differentiated L1 adipocytes (cells) were treated for 24 hours with palmitate (500 μM), either in the presence or in the absence of SLN1 or SLN10 (10 mM). Subsequently, the relative expression of inflammation markers was analyzed by RT and qPCR, using HPRT-1 as a normalizer and as a reference for expression levels of non-treated cells (MCP-1 and IL-12), and for those treated only with palmitate (proIL-1β, TNFα, iNOS, IL-6). Briefly, once finished, culture media treatments were collected for subsequent analysis, cells were washed with PBS, and RNA was extracted (illustra RNAspin Mini, GE Healthcare) and retro-transcribed (High Capacity cDNA Reverse Transcription Kit, Life Technologies); then, the genes under study were analyzed by using a quantitative PCR with specific probes (TaqMan® Gene Expression Assays, Life Technologies), estimating the relative quantification (RQ) with the ΔΔ Ct method.

Figure 80:
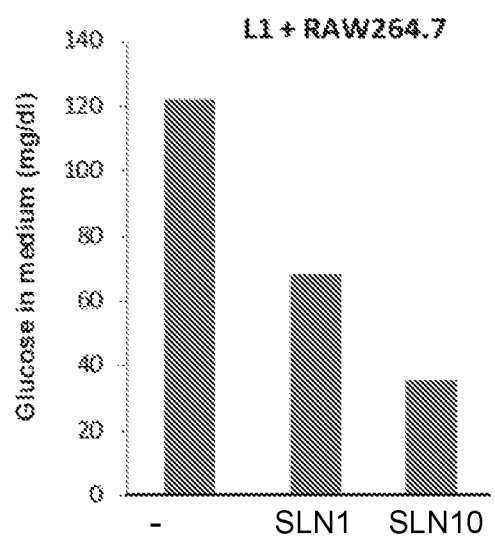

FIG. 80. Metformin amino acid compounds, such as metformin lysinate (SLN10), increase glucose consumption in macrophages and adipocytes cultures and co-cultures. RAW264.7 macrophages and L1 adipocytes co-cultures, obtained as shown in Table 6, and cultured in DMEM supplemented with 10% FBS and antibiotics, were treated with the indicated compounds (10 mM) for 30 hours, and glucose concentration after treatment was determined with a Glucocard (Arkray).

Figure 81:
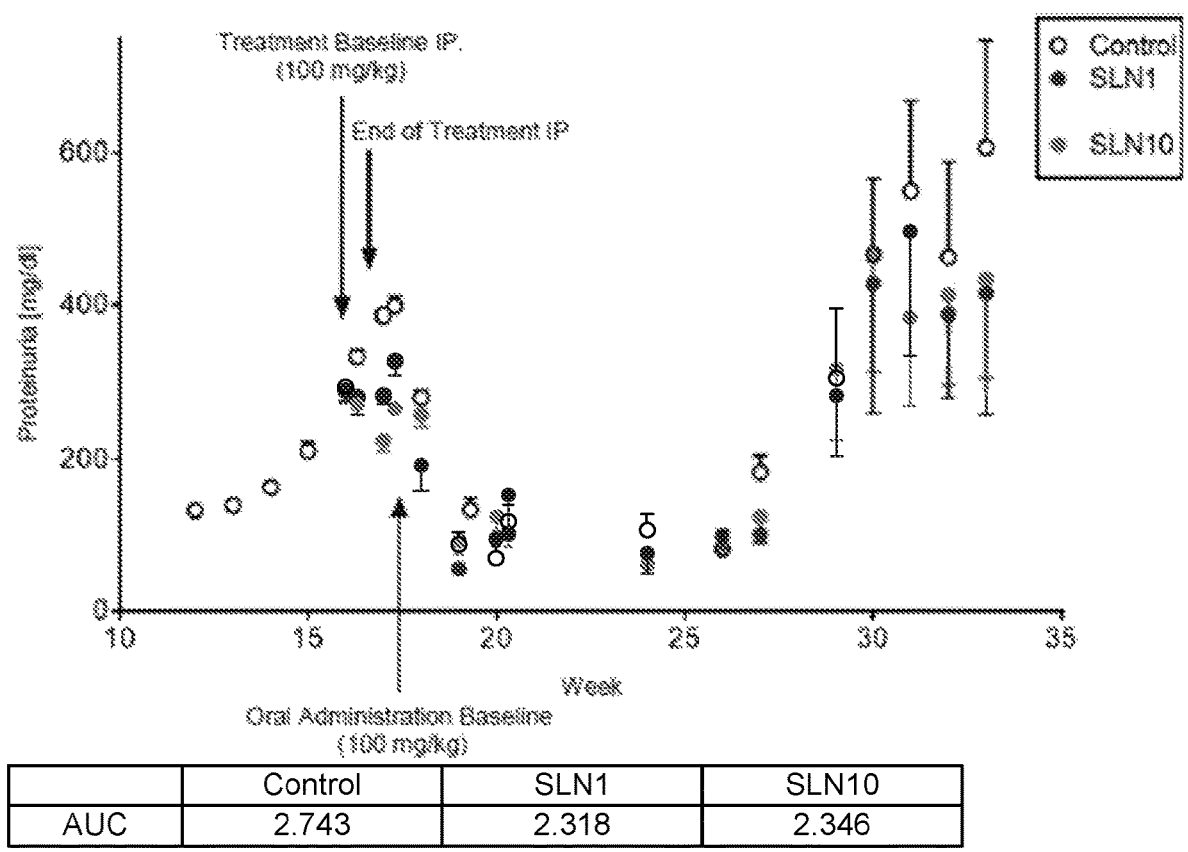

FIG. 81. Proteinuria evolution in (NZB×NZW) F1 mice, treated with a control, SLN1, and SLN10. F1 mice (NZB× NZW) were treated with SLN1 or SLN10 100 mg/kg/day in PBS, or with the vehicle (control), via intraperitoneal route (IP) for 5 days starting from week 16, and with 100 mg/kg/day of the same compounds, administered orally in drinking water starting from week 17, assuming that, on average, a baby mouse drinks 6 mL of water daily. Urine samples were taken periodically and protein concentration was determined. Proteinuria mean value (±SEM) for the mice groups mentioned above is shown in the graph. The Dunnett test shows that there are significant differences between the control group and SLN10 at week 31 (p<0.01). In the table below, areas under the curve (AUC) for each series from week 24, demonstrating greater efficacy for treatment with SLN10, are shown.

FIG. 82. Criteria used to determine the renal pathological grade in mice, by staining with haematoxylin-eosin.

Figure 83:
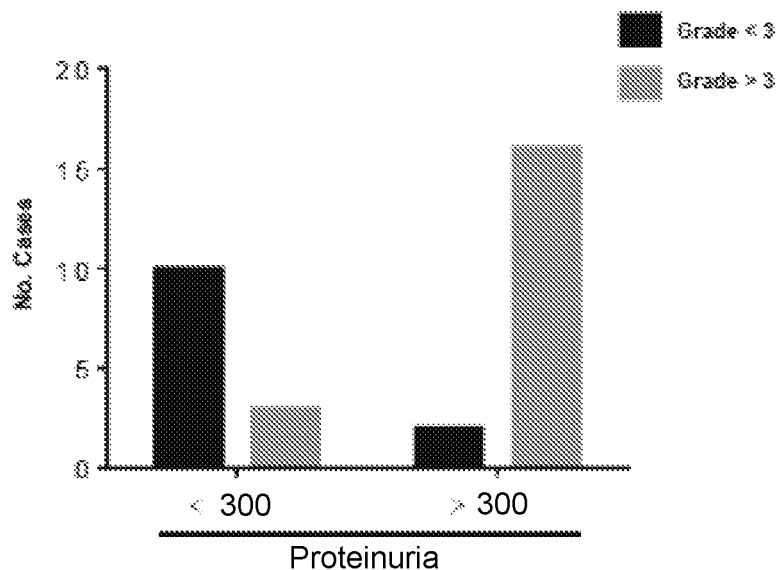

FIG. 83. (NZB×NZW) F1 mice with severe proteinuria show a high renal pathological grade. (NZB×NZW) F1 mice in the assay described in FIG. 81 were sacrificed at week 35; their kidneys were analyzed by staining with haematoxylin-eosin, and their pathological grade was estimated according to criteria in FIG. 82. The number of mice that developed low/moderate (<300 mg/dl) or high (>300 mg/dl) proteinuria at the end of the assay, classified according to their pathological grade, is shown. In FIG. 83, the chi-square test analysis showed that there is a significant correlation between proteinuria and pathological grade rates.

Figure 84:
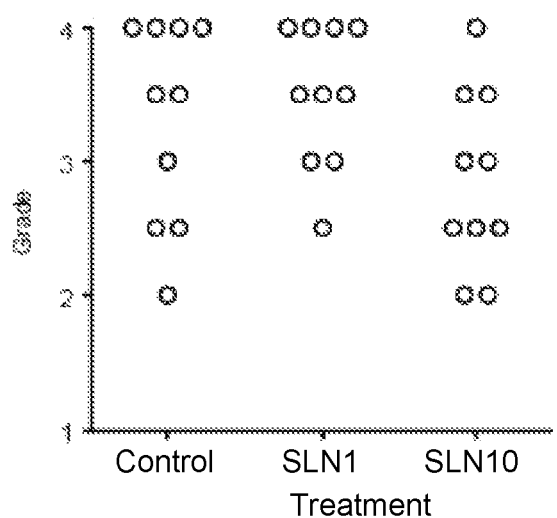

FIG. 84. Treatment with SLN10 reduces the number of mice with a renal pathological grade higher than 3. The renal pathological grade of each one of the mice in the assay described in FIG. 81, grouped according to treatment, is shown. Intermediate positions represent animals with renal lesions between the higher or lower grades.

Figure 85:
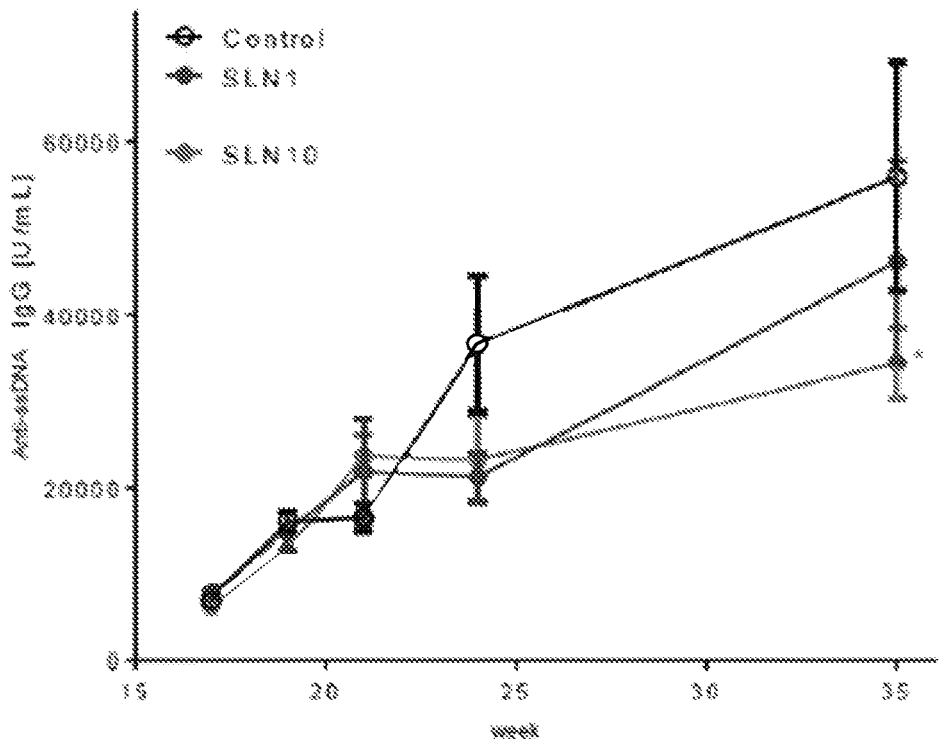

FIG. 85. Treatment with SLN10 reduces antibodies titers in (NZB×NZW) F1 mice. (NZB×NZW) F1 mice in the assay described in FIG. 81 were subjected to blood samples periodically, and antibodies titers (anti-ssDNA IgG) were determined using the Mouse anti-ssDNA ELISA kit (Alpha Diagnostic International), following the manufacturer's instructions. In the graph, the mean (±SEM) for each mice group over time is shown. A line was drawn to put together the points and see more clearly the evolution of all titers in each of the series. *Control vs. SLN10 p=0.0238 according to Dunnett test.

Figure 86:
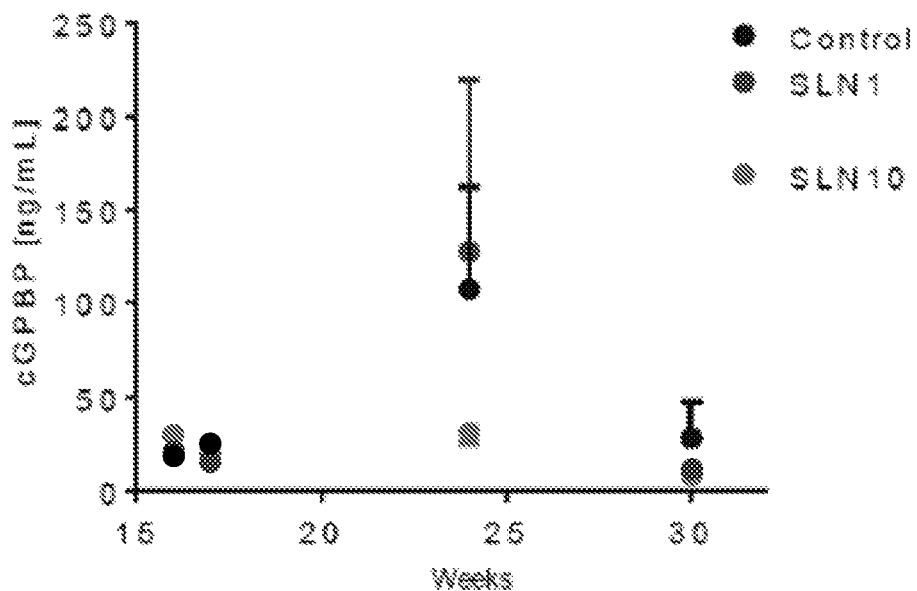

FIG. 86. cGPBP levels increase and decrease before the introduction of proteinuria in (NZB×NZW) F1 mice. The plasma of (NZB×NZW) F1 mice involved in the assay described in FIG. 81 was analyzed by the ELISA sandwich technique for cGPBP (Saus & Revert F, PCT/EP2009/005258; WO 2010/009856). Mean values (±SEM) for cGPBP in the mice groups during the indicated weeks.

Figure 87:
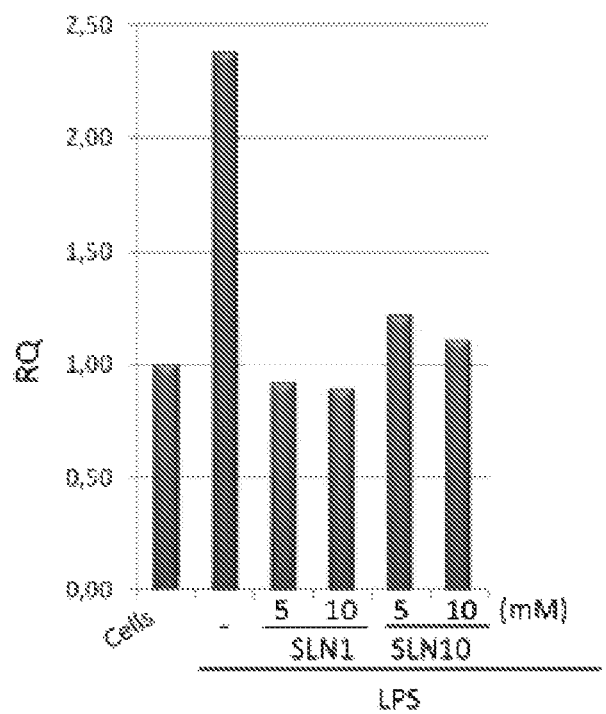

FIG. 87. Metformin amino acid compounds, such as metformin lysinate (SLN10), reduce the GPBP expression in RAW264.7 macrophages, stimulated with LPS. RAW264.7 macrophages cultured in DMEM, supplemented with 10% FBS and antibiotics, were treated with the indicated concentrations of either SLN1, SLN10 for 2 hours, after which LPS (1 µg/mL) was added to cultures. After incubating for 16 hours, the relative expression quantification (RQ) for GPBP was analyzed by RT-qPCR, using HPRT-1 as a normalizer and non-stimulated cells (cells) as a reference point.

Figure 88:
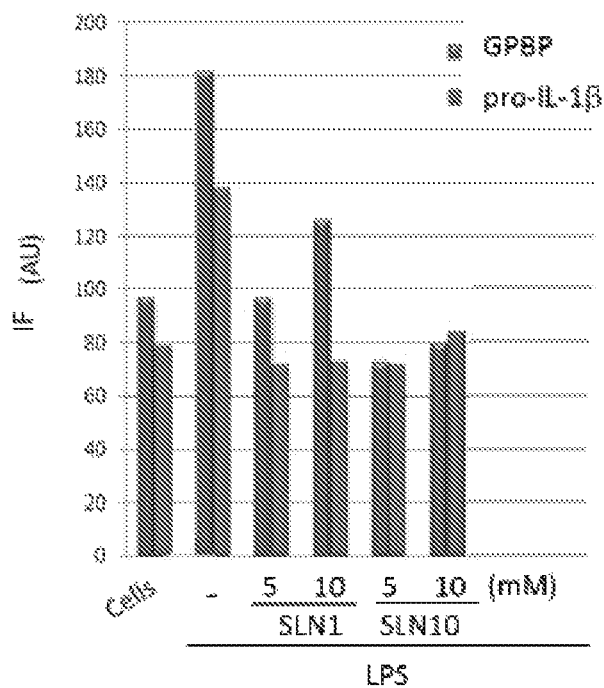

FIG. 88. Metformin amino acid compounds, such as metformin lysinate (SLN10), reduce GPBP and pro-IL-1β expression levels in RAW264.7 macrophages, stimulated with LPS. RAW264.7 macrophages were treated as shown in FIG. 87 and analyzed by flow cytometry, using for sample processing the Cytofix/Cytoperm (BD) kit, according to the manufacturer's instructions, as well as specific antibodies against GPBP (N27) and pro-IL-1β, conjugated with FITC and phycoerythrin (PE), correspondingly. The intensity of fluorescence (IF) emission median value is shown in arbitrary units (a.u.) for each of the series. Non-treated cells were used as a reference point and their corresponding isotype controls were carried out. The median is usually used in fluorescence quantitative studies to minimize the influence of extreme values that may distort the real mean value. Isotype controls were carried out to eliminate background, caused by nonspecific fluorescence; nonspecific antibodies from the same isotype of those used to detect GPBP and pro-IL-1β were used.

Figure 89A:
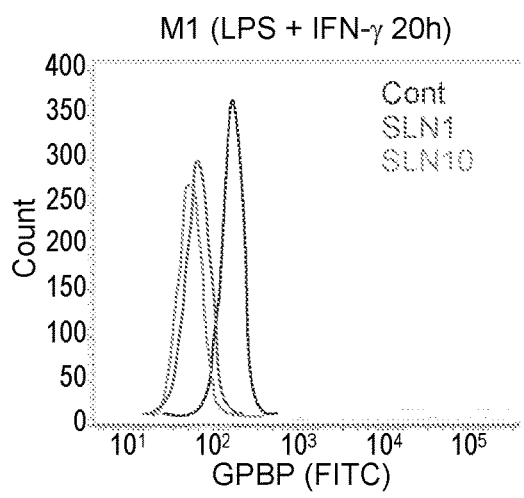
Figure 89B:
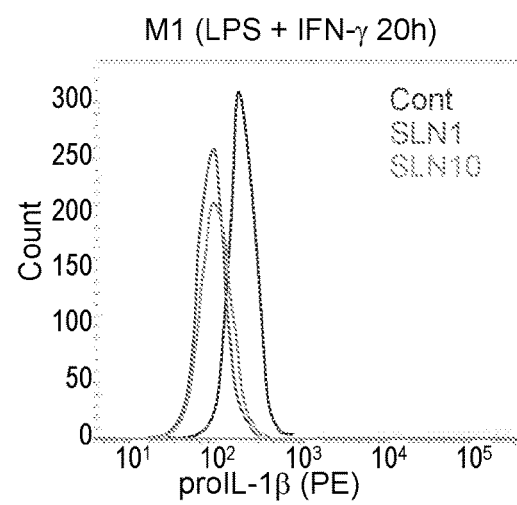

FIG. 89A-B. Metformin amino acid compounds, such as metformin lysinate (SLN10), reduce GPBP (FIG. 89A) and pro-IL-1β (FIG. 89B) levels in RAW264.7 cells, polarized to M1. RAW264.7 macrophages cultured in DMEM, supplemented with 10% FBS and antibiotics (cont.), were treated with 10 mM of SLN1 or SLN10 for 2 hours, after which LPS (0.5 µg/mL) and IFN-γ (20 ng/mL) were added to cultures. After 20 hours of incubation, cells were analyzed by flow cytometry, as shown in FIG. 88.

Figure 90A:
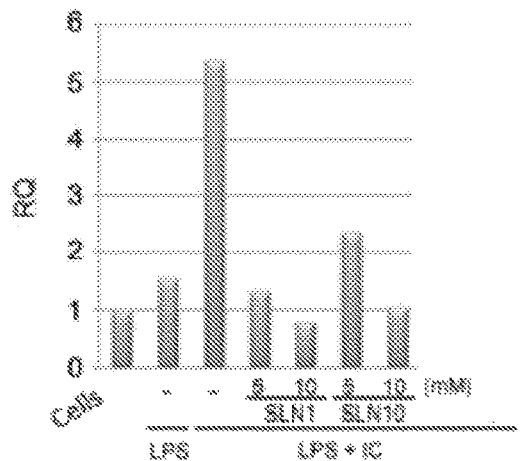
Figure 90B:
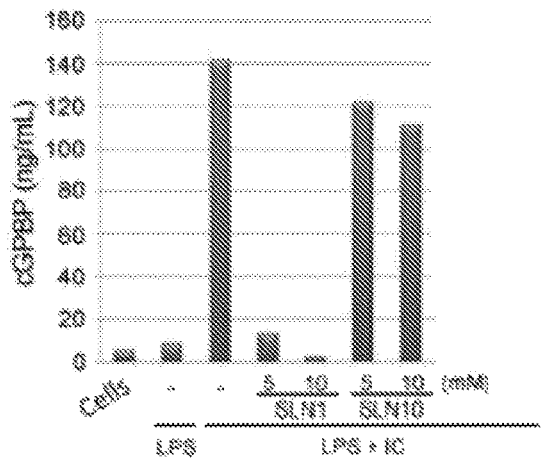

FIG. 90A-B. SLN10 reduces unevenly GPBP expression and secretion in RAW264.7 cells, stimulated with LPS and IC. FIG. 90A is a graph of RAW264.7 macrophages cultured in DMEM, supplemented with 10% FBS and antibiotics, were treated with the indicated concentrations of either SLN1 or SLN10 for 2 hours, after which LPS (1 µg/mL) was added to cultures. After incubating for 16 hours, IC was added. Following an additional incubation of 8 hours, cells were processed as shown in FIG. 79 for quantitative RT-PCR analysis, and the relative expression quantification (RQ) for GPBP was also analyzed using HPRT-1 as a normalizer and non-treated cells (cells) as a reference point. FIG. 90B is a graph of GPBP concentration in culture media of cells used in FIG. 90A that was determined by the ELISA sandwich technique for cGPBP (Saus J & Revert F, PCT/EP2009/005258; WO 2010/009856). For IC stimulation, sheep erythrocytes (Sigma Aldrich) were suspended in a Hanks (Sigma Aldrich) balanced salt solution mixture (1:1) and in 0.1 M EDTA, pH 7.4; then, they were opsonized with rabbit anti-sheep red blood cell (anti-SRBC, Sigma Aldrich) antibodies, to non-agglutinating titers, for 30 minutes at 37° C. Opsonized sheep erythrocytes (IC) were washed with Hanks (Sigma Aldrich) balanced salt solution, precipitated, and re-suspended in culture medium. The resulting IC were added to RAW264.7 cells, previously treated with SLNs and LPS, at a proportion of 10 sheep erythrocytes per macrophage.

Figure 91:
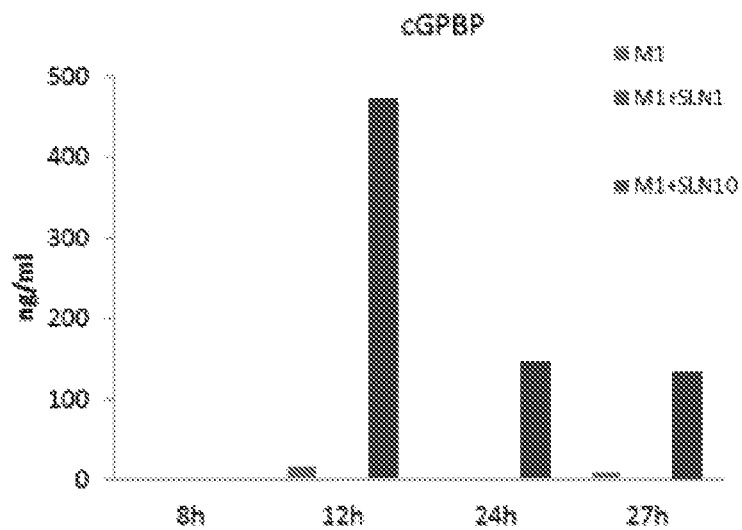

FIG. 91. SLN10 induces cGPBP secretion in RAW264.7 macrophages stimulated with LPS and IFN-γ. RAW264.7 macrophages were treated for 2 hours with SLN1 or SLN10 (10 mM), after which LPS (0.5 µg/mL) and IFN-γ (20 ng/mL) (M1) were added to culture media. At the indicated times, samples were taken from the culture media and the cGPBP concentration was determined by ELISA sandwich technique for cGPBP (Saus J& Revert F, PCTIEP2009/005258, WO 2010/009856).

Figure 92:
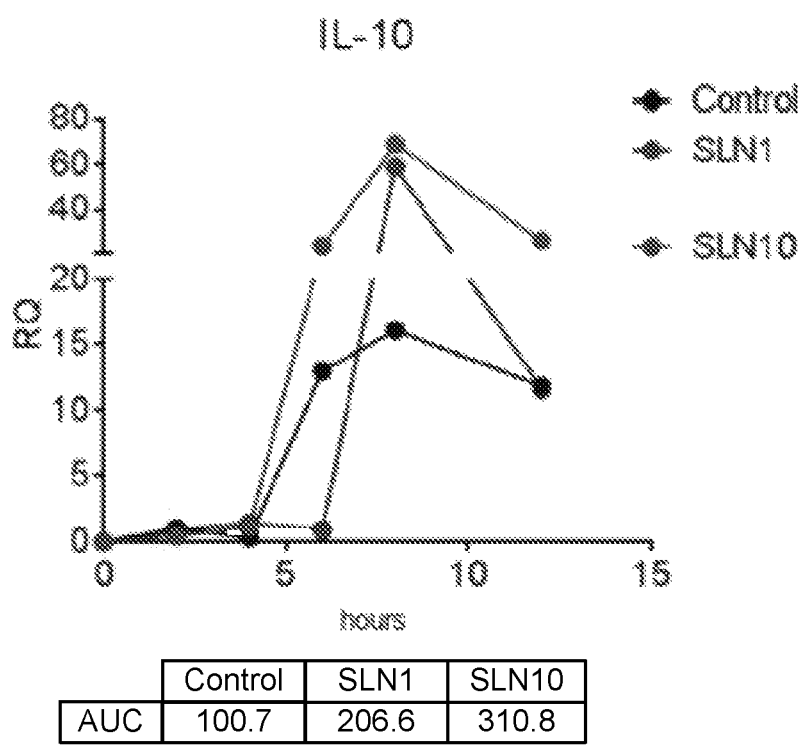

FIG. 92. SLN10 and SLN1 increase IL-10 expression in RAW264.7 macrophages, stimulated with LPS and IFN-γ. RAW264.7 macrophages were treated for 2 hours with SLN1 or SLN10 (10 mM), after which, LPS (0.5 µg/mL) and IFN-γ (20 ng/mL) (M1) were added to culture media. After several incubation times, cells were processed as shown in FIG. 79 for RT-qPCR analysis, and IL-10 relative quantification (RQ) was determined with a specific probe (Taqman®, Life Technologies) using HPRT-1 as a normalizer and non-stimulated cells as a reference point (time 0). In the Table in FIG. 92, the area under the curve (AUC) is indicated for each of the series.

FIG. 93. The IL-10 expression depends on GPBP-1. RAW264.7 1 (WT) macrophages with a reduced GPBP-1 expression (pSi-GPBP-1) were either non-treated (control)

or treated with SLN1 or SLN10 (10 mM) for 2 hours, and stimulated with LPS (0.5 µg/mL) and IFN-γ (20 ng/mL). After 8 hours, the IL-10 relative expression quantification (RQ) in cells was determined by RT-qPCR analysis, as shown in FIG. 79, using HPRT-1 as a normalizer and non-stimulated cells as a reference point. pSi-GPBP-1 macrophages were obtained by transfecting (Lipofectamine 2000, Life Technologies) RAW264.7 cells with a construction (pSi-GPBP-1) obtained with the pSilencer vector (Life Technologies), which expressed a short hairpin (sh)-RNA that inhibited specifically the isoform GPBP-1, and the corresponding antibiotic selection. The silencing efficacy was tested by Western blot with RAW264.7 (WT) and pSi-GPBP-1 cell lysates (50 µg), using specific antibodies (right).

FIG. 94. The IL-10 expression depends on cGPBP-1. In A, an assay scheme is shown; it was carried out specifically: RAW264.7 macrophages treated with 10 mM SLN10 for 2 hours were then stimulated with LPS (0.5 µg/mL) and IFN-γ (20 ng/mL) for 16 hours, resulting in a conditioned medium, where cGPBP levels were approximately 200 ng/mL (not shown). Subsequently, new RAW264.7 macrophages with the conditioned medium were cultured either in the presence or absence of a monoclonal antibody against cGPBP (αGPBP), and IL-10 expression in cultures was determined by RT-qPCR, as shown in FIG. 79, using a specific probe (Taqman®, Life Technologies). In B, the relative expression of IL-10 in RAW264.7 macrophages cultured with conditioned media, obtained as specified in A, is shown. The analysis was carried out by quantitative RT and PCR, using HPRT-1 as a normalizer. In this case, the reference point were cells treated with a conditioned medium in absence of N26 (RQ=1 value), and the increased IL-10 expression was verified; the analysis included non-stimulated cells cultured in a fresh, non-conditioned medium (cells).

Figure 95:
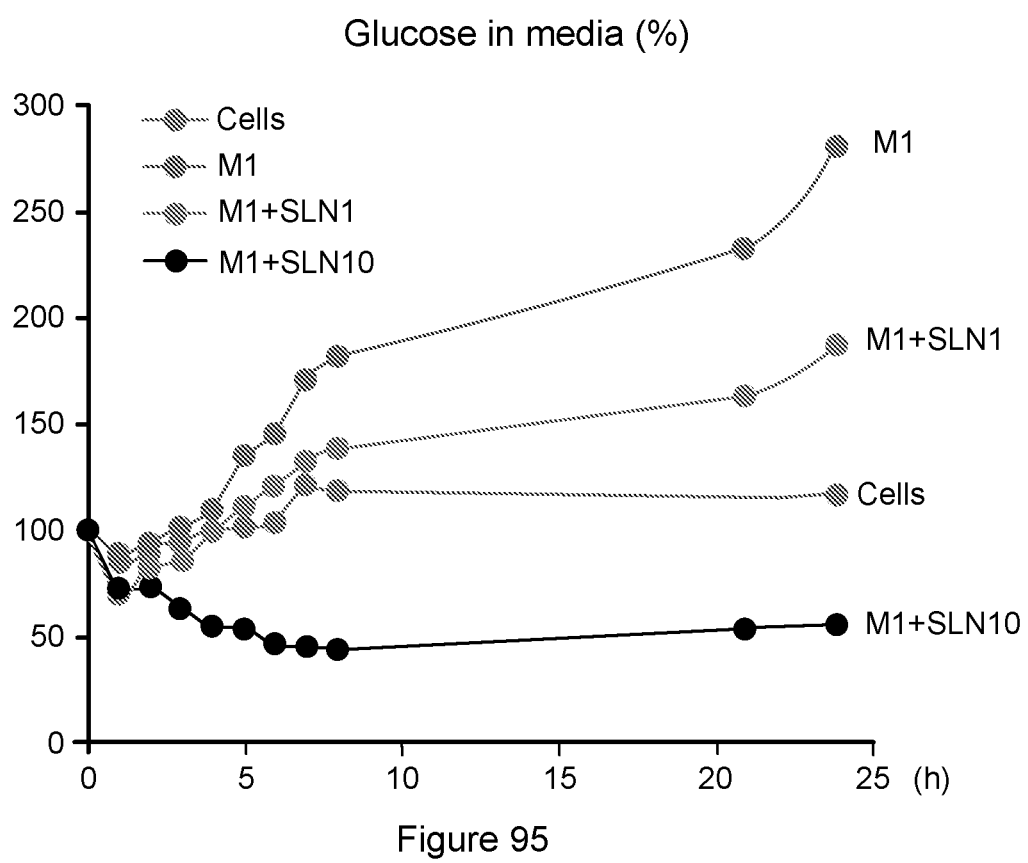

FIG. 95. C2C12 myotubes, treated with a conditioned RAW264.7 M1 macrophages medium (stimulated with LPS and IFN-γ [M1]), accumulate glucose in the culture medium: SLN compounds reduce the "hyperglycemic" effect of the M1 medium. RAW264.7 macrophages were treated with SLN1 or SLN10 (10 mM) for 2 hours and then stimulated with LPS (0.5 µg/mL) and IFN-γ (20 ng/mL) for 16 hours; then, the culture media were collected, and their glucose concentration adjusted to 100 mg/100 mL and used to culture C2C12 myoblasts that had been previously differentiated to myotubes in DMEM supplemented with 2% horse serum for 5 days. The glucose concentration in myotubes was determined at several times with a Glucocard (Arkray). C2C12 myotubes, cultured with conditioned media of non-stimulated (cells) macrophages, or similarly stimulated but not treated with a SLN (M1), were used as controls. The initial glucose levels (time 0) are used as a reference (100%) in each of the series.

Figure 96:
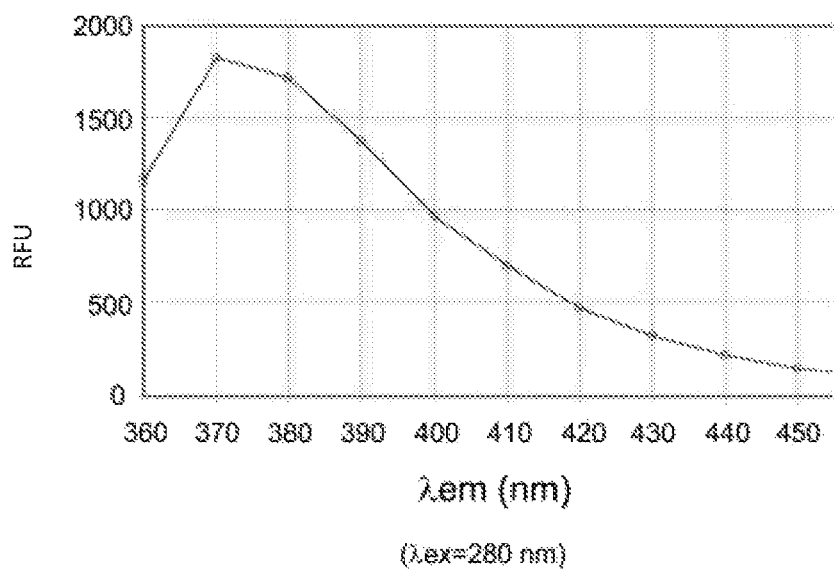

FIG. 96. GPBP fluorescence emission spectrum. The fluorescence emission spectrum of a 1 µM GPBP dissolution in PBS for a 280 nm excitation wavelength is shown; RFU: relative fluorescence units.

Figure 97:
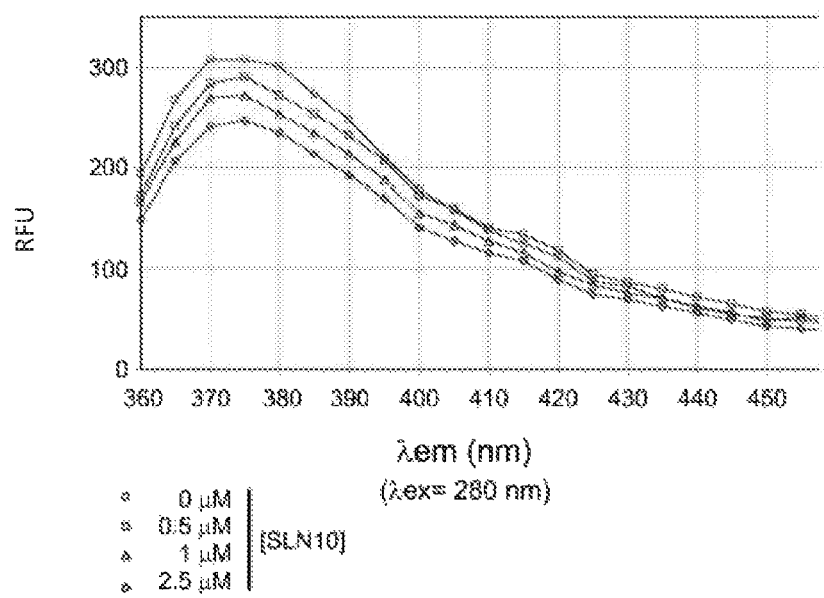

FIG. 97. The presence of SLN10 reduces GPBP fluorescence emission. The fluorescence emission between wavelengths of 360 and 500 nm of GPBP dissolved in 1 µM PBS with the indicated concentrations of SLN10, exciting at 280 nm, is shown. RFU: relative fluorescence units.

Figure 98:
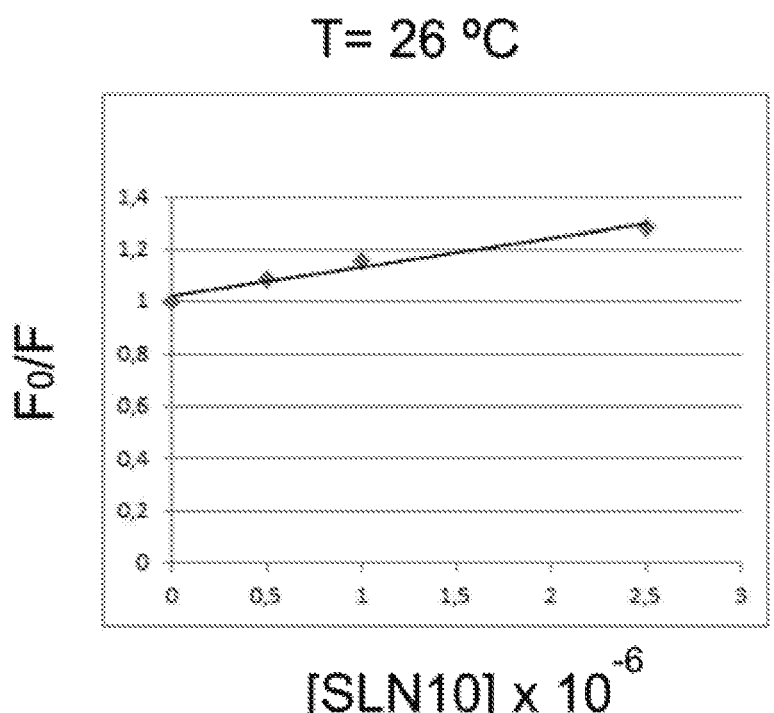

FIG. 98. Representation of the ratio of the fluorescence emission of the fluorophore (F0) with that of the fluorophore in the presence of the quencher molecule (F) (F0/F) versus concentration of SLN10 to estimate Ksv.

Figure 99:
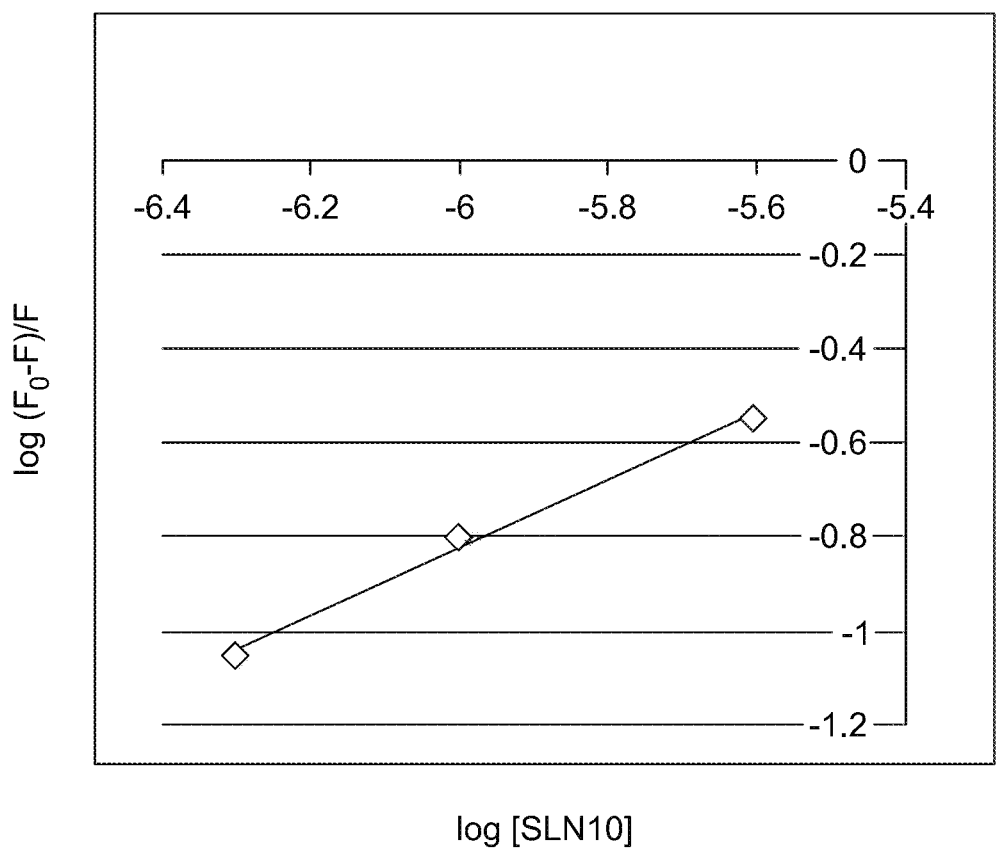

FIG. 99. Representation of log (F0−F)/F versus log of the concentration of SLN10 to estimate Ka.

Figure 100:
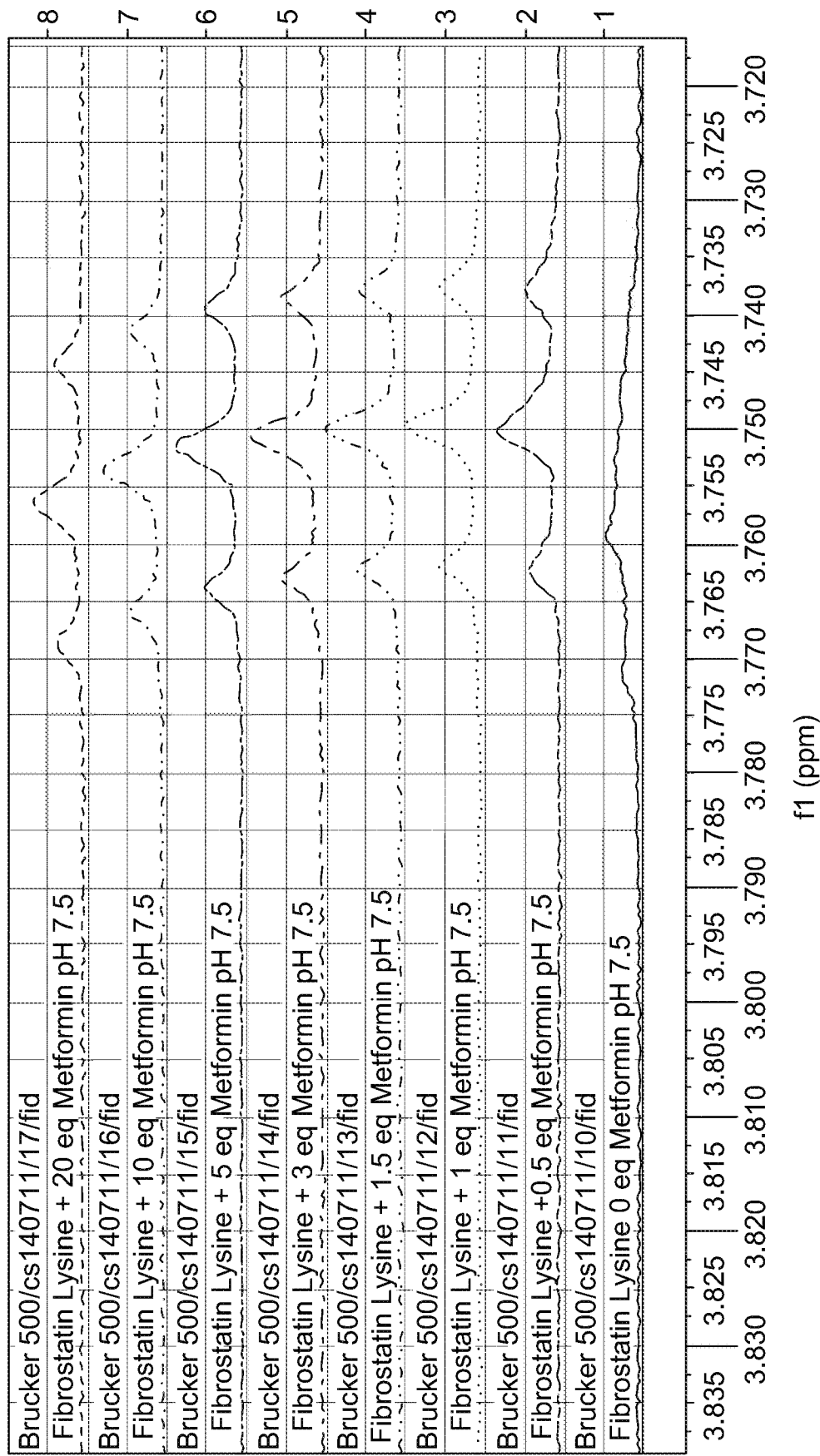
Figure 100:
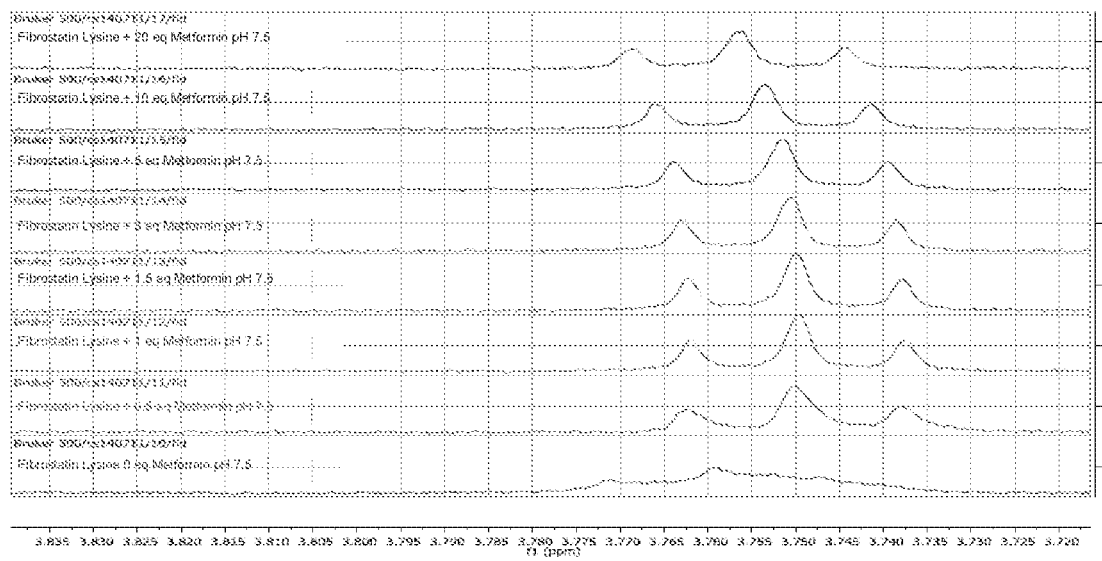

FIG. 100. Lysine alpha proton signal amplification framed in $^1$H RMN spectra.

Figure 101:
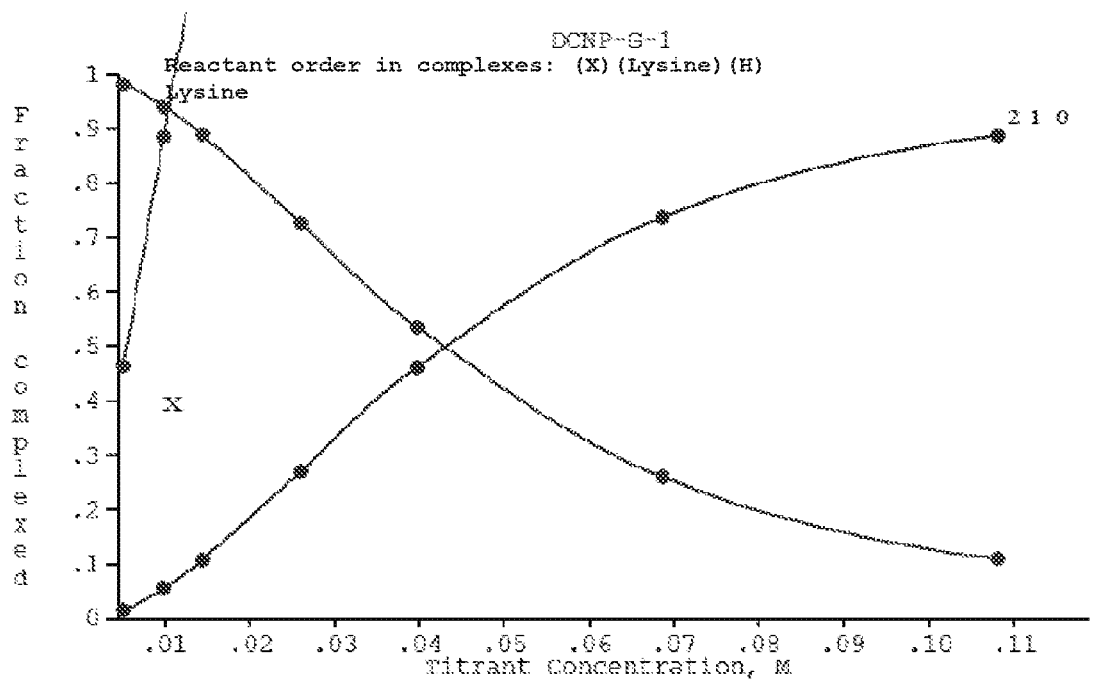

FIG. 101. Metformin association with lysine in aqueous solutions. Molar fractions of lysine (red) complex, according to the titrant concentration (metformin), estimated by the WINEQNMR2 software.

Figure 102:
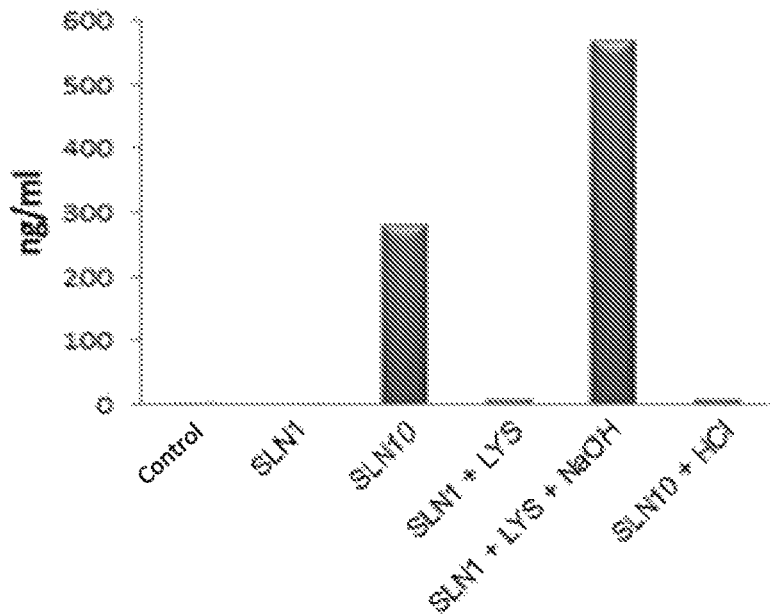

FIG. 102. The biological activity of SLN10 may be reproduced in an equimolar mixture of metformin hydrochloride, lysine, and NaOH. RAW264.7 cells were treated for 2 hours with: 1) vehicle (Control), 2) SLN1, 3) SLN10, 4) SLN1 and Lys, 5) SLN1, Lys, and NaOH, or 6) SLN10 and HCl, all of them in concentrations of 10 mM; then, they were stimulated with LPS (0.5 µg/mL) and IFN-γ (20 ng/mL) for 16 hours, after which the GPBP concentration in culture media was determined by ELISA. Results suggest that when dissolved, SLN10 forms a metformin lysine complex with its own biological activity, clearly different from that of metformin hydrochloride (SLN1).

Figure 103:
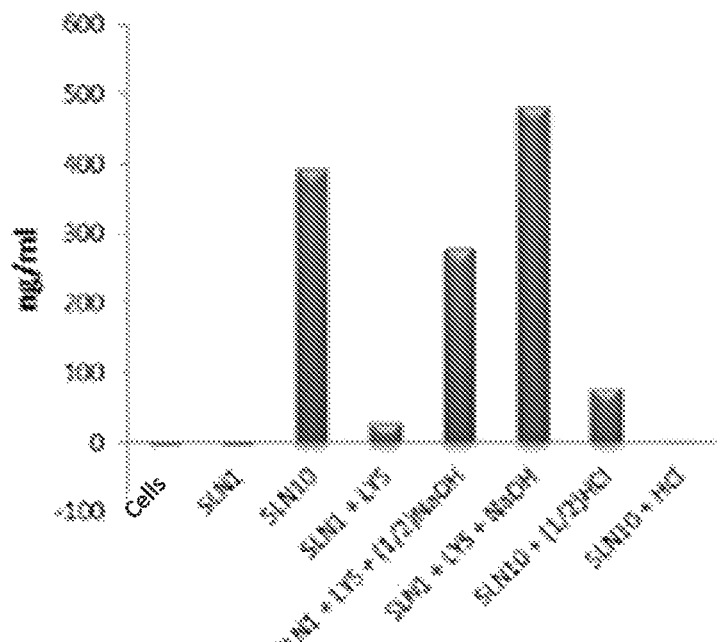
Figure 103:
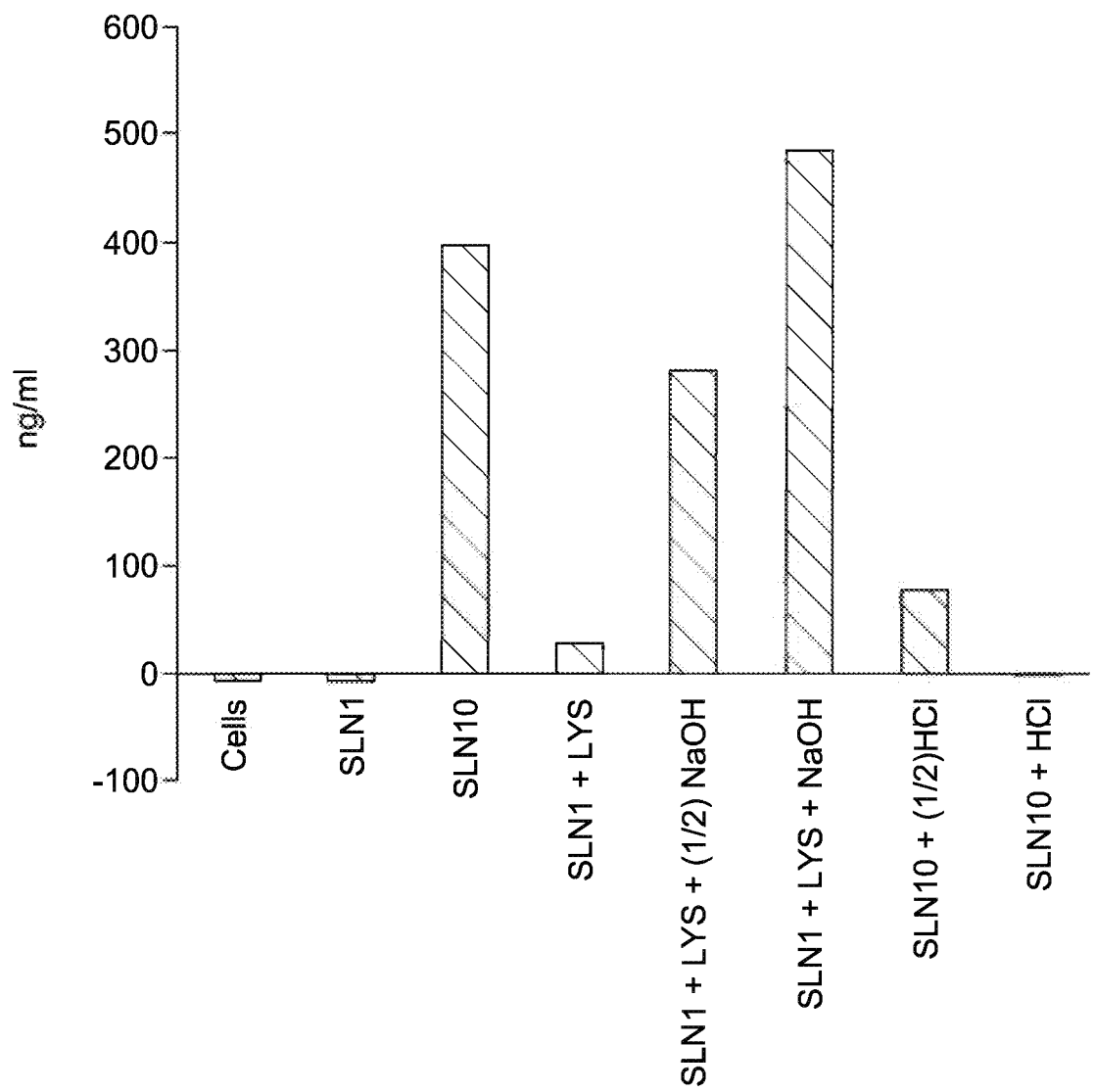

FIG. 103. The biological activity of SLN10 may be modulated by adding non-equimolar quantities of HCl and NaOH. RAW264.7 cells were treated for 2 hours (left to right) with: 1) vehicle (cells), 2) 10 mM SLN1, 3) 10 mM SLN10, 4) 10 mM SLN1+10 mM Lys, 5) 10 mM SLN1+10 mM Lys+5 mM NaOH, 6) 10 mM SLN1+10 mM Lys+10 mM NaOH, 7) 10 mM SLN10+5 mM HCl, or 8) 10 mM SLN10+10 mM HCl; then, they were stimulated with LPS (0.5 µg/mL) and IFN-γ (20 ng/mL) for 16 hours, after which the GPBP concentration in culture media was determined by ELISA.

Figure 104:
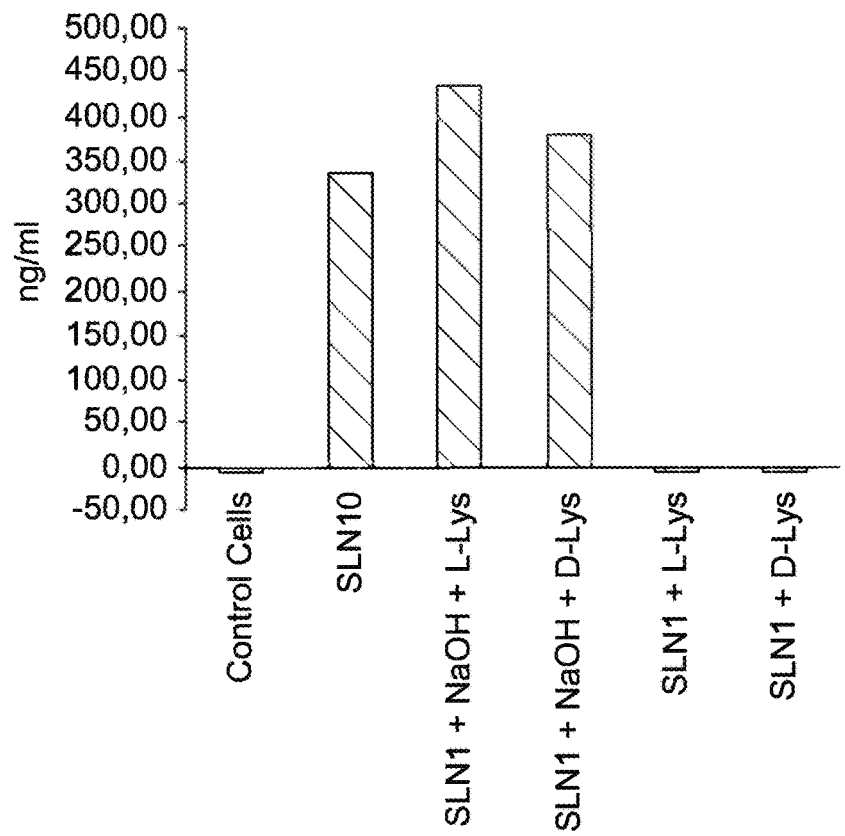

FIG. 104. The lysine side chain position in SLN10 does not determine its biological activity. RAW264.7 cells (control cells) were treated as indicated (10 mM) for 2 hours and subsequently stimulated with LPS (0.5 µg/mL) and IFN-γ (20 ng/mL) for 16 hours; then, the GPBP concentration in culture media was determined by ELISA. Both L-Lys and its enantiomer, D-Lys, produce SLN10 with a similar biological activity.

Figure 105:
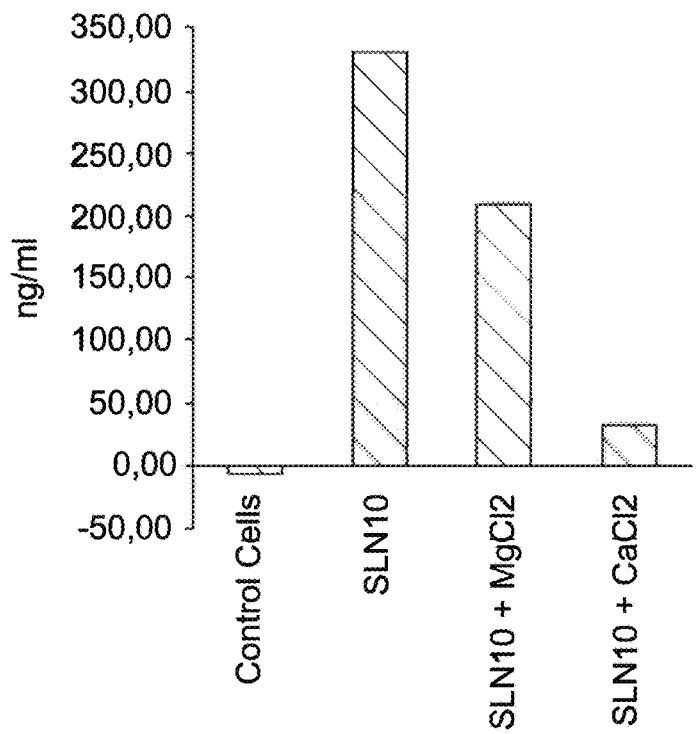

FIG. 105. Both $Mg^{2+}$ and $Ca^{2+}$ reduce the biological activity of SLN10. RAW264.7 cells (control cells) were treated either with 10 mM SLN10 for 2 hours or with 10 mM SLN10 together with equimolar quantities of $MgCl_2$ or $CaCl_2$, and subsequently stimulated with LPS (0.5 µg/mL) and IFN-γ (20 ng/mL) for 16 hours; then, the GPBP concentration in culture media was determined by ELISA.

Figure 106:
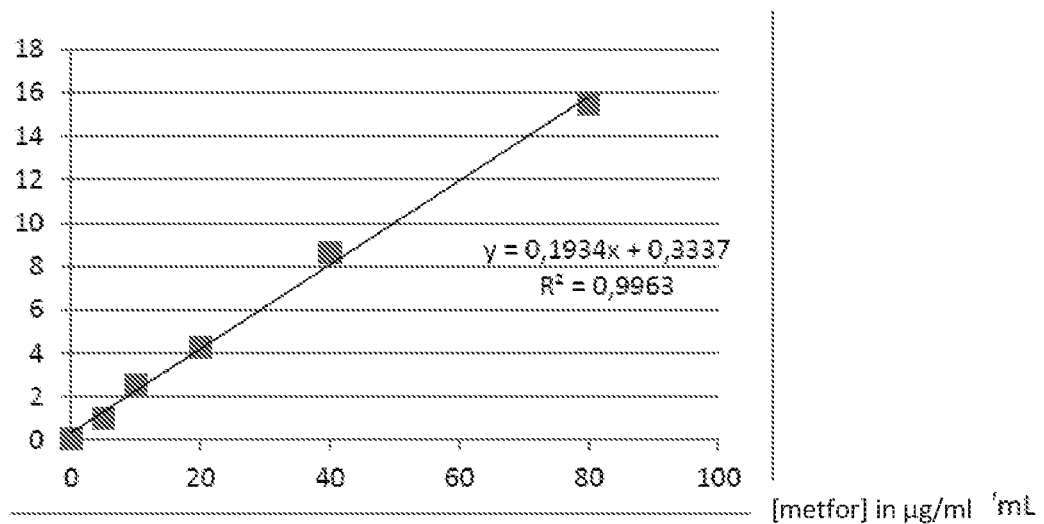

FIG. 106. Metformin calibration curve.

Figure 107:
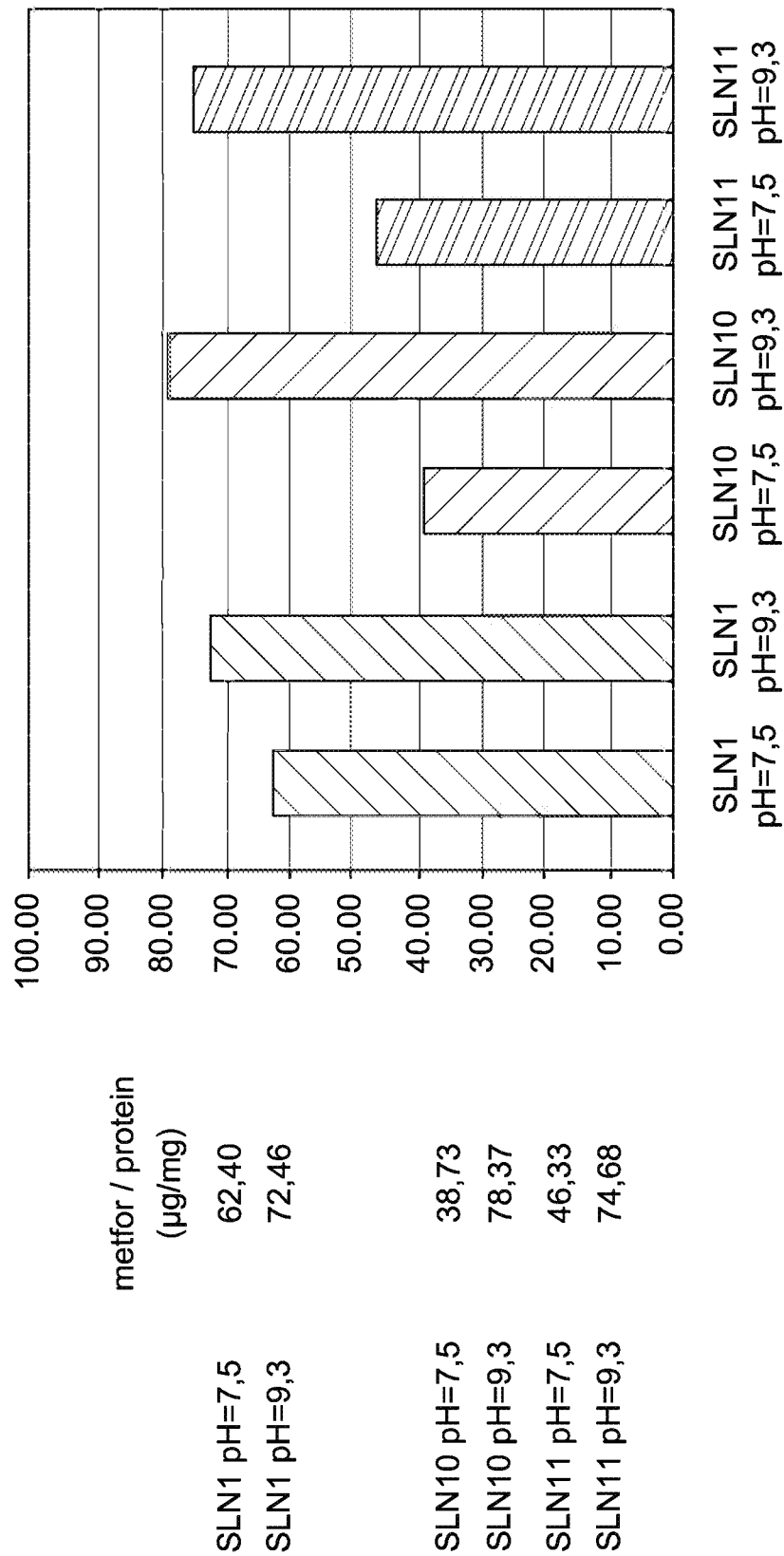
Figure 107:
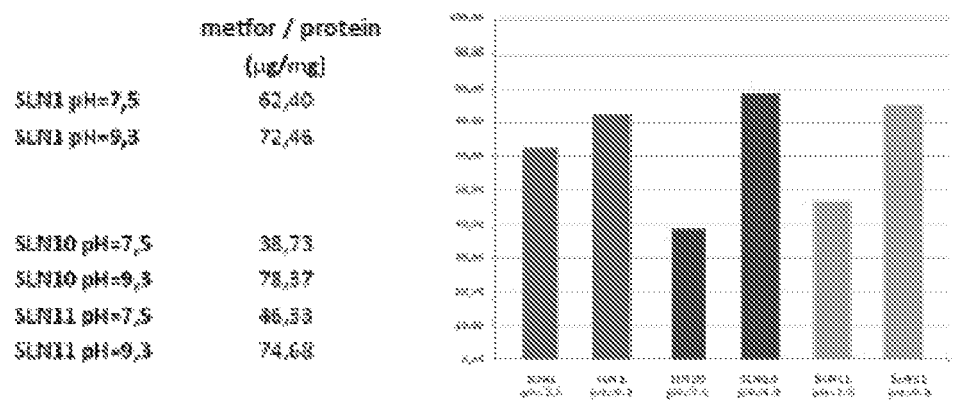

FIG. 107. Metformin quantification in A549 cells exposed to treatment as indicated.

Figure 108:
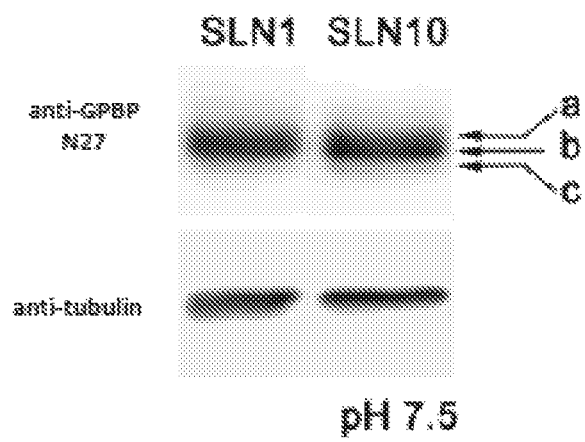

FIG. 108. Treatment with SLN10 at pH 7.5 reduces molecular weight in GPBP (I).

Figure 109:
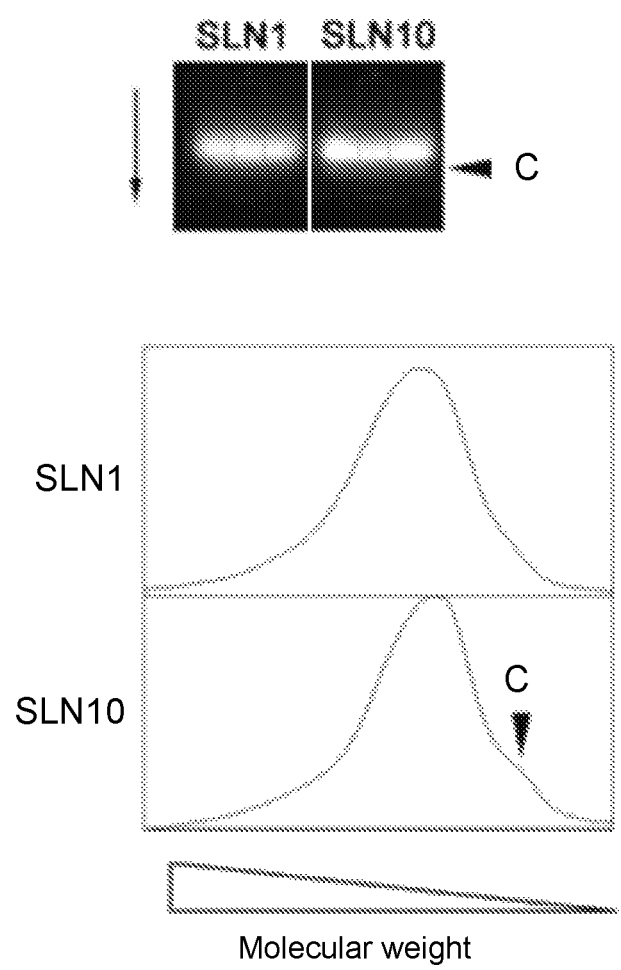

FIG. 109. Treatment with SLN10 at pH 7.5 reduces molecular weight in GPBP (II).

Figure 110:
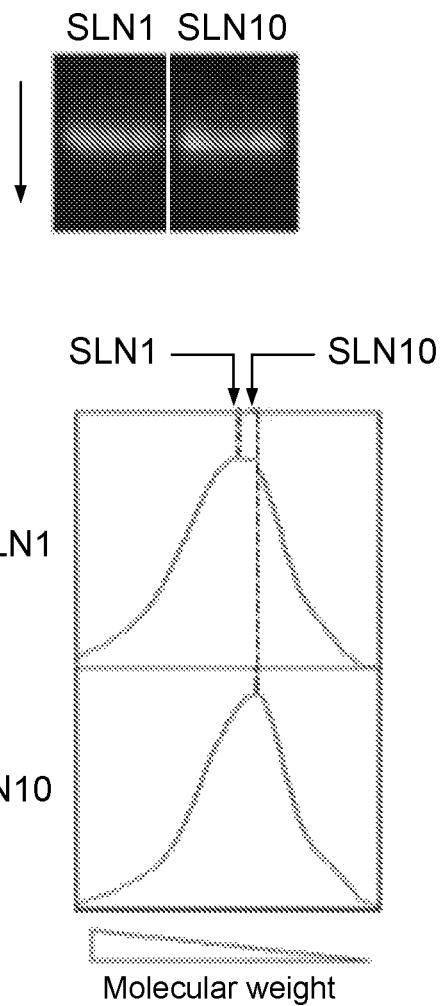

FIG. 110. Treatment with SLN10 at pH 7.5 reduces molecular weight in GPBP (III).

FIG. 111. Treatment with SLN10 at pH 9.3 reduces molecular weight in GPBP (I).

FIG. 112. Treatment with SLN10 at pH 9.3 reduces molecular weight in GPBP (II).

Figure 113:
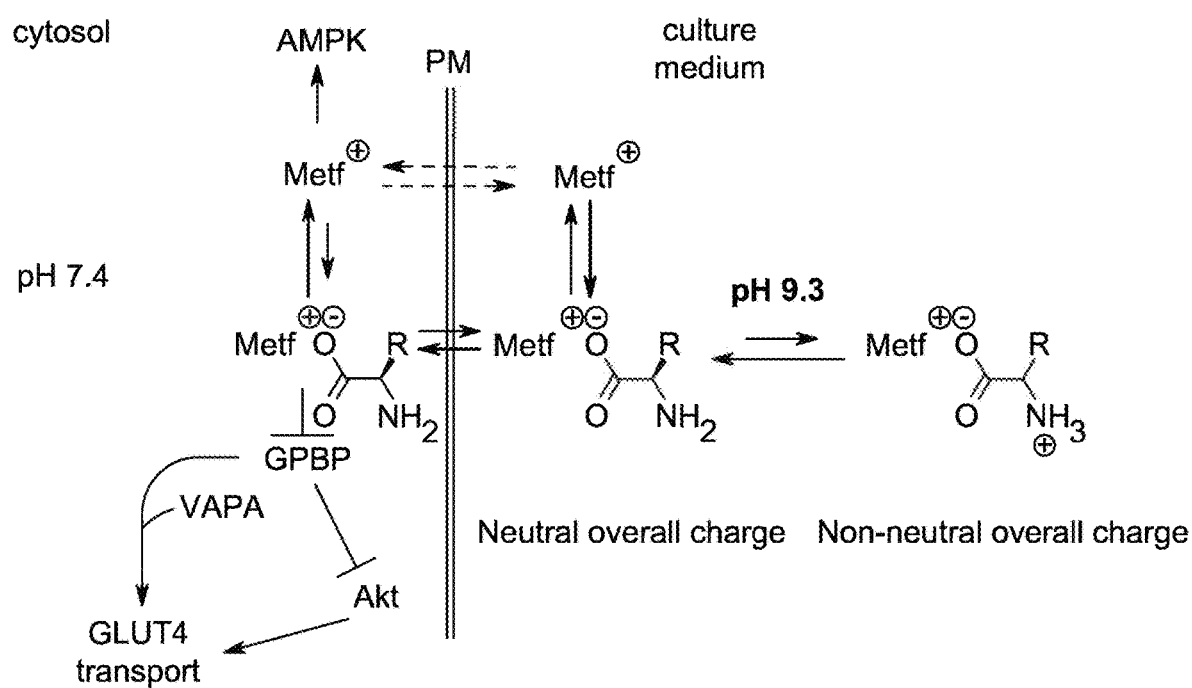

FIG. 113. Accumulation process model for metformin within cells.

Figure 114:
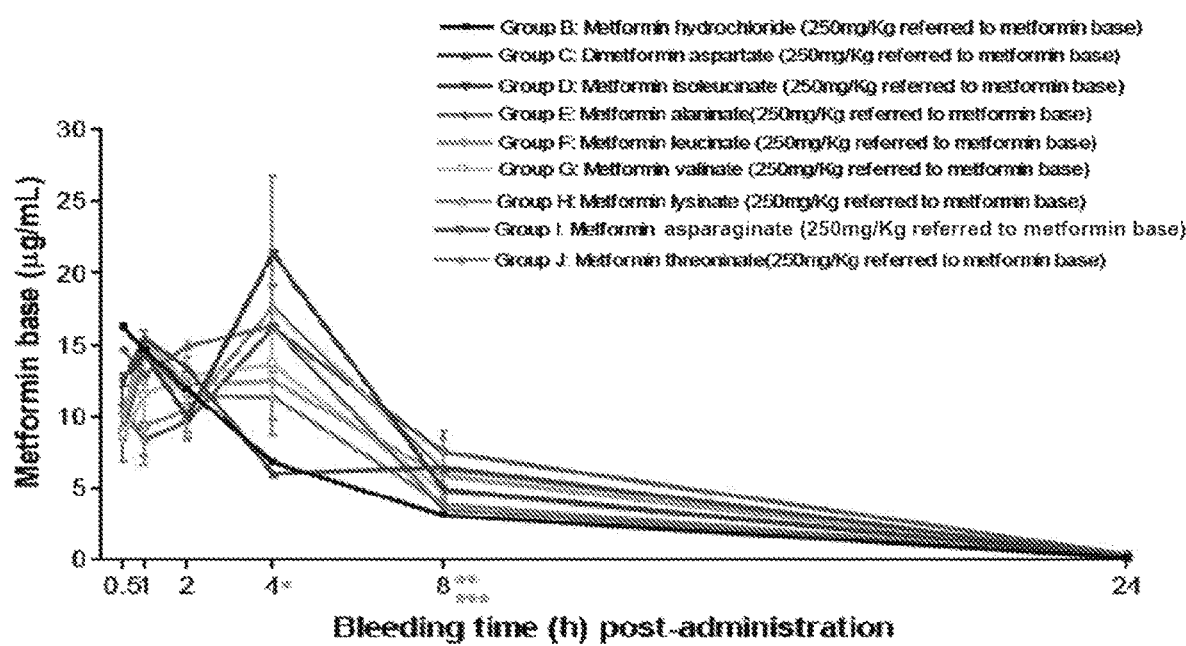

FIG. 114. Curves of metformin base concentration (µg/mL) in plasma. Groups B-J. Mean±standard deviation of three animals/group. *Data represent mean±SD of 2 animals in Group G (4 hours post-test item administration). Data represent mean±SD of 2 animals in Group 5 H (8 hours post-test item post-administration) * Data represent mean±SD of 2 animals in Group J (8 hours post-test item post-administration).

Figure 115:
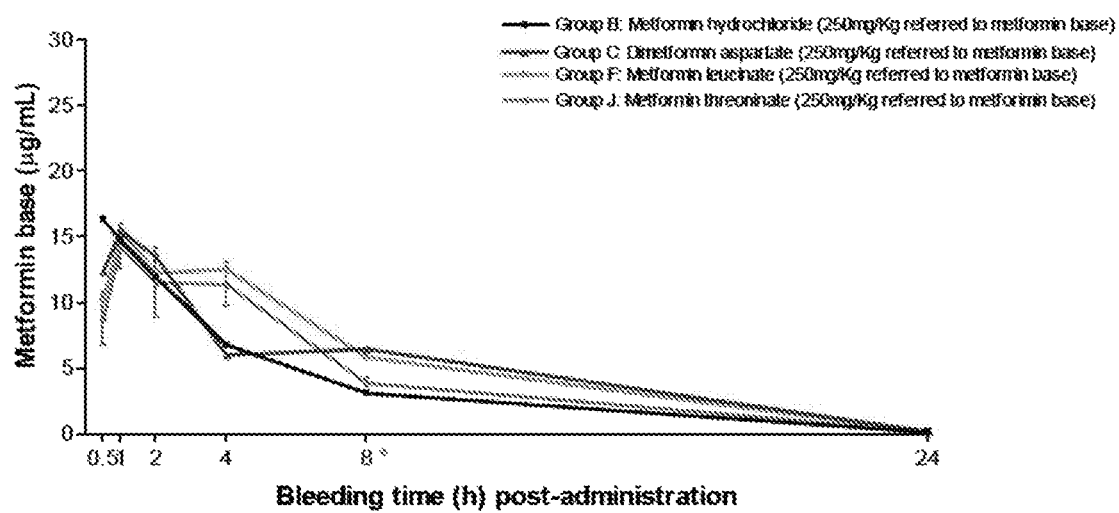

FIG. 115. Curves of metformin base concentration (µg/mL) in plasma. Metformin base concentration curves according to the time of maximum concentration ($T_{max}$). Groups with faster Metformin base absorption: Groups B and C.

Figure 116:
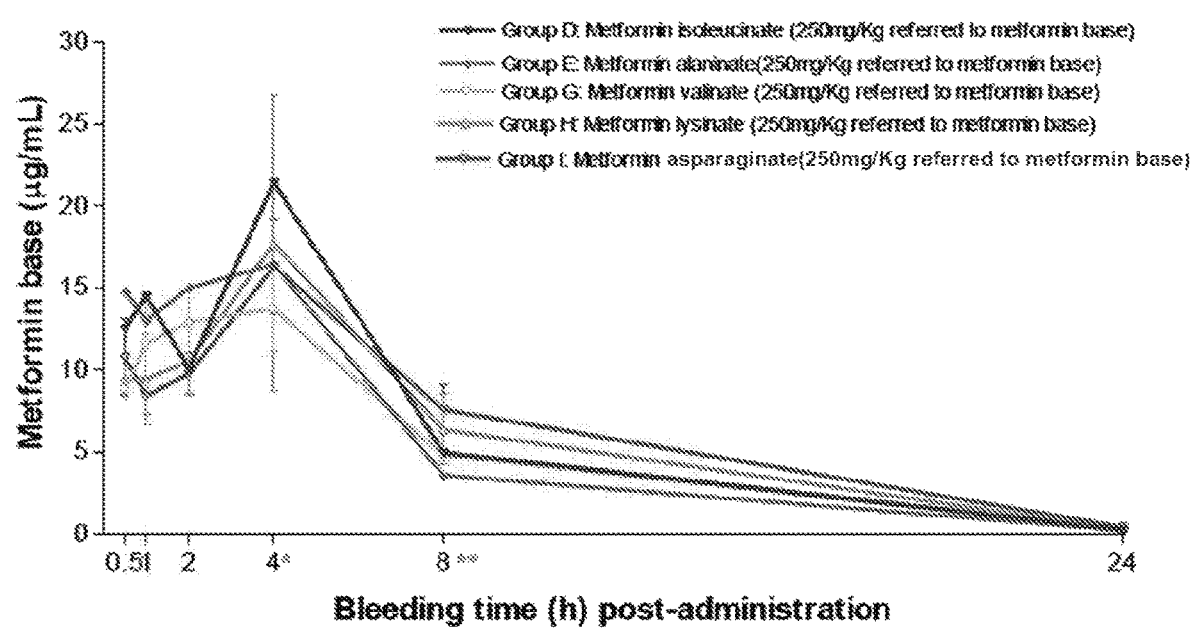

FIG. 116. Curves of metformin base concentration (µg/mL) in plasma. Metformin base concentration curves according to the time of maximum concentration ($T_{max}$). Groups with slower metformin base absorption: Groups D, E, H, and I. Mean±standard deviation of three animals/group. *Data represent mean±SD of 2 animals in Group G (4 hours post-test item administration). **Data represent mean±SD of 2 animals in Group H (8 hours post-test item post-administration).

FIG. 117. Curves of metformin base concentration (µg/mL) in plasma. Metformin base concentration curves according to the bioavailability ($AUC_{[0-24]}$). *Data represent mean=SD of 2 animals in Group G (4 hours post-test item administration). *Data represent mean±SD of 2 animals in Group J (8 hours post-test item post-administration).

Figure 118:
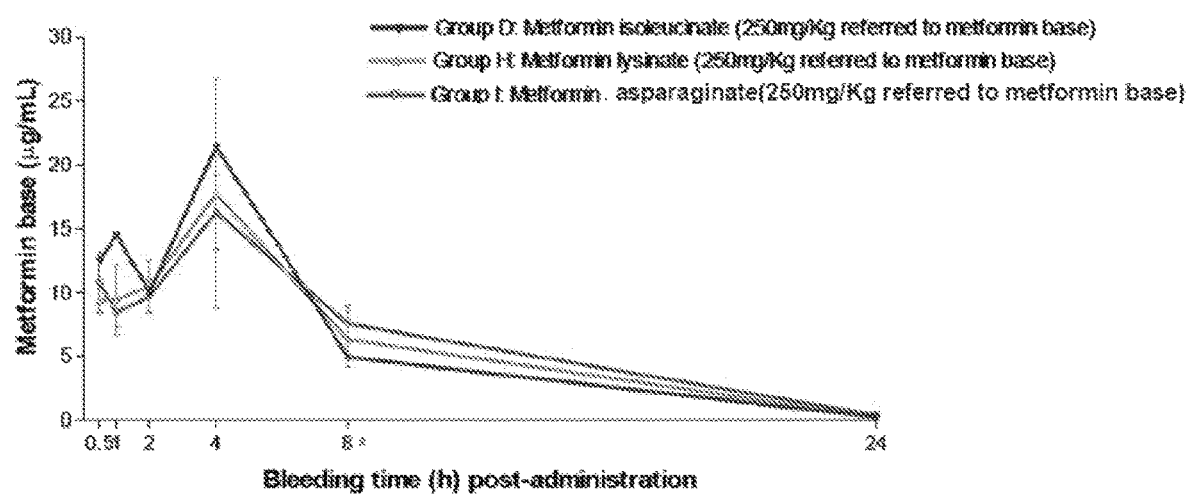

FIG. 118. Curves of metformin base concentration (µg/mL) in plasma. Metformin base concentration curves according to the bioavailability ($AUC_{[0-24]}$). Groups with higher bioavailability: Groups D, H, and I. Mean±standard deviation of three animals/group. *Data represent mean±SD of 2 animals in Group H (8 hours post test item post-administration).

Figure 119:
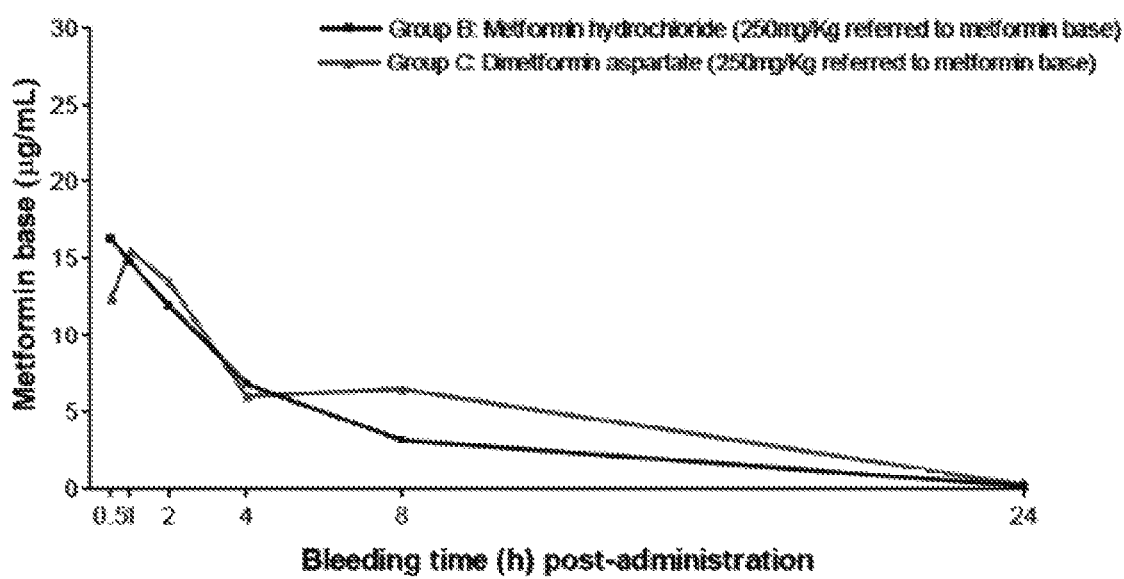

FIG. 119. Curves of metformin base concentration (µg/mL) in plasma. Metformin base concentration curves of Groups B and C compared to the rest of experimental groups. Groups B and C. Mean±standard deviation of three animals/group.

Figure 120:
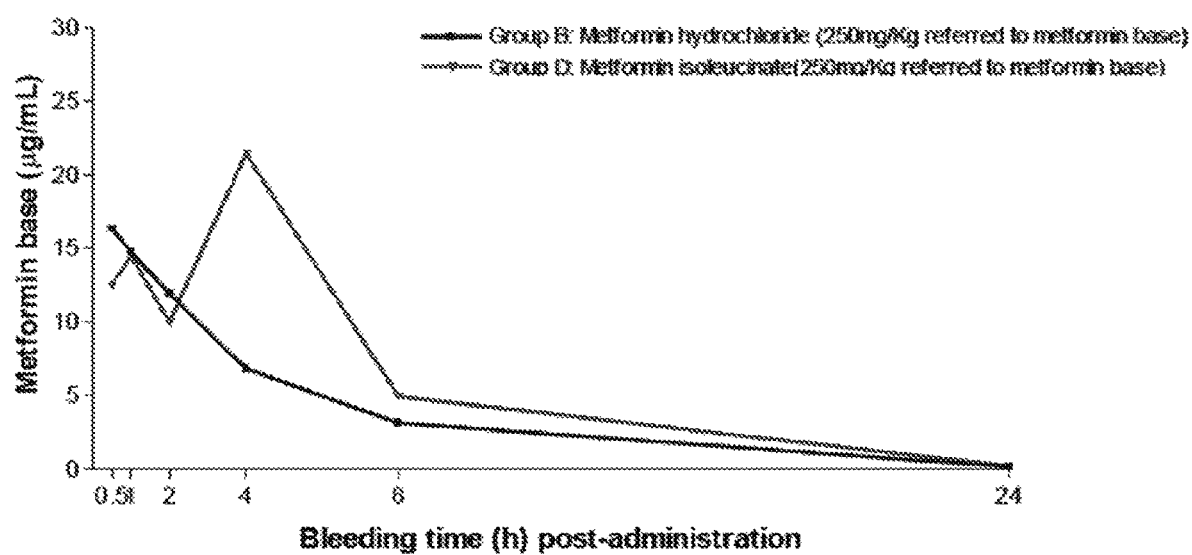

FIG. 120. Curves of metformin base concentration (µg/mL) in plasma. Metformin base concentration curves of Groups B and D compared to the rest of experimental groups. Groups B and D. Mean±standard deviation of three animals/group.

Figure 121:
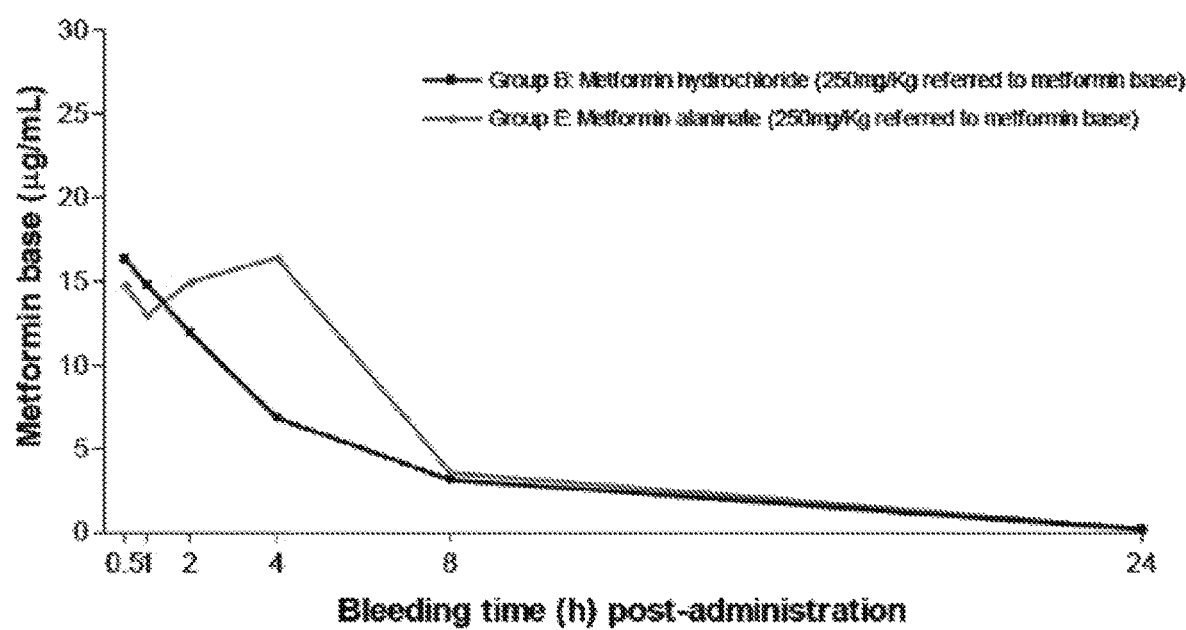

FIG. 121. Curves of metformin base concentration (µg/mL) in plasma. Metformin base concentration curves of Groups B and E compared to the rest of experimental groups. Groups B and E. Mean±standard deviation of three animals/group.

Figure 122:
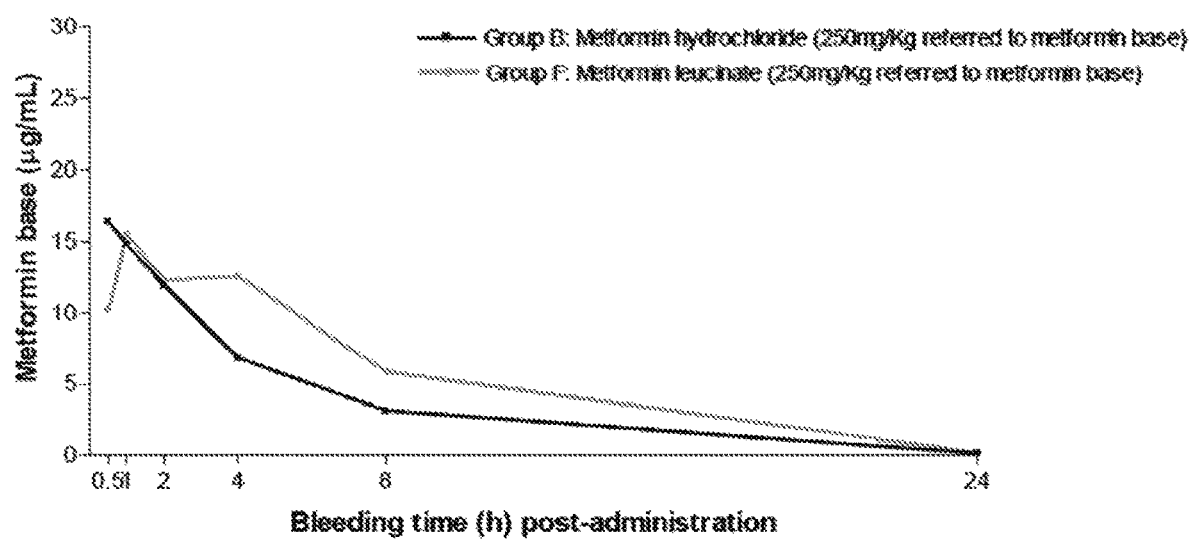

FIG. 122. Curves of metformin base concentration (µg/mL) in plasma. Metformin base concentration curves of Groups B and F compared to the rest of experimental groups. Groups B and F. Mean±standard deviation of three animals/group.

Figure 123:
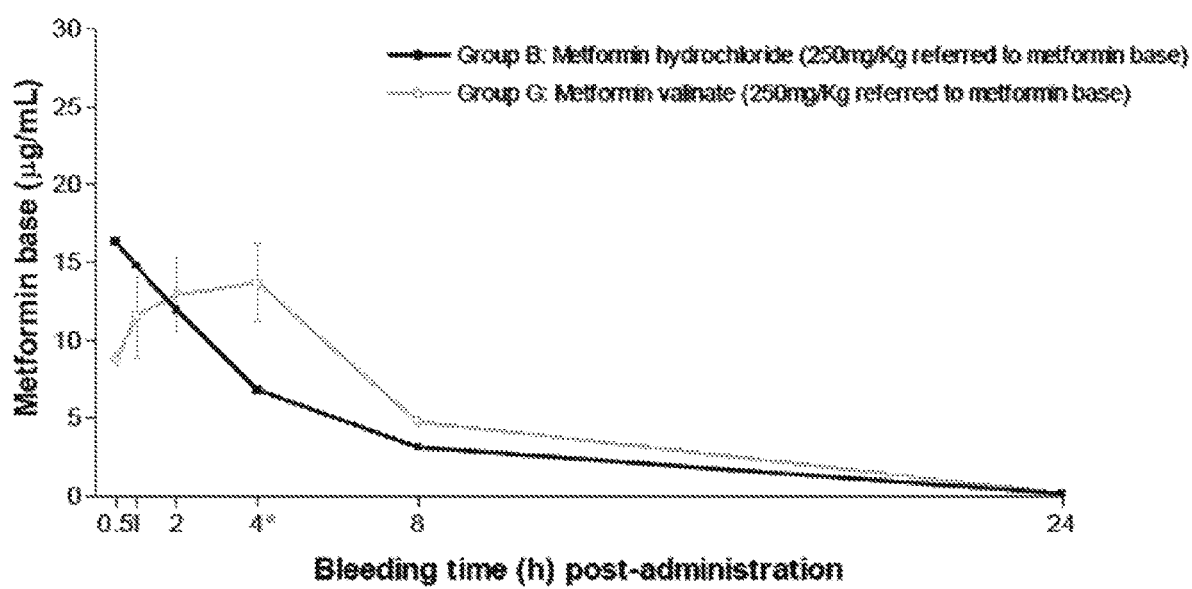

FIG. 123. Curves of metformin base concentration (µg/mL) in plasma. Metformin base concentration curves of Groups B and G compared to the rest of experimental groups. Groups B and G. Meant standard deviation of three animals/group. *Data represent mean±SD of 2 animals in Group G (4 hours post test item administration).

Figure 124:
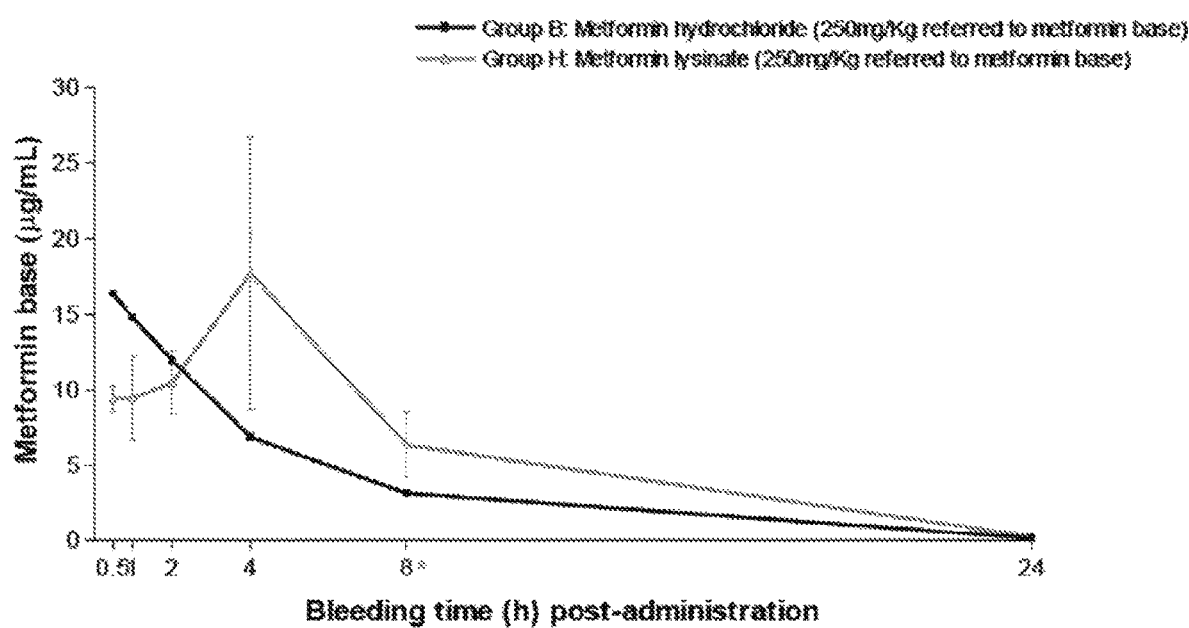

FIG. 124. Curves of metformin base concentration (µg/mL) in plasma. Metformin base concentration curves of Groups B and H compared to the rest of experimental groups. Groups B and H. Mean±standard deviation of three animals/group. *Data represent mean=SD of 2 animals in Group H (8 hours post test item post-administration).

Figure 125:
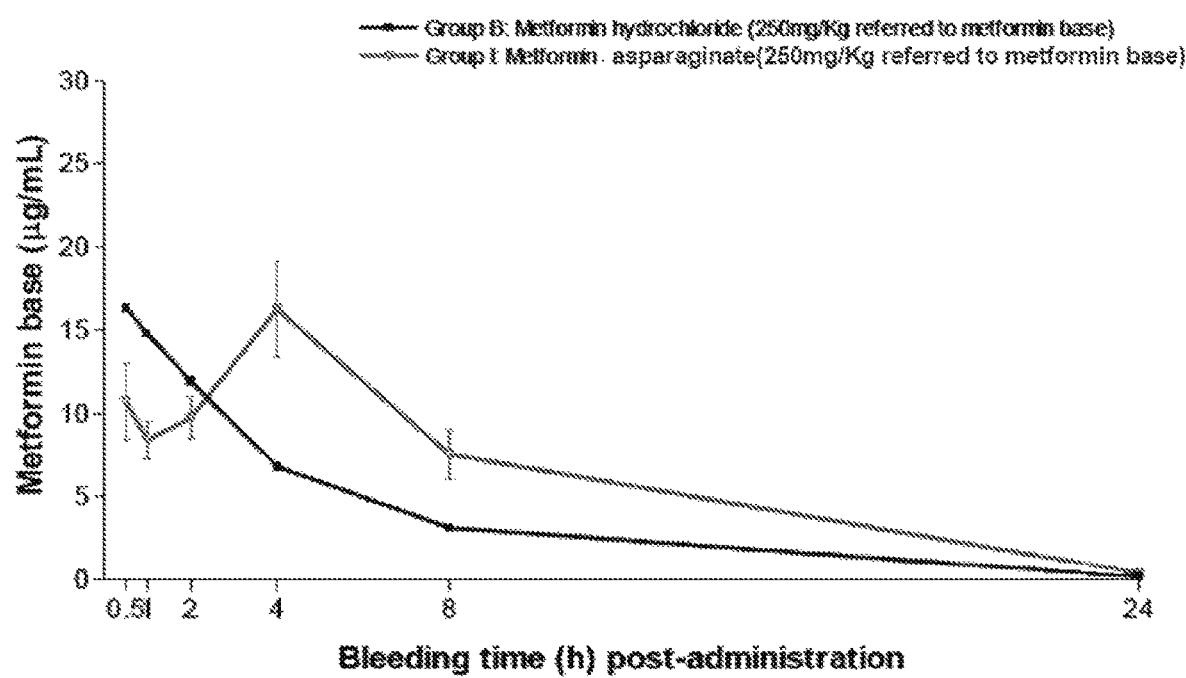

FIG. 125. Curves of metformin base concentration (µg/mL) in plasma. Metformin base concentration curves of Groups B and I compared to the rest of experimental groups. Groups B and I. Mean±standard deviation of three animals/group.

Figure 126:
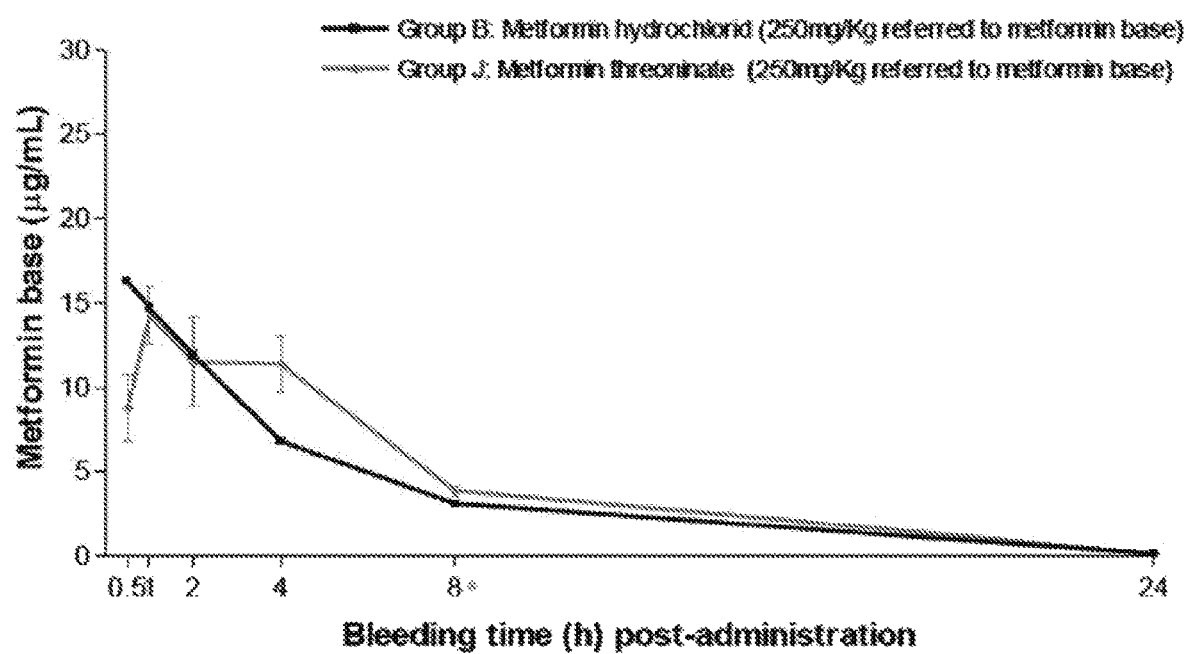

FIG. 126. Curves of metformin base concentration (µg/mL) in plasma. Metformin base concentration curves of Groups B and J compared to the rest of experimental groups. Groups B and J. Mean±standard deviation of three animals/group. *Data represent mean±SD of 2 animals in Group J (8 hours post test item post-administration).

Figure 127:
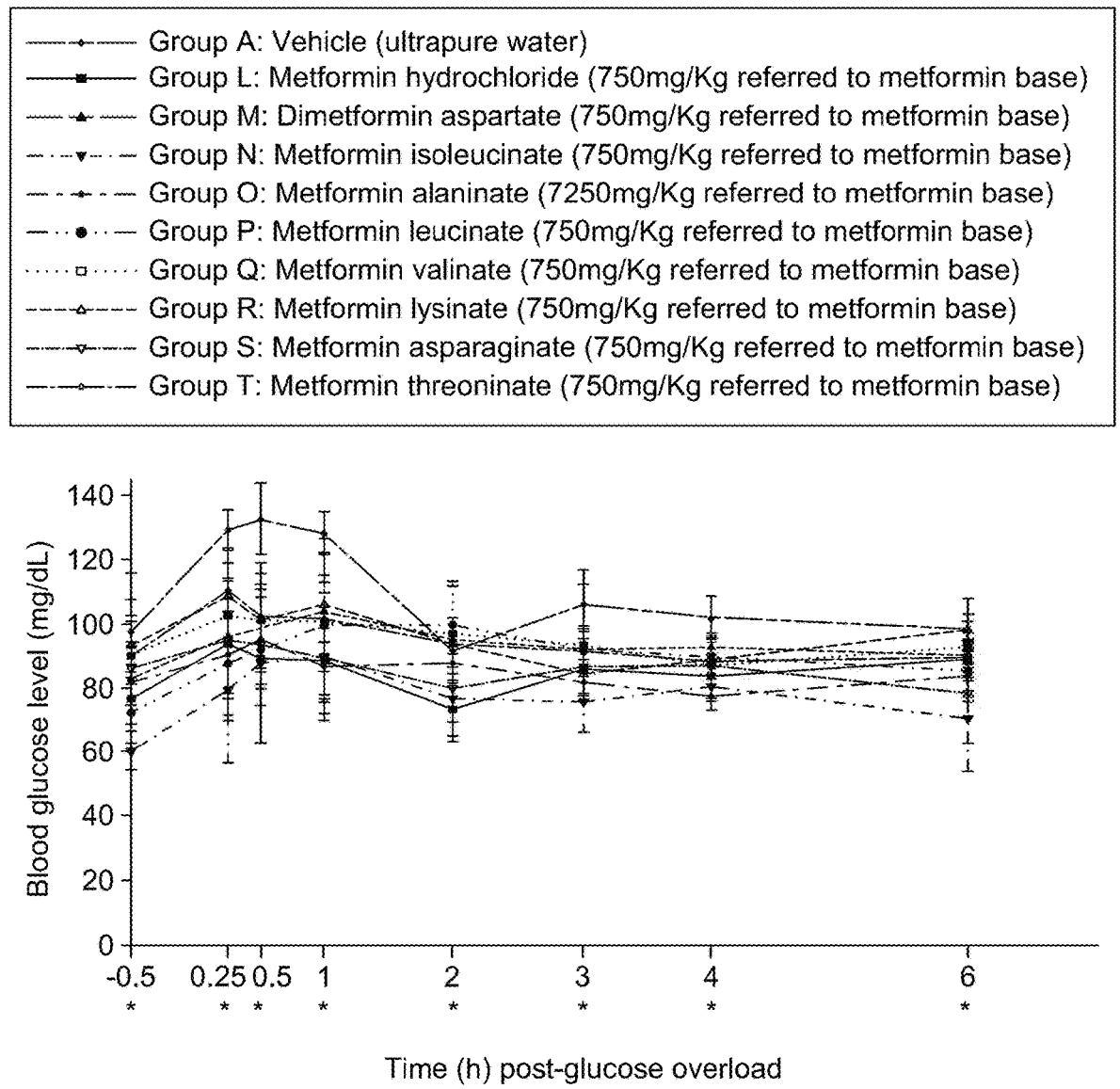
Figure 128:
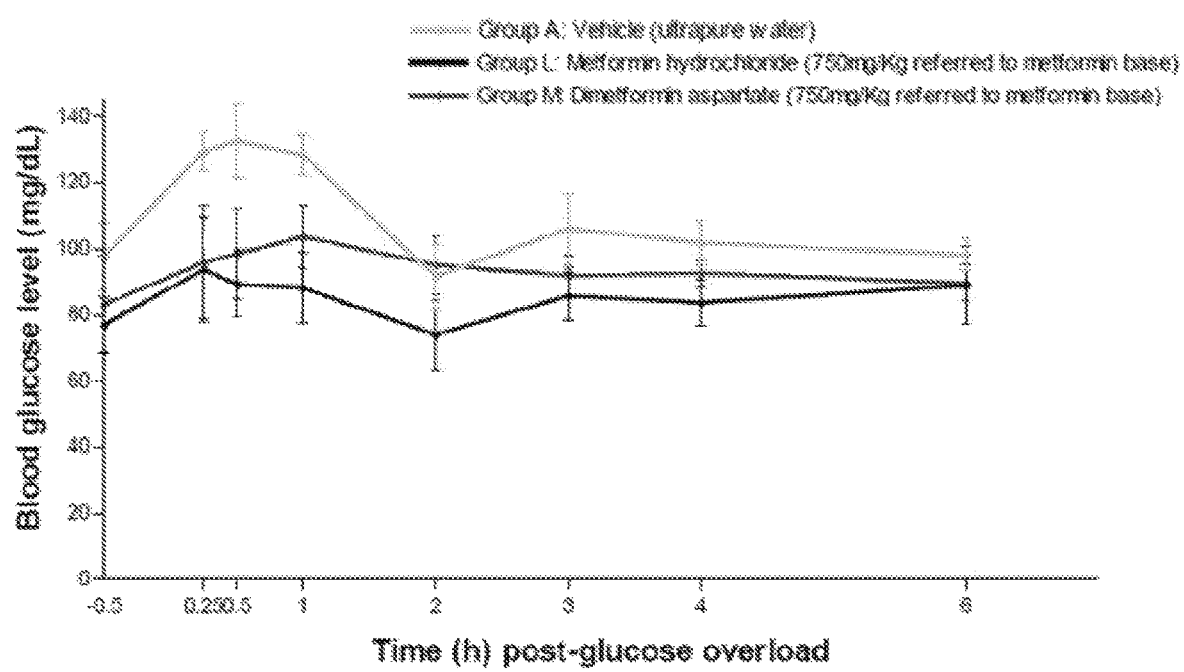

FIG. 127. Curves of blood glucose level (mg/dL). Groups A, L-T. Mean±standard deviation of four animals/group. * Data represent mean±SD of 3 animals in Groups R and T FIG. 128. Curves of blood glucose level (mg/dL). Groups A, L and M compared to the rest of experimental groups. Groups A, L, and M. Mean±standard deviation of four animals/group.

Figure 129:
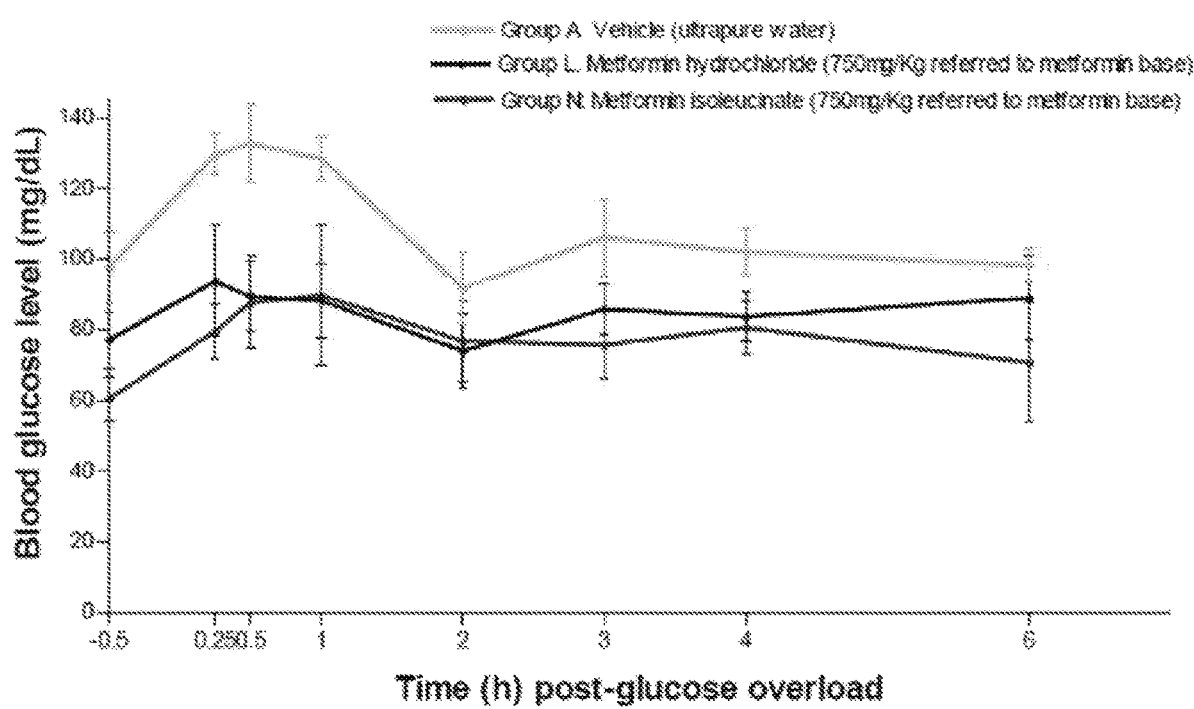

FIG. 129. Curves of blood glucose level (mg/dL). Groups A, L and N compared to the rest of experimental groups. Groups A, L, and M. Mean±standard deviation of four animals/group.

Figure 130:
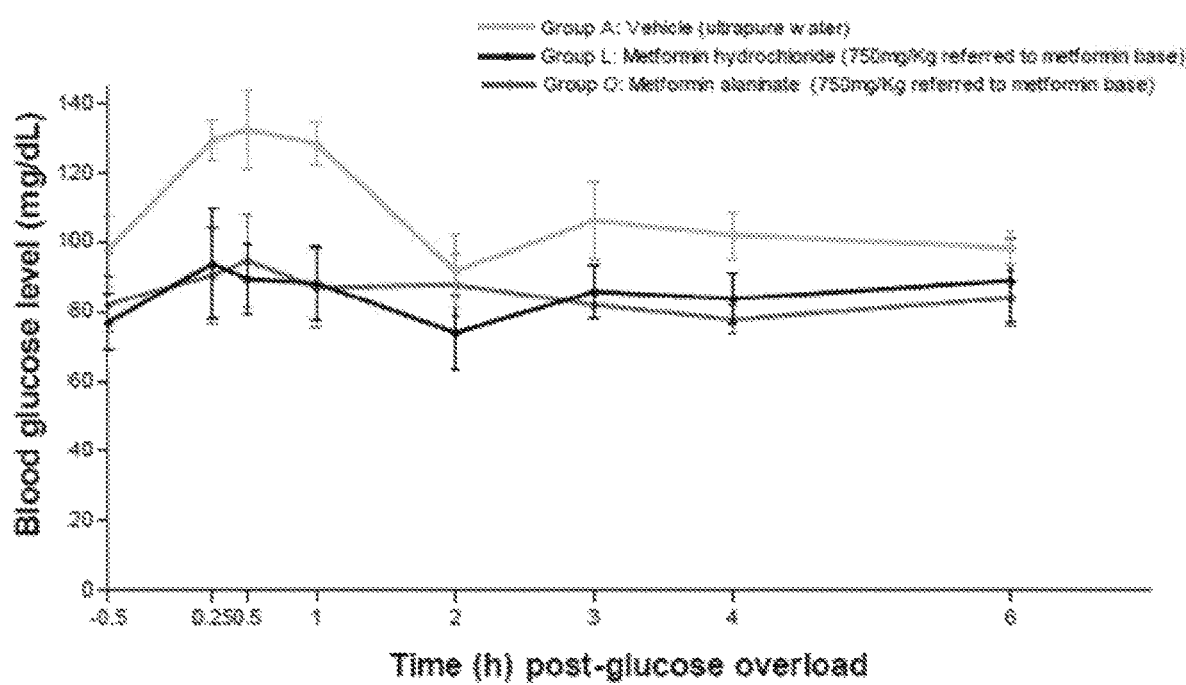

FIG. 130. Curves of blood glucose level (mg/dL). Groups A, L and O compared to the rest of experimental groups. Groups A, L, and O. Mean±standard deviation of four animals/group.

Figure 131:
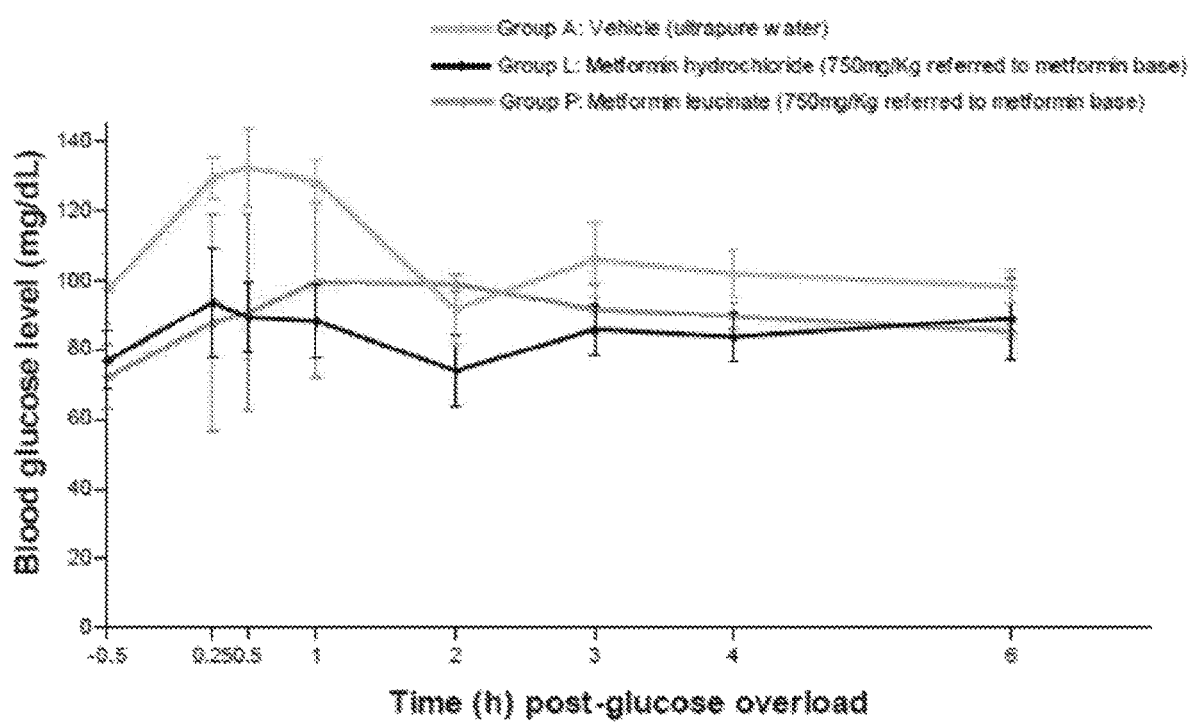

FIG. 131. Curves of blood glucose level (mg/dL). Groups A, L and P compared to the rest of experimental groups. Groups A, L, and P. Mean±standard deviation of four animals/group.

Figure 132:
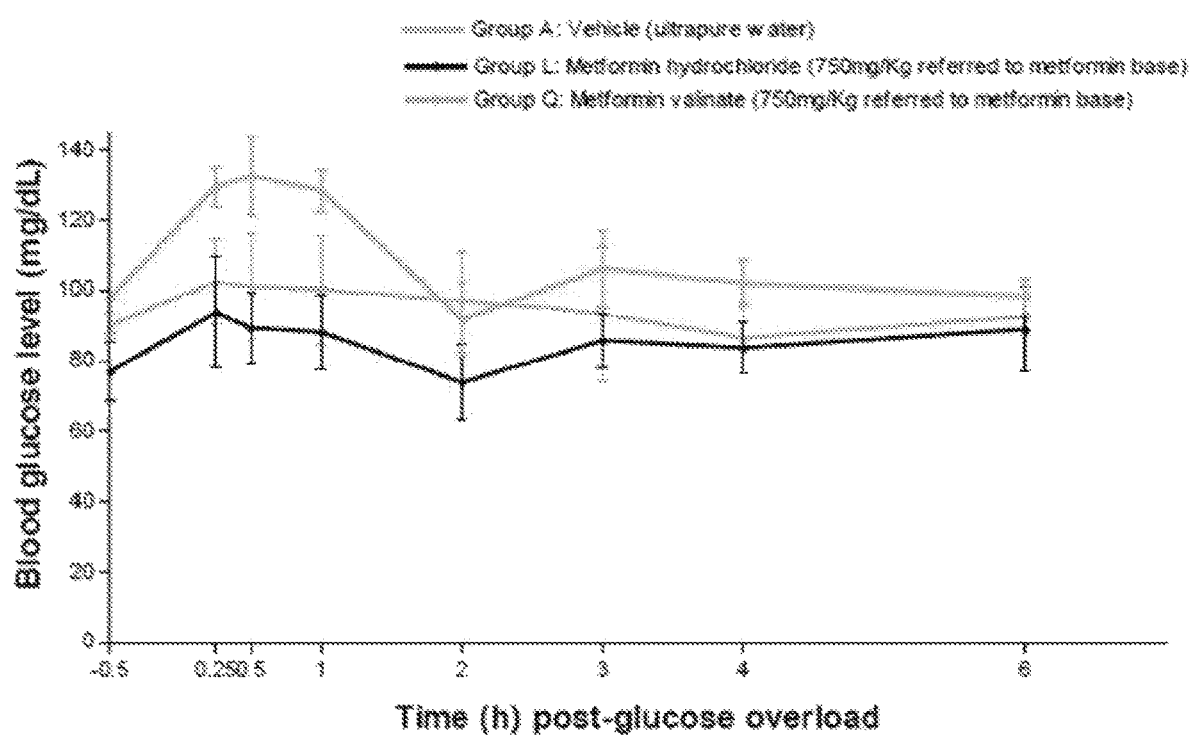

FIG. 132. Curves of blood glucose level (mg/dL). Groups A, L and Q compared to the rest of experimental groups. Groups A, L, and Q. Mean±standard deviation of four animals/group.

Figure 133:
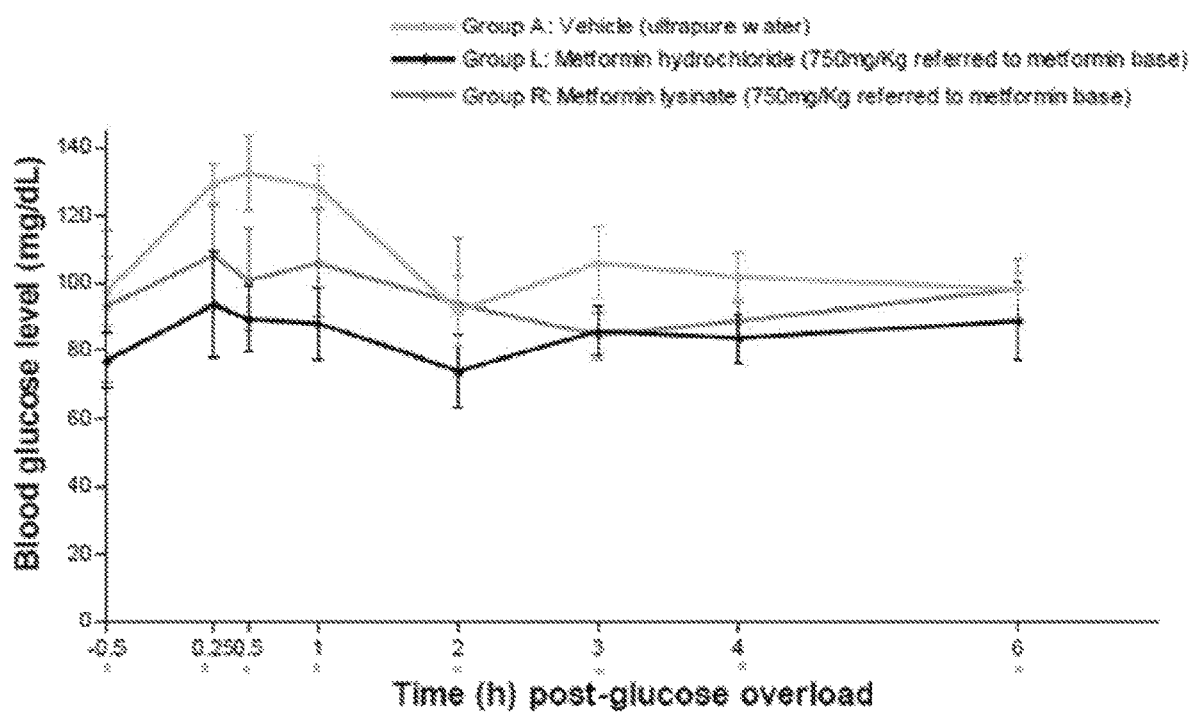

FIG. 133. Curves of blood glucose level (mg/dL). Groups A, L and R compared to the rest of experimental groups. Groups A, L, and R. Mean±standard deviation of four animals/group. *Data represent mean±SD of 3 animals in Groups R and T.

Figure 134:
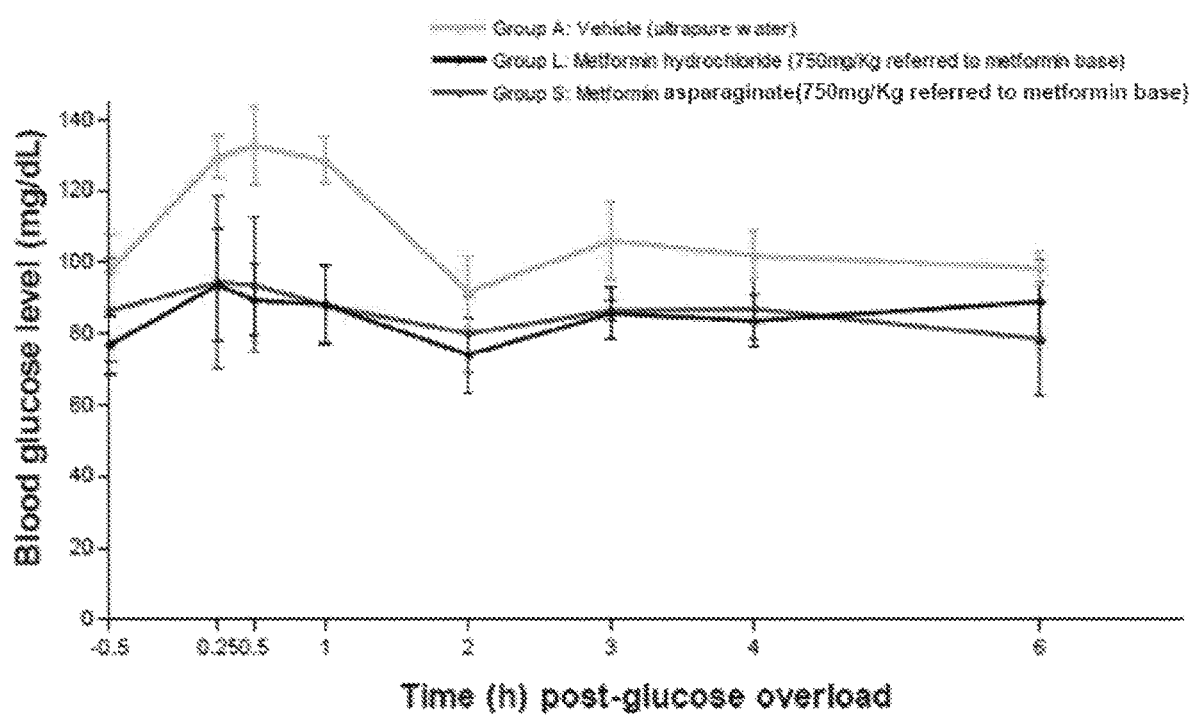

FIG. 134. Curves of blood glucose level (mg/dL). Groups A, L and S compared to the rest of experimental groups. Groups A, L, and S. Mean±standard deviation of four animals/group.

Figure 135:
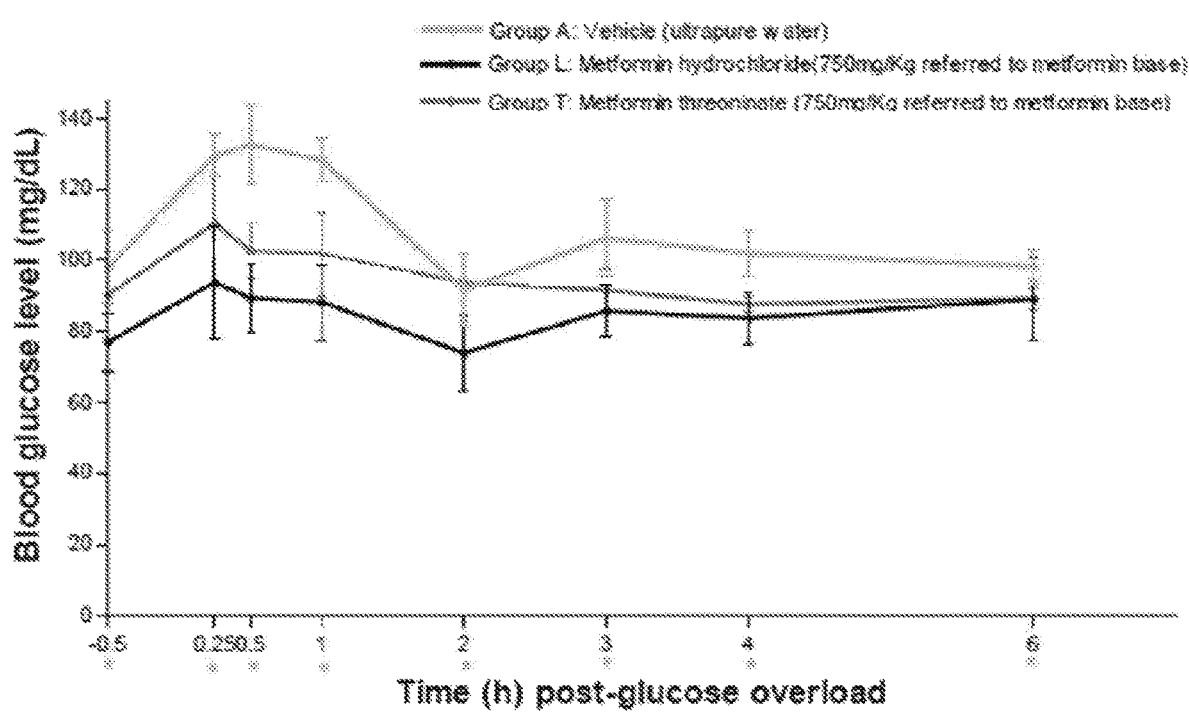

FIG. 135. Curves of blood glucose level (mg/dL). Groups A, L and T compared to the rest of experimental groups. Groups A, L, and T. Mean±standard deviation of four animals/group. *Data represent mean±SD of 3 animals.

Figure 136:
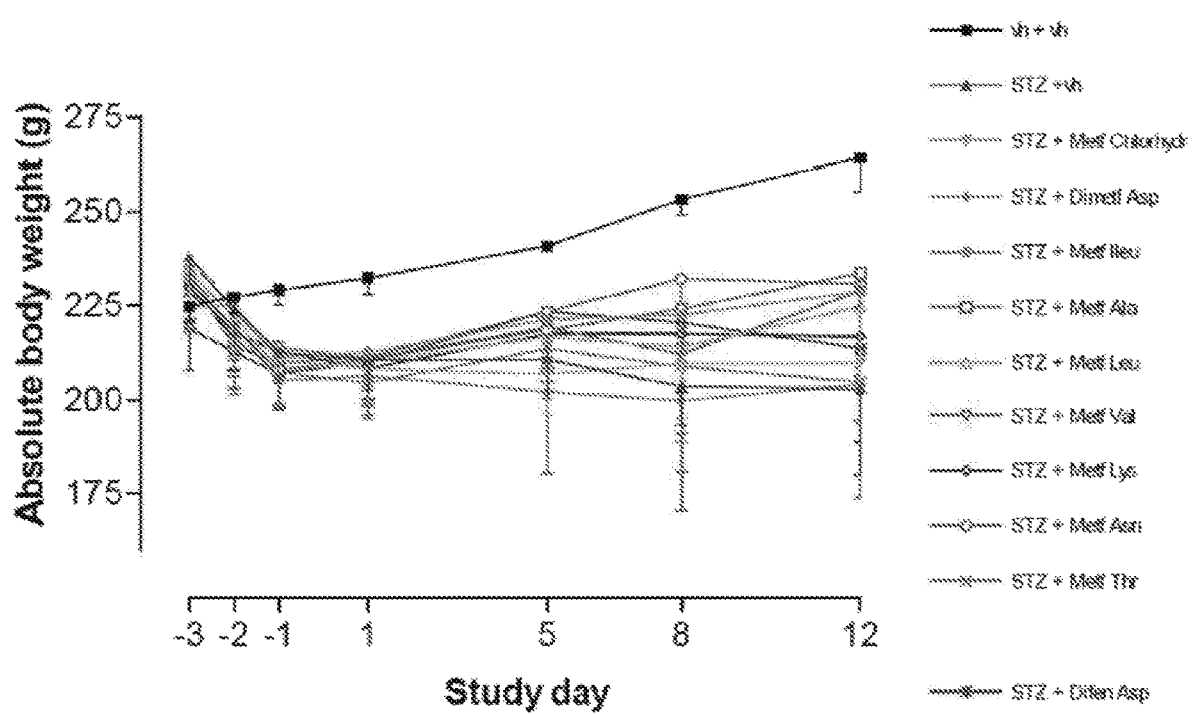

FIG. 136. Absolute body weight (g) throughout the study period. Mean±standard deviation.

Figure 137:
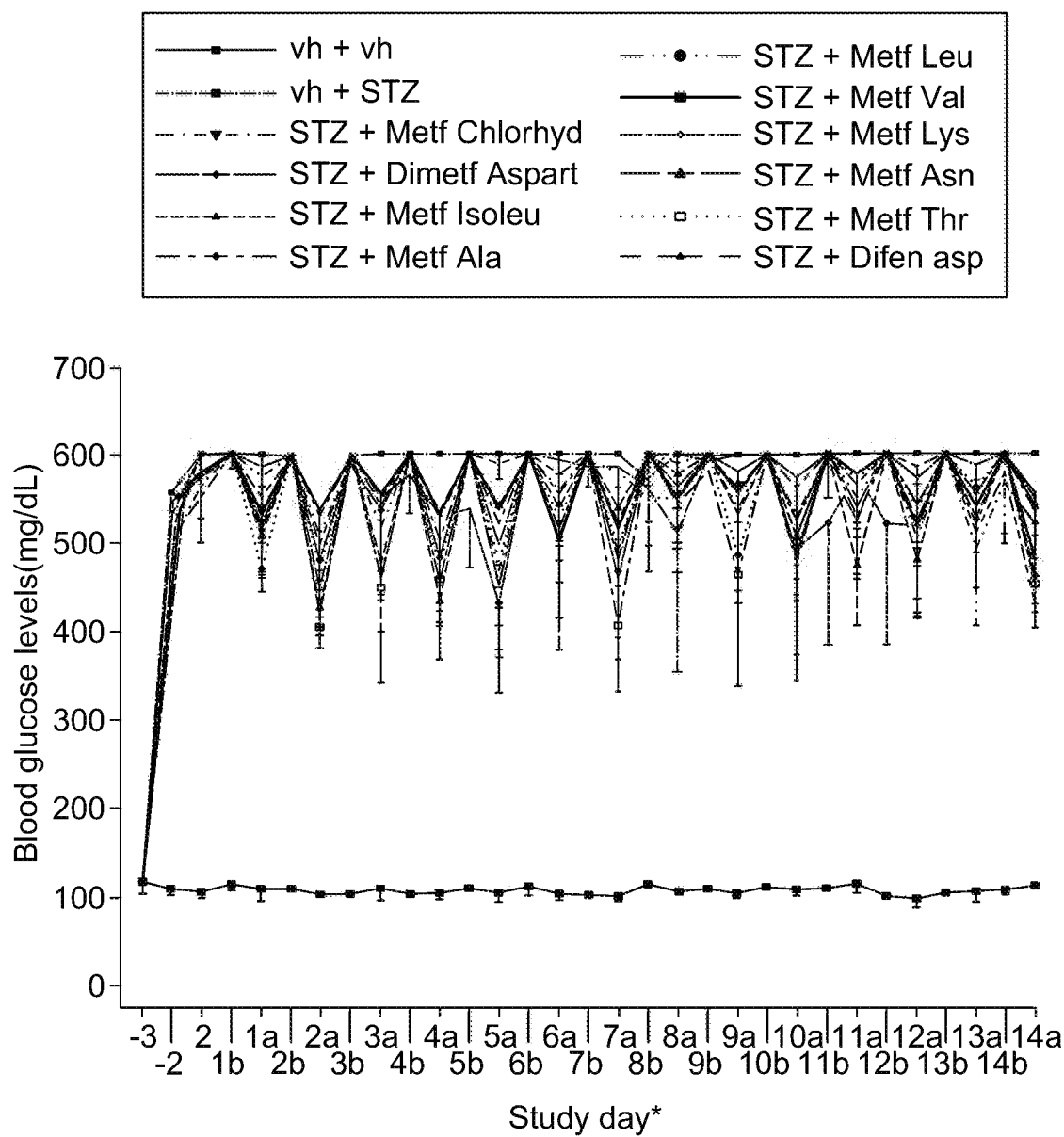

FIG. 137. Blood glucose levels (mg/dL) throughout the study period. Mean±standard deviation. (*) b: before administration of TI/RI, a: after administration of TI/RI.

FIG. 138. Chemical structures of the metformin amino acid compounds (SLNs).

DETAILED DESCRIPTION OF THE INVENTION

All references cited are herein incorporated by reference in their entirety.

Previous aspects and advantages related to the present invention will be more easily appreciated when better understood with reference to the following descriptions if taken together with the figures provided and the definitions below.

Definitions

The abbreviations used herein are: bp, base pair, DTT, dithiothreitol; DMEM, Dulbecco's modified Eagle's medium; EDTA, ethylenediamine tetraacetic acid; EGTA, ethylene glycol-bis (β-aminoethyl ether) N,N,N',N'-tetraacetic acid; HPLC, high performance liquid chromatography; Kb, thousand base pairs; kDa, thousand daltons; PMSF, phenylmethylsulfonyl fluoride; SDS-PAGE, sodium dodecylsulfate polyacrylamide gel electrophoresis; TBS, tris buffered saline.

Other abbreviations and reference numbers refer to metformin compounds of the present invention, also known as SLNs; whereas metformin hydrochloride and metformin lysinate, in particular, are cited and referred to as SLN1 and SLN10, respectively.

The term "and/or" as used in a phrase such as "A and/or B" herein is intended to include "A and B", "A or B", "A", and "B".

The term "about" generally refers to a range of numbers that one of skill in the art would consider equivalent to the recited value (i.e., having the same function or result). In many instances, the term "about" may include numbers that are rounded to the nearest significant figure.

Unless the context requires otherwise, the terms "comprise," "comprises," and "comprising" are used on the basis and clear understanding that they are to be interpreted inclusively, rather than exclusively, and that Applicant intends each of those words to be so interpreted in construing this patent, including the claims below.

The terms "improve" and "improving" have their plain and ordinary meaning to one skilled in the art of pharmaceutical or medical sciences and specifically include ameliorating the effects of hyperglycemia or an associated condition, or decreasing or lessening a side effects of hyperglycemia and/or diabetes.

The term "patient" includes mammals and humans, particularly humans.

The term "pharmaceutically acceptable carrier" or "pharmaceutically acceptable excipient" refers to any and all solvents, dispersion media, preservatives, antioxidants, coatings, isotonic and absorption delaying agents, and the like, that are compatible with pharmaceutical administration.

The terms "reduce" and "reducing" have their plain and ordinary meanings to one skilled in the art of pharmaceutical or medical sciences and specifically include diminishing or decreasing the number of occurrences, the duration, or the intensity, of hyperglycemia and/or diabetes.

The term "therapeutically effective amount" means an amount of a compound that, when administered to a patient suffering from or susceptible to hyperglycemia and/or diabetes is sufficient, either alone or in combination with additional therapies, to effect treatment for hyperglycemia and/or diabetes or the associated condition. The "therapeutically effective amount" will vary depending, for example, on the compound, the condition treated and its severity, and the age and weight of the patient to be treated.

The terms "treat" and "treating" have their plain and ordinary meaning to one skilled in the art of pharmaceutical or medical sciences and specifically include improving the quality of life or reducing the symptoms or side effects of hyperglycemia and/or diabetes.

Within this application, unless otherwise stated, the techniques utilized may be found in any of several well-known references to the technician in the art, such as: "Guide to Protein Purification" in Methods in Enzymology (M. P. Deutshcer, ed, (1990) Academic Press, Inc.); Culture of Animal Cells: A Manual of Basic Technique, 2nd Ed. (R. I. Freshney. 1987. Liss, Inc. New York, N.Y.).

GPBP (Goodpasture antigen-binding protein), also known as CERT (ceramide transfer protein), is a protein that has at least three related activities through a cycle: kinase protein (cytoplasm); chaperon (endoplasmic reticulum); and inflammatory cytokine (extracellular compartment). The cycle progression towards the outside of the cell is regulated by protein dephosphorylation and it is completed when the extracellular dephosphorylated protein is re-uptaken and returns to the cytoplasm, where its kinase activity is regained via phosphorylation. An increase in GPBP's expression has been associated with several disorders, including autoimmunity (renal and articular), inflammation (fibrosis), type 2 diabetes, and cancer. SLNs (e.g., metformin lysinate) have anti-inflammatory, antidiabetic and anti-tumoral activity, whose mode of action has not been characterized or exploited. Evidence also shows that metformin lysinate has better pharmacological properties than Metformin hydrochloride in Type 2 diabetes. We now provide evidence on how SLNs (e.g., metformin lysinate, or SLN10, thereon) are different from metformin hydrochloride's (SLN1, thereon), operating via a GPBP kinase activity inhibition, and are useful for diabetes, inflammation and cancer treatment.

COL4A3BP gen codes for a family of at least three proteins: one canonical, termed as GPBP-1 (previously, GPBP); and two alternative isoforms, termed as GPBP-2 (previously, GPBPΔ26/CERT) and GPBP-3 (previously, GPBP of 91-kDa). In most of the studied cell types, GPBP-1 is eminently extracellular, GPBP-2 is cytosolic, and GPBP-3 is bound to the external face of the plasma membrane. GPBP-2 is generated by means of an alternative exon splicing that eliminates a 26-residue region, rich in Ser, which is critical in protein exportation. GPBP-3 binds to the plasma membrane by means of additional N-terminal 83-residues that are gained by starting the translation in an alternative site (Thr), present in 5'-nontranslatable region. (Revert F, Ventura I, Martinez-Martinez P, Granero-Moltó F, Revert-Ros F, Macias J, Saus J. J Biol Chem. 2008, 283: 30246-55).

GPBP-1 is a non-conventional kinase protein that regulates the organization of the glomerular basement membrane (GBM) collagen net (type IV), a main compound in the glomerular filtration barrier. GPBP-1's glomerular overexpression induces alterations in the collagen net, dissociating GBM and causing glomerulonephritis (GN), due to (auto) antibodies or immune complexes (IC) deposits in altered GBM (Goodpasture disease, renal lupus and IgA nephropathy) (Revert F, Merino R, Monteagudo C, Macias J, Peydró A, Alcácer J, Muniesa P, Marquina R, Blanco M, Iglesias M, Revert-Ros F, Merino J, Saus J. Am J Pathol. 2007; 171: 1419-30). More recent results show that GPBP-1 plays a key role in maintaining homeostasis of the endoplasmic reticulum (ER) for correct protein folding. Specifically, GPBP-1 catalyzes conformational isomerization reactions on type IV collagen, essential for their correct binding in the GBM collagen net (Saus J. (2002) Appl. No. PCT/EP02/01010. Publication No. WO 02/061430; Calvete J J, Revert F, Blanco M, Cervera J, Tárrega C, Sanz L, Revert-Ros F, Granero F, Pérez-Payá E, Hudson B G, Saus J. Proteomics. 2006; 6 Suppl 1:501. S237-44). GPBP-2 is a cytosolic protein that transports ceramides between the ER and the Golgi apparatus, and promotes protein secretion; to do so, it needs to dephosphorylate in Ser (Raya A, Revert-Ros F, Martinez-Martinez P, Navarro S, Rosello E, Vieites B, Granero F, Forteza J, Saus J. J Biol Chem. 2000; 275:40392-9) and bind to VAPA (Hanada K, Kumagai K, Yasuda S, Miura Y, Kawano M, Fukasawa M, Nishijima M. Nature. 2003; 426:803-9; Fugmann T, Hausser A, Schöffler P, Schmid S, Pfizenmaier K, Olayioye M A. *J Cell Biol.* 2007; 178:15-22). GPBP is a membrane protein that promotes GPBP-1 secretion (Revert F, Ventura I, Martinez-Martinez P, Granero-Moltó F, Revert-Ros F, Macias J, Saus *J. J Biol Chem.* 2008; 283:30246-55).

ER is a passage organelle for a third part of proteins that are synthetized in cells, where they fold and modify. When proteins are not folded correctly in the ER, a reaction in the cell, known as UPR (unfolded protein response), occurs. First, UPR tries to solve the problem by synthetizing chaperones (enzymes that catalyze protein folding), but if it does not manage to do so, UPR activates cell death by apoptosis (Kaufman R J. Genes Dev. 30 1999; 13:1211-33; Szegezdi E, Logue S E, Gorman A M, Samali A. EMBO Rep. 2006; 7:880-5). Very recent results indicate that UPR is regulated, partly, by GPBP-1 and -2.

Evidence shows that COL4A3BP orchestrates a biological program that regulates Type IV glomerular collagen folding, secretion, and assembling (Revert F, Merino R, Monteagudo C, Macias J, Peydró A, Alcácer J, Muniesa P, Marquina R, Blanco M, Iglesias M, Revert-Ros F, Merino J, Saus J. Am J Pathol. (Revert F, Ventura I, Martinez-Martinez P, Granero-Moltó F, Revert-Ros F, Macias J, Saus J. J Biol Chem. 2008; 283:30246-55).

COL4A3BP is expressed in all tissues constitutively, but it is in striated muscle tissue (skeletal and heart muscle) where it has its maximum expression (Raya A, Revert F, Navarro S, Saus J. J Biol Chem. 1999; 274:12642-9), suggesting that GPBP proteins also play a key role in the cytoskeleton organization. According to this proposal, loss- and gain-of-function assays in zebrafish models have demonstrated that GPBP-1 is essential for muscle tissue development in lower vertebrates (Granero-Moltó F, Sarmah S, O'Rear L, Spagnoli A, Abrahamson D, Saus J, Hudson B G, Knapik E W. J Biol Chem. 2008; 283:20495-504). Recently, it has been demonstrated that the alternative expression of COL4A3BP (GPBP-2 and -3) in mice myotubes is reduced to undetectable levels and, consequently, GPBP-1, the gene's canonical form of expression, is not exported and remains in the cytosol, where it regulates the formation and elongation of myofibrils (Revert-Ros F, López-Pascual E, Granero-Moltó F, Macias J, Breyer R, ZentR, Hudson B G, Saadeddin A, Revert F, Blasco R, Navarro C, Burks D, Saus J. J Biol Chem 2011; 286:35030-43). Hence, evidence reveals that GPBP-1 regulates the supra molecular assembly of structural proteins in the intracellular as well as the extracellular compartment. However, in the intracellular compartment, this process is developed by a group of substrate proteins known as GIP (GPBP-Interacting Protein) (Revert-Ros F, López-Pascual E, Granero-Moltó F, Macias J, Breyer R, Zent R, Hudson B G, Saadeddin A, Revert F, Blasco R, Navarro C, Burks D, Saus J. J Biol Chem 2011; 286:35030-43). Finally, evidence indicates that GPBP-1 regulates fibrillar organization in muscle tissue, whereas GPBP-2 develops this role in other cell lines, where GPBP-1 is exported. (Revert-Ros F y Saus J. (2001). Appl. No. PCT/EP2012/13802. Publication No. WO03048193; Saus J y Revert F. Patent 7935492 (USA)).

TNFα (Tumor Necrosis Factor-alpha) induces COL4A3BP expression and stimulates GPBP kinase activity (Granero F, Revert F, Revert-Ros F, Lainez S, P Martinez-Martinez, J. Saus FEBS J. 2005; 272: 5291-305; Miralem T, Gibbs P E, Revert F, J Saus, Maines M D. J Biol Chem. 2010; 285:12551-8). TNF-α is a cytokine with a strong pro-inflammatory and autoimmune profile, which has been attributed an anti-tumoral activity, depending on the studied cell models (Aggarwal B B, Samanth A, Feldmann M (2001) Cytokine Reference Volume I. pp. 413434. Oppenheim & Feldmann Eds. Academic Press). All this suggests that COL4A3BP is a gene that regulates TNF-α-dependent processes, relevant to these Medicine fields: inflammation, autoimmunity, and cancer.

Biochemical and immunohistochemical studies reveal that GPBP proteins are expressed in all tissues and are found in the cytosol, plasma membrane, secretory pathways, endosomal pathway, mitochondria and nucleus, as well as the extracellular matrix and blood plasma. This indicates that proteins have a virtually biological function in all compartments: cellular and extracellular (Raya A, Revert F, Navarro S, Saus J. J Biol Chem. 1999; 274:12642-9; Raya A, Revert-Ros F, Martinez-Martinez P, Navarro S, Rosello E, Vieites B, Granero F, Forteza J, Saus J. J Biol Chem. 2000; 275:40392-9 Martinez-Martinez P. (2003) Doctoral Thesis; Saus J. (1999). Appl. No. PCT/EP2012/00324. Publication No. WO 00/50607).

The general opinion is that inflammation is a main pathogenic factor in both Type 1 diabetes, which has an autoimmune nature, (Bending D, Zaccone P, Cooke A. Int Immunol. 2012; 24:339-46) and Type 2 diabetes (Donath M Y, Shoelson S E. Nat Rev Immunol. 2011; 11:98-107), whose base has been related to amyloid material deposits in β cells, and defective folding in proteins (Westwell-Roper C Y, Ehses J A, Verchere C B. Diabetes. 2013 Nov. 12. [Epub ahead of print]). Pathogenic conjunction of autoimmunity, defective protein folding and inflammation suggest that a GPBP cycle hyperactivity has a key role in blood glucose homeostasis. Consistently, monitoring of circulating GPBP in a Type 2 diabetes model caused by a lack of substrate 2 expression of insulin receptor (IRS2$^{-/-}$), has revealed that the circulating GPBP levels are regulated, and that the early administration of GPBP blocking antibodies prevents hyperglycemia instauration and consequent death of animals, suggesting that, in this model at least, blood glucose homeostasis alteration is originated in a GPBP cycle hyperactivity. According to his proposal, Ser phosphorylation (Raya A, Revert-Ros F, Martinez-Martinez P, Navarro S, Rosello E, Vieites B, Granero F, Forteza J, Saus J. J Biol Chem. 2000; 275:40392-9), AMPK, a general sensor of the cell metabolic state that promotes glucose intake in response to 5'-AMP (Treebak J T, Glund S, Deshmukh A, Klein D K, Long Y C, Jensen T E, Jorgensen S B, Viollet B, Andersson L, Neumann D, Wallimann T, Richter E A, Chibalin A V, Zierath J R, Wojtaszewski J F. Diabetes. 2006; 55:2051-8), regulates the cycle progression when it enables the protein kinase activity, and is uptaken from the extracellular compartment. In our model, the activation by AMPK and autophosphorylation keeps the protein active in the cytoplasm, where it exerts its action on GIP130. Dephosphorylation by a phosphatase enables GPBP binding to VAPA in the ER (Saito S, Matsui H, Kawano M, Kumagai K, Tomishige N, Hanada K, Echigo S, Tamura S, Kobayashi T. J Biol Chem 2008; 283:6584-93) and its translocation to the lumen (Revert F, Ventura I, Martinez-Martinez P, Granero-Moltó F, Revert-Ros F, Macias J, Saus J. J Biol Chem. 2008; 283:30246-55) where a residual kinase activity coordinated with the chaperone activity of the protein intervenes actively in proteins folding an secretion (Type IV collagen) (Revert F, Penadés J R, Plana M, Bernal D, Johansson C, Itarte E, Cervera J, Wieslander J, Quinones S, Saus J. J Biol Chem. 1995; 270:13254-61; Saus J. (2002). Appl. No. PCT/EP2012/001010. Publication No. WO/2002/061430; Revert F, Merino R, Monteagudo C, Macias J, Peydró A, Alcacer J, Muniesa P, Marquina R, Blanco M, Iglesias M, Revert-Ros F, Merino J, Saus J. Am J Pathol. 2007; 171:1419-30). Finally, the protein secretion and subsequent IL-1β and IL-10 synthesis and secretion stimulation in macrophages (Saus J, Revert F, Merino R, Merino J, Revert-Ros F. (2012); Appl. No. PCT/EP2012/052923, Publication No. WO 2012/

113785) induce and limit the inflammatory response. In FIG. 6, the current state of knowledge for the GPBP cycle is illustrated.

Ser dephosphorylation (Raya A, Revert-Ros F, Martinez-Martinez P, Navarro S, Rosello E, Vieites B, Granero F, Forteza J, Saus J. J Biol Chem. 2000; 275:40392-9) has been associated with a close bind to VAPA and the ceramide transport between ER and the Golgi apparatus (Saito S, Matsui H, Kawano M, Kumagai K, Tomishige N, Hanada K, Echigo S, Tamura S, Kobayashi T. J Biol Chem. 2008; 283: 6584-93) with protein transport and secretion (Florin L, Pegel A, Becker E, Hausser A, Olayioye M A, Kaufmann H. J Biotechnol. 2009; 141:84-90), mediated by GPBP-2.

Other studies have demonstrated that GPBP-1 binding to VAPA is necessary for transport and subsequent secretion to the extracellular media (Revert F, Ventura I, Martinez-Martinez P, Granero-Moltó F, Revert-Ros F, Macias J, Saus J. J Biol Chem. 2008; 283:30246-55). Finally, more recent studies demonstrate that GPBP-2 can replace GPBP-1 in GPBP-1-deficient mice (Revert-Ros F, López-Pascual E, Granero-Moltó F, Macias J, Breyer R, Zent R, Hudson B G, Saadeddin A, Revert F, Blasco R, Navarro C, Burks D, Saus J. J Biol Chem 2011; 286:35030-43). Collectively, all these results suggest that GPBP-1 and -2 are highly interchangeable and that kinase activity, ceramide transport and protein secretion are closely related, and regulated, primarily, by Ser's phosphorylation state. (Raya A, Revert-Ros F, Martinez-Martinez P, Navarro S, Rosello E, Vieites B, Granero F, Forteza J, and J Biol Chem. 2000; 275:40392-9). Thus, when GPBP is phosphorylated, it would remain in the cytoplasm, but when it dephosphorylates, it would export and promote protein secretion (Bandyopadhyay A, Wang L, Agyin J, Tang Y, Lin S, Yeh I T, De K, Sun L Z. PLoS One. 2010; 5:e10365) and leads to the appearance of chemoresistance (Swanton C, Marani M, Pardo O, Warne P H, Kelly G, Sahai E, Elustondo F, Chang J, Temple J, Ahmed A A, Brenton J D, Downward J, Nicke B. Cancer Cell. 2007; 11:498-512) through a GPBP overexpression, which is promoted by the instauration of a UPR, as a result of GPBP inhibition in the ER (Swanton 5 C, Marani M, Pardo O, Warne P H, Kelly G, Sahai E, Elustondo F, Chang J, Temple J, Ahmed A A, Brenton J D, Downward J, Nicke B. Cancer Cell. 2007; 11:-512-et al. (2013) U.S. patent application Ser. No. 13/933,609). In low doses, T12 induces cell proliferation (Saus et al. (2013) U.S. patent application Ser. No. 13/933, 609). Finally, low doses of T12 do not induce UPR, but increase (synergically) the UPR that triggers doxorubicin (Saus et al. (2013) U.S. patent application Ser. No. 13/933, 609). Evidence also shows that kinase activity of GPBP inhibits cell growth through a negative regulation of AKT phosphorylation (Revert-Ros F, López-Pascual E, Granero-Moltó F, Macias J, Breyer R, Zent R, Hudson B G, Saadeddin A, Revert F, Blasco R, Navarro C, Burks D, Saus J. J Biol Chem 2011; 286:35030-43) and inhibits migration and cell nesting through GIP130 inhibiting phosphorylation (Revert-Ros F, López-Pascual E, Granero-Molto F, Macias J, Breyer R, Zent R, Hudson B G, Saadeddin A, Revert F, Blasco R, Navarro C, Burks D, Saus J. J Biol Chem 2011; 286:35030-43. According to this model: 1) T12 inhibits tumor cell migration (Saus et al. (2013) U.S. patent application Ser. No. 13/933,609); 2) T12 and doxorubicin are synergic, reducing tumor cells viability (Saus et al. (2013) U.S. patent application Ser. No. 13/933,609); and 3) T12 and doxorubicin are synergic, inhibiting tumor proliferation and metastasis in animal models (Saus et al. (2013) U.S. patent application Ser. No. 13/933,609).

There are two main signaling routes that regulate translocation of glucose transporters to plasma membrane: one induced by insulin and its receptor (IRS2/PI3K/Akt/AS160) (Leto D, Saltiel A R. Nat Rev Mol Cell Biol. 2012; 13:383-96), and the other one induced by physical exercise, operating through AMPK/AS160 (Treebak J T, Glund S, Deshmukh A, Klein D K, Long Y C, Jensen T E, Jorgensen S B, Viollet B, Andersson L, Neumann D, Wallimann T, Richter E A, Chibalin A V, Zierath J R, Wojtaszewski J F. Diabetes. 2006; 55:2051-8), which is also activated by metformin (Zhou G, Myers R, Li Y, Chen Y, Shen X, Fenyk-Melody J, Wu M, Ventre J, Doebber T, Fujii N, Musi N, Hirshman M F, Goodyear L J, Moller D E. J Clin Invest. 2001; 108:1167-74). Both routes converge in the induction of GLUT4 glucose transporter translocation to plasma membrane in adipose and muscular tissue.

GLUT4 is a transmembrane protein, that becomes part of the storage vesicles GSV (GLUT4 storage vesicles), which translocate to the plasma membrane in response to insulin in a natural way, after being synthetized in the ER and having travelled on to the Golgi apparatus. GLUT4 is internalized from the plasma membrane and passes to early endosomes, and thereon, to recycling endosomes.

From the two endosome types, vesicles can be formed; these return GLUT4 back to the plasma membrane directly. From recycling endosomes, GLUT4 can pass directly or indirectly to GSVs (via Golgi apparatus), which in the absence of stimuli remain around the nucleus in the so-called GLUT4 vesicles storage compartment (Leto D, Saltiel A R. Nat Rev Mol Cell Biol. 2012; 13:383-96). It is not known with certainty which type of binding maintains GSVs in perinuclear positions. TUG (tether containing UBX domain for GLUT4) is a cytosolic protein that interacts with GLUT4, and in the absence of stimuli may be the protein interfering with GSVs' migration towards the plasma membrane (Bogan J S, Hendon N, McKee A E, Tsao T S, Lodish H F. Nature. 2003; 425:727-33).

Apart from GLUT4, GSVs contain characteristic transmembrane proteins, such as IRAP (insulin regulated aminopeptidase) and VAMP2 (vesicle-associated membrane protein 2). VAMP2 is a vesicular protein in the SNARE (soluble N-ethylmaleimide-sensitive factor-attachment protein receptor) complex, essential for GSVs fusion and completion of GLUT4 translocation to the plasma membrane (Martin L B, Shewan A, Millar C A, Gould G W, James D E. J Biol Chem. 1998 January; 273(3):1444-52). VAMP2 interacts with ER membrane proteins, known as VAP (VAMP-associated proteins) (Skehel P A, Martin K C, Kandel E R, Bartsch D. Science, 1995; 269:1580-3) that also bind to GPBP (Saito S, Matsui H, Kawano M, Kumagai K, Tomishige N, Hanada K, Echigo S, Tamura S, Kobayashi T. J Biol Chem. 2008; 283:6584-93). VAPA's overexpression inhibits the regulated GLUT4 transport to plasma membrane (Foster L J, Weir M L, Lim D Y, Liu Z, Trimble W S, Klip A. Traffic. 2000, 1:512-21) and the non-regulated protein transport from the ER to the Golgi apparatus (Prosser D C, Tran D, Gougeon P Y, Verly C, Ngsee J K. J Cell Sci. 2008; 121:3052-61). It has been proven that a peptide including a FFAT (two phenylalanines in an acidic tract) motif counteracts the VAPA inhibitory effect on the RE-Golgi transport (Prosser D C, Tran D, Gougeon P Y, Verly C, Ngsee J K. J Cell Sci. 2008; 121:3052-61). Interestingly, GPBP contains a FFAT motif that is necessary for its interaction with VAPA (Kawano M, Kumagai K, Nishijima M, Hanada K. J Biol Chem. 2006; 281:30279-88), which suggests that the interaction between GPBP and VAPA could be one of the induction mechanisms in GPBP protein secretion.

Insulin receptor (IR) is a transmembrane tyrosine kinase that is activated by circulating insulin binding. IR activation produces its substrate (IRS1 and IRS2) phosphorylation, activating the Kinase (PI3K) that phosphorylates phosphatidylinositol 4,5-bisphosphate (PIP2) in the plasma membrane and produces phosphatidylinositol 3,4,5-trisphosphate (PIP3). PIP3 activates the phosphoinositide-dependent kinase protein (PDK) that phosphorylates and activates AKT. Finally, AKT phosphorylates AS160 (AKT substrate 160 kDa) (Leto D, Saltiel A R. Nat Rev Mol Cell Biol. 2012; 13:383-96).

The AMPK signaling route, activated by physical exercise, may also be pharmacologically induced by metformin (Lee J O, Lee S K, Kim J H, Kim N, You G Y, Moon J W, Kim S J, Park S H, Kim H S. J Biol Chem. 2012; 287: 44121-9). AMPK (5'-AMP-dependent kinase protein) is a heterotrimeric enzyme that has a catalytic subunit ($\alpha$ and two regulating subunits $\gamma$ and $\beta$).

5'-AMP also acts as an allosteric activator of subunit $\alpha$ (Hardic D G, Alessi D R. BMC Biol. 2013; 11:36). It is usually accepted that metformin acts provoking an increase in the AMP/ATP intracellular relationship, inhibiting either the electronic transport chain (Owen M R, Doran E, Halestrap A P. Biochem J. 2000; 348.607-14) or adenosine deaminase (Ouyang J, Parakhia R A, Ochs R S. J Biol Chem. 2011; 286:1-11). Both AKT and AMPK phosphorylate AS160, and at this point, signaling routes converge; they are initiated by insulin and physical exercise, and lead to GLUT4 translocation to the plasma membrane (Kramer H F, Witczak C A, Taylor E B, Fujii N, Hirshman M F, Goodyear L J. J Biol Chem. 2006; 281:31478-85).

AS160 is a GTPase-activating protein, recruited to GSVs by the IRAP protein. AS160 induces GTPase protein activities in family Rab (Rab8 and Rab14 in muscle and Rab10 in adipocytes). Rab proteins bound to GTP promote GSV transport to the plasma membrane, but when bound to GDP, they do not have this activity. When stimuli such as insulin physical exercise or metformin are absent, AS160 induces GTPase activity in Rab proteins, binding them to GDP and preventing GSVs transport. When AS160 is phosphorylated by AMPK or when AKT does not activate GTPases, Rab proteins remain bound to GTP and promote GSVs transport. This transport occurs mostly through the tubulin cytoskeleton; meanwhile, near the plasma membrane, the actin cortical cytoskeleton plays a key role in the last section of this transport. Nat Rev Mol Cell Biol. 2012; 13:383-96).

Type 2 diabetes affects mainly obese people, and it develops after the appearance of peripheral insulin resistance derived from a deficient insulin production by pancreatic $\beta$ cells. One of the main causes of peripheral insulin resistance is an existing low-intensity chronic inflammatory tissue state (Lumeng C N, Saltiel A R. J Clin Invest. 2011; 121:2111-7). In overfed obese individuals, macrophages are drawn by adipocytes and may represent up to 40% of tissue cells (Weisberg S P, McCann D, Desai M, Rosenbaum M, Leibel R L, Ferrante A W Jr. J Clin Invest. 2003; 112:1796-808). These macrophages are activated and secrete pro-inflammatory cytokines, such as TNFα, which acts as a paracrine in surrounding tissue and provokes insulin resistance by inhibitory phosphorylation of IRS-1 by c-Jun N terminal kinase (JNK) and IκB kinase (IKK). When cytokine secretion is too high, their plasma levels may increase and have an endocrine effect, causing insulin resistance in distant tissues, e.g. muscle and liver (Osborn O, Olefsky J M. Nat Med. 2012; 18:363-74).

In general, macrophage activation occurs in two steps (Rock K L, Latz E, Ontiveros F, Kono H. Annu Rev Immunol. 2010; 28:321-42; Strowig T, Henao-Mejia J, Elinav E, Flavell R. Nature. 2012; 481:278-86). In the first step, LPS or TNF-α initiate a signaling cascade through their corresponding membrane receptors, activating TNFκB, a class of transcription factors, which promote not only pro-IL-1β synthesis, but also GPBP activation and synthesis. (Granero F, Revert F, Revert-Ros F, Lainez S, Martinez-Martinez P, Saus J. FEBS J. 2005; 272:5291-305; Miralem T, Gibbs P E, Revert F, Saus J, Maines M D. J Biol Chem. 2010; 285:12551-8). In the second step, an additional signal, such as ATP, doxorubicin, IC, glucose, cholesterol crystals, or uric acid, among others, activates the inflammasome (caspase-1), and the processing and secretion of IL-1β is initiated. Interestingly, our studies have demonstrated that doxorubicin, a recognized inflammasome activator (Sauter K A, Wood L J, Wong J, Iordanov M, Magun B E. Cancer Biol Ther. 2011; 11:1008-16), induces GPBP secretion (Saus J, Revert F, Merino R, Merino J, Revert-Ros F. (2012). Appl. No. PCT/EP2012/052923. Publication No. WO/2012/113785). The pro-inflammatory phenotype of the activated macrophages is known as M1; it is mainly characterized by the secretion and synthesis of IL-10 and other pro-inflammatory mediators, such as iNOs and TNF-α (Edin S, Wikberg M L, Dahlin A M, Rutegård J, Öberg Å, Oldenborg P A, Palmqvist R. PLoS One. 2012; 7:e47045); it is also known that macrophage M1 synthetizes and secretes GPBP (Saus J, Revert F, Merino R, Merino J, Revert-Ros F. (2012). Appl. No. PCT/EP2012/052923. Publication No. WO/2012/113785). Activated macrophages tend to self-limit in time, and they differentiate into an M2 anti-inflammatory phenotype, which secretes other cytokines, among which IL-10 and arginase are the most important (for further review, see Biswas & Mantovani Nat Immunol. 2010; 11:889-96). Transition from M1 to M2 is mediated by receptor TLR4 internalization in LPS-stimulated cells and the activation of the promoter of cytokines, such as IL-10 (Iyer S S, Ghaffari A A, Cheng G. J Immunol. 2010; 185:6599-607). Studies have demonstrated that extracellular GPBP behaves as a pro-inflammatory cytokine, typical in M1 state, and promotes M1-M2 transition. In this respect, progressive accumulation of GPBP regulates macrophage activation to M1 (pro-inflammatory) (Saus J, Revert F, Merino R, Merino J, Revert-Ros F. (2012). Appl. No. PCT/EP2012/052923. Publication No. WO2012/113785) and its subsequent transformation to M2 (anti-inflammatory)

Metformin is a biguanide that not only promotes glucose uptake, but also inhibits hepatic gluconeogenesis (Natali A, Ferrannini E. Diabetologia. 2006; 49:434-41). This active principle has been used for decades for Type 2 diabetes treatment, but its mode of action has not been yet completely defined, or exploited. Although it activates AMPK through a rise in intracellular concentration of 5'-AMP, the identity of its pharmacologic target is still a matter of debate. Complex I of the electron transport chain of mitochondria (Brunmair B, Staniek K, Gras F, Scharf N, Althaym A, Clara R, Roden M, Gnaiger E, Nohl H, Waldhäusl W, Fürnsinn C. Diabetes. Biochem J. 2004; 53:1052-9) and AMP deaminase (Ouyang J, Parakhia R A, Ochs R S. J Biol Chem. 2011; 286:1-11) have already been described as metformin effectors. Although scientists have discarded AMPK as a direct target (Hardie D G. Gastroenterology. 2006; 131:973), metformin interacts with its subunit γ (Zhang Y, Wang Y, Bao C, Xu Y, Shen H, Chen J, Yan J, Chen Y. Mol Cell Biochem. 2012; 368:69-76). More recent evidence has demonstrated that metformin biguanide compounds (e.g. Metformin lysinate) have pharmacokinetics and pharmacodynamics different from those of metformin hydrochloride's (Lara Ochoa, J M F. (2008). Appl. No. PCT/EP2012/002665. Publication No. WO/2009/144527); however, so far their mode of action and pharmacologic targets have not been characterized or exploited.

Insulin resistance is a common feature in three pathologically related metabolic disorders, which have reached epidemic levels: Type 2 diabetes, obesity, and metabolic syndrome; thus, promoting Insulin sensitivity is an important goal within the therapeutic frame. Insulin receptor substrate proteins (IRS) regulate insulin physiological activity (Tamemoto H, Kadowaki T, Tobe K, Yagi T, Sakura H, Hayakawa T, Terauchi Y, Ueki K, Kaburagi Y, Satoh S, et al. Nature. 1994; 372:182-6). According to this proposal, deletion of Irs2 in mice causes diabetes due to a reduced development in the pancreatic β cell mass and to absence of proliferation from developed cells in response to peripheral insulin resistance (Withers D J, Gutierrez J S, Towery H, Burks D J, Ren J M, Previs S, Zhang Y, Bernal D, Pons S, Shulman G I, Bonner-Weir S, White M F. et al Nature. 1998; 391:900-4). Besides, Irs2 deficiency causes hepatic resistance to insulin and a defective suppression of hepatic production of glucose (Withers D J, Gutierrez J S, Towery H, Burks D J, Ren J M, Previs S, Zhang Y, Bernal D, Pons S, Shulman G I, Bonner-Weir S, White M F. Nature. 1998; 391:900-4; Kubota N, Tobe K, Terauchi Y, Eto K, Yamauchi T, Suzuki R, Tsubamoto Y, Komeda K, Nakano R, Miki H, Satoh S, Sekihara H, Sciacchitano S, Lesniak M, Aizawa S, Nagai R, Kimura S, Akanuma Y, Taylor S I, Kadowaki T. Diabetes. 2000; 49:1880-9; Previs S F, Withers D J, Ren J M, White M F, Shulman G I. J Biol Chem. 2000 275:38990-4). β Cell islets coming from Type 2 diabetes patients express a lower quantity of IRS2 than control islets; this shows that the molecule also plays an essential role in the development of diabetes in humans (Gunton J E, Kulkarni R N, Yim S, Okada T, Hawthorne W J, Tseng 25 Y H, Roberson R S, Ricordi C, O'Connell P J, Gonzalez F J, Kahn C R. Cell. 2005; 122:337-49). Irs2$^{-/-}$ male mice often die before 12 weeks due to diabetes complications, whereas Irs2$^{-/-}$ females develop a more benign diabetes form, and many survive up to 6 months. It is important to highlight that Irs2$^{-/-}$ females develop moderate obesity, partly because they eat more than control females; this suggests that Irs2$^{-/-}$ regulates the hypothalamic control of intake. According to this hypothesis, these females showed higher levels of leptin and leptin resistance (Burks D J, Font de Mora J, Schubert M, Withers D J, Myers M G, Towery H H, Altamuro S L, Flint C L, White M F. Nature. 2000; 407:377-82), suggesting that Irs2 could be a convergence point in leptin and insulin signaling pathways. Finally, recent studies have demonstrated a reduction of basal lipolysis in Irs2$^{-/-}$ females, which is consistent with the moderate obesity they develop (Garcia-Barrado M J, Iglesias-Osma M C, Moreno-Viedma V, Pastor Mansilla M F, Gonzalez S S, Carretero J, Moratinos J, Burks D J. Biochem Pharmacol. 2011; 81:279-88).

The present invention addresses and describes how metformin amino acid compounds, e.g. metformin lysinate, pharmacologically operate through GPBP. The present invention discloses and explains that the different electronic structure of these metformin amino acid compounds (SLNs) confront cytosolic GPBP and inhibit its kinase activity differently. This inhibiting characteristic is somewhat responsible for the pharmacological (anti-hyperglycemic and anti-inflammatory) differential activity that SLNs deploy (metformin amino acid compounds) in the IRS2$^{-/-}$ model of Type 2 diabetes.

Hence, the present invention describes metformin amino acid compounds as well as their synthesis; they display advantages over commercial metformin hydrochloride. Conceptual pharmacologic studies are described, and their results are compared to those obtained with commercial metformin hydrochloride; favorable results have been obtained, showing that new active principles can be widely used for treating diabetes mellitus, for example.

The use of metformin lysinate as a new molecule, or other amino acids, instead of the widely known metformin hydrochloride, is extremely important to define its assimilation pathway. metformin amino acid compounds of this invention exploit the presence of an amino acid to open a new assimilation pathway or route, different from that of commercial metformin hydrochloride's. This indicates that the ionized compound is not the one acting differently but rather that the existence of a new assimilation pathway shows a new chemical entity that is subsequently internalized by a different mechanism. When a metformin lysinate adduct is assimilated through a different route or by acting through a different receptor from that of separated (ionized) compounds, then, a differentiated mode of action different from metformin hydrochloride's (or even from the mix between betaine and metformin) is obtained.

In some embodiments, the metformin amino acid compound is selected from metformin aspartate, metformin isoleucinate, metformin alaninate, metformin valinate, metformin asparaginate, metformin threoninate, metformin leucinate, and metformin lysinate.

In some embodiments, the metformin amino acid compound is metformin aspartate. In some embodiments, the metformin aspartate is dimetformin aspartate. The chemical structure of dimetformin aspartate is represented by formula I:

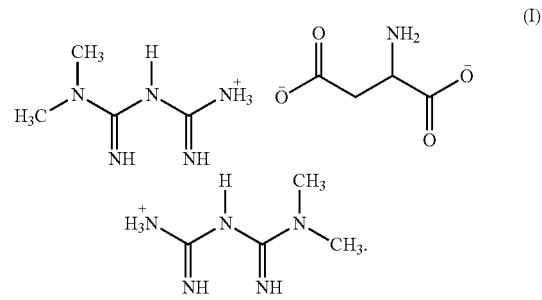

In some embodiments, the metformin amino acid compound is metformin isoleucinate. The chemical structure of metformin isoleucinate is represented by formula II:

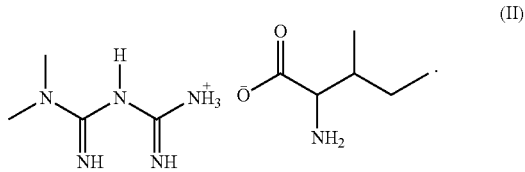

In some embodiments, the metformin amino acid compound is metformin alaninate. The chemical structure of metformin alaninate is represented by formula III:

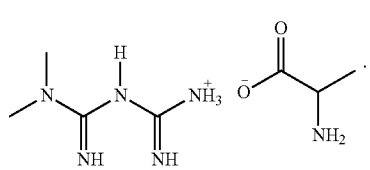

(III)

In some embodiments, the metformin amino acid compound is metformin valinate. The chemical structure of metformin valinate is represented by formula IV:

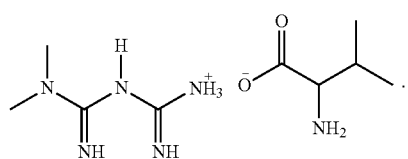

(IV)

In some embodiments, the metformin amino acid compound is metformin asparaginate. The chemical structure of metformin asparaginate is represented by formula V:

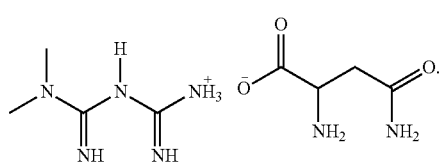

(V)

In some embodiments, the metformin amino acid compound is metformin threoninate. The chemical structure of metformin threoninate is represented by formula VI:

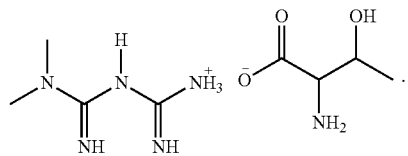

(VI)

In some embodiments, the metformin amino acid compound is metformin leucinate. The chemical structure of metformin leucinate is represented by formula VII:

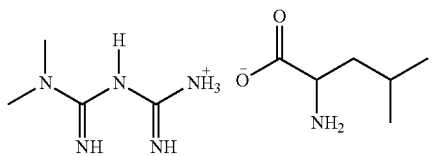

(VII)

In some embodiments, the metformin amino acid compound is metformin lysinate. The chemical structure of metformin lysinate is represented b formula VIII:

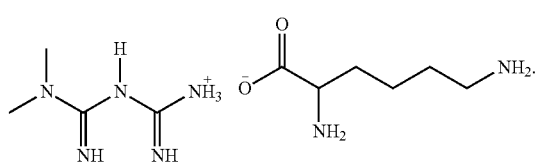

(VIII)

Several mechanism studies were conducted and demonstrated that metformin lysinate:
  differs from metformin hydrochloride and operates by inhibiting GPBP kinase activity;
  has an electronic structure that differs from metformin hydrochloride's electronic structure;
  confronts GPBP and inhibits its kinase activity;
  promotes glucose transporter translocation to membranes and glucose uptake (anti-hyperglycemic and anti-hypoglycemic activities);
  limits the inflammatory response (anti-inflammatory activity) by inhibiting GPBP kinase activity; and
  reduces peripheral insulin resistance in animal models of Type 2 diabetes due to their inhibiting action on GPBP kinase activity.

There are four protein complexes involved: AMPK, GPBP, LKB1, and AS160, characterizing the mode of action of the metformin amino acid compounds, wherein the amino acid is aspartate, isoleucinate, alaninate, valinate, asparaginate, threoninate, leucinate, or lysinate, which are essential in the regulation of GLUT4 expression as well as energy and glucose metabolism.

In some embodiments, metformin amino acid compounds, wherein the amino acid is selected from the group consisting of aspartate, isoleucinate, alaninate, valinate, asparaginate, threoninate, leucinate, and lysinate, participate and intervene in the AMPK, GPBP/CERT, and LKB1 activity in the following manner:
  They inhibit GPBP/CERT activity;
  They increase LKB1 activity;
  They have a different immune response modulation profile, especially in terms of increases IL10 synthesis;
  They translocate glucose transporter GLUT4 more efficiently;
  They act via VAPA-VAMP2 interaction; and/or
  They participate in AS160 regulation;
where AMPK increases GPBP/CERT activity; and GPBP/CERT and LKB1 power, in a synergic way, its kinase activity (reducing insulin level and improving lipid profile). In some embodiments, the metformin amino acid compound is metformin lysinate.

Another objective in the present invention is to use compositions, formulations and/or drugs containing metformin compounds (SLNs), such as metformin aspartate, metformin isoleucinate, metformin alaninate, metformin valinate, metformin asparaginate, metformin threoninate, metformin leucinate, or metformin lysinate, for Type 2 diabetes mellitus control, with an immediate release mechanism for a more effective treatment and less adverse effects.

The present invention also aims at using compositions, formulations and/or drugs containing metformin compounds (SLNs), such as metformin aspartate, metformin isoleucinate, metformin alaninate, metformin valinate, metformin asparaginate, metformin threoninate, metformin leucinate, or metformin lysinate.

Another objective in the present invention is to describe compositions, formulations and/or drugs containing the SLNs.

Metformin amino acid compounds (SLNs), which are biguanides, selected from the group consisting of metformin aspartate, metformin isoleucinate, metformin alaninate, metformin valinate, metformin asparaginate, metformin threoninate, metformin leucinate, and metformin lysinate, more particularly metformin lysinate, as well as compositions, formulations and/or drugs containing them, have an antihyperglycemic and coadjuvant, on the prevention, treatment and control of Type 2 diabetes in adults, as well as children and adolescents, always associated with diet and exercise.

In the present invention, compounds, as well as compositions, formulations and/or drugs containing them, are also useful for preventing, treating, and controlling Type 2 diabetes in obese or overweight patients, including patients who have failed to follow a diet or exercise regimen, who show failure with sulfonylureas and who have a tendency to gain weight; they are also useful for preventing, treating and controlling Type 2 diabetes in patients with lipid metabolism disorders secondary to diabetes.

Drugs, compositions and/or formulations containing the compounds in the present invention are optimized, robust, and useful in preventing, treating and controlling type 2 diabetes. These are replicable and have the required quality, stability and effectiveness for their purpose.

In some embodiments, the metformin amino acid compound is metformin lysinate, which is useful as an antihyperglycemic agent and as a coadjuvant compound in preventing, treating, and controlling Type 2 diabetes in adults, as well as children and adolescents.

In some embodiments, the dosage form used to administer the compounds and pharmaceutical compositions are tablets, caplets, gel, paste, powder, extended-release granules, capsules, extended-release tablets, liquids with buffering agents, effervescent tablets, suspensions, syrups, spray, and others. In some embodiments, the dosage form used to administer the compounds and pharmaceutical compositions is a tablet.

In some embodiments, the compounds and pharmaceutical compositions are administered orally, by intravenous injection, by intramuscular injection, nasally, by intraperitoneal injection, or sublingually. In some embodiments, the compounds and pharmaceutical compositions are administered orally.

In other embodiment, the present application discloses also pharmaceutical compositions comprising a compound of the present invention, or a pharmaceutically acceptable salt, solvate, and/or ester thereof, in combination with at least one additional therapeutic agent, and a pharmaceutically acceptable carrier or excipient.

In an embodiment, the present invention also describes drugs containing metformin amino acid compounds (SLNs), which are biguanides, selected from the group consisting of metformin aspartate, metformin isoleucinate, metformin alaninate, metformin valinate, metformin asparaginate, metformin threoninate, metformin leucinate, and metformin lysinate, more particularly metformin lysinate; and their solvates, hydrates, and/or polymorphs.

In the present invention, one embodiment of drugs, formulations and dosage forms may contain 100 mg up to 2.4 g of at least one of the new compounds (SLNs), which are metformin amino acid compounds (biguanides), selected from the group consisting of metformin aspartate, metformin isoleucinate, metformin alaninate, metformin valinate, metformin asparaginate, metformin threoninate, metformin leucinate, and metformin lysinate, more particularly metformin lysinate; and their solvates, hydrates, and/or polymorphs, and optionally, an excipient or a pharmaceutically acceptable vehicle.

In some embodiments, tablets are the preferred dosage form for administering compounds from this invention. In some embodiments, the selected formulation for administering the metformin amino acid compounds (SLNs, e.g., metformin lysinate) are aqueous coating tablets prepared via wet granulation, containing from about 100 mg to about 2.4 g of at least one of metformin amino acid compounds (SLNs), which are biguanides. In some embodiments, the formulations comprise from about 589-651 mg, from about 615-625 mg, or about 620 mg of metformin lysinate.

In some embodiments, the selected dosage form for administering the SLNs (e.g., metformin lysinate) are aqueous coating tablets prepared via wet granulation, containing from about 100 mg to about 2.4 g of at least one of the metformin amino acid compounds (SLNs), which are biguanides. In some embodiments, the dosage form comprises from about 997.5-1102.5 mg, from about 1035-1075 mg, or about 1050 mg of metformin lysinate.

In an additional embodiment, the present invention provides preclinical and clinical studies on these invention compounds (SLNs), as well as compositions, dosage forms and/or drugs containing them. Preclinical and clinical studies include; studies on pharmacokinetics, pharmacodynamics, and toxicology, as well as clinical trials phase I-III.

Synthesis and Characterization of Metformin Amino Acid Compounds

In some embodiments, metformin amino acid compounds were synthetized from reagents: dimethylamine hydrochloride and dicyandiamide. Dimethylamine hydrochloride is released from its anion by treating it in a strong base, as described in Example 2. Once released, the dimethylamine base dissolves in methanol, since at room temperature it is gas. The dimethylamine solution in methanol reacts in an appropriate organic dissolvent such as xylene or toluene, which produce better results; however, other hydrocarbons, such as heptane, pentane, cyclohexane and ethylbenzene, may be used. A dicyandiamide equivalent is added, keeping it at xylene's or toluene's reflux temperature, depending on the case. The product is separated by cooling at room temperature, and crystallizes on methanol (once or twice), depending on whether the residual dimethylamine concentration is lesser or greater than 10 ppm.

Dimethylamine should be monitored, even if this is not specified in the U.S. Pharmacopeia, in the National Formulary Metformin Hydrochloride (HCl) monograph, nor in the United Mexican States Pharmacopeia, as acid conditions of the reagent media may promote dimethylnitrosamine formation; this compound is thought, on a solid basis, to cause cancer in humans (for analysis techniques, see, for example: Application Note 298: Determination of Dimethylamine in Metformin HCl Drug Product Using IC with Suppressed Conductivity Detection Suparerk Tukkeeree, 1 Thunyarat Phesatcha, by authors Jeffrey Rohrer de Thermo Fisher Scientific Inc., Bangkok, Thailand and Thermo Fisher Scientific Inc., Sunnyvale, Calif. USA, see also Chung, S. W. C y Chan, B. T. P., Trimethylamine Oxide, dimethylamine, trimethylamine and formaldehyde levels in main traded fish species in Hong Kong, Food additives & Contaminants. Part B. Surveillance, June, v.2, No. 1 [2009]). Maximum levels of remaining dimethylamine in metformin should not surpass 10 ppm.

In some embodiments, the metformin base was synthesized by the following procedure: Under nitrogen flow, sodium methoxide is dissolved, keeping temperature below 40° C. Metformin hydrochloride is then added, and the reagent mixture is stirred for 60 to 70 minutes at a temperature between 26° and 30° C. Then, the solid that forms, which is sodium chloride, is separated by filtration, and metformin base remains as a solution (see Example 2).

Regardless of the technique used to obtain metformin base, the amino acid components were obtained following the procedure described below: An amino acid is added to a solution of metformin base in methanol. The reaction media is stirred vigorously while the reaction takes place. The solution is concentrated to a volume of around 50% to oversaturate and enable crystallization. It is then filtrated and dried, isolating the corresponding metformin amino acid compound.

In some embodiments, the metformin free base and the amino acid are admixed at a temperature from about 0° C. to about 60° C. In some embodiments, the metformin free base and the amino acid are admixed at a temperature from about 20° C. to about 50° C. In some embodiments, the metformin free base and the amino acid are admixed at a temperature from about 20° C. to about 25° C. In some embodiments, the metformin free base and the amino acid are admixed at a temperature from about 40° C. to about 45° C.

In some embodiments, the metformin free base and the amino acid are admixed for a time from about 30 minutes to about 30 hours. In some embodiments, the metformin free base and the amino acid are admixed for a time from about 2 hours to about 18 hours. In some embodiments, the metformin free base and the amino acid are admixed for a time of about 2 hours. In some embodiments, the metformin free base and the amino acid are admixed for a time of about 18 hours.

The compound obtained is identified by using nuclear magnetic resonance, infrared, mass spectrometry analysis, X-ray monocrystalline diffraction, among others.

X-ray monocrystalline diffraction. The X-ray monocrystalline diffraction experiments were conducted in a Bruker AXS SMART APEX CCD diffractometer, equipped with a Bruker AXS [graphite monochromated Mo-KR radiation ($\lambda$) 0.71073 Å]. Data integration and unit-cell parameters were obtained by using SAINT. The structure of crystals was solved with direct techniques using SHELXS-97. All atom positions, different from those of hydrogen, were located using Fourier transform techniques.

For X-ray powder diffraction, samples were ground in an agate mortar, mounted in a glass sample holder by powder mounting in a cavity, and analyzed with a SIEMENS D5000 diffractometer, using K$\alpha$ radiation ($\Delta$=1.5406 Å); at 35 kV, 30 mA; for 58 minutes, in intervals of $2°<2\theta<60°$.

The equipment used to determine the solid-state nuclear magnetic resonance spectra is a Bruker NMR Avance II, 5300 MHz multinuclear spectrometer.

The nuclear magnetic resonance spectrum of $^1H$ was run on a Varian NMR Inova, 400 MHz, multinuclear spectrometer, using deuterated water ($D_2O$) as a dissolvent; the nuclear magnetic resonance spectrometer spectrum of $^{13}C$ was run on a Varian NMR, at 100 MHz.

Additionally, samples were run by nuclear magnetic resonance spectrum of $^1H$ and $^{13}C$ on a Bruker NMR Avance III, 500 MHz, multinuclear spectrometer, using deuterated water ($D_2O$) as a dissolvent. The structure assignment was based on chemical shifts, integration, coupling and correlation studies of $^1H$ and $^{13}C$. Note: The use of deuterated water as a dissolvent in a $^1H$ NMR prevents NH and OH proton images from being observed. Mass tests were conducted in a MStation 700 high resolution mass spectrophotometer.

The infrared spectrum is applied to characterize molecules that give a good pattern of infrared light absorption lines, specific to each molecule. A Nicolet Avatar 360 FT-IR E.S.P. infrared spectrophotometer was used to determine the infrared spectra. Spectra in potassium bromide were obtained.

Elemental tests were carried out in a Perkin Elmer PE2400 elemental analyzer under the following operating conditions:
Carrier gas: UHP Helium
Pressure: 116.2 mm Hg
Detector: Thermal conductivity
Reduction reactor temperature: 501° C.
Combustion reactor temperature: 975° C.
Calibration compound: Acetanilide (Perkin Elmer)

Identity tests corresponding to metformin were analyzed using a High-Performance Liquid Chromatography (HPLC), in which retention times of the main sample analyte corresponded in time and form to the one obtained with a reference solution of metformin hydrochloride (FIGS. 47-54).

In another embodiment, identity test by spectrophotometry UV-Vis (FIGS. 39-46) showed a maximum absorption of each one of the metformin compounds at 223 nm, with a characteristic valley between 216 and 217 nm.

In another embodiment, peak purity tests showed that the separated analyte was pure, since only signals attributed to the concerned analyte were observed (FIGS. 55-63).

Also, the analysis of volatile organic impurities (where methanol was included) proved residual concentrations specifications for solvents that could be present in the final product, such as methanol (less than 3000 ppm), benzene (less than 2 ppm), methylene chloride (less than 600 ppm), chloroform (less than 60 ppm), trichloroethylene (less than 80 ppm), and 1,4-dioxane (less than 380 ppm).

In another embodiment, the content test was carried out by using HPLC, showing results with a recovered percentage between 90.0% and 97.0%, whereas for the metformin-related substances test, in which the cyanoguanidine impurity was estimated, values near 0.2% were identified; only the aspartate compound complied with the specification (less than 0.02%), as all the other metformin amino acid compounds (SLNs) showed values higher than 0.15%. Finally, in terms of unknown individual impurities, there were impurities between 0.15% and 0.20%.

In some embodiments, the weight percentage of the recovered metformin amino acid compound was from about 90.0% to about 99.9%, about 90% h to about 98%, about 90% to about 97%, about 97% to about 99.9%, about 97% to about 98%, about 98% to about 99.9%.

In some embodiments, the metformin amino acid compounds contained impurities (w/w) from about 0.20% to about 0.01%, about 0.20% to about 0.02%, about 0.20% to about 0.05%, about 0.15% to about 0.01%, about 0.15% to about 0.02%, about 0.15% to about 0.05%, about 0.05% to about 0.01%, about 0.02% to about 0.01%. In some embodiments, the metformin amino acid compounds contained impurities less than about 0.20% (w/w). In some embodiments, the metformin amino acid compounds contained impurities less than about 0.15% (w/w).

In an additional embodiment, an infrared spectrum was taken for each SLN compound analyzed, in order to have enough evidence to demonstrate the integrity of each molecule.

Drugs of this invention involving metformin amino acid compounds (SLNs), which are biguanides, selected from the group consisting of metformin aspartate, metformin isoleucinate, metformin alaninate, metformin valinate, metformin asparaginate, metformin threoninate, metformin leucinate, and metformin lysinate, more particularly metformin lysinate, have unique physicochemical characteristics, a distinct mode of action different from metformin hydrochloride, translocating GLUT4 more efficiently, with a better anti-inflammatory profile; also, they reduce insulin and leptin levels in Type 2 diabetes models. They have an anti-hyperglycemic effect as coadjuvant on prevention, treatment, and control of Type 2 diabetes in adults, as well as children and adolescents, always associated with diet and exercise.

Compositions or Pharmaceutical Formulations

The present application discloses pharmaceutical compositions comprising a compound of the present invention, or a pharmaceutically acceptable salt, solvate, and/or ester thereof, in combination with at least one additional therapeutic agent, and a pharmaceutically acceptable carrier or excipient.

In an embodiment, the present invention also describes drugs containing metformin amino acid compounds (SLNs), which are biguanides, selected from the group consisting of metformin aspartate, metformin isoleucinate, metformin alaninate, metformin valinate, metformin asparaginate, metformin threoninate, metformin leucinate, and metformin lysinate more particularly metformin lysinate; and their solvates, hydrates, and/or polymorphs thereof.

This invention also describes a drug comprising a compound of metformin lysinate.

This invention also describes a drug containing metformin amino acid compounds (SLNs), which are biguanides, selected from the group consisting of metformin aspartate, metformin isoleucinate, metformin alaninate, metformin valinate, metformin asparaginate, metformin threoninate, metformin leucinate, or metformin lysinate for controlling Type 2 diabetes, with an immediate release mechanism, resulting in a more effective treatment, with fewer adverse effects.

This invention also describes a drug comprising at least one of the SLNs (e.g., metformin lysinate), for controlling type II diabetes mellitus, with an immediate release mechanism for a more effective treatment with fewer adverse effects.

This invention also describes a drug comprising metformin lysinate, for controlling type 1 diabetes mellitus, with an immediate release mechanism for a more effective treatment with fewer adverse effects.

Moreover, this invention also describes a drug comprising metformin compounds (biguanides, SLNs), selected from the group consisting of metformin aspartate, metformin isoleucinate, metformin alaninate, metformin valinate, metformin asparaginate, metformin threoninate, metformin leucinate, and metformin lysinate, with unique physicochemical characteristics, a distinct mode of action different from metformin hydrochloride's, translocating GLUT4 more efficiently, with a better anti-inflammatory profile; also, it reduces insulin and leptin levels in Type 2 diabetes models.

This invention also describes a drug comprising Metformin lysinate, with unique physicochemical characteristics, a distinct mode of action different from Metformin hydrochloride's, translocating GLUT4 more efficiently, with a better anti-inflammatory profile; also, it reduces insulin and leptin levels in Type 2 diabetes models.

Within the scope of this invention is the description of drugs comprising metformin compounds (SLNs), selected from the group consisting of metformin aspartate, metformin isoleucinate, metformin alaninate, metformin valinate, metformin asparaginate, metformin threoninate, metformin leucinate, and metformin lysinate, more particularly metformin lysinate, participate and intervene in the AMPK, GPBP/CERT and LKB1 activity, where AMPK increases the GPBP/CERT activity, and GPBP/CERT as well as LKB1 power, in a synergic way, its kinase activity, as follows:
They inhibit GPBP/CERT activity;
They increase LKB1 activity;
increases IL10 synthesis;
They translocate glucose transporter GLUT4 more efficiently;
They act via VAPA-VAMP2 interaction; and/or
They participate in AS160 regulation.

The compounds of the present invention, which are useful for drug manufacturing, have an anti-hyperglycemic effect as coadjuvants on prevention, treatment and control of Type 2 diabetes in adults, as well as children and adolescents, always associated with diet and exercise.

The compounds and drugs containing them, from the present invention, are also useful for preventing, treating, and controlling Type 2 diabetes in obese or overweight patients, including patients who have failed to follow a diet or an exercise regimen, who show failure with sulfonylureas, and who have a tendency to gain weight; they are also useful for preventing, treating and controlling Type 2 diabetes in patients with lipid metabolism disorders secondary to diabetes.

A preferred compound in the present invention is metformin lysinate, which is useful as an anti-hyperglycemic agent and as a coadjuvant compound in preventing, treating and controlling Type 2 diabetes in adults, as well as children and adolescents.

It has been determined that metformin amino acid compounds (SLNs), which are biguanides, selected from the group consisting of metformin aspartate, metformin isoleucinate, metformin alaninate, metformin valinate, metformin asparaginate, metformin threoninate, metformin leucinate, or metformin lysinate, more particularly metformin lysinate, have unique physicochemical characteristics, a distinct mode of action different from metformin hydrochloride, translocating GLUT4 more efficiently, with a better anti-inflammatory profile; also, they reduce insulin and leptin levels in Type 2 diabetes models.

While it is possible for the active principles to be administered alone it may be preferable to present them as pharmaceutical formulations. The formulations of the invention comprise at least one active principle, as above defined, together with one or more acceptable carriers and, optionally, other therapeutic principles. The carrier(s) must be "acceptable" in the sense of being compatible with the other principles of the formulation and physiologically innocuous to the recipient thereof.

In one embodiment, the present application discloses also pharmaceutical compositions comprising a compound of the present invention, or a pharmaceutically acceptable salt, solvate, and/or ester thereof, in combination with at least one additional therapeutic agent, and a pharmaceutically acceptable carrier or excipient. The additional therapeutic agent is selected from other anti-diabetic drugs, such as sulfonylureas, iDPP4, SGL2, thiazolidinediones (TZD), insulins, glinides, etc.

Thus, the compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration, they will generally be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkyl cellulose, hydroxyalkyl methylcellulose, stearic acid and the like. In some embodiments, the excipient is microcrystalline cellulose, anhydrous dibasic calcium phosphate, sodium starch glycolate, magnesium stearate, or combinations thereof.

The formulations include those suitable for the foregoing administration routes. The formulations may conveniently be presented in unit dosage form and may be prepared by any of the methods well known in the art of pharmacy. Techniques and formulations generally are found in *Remington's* Pharmaceutical Sciences (Mack Publishing Co., Easton, Pa.) Such methods include the step of bringing into association the active ingredient with the carrier, which constitutes one or more accessory ingredients. In general, the formulations are prepared uniformly and intimately, bringing into association the active principle with liquid carriers or finely divided solid carriers, or both, and then, if necessary, shaping the product.

Pharmaceutical forms for administering the compounds of the present invention may include the following: tablet, caplet, powder, extended-release granule, capsule, extended-release tablet, liquid with buffering agents, effervescent tablet, suspension, and other forms. The route of administration may be oral, intravenous injection, intramuscular injection, etc.

Formulations of the present invention suitable for oral administration may be presented as discrete units, such as capsules, cachets, or tablets, each containing a predetermined amount of the active principle (as a powder or granules).

A tablet is made by compression or molding, optionally with one or more accessory ingredients. Compressed tablets may be prepared by compressing in a suitable machine the active ingredient in a free-flowing form, such as a powder or granules, optionally mixed with a binder, lubricant, inert diluent, preservative, surface active, or dispersing agent. Molded tablets may be made by molding, in a suitable machine, a mixture of the powdered active ingredient moistened with an inert liquid diluent. The tablets may optionally be coated or scored and formulated so as to provide slow or controlled release of the active ingredient therefrom.

Pharmaceutical formulations according to the present invention comprise one or more compounds of the invention together with one or more pharmaceutically acceptable carriers or excipients, and optionally, other therapeutic agents. Pharmaceutical formulations containing the active ingredient may be in any form suitable for the intended method of administration. When administered for oral use, for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions, and such compositions may contain one or more agents, including sweetening agents, flavoring agents, coloring agents and preserving agents, in order to provide a palatable preparation. Tablets containing the active ingredient in a mixture with non-toxic pharmaceutically acceptable excipient suitable for manufacture of tablets are acceptable. These excipients may be, for example, inert diluents, such as calcium or sodium carbonate, lactose, lactose monohydrate, croscarmellose sodium, povidone, calcium, or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques, including microencapsulation to delay disintegration and adsorption in the gastrointestinal tract and thereby provide a sustained action over a longer period. For example, a time delay material, such as glyceryl monostearate or glyceryl distearate alone or with a wax, can be employed.

Formulations for oral use may be also presented as hard gelatin capsules, where the active ingredient is mixed with an inert solid diluent, for example calcium phosphate or kaolin, or as soft gelatin capsules wherein the active ingredient is mixed with water or an oil medium, such as peanut oil, liquid paraffin, or olive oil.

Aqueous suspensions of the invention contain the active materials in admixture with excipients suitable for the manufacture of aqueous suspensions. Such excipients include a suspending agent, such as sodium carboxymethyl cellulose, methylcellulose, hydroxypropyl methylcellulose, sodium alginate, polyvinylpyrrolidone, gum tragacanth and gum acacia, and dispersing or wetting agents, such as a naturally occurring phosphatide (e.g., lecithin), a condensation product of an alkylene oxide with a fatty acid (e.g. polyoxyethylene stearate), a condensation product of ethylene oxide with a long chain aliphatic alcohol (e.g. heptadecaethyleneoxycetanol), a condensation product of ethylene oxide with a partial ester derived from a fatty acid and a hexitol anhydride (e.g. polyoxyethylene sorbitan monooleate). The aqueous suspension may also contain one or more preservatives, such as ethyl or n-propyl p-hydroxybenzoate, one or more coloring agents, one or more flavoring agents, and one or more sweetening agents, such as sucrose or saccharin.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, such as a solution in 1,3-butanediol, or prepared as a lyophilized powder. Among the acceptable vehicles and solvents that may be employed are water, Ringer's solution, and isotonic sodium chloride solution. In addition, sterile fixed oils may conventionally be employed as a solvent or suspending medium. For this purpose, any bland fixed oil may be employed, including synthetic mono- or diglycerides. In addition, fatty acids, such as oleic acid, may be used in the preparation of injectables.

Formulations suitable for parenteral administration include aqueous and non-aqueous sterile injection solutions, which may contain anti-oxidants, buffers, bacterostats, and solutes, which render the formulation isotonic with the blood of the intended recipient, as well as aqueous and non-aqueous sterile suspensions, which may include suspending agents and thickening agents.

The formulations are presented in unit-dose or multi-dose containers, for example, sealed ampoules and vials, and may be stored in a freeze-dried (lyophilized) condition, requiring only the addition of the sterile liquid carrier, for example, water for injection, immediately prior to use. Extemporaneous injection solutions and suspensions are prepared from sterile powders, granules, and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above, the formulations of this invention may include other agents conventional in the art having regard to the type of formulation in question, for example, those suitable for oral administration may include flavoring agents.

In one embodiment of the invention, the pharmaceutical form preferred for administering the compounds of this invention is the tablet, due to its dose accuracy and coating simplicity, besides being the most acceptable one as it is easy to administrate. Although capsules are one alternative, it is not possible to dose such a high concentration of drug due to the small size of the capsules. In the case of tablets, it is possible to reduce the volume of the powders, thus facilitating the managing and administration. Caplet-shaped tablets facilitate swallowing and have the smallest possible size for the amount and weight thereof. A slot is also included in the design for an easy administration.

In yet another embodiment, the present application discloses pharmaceutical compositions comprising a compound of the present invention, or a pharmaceutically acceptable salt, solvate, and/or ester thereof, in combination with at least one additional therapeutic agent, and a pharmaceutically acceptable carrier or excipient.

In the present invention, one embodiment of drugs, formulations and dosage forms may contain 100 mg up to 2.4 g of at least one of the new compounds (SLNs), which are new-generation biguanides, selected from the group consisting of metformin aspartate, metformin isoleucinate, metformin alaninate, metformin valinate, metformin asparaginate, metformin threoninate, metformin leucinate, or metformin lysinate, more particularly metformin lysinate; and their solvates, hydrates, and/or polymorphs, and optionally, an excipient or a pharmaceutically acceptable vehicle.

The formulation selected for the administration of the compounds of the present invention, selected from the group consisting of metformin aspartate, metformin isoleucinate, metformin alaninate, metformin valinate, metformin asparaginate, metformin threoninate, metformin leucinate, and metformin lysinate, more particularly metformin lysinate, are tablets with aqueous coating by wet granulation.

Particularly, the formulation used for the administration of the metformin amino acid compounds are tablets with aqueous coating prepared by wet granulation, comprising from about 100 mg to about 2.4 g of at least one of the metformin amino acid compounds (SLNs), which are biguanides (from this invention). In some embodiments, the formulation comprises between about 589-651 mg, from about 615-625 mg, or about 620 mg of at least one metformin amino acid compound (SLN). In some embodiments, the formulation comprises metformin lysinate.

In some embodiments, the pharmaceutical composition for administering metformin amino acid compounds are aqueous coating tablets prepared via wet granulation, containing from about 100 mg to about 2.4 g of at least one of the metformin amino acid compounds (SLNs), which are biguanides. In some embodiments, the formulations comprise from about 997.5-1102.5 mg, from about 1035-1075 mg or about 1050 mg of at least one SLNs (e.g., metformin lysinate).

The formulation was designed based on the physicochemical characteristics of the compounds of this invention (SLNs), and on the desired characteristics of the product in order to ensure effectiveness, safety, and quality for the drug manufacturing process. The components of the formulation were selected based on their function, and their concentration was established depending on the product performance.

EXAMPLES

These examples have been included to illustrate the embodiments of this invention. Certain aspects in these examples are described in terms of techniques and procedures that are found or considered by creators involved in the present invention to work correctly in the invention practice. Given the present description and general level of the technique ability, the following examples are models only, and changes, modifications and alterations may occur, without deviating from this invention's scope.

The invention will now be illustrated by the following non-limiting examples.

Example 1

Synthesis and Characterization of Compounds in this Invention

Following the general process described above, metformin amino acid compounds were synthetized with the following amino acids: Aspartic, Isoleucine, Alanine, Valise, Asparagine, Threonine, Leucine, Lysine. In examples 3, 4, 5, 6, 7, 8, 9, 10, the particular process for the synthesis of some amino acids is described. The process for the remaining compounds is very similar and easily inferable from the general process and specific processes. Each active principle structure elucidation was carried out by solid-state $^{13}$C nuclear magnetic resonance spectrum, FT-infrared, differential scanning analysis, and mass spectrometry. In FIGS. 6, 7, 8, 9A, and 9B, the corresponding spectra and physicochemical analyses for the compound obtained from the reaction between metformin and aspartic, are shown, and their results confirm the corresponding dimetformin aspartate obtention. In FIGS. 10, 11, 12, 13A, and 13B the corresponding spectra and physicochemical analyses for compound obtained from the reaction between metformin and isoleucine, are shown, and their results confirm the corresponding metformin isoleucinate obtention. In FIGS. 14, 15, 16, 17A, and 17B the corresponding spectra and physicochemical analyses for alanine are shown, and their results confirm the corresponding metformin alaninate obtention. In FIGS. 18, 19, 20, 21A, and 21B the corresponding spectra and physicochemical analyses for valine are shown, and their results confirm the corresponding metformin valinate obtention. In FIGS. 22, 23, 24, 25A, and 25B the corresponding spectra and physicochemical analyses for asparagine are shown, and their results confirm the corresponding metformin asparaginate obtention. In FIGS. 26, 27, 28, 29A, and 29B the corresponding spectra and physicochemical analyses for threonine are shown, and their results confirm the corresponding metformin threoninate obtention. In FIGS. 30, 31, 32, 33A, and 33B the corresponding spectra and physicochemical analyses for leucine are shown, and their results confirm the corresponding metformin leucinate obtention. In FIGS. 34, 35, 36, 37A, and 37B the corresponding spectra and physicochemical analyses for lysine are shown, and their results confirm the corresponding metformin lysinate obtention.

Mass spectrometry for each compound was made by $FAB^+$ and $FAB^-$; both molecular ions, the cation and the anion, are observed to ensure the metformin compound formation. The constitution of metformin amino acid compounds is observed by using the following technique: isoleucinate, leucinate, valinate, asparaginate, threoninate, and lysinate are formed by metformin: an amino acid in a 1:1 molar proportion; in the specific case of dimetformin aspartate the metformin proportion is: amino acid in a 2:1 proportion (FIGS. 9A and 9B). This is easy to understand given that amino acids have two carboxylic acids. For dimetformin aspartate, the stoichiometry was checked through elemental analysis and $^1H^+$ nuclear magnetic resonance.

Regarding the active principles' physicochemical properties, in Tables 7 and 8, water solubility of each one of the compounds is shown. Their solubility may be compared with the solubility of metformin hydrochloride, which is 0.4 g/mL. SLNs showed a high solubility in purified water at room temperature; this was observed during the sample preparation for the pH test. These metformin molecules could be classified as easily soluble substances in water, considering that when 1.0 g of the sample was dissolved in 10 mL of purified water, it was completely solubilized, without the need of external action. On the other hand, the pH of these solutions ranges between the values of 10 and 12, which means that in aqueous solutions, they have a very basic pH, compared with that of metformin hydrochloride's, which has a 6.86 pH. Likewise, each compound's melting point and hygroscopicity are reported. Generally, compounds show hygroscopic features; in the case of metformin lysinate, hygroscopicity complies with specifications of the European Pharmacopeia 7.0 Vol. 1, Section 5.11, page 637, as a "deliquescent compound." This is similar for asparagine, threonine, and leucine. Compounds containing isoleucine, alanine, and valine are hygroscopic, and aspartic acid is slightly hygroscopic (Table 1).

TABLE 1

Synthetized metformin amino acid compounds and their solubility.

| Amino acid | R group | Physical form | WATER SOLUBILITY g/mL | PH |
|---|---|---|---|---|
| 11. ASPARTIC ACID* | 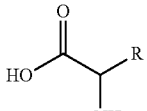 | Slightly hygroscopic solid | 0.455 | 11.03 |
| 12. ISOLEUCIN | 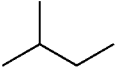 | Hygroscopic solid | 1.25 | 11.26 |
| 13. ALANINE | $CH_3$ | Hygroscopic solid | 1.25 | 11.34 |
| 14. VALINE |  | Hygroscopic solid | 1.67 | 11.11 |
| 15. ASPARAGINE |  | Deliquescent | 1.67 | 10.53 |
| 16. THREONINE | 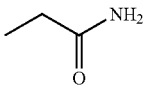 | Deliquescent | 1.67 | 10.73 |
| 17. LEUCINE |  | Deliquescent | 1.00 | 11.08 |
| 18. LYSINE | 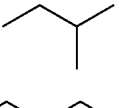 | Deliquescent | 1.25 | 12.04 |
| 19. Metformin hydrochloride | HCl | White or whitish crystals | Very soluble | 6.86 |
| 20. Metformin glycinate | 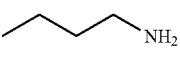 | White or whitish powder | 1.4 | 10.8 |

*Value R is shown in the second column for each amino acid

TABLE 2

Physicochemical properties of the present invention's new active principles

| Test | Dimetformin aspartate | Metformin isoleucinate | Metformin alaninate | Metformin valinate | Metformin asparaginate | Metformin lysinate |
|---|---|---|---|---|---|---|
| Description | Fine and white powder, free of foreign particles | Fine and slightly yellow powder, free of foreign particles | Fine and slightly yellow powder, free of foreign particles | Fine and slightly yellow powder, free of foreign particles | Fine and white powder, free of foreign particles | Yellow powder free of foreign particles |
| HPLC id | Tr standard (min.) = .95 Tr sample (min.) = 2.95 $\lambda$(max. nm) = 232.0 | Tr standard (min.) = 2.95 Tr sample (min.) = 2.95 $\lambda$(max. nm) = 232.0 232.°$\gamma$max | Tr standard (min.) = 2.95 Tr sample (min.) = 2.95 $\lambda$(max. nm) = | Tr standard (min.) = 2.95 Tr sample (min.) = 2.95 $\lambda$(max. nm) = 232.0 | Tr standard (min.) = 2.95 Tr sample (min.) = 2.94 $\lambda$(max. nm) = 232.0 | Tr standard (min.) = 2.95 Tr sample (min.) = 2.94 $\lambda$(max. nm) = 232.0 |
| Identity UV-Vis | (nm) 233.0 valleymax(nm) 216.0 | $\lambda$max (nm) 233.0 valleymax(nm) 216.0 | $\lambda$max (nm) 233.0 valleymax(nm) 216.0 | $\lambda$max (nm) 233.0 valleymax(nm) 216.0 | $\lambda$max (nm) 233.0 valleymax(nm) 217.0 | $\lambda$max (nm) 233.0 valleymax(nm) 217.0 |
| Solution pH | 11.03 | 11.26 | 11.34 | 11.11 | 10.53 | 12.04 |
| Metformin Content (98.5%-101.0%) | 96.08% 96.14 mg Metformin | 94.68% 94.97 mg Metformin | 95.83% 95.64 mg Metformin | 95.52% 96.16 mg Metformin | 93.32% 94.25 mg Metformin | 91.21% 91.23 mg Metformin |
| DSC | Melting point: 221.74° C. | Melting point 149.60° C. | Melting point 178.61° C. | Melting point 163.36° C. | Melting point 165.87° C. | Melting point 151.91° C. |
| Related substances, Cyanoguanidine Less than 0.020% Impurity rate. Unknown, Less than 0.10%, Total impurities: No more than 0.60% | % Cyanoguanidine 0.010 % Impurity rate. 0.416 % Total Imp. 0.448 | % Cyanoguanidine 0.166 % Impurity rate. 0.025 % Total Imp. 0.127 | % Cyanoguanidine 0.205 % Impurity rate. 0.196 % Total Imp. 0.422 | % Cyanoguanidine 0.227, % Impurity rate. 0.168 % Total Imp. 0.248 | % Cyanoguanidine 0.156 % Impurity rate. 0.414 % Total Imp. 2.335 | % Cyanoguanidine 0.159 % Impurity rate. 0.224 % Total Imp. 0.596 |

| Test | Metformin threoninate | Metformin leucinate | Metformin hydrochloride | Metformin glycinate |
|---|---|---|---|---|
| Description | Yellow powder free of foreign particles | Fine and slightly yellow powder, free of foreign particles | White or whitish crystals | White or whitish powder |
| HPLC id | Tr standard (min.) = 2.95 Tr sample (min.) = 2.94 A(max. nm) = 232.0 | Tr standard (min.) = 2.95 Tr sample (min.) = 2.94 A(max.nm) = 232.0 | Tr standard (min.) = 2.95 Tr sample (min.) = 2.95 A(max. nm) = 232.0 | |
| Identity UV-Vis | $\lambda$max (nm) 233.0 valleymax(nm) 216.0 | $\lambda$max (nm) 233.0 valleymax(nm) 216.0 | $\lambda$max (nm) 233.0 valleymax(nm) 216.0 | |
| Solution pH | 10.73 | 11.08 | 6.86 | 10.8 |
| Metformin content (98.5%-101.0%) | 95.10% 95.35 mg Metformin | 95.09% 95.38 mg Metformin | 99.24% | |
| DSC | Melting point 145.90° C. | Melting point 142.80° C. | Melting point 228.44° C. (FIG. 49) | Melting point 166.0° 166.0° C. |
| Related substances Cyanoguanidine Less than 0.020% Impurity rate. Unknown, Less than 0.10%, Total impurities: No more than 0.60% | % Cyanoguanidine 0.177, % Impurity rate. 0.168 % Total Imp. 0.514 | % Cyanoguanidine 0.172, % Impurity rate. 0.146% % Total Imp. 0.217 | % Cyanoguanidine Less than 0.02% % Impurity rate. Less than 0.1% % Total Imp. Less than 0.6% | % Cyanoguanidine 0.00 % Impurity rate. <0.10% % Total Imp. 0.03% |

Example 2

Process for Producing Dimethylamine Base

A total of 183 mL of methanol was poured in a round bottom flask and cooled between 0° C. and −10° C.; sodium methoxide of 95.2% purity was added, keeping temperature below 35° C. It was cooled to 0° C., and dimethylamine hydrochloride was poured and stirred for 45 minutes, keeping temperature below 50° C. The solution was titrated and dicyandiamide is added.

Example 3

General Method for Obtaining Metformin Base

A total of 183 mL of methanol was poured in a 3-neck round bottom flask and cooled between −10° C. and 0° C. Then, 19.8 g of sodium methoxide was added, keeping temperature below 35° C. Temperature was adjusted between 26° C. and 35° C., and 57.8 g of metformin hydrochloride was added. Suspension was stirred for 1 hour between 26° C. and 30° C. and vacuum filtered; the filtrate was evaporated under vacuum, and the resulting solid was treated with 300 mL of isopropanol, filtrated and evaporated to give a solid weighing 41.5 g for a 92% yield.

Example 4

Production of Dimetformin Aspartate

A total of 53.45 g L-aspartic acid was added to 104.8 g of a metformin base solution in methanol 1050 mL and stirred at room temperature. The mixture was stirred at room temperature for 2 hours, giving a suspension that was filtrated; the solid was washed with cold methanol and dried for 4 hours/40° C.-45° C., 115 g (73%) were obtained.

Example 5

Production of Metformin Isoleucinate

A total of 16.55 g L-isoleucine was added to 16.3 g of a Metformin base solution in methanol 163 mL and stirred at room temperature. The mixture was stirred at room temperature for 18 hours and filtered to remove any solids; the filtrate was concentrated under vacuum until solid was formed. Then, it was cooled between 0° C. and 10° C. for 4 hours, filtered and dried, giving 17.74 g (54%).

Example 6

Production of Metformin Alaninate

A total of 12.07 g L-alanine was added to 17.5 g of a metformin base solution in methanol 175 mL and stirred at room temperature. The mixture was stirred at room temperature for 18 hours and filtered to remove any solids; the filtrate was concentrated under vacuum until solid was formed. Then, it was cooled between 0° C. and 10° C. for 4 hours, filtered and dried, giving 16.88 g (57%).

Example 7

Production of Metformin L-Valinate

A total of 14.96 g L-valine was added to 16.5 g of a metformin base solution in methanol 165 mL and stirred at room temperature. The mixture was stirred at room temperature for 18 hours and filtered to remove any solids; the filtrate was concentrated under vacuum until solid was formed. Then, it was cooled between 0° C. and 10° C. for 4 hours, filtered and dried, giving 16.72 g (53%).

Example 8

Production of Metformin L-Asparaginate

A total of 15.34 g L-asparagine was added to 15.0 g of a metformin base solution in methanol 150 mL and stirred at room temperature. The mixture was stirred at room temperature for 18 hours and filtered to remove any solids; the filtrate was concentrated under vacuum until solid was formed. Then, it was cooled between 0° C. and 10° C. for 4 hours, filtered and dried, giving 15.19 g (50%).

Example 9

Production of Metformin Threoninate

A total of 15.22 g L-threonine was added to 16.5 g of a metformin base solution in methanol 165 mL and stirred at room temperature. The mixture was stirred at room temperature for 18 hours and filtered to remove any solids; the filtrate was concentrated under vacuum until solid was formed. Then, it was cooled between 0° C. and 10° C. for 4 hours, filtered and dried, giving 18.7 g (59%).

Example 10

Production of Metformin Leucinate

A total of 12.19 g L-leucine was added to 12.0 g of a metformin base solution in methanol 120 mL and stirred at room temperature. The mixture was stirred at room temperature for 18 hours and filtered to remove any solids; the filtrate was concentrated under vacuum until solid was formed. Then, it was cooled between 0° C. and 10° C. for 4 hours, filtered and dried, giving 11.62 g (48%).

Example 11

Production of Metformin L-Lysinate

A total of 31.78 g of monohydrate L-lysine was added to 25.0 g of a metformin base solution in methanol 250 mL and stirred at room temperature. The mixture was stirred at room temperature for 18 hours, filtered to remove any solids; the filtrate was concentrated under vacuum until solid was formed. Then, it was cooled between 0° C. and 10° C. for 4 hours, filtered and dried, giving 24.43 g (43%).

Example 12

Infrared Spectrum

The infrared spectrum is applied to characterize molecules that give a good pattern of infrared light absorption lines, characteristic of each molecule. The equipment used to determine the infrared spectra was a Hewlett Packard 8453 infrared spectrophotometer or Nicolet Avatar 360 FTIR E.S.P. Spectra in potassium bromide were obtained.

Example 13

Identity by UV-Vis

Sample Preparation

A total of 100 mg of Metformin base was weighed and transferred to a 100 mL volumetric flask, where 80 mL of phosphate buffer pH 6.80 was added and mechanically stirred for 15 minutes. Then, it was brought to volume with phosphate buffer pH 6.80 and mixed. An aliquot of 5 mL of this solution was taken and transferred to a 50 mL volumetric flask. Then, it was brought to volume with purified water and mixed.

Reference Solution Preparation

A reference solution of metformin hydrochloride at the same concentration of the sample (concentration±100 μg/mL metformin base) was prepared.

Procedure

Scans were performed on each prepared solution (sample and reference solution) of 200 to 450 nm, and the wavelength of maximum absorbance was determined. The absorption spectrum of UV-Vis of 200 to 450 nm carried out in the studied raw materials showed a maximum absorption at 233 nm, with no absorbance from 265 nm onwards. In the corresponding spectrograms, a characteristic valley was detected between 216 and 217 nm.

The spectrograms obtained are similar to those of a reference solution of hydrochloride metformin treated the same way as the sample solution. Ultraviolet absorption spectrograms are shown in Table 3 and FIGS. 39-46.

TABLE 3

Identity by UV-Vis spectrophotometry. Wavelength of maximum absorbance in different metformin compounds (SLNs).
Maximum Absorbance Wavelength

| Raw Material | Wavelength | Valley |
|---|---|---|
| Dimetformin aspartate | 233.0 | 216.0 |
| Metformin isoleucinate | 233.0 | 216.0 |
| Metformin alaninate | 233.0 | 216.0 |
| Metformin valinate | 233.0 | 216.0 |
| Metformin asparaginate | 233.0 | 217.0 |
| Metformin lysinate | 233.0 | 217.0 |
| Metformin threoninate | 233.0 | 216.0 |
| Metformin leucinate | 233.0 | 216.0 |
| Metformin hydrochloride | 233.0 | 216.0 |

Example 14

Solution pH of the Metformin Compounds

Sample Preparation

About one gram of sample was weighed and dissolved in 10 mL of purified water. Complete dissolution of the sample was verified and the pH of the solution was determined using a calibrated potentiometer within the pH range of 7.0 to 10.0.

To determine the pH of the solution, a 1:10 solution in purified water was prepared for each analyzed sample, resulting in pH values between 10 and 12. Therefore, these basic raw materials showed basic characteristics in aqueous solution. Only for comparative purposes, a metformin hydrochloride solution was prepared in the same way and the pH value was determined, obtaining a result of 6.86. Individual values of pH for each compound (SLNs) are shown in Table 4.

TABLE 4 pH of the solution in different compounds of metformin (SLNs)
Solution pH

| Raw Material | Result |
|---|---|
| Dimetformin aspartate | 11.03 |
| Metformin isoleucinate | 11.26 |
| Metformin alaninate | 11.34 |
| Metformin valinate | 11.11 |
| Metformin asparaginate | 10.53 |
| Metformin lysinate | 12.04 |
| Metformin threoninate | 10.73 |
| Metformin leucinate | 11.08 |
| Metformin hydrochloride | 6.86 |

Example 15

Metformin Content

Diluent Solution

About 6.8 g of monobasic potassium phosphate and 0.9 g of sodium hydroxide were weighed and put into a 1000 mL volumetric flask. It was dissolved and brought to volume with purified water. The pH of the solution was checked to a value of 6.80±0.05 and adjusted with saturated sodium hydroxide solution.

Reference Solution

About 64.12 mg of metformin hydrochloride (reference substance) was weighted in duplicate and transferred separately to 20 mL volumetric flasks; then, it was dissolved and brought to volume with diluent solution. Aliquots of 2 mL were separately transferred to 50 mL volumetric flasks and brought to volume with purified water; then, they were mixed (solutions R1 and R2 concentration±100 µg/mL metformin base).

Sample Solution

An equivalent of 100.0 mg of metformin base of the different metformin compounds (SLNs) was weighted in duplicate and transferred to 100 mL volumetric flasks. A total of 80 mL diluent solution was added into each flask, after which they were mechanically stirred for 15 minutes, brought to volume with diluent solution and mixed. An aliquot of 5 mL of these solutions was transferred to 50 mL volumetric flasks. Then, they were brought to volume with purified water and mixed. (M1 and M2 solutions).

Chromatographic Conditions

Mobile Phase: Preparation of The Buffer Solution

A total of 2.6 g of potassium phosphate monobasic and 1.31 g of sodium hexanesulfonate were weighed and transferred to a 1000 mL volumetric flask; they were dissolved and brought to volume with purified water.

Preparation of Mobile Phase

A total of 700 mL of buffer solution and 300 mL of chromatographic grade methanol were transferred into a 1000 mL beaker, measured separately and mixed. The solution was filtered through a 0.45 µm pore size Millipore membrane and degassed in ultrasound.

FLOW VELOCITY 1.0 mL/minute.

COLUMN: Stainless steel, length of 15 cm and internal diameter of 4.6 mm, packed with totally porous silica particles of a 5 µm diameter, coated with octadecylsilane groups (C18), Moon type of brand Phenomenex.

COLUMN TEMPERATURE 25.0° C.

DETECTOR: U.V. at 232 nm.

INJECTION VOLUME: 5 µL

RETENTION TIME 2.8 minutes approximately

Run time 4.0 minutes

Metformin base results obtained from 100 mg of each metformin compound are: 63.38 mg for dimetformin aspartate, batch: 021-JAT-05; 46.97 mg for metformin isoleucinate, batch: 021-JAT-24; 56.73 mg for metformin alaninate, batch 021-JAT-26; 50.08 mg for metformin valinate, batch: 021-JAT-05; 46.13 mg for metformin asparaginate, batch: 021-JAT-05; 42.79 mg for metformin lysinate, batch: 021-JAT-05; 49.48 mg for metformin threoninate, batch: 021-JAT-05; 47.17 mg for metformin leucinate, batch: 021-JAT-31. Table 5 shows individual results of metformin base mgs recovered.

TABLE 5

Metformin content
Metformin Content

| Raw Material | Sample 1 (%) | Sample 2 (%) | Sample 3 (%) | Average (%) | CV | Mg Metformin/100 mg sample |
|---|---|---|---|---|---|---|
| Dimetformin aspartate | 95.70 | 96.44 | 96.01 | 96.08 | 0.33 | 63.38 mg |
| Metformin isoleucinate | 94.79 | 95.12 | 94.14 | 94.68 | 0.32 | 46.97 mg |
| Metformin alaninate | 95.31 | 95.81 | 96.38 | 95.83 | 0.30 | 56.73 mg |
| Metformin valinate | 95.23 | 94.68 | 96.12 | 95.52 | 0.38 | 50.08 mg |
| Metformin asparaginate | 92.35 | 93.87 | 91.74 | 93.32 | 0.90 | 46.13 mg |
| Metformin lysinate | 91.97 | 91.54 | 90.12 | 91.21 | 1.06 | 42.79 mg |
| Metformin threoninate | 94.49 | 96.40 | 94.42 | 95.10 | 1.08 | 49.48 mg |
| Metformin leucinate | 95.47 | 94.47 | 95.33 | 95.09 | 0.37 | 47.17 mg |

Example 16

Related Substances

Diluent Solution
Purified Water
Standard Solution of Cyanoguanidine

About 10 mg of Cyanoguanidine (reference substance) was weighted in duplicate and transferred separately to 100 mL volumetric flasks; then, it was dissolved, brought to volume with diluent solution, and mixed. (Solutions P1 and P2, concentration±100 µg/mL of Cyanoguanidine).

Standard Solution of Metformin

About 16.0 mg of metformin hydrochloride was weighted in duplicate and transferred separately to 100 mL volumetric flasks; then, it was dissolved, brought to volume with diluent solution, and mixed. (Solutions P1 and P2, concentration±125 µg/mL of metformin base).

Reference Solutions

Prepared in duplicate. A total of 1 mL of the standard solutions of Cyanoguanidine (C1 and C2) and 4 mL of the standard solutions of metformin (P1 and P2) were put separately into 100 mL volumetric flasks, brought to volume with diluent solution, and mixed (solutions R1 and R2, concentration±1.0 µg/mL de Cyanoguanidine, ±5 µg/mL of metformin base)

Resolution Solution

It was dissolved and brought to volume with diluent solution in a 50 mL volumetric flask. A 4 mL aliquot of the above mentioned solution was poured into a 100 mL volumetric flask, and a 1 mL aliquot of the standard solution, cyanoguanidine C1, and a 4 mL aliquot of the standard solution metformin P1 were added. It was brought to volume with diluent solution and mixed. (Solution R3, concentration±2 µg/mL of Melamine, ±1.0 µg/mL of Cyanoguanidine, ±5 µg/mL of metformin base).

Sample Solution

An equivalent of 500 mg of metformin base of each raw material was weighed and poured into a 100 mL volumetric flask; approximately 80 mL of diluent solution was added and mechanically stirred for 30 minutes. It was brought to volume with diluent solution and mixed. (Solutions M1).

Instrumental Parameters
Chromatographic Conditions
Mobile Phase: Preparation of The Buffer Solution A total of 2.6 g of potassium phosphate monobasic and 1.31 g of sodium hexanesulfonate were weighed and transferred to a 1000 mL volumetric flask; they were dissolved and brought to volume with purified water.

Preparation of Mobile Phase

A total of 950 mL of buffer solution and 50 mL of chromatographic grade methanol were transferred into a 1000 mL beaker, measured separately and mixed. The solution was filtrated through a 0.45 µm pore size Millipore membrane and degassed in ultrasound.

FLOW VELOCITY 1.5 mL/minute.
COLUMN Stainless steel, length of 15 cm and internal diameter of 4.6 mm, packed with totally porous silica particles of a 5 µm diameter, coated with octadecylsilane groups (C18), Aqua type of brand Phenomenex.
COLUMN TEMPERATURE 25.0° C.
DETECTOR: U.V. at 218 nm.
INJECTION VOLUME 20 µl Retention Time
Cyanoguanidine 1.6 minutes approximately.
Melamine 10.5 minutes approximately.
Metformin 14.0 minutes approximately.

Run Time
Solution R3 17 minutes
Solutions R1 and R2 17 minutes
Blank solution and sample solution 30 minutes For this test, only the raw material of batch No. 021-JAT-05, corresponding to dimetformin aspartate, shows a lower than 0.02% (0.01%) percentage for Cyanoguanidine impurity. In all remaining raw materials, percentages are above 0.15% for that impurity. Regarding individual impurities, only the raw material of batch 021-JAT-24 (metformin isoleucinate) shows individual impurities below 0.1%. In all other raw materials, there are individual impurities ranging from 0.15% to 0.40%.

Finally, for the quantification of total impurities, the metformin asparagine raw material with batch 021-JAT-28 shows a total sum of 2.34%; the other raw materials show percentages of total impurities of less than 0.6%. Individual values of related substances, in raw materials, are shown in Table 6.

TABLE 6

Related substances of Metformin
Related Substances

| Material | Cyano-guanidine No more than 0.02% (%) | Individual impurities No more than 0.1% (%) | Total impurities No more than 0.6% (%) |
|---|---|---|---|
| Dimetformin aspartate | 0.010 | 0.416 | 0.448 |
| Metformin isoleucinate. | 0.166 | 0.025 | 0.127 |
| Metformin alaninate | 0.205 | 0.196 | 0.422 |
| Metformin valinate | 0.227 | 0.168 | 0.248 |
| Metformin asparaginate | 0.156 | 0.414 | 2.335 |
| Metformin lysinate | 0.159 | 0.224 | 0.596 |
| Metformin threoninate | 0.177 | 0.247 | 0.514 |
| Metformin leucinate | 0.172 | 0.146 | 0.217 |

Example 17

Identity by Liquid Chromatography

Sample Preparation

The sample solutions, reference solutions, diluent solution, and chromatographic conditions described in the above examples are used for the analysis of metformin compounds. Chromatograms of raw materials classified as metformin amino acid compounds (SLNs) showed the same retention time and peak shape as a reference solution of metformin hydrochloride. The retention time of the standard solution is 2.95 minutes, whereas the retention time for the metformin amino acid compounds range from 2.94 to 2.95 minutes.

Individual retention times for each raw material are shown in Table 7 and the respective chromatogram in FIG. 47-54.

TABLE 7

Identity by High Resolution Liquid Chromatography,
Retention times in different compounds of metformin (SLNs).
Retention times in different compounds of Metformin

| Raw material | Time in minutes |
|---|---|
| Metformin aspartate | 2.95 |
| Metformin isoleucinate | 2.95 |
| Metformin alaninate | 2.95 |
| Metformin valinate | 2.95 |
| Metformin asparaginate | 2.94 |
| Metformin lysinate | 2.94 |
| Metformin threoninate | 2.94 |
| Metformin leucinate | 2.94 |
| Metformin hydrochloride | 2.95 |

Example 18

TABLE 8

Peak purity of different compounds of metformin (SLNs)
Peak purity

| Raw material | Purity angle | Purity threshold |
|---|---|---|
| Dimetformin aspartate | 0.058 | 0.242 |
| Metformin isoleucinate | 0.058 | 0.242 |
| Metformin alaninate | 0.060 | 0.241 |
| Metformin valinate | 0.065 | 0.242 |
| Metformin asparaginate | 0.061 | 0.242 |
| Metformin lysinate | 0.068 | 0.246 |
| Metformin threoninate | 0.072 | 0.245 |
| Metformin leucinate | 0.063 | 0.243 |
| Metformin hydrochloride | 0.065 | 0.245 |

FIGS. 55-63 show the identity and peak purity of each metformin compound by HPLC.

Example 19

Organic Volatile Impurity

Preparation of Reference Solution

A total of 455 µl of methylene chloride, 40 µl of chloroform, 570 µl of benzene, 370 µl of 1,4-dioxane, and 55 µl of trichlorethylene were added in a 25 mL volumetric flask with 20 mL of dimethylsulfoxide; it was brought to volume with dimethylsulfoxide and manually homogenized. An aliquot of 1.0 mL was transferred to a 100 mL volumetric flask and brought to volume with purified water. An aliquot of 5 mL was transferred to a 100 mL volumetric flask and brought to volume with purified water.

Sample Preparation

A total of 0.250 g of the testing substance was weighed and put into a 25 mL volumetric flask; it was dissolved and brought to volume with purified water.

Procedure

A total of 5 mL of the sample solution and reference solution were transferred separately into headspace vials, capped with a rubber septa coated with polytetrafluoroethylene, and closed with an aluminum cap.

Instrumental Parameters

Chromatographic Conditions
 MOBILE PHASE: Chromatographic grade helium
 FLOW VELOCITY: 25 cm/sec
 SPLIT: Off
 INJECTOR TEMPERATURE: 110° C.
 DETECTOR: FID (Flame Ionization Detector)
 INJECTOR TEMPERATURE: 200° C.
 COLUMN: Capillary of 0.53 mm of internal diameter×30 m in length, packed with coated fused silica of G27 stationary phase of 5 µm of thickness. HP-5 type, Agilent Technologies. COLUMN TEMPERATURE (Table 9):

TABLE 9

Column temperature

| Time (minutes) | Temperature (° C.) | Temperature ramp |
|---|---|---|
| 0.10 | 35 | Isothermal |
| 10.2605 | 35 → 200 | 10° C./min |
| 26.5-36.5 | 200 | Isothermal |

Temperature of the transference line 95° C.
Headspace conditions: 85.0° C./15
VOL. OF INJECTION: 1 mL Raw materials classified metformin amino acid compounds (SLNs) were analyzed according to the 8th edition FEUM method. Results of the analysis of residual solvents for different raw materials are shown in Table 4. All chromatograms indicate that volatile residues are within specification limits as well as any other volatile material that might be contaminating the product.

TABLE 10

Organic volatile impurities for the metformin amino acid compounds (SLNs).

| METHANOL REFERENCE SOLUTIONS REFERENCE AREA 1 | | |
|---|---|---|
| | | 4227.1 |
| Average | | 4227.10 |

METFORMIN ISOLEUCINATE

| Batch/Request no. | Sample weight in g | Name | AREA | ppm result | ppm specification |
|---|---|---|---|---|---|
| 021-JAT 24 | 0.250 | Methanol | 622.4 | 0.2094 | 3000 |
| SDF 11.384 | | Unknown peak | 626.8 | 0.2761 | 3000 |
| | | methane hydrochloride | 342.5 | 0.0224 | 600 |
| | | Benzene | 237.9 | 0.00001 | 2 |

METFORMIN ALANINATE

| Batch/Request no. | Sample weight in g | Name | AREA | ppm result | ppm specification |
|---|---|---|---|---|---|
| 021-JAT 26 | 0.250 | Methanol | 186.5 | 0.0627 | 3000 |
| SDF 11.381 | | Unknown peak | 1660.9 | 0.5587 | 3000 |
| | | methane hydrochloride | 40.5 | 0.0027 | 600 |

METFORMIN VALINATE

| Batch/Request no. | Sample weight in g | Name | AREA | ppm result | ppm specification |
|---|---|---|---|---|---|
| 021-JAT 27 | 0.250 | Methanol | 140.9 | 0.0474 | 3000 |
| SDF 11.382 | | Unknown peak 1 | 117.1 | Illegible | 3000 |
| | | Unknown peak 2 | 11.2 | 0.0038 | 3000 |
| | | methane hydrochloride | 22.4 | 0.0015 | 600 |
| | | ILLEGIBLE | 18.2 | 0.00000 | illegible |

METFORMIN ASPARTATE

| Batch/Request no. | Sample weight in g | Name | AREA | ppm result | ppm specification |
|---|---|---|---|---|---|
| 021-JAT 28 | 0.250 | Methanol | 2733.5 | illegible | 3000 |
| SDF 11.385 | | Unknown peak 2 | 45.2 | 0.952 | 3000 |
| | | methane hydrochloride | illegible | illegible | 600 |

METFORMIN LYSINATE

| Batch/Request no. | Sample weight in g | Name | AREA | ppm result | ppm specification |
|---|---|---|---|---|---|
| 021-JAT 29 | 0.250 | Methanol | 311.3 | 0.1047 | 3000 |
| SDF 11.383 | | Unknown peak | 3007.9 | 1.5449 | 3000 |
| | | methane hydrochloride | illegible | 0.0041 | 600 |

METFORMIN THREONINATE

| Batch/Request no. | Sample weight in g | Name | AREA | ppm result | ppm specification |
|---|---|---|---|---|---|
| 021-JAT 28 | 0.250 | Methanol | illegible | 0.632 | 3000 |
| SDF 11.348 | | Unknown peak 1 | 850.5 | 0.2951 | 3000 |
| | | methane hydrochloride | illegible | illegible | 600 |

METFORMIN LEUCINATE

| Batch/Request no. | Sample weight in g | Name | AREA | ppm result | ppm specification |
|---|---|---|---|---|---|
| 021-JAT 31 | 0.250 | Methanol | 190.1 | 0.0370 | 3000 |
| SDF 11.348 | | Unknown peak 1 | 389.2 | illegible | 3000 |
| | | methane hydrochloride | 28.4 | 0.0019 | 600 |
| | | Benzene | 176.1 | 0.000004 | illegible |
| | | illegible | 15.5 | illegible | 80 |

DIMETFORMIN ASPARAGINATE

| Batch/Order No. | Sample weight in g | Name | AREA | Ppm result | Ppm specification |
|---|---|---|---|---|---|
| 021-JAT-05 | | Methanol | 7712 | 0.2594 | 3000 |
| SDF11-307 | | Unknown peak 1 | 826.8 | 0.2781 | 3000 |
| | | Unknown peak 2 | 11.4 | 0.0038 | 3000 |
| | | Methylene chloride | 15.5 | 0.0010 | 600 |
| | | Trichloroethylene | 12.8 | 0.00006 | 80 |

Example 20

Differential Scanning Calorimetry (DSC)

Sample Solution Preparation

A sample was weighed in 40 uL aluminum crucibles with lid and encapsulated; a hole in the center of the lid was opened, and heating from 30° C. to 300° C. was initiated, with a heating rate of 10° C./min. The procedure was repeated for each compound (SLNs).

According to the results, dimetformin aspartate was the compound with the highest meting point (221.74° C.) when compared with the other metformin compounds (SLNs) analyzed. However, this value is below the melting point of metformin hydrochloride's, which is 228.44° C.

Table 11 shows melting points obtained for different metformin amino acid compounds (SLNs).

TABLE 11A

Melting points for the metformin amino acid compounds (SLNs).

|  | Dimetformin aspartate | Metformin isoleucinate | Metformin alaninate | Metformin valinate |
|---|---|---|---|---|
| Melting point (° C.) | 221.74 | 149.60 | 178.61 | 163.36 |

TABLE 11B

Melting points for the Metformin amino acid compounds (SLNs).

|  | Metformin asparaginate | Metformin lysinate | Metformin threoninate | Metformin leucinate | Metformin hydrochloride |
|---|---|---|---|---|---|
| Melting point (° C.) | 165.87 | 151.91 | 145.90 | 142.80 | 228.44 |

Several changes in form and details may be carried out therein without deviating from the spirit and scope of the invention. Unless it is otherwise clear from context, any form, appearance, element, function, step, or the like may be used in combination with any other. To the extent that information associated with an appointment changes over time, the information associated with the appointment shall be that of the earliest effective date of presentation, being the earliest effective date of presentation the presentation date of this application or the earliest priority application disclosed in this appointment. All references, issued patents, and patent applications mentioned in this specification body are incorporated by reference in their entirety for all purposes. Any mode, appearance, feature, element, step, or the like may be combined with any other unless otherwise indicated by context.

Example 21

Mode of Action of Compounds of this Invention

The metformin amino acid compounds, selected from metformin aspartate, metformin isoleucinate, metformin alaninate, metformin valinate, metformin asparaginate, metformin threoninate, metformin leucinate, or metformin lysinate modulate the GPBP kinase activity differently. metformin lysinate (SLN10) modulates GPBP activity differently than metformin hydrochloride.

To investigate the relationship between GPBP and metformin lysinate, we performed in vitro (auto) phosphorylation tests of GPBP (Raya A, Revert F, S Navarro, J. Saus 1999 J Biol Chem, 1999; 274:12642-9) (FIG. 64).

Interestingly, under the same experimental conditions in which T12 inhibited the GPBP kinase activity, SLN1 appeared as a moderate activator, and SLN10 behaved as kinase activity inhibitors. In the regulatory mechanism of the new molecule on the GPBP activity, the GPBP phosphorylation status in myotubes stimulated with compound SLN10 was analyzed (FIG. 65). The presence of equimolecular amounts of individual compounds in the culture medium showed different resulting states regarding GPBP phosphorylation. Therefore, while SIN1 barely altered the phosphorylation state, SLN10 induced a remarkable GPBP dephosphorylation.

Other phosphorylation assays including the following conditions were conducted: protein FLAG-GPBP-1 (270 ng), expressed in Pichia pastoris yeast and purified with anti-FLAG (Sigma) resin, was used in phosphorylation assays in the absence (Control) or presence of metformin hydrochloride (SLN1) or metformin lysinate (SLN10) at the indicated concentrations for each case, in two different phosphorylation solutions: a) Na buffer: 25 mM Tris-HCl pH 7.4, 150 mM NaCl, 10 mM MgCl2, 1 mM DTT, 0,132 mM g[32P] ATP or b) K buffer: 15 25 mM Tris-HCl pH 7.4, 150 mM KCl, 10 mM MgCl2, 1 mM DTT, 0,132 mM g[32P] ATP. The reaction volume was 25 mL, reaction time 15 minutes, and temperature 37° C. Reactions were stopped with reducing loading buffer for SDS-PAGE and incubated at 95° C. for 3 minutes. Then, electrophoresis in 10% polyacrylamide gel and electroblotting to PVDF membrane were applied. Autoradiography was applied to membranes by exposure to photographic films (Amersham Hyperfilm MP, GE Healthcare Lifesciences). After autoradiography, the membranes were blocked with 5% skimmed milk in TBST and incubated with anti-FLAG (Sigma) monoclonal antibodies and secondary antibodies against mouse IgG conjugated to peroxidase (Promega). Western blots (WB) were revealed with ECL (GE Healthcare Lifesciences).

The composition of the reaction medium affects the inhibitory activity of the metformin compounds over GPBP. SLN10 inhibits GPBP in Na buffer. This suggests that SLN10 inhibits GPBP in extracellular media, where Na ions are predominant. These results might reflect SLN10 capacity to induce GPBP secretion by macrophages (FIG. 66).

The GPBP kinase activity is regulated in part by its aggregation state; moreover, T12 is an destabilizing inhibitor of the quaternary structure of GPBP in the cytosol of cells in culture (Raya A, Revert-Ros F, Martinez-Martinez P, Navarro S, Rosello E, Vieites B, Barn F, J Forteza, Saus J. J Biol Chem. 2000; 275:40392-9). The activity of metformin compounds, for example, metformin lysinate, on the GPBP kinase activity was analyzed by the aggregation state of GPBP in these compounds-treated cells.

Example 22

The differential "anti-hyperglycaemic" effect of metformin compounds of this invention, like metformin lysinate, depends on the modulation of the GPBP kinase activity.

GPBP kinase activity has not been associated with the "anti-hyperglycaemic" activity of metformin. For this purpose, the evolution of glucose uptake was studied in the culture medium of myotubes in response to different molecules studied (FIG. 67).

Interestingly, the activity of the SLN10 compound was higher than that of compound SLN1, consistent with its differential ability to inhibit the GPBP kinase activity in vitro (see FIG. 73), suggesting that the GPBP kinase activity is a negative regulator of GLUT4 translocation and glucose uptake. In contrast, the SLNs (e.g., SLN10) inhibit GPBP kinase activity. When the initial concentration of glucose in the culture medium was "normoglycemic", the SLNs compounds showed no difference in their ability to stimulate glucose uptake (FIGS. 68A and 68B).

These results suggested that the inhibition of the GPBP kinase activity and its "anti-hyperglycaemic" activity were related. To investigate this possibility, C2C12 myotubes were cultured with increasing glucose concentrations, and the GPBP intracellular expression was determined by Western blot (FIG. 69). Of particular interest was the coordinated increase of the GPBP expression with glucose concentration in the culture medium, suggesting that the differential "anti-hyperglycaemic" activity of SLNs compounds depended on the inhibition of an increased GPBP activity.

Glucose uptake in response to biguanides is expected to be directly related to translocation of the glucose transporter GLUT4 to the plasma membrane, a process that depends mainly on the phosphorylation of AS160 by AMPK activation (Lee J O, Lee S K, Jung J H Kim J H, You G Y, Kim S J, Park S H, Uhm K O, Kim H S *J Cell Physiol.* 2011; 226:974-81. Confirmation regarding the relationship between glucose consumption stimulation by SLNs and AMPK activation as well as the increase in GLUT4 translocation was obtained by analyzing plasma membranes and cell extracts by Western blot (FIGS. 70A-C).

The differential GPBP inhibition by metformin compounds, for example, metformin lysinate, and their role in the activation of the LKB1/AMPK pathway was first investigated in myotubes in culture (FIG. 71). Interestingly, LKB1 and GPBP co-localized extensively in the cytoplasm in granular aggregates, visible by microscopy, indicating that they are large structures. Stimulation by metformin compounds, for example, metformin lysinate, affected the distribution of these structures, while SLN1 moved LKB1-GPBP aggregates from peripheral positions to areas around the nuclei. SLN10-treated cells were associated with delocalization of LKB1 and virtual absence of kinase in granular aggregates.

Delocalization of LKB1 aggregates suggests that treatment with SLN10 is associated with LKB1 release from the granular structure, where both kinases are associated. To understand this phenomenon at the molecular level, we conducted in vitro phosphorylation experiments with GPBP and the commercial protein complex LKB1/STRADα/MO25 (Millipore) (FIG. 72). STRADα and MO25 are supporters necessary to activate LKB1. Besides, STRADα is a substrate of LKB1 (Baas A F, 15 Boudeau J, Sapkota G P, Smit L, R Medema, Morrice N A, Alessi D R, Clevers H C. *EMBO J.* 2003; 22: 3062-72), and its phosphorylation status monitors the kinase activity of LKB1. We have observed that GPBP induces the phosphorylation and activation of LKB1 (compare lanes 2 and 3) and that the level of GPBP phosphorylation also increases in the presence of LKB1 (compare lanes 1 and 3). This suggests that LKB1 and GPBP regulate positively and reciprocally their kinase activity by cross phosphorylation. It cannot be excluded, however, that the simple interaction of kinases activates corresponding autophosphorylation processes.

Although it has been claimed that LKB1 is not a target of metformin (Hardie D G. *Gastroenterology* 2006; 131:973), our experiments show that both metformin and SLN10 trigger a discrete LKB1 autophosphorylation and the phosphorylation of STRADα, suggesting that metformin and SLN10 activate LKB1. The presence of GPBP in the reaction mixture had consequences; SLN10, but not SLN1, inhibited the incorporation of phosphate by LKB1/STRADα efficiently, suggesting that GPBP activates LKB1 by cross phosphorylation and that SLN10, but not SLN1, inhibits the GPBP kinase activity.

To further explain the above results, a more physiological approach in the in vitro assays was performed. A combination of LKB1/STRADα, GPBP, and AMPK/AS160 was used, i.e., each kinase was added with its own substrate except GPBP, which acted as both an enzyme and substrate at the same time (autophosphorylation) (FIG. 73).

As expected, SLN1 stimulated GPBP autophosphorylation, whereas SLN10 and T12 inhibited it progressively. As autophosphorylation (GPBP kinase activity) was inhibited, the phosphorylated STRADα amount increased, indicating that in the presence of GPBP, the AMPK inhibition increased the phosphorylation of the LKB1 effector. However, under these conditions, we did not identify an increase in the amount of phosphorylated AS160, which is the end point of the signaling pathway, probably because AMPK is activated and not susceptible to further activation (results not shown). Nevertheless, T12 showed a strong inhibition of the phosphorylation of a AMPK polypeptide, and through specific antibodies, we were able to demonstrate that it was a regulatory subunit γ (results not shown): the subunit that others had postulated as a molecular target of metformin (Zhang Y, Wang Y, C Bao, Xu Y, Shen H, Chen J, Yan J, Chen Y. *Mol Cell Biochem.* 2012; 368:69-76). All the evidence indicated that SLN1 and SLN10 induce the LKB1-AMPK AS160 pathway gradually, releasing LKB1- and dephosphorylated GPBP-activated forms.

Our results show that in cells: 1) SLN10 induces GPBP dephosphorylation, cause disintegration of GPBP-LKB1 aggregates, and promotes translocation of glucose transporters more efficiently than SLN1; 2) the differential "anti-hyperglycemic" activity between SLN1 and SLN10 occurs mainly in "hyperglycemic" conditions and with the overexpression of GPBP.

Studies conducted by other researchers show that: 1) The dephosphorylated form of GPBP binds strongly to VAPA (Saito S. Matsui H, Kawano M, Kumagai K, Tomishige N, Hanada K, Echigo S, Tamura S, Kobayashi T. *J Biol Chem* 2008; 283: 6584-93) and activates the constitutive protein secretion (Florin L, Pegel A, Becker E, Hausser A, Olayioye M A, H. Kaufmann *J Biotechnol* 2009; 141:84-90), and 2) VAPA overexpression inhibits the regulated secretion of GLUT4 to the plasma membrane (Foster L J, Weir M L, Lim D Y, Liu Z, Trimble W S, Klip A. *Traffic* 2000; 1:512-21. Besides, VAPA inhibits the constitutive protein transport from the ER to the Golgi apparatus, and that inhibition is counteracted by peptides containing the FFAT motif (Prosser D C, Tran D, Gougeon P Y, Verly C, Ngsee J K. *J Cell Sci.* 2008; 121:3052-61). GPBP contains a FFAT motif necessary to interact with VAPA (Kawano M, Kumagai K, Nishijima M, Hanada K. *J Biol Chem* 2006; 281:30279-88). Thus, it is plausible that SLN10 promotes a free-dephosphorylated GPBP increase, favoring GPBP-VAPA aggregate formation, VAPA-VAMP2 disassociation, and the regulated and constitutive transport of protein.

These results suggest that the compounds of metformin, for example, metformin lysinate, inhibit the interaction between VAPA and VAMP2, thus facilitating controlled secretion of vesicles containing GLUT4. The participation of GPBP in this process was demonstrated, as metformin compounds of this invention also decolocalized GPBP and VAPA (FIGS. 74A and 74B), suggesting that such compounds dissociate VAPA of secretory vesicles containing GPBP and GLUT4, and that controlled secretion of vesicles with GLUT4 depended on GPBP and was induced by metformin. No significant differences between the different compounds at experimental conditions were observed, and therefore, the participation of the GPBP dephosphorylation in the process was uncertain. "Hyperglycemic" culture conditions induce myotubes to overexpress GPBP with significant amounts of dephosphorylated GPBP (see FIG. 69). An excess of dephosphorylated GPBP could mask the presence of more dephosphorylated GPBP resulting from the inhibitory activity of SLN10 on GPBP; thus, the differential "anti-hyperglycaemic" activity of SLN10 through VAPA should be analyzed in conditions of GPBP overexpression, eminently in a phosphorylated state.

To determine whether SLN10 uses the VAPA pathway for over-inducing GLUT4 translocation through dephosphorylated GPBP, the distribution of GPBP and GLUT4 in L1 adipocytes in response to metformin compounds of this invention, such as metformin lysinate, (FIG. 75) was studied.

In the absence of stimulation, GLUT4 accumulated in large structures in the secretory pathway near the core (trans-Golgi region), with limited colocalization with GPBP occupying the surroundings. Stimulation with metformin compounds, for example, metformin lysinate, had different consequences. Thus, with SLN1, an extensive colocalization of both proteins was observed in juxtanuclear structure, but with a low presence in secretory vesicles. Finally, in the presence of SLN10, vesicles scattered throughout the cytoplasm and the two proteins were widely located in the plasma membrane, where an extensive colocalization was observed. Interestingly, the juxtanuclear structure was free of GPBP and two types of secretory vesicles-one containing both proteins and the other one containing only GLUT4.

These results demonstrate that there are two types of secretory vesicles transporting GLUT4 to the plasma membrane: those that contain GPBP and those that do not. The first would depend primarily on the dissociation of VAMP2-VAPA, caused by GPBP dephosphorylation, whereas the other would depend largely on the dissociation of IRAP-AS160, caused by AS160 phosphorylation by AMPK (Treebak J T, Glund S, Deshmukh A, Klein D K Long Y C, T E Jensen, Jorgensen S B, Viollet B, Andersson L, D Neumann, Wallimann T, Richter E A, Chibalin A V, Zierath J R, Wojtaszewski J F. *Diabetes.* 2006; 55:2051-8) y Akt (Leto D, Saltiel A R. *Nat Rev Mol Cell Biol.* 2012; 13:383-96).

Further evidence suggested that GPBP could also be involved in the signaling pathway of insulin, for AKT was overactivated in poor GPBP-1 myotubes (see activation of AKT in GPBP myotubes –/–) (Revert-Ros F, Lopez-Pascual E, Granero-Moltó F, J Macias, Breyer R, Zent R, Hudson B G, Saadeddin A, Revert F, Blasco R, Navarro C, D Burks, Saus J. *J Biol Chem* 2011; 286: 35030-43). That is, the inhibition of the GPBP kinase activity by SLN10 could be positively controlling the pathway of insulin. To investigate whether differential stimulation of cells with the metformin compounds of this invention, such as metformin lysinate, had a counterpart in the signaling pathway of insulin, the expression of the insulin receptor was analyzed, and we observed that SLN10 promotes accumulation in the plasma membrane (FIG. 76), which is consistent with its ability to inhibit the in vitro GPBP kinase activity (see FIG. 73). Precursors of the insulin receptor dimerize in the ER and are processed in the Golgi apparatus by limited proteolysis, forming two peptides ($\alpha$ and $\beta$) per molecule of precursor. In the plasma membrane, the functional form of the insulin receptor is a tetramer [$(\alpha\beta)_2$] (Hwang J B, Hernandez J, Leduc R, Frost S C. *Biochim Biophys Acta.* 2000; 1499:74-84). In our sample, the plasma membrane co-purifies with fragments of other cell membranes, including the Golgi apparatus, allowing to determine that the processing of the precursor is induced mainly in response to SLN10. This result suggests that GPBP inhibits the insulin pathway, regulating the processing of receptor precursors negatively, and that GPBP phosphorylation exerts a negative regulation on the unregulated transport of proteins.

Similarly, activated and purified kinases were used to investigate GPBP and AKT interactivity in vitro.

In basal conditions, GLUT4 is found in the perinuclear region, corresponding to the Golgi. Upon insulin administration, the GLUT4 distribution to the cell membrane increased. In the case of metformin glycinate, a very intense accumulation of GLUT4 in the perinuclear region and in the plasma membrane was observed; the amounts were higher than those found with insulin. In the case of metformin, levels lower than insulin were found, with perinuclear distribution and poor distribution in the cell membrane. (FIGS. 77 and 78).

Globally, our results suggest that metformin hydrochloride (SLN1) decreases hyperglycemia by inducing a controlled secretion of vesicles (GLUT4), which results from the activation of the LKB1-AMPK-AS160 pathway. In contrast, metformin lysinate (SLN10) reduces hyperglycemia by an over-induction of the controlled secretion of vesicles, which results from the synergistic cooperation of three mechanisms that depend on the inhibition of the GPBP kinase activity: (1) Overactivation of the LKB1-AMPK-AS160 pathway as a result of the massive release of LKB1 from LKB1-GPBP aggregates; (2) Activation of insulin pathway by receptor accumulation in the plasma membrane and counteraction of the negative regulatory effect that GPBP exerts on this pathway; and (3) Activation of an auxiliary controlled secretory pathway of vesicles, dependent on dephosphorylated GPBP and VAPA.

Example 23

Anti-Inflammatory Effects of Metformin Lysinate

The overexpression of GPBP causes GN-IC in mice (Revert F, Merino R, Monteagudo C, Macias J, Peydró A, Alcacer J, Muniesa P, Marquina R, Blanco M. Iglesias M, Revert-Ros F, Merino J, Saus J. *Am J. Pathol* 2007; 171: 1419-30. The administration of blocking antibodies of extracellular GPBP has pharmacological anti-inflammatory effects on this model and in other disease models, mediated by an increase of extracellular GPBP, including diabetes in mouse iRS2–/– (Saus J, Revert F, Merino R, Merino J, Revert-Ros F. (2012). Appl. No. PCT/EP2012/052923. Publication No. WO/2012/113785; Saus J, F. Revert 2013. U.S.

Provisional Patent 61/883,792). In obesity, an increased fatty acid release triggers a cross proinflammatory stimulation between preadipocytes/adipocytes that secrete TNF-α as well as MCP-1 (among other adipokines) and monocytes/macrophages that secrete TNF-α and IL-1β (among other cytokines). A peripheral insulin resistance of an unknown molecular basis results from this binomial, causing hyperglycemia. TNF-α induces the expression and kinase activity of GPBP (Granero F, Revert F, Revert-Ros F, Lainez S, P Martinez-Martinez, J. Saus FEBS J. 2005; 272: 5291-305; Miralem T, Gibbs P E, Revert F, J Saus, Maines M D. J Biol Chem. 2010; 285: 12551-8), GPBP inhibits the insulin pathway (Revert-Ros F, Lopez-Pascual E, Granero-Molto F, J Macias, Breyer R, R Zent, Hudson B G, Saadeddin A, Revert F, R Blasco Navarro C, D Burks, J. Saus J Biol Chem. 2011; 286: 35030-43) (see AKT activation in myotubes GPBP −/−), and inhibitory compounds of GPBP kinase activity (SLN10) induce insulin pathway (see above FIG. 76). All these observations suggested that the increased activity of GPBP in both extracellular and intracellular sides underlies the peripheral insulin resistance that mediates hyperglycemia in obese individuals by pro-inflammatory stimulus, such as palmitate, which is a saturated fatty acid (R L Bradley, F F Fisher, E. Maratos-Flier *Obesity* 2003; 16: 938-44; McCall K D, Holliday D, E Dickerson, Wallace B, Schwartz A L, C Schwartz, C J Lewis, L D Kohn, Schwartz F L. *J Endocrinol.* 2010; 207:343-53).

Palmitate is a saturated fatty acid that simulates an experimental obese state. It can be used as a pro-inflammatory stimulant for cytokines such as proIL-1β, TNFα, INOS, IL-6, MCP-1, and IL-12. Adipocytes cultured in the absence or presence of palmitate were treated with SLN1 or SLN10, and the expression of inflammation markers was determined by quantitative RT-PCR (FIG. 79). As shown in FIG. 79, SLN10 was much more effective in attenuating the inflammatory response of adipocytes stimulated with palmitate. These anti-inflammatory effects are consistent with the inhibitory activity that these compounds have on GPBP in vitro (See FIG. 73), suggesting that the kinase activity of GPBP affects the pro-inflammatory response induced by palmitate.

The role of GPBP in inflammatory macrophage RAW264.7 activation was investigated using an mRNA silencer specific for GPBP. Stimulation with macrophage palmitate induced not only the expression and secretion of GPBP, but also the synthesis and secretion of cytokines characteristic of inflammatory phenotypes M1 (IL-β1) and M2 (IL-10). Interestingly, the presence of a GPBP silencer inhibited induced synthesis and secretion of IL-1β, and even more of IL-10, suggesting that GPBP controls the entry to M1, as well as M1 transition to M2, in inflammatory macrophage activation by palmitate.

The role of GPBP in inflammatory macrophage RAW264.7 activation was investigated using an mRNA silencer specific for GPBP. Stimulation with macrophage palmitate induced not only the expression and secretion of GPBP, but also the synthesis and secretion of cytokines characteristic of inflammatory phenotypes M1 (IL-β1) and M2 (IL-10). Interestingly, the presence of a GPBP silencer inhibited induced synthesis and secretion of IL-1β, and even more of IL-10, suggesting that GPBP controls the entry to M1, as well as M1 transition to M2, in inflammatory macrophage activation by palmitate.

One of the key pathogenic events in hyperglycemia of obese patients is the emergence of a pathogenic feedback between adipose tissue and macrophages of the immune system, in which adipocytes attract macrophages, polarizing them to pro-inflammatory phenotypes, and polarized macrophages secrete cytokines, promoting resistance to adipocyte insulin (Johnson A M, Olefsky J M. *Cell.* 2013; 152:673-84). To reproduce this pathogenic dialogue ex vivo and investigate the activity of SLNs compounds thereon, cytometric techniques allowing the discrimination between these cell lines and determination of phenotypic changes in macrophages in response to individual compounds (Table 18) were used.

Metformin compounds, like metformin lysinate, reduced the proportion of macrophages in M1, with SLN10 showing the strongest effect and SLN1 showing the lowest activity. In a first attempt to determine the ability of metformin compounds of this invention to counteract peripheral resistance to insulin, glucose consumption of co-cultures in the presence of individual SLNs compounds (FIG. 80) was determined. The consumption of glucose increased in the presence of SLNs but with some differences with respect to individual myotube cultures (see FIG. 67), L1 adipocytes, or macrophages (data not shown), since SLN10 showed a stronger "anti-hyperglycemic" and "hypoglycemic" effect in co-cultures. The increase in glucose uptake as a response to SLNs was not attributable to an increase in the corresponding glucose carrier expression (GLUT1 and GLUT4, respectively).

The results suggested rather that the increased consumption of glucose in the presence of metformin compounds of this invention was due to an accumulation of carriers in the plasma membrane (see FIGS. 70A-C and 75), induced by activation of the pathway LKB1/AMPK/AS160 (SLN1 and SLN10) and the insulin pathway (SLN2), due to a decrease in peripheral resistance to insulin (see FIG. 76).

TABLE 12

Cytometric analysis of RAW + L1 co-cultures in the absence or presence of individual metformin compounds of the present invention.

| RAW + 3T3L1 | | EVENTS % | |
|---|---|---|---|
| Cont. | FSC/SSC | 945 | — |
| | F4/80+ | 607 | 100.00 |
| | F4/80+CD86− | 197 | 32.45 |
| | F4/80+CD86− | 410 | 67.55 |
| SLN1 | FSC/SSC | 2.322 | — |
| | F4/80+ | 1.609 | 100.00 |
| | F480+CD86− | 551 | 34.24 |
| | F480+CD86− | 1,058 | 65.76 |
| | | | |
| SLN10 | FSC/SSC | 2.163 | — |
| | F4/80+ | 1.528 | 100.00 |
| | F480+CD86− | 566 | 37.04 |
| | F480+CD86− | 962 | 62.96 |

Table 12 shows that NIH-3T3-L1 pre-adipocytes were differentiated to adipocytes, as in FIG. 70A-C, for 10 days. RAW264.7 macrophages were added to adipocyte cultures, and the co-culture was maintained in DMEM supplemented with 10% FBS and antibiotics for 8 hours. Then, co-cultures were treated with 10 mM SLN1 or SLN10 for 24 hours. Next, cells were washed with PBS and collected by mechanical methods (without trypsin) to prevent protein loss from the cell surface. Cells were then blocked (FcBlock, BD Pharmingen) for 15 minutes at 4° C., and incubated for 20-30 minutes at 4° C. in darkness with anti-mouse F4/80 (eBioscience), conjugated with PerCP-Cy5.5, to mark macrophages, and anti-mouse CD86 (BioLegend), conjugated with PE-Cy7.7, to mark macrophages M1 specifically. Afterwards, cells were washed three times with PBS and centrifuged (500×g, 10 minutes, 4° C.), after which they were analyzed with a cytometer (FACSVerse, BD). In Table 6, the M1 macrophage percentage of the total macrophages analyzed (burgundy) for each treatment is highlighted in yellow.

SLN10 showed an additional "anti-inflammatory" and "anti-hyperglycemic" activity with respect to SLN1, that was attributable to their condition as inhibitors of the GPBP kinase activity, as evidence suggested that phosphorylation/dephosphorylation of Ser (Raya A Revert-Ros F, Martinez-Martinez P, S Navarro, Rosello E, Vieites B, Barn F, J Forteza, Saus J. J Biol Chem. 2000; 275: 40392-9) is the engine of the GPBP cycle. In this model, the differential effect of the metformin amino acid compounds on the inflammatory response would show the interdependence of intracellular and extracellular stages of GPBP through its cycle, suggesting that GPBP secretion affects the pro-inflammatory relation, which eventually causes peripheral insulin resistance.

In a determined attempt to demonstrate the interdependence between the intracellular kinase activity and the pro-inflammatory extracellular activity of GPBP, proteinuria was monitored in an animal model of extracellular GPBP-dependent kidney disease (unpublished results), to which individual SLNs (FIG. 81) compounds were administrated. A proteinuria peak that spontaneously decreased, regardless of the treatment, was observed in weeks 16 and 17. Proteinuria levels remained normal until week 29 when a steady increase thereof was observed in the control group. From week 29, treatments with SLNs reduced proteinuria, when compared with the control group, SLN10 being the most effective, as it achieved statistical significance at week 31 (FIG. 81).

From week 33 onwards, mice in the control group and those treated with SLN1 began to die. At week 35, the remaining animals were sacrificed to analyze their plasma and tissues. The degree of proteinuria of each mouse from week 21 until the moment of their death to sacrifice was determined. Mice treated with SLN10 showed significantly less proteinuria. The number of mice with severe proteinuria (red) or dying prematurely (dark gray) decreased with either of the two treatments.

The kidneys were analyzed by standard techniques of histochemistry. A gradation in the pathological condition was established based on severity criteria in glomerular and tubular lesions, as shown in FIG. 82.

The severity of glomerular and tubular lesions seems to be the cause of death, therefore, mice that died prematurely were assigned a pathological grade of 4, although the corresponding pathological analysis was not carried out. Significant alterations were not observed in other vital organs, such as the liver, heart, and lungs (results not shown).

Interestingly, a direct relationship between proteinuria before sacrifice and the renal pathological grade was observed (FIG. 83). All test mice showed a pathological grade equal or greater than 2, indicating that all animals developed renal lupus. Treatment with SLN10 reduced the number of mice with a pathological grade above 3 (Control: 6; SLN1: 7; SLN10: 3) (FIG. 84). Autoantibody levels were significantly higher during week 19 and increased over time up to titers of 60,000 U/mL. Interestingly, treatment with SLN10 reduced titers by half (FIG. 85).

The analysis of IC glomerular deposits (IgG, IgA, IgM) showed that all groups had IgG deposits, as well as IgM deposits in a lesser extent, and no significant differences between groups of mice were observed (not shown). In general, mice showed inflammatory infiltrates in their kidneys, most evident in the pathological grade of 4. However, no relationship between the extension and treatments was observed.

Circulating GPBP levels (cGPBP) were measured, and although the differences between series were not statistically significant, an increase in cGPBP levels, prior to the steady increase of proteinuria in the control group, was observed. Those treated with SLN10 showed no increase (FIG. 86).

In order to assess whether SLNs were altering the inflammatory response, plasma cytokines and chemokines were analyzed at week 30, when the SLN2 was comparatively more effective in reducing proteinuria. Quantified analytes included:

Cytokines: IL-1α, IL-1β, IL-2, IL-4, IL-5, IL-6, IL-7, IL-9, IL-10, IL-12p40, IL-12p70, IL-13, IL-15, IL-17, IFN-γ, TNF-α

Chemokines: MCP-1 (CCL2), MIP-1α (CCL3), MIP-1β (CCL4), RANTES (CCL5), Eotaxin (CCL11), KC (CXCL1), MIP-2 (CXCL2), LIX (CXCL5), MIG (CXCL9), and IP-10 (CXCL10)

Growth factors: IL-3 (MULTI-CSF), G-CSF, GM-CSF, M-CSF, VEGF, LIF (leukemia-inhibitory factor)

No significant differences between groups were observed at week 30 nor significant increases in inflammation markers in the control group (results not shown). Therefore, the effect of treatment on serum inflammation markers was not clarified. In other animal models of disease also mediated by an overactivation of the GPBP cycle, such as collagen-induced arthritis (CIA), a rheumatoid arthritis model (J Saus, Revert F, Merino R, Merino J, Revert-Ros F. (2012). Appl. No. PCT/EP2012/052923. Publication No. WO/2012/113785) or Type 2 diabetes model IRS2−/− (Saus J, F. Revert 2013. U.S. Provisional Patent 61/883,792), we observed that the cGPBP plasma levels underwent a limited increase over time immediately before the establishment of the cardinal clinical manifestations, such as hyperglycemia and arthritis, or proteinuria, in this case. In all cases, including the case in question, the administration of GPBP blocking antibodies in early stages had therapeutic effects on clinical manifestations (Revert F, R Merino, Merino J, Revert-Ros F. (2012). Appl. No. PCTIEP2012/052923. Publication No. WO/2012/113785). These results demonstrated that extracellular GPBP plays a central role in the pathogenic inflammatory response in all three cases. However, our results clearly show that SLN10 reduced proteinuria.

To investigate the role GPBP plays in inflammatory macrophage activation, a LPS-stimulated RAW264.7 cell model was used, and transcription, expression, and secretion of GPBP in response to the metformin compounds of this invention, such as metformin lysinate, were analyzed. LPS stimulation induced the expression of Col4a3 bp, but pretreatment with SLNs counteracted this induction (FIG. 87), suggesting that the SLNs compounds inhibit the transcription of GPBP in response to LPS, and that they are agents with a very early anti-inflammatory activity.

Accordingly, when the macrophage was LPS-stimulated, treatment with the SLNs compounds was associated with a coordinated inhibition of the induced expression of GPBP and pro-IL-1 (FIG. 88).

Similar results were obtained by stimulating the macrophage with LPS and IFN-γ, a more conventional and powerful way of inducing phenotype M1 (FIG. 89). However, while in both cases no significant differences were observed between compounds inhibiting the induced expression of pro-IL-1β, the induced expression of GPBP was more efficiently inhibited by SLN10.

Finally, to approach our animal model (see FIG. 81), we analyzed the expression and secretion of GPBP by macrophages in response to LPS and IC (FIG. 90). Additional macrophage activation by IC induced the expression and secretion of GPBP, and such an induction was counteracted by SLNs compounds, although unevenly. So, whereas all of them neutralized the induction of transcription, SLN10 showed less ability to reduce GPBP secretion, induced by LPS and IC.

To investigate the significance of our findings in inflammation, we stimulated macrophages with LPS and IFN-γ, and we analyzed GPBP secretion in response to SLNs compounds (FIG. 91). Results show that when the transformation to M1 was performed, GPBP was not secreted significantly, as opposed to when the macrophage was stimulated with LPS and IC, a well-known inflammasome activator (Shin M S, Kang Y, Lee N, Wahl E R, Kim S H, Kang K S, Lazova R, Kang J I. *Immunol.* 2013; 190:1407-15) (see FIG. 90B above). Interestingly, SLN1 did not induce significantly the secretion of GPBP, but the presence of SLN10 in the medium induced GPBP secretion strongly. This model provided an excellent opportunity to confirm that the accumulation of GPBP facilitated the M1 transition (pro-inflammatory) to M2 (anti-inflammatory). For this, the analysis of the expression of IL-10 was monitored (FIG. 92). Interestingly, although the maximum expression of IL-10 occurred in all cases, at the same time, the increase of IL-10 was markedly superior in all cultures treated with SLN10 (compare the area below the curve in all treatments).

This indicated that the M1 transition to M2 kept occurring in all cases, but more efficiently in SLN10-treated cultures. The GPBP participation in the differential stimulation of IL-10 was initially revealed by studying the expression levels of IL-10 in deficient GPBP macrophages (FIG. 93). The IL-10 expression in control cultures or SLN10-treated cultures depended largely on the GPBP expression, whereas the IL-10 expression in cultures treated with SLN1 was virtually GPBP independent. These results were consistent with the GPBP secretion levels in cultures (see FIG. 91), as well as with the modulating activity of SLNs in the in vitro GPBP kinase activity (see FIG. 73). The participation of extracellular GPBP in the differential stimulation of the IL-10 expression by SLN10 was finally confirmed by demonstrating that the IL-10 expression decreased strongly in the presence of a GPBP blocking antibody (N26) in the culture medium (FIG. 94).

The above results showed that in macrophages stimulated with LPS and doxorubicin, the expression and secretion of GPBP regulates the expression and secretion of IL-1β, characteristic of phenotype M1 (Saus J, Revert F, R Merino, Merino J, Revert-Ros F. (2012). Appl. No. PCT/EP2012/052923. Publication No. WO/2012/113785). We have now demonstrated that GPBP secretion, induced by SLN10, upregulates the expression of IL-10 in macrophages stimulated with LPS and IFN-γ. All our results suggest that extracellular GPBP levels regulate the inflammatory response since its inception (M1) until its resolution (M2). Kinase activity of GPBP downregulates its own secretion because autophosphorylation is probably a strategy of GPBP to remain within the cell. Consequently, the differential regulation of SLNs on GPBP secretion is partially attributable to its different capacity to inhibit kinase activity and autophosphorylation. Similarly, the differential therapeutic activity of SLN10 in the model of autoimmune GN-IC depends on its condition as inhibitors of the GPBP kinase activity and their ability to produce GPBP secretion into the extracellular space and stop the inflammatory M1 process.

Consistently, severe clinical inflammatory manifestations in males of CIA or diabetes IRS2−/− models (arthritis and hyperglycemia, respectively) are preceded by a dramatic reduction in circulating levels of GPBP that increase in asymptomatic early stages. On the contrary, the maintenance of GPBP levels was associated with much milder clinical symptoms in the females of these models (J Saus, Revert F, R Merino, Merino J, Revert-Ros F. (2012). Appl. No. PCT/EP2012/052923. Publication No. WO/2012/113785; Saus J, F. Revert 2013. U.S. Provisional Patent 61/883,792).

The treatment of an F1 model (NZB×NZW) with SLN10 is associated with a similar reduction of proteinuria, but with a lower impact on the inflammatory response (see above). The varied pharmacological response to N26 and SLN10 suggests that there are two distinguishable GPBP-dependent pathomechanisms, namely: 1. Alterations in the type IV collagen network that cause structural alterations (Revert F, Merino R, Monteagudo C, Macias J, Peydró A, Alcacer 20J, Muniesa P, Marquina R, White M, Iglesias M, Revert-Ros F, Merino J, Saus J. Am J Pathol J. 2007; 171:1419-30); 2. IC deposits and the associated inflammatory reaction. In the first case, the increased GPBP (in the ER) kinase/chaperone activity produces the synthesis of aberrant collagen conformations that cause the expansion and disruption of the glomerular collagen (MBG dissociation and sclerosis). In the second case, the accumulation of GPBP in the extracellular space (plasma) promotes and regulates the inflammatory response induced by the IC deposit (IgG autoantibodies) in the dissociated MBG (inflammatory infiltrates and fibrosis). In this pathogenic scenario, it is expected that treatment with inhibitors of the kinase activity (SLN10) will affect primarily the activity of GPBP within the cell (phosphorylated GPBP) and N26 will interfere primarily in the extracellular signaling (dephosphorylated GPBP). In both cases, proteinuria decreases significantly, suggesting that functional alteration of the glomerular filtration barrier in this model is twofold: structural and inflammatory. Significantly, the pharmacological effects associated with the treatment of a less severe GN-IC model with N26 surpassed the simple anti-inflammatory action. Furthermore, N26 clearly decreased structural alterations. On the other hand, the results in this report demonstrate that SLN10 limits the inflammatory M1 response. This suggests that the GPBP intracellular (phosphorylated with kinase activity) and extracellular (dephosphorylated without kinase activity) levels are related, and that GPBP phosphorylation/dephosphorylation occurs reversibly on a single pool of GPBP circulating inside and outside the cell: It is secreted dephosphorylated, returns to the cell (where it is phosphorylated), and passes through the same intracellular compartments to be dephosphorylated and secreted again. Upon inflammasome with doxorubicin activation, a GPBP secretion occurs, producing IL-1β synthesis and secretion and keeping M1174 response. When macrophages are stimulated with LPS and IFN-γ, but in the absence of an inflammasome activation, GPBP secretion induces IL-10 synthesis and M1 transition to M2 (see FIG. 87). Besides demonstrating that GPBP oversees the inflammatory response, these observations suggest that extracellular GPBP is not homogeneous, since high levels of GPBP may be pro-inflammatory when inducing IL-1β secretion, or anti-inflammatory when inducing IL-10 secretion. Therefore, high levels of GPBP in response to SLN10 in LPS- and IFN-γ-stimulated macrophages occurred along with a reduction in the synthesis and secretion of IL-1β (results not shown).

Evidence suggests that there are at least two different secretory pathways of GPBP, namely: one that depends on caspase-1 activation (inflammasome) and another one that depends on regulated secretion vesicles (SLN10). The first track is expected to use a secretion route shared with IL-1β, where the GPBP kinase activity intervention may not play a controlling role. This pathway may be responsible for the SLNs anti-inflammatory activity in early stages, suppressing GPBP and IL-1β expressions (see FIGS. 87, 88, 89A, and 89B).

Evidence also shows that inflammation and hyperglycemia are related, and that inflammation induces hyperglycemia (Johnson A M, Olefsky J M. *Cell*. 2013; 152: 673-84), and hyperglycemia produces inflammation (Aljada A, Friedman J, Ghanim H, P Mohanty, Hofmeyer D, Chaudhuri A, Dandona P. *Metabolism*. 2006; 55: 1177-1185), but so far the molecular basis of this pathogenic binomial has yet to be clarified. In order to explore the involvement of GPBP in this binomial, we monitored glucose consumption of myotubes cultured in "normoglycemic" conditions with macrophage-conditioned media, stimulated and treated with individual SLNs compounds (FIG. 95). Interestingly, the glucose concentration in cultured myotubes kept at the M1 macrophage-conditioned medium increased steadily until reaching "hyperglycemic" levels, whereas the "hyperglycemic" effect was counteracted by individual SLNs, but with considerable differences between them. While SLN1 slowed progression towards "hyperglycemia", SLN2 kept values at "normoglycemic" levels, and SLN10 took them to "hypoglycemic" levels. These results show that SLNs differentially modulate the metabolic response to hyperglycemic soluble factors released from stimulated macrophages. Evidence suggests that GPBP extracellular levels when limiting the M1 response and facilitating M2 transition may reduce the levels of these diabetogenic factors.

Example 24

GPBP and SLN10 Form Stable Complexes in Saline Solution

Taking advantage of the intrinsic fluorescence of GPBP, we found that SLN10 forms complexes with GPBP in vitro. GPBP has a maximum emission at 370 nm when excited at 280 nm (FIG. 96).

The addition of increasing concentrations of SLN10 (0-2.5 μM) to a solution of 1 μM GPBP caused a steady reduction (extinction) of the intensity of fluorescence emission at 370 nm (F370) (FIG. 97).

This phenomenon suggests that GPBP and SLN10 interact.

There are two mechanisms by which a molecule can cause a fluorophore fluorescence extinction (quenching):

a) Static: the fluorophore (F), in this case GPBP, and the quencher molecule (ME), SLN10, form a stable complex (F-ME) less fluorescent than F.

b) Dynamic: F and ME do not form stable complexes but collide. Collisions dissipate energy stored by F in excited state (F*), reducing its fluorescence emission.

Increases in temperature produce opposite effects on each type of extinction: increase in temperature decreases the static-type extinction because the F-ME complex is less stable, while the dynamic extinction is favored because the frequency of collisions between F and ME increases. Static and dynamic extinctions are not mutually exclusive and can coexist in the same F and ME solution. If the extinction is of one single type (static or dynamic), the ratio of the fluorescence emission of the fluorophore (F0) with that of the fluorophore in the presence of ME (F) is linear and proportional to the concentration of ME, and it is defined by the Stern-Volmer equation (Agudelo D, Beauregard M, G Bérubé, Tajmir-Riahi H A. *J Photochem Photobiol B*. 2012; 117: 185-92), which in the case of GPBP and SLN10 is:

$$\frac{F_0}{F} = 1 + Ksv \cdot [SLN10] \quad \text{(Equation 1)}$$

where F0 is the intensity of fluorescence emission at 370 nm of a solution of 1 μM GPBP excited at 280 nm, in the absence of SLN10, F is the intensity of fluorescence emission at 370 nm for each concentration of SLN10, and Ksv is the Stern-Volmer constant extinction.

Calculating Ksv at two different temperatures allows to determine whether the extinction occurs by mere collision (dynamic) or by the formation of a stable complex (static). In the first case, Ksv increases with temperature, and in the second case, it decreases.

This procedure has been used to determine the type of interaction between GPBP and SLN10, calculating Ksv at 26° C. (FIG. 98) and 32° C. (not shown):

The equation calculated for the line in FIG. 98 is:

F0/F=1.0236+0.1088×[SLN10]

R2=0.9659 where the slope (0.1088) is Ksv/10⁶, from which it is deducted that at 26° C.

Ksv=1.088×10⁵ M⁻¹

At 32° C., we calculated that Ksv=1.044×10 M⁻¹ (not shown).

The decrease of Ksv upon passing to 26-32° C. indicated a static fluorescence quenching of GPBP by SLN10, and the formation of a GPBP-SLN10 complex.

Therefore, there must be a phenomenon of association between GPBP and SLN10 with an affinity constant (Ka):

$$Ka \; GPBP + nSLN10 \xrightleftharpoons{Ka} GPBP \cdot SLN10n \quad \text{(Equation 2)}$$

where $$Ka = \frac{[GPBP - SLN10n]}{[GPBP] \times [SLN10]^n} \quad \text{(Equation 3)}$$

In this case the following equation can be derived (Mandal G, M Bardhan, Ganguly T. Colloids Surf B Biointerfaces. 2010; 81:178-84):

$$\log\left[\frac{F_0 \cdot F}{F}\right] = \log K_a + n\log[SLN10] \quad \text{(Equation 4)}$$

where F0 is the fluorescence emission of GPBP, F fluorescence emission of GPBP at a concentration of SLN10, Ka the constant of affinity, and n the number of SLN10 molecules bound to GPBP.

The equation above was represented with the F data obtained at 26° C. (FIG. 99):

The equation of the line is:

log(F0−F)/F=3.4935+0.7196×log[SLN10]R²=0.9939 (Equation 5)

Considering Equation 2, it follows that Ka=10³·⁴⁹³⁵=3.115×10³ and that n=0.7

Ka can be considered moderate according to previous similar studies, conducted in other proteins and ligands (Agudelo D, Beauregard M, G Bérubé, Tajmir-Riahi H A. J Photochem Photobiol B. 2012; 35 117:185-92). The fact that n<1 indicates that not all GPBP molecules are accessible to SLN10.

Example 25

Metformin Lysinate Decreases Hyperglycemic Levels of in C2C12 Myotubes Induced by M1 Macrophage Conditioned Media There is considerable evidence showing that inflammation and hyperglycemia are interconnected: Inflammation induces hyperglycemia and reciprocally hyperglycemia induces inflammation with the molecular bases not elucidated yet. To explore the participation of GPBP, glucose intake under normoglycemic conditions with conditioned media generated by macrophages differentiated to a proinflammatory M1 phenotype was monitored.

In the experiments, RAW264.7 macrophages were treated with metformin HCl or metformin lysinate (10 mM) for 2 hours and then stimulated with LPS (0.5 µg/mL) and IFNγ (20 ng/mL) for 16 hours. Then the culture media were collected, their glucose concentration adjusted to 100 mg/100 mL and used to culture C2C12 myoblasts that had been previously differentiated to myotubes in DMEM supplemented with 2% horse serum for 5 days. The glucose concentration of the myotube cultures was determined at different times with Glucocard (Arkray). The controls used were the C2C12 cultured with media conditioned with no stimulated macrophages (cells) or with M1 conditioned media. The initial glucose levels (time 0) were used as a reference (100%) in each series. The results are shown in FIG. 95.

As shown in FIG. 95, hyperglycemic levels were induced in myotubes grown by a proinflammatory M1 macrophage-derived conditioned media. Treatment with metformin lysinate, but not metformin HCl, reduced the hyperglycemic levels. In other words, whereas metformin HCl slowed down the progression towards hyperglycemia, metformin lysinate reduced the glucose concentration to hypoglycemic levels. These results are consistent with the GPBP inhibition capacity revealing that the metabolic response to soluble hyperglycemic factors released by proinflammatory macrophages can effectively modulated by GPBP specific inhibitors.

Example 26

Metformin Association with Lysine in Aqueous Solutions

Results from this example support that lysine (and by extension potentially other amino acid) forms stable complexes with metformin in aqueous solutions. In aqueous solution, metformin acts as a base ($pK_a$=12.4) and tends to subtract protons present in the solution, so the correct way to represent it is in a positively charged protonated way (MetF-H'). Moreover, in aqueous solution and at physiological pH, most of the amino acids are in zwitterionic form, i.e., electrically neutral, but with formal positive charges in the amino group and negative charges in the carboxyl group. It is therefore expected that the positively charged metformin (MetF-H$^+$) and the negatively charged carboxyl group (COO—) undergo an electrostatic attraction, SLN10 will form a metformin-amino acid aggregate or complex stable in solution. However, such an interaction may not be strong due to an impairment produced by the solvation sphere surrounding both species.

To evaluate the degree of metformin association with lysine an aqueous solution of lysine (concentration known) was titrated with an increasing amount of metformin, and the generation of stable metformin lysinate complexes was quantified by the variation of proton signal displacement using nuclear magnetic resonance (NMR).

Specifically, 500 µL of a 10 mM lysine solution in buffer 1×30 PBS were introduced in an NMR tube, and the pH was adjusted to 7.5; moreover, 50 mL of deuterated methanol was added, and the NMR proton spectrum was recorded ($^1$H). On the other hand, a solution of metformin hydrochloride was prepared in 500 mM buffer 1×PBS, and the pH was adjusted to 7.5. Increasing amounts of the metformin dissolution were added to the amino acid dissolution, and the $^1$H NMR spectrum was recorded after each addition until reaching 20 equivalents.

The alpha proton signal of lysine (triplet to 3.76 ppm, FIG. 100) first shifted to lower S values below 96 and then to higher values. The formation of the metformin lysinate complexes was analyzed using the WINEQNMR2 program, which calculates the association constant by adjusting the real chemical displacement according to the concentrations of the components. The complexation constant was calculated to be 828±42 (FIG. 101).

Example 27

Tests of Metformin Lysinate on Mouse 3t3-11 Adipocytes

Differentiation Protocol

3T3-L1 cells are mouse pre-adipocytes that can differentiate to adipocytes with appropriate stimuli. 3T3-L1 cells propagate in DMEM (with L-glutamine and 4.5 g/L glucose) supplemented with 10% calf serum and penicillin/streptomycin. To differentiate them to adipocytes, 3T3-L1 cells are first cultured to confluence in DMEM with 10% calf serum. Two days after reaching confluence (day 0), cultures are incubated for two days in DMEM with 10% fetal bovine serum, supplemented with 1 mM dexamethasone, 2 mM rosiglitazone, 167 nM insulin, and 115 mg/mL 3-isobutyl-1-methyl xanthine (IBMX). Then (day 2), cultures are maintained for two days in DMEM with 10% fetal bovine serum, supplemented with 167 nM insulin. Afterwards (day 4), cultures are maintained in DMEM with 10% fetal bovine serum, which is renewed every two days until full culture differentiation, which occurs at 8-10 days from the beginning of the process; this can be checked with an inverted microscope (Motic AE31) by the appearance of lipid droplets in the cytoplasm of cells.

Example 28

Compositions or Pharmaceutical Formulations, Pharmaceutical Forms and Drugs Comprising the Compounds of the Present Invention The formulation or composition for the manufacturing process of a drug comprising the metformin compounds (SLNs) of the present invention includes diluents, binders, disintegrants, slidings, lubricants, non-adherent agents, coating or film, and solvent.

A qualitative-quantitative formula of the present invention, that depends on the formulation for the manufacture of a drug comprising metformin compounds (SLNs), selected from the group comprising metformin aspartate, isoleucinate, alaninate, valinate, asparaginate, threoninate, leucinate or lysinate, more particularly metformin lysinate, has the active ingredient and excipient cbp, for example:

Active Substance: 95-105%
Diluent: 19-23%
Binder: 3-6%
Disintegrant: 3-6%
Sliding: 0.15-0.45%
Lubricant and/or non-adherent agent: 3-7%
Film or coating: 0.5-0.7%
Diluent:
A qualitative-quantitative formula, not limiting the scope and variants to implement the present invention, is characterized by:
Active Substance: 620 mg or 1050 mg
Dibasic calcium phosphate: 21-22%
Povidone: 4-5%
Starch sodium glycolate: 4-5%
Colloidal silicon dioxide: 0.28-0.32%
Talcum: 4.7-5.3%
Magnesium stearate: 0.9-1.1%
Anionic copolymer film based on methacrylic acid and ethylacrylate, as well as talcum: 0.6-0.7%
Purified Water The manufacturing procedure comprises a wet granulation process involving granulation of the drug with water in order to ensure functionality of the formulation and its suitable performance in the pharmaceutical form. To an expert, the existing methods and variations for wet-granulation and coating of solid pharmaceutical forms in the pharmaceutical industry are well known; therefore, without limiting the scope of the invention, the manufacturing processes of solid pharmaceutical forms, such as tablets, are well known and common in the pharmaceutical literature, and examples herein are intended to illustrate embodiments of the present invention, without limiting its scope.

A high-speed granulator is used in the manufacturing process, and the result is a granulate suitable for compression, which is carried out in rotary tablet presses that are capable of handling tools for tablets containing doses from 100 mg up to 2.4 g, specially 589-651 mg, preferably 615-625 mg, and more particularly 620 mg; or 997.5-1102.5 mg, preferably 1035-1075 mg, and more particularly 1050 mg of a compound selected from the group consisting of metformin aspartate, metformin isoleucinate, metformin alaninate, metformin valinate, metformin asparaginate, metformin threoninate, metformin leucinate, and metformin lysinate, more particularly metformin lysinate.

The coating process was carried out in a conventional drum system by set conditions, ensuring functionality of the formulation and its proper performance. Particularly, the formulation used for administering at least one SLNs (e.g., mMetformin lysinate) are tablets with aqueous coating by wet granulation, comprising from 100 mg up to 2.4 g, specially 589-651 mg, preferably 615-625 mg of at least one SLNs (e.g., metformin lysinate), and more particularly 620 mg of at least one SLNs (e.g., metformin lysinate).

In another particular embodiment of this invention, the formulation used for administering metformin glycinate were tablets with aqueous coating by wet granulation, comprising from 100 mg up to 2.4 g, specially 997.5-1102.5 mg, preferably 1035-1075 mg of at least one SLNs (e.g., metformin lysinate), and more particularly 1050 mg of at least one SLNs (e.g., metformin lysinate).

The wet-manufacturing steps of the present invention include the following steps, without limiting the scope and variants for the implementation thereof:
a. weight the raw material
b. sieve the active ingredient together with the excipients
c. Mix
d. granulate with purified water
e. dry to a moisture below 2.0%
f. sieve
g. mix
h. granulate with purified water
i. dry to moisture below 3.5%
j. sieve
k. mix lubricants and/or non-adherent agents
l. compress according to the desired specifications
m. coat with film Tablets can be packaged in aluminum/aluminum blister, PVDC/aluminum blister, and HDPE/PP bottles.

In one embodiment, the present application discloses also pharmaceutical compositions comprising a compound of the present invention, or a pharmaceutically acceptable salt, solvate, and/or ester thereof, in combination with at least one additional therapeutic agent, and a pharmaceutically acceptable carrier or excipient. The additional therapeutic agent is selected from other anti-diabetic drugs, such as sulfonylureas, iDPP4, SGL2, thiazolidinediones (TZD), insulins, glinides, etc.

The scope of the invention is not limited and these are only embodiments that do not limit the invention, every time that the tablets or caplets of the compounds of the present invention, such as metformin aspartate, metformin isoleucinate, metformin alaninate, metformin valinate, metformin asparaginate, metformin threoninate, metformin leucinate, or metformin lysinate contain from 100 mg up to 2.4 g, especially 589-651 mg, preferably 615-625, and more particularly 620 mg; or from 997.5 up to 1102.5 mg, especially 1035-1075 mg, and more particularly 1050 mg. Likewise, stability data of at least 3 months under conditions of 25° C.-45° C. and 60-80% RH, more particularly 25° C., 30° C., and 40° C., and 60%, 65%, and 75% RH, show that the tablets of the compounds of the present invention, such as metformin lysinate, are very stable and can keep appropriate titrated concentrations for its implementation in different packaging or conditioning. A skilled person in the art will appreciate that, in exposed weather conditions, the present invention is stable and can be implemented without limiting to the scope of the invention herein exemplified and implemented.

A preferred but not a limiting embodiment of a stability test for a drug and/or formulation comprising 620 mg of at least one SLNs (e.g., metformin lysinate) is indicated. A skilled person in the art will appreciate that the present invention may routinely and/or evidently include within its scope stability tests for a drug and/or formulation comprising 1050 mg of at least one SLNs (e.g., metformin lysinate), or any other concentration from 100 mg up to 2.4 g. Likewise, someone skilled in the art will appreciate that the present invention may include in its scope, with no limitations, drugs and/or formulations comprising any of the following compounds of metformin of the present invention, selected from the group consisting of metformin aspartate, metformin isoleucinate, metformin alaninate, metformin valinate, metformin asparaginate, metformin threoninate, metformin leucinate, and metformin lysinate.

Preclinical Evidence Pharmacokinetic and Pharmacodynamic Studies

Example 29

Bioavailability Studies of the Metformin Compounds (SLNs) in Cultured Cells

Objective

Evaluated bioavailability differences between the compounds of the present invention (metformin compounds (SLNs)) and metformin hydrochloride by determining the intracellular concentration of metformin in cultures of A549 cells and to develop an explanatory model.

Materials and Method

Treatment and Lysate of A549 Cells.

A total of 9 large culture plates were inoculated with A549 cells and incubated in an oven at 37° C. and 5% of C02 atmosphere to reach confluence in medium DMEM/F12 1:1 Modified (L-glutamine 2.5 mM, buffer HEPES 15 mM, sodium pyruvate 110 mg/L), with 10% fetal bovine serum and 1% antibiotics. With the same medium, 40 mL of 10 mM metformin hydrochloride (SLN1), metformin lysinate (SLN10), and metformin asparaginate (SLN11) were prepared. Based on these solutions, 20 mL at 7.5 and 9.3 pH for each compound were prepared. Thus, eight different solutions (4 SLNs at 2 values of pH) of 20 mL each were obtained.

The culture medium of the 9 confluent plates was eliminated, and each plate received one of the 8 above mentioned solutions (20 mL). The ninth plate was added with only 20 mL of culture medium (CONTROL). The plates were incubated in an oven for 3 hours and the administrated medium was eliminated afterwards. Each plate was washed twice with PBS solution (10 mL) to remove any remaining metformin, and 4 mL of trypsin was added to separate cells from the plate. Cells were washed with 10 mL of PBS and centrifuged at 500×g for 10 min. The supernatant was decanted and, the sediment was lysed by adding 300 mL of hypotonic buffer (10 mM HEPES, pH 7.9, 1.5 mM $MgCl_2$, 10 mM KCl, 10 µ/mL leupeptin, 1 mM dithiothreitol and 1 mM PMSF) and incubated on ice for 30 min. Then, lysates were centrifuged at 16,000×g for 10 min at 4° C., and the supernatants were collected and preserved at −20° C. The supernatants were thawed and centrifuged again at 16,000×g for 10 min at 4° C., the protein concentration was determined (Bio-Rad Protein Assay), and the metformin content quantified.

The HPLC chromatograph used consists of a pump (LaChrom Elite L-2130, VWR Hitachi High Technologies, Tokyo, Japan), a UV/Vis detector (LaChrom Ultra L-2455U, VWR Hitachi High Technologies, Tokyo, Japan), a column oven (Ultra LaChrom L-2300, Hitachi High VWR Technologies, Tokyo, Japan) and an automatic injector (LaChrom Elite L-2200, VWR Hitachi High Technologies, Tokyo, Japan). The separation of the analytes was performed at 25° C. in a Phenomenex Aeris widepore XB-C18 column (150 mm×4.60 mm, 3.6 µm). The mobile phase (pH 5.0) was pumped at a flow of 1.0 mL/min, and it consisted of a mixture of acetonitrile-water (33:66, v/v) containing 2 mM sodium dodecyl sulfate, 12.5 mM potassium dihydrogen phosphate, and 15 mM triethylamine. The wavelength of the UV detector was 236 nm.

Standard solutions of the metformin hydrochlorides and ranitidine (Pharmaceutical secondary standard, Sigma-Aldrich) were prepared by dissolving 5 mg of each solution in 1 mL of methanol. They were diluted in methanol to prepare adequate working dilutions and were stored at 4° C. The internal standard solution (ranitidine) was diluted in methanol until reaching a final concentration of 120 µg/mL. Calibration standards were prepared, enriching 90 µL of sample lysate without metformin (CONTROL), with 10 µL of the working standards to achieve final metformin concentrations of 5, 10, 20, 40, and 80 µg/mL. An aliquot of 5 µL of internal standard (ranitidine, 120 µm/mL) was added to 100 µL of the lysed samples. The mixture was shaken vigorously (vortex) for 30 seconds, and 25 µL of acetonitrile acidic solution (pH 1.0) was added to it, as to precipitate proteins. Subsequently, the samples were vigorously (vortex) mixed for 30 sec, centrifuged at 16,000×g for 15 min at 4° C., and the supernatant (15 µL) was injected into the chromatograph. After analyzing the standard calibration samples, a calibration curve representing the ratio of the peak areas of metformin/ranitidine (y) against the corresponding concentrations of metformin (0, 5, 10, 20, 40, and 80 µg/mL, x) was obtained. The curve was adjusted by linear least squares regression (FIG. 106).

Western Blot Analysis.

A549 cells cultured to confluence in DMEM/F12 supplemented with 2.5 mM L-glutamine, 15 mM HEPES, 110 mg/L sodium pyruvate, 10% fetal bovine serum and 1% antibiotic, were treated for 3 hours with 10 mM SLN1 (metformin hydrochloride) or 10 mM SLN10 (metformin lysinate) in culture medium, whose pH was adjusted to 7.5 or 9.3. After the incubation time, cells were washed twice with PBS and lysed in 25 mM Tris-HCl, pH 7.4, 140 mM NaCl, 3 mM KCl, 20 mM NaF, 1 mM PMSF, 10 µg/mL leupeptin, 1% Triton X-100 for 20 min at 4° C. The lysates were centrifuged at 20,000×g for 10 min at 4° C., supernatants were recovered, and protein concentration determined (Bio-Rad Protein Assay).

Equal amounts of each lysate (40 µg) were analyzed by Western blot, with monoclonal antibodies against GPBP N27 (Fibrostatin SL) and against tubulin (Sigma). Electrophoresis was performed in polyacrylamide gel (6.5%) with SDS, after which electroblotting was carried out to PVDF membrane (Immobilon P, Millipore Merck). After transfer, the membranes were blocked in 5% skim milk in 25 mM Tris-HCl, pH 7.5, 150 mM NaCl, 0.05% Tween-20 (TBST) for 45 min, and then incubated with primary antibodies diluted in blocking solution for 16 hours at 4° C. Thereafter, the membranes were washed with TBST (3×5 minutes) and incubated with secondary antibodies against mouse IgG, conjugated to horseradish peroxidase (HRP) (Sigma) for 1 hours at room temperature while stirring. After further washes with TBST (3×5 minutes), the chemiluminescence disclosure was performed by using the ECL Prime reagent (GE Healthcare) and the image generation system ImageQuant LAS 4000 Mini (GE Healthcare).

The Western blots disclosure images were analyzed with the ImageJ WCIF program.

Results

To standardize all data, metformin concentrations (µg/mL) were divided among protein concentrations (mg/mL) of each sample. FIG. 107 shows the results for the first experiment. In all cases, higher amounts of metformin can be seen in cells treated in basic medium than in cells treated in neutral medium. This suggests that medium basification facilitates metformin entry into cells. The experiment was repeated 4 times, but without the thawing intermediate step. The findings of this experiment are similar to those of the previous experiment.

To investigate the effects that the increase of intracellular metformin levels had on GPBP, studies similar to those shown in FIG. 107 with SLN1 and SLN10 were carried out. Cell extracts were analyzed by Western blot. A549 cell extracts contained at least three polypeptides (a, b, and c) reactive with N27, an antibody that recognizes all molecular species and generates the COL4A3BP gene (FIG. 108). However, the proportion of reactive species varied, and different exposures were necessary to identify them and to carry out the comparative analysis. At pH of 7.5, cultures treated with SLN1 showed two polypeptides, a and b, with similar reactivity, while in corresponding counterparts of treated with SLN10, there was an increase in the reactivity of peptides b and c, which was demonstrable by an image analysis program that revealed that SLN10 treatments took the maximum reactivity towards smaller values in the presence of a "reactivity shoulder," corresponding to polypeptide c (FIGS. 109 and 110). At pH of 9.3 (FIG. 111), the image analysis revealed that treatment with SLN10 induced a shift of the maximum reactivity peak towards smaller values (polypeptide b), when compared with SLN1 treatment, although a different "reactivity shoulder" was not observed in the position corresponding to polypeptide c (FIG. 112).

Discussion

According to the results described herein and knowing that it is more difficult for charged molecules pass through cell membranes than for molecules with neutral charge, the following mechanism regarding the process of metformin entry into cells is displayed (FIG. 113). Metformin in aqueous solution and physiological pH has a positive charge (MetF+) due to its high basic character (pKa 12.4), whereas amino acids are found in zwitterionic form, i.e., electrically charged but with positive formal charges in the amino group ($NH3^+$) and a negative charge in the carboxyl group ($COO^-$). It is therefore expected that metformin with a positive charge and the negatively charged carboxyl group experiment an electrostatic attraction, and that an adduct or metformin-amino acid complex is formed, being stable in solution. Although at pH of 7.4, such a complex has a non-neutral overall charge; as pH increases, the $NH3+$ group loses a proton, in a way that the net charge of the metformin-amino acid complex gets neutralized and can easily penetrate through the cell membrane. Once inside the cell, where the pH is 7.4, a balance favoring the presence of charged metformin is achieved, with limited capability to spread outwards.

Therefore, we would have two active ingredients within balance with a high shift towards the release of charged metformin. Through the Henderson-Hasselbalch equation, the concentration of the amino acid with the protonated amino group (charged) may be calculated. When assuming a 100% complexation, the theoretical maximum of the active ingredient responsible for inhibiting the GPBP would be of 214 µM (SLN10), and 427 µM (SLN11); these are values that are close to the normal range of concentrations for kinase inhibitors, and this would also justify the high concentration of compounds required to inhibit kinase activity in vitro at pH of 7.0 (see previous final report). In this sense, at this pH, the SLNs showed an inhibitory capacity at 1 mM, which according to our estimates, corresponds to an active ingredient concentration of 8.6 µM for SLN10 in in vitro assays.

Inside the cell, the neutral adduct would inhibit the kinase activity of GPBP, resulting in a reduction in the autophosphorylation state, with an increase in electrophoretic mobility and VAPA affinity. This results in induction or stimulation of the GLUT4 translocation to the plasma membrane. In contrast, charged metformin would activate AMPK kinase activity, having the same consequences on the glucose carrier.

A549 cells extracts treated with 10 mM SLN1 or SLN10, for 3 hours at pH of 7.5 were analyzed by Western blot, with the indicated antibodies. Polypeptides a, b, and c, of different electrophoretic mobility, recognized by the N27 antibody are indicated with arrows. Polypeptide c, of greater mobility and lower molecular mass, is more abundant in culture extracts treated with SLN10 than in those treated with SLN1.

The optimized image in FIG. 108 was analyzed with the ImageJ WCIF program. At the upper part, the optimized image with the analyzed areas is shown. The left vertical arrow indicates the direction of the image analysis, whose result is shown in the charts below. The tip of right horizontal arrow points the polypeptide c, of higher electrophoretic mobility, which is more abundant in culture extracts treated with SLN10. The charts below show signal intensity distributions in the regions analyzed, in the direction indicated by the arrow of the image above. The tips of vertical arrows indicate the "reactivity shoulders" corresponding to polypeptide c, best seen in cell cultures treated with SLN10 than in cultures treated with SLN1.

The image in FIG. 108 was analyzed with the ImageJ WCIF program similarly to what is shown in FIG. 109. It is observed that the maximum of the signal intensity curves shifts to positions of less molecular weight in cell extracts treated with SLN10, compared with cell extracts treated with SLN1.

A549 cell extracts treated with 10 mM SLN1 or SLN10 for 3 hours at pH of 9.3 were analyzed with Western blot, with the indicated antibodies.

A549 cell extracts treated with 10 mM SNL12 or SLN10 for 3 hours at pH of 9.3 were analyzed with Western blot, with anti-GPBP N27 monoclonal antibodies. Then, the image in FIG. 111 was analyzed with the ImageJ WCIF program as with FIGS. 108 and 109. It is observed that the maximum of the signal intensity curves shifts to positions of less molecular weight in cell extracts treated with SLN10, compared with cell extracts treated with SLN1.

Example 30

Determination of Metformin in Rat Plasma Using LC-MS/MS

Principle

Metformin is determined in rat plasma by protein precipitation followed by HPLC analysis with tandem mass spectrometric detection.

COSHH Assessment

Normal precautions are necessary when handling the test item i.e. disposable gloves, safety glasses, and laboratory coats.

Apparatus/Glassware/Consumables

Apparatus: Agilent, HPLC pump with Presearch autosampler coupled to a MDS Sciex Mass Spectrometer.

Reagents/Solutions

Reagent:
  Ammonium formate
  Acetonitrile
  Methanol
  Propan-2-ol
  Formic acid
  UHP water Reagent Solutions
4.2.1 10 mM Ammonium Formate pH of 3.5—Mobile Phase A 0.631 g of ammonium formate is dissolved and diluted to 1 L with 5 UHP water in a 1 L measuring cylinder. Formic acid is added dropwise until a pH of 3.5 is achieved. The solution is transferred to a storage vessel and is stored at room temperature for up to 2 weeks.

Acetonitrile—Mobile Phase B 1000 mL of acetonitrile is added to a suitable storage vessel. The solvent is stored at room temperature for up to 3 months.

50% (v/v) Methanol 250 mL of methanol is added to 250 mL of UHP water in a suitable vessel and mixed. The solution is stored at room temperature for up to 3 months.

0.1% (v/v) Formic Acid in Acetonitrile:Propan-2-Ol:UHP Water [4:3:3 (v/v)]—Needle Rinse 1

400 mL of acetonitrile, 300 mL of propan-2-ol, and 300 mL of UHP water are added to a 1 L measuring cylinder. 1 mL of formic acid is added and the contents are mixed. The solution is transferred to a storage vessel and stored at room temperature for up to 3 weeks.

Methanol—Needle Rinse 2

500 mL of methanol is added to the auto sampler needle rinse bottle. The solution is stored at room temperature for up to 3 months.

Test Items/Reference Standards
Metformin

Metformin (reference standard)

Analytical Stock Solutions

Accurately weigh out approximately 100 mg of metformin and dissolve in 50% methanol, with sonication if necessary, and dilute to volume with 50% methanol in a 10 mL Grade A volumetric flask to give a solution with a concentration of 10000 µg/mL. Prepare two solutions, one for preparation of calibration standards (A) and the other one for Quality Control samples (B). The amount weighed should be corrected for purity and compound form. These solutions should be stored at approximately 4° C.

Diluted Solutions

The duplicate analytical stock solutions (A and B) should be diluted with 50% methanol to produce two sets of diluted solutions, each set prepared as indicated in the Table 13 below:

TABLE 13

Diluted solutions

| Volume taken (µL) | Concentration (µg/mL) | Final volume (mL) | Concentration (µg/mL) |
|---|---|---|---|
| 100 | 10000 | 1 | 1000 |
| 200 | 1000 | 1 | 200 |
| 250 | 200 | 1 | 50.0 |
| 100 | 50.0 | 1 | 5.00 |

Internal Standard Stock Solution

SIL-metformin is purchased in small quantities and is dissolved in 50% methanol on receipt to a concentration of approximately 1000 µg/mL and the solution stored at approximately −20° C. long term.

Internal Standard Working Solution

On the day of an analytical run the internal standard stock solution should be diluted with acetonitrile, to produce a working solution, used in the sample preparation procedure, as detailed in the following Table 14:

TABLE 14

Working solution

| Volume taken (µl) | Concentration (µg/mL) | Final volume (mL) | Concentration (ng/mL) |
|---|---|---|---|
| 5.00 | 1000 | 50 | 100 |

The volumes specified in Table 14 are illustrative and may be scaled up or down as required where different volumes of internal standard are required.

Procedures
Calibration Standards

Calibration standards are prepared by aliquoting volumes of the diluted solutions (A) into polypropylene tubes and adding the appropriate volume of rat plasma (lithium heparin). The samples are then mixed briefly. Calibration standards should be aliquoted into polypropylene tubes in appropriate portions and stored at approximately −20° C. if necessary. The calibration standards are prepared as indicated in the Table 15 below.

TABLE 15

Calibration standards

| Calibration standard | Spiking solution conc. (µg/mL) | Spike volume (µl) | Final volume (rat plasma) (mL) | Calibration standard conc. (ng/mL) |
|---|---|---|---|---|
| A | 5.00 | 10.0 | 0.5 | 100 |
| B | 5.00 | 25.0 | 0.5 | 250 |
| C | 50.0 | 6.00 | 0.5 | 600 |
| D | 50.0 | 14.0 | 0.5 | 1400 |
| E | 200 | 8.00 | 0.5 | 3200 |
| F | 200 | 20.0 | 0.5 | 8000 |
| G | 1000 | 10.0 | 0.5 | 20000 |
| H | 1000 | 25.0 | 0.5 | 50000 |

The volumes specified in the Table 15 are illustrative and may be scaled up or down when different volumes of Calibration Standards are required.

Validation Samples/Quality Control Samples

Validation Samples/Quality Control (QC) samples are prepared by aliquoting volumes of the diluted solutions (B) into polypropylene tubes and adding the appropriate volume of rat plasma (lithium heparin).

The samples are then mixed briefly. Validation/QC samples should be aliquoted into polypropylene tubes and stored at approximately −20° C. The Validation/QC samples are prepared as indicated in the Table 16 below:

TABLE 16

Validation/QC samples

| Validation/QC sample | Spiking solution conc. (µg/mL) | Spike volume (µl) | Final volume (rat plasma) (mL) | Validation/QC sample conc. (ng/mL) |
|---|---|---|---|---|
| VS1 | 5.00 | 20.0 | 1 | 100 |
| VS2/QC low | 5.00 | 50.0 | 1 | 250 |
| VS3/QC med | 50.0 | 40.0 | 1 | 2000 |
| VS4/QC high | 1000 | 40.0 | 1 | 40000 |
| VS5 | 1000 | 50.0 | 1 | 50000 |

The volumes specified in the Table 16 are illustrative and may be scaled up or down when different volumes of Validation/QC samples are required. Validation samples prepared at concentrations greater than 50000 ng/mL may be prepared directly from the stock analyte solutions if necessary, or from diluted solutions other than those detailed in section 5.2.

Sample Preparation

Samples are extracted from rat plasma by protein precipitation according to the procedure in Table 17:

TABLE 17

Procedure for protein precipitation

1. Aliquot 10 μl of calibration standard, Validation/QC sample, study sample, blank rat plasma into the appropriate wells of the protein plate.
2. Aliquot 300 μl of acetonitrile, into the wells of the protein plate which are intended for the double blank samples.
3. Aliquot 300 μl of working internal standard solution (100 ng/mL) into all other wells.
4. Agitate the liquids in the wells by placing the protein plate onto a vortex mixer. Grip the protein plate and mix the samples at a moderate speed for approximately 10 seconds.
5. Place a collection plate or a rack of 1.4 mL micronic tubes within the extraction manifold, and place the protein plate on top of the manifold. Draw the supernatants through the filters into the collection tubes by applying vacuum to the manifold.
6. Seal tubes, vortex mix for 30 seconds, centrifuge, and inject samples into LC- MS/MS system.

HPLC Conditions:

TABLE 18

HPLC Conditions

| | |
|---|---|
| HPLC column | 50 × 2.1 mm Atlantis Hilic Silica 5 μm |
| Column temperature | ambient |
| Flow rate | 0.3 mL/min |
| Mobile phase A | 10 mM ammonium formate pH 3.5 |
| Mobile phase B | Acetonitrile |
| HPLC mode | gradient |
| Typical injection volume | 2-15 μl |
| Needle rinse 1 | 0.1% (v/v) formic acid in acetonitrile:propan-2-ol:water [4:3:3 (v/v)] |
| Needle rinse 2 | Methanol |

TABLE 19

HPLC Mobile Phase Gradient

| Time | Composition (%) A | Composition (%) B |
|---|---|---|
| 0 | 10 | 90 |
| 2 | 50 | 50 |
| 2.5 | 50 | 50 |
| 2.6 | 10 | 90 |
| 6.0 | 10 | 90 |

Mass Spectrometer Conditions (Tables 20 and 21)

TABLE 20

Mass Spectrometer Conditions

| | |
|---|---|
| Ionization mode | Electro spray |
| Polarity | Positive |
| Curtain gas (nitrogen) | 12* |
| Nebulizer gas (air) | 8* |
| Auxiliary gas (air) | 6 l/min* |
| Collision gas (nitrogen) | 10* |
| Source/auxiliary gas temperature | 500° C. |
| LC effluent split ratio | 100% |

*The values given are approximate

TABLE 21

Mass Spectrometer Analyte Detection Conditions

| Analyte | Precursor ion (m/z) | Product ion (m/z) | Dwell time (ms) | Typical retention time (min) |
|---|---|---|---|---|
| Metformin | 130 | 60 | 100 | 3.4 |
| SIL-metformin | 136 | 60 | 100 | 3.4 |

Quantification

The peak area ratios of the calibration standards are plotted against theoretical concentration and a regression analysis carried out (Quadratic fit) using the proprietary software Analyst® (Applied Biosystems Ltd. MDS Sciex Ltd). The calibration line is weighted by a factor $1/X2$. Validation sample, Quality Control sample, and study sample concentrations are interpolated from the calibration line.

Example 31

Determination of the Pharmacokinetic Profiles of Different Metformin Compounds after Oral Administration to Female Sprague Dawley Rats and Evaluation of the Effect of Said Compounds on the Glucokinetic Profile after an Oral Glucose Overload Objective The two main objectives of the current study were to determine the pharmacokinetic profiles of different metformin compounds after a single oral administration to female Sprague Dawley rats and to evaluate the effect of said compounds on the glucokinetic profile after an oral glucose overload. A correction factor referred to metformin compound was applied for each test item to make sure that all animals received the same amount of metformin.

In order to achieve them, the study was divided into two parts that were carried out consecutively with the following specific goals Pharmacokinetics of metformin compounds at 250 mg/kg (referred to metformin base): the particular aim was to determine exploratory pharmacokinetic profiles of the different metformin compounds after a single oral administration.

Effect of the metformin compounds on the glucokinetic profile at 750 mg/kg (referred to metformin base): the particular aim was to evaluate the variation of blood glucose levels after an oral blood glucose overload in rats previously administered during five consecutive days with the different metformin compounds by oral route.

Additionally, possible differences in toxicity profile of the metformin compounds given to animals at 750 mg/kg (referred to metformin base) for 5 days were also evaluated in this part of the study.

Metformin hydrochloride was considered as reference item and assayed in parallel in the two parts of the study.

Test System Characterization (Table 22).

TABLE 22

Test system characterization

| | |
|---|---|
| Species: | Rat |
| Strain: | Hsd: Sprague Dawley ®TM SD ®TM |

TABLE 22-continued

Test system characterization

| | |
|---|---|
| Sex: | Female |
| Color: | Albine |
| Health status: | Specific Pathogen Free (SPF) |
| Total number of animals (including reserve): | 130 (110 were used in the study and 20 spare animals) |
| Approx. age of the animals on arrival: | 6 weeks |
| Acclimatization period: | 17 days |

The target parameters of the animal facilities include a light cycle of 12:12, air exchange of >15 changes per hour, pressure gradient with animal holding room positive to corridors, temperature 22±3° C. and relative humidity of 30-70%.

Regarding the animal housing: pharmacokinetic assays with metformin compounds had 6 animals per cage; while in the determination of the effect of the metformin compounds on the glucokinetic profile had 6 or 4 animals per cage depending on the number of animals from each group. On the study day 3, half of the animals from each group were separated into different cages and remained there until sacrifice to separate the animals from round 1 and 2 of the study part for determining the effect of metformin compounds on glucokinetic/toxicity profile. The cage floor area was 1815 cm$^2$ with a cage size of 590×390×200 mm, while the change of cages and bedding was done at least 2 times/week. Enrichment devices (nesting material, tubes and chew blocks) were provided as a default husbandry practice.

The applicable guidelines include the European Directive 2010/63EC from the European Economic Community on the Protection of Animals used for Experimental and other Scientific purposes; the European Directive 2004/10/EC about Good Laboratory Practices; FELASA Guidelines; Humane Endpoints Guidance Document of the OECD (ENV/JM/MONO(2000)7) about the recognition, assessment, and use of clinical signs as humane endpoints for experimental animals used in safety evaluation.

Food and water (tap water) availability was ad libitum.

Test Item Identification

TABLE 23

Test item identification

Test item 1: Dimetformin aspartate

| Batch: | 021-JAT-05 |
|---|---|
| Physicochemical properties: | |
| Physical state: | Powder |
| Purity/Composition | >99.00% |
| Color: | Slightly white |
| Molecular weight: | 391.43 g/mol |
| Correction factor (referred to metformin base): | 1.515 |

Test item 2: Metformin isoleucinate

| Batch: | 021-JAT-024 |
|---|---|
| Physicochemical properties: | |
| Physical state: | Powder |
| Purity: | >99% |
| Color: | Slightly white |
| Molecular weight: | 260.34 g/mol |
| Correction factor (referred to metformin base): | 2.015 |

TABLE 23-continued

Test item identification

Test item 3: Metformin alaninate

| Batch: | 021-JAT-26 |
|---|---|
| Physicochemical properties: | |
| Physical state: | Powder |
| Purity: | >99% |
| Color: | Slightly white |
| Molecular weight: | 218.26 g/mol |
| Correction factor (referred to metformin base): | 1.690 |

Test item 4: Metformin leucinate

| Batch: | 021-JAT-31 |
|---|---|
| Physicochemical properties: | |
| Physical state: | Powder |
| Purity: | >99% |
| Color: | Slightly white |
| Molecular weight: | 260.339 g/mol |
| Correction factor (referred to metformin base): | 2.015 |

Test item 5: Metformin valinate

| Batch: | 021-JAT-27 |
|---|---|
| Physicochemical properties: | |
| Physical state: | Powder |
| Purity: | >99% |
| Color: | Slightly white |
| Molecular weight: | 246.313 g/mol |
| Correction factor (referred to metformin base): | 1.907 |

Test item 6: Metformin lysinate

| Batch: | 021-JAT-29 |
|---|---|
| Physicochemical properties: | |
| Physical state: | Powder |
| Purity: | >99% |
| Color: | Slightly white |
| Molecular weight: | 275.354 g/mol |
| Correction factor (referred to metformin base): | 2.132 |

Test item 7: Metformin asparaginate

| Batch: | 021-JAT-28 |
|---|---|
| Physicochemical properties: | |
| Physical state: | Powder |
| Purity: | >99% |
| Color: | Slightly white |
| Molecular weight: | 261.284 g/mol |
| Correction factor (referred to metformin base): | 2.023 |

Test item 8: Metformin threoninate

| Batch: | 021-JAT-30 |
|---|---|
| Physicochemical properties: | |
| Physical state: | Powder |
| Purity: | >99% |
| Color: | Slightly white |

TABLE 23-continued

Test item identification

| | |
|---|---|
| Molecular weight: | 248.285 g/mol |
| Correction factor (referred to metformin base): | 1.922 |

Reference Item Identification (Table 24)

TABLE 24

Reference item identification
Reference item: Metformin hydrochloride

| | |
|---|---|
| Batch: | 1002002898 |
| Physicochemical properties: | |
| Physical state: | Powder |
| Purity: | 100.05% |
| Color: | White |
| Molecular weight: | 165.6 g/mol |
| Correction factor (referred to metformin base): | 1.282 |

Vehicle Identification
  Clear and transparent ultrapure water.
Additional Reagents and Working Solutions (Table 25)

TABLE 25

Additional reagents and working solutions
Reagent: D-(+)-glucose monohydrate

| | |
|---|---|
| Batch: | SZBA17920V |
| Supplier: | Sigma Aldrich |
| Physicochemical properties: | |
| Physical state: | Solid |
| Appearance: | Powder |
| Color: | White to off white |
| Molecular weight: | 198.17 g/mol |

Experimental Design

In the present study, the pharmacokinetic profiles of different metformin compounds after a single oral administration to female Sprague Dawley rats and the effect of said compounds on the glucokinetic profile after an oral glucose overload were determined. Complementarily, possible differences in toxicity profile of said metformin compounds orally given to the animals for 5 days were also evaluated. The study consisted of two parts designed as Pharmacokinetics of metformin compounds and Effect of the metformin compounds on the glucokinetic/toxicity profile, that were performed in the following manner:

Pharmacokinetics of metformin compounds: nine experimental groups with six animals each were administered orally with the test items consisting in nine metformin compounds at a dose of 250 mg/kg (referred to metformin base). In parallel, Metformin hydrochloride, considered as reference item, was administered to a tenth experimental group in the same way. The animals were single dosed by oral gavage and blood samples were collected in commercial lithium-heparin tubes by sublingual puncture at 0.5, 1, 2, 4, 8, and 24 hours after test or reference item administration. Each animal was bled three times and three animals per time point were used. After plasma separation, the samples were stored at ca.−80° C. until the delivery to the bioanalytical test site for the bioanalysis. PK parameters (Cmax, Tmax and AUC) were evaluated. After the last blood sampling, all animals were sacrificed by $CO_2$ inhalation.

Effect of the metformin compounds on the glucokinetic profile: this part of the study consisted of a total of eleven groups: ten with four animals each treated with the corresponding test item or reference item (metformin hydrochloride), and an additional one with six animals administered in the same manner with the vehicle (ultrapure water). The animals were dosed at 750 mg/kg (referred to metformin compounds) for five times (once a day for five consecutive days) by oral gavage. On the fifth day of treatment and two hours after the last test item/reference item/vehicle administration, the animals received an oral glucose overload (3 g/kg). Thereafter, the blood glucose level was measured and recorded by means of reactive strips and a glucometer at 0.25, 0.5, 1, 2, 3, 4, and 6 hours post-glucose overload. Additionally, clinical signs, body weight and macroscopic observations at necropsy were evaluated as toxicity parameters. Animals were killed by $CO_2$ inhalation and a gross necropsy was performed to them approximately 24 hours after the last test item/reference item/vehicle administration.

Experimental Groups

Only animals that met the inclusion criteria were recruited for the study and distributed into experimental groups according to the body weight stratification method (Table 50).

Inclusion Criteria and Stratification Method
  Inclusion criteria: 20% of the mean body weight
  Stratification method: Animals were randomly distributed by means of the body weight stratification method.
  Schedule: The animal distribution was performed along the week previous to the administration for determining the pharmacokinetic profile of metformin compounds

TABLE 26

Experimental groups. Twenty one animal experimental groups were used in the present study.

| Group | Treatment | Administration route | Dose[a] (mL/kg) | Dose volume (mL/kg) | Animal ID's | Number of animals | Sex |
|---|---|---|---|---|---|---|---|
| A | Vehicle (ultrapure water) | Oral | — | 10 | 1-6 | 6 | Female |
| B | Reference Item (Metformin hydrochloride) | | | | 7-12 | 6 | |

TABLE 26-continued

Experimental groups. Twenty one animal experimental groups were used in the present study.

| Group | Treatment | Administration route | Dose$^a$ (mL/kg) | Dose volume (mL/kg) | Animal ID's | Number of animals | Sex |
|---|---|---|---|---|---|---|---|
| C | Test item 1 (Dimetformin aspartate | | | | 13-18 | 6 | |
| D | Test item 2 (Metformin isoleucinate) | Oral | 250 | 10 | 19-24 | 6 | |
| E | Test item 3 (Metformin alaninate) | | | | 25-30 | 6 | |
| F | Test item (Metformin leucinate) | | | | 31-36 | 6 | |
| G | Test item 5 (Metformin valinate) | | | | 37-42 | 6 | |
| H | Test item 6 (Metformin lysinate) | | | | 43-48 | 6 | |
| I | Test item 7 (metformin asparaginate) | | | | 49-54 | 6 | |
| T | Test item 9 (Metformin threoninate) | | | | 55-60 | 6 | |
| M | Reference Item (Metformin hydrochloride) | Oral | — | 10 | 67-70 | 4 | Female |
| M | Test item 1 (Dimetformin aspartate) | Oral | 750 | 10 | 71-74 | 4 | |
| N | Test item 2 (Metformin isoleucinate) | | | | 75-78 | 4 | |
| O | Test item 3 (Metformin alaninate) | | | | 79-82 | 4 | |
| P | Test item 4 (Metformin leucinate) | | | | 83-86 | 4 | |
| Q | Test item 5 (Metformin valinate) | | | | 87-90 | 4 | |
| R | Test item 6 (Metformin lysinate) | | | | 91-94 | 4 | |
| S | Test item 7 (Metformin asparaginate) | | | | 95-98 | 4 | |
| T | Test item 8 (Metformin threoninate) | | | | 99-102 | 4 | |

$^a$Dose is referred to metformin base

Administration

Test and reference item were administered according to the following parameters.

Test procedure: Test and reference item administration

Route of administration: Oral (gavage)

Doses tested (mg/kg): 250 and 750 (dose is referred to metformin base).

Rationale for dose selection: Doses suggested by the sponsor based on previous studies Dose volume: 10 mL/kg Dose regimen: Pharmacokinetics of metformin compounds: single dose at 250 mg/kg. Effect of metformin compounds on glucokinetic/toxicity profile: five times at 750 mg/kg (once a day for five consecutive days).

Other: Pharmacokinetic of metformin compounds: Animals were weighed prior to administration for dosing purposes. Effect of metformin compounds on glucokinetic/toxicity profile: Animals were weighed prior to the first and fifth administrations for dosing purposes. Additionally, animals were fasted (food but not water was withheld overnight) prior to the fifth administration.

In the study part of Effect of metformin compounds on glucokinetic/toxicity profile, the vehicle was administered in the same manner than the test items, as control.

Formulation of Test and Reference Items

Formulation of reference item 1 and test items 1-9 (Table 51).

Dosage form: liquid

Vehicle: ultrapure water

Formulation procedure: The test items were weighed directly into a volumetric flask and dissolved with the corresponding volume of the vehicle by gently mixing at room temperature.

TABLE 27

Concentration and formulation test items.

| Test Item | Group | Dose[a] (mg/kg) | Formulated TI concentration referred to metformin base (mg/mL) | Correction factor | Dose metformin (mg/kg) | Formulated concentration referred metformin compound (mg/mL) | TI to |
|---|---|---|---|---|---|---|---|
| Reference Item | B | 250 | 25 | 1.282 | 320.5 | 32.05 | |
| (Metformin hydrochloride) | L | 750 | 75 | | 2961.5 | 96.15 | |
| Test item 1 | C | 250 | 25 | 1.515[b] | 378.6 | 37.86 | |
| (Dimetformin aspartate) | M | 750 | 75 | | 1136.3 | 113.63 | |
| Test item 2 | D | 250 | 25 | 2.015 | 503.8 | 50.38 | |
| (Metformin isoleucinate) | N | 750 | 75 | | 1511.25 | 151.125 | |
| Test item 3 | E | 250 | 25 | 1.690 | 422.5 | 42.25 | |
| (Metformin alaninate) | O | 750 | 75 | | 1267.5 | 126.75 | |
| Test item 4 | F | 250 | 25 | 2.015 | 503.8 | 50.38 | |
| (Metformin leucinate) | P | 750 | 75 | | 1511.25 | 151.125 | |
| Test item 5 | G | 250 | 25 | 1.907 | 476.75 | 47.675 | |
| (Metformin valinate) | Q | 750 | 75 | | 1430.3 | 143.03 | |
| Test item 6 | H | 250 | 25 | 2.132 | 533.0 | 53.3 | |
| (Metformin lysinate) | R | 750 | 75 | | 1599.0 | 159.9 | |
| Test item 7 | I | 250 | 25 | 2.023 | 505.75 | 50.575 | |
| (Metformin asparaginate) | S | 750 | 75 | | 1517.3 | 151.73 | |
| Test item 8 | J | 250 | 25 | 1.922 | 480.5 | 48.05 | |
| (Metformin threoninate) | T | 750 | 75 | | 1441.5 | 144.15 | |

Unknown

Dose is referred to metformin base.

Considering two moieties of metformin for each molecule of dimetformin.

TI/RI were not stored after administration, while items were formulated prior to each administration.

Experimental Data

In Life Observation

General Clinical Signs

Animals were observed for clinical signs after being administered and daily thereafter until sacrifice.

Observations included changes in the skin, eyes and mucous membranes. Alterations in respiratory pattern, behavior, posture response to handling and the presence of abnormal movements were also recorded. Animals were checked regularly for any clinical signs, discomfort and mortality according to the Humane Endpoints Guidance Document of the OCDE.

Body Weight

Body weight was recorded along the week before to the test item administration for group distribution, prior to the single administration for pharmacokinetic assays, and previously to the first and fifth administrations of the study part for determining the effect of metformin compounds on glucokinetic/toxicity profile.

Pharmacokinetics of Metformin Compounds

On study day 1, animals from experimental groups B-K were single dosed orally at 250 mg/kg by gavage with the corresponding test item.

Plasma Collection for Pharmaceutical Analysis

Time points for blood extraction were right at 0.5, 1, 2, 4, 8, and 24 hours after oral administration.

At each time point, a volume of 0.5 mL whole blood was extracted from isoflurane anesthetized animals by sublingual puncture and transferred directly to commercial tubes containing lithium-heparin according to the following Table 28.

TABLE 28

Time points after dosing

| Group | Treatment | Animal ID's | Time points (hours) after dosing | | | | | |
|---|---|---|---|---|---|---|---|---|
| | | | 0.5 | 1 | 2 | 4 | 8 | 24 |
| B | Reference Item | 7-9 | | * | | * | | * |
| | (Metformin hydrochloride) | 10-12 | * | | * | | * | |
| C | Test item 1 | 13-15 | | * | | * | | * |
| | (Dimetformin aspartate) | 16-18 | * | | * | | * | |
| D | Test item 2 | 19-21 | | * | | * | | * |
| | (Metformin isoleucinate) | 22-24 | * | | * | | * | |
| E | Test item 3 | 25-27 | | * | | * | | * |
| | (Metformin alaninate) | 28-30 | * | | * | | * | |
| F | Test item 4 | 31-33 | | * | | * | | * |
| | (Metformin leucinate) | 34-36 | * | | * | | * | |
| G | Test item 5 | 37-39 | | * | | * | | * |
| | (Metformin valinate) | 40-42 | * | | * | | * | |
| H | Test item 6 | 43-45 | | * | | * | | * |
| | (Metformin lysinate) | 46-48 | * | | * | | * | |
| I | Test item 7 | 49-51 | | * | | * | | * |
| | (Metformin asparaginate) | 52-54 | * | | * | | * | |

TABLE 28-continued

<table>
<tr><th colspan="9">Time points after dosing</th></tr>
<tr><th>Group</th><th>Treatment</th><th>Animal ID's</th><th colspan="6">Time points (hours) after dosing</th></tr>
<tr><th></th><th></th><th></th><th>0.5</th><th>1</th><th>2</th><th>4</th><th>8</th><th>24</th></tr>
<tr><td>T</td><td>Test item 8 (Metformin threoninate)</td><td>55-57<br>58-60</td><td><br>*</td><td>*<br></td><td><br>*</td><td>*<br></td><td><br>*</td><td>*<br></td></tr>
</table>

Blood sampling = marked boxes (*)

The heparinized blood tubes were placed in ice water or crushed ice until being centrifuged for 10 min at approximately 1.634 g and ca. 4° C.

The plasma obtained after centrifugation was divided into two aliquots and preserved in polypropylene tubes at ca.−80° C. Samples were processed and frozen within the first hour following each extraction.

Pharmacokinetic Evaluation

A graphic representation of the mean metformin plasma level versus time was plotted.

The following pharmacokinetic parameters were obtained:

Maximum concentration ($C_{max}$): the highest observed plasma concentration of the measured concentration-time profile.

Time of maximum concentration ($T_{max}$): the time after administration at which $C_{max}$ occurs.

Additionally, area under the curve (AUC [0-24]) defined as the integration of the metformin base concentration measurements over time were calculated by using WinNonLin software (Professional Version 5.2., Pharsight Corporation).

For every pharmacokinetic parameter calculated, the metformin plasma level prior to administration was considered 0 μg/mL.

Effect of Metformin Compounds on Glucokinetic Profile

Animals from the experimental groups L-U were administered orally by gavage five times (once a day during five consecutive days) with the corresponding test and reference items at a dose of 750 mg/kg/day. Similarly, animals from group A were administered with the same volume of vehicle and served as control. Animals from each group were further separated into two different rounds exposed to identical conditions and readouts, but the experimental part was performed at different study days. The rounds 1 and 2 consisted of half of the animals from each group which were separated into different cages on the study day 3. The administration of animals from rounds 1 and 2 started on study days 4 and 5, respectively. As a consequence, some of the follow up readouts were planned accordingly.

Blood Glucose Level Record

On the fifth day of treatment and two hours after the test item/reference item/vehicle administration, the animals received an oral glucose overload, as follows:

Glucose Overload

Route of administration: Oral (gavage)
Dose (g/kg): 3
Dose volume: 10 mL/kg
Dose regimen: Single (two hours after the last test item/reference item/vehicle administration)
Formulated glucose concentration (mg/mL): 300
Vehicle for formulation: Ultrapure water
Other: Animals were fasted (food but not water was withheld overnight) prior to the fifth administration and, consequently, to the glucose overload.

Prior to glucose overload (approximately 30 min) and 0.25, 0.5, 1, 2, 3, 4, and 6 hours thereafter, blood glucose levels were measured and recorded by means of reactive strips (supplier: Roche; ref: 05987431) and a glucometer (Accu-check Aviva) in a drop of blood collected by tail vein puncture. After the last blood glucose level record, animals had free access to the food.

Terminal Investigation

Animals employed for the pharmacokinetic assays were sacrificed by $CO_2$ overdosing after the 24 hours blood sampling.

Animals allocated to the study part for determining the effect of metformin compounds on glucokinetic/toxicity profile were killed by $CO_2$ inhalation approximately 24 hours after the last test item/reference item/vehicle administration, and a gross necropsy consisting of a macroscopic evaluation of all the external body orifices and the examination of the abdominal, thoracic cavities and contents were performed to them.

Spleens with macroscopic changes from some animals were initially preserved. After judgment that the changes were clearly not treatment related and upon agreement with the sponsor spleens were discarded.

Animals with severe pain or enduring signs of severe distress during the study were killed by $CO_2$ overdosing and a gross necropsy was performed to them as it is indicated above.

Statistical Analysis

As the sample size (n) was too small to perform the normality test, a Kruskal Wallis test (non-parametric) followed by Dunn's multiple comparison test of all groups included in the study part for determining the effect of metformin compounds on glucokinetic/toxicity profile (Groups A, L-U) was performed. A value of $p<0.05$ was considered as statistically significant.

Results

In Life Observations

Mortality and General Clinical Signs

Neither mortality nor clinical signs were observed in the animals from groups B-K used in the pharmacokinetic assay, except for the animal ID45 from group H treated with Metformin lysinate (250 mg/kg referred to metformin base) which presented respiratory noises approximately 30 min after the test item administration.

In the case of the groups employed for determining the effect of metformin compounds on the glucokinetic profiles (Groups A, L-U), the animal ID102 from group T treated with Metformin threoninate (750 mg/kg, referred to metformin base) died during the study just after the fifth test item administration. No anomaly was observed neither during the days prior to its death nor at the macroscopic necropsy. Therefore, it could be attributable to the stress that could involve the administration and handling of the animal.

In addition, the animal ID93 from the group R treated with Metformin lysinate (750 mg/kg, referred to metformin base) had to be humanely killed by $CO_2$ overdose after the last blood glucose record due to the fact that it presented hypothermia, lack of activity and tear excess prior and after the glucose overload on the fifth test item administration day. These clinical signs could be explained by the hypoglycemia that said animal showed throughout the fifth day of the test item administration (blood glucose level with values as low as 16 mg/dl at six hours after the glucose overload).

Minor clinical signs that seem not to be related to the test item treatments such as chromodacryorrhea were observed in the animal ID91 on the fourth and fifth treatment days, in the animals ID93 and 99 on the third administration day and in the animal ID95 on fourth day of treatment. This same clinical sign was presented by the animals ID76, 79, and 80 on the sacrifice day. On the other hand, a wound in the left limb of the animal ID75 and in both sides of the neck from the animal ID99 were observed on the two last days of test item administration. Respiratory noises were also noticed in the animals ID73 and 85 at 30 minutes post-glucose overload.

Body Weight

Body weights of the animals were the expected for this strain and sex, according to provider information (Harlan Laboratories).

In the specific case of groups employed for determining the effect of metformin compounds on glucokinetic/toxicity profile, the body weight from animals treated with the different metformin compounds was similar to the observed in the group A administered with the vehicle (ultrapure water).

Pharmacokinetics of the Different Metformin Compounds
Analyses of Plasma Samples The metformin base concentration obtained in all the study samples from treated animals was over the lower limit of quantification established as 0.05 μg/mL in the analytical phase plan.

In addition to the graphic representation of the plasma levels from the twenty experimental groups involved in this study part vs time, Figures comparing the pharmacokinetic profiles of each metformin compound to the reference item, metformin hydrochloride (group B), and to metformin glycinate (group K), assessed in previous studies, have also been included.

TABLE 29

Body weight (g). Mean ± standard deviation. Groups B-K

| Group | Treatment | Dose (mg/kg)* | On distribution day n | On distribution day Mean ± SD | On administration day n | On administration day Mean ± SD |
|---|---|---|---|---|---|---|
| B | Metformin hydrochloride | 250 | 6 | 186.93 ± 10.39 | 7 | 190.39 ± 9.88 |
| C | Dimetformin aspartate | 250 | 6 | 186.02 ± 5.04 | 6 | 188.42 ± 5.42 |
| D | Metformin isoleucinate | 250 | 6 | 189.10 ± 7.62 | 6 | 197.30 ± 10.62 |
| E | Metformin alaninate | 250 | 6 | 187.52 ± 10.28 | 8 | 202.49 ± 12.79 |
| F | Metformin leucinate | 250 | 6 | 187.38 ± 6.74 | 7 | 195.70 ± 9.85 |
| G | Metformin valinate | 250 | 6 | 186.67 ± 11.37 | 6 | 193.85 ± 7.65 |
| H | Metformin lysinate | 250 | 6 | 184.42 ± 11.94 | 6 | 189.83 ± 11.17 |
| I | Metformin asparaginate | 250 | 6 | 186.85 ± 11.32 | 6 | 191.98 ± 10.26 |
| T | Metformin threoninate | 250 | 6 | 186.22 ± 10.13 | 6 | 193.13 ± 9.66 |

Body weight (g). Mean ± standard deviation. Groups A, L-U

| Group | Treatment | Dose (mg/kg)* | On distribution day n | On distribution day Mean ± SD | On first administration day N | On first administration day Mean ± SD | On first administration day n | On first administration day Mean ± SD |
|---|---|---|---|---|---|---|---|---|
| A | Vehicle | — | 6 | 187.20 ± 10.60 | 6 | 209.07 ± 12.67 | 6 | 201.98 ± 15.20 |
| L | Metformin hydrochloride | 750 | 4 | 189.03 ± 15.13 | 4 | 202.20 ± 18.12 | 4 | 197.78 ± 19.66 |
| M | Dimetformin aspartate | 750 | 4 | 192.05 ± 6.89 | 4 | 207.73 ± 9.57 | 4 | 197.30 ± 10.15 |
| N | Metformin isoleucinate | 750 | 4 | 190.40 ± 7.71 | 4 | 203.33 ± 5.11 | 4 | 196.80 ± 11.54 |
| O | Metformin alaninate | 750 | 4 | 186.18 ± 8.04 | 4 | 200.80 ± 10.15 | 4 | 195.43 ± 11.23 |
| P | Metformin leucinate | 750 | 4 | 185.53 ± 12.04 | 4 | 199.25 ± 9.43 | 4 | 193.53 ± 11.92 |
| Q | Metformin valinate | 750 | 4 | 190.28 ± 6.26 | 4 | 206.48 ± 10.52 | 4 | 194.90 ± 4.71 |
| R | Metformin lysinate | 750 | 4 | 186.73 ± 8.05 | 4 | 203.38 ± 13.38 | 4 | 192.83 ± 9.65 |
| S | Metformin asparaginate | 750 | 4 | 188.40 ± 10.50 | 4 | 201.60 ± 5.61 | 4 | 196.93 ± 10.40 |
| T | Metformin threoninate | 750 | 4 | 188.55 ± 6.35 | 4 | 202.15 ± 5.48 | 4 | 194.20 ± 4.58 |

(a) Dose is referred to metformin base

TABLE 30

Metformin base concentration (µg/mL) in plasma. Mean ± standard deviation

| | | | \multicolumn{6}{c}{Metformin base concentration (µg/mL) at the corresponding bleeding times (hours) post-administration} |
| | | | 0.5 | | 1 | | 2 |
| t | Treatment | Dose (mg/kg)* | n | Mean ± SD | n | Mean ± SD | n |
|---|---|---|---|---|---|---|---|
| B | Metformin hydrochloride | 250 | 3 | 16.33 ± 5.10 | 3 | 14.77 ± 5.07 | 3 |
| C | Dimetformin aspartate | 250 | 3 | 12.43 ± 2.05 | 3 | 15.50 ± 4.49 | 3 |
| D | Metformin isoleucinate | 250 | 3 | 12.53 ± 1.91 | 3 | 14.47 ± 2.58 | 3 |
| E | Metformin alaninate | 250 | 3 | 14.77 ± 3.29 | 3 | 13.00 ± 1.39 | 3 |
| F | Metformin leucinate | 250 | 3 | 10.21 ± 1.77 | 3 | 15.43 ± 0.81 | 3 |
| G | Metformin valinate | 250 | 3 | 8.75 ± 0.50 | 3 | 11.56 ± 2.71 | 3 |
| H | Metformin lysinate | 250 | 3 | 9.39 ± 0.88 | 3 | 9.42 ± 2.78 | 3 |
| I | Metformin asparaginate | 250 | 3 | 10.72 ± 2.33 | 3 | 8.40 ± 1.12 | 3 |
| J | Metformin threoninate | 250 | 3 | 8.81 ± 2.00 | 3 | 14.30 ± 1.70 | 3 |

| | \multicolumn{6}{c}{Metformin base concentration (µg/mL) at the corresponding bleeding times (hours) post-administration} |
| | 2 | | 4 | | 8 | | 24 | |
| t | Mean ± SD | n | Mean ± SD | n | Mean ± SD | n | Mean ± SD |
|---|---|---|---|---|---|---|---|
| B | 11.94 ± 3.24 | 3 | 6.83 ± 1.65 | 3 | 3.14 ± 1.05 | 3 | 0.19 ± 0.10 |
| C | 13.47 ± 3.13 | 3 | 6.05 ± 0.98 | 3 | 6.50 ± 1.57 | 3 | 0.22 ± 0.11 |
| D | 10.05 ± 2.33 | 3 | 21.43 ± 3.35 | 3 | 4.94 ± 0.80 | 3 | 0.24 ± 0.08 |
| E | 14.97 ± 3.57 | 3 | 16.40 ± 5.23 | 3 | 3.56 ± 1.19 | 3 | 0.22 ± 0.08 |
| F | 12.30 ± 2.41 | 3 | 12.57 ± 4.13 | 3 | 5.88 ± 0.80 | 3 | 0.21 ± 0.08 |
| G | 12.90 ± 2.38 | 2 | 13.70 ± 2.55 | 3 | 4.79 ± 0.38 | 3 | 0.21 ± 0.09 |
| H | 10.47 ± 2.09 | 3 | 17.70 ± 8.99 | 2 | 6.32 ± 2.14 | 3 | 0.26 ± 0.07 |
| I | 9.74 ± 1.24 | 3 | 16.27 ± 2.89 | 3 | 7.56 ± 1.49 | 3 | 0.39 ± 0.13 |
| J | 11.53 ± 2.61 | 3 | 11.43 ± 1.66 | 2 | 3.91 ± 0.33 | 3 | 0.23 ± 0.08 |

(a) Dose is referred to metformin base

TABLE 31

Blood glucose level (mg/dL). Mean ± standard deviation

| | | | | \multicolumn{2}{c}{Blood glucose level (mg/dL) at the corresponding bleeding times (hours) post- glucose overload} |
| | | | | Pre-glucose overload | 0.25 |
| Group | Treatment | Dose (mg/kg)* | n | Mean ± SD | Mean ± SD |
|---|---|---|---|---|---|
| A | Vehicle | — | 4 | 97.67 ± 9.99 | 129.50 ± 5.89 |
| L | Metformin hydrochloride | 750 | 4 | 77.00 ± 8.08 | 93.75 ± 15.78 |
| M | Dimetformin aspartate | 750 | 4 | 83.25 ± 14.89 | 96.00 ± 17.15 |
| N | Metformin isoleucinate | 750 | 4 | 60.50* ± 6.14 | 79.50* ± 7.72 |
| O | Metformin alaninate | 750 | 4 | 82.25 ± 7.68 | 90.50 ± 13.72 |
| P | Metformin leucinate | 750 | 4 | 72.25 ± 9.29 | 87.75 ± 31.40 |
| Q | Metformin valinate | 750 | 4 | 90.25 ± 3.86 | 102.50 ± 12.07 |
| R | Metformin lysinate | 750 | 3 | 93.33 ± 22.48 | 108.33 ± 14.57 |
| S | Metformin asparaginate | 750 | 4 | 86.50 ± 14.62 | 94.50 ± 24.31 |
| T | Metformin threoninate | 750 | 3 | 90.33 ± 12.34 | 110.33 ± 16.92 |
| A | Vehicle | — | 4 | 97.67 ± 9.99 | 129.50 ± 5.89 |
| L | Metformin hydrochloride | 750 | 4 | 77.00 ± 8.08 | 93.75 ± 15.78 |
| M | Dimetformin aspartate | 750 | 4 | 83.25 ± 14.89 | 96.00 ± 17.15 |
| N | Metformin isoleucinate | 750 | 4 | 60.50* ± 6.14 | 79.50* ± 7.72 |
| O | Metformin alaninate | 750 | 4 | 82.25 ± 7.68 | 90.50 ± 13.72 |
| P | Metformin leucinate | 750 | 4 | 72.25 ± 9.29 | 87.75 ± 31.40 |
| Q | Metformin valinate | 750 | 4 | 90.25 ± 3.86 | 102.50 ± 12.07 |
| R | Metformin lysinate | 750 | 3 | 93.33 ± 22.48 | 108.33 ± 14.57 |
| S | Metformin asparaginate | 750 | 4 | 86.50 ± 14.62 | 94.50 ± 24.31 |
| T | Metformin threoninate | 750 | 3 | 90.33 ± 12.34 | 110.33 ± 16.92 |

TABLE 31-continued

Blood glucose level (mg/dL). Mean ± standard deviation

| | Group | Blood glucose level (mg/dL) at the corresponding bleeding times (hours) post- glucose overload | | | | | |
|---|---|---|---|---|---|---|---|
| | | 0.5 Mean ± SD | 1 Mean ± SD | 2 Mean ± SD | 3 h Mean ± SD | 4 h Mean ± SD | 6 Mean ± SD |
| | A | 132.50 ± 11.18 | 128.50 ± 6.25 | 91.83 ± 10.15 | 106.17 ± 10.94 | 102.00 ± 6.66 | 98.33 ± 4.84 |
| | L | 89.50 ± 9.98 | 88.25 ± 10.63 | 74.00 ± 10.58 | 85.75 ± 7.37 | 83.75 ± 7.23 | 89.00 ± 11.80 |
| | M | 98.50 ± 13.70 | 103.75 ± 9.29 | 95.25 ± 8.77 | 92.00 ± 6.16 | 92.75 ± 4.11 | 89.75 ± 5.50 |
| | N | 87.75 ± 12.97 | 89.75 ± 19.77 | 76.75 ± 11.44 | 75.75** ± 9.57 | 80.50 ± 7.51 | 70.75 ± 17.04 |
| | O | 94.75 ± 13.52 | 87.00* ± 11.52 | 87.75 ± 9.00 | 82.00* ± 3.74 | 77.75* ± 4.11 | 84.00 ± 7.83 |
| | P | 90.75 ± 28.16 | 99.50 ± 27.50 | 99.00 ± 2.45 | 91.75 ± 6.99 | 89.75 ± 3.69 | 85.25 ± 2.22 |
| | Q | 101.00 ± 14.90 | 100.25 ± 15.44 | 97.00 ± 14.54 | 93.50 ± 18.91 | 86.50 ± 10.15 | 92.75 ± 5.56 |
| | R | 101.00 ± 15.13 | 106.00 ± 15.72 | 94.00 ± 19.47 | 84.67 ± 7.09 | 89.00 ± 5.29 | 98.33 ± 9.07 |
| | S | 93.75 ± 19.14 | 88.00* ± 11.17 | 80.00 ± 10.68 | 86.50 ± 2.65 | 87.00 ± 8.60 | 78.50 ± 16.03 |
| | T | 102.67 ± 8.02 | 101.67 ± 11.85 | 93.67 ± 10.69 | 91.67 ± 6.03 | 87.67 ± 2.08 | 89.33 ± 3.06 |
| | A | 132.50 ± 11.18 | 128.50 ± 6.25 | 91.83 ± 10.15 | 106.17 ± 10.94 | 102.00 ± 6.66 | 98.33 ± 4.84 |
| | L | 89.50 ± 9.98 | 88.25 ± 10.63 | 74.00 ± 10.58 | 85.75 ± 7.37 | 83.75 ± 7.23 | 89.00 ± 11.80 |
| | M | 98.50 ± 13.70 | 103.75 ± 9.29 | 95.25 ± 8.77 | 92.00 ± 6.16 | 92.75 ± 4.11 | 89.75 ± 5.50 |
| | N | 87.75 ± 12.97 | 89.75 ± 19.77 | 76.75 ± 11.44 | 75.75** ± 9.57 | 80.50 ± 7.51 | 70.75 ± 17.04 |
| | O | 94.75 ± 13.52 | 87.00* ± 11.52 | 87.75 ± 9.00 | 82.00* ± 3.74 | 77.75* ± 4.11 | 84.00 ± 7.83 |
| | P | 90.75 ± 28.16 | 99.50 ± 27.50 | 99.00 ± 2.45 | 91.75 ± 6.99 | 89.75 ± 3.69 | 85.25 ± 2.22 |
| | Q | 101.00 ± 14.90 | 100.25 ± 15.44 | 97.00 ± 14.54 | 93.50 ± 18.91 | 86.50 ± 10.15 | 92.75 ± 5.56 |
| | R | 101.00 ± 15.13 | 106.00 ± 15.72 | 94.00 ± 19.47 | 84.67 ± 7.09 | 89.00 ± 5.29 | 98.33 ± 9.07 |
| | S | 93.75 ± 19.14 | 88.00* ± 11.17 | 80.00 ± 10.68 | 86.50 ± 2.65 | 87.00 ± 8.60 | 78.50 ± 16.03 |
| | T | 102.67 ± 8.02 | 101.67 ± 11.85 | 93.67 ± 10.69 | 91.67 ± 6.03 | 87.67 ± 2.08 | 89.33 ± 3.06 |

(a) Dose is referred to metformin base
*p < 0.05 vs group A, Kruskal-Wallis + Dunn's multiple comparison test
**p < 0.01 vs group A, Kruskal-Wallis + Dunn's multiple comparison test Pharmacokinetic Parameters The pharmacokinetic parameters calculated with the obtained metformin base concentrations in plasma are detailed in the following Table 32:

TABLE 32

Pharmacokinetic parameters

| Group | Treatment | Dose (mg/kg)a | $C_{max}$ (µg/mL) | $T_{max}$ (h) | AUC(0-24) (µg*h/mL) |
|---|---|---|---|---|---|
| B | Metformin hydrochloride | 250 | 16.33 | 0.5 | 90.56 |
| C | Dimetformin aspartate | 250 | 15.50 | 1 | 122.96 |
| D | Metformin isoleucinate | 250 | 21.43 | 4 | 148.77 |
| E | Metformin alaninate | 250 | 16.40 | 4 | 126.09 |
| F | Metformin leucinate | 250 | 15.43 | 1 | 133.32 |
| G | Metformin valinate | 250 | 13.70 | 4 | 123.05 |
| H | Metformin lysinate | 250 | 17.70 | 4 | 145.85 |
| I | Metformin asparaginate | 250 | 16.27 | 4 | 153.76 |
| J | Metformin threoninate | 250 | 14.30 | 1 | 107.62 |
| | | 250 | | | | aDose is referred to metformin base

As the above Table 32 details, the Cmax ranged between 13.7 and 21.43 µg/mL corresponding to the groups G and D (treated with metformin valinate and isoleucinate, respectively). This pharmacokinetic parameter was similar in the tested metformin compounds when compared to the reference item, metformin hydrochloride.

Regarding the $T_{max}$, two groups of metformin compounds could be established: one group with a faster absorption ($T_{max}$ between 0.5 and 1 hour) including metformin hydrochloride (the fastest), dimetformin aspartate, metformin leucinate and metformin threoninate, and a second group encompassing the rest of metformin compounds tested (metformin isoleucinate, alaninate, valinate, lysinate, asparaginate and glycinate) which exhibited a $T_{max}$ of 4 hours.

Likewise, and considering the bioavailability, two groups of metformin compounds could be also defined: one group with a lower $AUC_{(0-24)}$ (ranging between 82.03 and 125.80 µg*h/mL) including dimetformin aspartate, metformin hydrochloride, alaninate, leucinate, valinate and threoninate, and a second group showing a higher bioavailability (with $AUC_{(0-24)}$ values between 139.00 and 164.10 µg*h/mL) and encompassing metformin isoleucinate, lysinate, asparaginate and glycinate. However, and regardless the groups distinguished above, the reference item, the metformin compound of hydrochloride, exhibited the lowest ($AUC_{(0-24)}$ 82.03 µg*h/mL) when compared to rest of metformin compounds tested in the current study.

Effect of Different Metformin Compounds on Glucokinetic/Toxicity Profiles

FIGS. 127-135. Table 31.

In general, blood glucose levels from the animals treated orally during five consecutive days with all the metformin compounds tested were lower than the measured in the animals receiving vehicle, ultrapure water, before the oral glucose overload. Nevertheless, said decrease in blood glucose levels was only statistically significant (p<0.05, Dunn's test) in the case of metformin isoleucinate.

After the oral glucose overload, blood glucose levels in the animals from all the groups treated with the metformin compounds were also lower than the ones found in the control animals administered vehicle, with isolated statistically significant decreases respect to control being found in some groups at different time points after glucose administration: Metformin isoleucinate at the time points of 0.25 (p<0.05, Dunn's test) and 3 hours (p<0.01, Dunn's test), metformin alaninate at 1, 3 and 4 hours (p<0.05, Dunn's test), and metformin asparaginate at the time point of 1 hours (p<0.05, Dunn's test).

The profiles of the curves obtained with the different compounds, including the metformin hydrochloride, were very similar, and statistically significant differences between the reference item and the remaining metformin compounds among the various time points have not been found.

One hour after glucose overload, the blood glucose levels decreased in most of the experimental groups until achieving the values found before it, approximately, at 6 hours after the glucose overload. In terms of toxicity of the metformin compounds, no adverse effect was observed in the animals from groups treated for five days with a metformin base dose of 750 mg/kg. Only the animal ID93 from the group administered with metformin lysinate had to be sacrificed for humane reasons as it presented severe hypoglycemia (blood glucose level with values as low as 16 mg/dl at six hours after the glucose overload) throughout the fifth administration day as well as hypothermia, lack of activity, and tear excess.

Terminal Investigation
Necropsy Findings

No findings were observed during the macroscopic necropsy of the animals from groups A and L-U. Only the spleen of the animals ID80 and 89 belonging to the groups O (treated with metformin alaninate) and Q (treated with metformin valinate) presented a small additional lobe. These findings are considered incidental and not related to the test item administration.

Conclusions and Discussion

Taking together the data obtained in the current study, it can be concluded that under the assay experimental conditions:

Concerning the maximum concentration of metformin base measured in plasma ($C_{max}$), no relevant differences were observed among the metformin compounds after a single dose of 250 mg/kg (referred to metformin base). However, according to the time when $C_{max}$ occurs ($T_{max}$), two groups of metformin compounds could be distinguished: those that were absorbed faster and included the reference item, metformin hydrochloride ($T_{max}$=0.5 hour), dimetformin aspartate, metformin leucinate and threoninate $T_{max}$=1 hour), and those absorbed more slowly comprising metformin isoleucinate, valinate, alaninate, lysinate, and asparaginate ($T_{max}$=4 hours).

According to the bioavailability, two groups could be also established: a first one encompassing the metformin compounds of isoleucinate, lysinate, and asparaginate with a higher bioavailability that almost duplicated the one found in the reference item, metformin hydrochloride, which is included in the second group, together with dimetformin aspartate and metformin alaninate, leucinate, valinate and threoninate, as they showed a lower bioavailability. However, and regardless of the groups distinguished above, the reference item, metformin hydrochloride, exhibited the lowest $AUC_{(0-24)}$ 82.03 µg*h/mL) when compared to rest of metformin compounds tested in the current study.

The metformin compounds at a dose of 750 mg/kg (referred to metformin base) and administered for five days decreased the blood glucose level when compared to the vehicle, ultrapure water.

The metformin compounds at a dose of 750 mg/kg (referred to metformin base) and administered for five days tended to prevent the blood glucose level increase induced by the oral glucose overload.

Regarding the effect of metformin compounds on the glucokinetic profile, only metformin isoleucinate and metformin alaninate showed a statistically significant decrease of blood glucose levels at different times after the five test item administrations (750 mg/kg referred to metformin base) and oral glucose overload on the fifth day of treatment when compared to the vehicle (ultrapure water). The blood glucose level also tended to be lower in animals treated with the remaining metformin compounds after the glucose overload, but not significant differences were observed.

Similar effect on glucokinetic profiles was shown by the reference item, metformin hydrochloride, and the rest of compounds, as non-significant differences were observed after the five test item administrations (750 mg/kg referred to metformin base) and oral glucose overload on the fifth day of treatment.

The metformin compounds at a dose of 750 mg/kg (referred to Metformin base) and administered for five days did not produce any adverse effects during the study period.

Example 32

Evaluation of the Efficacy of Different Compounds of Metformin to Modulate Glycemia in a Rat Model of Streptozotocin-Induced Diabetes after Daily Oral Administration for 14 Consecutive Days Objective The objective of the present study was to determine the efficacy of different compounds of metformin administered at the same dose calculated as base, to modulate glycemia a rat model of streptozotocin-induced diabetes, when administered daily by oral route over a period of 14 consecutive days. The efficacy of a compound of diphenformin to modulate glycemia was also determined when administered using the same dosing regimen.

Test System and Conditions (Table 33)

TABLE 33

| Test system and conditions | |
|---|---|
| Species: | Rat |
| Strain: | Sprague Dawley |
| Sex: | Male |
| Color: | Albino |
| Health status: | Specific Pathogen Free (SPF) |
| Rationale for selection of species/strain: | Rat is a common model for diabetes research due to its good response to streptozotocin (Lenzen S; The mechanism of alloxan and streptozotocin-induced diabetes; Diabetologia, 2008, 51: 216-26) |
| Total number of animals (including reserve): | 46 (39 used in the study) |
| Approx. age of the animals on arrival: | 6 weeks |
| Acclimatization period: | 13 days |

The target parameters of animal facilities include a light cycle of 12:12, air exchange of ≥changes per hour, pressure gradient with animal holding room positive to corridors, temperature 22±3° C., and relative humidity of 30-70%. Regarding the animal housing, 3 animals per cage were kept in a cage floor area of 800 cm² of 18 cm height, while the change of cages and bedding was done daily based on the increased urination produced by the diabetic condition of the animal. Enrichment devices (nesting material, tubes and chew blocks) were provided as a default husbandry practice. Hydrogel™ G-400 polymer was administered to all rats included in the study on day of study 6 to prevent diabetes-induced dehydration.

The applicable guidelines include the European Directive 2010/63EC from the European Economic Community on the Protection of Animals used for Experimental and other scientific purposes; the European Directive 2004/10/EC about Good Laboratory Practices; FELASA Guidelines; Humane Endpoints Guidance Document of the OECD (ENV/JM/MONO(2000)7) about the recognition, assessment, and use of clinical signs as humane endpoints for experimental animals used in safety evaluation; and Evaluation of safety of veterinary vaccines, European Pharmacopoeia.

Food and water (tap water) availability was ad libitum.
Test Item Identification (Table 34)

TABLE 34

Test item identification

Test item 1: Dimetformin aspartate

| | |
|---|---|
| Batch: | 021-JAT-05 |
| Physicochemical properties: | |
| Physical state: | Powder |
| Purity/Composition | >99.00% |
| Color: | Slightly white |
| Molecular weight: | 391.43 g/mol |
| Correction factor (referred to metformin base): | 1.515 |

Test item 2: Metformin isoleucinate

| | |
|---|---|
| Batch: | 021-JAT-024 |
| Physicochemical properties: | |
| Physical state: | Powder |
| Purity: | >99% |
| Color: | Slightly white |
| Molecular weight: | 260.34 g/mol |
| Correction factor (referred to metformin base): | 2.015 |

Test item 3: Metformin alaninate

| | |
|---|---|
| Batch: | 021-JAT-26 |
| Physicochemical properties: | |
| Physical state: | Powder |
| Purity: | >99% |
| Color: | Slightly white |
| Molecular weight: | 218.26 g/mol |
| Correction factor (referred to metformin base): | 1.690 |

Test item 4: Metformin leucinate

| | |
|---|---|
| Batch: | 021-JAT-31 |
| Physicochemical properties | |
| Physical state: | Powder |
| Purity: | >99% |
| Color: | Slightly white |
| Molecular weight: | 260.339 g/mol |
| Correction factor (referred to metformin base): | 2.015 |

Test item 5: Metformin valinate

| | |
|---|---|
| Batch: | 021-JAT-27 |
| Physicochemical properties: | |
| Physical state: | Powder |
| Purity: | >99% |

TABLE 34-continued

Test item identification

| | |
|---|---|
| Color: | Slightly white |
| Molecular weight: | 246.313 g/mol |
| Correction factor (referred to metformin base): | 1.907 |

Test item 6: Metformin lysinate

| | |
|---|---|
| Batch: | 021-JAT-29 |
| Physicochemical properties: | |
| Physical state: | Powder |
| Purity: | >99% |
| Color: | Slightly white |
| Molecular weight: | 275.354 g/mol |
| Correction factor (referred to metformin base): | 2.132 |

Test item 7: Metformin asparaginate

| | |
|---|---|
| Batch: | 021-JAT-28 |
| Physicochemical properties: | |
| Physical state: | Powder |
| Purity: | >99% |
| Color: | Slightly white |
| Molecular weight: | 261.284 g/mol |
| Correction factor (referred to Metformin base): | 2.023 |

Test item 8: Metformin threoninate

| | |
|---|---|
| Batch: | 021-JAT-30 |
| Physicochemical properties: | |
| Physical state: | Powder |
| Purity: | >99% |
| Color: | Slightly white |
| Molecular weight: | 248.285 g/mol |
| Correction factor (referred to metformin base): | 1.922 |

Test item 10: Diphenformin aspartate

| | |
|---|---|
| Batch: | 021-JAT-54 |
| Supplier: | |
| Physicochemical properties: | |
| Physical state: | Powder |
| Purity: | >99% |
| Color: | White |
| Molecular weight: | 543.629 g/mol |

Reference and Reagent Item Identification (Table 35)

TABLE 35

Reference item identification

Reference item: Metformin hydrochloride

| | |
|---|---|
| Batch: | 1002002898 |
| Physicochemical properties: | |
| Physical state: | Powder |
| Purity: | 100.05% |
| Color: | White |
| Molecular weight: | 165.6 g/mol |
| Correction factor (referred to metformin base): | 1.282 |

Reagent: Streptozotocin

| | |
|---|---|
| Batch: | 031M1287V |
| Supplier: | SIGMA ALDRICH |

TABLE 35-continued

| Reference item identification | |
|---|---|
| Physicochemical properties: | |
| Physical state: | Powder |
| Appearance: | ≥98% |
| Color: | Off White |
| Handling and storage conditions: | At −20 ± 3° C. Handle with care due to toxicity. |
| Reagent: Hydrogel ™ | |
| Batch: | G-400 |
| Supplier: | HARLAN |
| Physicochemical properties: | |
| Physical state: | Powder |
| Color: | Brown |
| Storage conditions: | Room temperature |

Reagent Grade Deionized Water (MiliQ) was Used as Vehicle.

Storage conditions of the test and reference items, as the vehicle, were at room temperature in a closed container and protected from light.

Experimental Design

On day −3, 43 animals (36 to be used in the study and γ extra) were intravenously administered with streptozotocin (STZ, 60 mg/kg) to induce diabetes. Control animals (3) were intravenously administered with vehicle. Approximately 24 hours following diabetes induction (day −2), blood glucose levels were determined; animals were considered diabetic if glucose levels were above 250 mg/dl. On the same day, animals fulfilling the diabetic condition and with an acceptable health status were assigned to one of twelve groups (B to M) by means of the weight stratification method. Control animals were assigned to group A. Each experimental group had a total number of 3 animals before Test item/Reference item (TI/RI) administration.

TI/RI administration regimen started approximately 72 hours after diabetes induction (day 1) and was performed at the same hour of the day throughout the entire study. During the administration regimen animals from groups A to M were administered once daily with either vehicle (groups A and B), reference item (metformin hydrochloride, group C), one of nine different metformin compounds (groups D to L), or a diphenformin compound (group M) through oral route by gavage. Reference item and metformin compounds were administered at the same dose referred as base (250 mg/kg). A correction factor referred to metformin compound was applied for each test item to make sure that all animals received the same amount of metformin. Diphenformin aspartate was administered at a dose of 9.42 mg/kg referred as base.

Blood glucose levels were measured before STZ administration (day −3), 24, and 48 hours after induction of diabetes (day −2 and day −1) and then twice daily until the end of the study, once approximately 1 hour before dosing and again approximately 2 hours after administration of TI/RI. Blood glucose levels were determined using reactive strips and a glucometer, after tail-vein puncture. Approximately 24 hours after last administration (day 15), overnight-fasted animals were sacrificed by $CO_2$ overdose. Before sacrifice, animals were anaesthetized with isoflurane and blood from all animals was collected in lithium heparin tubes through the retro-orbital sinus puncture procedure. Plasma was extracted and triglycerides, total cholesterol and glucose levels were determined. Additionally, a gross necropsy was performed in all animals. Organs showing gross abnormalities were collected and preserved in 4% formaldehyde.

Experimental Groups

Only animals that met the inclusion criteria were recruited for the study and distributed into experimental groups according to the body weight stratification method.

Inclusion Criteria and Stratification Method

Inclusion criteria: Diabetic animals: blood glucose levels above 250 mg/dl on day −2; Acceptable health status.

Stratification method: Animals were randomly distributed by means of the body weight stratification method on day −2.

Thirteen groups of 3 male rats each were used in the present study. Groups and treatments are stated in the following Table 36:

TABLE 36

Groups and treatments of the study

| Group | STZ (mg/kg, IV) | TI/RI | Metformin dose (mg/kg/day calculated as base, p.o.) | Animal ID |
|---|---|---|---|---|
| A | — | Vehicle | | 1-3 |
| B | 60 | Vehicle | | 4-6 |
| C | 60 | Metformin hydrochloride | 250 | 7-9 |
| D | 60 | Dimetformin aspartate | 250 | 10-12 |
| E | 60 | Metformin isoleucinate | 250 | 13-15 |
| F | 60 | Metformin alaninate | 250 | 16-18 |
| G | 60 | Metformin leucinate | 250 | 19-21 |
| H | 60 | Metformin valinate | 250 | 22-24 |
| I | 60 | Metformin lysinate | 250 | 25-27 |
| J | 60 | Metformin asparaginate | 250 | 28-30 |
| K | 60 | Metformin threoninate | 250 | 31-33 |
| M | 60 | Diphenformin aspartate | 9.42 | 37-39 |

Administration

Streptozotocin was administered according to the following parameters:

Test procedure: Streptozotocin diabetes-induced model

Route of administration: Intravenous, on the lateral tail vein

Dose: 60 mg/kg

Rationale for dose selection: This dose has been demonstrated to induce diabetes in approximately 24 hours in Sprague Dawley rats (Lenzen S; The mechanism of alloxan and streptozotocin-induced diabetes; Diabetologia, 2008, 51:216-26)

Dose volume: 2 mL/kg

Dose regimen: Single, on day −3 of the study

The test items were administered according to the following parameters:

Test procedure: test item administration

Route of administration: Oral (gavage)

Dose volume: 10 mL/kg

Duration: 14 days. Animals were dosed until the day prior to terminal sacrifice

Procedure: The dose volume was adjusted according to the last body weight recorded Dose regimen: Daily over a period of 14 consecutive days Doses tested metformin compounds, groups C-L: 250 mg/kg, referred as metformin base Rationale for dose selection: Dose suggested by sponsor according to previous experiments.

Diphenformin aspartate, group M: 9.42 mg/kg, referred as diphenformin base

Rationale for dose selection: Dose suggested by sponsor considering equivalence of efficacy between metformin hydrochloride and diphenformin base.

The reference item was administered according to the following parameters:

Test procedure: reference item administration (metformin hydrochloride)
Route of administration: Oral (gavage)
Doses tested. 250 mg/kg
Rationale for dose selection: Dose suggested by sponsor according to previous experiments.
Dose volume: 10 mL/kg Formulated item storage conditions: No storage when formulated
Frequency of formulation: Prior to each administration
Test and Reference Item Formulation
Dosage form: Liquid
Vehicle: Reagent grade deionized water (MiliQ)
Formulation procedure: The test item was weighed directly into a volumetric flask by means of a funnel and dissolved with the corresponding volume of the vehicle by gently moving at room temperature. The test item amount to weigh was calculated using the appropriate base to compound correction factor as shown below (Table 38):

TABLE 38

Concentration and formulation test items

| Group | TI/RI | Dose referred to base (mg/kg/day) | Correction factor | Dose referred to compound (mg/kg/day) | Administration volume (mL/kg) | Formulated TI/RI concentration (mg/mL) |
|---|---|---|---|---|---|---|
| A | Vehicle | — | — | — | — | — |
| B | Vehicle | — | — | — | — | — |
| C | Metformin hydrochloride | 250 | 1.282 | 302.5 | 10 | 30.25 |
| D | Dimetformin aspartate | 250 | 1.515* | 378.7 | 10 | 37.87 |
| E | Metformin isoleucinate | 250 | 2.016 | 504.0 | 10 | 50.40 |
| F | Metformin alaninate | 250 | 1.690 | 422.5 | 10 | 42.25 |
| G | Metformin leucinate | 250 | 2.016 | 504.0 | 10 | 50.40 |
| H | Metformin valinate | 250 | 1.907 | 476.7 | 10 | 47.67 |
| I | Metformin lysinate | 250 | 2.132 | 533.0 | 10 | 53.30 |
| J | Metformin asparaginate | 250 | 2.023 | 505.7 | 10 | 50.57 |
| K | Metformin threoninate | 250 | 1.922 | 480.5 | 10 | 48.05 |
| M | Diphenformin aspartate | 9.42 | 2.104 | 198.2 | 10 | 19.82 |

*Considering two moieties of metformin base by each molecule of Dimetformin aspartate.

Duration: 14 days. Animals were dosed until the day prior to terminal sacrifice

Procedure: The dose volume was adjusted according to the last body weight recorded Dose regimen: Daily over a period of 14 days Formulation of Streptozotocin and Test Item (Table 61)

Streptozotocin formulation

Dosage form: Liquid

Vehicle: Water for injection

Formulation procedure: Sterile vials containing streptozotocin were transferred to the animal room and reconstituted in water for injection to the appropriate concentration.

TABLE 37

Concentration and doses for each group

| Group | Dose (mg/kg) | Formulated STZ concentration (mg/mL) |
|---|---|---|
| A | — | — |
| B | 60 | 30 |
| C | 60 | 30 |
| D | 60 | 30 |
| E | 60 | 30 |
| F | 60 | 30 |
| G | 60 | 30 |
| H | 60 | 30 |
| I | 60 | 30 |
| J | 60 | 30 |
| K | 60 | 30 |
| M | 60 | 30 |

Stability of formulation: Formulated STZ was administered within three minutes following formulation.

Stability of Formulation

Test and reference items were prepared fresh daily.

Formulated item storage conditions: Test and reference item were not stored after administration. Frequency of formulation: Test and reference item were formulated daily.

Experimental Data

In-Life Observations

Mortality and General Clinical Signs

Animals were observed once a day. Observations included changes in skin, eyes and mucous membranes. Alterations in respiratory pattern, behavior, posture, response to handling and the presence of abnormal movements were also recorded. Animals were checked regularly for any clinical signs, discomfort and mortality according to the OCDE Humane Endpoints Guidance Document.

Body Weight

Body weight was recorded prior to induction of diabetes (day −3), at the time of group distribution (day −2), one day prior to administration (day −1), the first day of administration of TI/RI (day 1) and twice weekly thereafter until sacrifice.

Blood Glucose Determination

Blood glucose was determined using a drop of blood collected from tail vein puncture that was directly placed on a reactive strip inserted into a glucometer (ACCU-Check AVIVA, Roche). Blood glucose was determined before STZ administration (day −3), approximately 24 and 48 hours after diabetes induction (day −2 and −1), and twice daily thereafter until the end of the study period, once approximately 1 hour before administration of TI/RI and again approximately 2 hours after administration. Blood glucose measurements were performed at the same time of the day.

Clinical Pathology
Blood Collection for Clinical Biochemistry Analysis

Animals were fasted overnight and anaesthetized with isoflurane. 1-mL blood samples were obtained before sacrifice and approximately 18 hours after last TI administration by retro-orbital sinus puncture procedure. Blood was collected in 1 mL tubes containing lithium heparin as an anticoagulant.

Following each blood collection, samples were gently mixed and placed on ice until processing. Tubes containing heparinized blood were centrifuged at approximately 1000 g for 10 minutes at 5° C.±3. Plasma samples were analyzed immediately after collection by means of a biochemistry analyzer (Cobas, INTEGRA 400 plus). Biochemistry analysis included plasma triglycerides, total cholesterol and glucose levels determination in all animals.

Terminal Investigation

At the end of day 14 of the study, after last glucose measurement all animals were fasted overnight and were sacrificed by $CO_2$ overdose on day 15. Immediately thereafter, a gross necropsy was performed. Organs showing gross abnormalities were collected and preserved in 4% formaldehyde.

Additional Methods

To prevent diabetes-induced dehydration, free access to G-400 Hydrogel™ was allowed to all animals at day 6 of study, when severe dehydration signs such as presence of cutaneous fold, were first observed.

Statistical Analysis

The following comparisons were made using One-Way ANOVA followed by a Dunnet's test, considering a value of $P<0.05$ as statistically significant.

Blood Glucose Levels

Blood glucose levels, especially before TI/RI administration, were beyond the upper limit of detection (ULOD) of the glucometer and no quantitative values were obtained. As a consequence the following statistical comparisons were not performed:
  Basal blood glucose levels (i.e. before administration of TI/RI) vs basal blood glucose levels from diabetic control group (B).
  Basal blood glucose levels vs basal blood glucose levels from diabetic animals treated with RI (group C).
  Blood glucose levels differential (i.e. blood glucose level after administration subtracted from blood glucose level before administration) vs blood glucose levels differential from diabetic control group (B).
  Blood glucose levels differential vs blood glucose levels differential from diabetic animals treated with RI (group C).

On the other hand, when upper glucometer detection limit allowed quantitative values, the following statistical comparisons were made (in the case the experimental group contained one value beyond the glucometer limit, this value was excluded from mean and SD calculation):
  Blood glucose levels after administration vs blood glucose levels from diabetic control group (B).
  Blood glucose levels after administration vs blood glucose levels from diabetic animals treated with RI (group C).

Body Weight, Plasma Triglycerides, Total Cholesterol and Glucose Levels

Experimental groups were compared vs diabetic control group (group B) and vs diabetic animals treated with RI (group C).

Results
In-Life Observations
Mortality

Animal ID 23 (group H, diabetic animals treated with metformin valinate) was found dead on the day 9 of study and it was not possible to obtain any blood for biochemistry analysis. A gross necropsy was carried out at the time of finding. An air-filled cavity with black spots inside was found in the stomach at the level of pylorus. No macroscopic alteration was found in trachea and esophagus. Pancreas and spleen were collected as a reduction in normal size was noted. Stomach was collected as well. The cause of death could not be precisely determined.

Animal ID 5 (group B, diabetic animals treated with vehicle) and animal ID 38 (group M, diabetic animals treated with diphenformin aspartate) were sacrificed for humane reasons (weight loss above 20%) on days 10 and 14 of study respectively. Blood was collected before sacrifice and plasma was frozen at −80° C. until the analysis. A significant reduction in spleen size was observed in animal ID 5 and this organ was collected as well. Biochemistry parameters revealed no remarkable results. The cause of death could not be precisely determined.

Clinical Signs and Observations

No clinical signs were observed in the control group, with the exception of chromodacryorrhea in one animal and noisy breath in another animal. These clinical signs were observed just once during the study and are considered incidental. By contrast, chromodacryorrhea, hunched posture, unkept hair, skin fold, and noisy breath were consistently observed among diabetic animals at different days throughout the study. These clinical signs occur normally in diabetic animals and were also observed in diabetic animals treated with vehicle, thus no relation to the test item can be attributed. Other clinical signs observed during the study with lower incidence include apparent thinness, piloerection, palpebral ptosis, crooked tail and prostration. These clinical signs were randomly distributed among all diabetic groups (including diabetic animals treated with vehicle) and were not attributed to the administration of the TI/RT.

Finally, the presence of red tail, swollen tail or a scab on tail were only observed in diabetic animals and are attributed to the repetitive blood collection by tail puncture and the impaired wound healing capacity typical of diabetic animals. Betadine was administered topically twice a day to these rats to prevent infections.

Body Weight

FIG. 136, Tables 39-40

There was an evident decrease on body weight in diabetic animals compared to normoglycemic animals. Weight loss is a very well reported effect on streptozotocin-induced diabetes in Sprague-Dawley rats (Akbarzadeh et al., 2007). Nevertheless, this trend to a weight loss in diabetic animals did not reach statistical significance in the present study, probably due to the low number of animals in the experimental groups. A significant effect of TI/RI on body weight was not observed in the present study.

Blood Glucose Levels

FIG. 137, Table 41 (blood glucose levels before first TI/RI administration), Tables 66-68 (blood glucose levels 1 hour before TI/RI administration), Tables 69-71 (blood glucose levels 2 hours after TI/RI administration).

The streptozotocin-induced diabetes rat model results in very high blood glucose levels; therefore, glucose levels in this study, especially before TI/RI administration were frequently beyond the upper limit of detection (ULOD) of the glucometer (600 mg/dl). As a consequence, blood glucose levels values before and after TI/RI administration, as well as blood glucose levels differential values (i.e. blood glucose levels after TI/RI administration−blood glucose levels before TI/RI administration) could not be precisely determined in some animals. Mean and SD calculations as well as statistic comparisons were only carried out in experimental groups that contained at least 2 quantifiable values.

There was a significant increase in blood glucose levels 24 hours following streptozotocin administration in all diabetes-induced animals (FIG. 137, Table 41, $p<0.01$ groups B-M vs group A). Blood glucose levels in the control group were around 109 mg/dl whereas blood glucose levels in diabetic groups were above 400 mg/dl on day −2 (24 hours following diabetes induction). On day −1 (48 hours following diabetes induction) blood glucose levels of the diabetic animals had risen above 550 and exceeded in some groups the glucometer detection limit (600 mg/dl) while in control animals remained around 106 mg/dl.

Blood glucose levels 1 hour before each daily TI/RI administration were beyond the ULOD of the glucometer (600 mg/dl) in all diabetic animals (group B to group M) throughout the study with few occasional exceptions. No clear difference was observed when diabetic animals treated with any of the compounds of metformin tested (group D to L) were compared to diabetic animals treated with vehicle (group B) or to diabetic animals treated with the RI metformin hydrochloride (group C) as glucose levels were almost always above the ULOD. By contrast, normoglycemic animals treated with vehicle (group A) were always under the detection limit of the glucometer and within expected normal range (99-124 mg/dl) throughout the study.

Similarly, blood glucose levels 2 hours after each daily TI/RI administration were notably lower in normoglycemic animals treated with vehicle (group A) compared to diabetic animals treated with vehicle (group B) or diabetic animals treated with the RI metformin hydrochloride (group C). In addition, a reduction of blood glucose levels was observed in diabetic animals 2 hours after the administration of the RI, of any of the compounds of metformin (group C to L) or diphenformin aspartate (group M) when compared to diabetic animals treated with vehicle (group B).

Statistical comparisons between experimental groups were not possible as blood glucose levels in diabetic animals treated with vehicle (group B) were beyond the ULOD and only in day 2 at least two values within range could be obtained. On day 2, normoglycemic animals (group A) and diabetic animals treated with metformin alaninate (group F) and diabetic animals treated with metformin valinate (group H) presented significantly lower blood glucose levels when compared to diabetic animals treated with vehicle (group B). In addition, only blood glucose levels from normoglycemic animals (group A) were significantly lower than blood glucose levels after 2 hours of TI/R administration from diabetic animals treated with the RI metformin hydrochloride (group C).

Blood glucose levels differential values (i.e. blood glucose levels after TI/RI administration−blood glucose levels before TI/RI administration) could only be calculated in normoglycemic animals. In the rest of experimental groups (B to M) quantification of blood glucose differential could not be obtained since at least one blood glucose level (i.e. before or after TI/RI administration) was beyond the ULOD.

Overall, all metformin compounds evaluated in this study showed pharmacological activity on hyperglycemic animals, reducing qualitatively blood glucose levels after treatment.

Clinical Pathology

Biochemistry

No significant differences on plasma glucose levels at the time of sacrifice (approximately 18 hours after last TI administration) were found when diabetic animals treated with any of the metformin compounds (groups D-K) or diphenformin aspartate (group M) were compared to diabetic animals treated with vehicle (group B) or to diabetic animals treated with the RI metformin hydrochloride (group C). Plasma glucose levels were significantly higher ($p<0.05$, Dunnet test) in diabetic animals treated with metformin valinate (group H), metformin asparaginate (group J) when compared to normoglycemic animals treated with vehicle (group A).

Normoglycemic animals treated with vehicle (group A) showed plasma cholesterol levels significantly higher than diabetic animals treated with vehicle (group B) ($p<0.01$, Dunnett test). No other significant differences were found when plasma cholesterol levels from animals treated with any of the Tis were compared to diabetic animals treated with vehicle (group B). Similarly, no statistical differences were found when plasma cholesterol levels from animals belonging to groups A, B and to groups D-K were compared to diabetic animals with RI metformin hydrochloride (group C).

No significant differences on plasma triglycerides levels at the time of sacrifice were found when diabetic animals treated with any of the compounds of metformin (groups C to K) or with diabetic animals treated with diphenformin aspartate (group M) were compared to diabetic animals treated with vehicle (group B) or to diabetic animals treated with the RI metformin hydrochloride (group C).

Necropsy Finings

No macroscopic abnormalities were observed during necropsy in normoglycemic animals treated with vehicle (group A). The main abnormalities that were found in the present study at the time of necropsy were the following:

Thymus atrophy:
    ID 4 and 6 from group B (diabetic animals treated with vehicle)
    ID 7 from group C (diabetic animals treated with metformin hydrochloride)
    ID 31 from group K (diabetic animals treated with metformin threoninate)
    ID 39 from group M (diabetic animals treated with diphenformin aspartate)

Seminal vesicles atrophy
    ID 6 from group B (diabetic animals treated with vehicle)
    ID 19 from group G (diabetic animals treated with metformin leucinate)

Pancreas atrophy
    ID 23 from group H (diabetic animals treated with metformin valinate)

Spleen atrophy
    ID 23 from group H (diabetic animals treated with metformin valinate)
    ID 39 from group M (diabetic animals treated with diphenformin aspartate)

Kidney hypertrophy
    ID 23 from group H (diabetic animals treated with metformin valinate)
    ID 39 from group M (diabetic animals treated with diphenformin aspartate)

Kidney hypertrophy
    ID 30 from group J (diabetic animals treated with metformin asparaginate
    ID 33 from group K (diabetic animals treated with metformin threoninate)

All of these are all well-documented alterations found in diabetes and are not attributed to the TI/RI.

The present study was aimed towards evaluating the efficacy of different compounds of metformin and a compound of diphenformin to regulate glycemia. For this purpose a model of diabetes induced by streptozotocin was used. One of the disadvantages of using a STZ-induced model of diabetes is that glucose levels are sometimes above the detection limit of the glucometer and blood glucose levels as well as differences among experimental groups could not be determined quantitatively. However, the nature of this study, where two blood samples per day needed to be obtained in diabetic animals during 14 days, pointed out the use of glucometer as the best option to measure blood glucose levels. Blood sampling using other methods (such as obtaining 0.5 mL per sampling by sublingual or retro-orbital puncture and quantification of blood glucose levels by means of a biochemistry analyzer) were not followed to prevent animal deaths due to excessive blood sampling throughout the study. Nevertheless, the information obtained from this study is considered valid taking into account the prospective nature thereof, where 10 different compounds of metformin and one compound of diphenformin were explored on their capacity on modulation of glycemia, although the diabetes model used in this study does not allow determining accurately the magnitude of such modulation. The results presented here will allow to select a few of them and test their glycemic regulatory properties in future studies.

Taking together the data obtained in the present study it can be concluded that:

Diabetic condition was successfully reached taking into account the levels of blood glucose achieved after streptozotocin administration. In addition, all the diabetic animals showed a progressive weight loss during the first days after diabetes induction. Body weight from diabetic animals was clearly lower than normoglycemic rats throughout the study. No effect of TI/RI on body weight was observed throughout the study.

The clinical signs and necropsy findings observed were related to the model of diabetes itself and none could be attributed to the test/reference items.

Blood glucose levels before daily TI/RI administration were similar in all diabetic animals (near or above 600 mg/dL) and significantly higher to normoglycemic animals (around 110 mg/dL). A reduction on blood glucose levels in diabetic rats was observed at all days of study 2 hours after administration of the reference item, metformin hydrochloride, any of the compounds of metformin and diphenformin aspartate. This reduction was transient as blood glucose levels returned above 600 mg/dL the following day throughout the entire study.

No statistical differences were found on plasma glucose levels and plasma triglycerides levels among the experimental groups at the end of the study. On the other hand, plasma cholesterol levels were found to be significantly higher in normoglycemic animals treated with vehicle when they were compared to diabetic animals treated with vehicle.

No clear difference was observed between animals treated with any of the metformin compounds or the compound of diphenformin and animals treated with the reference item, metformin hydrochloride, on blood glucose levels (before or after TI/RI), body weight and biochemistry parameters.

TABLE 39

Absolute body weight (g). Mean ± standard deviation

| Group | TI/RI | N | Day −3 (before STZ administration) | Day −2 (distribution of groups) | Day −1 | Day −2 |
|---|---|---|---|---|---|---|
| A | vehicle + vehicle | 3 | 224.90 ± 4.29 | 227.40 ± 4.06 | 229.17 ± 3.98 | 232.33 ± 4.13 |
| B | STZ + vehicle | 3 | 238.00 ± 7.28 | 223.87 ± 9.77 | 212.77 ± 8.54 | 210.53 ± 7.94 |
| C | STZ + Metformin hydrochloride | 3 | 231.30 ± 11.83 | 223.73 ± 10.88 | 210.43 ± 11.90 | 208.27 ± 9.80 |
| D | STZ + Dimetformin aspartate | 3 | 228.17 ± 10.17 | 219.53 ± 13.36 | 205.23 ± 6.83 | 206.33 ± 7.31 |
| E | STZ + Metformin isoleucinate | 3 | 224.63 ± 9.17 | 225.17 ± 10.85 | 211.30 ± 7.51 | 212.57 ± 11.04 |
| F | STZ + Metformin alaninate | 3 | 232.07 ± 6.17 | 219.20 ± 4.18 | 208.00 ± 2.65 | 210.60 ± 4.30 |
| G | STZ + Metformin leucinate | 3 | 234.57 ± 1.87 | 221.90 ± 6.16 | 207.93 ± 0.99 | 210.00 ± 3.82 |
| H | STZ + Metformin valinate | 3 | 233.50 ± 9.71 | 217.43 ± 14.43 | 213.90 ± 16.31 | 211.10 ± 12.78 |
| I | STZ + Metformin lysinate | 3 | 229.63 ± 1.92 | 217.67 ± 9.71 | 212.73 ± 0.23 | 208.33 ± 8.24 |
| J | STZ + Metformin asparaginate | 3 | 233.47 ± 15.23 | 214.13 ± 12.67 | 209.73 ± 12.66 | 211.33 ± 16.23 |
| K | STZ + Metformin threoninate | 3 | 231.13 ± 10.20 | 216.43 ± 8.74 | 207.33 ± 8.52 | 204.53 ± 8.39 |
| M | STZ + Diphenformin aspartate | 3 | 219.17 ± 19.71 | 212.77 ± 8.22 | 207.03 ± 1.61 | 210.00 ± 1.57 |

TABLE 40

Absolute body weight (g). Mean ± standard deviation (cont.)

| Group | TI/RI | N | Day 5 | Day 8 | Day 12 | Day 15 (day of sacrifice)* |
|---|---|---|---|---|---|---|
| A | vehicle + vehicle | 3 | 240.90 ± 1.47 | 253.23 ± 4.11 | 264.30 ± 9.15 | 260.20 ± 8.25 |
| B | STZ + vehicle | 3¥ | 210.73 ± 10.42 | 203.63 ± 10.21 | 202.90 ± 22.91 | 177.95 ± 29.06 |
| C | STZ + Metformin hydrochloride | 3 | 206.87 ± 10.77 | 209.70 ± 14.73 | 209.80 ± 16.21 | 183.27 ± 21.56 |
| D | STZ + Dimetformin aspartate | 3 | 202.10 ± 21.97 | 199.77 ± 29.45 | 204.17 ± 30.21 | 183.23 ± 24.13 |
| E | STZ + Metformin isoleucinate | 3 | 221.47 ± 17.53 | 222.63 ± 30.37 | 228.77 ± 24.82 | 209.10 ± 35.62 |
| F | STZ + Metformin alaninate | 3 | 218.60 ± 10.18 | 224.17 ± 11.76 | 233.67 ± 8.96 | 207.50 ± 6.01 |
| G | STZ + Metformin leucinate | 3 | 216.67 ± 14.23 | 214.00 ± 25.03 | 224.80 ± 30.85 | 197.67 ± 28.40 |
| H | STZ + Metformin valinate | 3¥ | 219.23 ± 14.36 | 212.23 ± 31.37 | 228.85 ± 8.41 | 206.30 ± 7.21 |

TABLE 40-continued

Absolute body weight (g). Mean ± standard deviation (cont.)

| Group | TI/RI | N | Day 5 | Day 8 | Day 12 | Day 15 (day of sacrifice)* |
|---|---|---|---|---|---|---|
| I | STZ + Metformin lysinate | 3 | 217.60 ± 10.44 | 217.50 ± 15.60 | 216.87 ± 27.95 | 196.53 ± 24.71 |
| J | STZ + Metformin asparaginate | 3 | 223.57 ± 12.27 | 232.13 ± 15.00 | 230.77 ± 22.08 | 210.57 ± 20.20 |
| K | STZ + Metformin threoninate | 3 | 213.60 ± 5.97 | 208.90 ± 18.00 | 204.80 ± 24.77 | 197.83 ± 20.26 |
| M | STZ + Diphenformin aspartate | 3¥ | 223.57 ± 3.04 | 220.53 ± 10.23 | 213.73 ± 32.71 | 183.90 ± 11.74 |

*Overnight fasted animals
¥n = 3 in all days of study points except day 12 and day 15 (n = 2)
(£): n = 3 in all days of study points except day 15 (n = 2)

TABLE 41

Blood glucose levels before TI/RI administration (mg/dL). Mean ± SD

| Group | TI/RI | N | Day −3 (before STZ administration) | Day −2 (distribution of groups) | Day −1 |
|---|---|---|---|---|---|
| A | vehicle + vehicle | 3 | 117.67 ± 10.69 | 109.67 ± 5.51 | 106.67 ± 6.81 |
| B | STZ + vehicle | 3 | 121.00 ± 1.00 | 556.67** ± 30.66 | n.d. ± n.d. |
| C | STZ + Metformin hydrochloride | 3 | 120.00 ± 8.72 | 514.00** ± 38.74 | 525.00€ ± 32.53€ |
| D | STZ + Dimetformin aspartate | 3 | 120.00 ± 2.65 | 546.33** ± 46.70 | 572.00§ ± n.d.§ |
| E | STZ + Metformin isoleucinate | 3 | 115.33 ± 4.93 | 531.00** ± 63.66 | n.d. ± n.d. |
| L | STZ + Metformin alaninate | 3 | 121.33 ± 6.51 | 485.33** ± 38.68 | 577.00€ ± 26.87€ |
| G | STZ + Metformin leucinate | 3 | 118.33 ± 10.02 | 498.00** ± 87.43 | 563.00 ± 36.39 |
| H | STZ + Metformin valinate | 3 | 120.00 ± 1.73 | 449.33** ± 22.19 | 592.00§ ± n.d.§ |
| I | STZ + Metformin lysinate | 3 | 114.00 ± 6.93 | 460.33** ± 25.17 | 577.00§ ± n.d.§ |
| J | STZ + Metformin asparaginate | 3 | 116.33 ± 5.51 | 515.67** ± 73.55 | 573.00§ ± n.d.§ |
| K | STZ + Metformin threoninate | 3 | 117.33 ± 14.05 | 442.33** ± 18.77 | n.d. ± n.d. |
| M | STZ + Diphenformin aspartate | 3 | 115.33 ± 10.02 | 483.33** ± 74.81 | n.d. ± n.d. |

(n.d) Mean and SD not calculated because all values were beyond ULOD of the glucometer (600 mg/dl).
§n = 1. SD is not calculated in these groups and is shown in tables as n.d.
€n = 2
**p < 0.01 vs group A, Dunnet

TABLE 42

Blood glucose levels 1 hour before TI/RI administration (mg/dL). Mean ± standard deviation

| Group | TI/RI | N | Day 1 | Day 2 | Day 3 | Day 4 |
|---|---|---|---|---|---|---|
| A | vehicle + vehicle | 3 | 115.00 ± 7.81 | 109.67 ± 1.53 | 105.33 ± 3.21 | 104.67 ± 1.53 |
| B | STZ + vehicle | 3 | n.d. ± n.d. | 591.00§ ± n.d.§ | 588.00€ ± 2.83€ | n.d. ± n.d. |
| C | STZ + Metformin hydrochloride | 3 | n.d. ± n.d. | n.d. ± n.d. | n.d. ± n.d. | n.d. ± n.d. |
| D | STZ + Dimetformin aspartate | 3 | n.d. ± n.d. | n.d. ± n.d. | n.d. ± n.d. | 560.50€ ± 47.38€ |
| E | STZ + Metformin isoleucinate | 3 | n.d. ± n.d. | n.d. ± n.d. | 576.00§ ± n.d.§ | n.d. ± n.d. |
| F | STZ + Metformin alaninate | 3 | n.d. ± n.d. | 597.00§ ± n.d.§ | n.d. ± n.d. | 592.00§ ± n.d.§ |
| G | STZ + Metformin leucinate | 3 | 596.00§ ± n.d. | n.d. ± n.d. | 593.00§ ± n.d.§ | n.d. ± n.d. |
| H | STZ + Metformin valinate | 3 | n.d. ± n.d. | n.d. ± n.d. | n.d. ± n.d. | n.d. ± n.d. |
| I | STZ + Metformin lysinate | 3 | 583.00§ ± n.d. | 599.00§ ± n.d.§ | n.d. ± n.d. | n.d. ± n.d. |
| J | STZ + Metformin asparaginate | 3 | n.d. ± n.d. | n.d. ± n.d. | n.d. ± n.d. | n.d. ± n.d. |
| K | STZ + Metformin threoninate | 3 | n.d. ± n.d. | n.d. ± n.d. | 573.00§ ± n.d.§ | n.d. ± n.d. |
| M | STZ + Diphenformin aspartate | 3 | n.d. ± n.d. | 563.00§ ± n.d.§ | n.d. ± n.d. | n.d. ± n.d. |

(n.d) Mean and SD not calculated because all values were beyond ULOD of the glucometer (600 mg/dl).
§n = 1. SD is not calculated in these groups and is also shown in tables as n.d.
€n = 2

TABLE 43

Blood glucose levels 1 hour before TI/RI administration (mg/dL). Mean ± standard deviation (cont. I)

| Group | TI/RI | N | Day 5 | Day 6 | Day 7 | Day 8 | Day 9 |
|---|---|---|---|---|---|---|---|
| A | vehicle + vehicle | 3 | 111.00 ± 3.61 | 112.□7 ± 10.02 | 103.67 ± 2.52 | 115.00 ± 3.00 | 109.67 ± 1.15 |
| B | STZ + vehicle | 2 | n.d. ± n.d. | n.d. ± n.d. | n.d. ± n.d. | 517.00§ ± n.d.§ | 574.00§ ± n.d.§ |
| C | STZ + Metformin hydrochloride | 3 | n.d. ± n.d. | n.d. ± n.d. | n.d. ± n.d. | n.d. ± n.d. | n.d. ± n.d. |
| D | STZ + Dimetformin aspartate | 3 | 506.50€ ± 51.62€ | n□d. ± n.d. | 592.00§ ± n.d.§ | n.d. ± n.d. | n.d. ± n.d. |
| E | STZ + Metformin isoleucinate | 3 | n.d. ± n.d. | n.d. ± n.d. | n.d. ± n.d. | n.d. ± n.d. | n.d. ± n.d. |
| F | STZ + Metformin alaninate | 3 | 588.50€ ± 4.95€ | n.d. ± n.d. | 584.00 ± 0.00 | n.d. ± n.d. | 543.00§ ± n.d.§ |
| G | STZ + Metformin leucinate | 3 | n.d. ± n.d. | n.d. ± n.d. | n.d. ± n.d. | n.d. ± n.d. | n.d. ± n.d. |
| H | STZ + Metformin valinate | 2 | n.d. ± n.d. | n.d. ± n.d. | 560.00§ ± n.d.§ | 488.00§ ± n.d.§ | n.d. ± n.d. |
| I | STZ + Metformin lysinate | 3 | n.d. ± n.d. | n.d. ± n.d. | n.d. ± n.d. | n.d. ± n.d. | n.d. ± n.d. |
| J | STZ + Metformin asparaginate | 3 | n.d. ± n.d. | n.d. ± n.d. | n.d. ± n.d. | n.d. ± n.d. | n.d. ± n.d. |
| K | STZ + Metformin threoninate | 3 | n.d. ± n.d. | 589.00§ ± n.d.§ | 582.00§ ± n.d.§ | 456.00§ ± n.d.§ | n.d. ± n.d. |
| M | STZ + Diphenformin aspartate | 3¥ | n.d. ± n.d. | n.d. ± n.d. | 589.00§ ± n.d.§ | n.d. ± n.d. | n.d. ± n.d. |

(n.d) Mean and SD not calculated because all values were beyond ULOD of the glucometer (600 mg/dL).
§n = 1, SD is not calculated in these groups and is also shown in tables as n.d.,
€n = 2
¥n = 3 in all study days except day 9 (n = 2)

TABLE 44

Blood glucose levels 1 hour before TI/RI administration (mg/dL). Mean ± standard deviation (cont. II)

| Group | TI/RI | N | Day 10 | Day 11 | Day 12 | Day 13 | Day 14 |
|---|---|---|---|---|---|---|---|
| A | vehicle + vehicle | 3 | 111.67 ± 1.53 | 111.00 ± 2.65 | 102.67 ± 3.51 | 105.67 ± 3.06 | 109.00 ± 4.58 |
| B | STZ + vehicle | 2 | n.d. ± n.d. | n.d. ± n.d. | n.d. ± n.d. | n.d. ± n.d. | n.d. ± n.d. |
| C | STZ + Metformin hydrochloride | 3 | 579.00§ ± n.d.§ | 547.00§ ± n.d.§ | n.d. ± n.d. | n.d. ± n.d. | n.d. ± n.d. |
| D | STZ + Dimetformin aspartate | 3 | n.d. ± n.d. | 364.00§ ± n.d.§ | 365.00§ ± n.d.§ | n.d. ± n.d. | n.d. ± n.d. |
| E | STZ + Metformin isoleucinate | 3 | n.d. ± n.d. | n.d. ± n.d. | n.d. ± n.d. | n.d. ± n.d. | n.d. ± n.d. |
| F | STZ + Metformin alaninate | 3 | n.d. ± n.d. | n.d. ± n.d. | n.d. ± n.d. | n.d. ± n.d. | 572.00§ ± n.d.§ |
| G | STZ + Metformin leucinate | 3 | n.d. ± n.d. | n.d. ± n.d. | n.d. ± n.d. | 580.00§ ± n.d.§ | 502.00§ ± n.d.§ |
| H | STZ + Metformin valinate | 2 | n.d. ± n.d. | n.d. ± n.d. | n.d. ± n.d. | n.d. ± n.d. | n.d. ± n.d. |
| I | STZ + Metformin lysinate | 3 | n.d. ± n.d. | n.d. ± n.d. | n.d. ± n.d. | 582.00§ ± n.d.§ | n.d. ± n.d. |
| J | STZ + Metformin asparaginate | 3 | n.d. ± n.d. | n.d. ± n.d. | 576.00§ ± n.d.§ | n.d. ± n.d. | 573.00§ ± n.d.§ |
| K | STZ + Metformin threoninate | 3 | n.d. ± n.d. | n.d. ± n.d. | 592.00§ ± n.d.§ | n.d. ± n.d. | n.d. ± n.d. |
| M | STZ + Diphenformin aspartate | 3¥ | n.d. ± n.d. | n.d. ± n.d. | n.d. ± n.d. | n.d. ± n.d. | 490.00§ ± n.d.§ |

(n.d) Mean and SD not calculated because all values were beyond ULOD of the glucometer (600 mg/dl).
§n = 1. SD is not calculated in these groups and is also shown in tables as n.d.
¥n = 3 in all study days except day 14 (n = 2)

TABLE 45

Blood glucose levels 2 hours after daily TI/RI administration (mg/dl). Mean ± standard deviation

| Group | TI/RI | N | Day 1 | Day 2 | Day 3 | Day 4 | Day 5 |
|---|---|---|---|---|---|---|---|
| A | vehicle + vehicle | 3 | 110.33 ± 13.80 | 104.00**,†† ± 3.00 | 110.33 ± 10.50 | 105.33 ± 5.03 | 106.33 ± 11.06 |
| B | STZ + vehicle | 3 | n.d. ± n.d. | 550.00$^ɛ$ ± 11.31$^ɛ$ | n.d. ± n.d. | n.d. ± n.d. | n.d. ± n.d. |
| C | STZ + Metformin hydrochloride | 3 | 496.00$^ɛ$ ± 43.84 | 468.33 ± 30.55 | 541.00 ± 50.71 | 445.00$^ɛ$ ± 130.11$^ɛ$ | 357.00§ ± n.d. |
| D | STZ + Dimetformin aspartate | 3 | 561.00§ ± n.d.§ | 505.00 ± 28.16 | 472.00§ ± n.d.§ | 496.00$^ɛ$ ± 31.11$^ɛ$ | 429.00 ± 97.41 |
| E | STZ + Metformin isoleucinate | 3 | 509.00 ± 45.08 | 467.67 ± 85.99 | 445.00 ± 48.08 | 424.00 ± 12.29 | 513.50$^ɛ$ ± 13.44$^ɛ$ |
| F | STZ + Metformin alaninate | 3 | 515.33 ± 68.82 | 407.67** ± 12.86 | 451.33 ± 108.65 | 463.67 ± 57.01 | 457.33 ± 85.68 |
| G | STZ + Metformin leucinate | 3 | 524.00§ ± n.d.§ | 461.00$^ɛ$ ± 14.14$^ɛ$ | 476.50$^ɛ$ ±36.06$^ɛ$ | 492.50$^ɛ$ ± 16.26$^ɛ$ | 482.00$^ɛ$ ± 28.28$^ɛ$ |
| H | STZ + Metformin valinate | 3 | 526.67 ± 26.03 | 447.33* ± 9.29 | 479.33 ± 41.86 | 464.67 ± 18.23 | 498.33 ± 46.36 |
| I | STZ + Metformin lysinate | 3 | 520.33 ± 56.98 | 498.50$^ɛ$ ± 72.83$^ɛ$ | 485.33 ± 22.55 | 504.67 ± 35.53 | 506.00$^ɛ$ ± 36.77$^ɛ$ |
| J | STZ + Metformin asparaginate | 3 | 571.50$^ɛ$ ± 31.82$^ɛ$ | 495.00 ± 17.69 | 530.50$^ɛ$ ± 41.72$^ɛ$ | 532.33 ± 64.47 | 519.67 ± 67.00 |
| K | STZ + Metformin threoninate | 3 | 468.67 ± 23.59 | 475.33 ± 55.01 | 476.00 ± 40.04 | 477.00 ± 32.05 | 462.00 ± 16.64 |
| M | STZ + Diphenformin aspartate | 3 | 550.33 ± 7.37 | 495.00$^ɛ$ ± 41.01$^ɛ$ | 524.50$^ɛ$ ± 27.58$^ɛ$ | 529.00 ± 48.66 | 571.00§ ± n.d.§ |

(n.d) Mean and SD not calculated because all values were beyond ULOD of the glucometer (600 mg/dl).
§n = 1. SD is not calculated in these groups and is also shown in tables as n.d.,
$^ɛ$n = 2
*p < 0.05 vs group B, Dunnett's test,
**p < 0.01 vs group B, Dunnett's test
†p < 0.01 vs group C, Dunnett's test

TABLE 46

Blood glucose levels 2 hours after daily TI/RI administration (mg/dl). Mean ± standard deviation (cont. I)

| Group | TI/RI | N | Day 6 | Day 7 | Day 8 | Day 9 | Day 10 |
|---|---|---|---|---|---|---|---|
| A | vehicle + vehicle | 3 | 104.67 ± 4.73 | 102.00 ± 4.58 | 107.33 ± 2.52 | 105.00 ± 5.20 | 110.00 ± 5.00 |
| B | STZ + vehicle | 3¥ | n.d. ± n.d. | n.d. ± n.d. | n.d. ± n.d. | n.d. ± n.d. | n.d. ± n.d. |
| C | STZ + Metformin hydrochloride | 3 | 500.67 ± 73.36 | 498.50$^ɛ$ ± 38.69$^ɛ$ | n.d. ± n.d. | 543.00§ ± n.d.§ | 564.00$^ɛ$ ± 49.50$^ɛ$ |
| D | STZ + Dimetformin aspartate | 3 | 538.00§ ± n.d.§ | 469.00$^ɛ$ ± 172.53$^ɛ$ | 492.00§ ± n.d.§ | 432.00§ ± n.d.§ | 443.00$^ɛ$ ± 117.38$^ɛ$ |
| E | STZ + Metformin isoleucinate | 3 | 540.33 ± 42.71 | 508.50$^ɛ$ ± 71.42$^ɛ$ | 537.00§ ± n.d.§ | 500.00$^ɛ$ ± 90.51$^ɛ$ | 508.33 ± 73.42 |
| F | STZ + Metformin alaninate | 3 | 539.00$^ɛ$ ± 29.70$^ɛ$ | 406.67 ± 74.10 | 541.00 ± 47.13 | 466.00 ± 33.18 | 503.00$^ɛ$ ± 32.53$^ɛ$ |
| G | STZ + Metformin leucinate | 3 | 471.00§ ± n.d.§ | 434.00 ± 14.14 | 580.00§ ± n.d.§ | 513.50$^ɛ$ ± 27.58$^ɛ$ | 491.00$^ɛ$ ± 32.53$^ɛ$ |
| H | STZ + Metformin valinate | 3† | 591.50$^ɛ$ ± 10.61$^ɛ$ | 559.00§ ± n.d.§ | 331.00§ ± n.d.§ | 568.00 ± 45.25 | n.d. ± n.d. |
| I | STZ + Metformin lysinate | 3 | 464.50$^ɛ$ ± 72.83$^ɛ$ | 472.33 ± 52.25 | 546.50$^ɛ$ ± 48.79$^ɛ$ | 562.67 ± 24.91 | 413.50$^ɛ$ ± 106.77$^ɛ$ |
| J | STZ + Metformin asparaginate | 3 | 535.50$^ɛ$ ± 6.36$^ɛ$ | 526.33 ± 50.84 | 454.00§ ± n.d.§ | 559.00 ± 17.06 | 504.00 ± 63.38 |
| K | STZ + Metformin threoninate | 3 | 528.67 ± 72.45 | 544.00 ± n.d.§ | 519.50$^ɛ$ ± 3.54$^ɛ$ | 481.33 ± 142.42 | 594.00§ ± n.d.§ |
| M | STZ + Diphenformin aspartate | 3 | 534.00§ ± n.d.§ | 481.00 ± 0.00 | 573.00§ ± n.d.§ | n.d. ± n.d. | 542.00$^ɛ$ ± 35.36$^ɛ$ |

¥n = 3 in all study days except day 10 (n = 2),
†n = 3 in all study days except day 9 and day 10 (n = 2)
(n.d) Mean and SD not calculated because all values were beyond ULOD of the glucometer (600 mg/dL).
§n = 1. SD is not calculated in these groups and is also shown in tables as n.d.
$^ɛ$n = 2

TABLE 47

Blood glucose levels 2 hours after daily TI/RI administration (mg/dl). Mean ± standard deviation (cont. II)

| Group | TI/RI | N | Day 11 | Day 12 | Day 13 | Day 14 |
|---|---|---|---|---|---|---|
| A | vehicle + vehicle | 3 | 116.33 ± 9.07 | 97.67 ± 8.74 | 107.33 ± 11.85 | 113.33 ± 4.93 |
| B | STZ + vehicle | 2 | n.d. ± n.d. | n.d. ± n.d. | n.d. ± n.d. | n.d. ± n.d. |
| C | STZ + Metformin hydrochloride | 3 | 491.00$^ε$ ± 11.31$^ε$ | 531.00 ± 26.89 | 528.50$^ε$ ± 50.20$^ε$ | 503.00$^ε$ ± 46.67$^ε$ |
| D | STZ + Dimetformin aspartate | 3 | 570.00$^ε$ ± 16.97$^ε$ | 519.00 ± 80.54 | 554.33 ± 51.59 | 532.67 ± 45.57 |
| E | STZ + Metformin isoleucinate | 3 | 474.33 ± 66.56 | 480.00 ± 65.05 | 491.50$^ε$ ± 64.35$^ε$ | 467.00 ± 41.33 |
| F | STZ + Metformin alaninate | 3 | 518.00$^ε$ ± 62.23$^ε$ | 516.50$^ε$ ± 23.33$^ε$ | 513.33 ± 23.09 | 455.67 ± 33.38 |
| G | STZ + Metformin leucinate | 3 | 446.00 ± n.d.§ | 459.50$^ε$ ± 24.75$^ε$ | 446.00 ± 1.41 | 485.50 ± 69.76 |
| H | STZ + Metformin valinate | 2 | n.d. ± n.d. | 575.00 ± 8.49 | 577.00§ ± n.d.§ | n.d. ± n.d. |
| I | STZ + Metformin lysinate | 3 | 566.50$^ε$ ±41.72$^ε$ | 454.00$^ε$ ± 24.04$^ε$ | 541.00 ± 13.11 | 480.00 ± 73.75 |
| J | STZ + Metformin asparaginate | 3 | 552.33 ± 36.23 | 521.00 ± 45.31 | 491.67 ± 40.27 | 535.00 ± 2.83 |
| K | STZ + Metformin threoninate | 3 | 516.00 ± n.d.§ | 468.00$^ε$ ± 77.78$^ε$ | 562.00 ± 26.96 | 424.00§ ± n.d.§ |
| M | STZ + Diphenformin aspartate | 3¥ | 549.50$^ε$ ± 50.20$^ε$ | 562.00§ ± n.d.§ | 531.50$^ε$ ± 30.41$^ε$ | 433.50 ± 2.12 |

¥n = 3 in all study days except day 10 (n = 2),
(n.d) Mean and SD not calculated because all values were beyond ULOD of the glucometer (600 mg/dl).
§n = 1. SD is not calculated in these groups and is shown in tables as n.d.
$^ε$n = 2

TABLE 48

Clinical pathology: Plasma clinical biochemistry parameters

| | | | Plasma clinical biochemistry parameters | | |
|---|---|---|---|---|---|
| Group | TI/RI | N | Cholesterol (mmol/L) | Glucose (mg/dL) | Triglycerides (mmol/L) |
| A | vehicle + vehicle | 3 | 2.43** ± 0.41 | 94.55 ± 3.15 | 0.58 ± 0.21 |
| B | STZ + vehicle | 2 | 1.49 ± 0.28 | 417.27 ± 88.71 | 0.41 ± 0.02 |
| C | STZ + Metformin hydrochloride | 3 | 1.75 ± 0.53 | 279.39 ± 202.07 | 0.42 ± 0.17 |
| D | STZ + Dimetformin aspartate | 3 | 1.68 ± 0.28 | 329.09 ± 233.21 | 1.10 ± 0.68 |
| E | STZ + Metformin isoleucinate | 3 | 1.60 ± 0.12 | 278.79 ± 217.77 | 1.15 ± 0.57 |
| F | STZ + Metformin alaninate | 3 | 1.62 ± 0.22 | 206.06 ± 65.08 | 0.77 ± 0.29 |
| G | STZ + Metformin leucinate | 3 | 1.49 ± 0.28 | 109.70 ± 26.12 | 0.58 ± 0.04 |
| H | STZ + Metformin valinate | 2 | 1.79 ± 0.06 | 467.27 ± 90.00 | 1.19 ± 0.19 |
| I | STZ + Metformin lysinate | 3 | 1.50 ± 0.27 | 302.42 ± 78.00 | 1.00 ± 0.45 |
| J | STZ + Metformin asparaginate | 3 | 1.86 ± 0.36 | 471.52 ± 61.29 | 1.08 ± 0.28 |
| K | STZ + Metformin threoninate | 3 | 1.90 ± 0.17 | 335.15 ± 201.73 | 1.00 ± 0.50 |
| M | STZ + Diphenformin aspartate | 2 | 1.99 ± 0.23 | 220.00 ± 280.27 | 0.52 ± 0.18 |

**p < 0.01 vs group B, Dunnett test

TABLE 49

Incidence of necropsy findings (animals with findings/total number of animals)

| | A | B | C | D | E | F |
|---|---|---|---|---|---|---|
| Macroscopic Finding | Vehicle + Vehicle | STZ + vehicle | STZ + Metformin hydrochloride | STZ Dimetformin aspartate | STZ + Metformin Isoleucinate | STZ + Metformin alaninate |
| Thymus reduced size | — | 2/3 | 1/3 | — | — | — |
| Red-colored adrenal glands | — | — | 2/3 | — | — | — |
| Red-colored yeyunum and duodenum | — | 1/3 | — | — | — | — |
| Seminal vesicles reduced size | — | 1/3 | — | — | — | — |
| Prostate reduced size | — | — | — | — | — | — |
| Kidney hypertrophy | — | — | — | — | — | — |
| Pancreas reduced size | — | — | — | — | — | — |
| Spleen reduced size | — | 1/3 | — | — | — | — |

TABLE 49-continued

Incidence of necropsy findings (animals with findings/total number of animals)

| | G | H | I | J | K | M |
|---|---|---|---|---|---|---|
| Macroscopic Finding | STZ + Metformin Leucinate | STZ + Metformin valinate | STZ + Metformin Lysinate | STZ + Metformin asparaginate | STZ + Metformin threoninate | STZ + Metformin aspartate |
| Thymus reduced size | — | — | — | — | 1/3— | 1/3 |
| Red-colored adrenal glands | 1/3 | — | — | — | — | — |
| Red-colored yeyunum and duodenum | | | | | | |
| Seminal vesicles reduced size | 1/3 | — | — | — | — | — |
| Prostate reduced size | 1/3 | — | — | — | — | — |
| Kidney hypertrophy | — | — | — | 1/3 | 1/3 | — |
| Pancreas reduced size | — | 1/3 | — | — | — | — |
| Spleen reduced size | — | 1/3 | — | — | — | — |

—No macroscopic abnormalities were observed

According to the above studies, it was observed that metformin compounds of the present invention, selected from the group consisting of metformin aspartate, metformin isoleucinate, metformin alaninate, metformin valinate, metformin asparaginate, metformin threoninate, metformin leucinate, and metformin lysinate, more particularly metformin lysinate, are efficient and all of them are able to reduce blood glucose. Also, the different compounds of metformin of the present invention, particularly metformin lysinate, also inhibit GPBP inhibitors and not just biguanides.

The present invention shows that SLNs, such as metformin lysinate, are active ingredients different from metformin hydrochloride for Type 2 Diabetes, operating by inhibiting GPBP kinase activity. In this invention, it is disclosed and protected that: 1. SLN10 has an electronic structure different from metformin hydrochloride's, which confronts GPBP and inhibits its kinase activity; 2. SLN10 promotes glucose transporter translocation to membranes and glucose uptake (anti-hyperglycemic and anti-hypoglycemic activities), and limit the inflammatory response (anti-inflammatory activity) by inhibiting GPBP kinase activity; 3. SLN10 reduces peripheral insulin resistance, and it is a better antidiabetic agent than SLN1 in animal models of Type 2 Diabetes due to its inhibiting action over the GPBP kinase activity.

This is how this invention proposes drugs, compositions and/or formulations, such as tablets, more particularly tablets with aqueous coating comprising metformin compounds (SLNs) from 100 mg up to 2.4 g, selected from the group consisting of metformin aspartate, metformin isoleucinate, metformin alaninate, metformin valinate, metformin asparaginate, metformin threoninate, metformin leucinate, and metformin lysinate, more particularly metformin lysinate, from 100 mg up to 2.4 g, preferably 589-651 mg, specially 615-625 mg, and more particularly 620 mg, or 997.5-1102.5 mg, preferably 1035-1075 mg, and more particularly 1050 mg. The SLNs participate and intervene in the AMPK, GPBP/CERT, and LKB1 activity in the following manner:

They inhibit GPBP/CERT activity
They increase LKB1 activity
They inhibit GPBP/CERT and LKB1 cross-activation
They increase IL10 synthesis
They translocate glucose transporter GLUT4 more efficiently
They act via VAPA-VAMP2 interaction; and/or
They participate in AS160 regulation where AMPK increases GPBP/CERT activity; and GPBP/CERT and LKB1 power, in a synergic way, its kinase activity (reducing insulin and leptin levels, and improving lipids profile).

METHODS OF USE

The present application discloses pharmaceutical compositions and medicaments comprising at least one compound of the present invention, or a pharmaceutically acceptable salt, solvate, and/or ester thereof, and optionally in combination with at least one additional therapeutic agent, and a pharmaceutically acceptable carrier or excipient. The compounds are selected from the group comprising metformin aspartate, metformin isoleucinate, metformin alaninate, metformin valinate, metformin asparaginate, metformin threoninate, metformin leucinate, or metformin lysinate, more particularly Metformin lysinate.

The metformin compounds of the present invention, such as metformin aspartate, metformin isoleucinate, metformin alaninate, metformin valinate, metformin asparaginate, metformin threoninate, metformin leucinate, or metformin lysinate, have an anti-hyperglycemic effect as coadjuvant on prevention, treatment and control of Type 2 diabetes in adults, as well as children and adolescents.

The compounds of the present invention are also useful for preventing, treating, and controlling Type 2 Diabetes in obese or overweight patients, including patients who have failed to follow a diet or an exercise regimen, who show failure with sulfonylureas, and who have a tendency to gain weight; they are also useful for preventing, treating and controlling Type 2 Diabetes in patients with lipid metabolism disorders secondary to Diabetes.

A preferred compound in the present invention is metformin lysinate, which is useful as an anti-hyperglycemic agent and as a coadjuvant compound in preventing, treating and controlling Type 2 Diabetes in adults, as well as children and adolescents.

Tablets constitute the preferred dosage form for the administration of the compounds of this invention.

In some embodiments, the metformin amino acid compounds, which are biguanides, selected from the group consisting of metformin aspartate, metformin isoleucinate, metformin alaninate, metformin valinate, metformin asparaginate, metformin threoninate, metformin leucinate, and metformin lysinate, are effective and capable of lowering blood glucose levels. In some embodiments, metformin lysinate is effective and capable of lowering blood glucose levels. In some embodiments, the metformin amino acid compounds, selected from the group consisting of metformin aspartate, metformin isoleucinate, metformin alaninate, metformin valinate, metformin asparaginate, metformin threoninate, metformin leucinate, and metformin lysinate, inhibit GPBP. In some embodiments, metformin lysinate inhibits GPBP.

The present invention shows that the metformin amino acid compounds (SLNs), such as metformin lysinate, are different from metformin hydrochloride for Type 2 diabetes, operating by inhibiting GPBP kinase activity. In the present invention, the following is disclosed and protected: 1. Metformin of SLN10 has an electronic structure different from metformin of SLN1, that confronts GPBP and inhibits its kinase activity; 2. SLN10 promote glucose transporter translocation to membranes and glucose uptake (anti-hyperglycemic and anti-hypoglycemic activities), and limit the inflammatory response (anti-inflammatory activity) by inhibiting GPBP kinase activity.

In some embodiments, the metformin amino acid compound is metformin aspartate, metformin isoleucinate, metformin alaninate, metformin valinate, metformin asparaginate, metformin threoninate, metformin leucinate, or metformin lysinate, more particularly metformin lysinate, administered in a dosage form of from about 100 mg to about 2.4 g, from about 589-651 mg, from about 615-625 mg, and about 620 mg. In some embodiments, the metformin amino acid compound is administered in a dosage form of from about 997.5-1102.5 mg, from about 1035-1075 mg, or about 1050 mg. The SLNs participate and intervene in the AMPK, GPBP/CERT, and LKB1 activity.

Drugs, compositions and/or formulations containing the compounds in the present invention are optimized, robust, and useful in preventing, treating and controlling Type 2 Diabetes. These are replicable and have the required quality, stability, and effectiveness for their purpose.

In some embodiments, pharmaceutical compositions comprising a metformin amino acid compounds, or a pharmaceutically acceptable salt, solvate, and/or ester thereof are disclosed, in combination with at least one additional therapeutic agent, and a pharmaceutically acceptable carrier or excipient. The additional therapeutic agent is selected among other antidiabetic drugs, such as sulfonylureas, iDPP4, SGL2, thiazolidinediones (TZD), insulin, glinides, etc. In some embodiments, the pharmaceutical composition comprising another anti-hyperglycemic agent. In some embodiments, the other anti-hyperglycemic agent is glyburide, glipizide, glimepiride, acarbose, miglitol, troglitazone, or insulin.

While various embodiments have been described above, it should be understood that they have been presented by way of example only, and not limitation. It will be apparent to persons skilled in the art that various changes in form and detail can be made therein without departing from the spirit and scope of the invention. Thus, the breadth and scope should not be limited by any of the above-described exemplary embodiments, but should be defined only in accordance with the following claims and their equivalents.

All publications, patents, and patent applications mentioned in this specification are indicative of the level of skill of those skilled in the art to which this invention pertains, and are herein incorporated by reference to the same extent as if each individual publication, patent, or patent application was specifically and individually indicated to be incorporated by reference.

What is claimed:

1. A method of producing a metformin lysinate complex, the method comprising:
   (a) preparing the free base of metformin from a metformin compound;
   (b) admixing the metformin free base of (a) with lysine at a temperature from about 0° C. to about 60° C.;
   (c) stirring the metformin free base and the lysine for from about 30 minutes to about 30 hours;
   (d) filtering the admixture of metformin base and lysine; and
   (e) concentrating the filtrate of (d).

2. The method of claim 1, wherein about one equivalent of the metformin free base is reacted with about one equivalent of lysine.

3. The method of claim 1, further comprising:
   (f) cooling the concentrated filtrate of (e) to below room temperature.

4. The method of claim 1, wherein the metformin compound is metformin hydrochloride.

* * * * *

UNITED STATES PATENT AND TRADEMARK OFFICE
CERTIFICATE OF CORRECTION

| | |
|---|---|
| PATENT NO. | : 11,510,886 B2 |
| APPLICATION NO. | : 16/337994 |
| DATED | : November 29, 2022 |
| INVENTOR(S) | : J. González-Canudas |

It is certified that error appears in the above-identified patent and that said Letters Patent is hereby corrected as shown below:

On the Title Page

Column 1, Item (71), in "Applicant", Line 1, delete "Silancs" and insert --Silanes--, therefor.

In the Specification

In Column 5, Line 20, please replace "(NCI)" with --(NC1)--, therefor.
In Column 8, Line 44, please replace "tract Plasma" with --tract. Plasma--, therefor.
In Column 8, Line 46, please replace "g/mL" with --ηg/mL--, therefor.
In Column 14, Line 47, please replace "morcover" with --moreover--, therefor.
In Column 19, Line 18, please replace "S00" with --500--, therefor.
In Column 28, Line 17, please replace "(IRP)" with --(IRβ)--, therefor.
In Column 30, Lines 51-52, please replace "PCTIEP2009/005258" with --PCT/EP2009/005258--, therefor.
In Column 42, Line 22, please replace "IL-10" with --IL-1β--, therefor.
In Column 45, Line 67, please replace "represented b formula" with --represented by formula--, therefor.
In Column 49, Line 52, please replace "Δ=1.5406 Å" with --λ=1.5406 Å--, therefor.
In Column 50, Line 51, please replace "about 90% h to" with --about 90% to--, therefor.
In Column 51, Line 47, please replace "type H" with --type II--, therefor.
In Column 51, Line 51, please replace "type 1" with --type II--, therefor.
In Column 56, Line 34, please replace "Valise" with --Valine--, therefor.
In Column 72, Line 12, please replace "SIN1" with --SLN1--, therefor.
In Column 80, Line 42, please replace "PCTIEP2012/052923" with --PCT/EP2012/052923--, therefor.
In Column 86, Line 21, please replace "lower S values" with --lower δ values--, therefor.
In Column 89, Line 18, please replace "C02" with --$CO_2$--, therefor.
In Column 117, Line 26, please replace "γ" with --7--, therefor.

Signed and Sealed this
Twenty-first Day of February, 2023

*Katherine Kelly Vidal*

Katherine Kelly Vidal
*Director of the United States Patent and Trademark Office*